US011753381B2

(12) United States Patent
Lewis et al.

(10) Patent No.: US 11,753,381 B2
(45) Date of Patent: Sep. 12, 2023

(54) INHIBITORS OF RECEPTOR INTERACTING PROTEIN KINASE I FOR THE TREATMENT OF DISEASE

(71) Applicant: Board of Regents, The University of Texas System, Austin, TX (US)

(72) Inventors: Richard T. Lewis, Missouri City, TX (US); Matthew Michael Hamilton, Missouri City, TX (US); William J. Ray, Houston, TX (US); Fernando Alvarez, Austin, TX (US); Dana E. Pfaffinger, Houston, TX (US); Naphtali Reyna, Arlington, TX (US); Jason Cross, Pearland, TX (US); Suyambu Kesava Vijayan Ramaswamy, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 37 days.

(21) Appl. No.: 17/033,104

(22) Filed: Sep. 25, 2020

(65) Prior Publication Data

US 2021/0094921 A1 Apr. 1, 2021

Related U.S. Application Data

(60) Provisional application No. 62/907,146, filed on Sep. 27, 2019.

(51) Int. Cl.
| | | |
|---|---|---|
| C07D 231/06 | (2006.01) | |
| A61K 31/4965 | (2006.01) | |
| A61K 31/415 | (2006.01) | |
| A61K 31/416 | (2006.01) | |
| C07D 231/56 | (2006.01) | |
| C07D 403/12 | (2006.01) | |
| A61K 31/506 | (2006.01) | |
| A61K 31/5377 | (2006.01) | |
| C07D 401/14 | (2006.01) | |
| A61K 31/4439 | (2006.01) | |
| C07D 471/04 | (2006.01) | |
| A61K 31/437 | (2006.01) | |
| C07D 403/08 | (2006.01) | |
| A61K 31/4155 | (2006.01) | |
| C07D 413/08 | (2006.01) | |
| A61K 31/4245 | (2006.01) | |
| A61K 31/4184 | (2006.01) | |
| C07D 207/10 | (2006.01) | |
| A61K 31/40 | (2006.01) | |
| A61K 31/4015 | (2006.01) | |
| C07D 401/12 | (2006.01) | |
| C07D 403/14 | (2006.01) | |
| A61K 31/497 | (2006.01) | |
| A61K 31/4192 | (2006.01) | |
| C07D 487/04 | (2006.01) | |
| A61K 31/4985 | (2006.01) | |
| C07D 417/14 | (2006.01) | |

(Continued)

(52) U.S. Cl.
CPC ............ *C07D 231/06* (2013.01); *A61K 31/40* (2013.01); *A61K 31/4015* (2013.01); *A61K 31/415* (2013.01); *A61K 31/416* (2013.01); *A61K 31/4155* (2013.01); *A61K 31/4184* (2013.01); *A61K 31/4192* (2013.01); *A61K 31/427* (2013.01); *A61K 31/4245* (2013.01); *A61K 31/437* (2013.01); *A61K 31/4439* (2013.01); *A61K 31/497* (2013.01); *A61K 31/4965* (2013.01); *A61K 31/4985* (2013.01); *A61K 31/506* (2013.01); *A61K 31/5377* (2013.01); *A61K 45/06* (2013.01); *C07D 207/10* (2013.01); *C07D 231/56* (2013.01); *C07D 241/24* (2013.01); *C07D 401/12* (2013.01); *C07D 401/14* (2013.01); *C07D 403/08* (2013.01); *C07D 403/12* (2013.01); *C07D 403/14* (2013.01); *C07D 413/08* (2013.01); *C07D 417/14* (2013.01); *C07D 471/04* (2013.01); *C07D 487/04* (2013.01)

(58) Field of Classification Search
CPC .. C07D 231/06; C07D 207/10; C07D 231/56; C07D 241/24; C07D 401/12; C07D 401/14; C07D 403/08; C07D 403/12; C07D 403/14; C07D 413/08; C07D 417/14; C07D 471/04; C07D 487/04
See application file for complete search history.

(56) References Cited

U.S. PATENT DOCUMENTS 6,291,476 B1  9/2001 Kordik
2012/0122889 A1  5/2012 Yuan
(Continued)

FOREIGN PATENT DOCUMENTS

WO  2010075561  7/2010
WO  2010122088  10/2010
(Continued)

OTHER PUBLICATIONS

Degterev; PNAS 2019, 116, 9714-9722. https://doi.org/10.1073/pnas.1901179116 (Year: 2019).*

(Continued)

*Primary Examiner* — Daniel R Carcanague
(74) *Attorney, Agent, or Firm* — Cynthia Hathaway; Lauren L. Stevens; Erik M. Larsen

(57) ABSTRACT

Disclosed herein are compounds which inhibit RIPK1, pharmaceutical compositions, and methods of treatment of RIPK1-mediated diseases, such as neurodegenerative disorders, inflammatory disorders, and cancer.

8 Claims, No Drawings

(51) Int. Cl.
*A61K 31/427* (2006.01)
*C07D 241/24* (2006.01)
*A61K 45/06* (2006.01)

(56) References Cited

U.S. PATENT DOCUMENTS

| | | |
|---|---|---|
| 2013/0184287 A1 | 7/2013 | Gray |
| 2013/0281428 A1 | 10/2013 | Ohki |
| 2014/0066466 A1 | 3/2014 | Yuan |
| 2014/0228367 A1 | 8/2014 | Flynn |
| 2014/0364431 A1 | 12/2014 | Gong |
| 2015/0353533 A1 | 12/2015 | Bandyopadhyay |
| 2016/0002255 A1 | 1/2016 | Brockunier |
| 2016/0075654 A1* | 3/2016 | Bunker ............... C07C 215/42 514/630 |
| 2016/0221963 A1 | 8/2016 | Beigelman |
| 2017/0008877 A1 | 1/2017 | Patel |
| 2017/0226127 A1 | 8/2017 | Estrada |
| 2017/0266199 A1 | 9/2017 | Berger |
| 2018/0170927 A1 | 6/2018 | Patel |
| 2018/0319819 A1 | 11/2018 | Yogo |
| 2019/0092714 A1 | 3/2019 | Suzuki |
| 2019/0241565 A1 | 8/2019 | Patel |
| 2020/0062735 A1 | 2/2020 | Anbari |
| 2021/0032271 A1 | 2/2021 | Patel |
| 2021/0094951 A1 | 4/2021 | Lewis |
| 2021/0115010 A1* | 4/2021 | Soth ............... C07D 401/04 |
| 2021/0154204 A1 | 5/2021 | Lewis |

FOREIGN PATENT DOCUMENTS

| | | |
|---|---|---|
| WO | 2011115725 | 9/2011 |
| WO | 2012125544 | 9/2012 |
| WO | 2014125444 | 8/2014 |
| WO | 2016027253 | 2/2016 |
| WO | 2016044331 | 3/2016 |
| WO | 2016101887 | 6/2016 |
| WO | 2016185423 | 11/2016 |
| WO | 2017069279 | 4/2017 |
| WO | 2017096301 | 6/2017 |
| WO | 2017136727 | 8/2017 |
| WO | 2018100070 | 6/2018 |
| WO | 2018107060 | 6/2018 |
| WO | 2019051038 | 3/2019 |
| WO | 2019110832 | 6/2019 |
| WO | 2019213445 | 11/2019 |
| WO | 2019213447 | 11/2019 |
| WO | 2021046515 | 3/2021 |
| WO | 2021062199 | 3/2021 |
| WO | 2021108198 | 6/2021 |
| WO | 2021173917 | 9/2021 |

OTHER PUBLICATIONS

Chemical Abstracts STN Registry Database, record for RN 2373678-19-2, "3-[[2-(3-Methoxyphenyl)-1-pyrrolidinyl]carbonyl] bicyclo[1.1.1]pentane-1-carboxylic acid", Entered STN Sep. 4, 2019. (Year: 2019).*
Chemical Abstracts STN Registry Database, record for RN 2323881-41-8, "[3-(4-Cyclopropyl-1H-1,2,3-triazol-1-yl)-1-pyrrolidinyl][3-(trifluoromethyl)bicyclo[1.1.1]pent-1-yl]methanone", Entered STN Jun. 4, 2019. (Year: 2019).*
Caputo; Chem. Sci., 2018,9, 5295-5300. https://doi.org/10.1039/c8sc01355a (Year: 2018).*
Goh; ACS Med. Chem. Lett. 2017, 8, 516-520. http://dx.doi.org/10.1021/acsmedchemlett.7b00018 (Year: 2017).*
Pellicciari; J. Med. Chem. 1996, 39, 2874-2876. https://doi.org/10.1021/jm960254o (Year: 1996).*
Stepan; J Med Chem. 2012, 55, 3414-3424. https://doi.org/10.1021/jm300094u (Year: 2012).*
Thirumoorthi; Chem. Commun., 2015,51, 3139-3142. https://doi.org/10.1039/C4CC09655J (Year: 2015).*
International Application No. PCT/US2020/049667; International Search Report and Written Opinion of the International Searching Authority, dated Feb. 4, 2021; 11 pages.
International Application No. PCT/US2020/052789; International Search Report and Written Opinion of the International Searching Authority, dated Feb. 17, 2021; 10 pages.
International Application No. PCT/US2020/061171; International Search Report and Written Opinion of the International Searching Authority, dated Mar. 17, 2021; 9 pages.
PubChem CID 122183864 Create Date: Oct. 26, 2016 (Oct. 26, 2016), especially p. 2 formula.
PubChem CID 1481295, N-Methyl-4-oxo-1-phenyl-1,4-dihydro-3-pyridazinecarboxamide, create date Jul. 11, 2005.
PubChem CID 58072278, 1-Methyl-4-oxopyridazine-3-carboxamide, create date Aug. 19, 2012.
PubChem CID 891989 Create Date: Jul. 9, 2005 (Jul. 9, 2005), especially p. 2 formula.
PubChem Compound Record for CID 132165444, CN(C(=O)C12CC(C1)(C2)C(=O)O)C, Create Date: Jan. 29, 2018.
PubChem Compound Record for CID 86010391, 3-Methylbicyclo[1.1.1]pentane-1-carboxamide, Create Date: Nov. 3, 2014.
Ameriks, M. et al., "Diazinones as P2 replacements for pyrazole-based cathepsin S inhibitors", Bioorg Med Chem Lett., 20(14):4060-4, (2010).
International Application No. PCT/US2020/049667; International Preliminary Report on Patentability, dated Mar. 17, 2022; 8 pages.
International Application No. PCT/US2020/052789; International Preliminary Report on Patentability, dated Apr. 7, 2022; 7 pages.
International Application No. PCT/US2020/061171; International Preliminary Report on Patentability, dated Jun. 9, 2022; 6 pages.
Berger, S. et al., "Characterization of GSK'963: A Structurally Distinct, Potent and Selective Inhibitor of RIP1 Kinase", Cell Death Discov., 1:15009, (2015).
Choi, S. et al., "Optimization of Tricyclic NEC-3 Necroptosis Inhibitors for In Vitro Liver Microsomal Stability", Bioorg Med Chem Lett., 22(17):5685-8, (2012).
Harris, P. et al., "Identification of a RIP1 Kinase Inhibitor Clinical Candidate (GSK3145095) for the Treatment of Pancreatic Cancer", ACS Med Chem Lett., 10(6):857-62, (2019).
Jagtap, P. et al., "Structure-Activity Relationship Study of Tricyclic Necroptosis Inhibitors", J Med Chem., 50(8):1886-95, (2007).
Ren, Y. et al., "Discovery of a Highly Potent, Selective, and Metabolically Stable Inhibitor of Receptor-Interacting Protein 1 (RIP1) for the Treatment of Systemic Inflammatory Response Syndrome", J Med Chem., 60(3):972-86, (2017).
U.S. Appl. No. 16/952,422, filed Nov. 19, 2020; 143 pages.
U.S. Appl. No. 17/014,184, filed Sep. 8, 2020; 245 pages.
Yoshikawa, M. et al., "Discovery of 7-Oxo-2,4,5,7-tetrahydro-6 H-pyrazolo[3,4- c]pyridine Derivatives as Potent, Orally Available, and Brain-Penetrating Receptor Interacting Protein 1 (RIP1) Kinase Inhibitors: Analysis of Structure-Kinetic Relationships", J Med Chem., 61(6):2384-409, (2018).
Chemical Abstracts STN Database, Record for RN 1277246-48-6, "1-(2-Fluorophenyl)-N-(hexahydro-2-oxo-1 H-azepin-3-yl)-1,4-dihydro-6-methyl-4-oxo-3-pyridazinecarboxamide", Entered STN Apr. 11, 2011, (2011).
Chemical Abstracts STN Database, Record for RN 924068-54-2, "N-(3-Chlorophenyl)-1,4-dihydro-6-methyl-4-oxo-1-phenyl-3-pyridazinecarboxamide", Entered STN Mar. 1, 2007, (2007).
U.S. Appl. No. 16/952,422, Non-Final Office Action, dated Oct. 14, 2022; 36 pages.
U.S. Appl. No. 16/952,422; Examiner-Initiated Interview Summary, dated Jan. 19, 2023; 1 page.
U.S. Appl. No. 16/952,422; Notice of Allowance, dated Feb. 17, 2023; 12 pages.
U.S. Appl. No. 17/014,184, Non-Final Office Action, dated Sep. 27, 2022; 31 pages.
U.S. Appl. No. 17/014,184; Examiner-Initiated Interview Summary, dated Feb. 28, 2023; 1 page.
U.S. Appl. No. 17/014,184; Notice of Allowance, dated Mar. 9, 2023; 16 pages.

* cited by examiner

INHIBITORS OF RECEPTOR INTERACTING PROTEIN KINASE I FOR THE TREATMENT OF DISEASE

This application claims the benefit of priority of U.S. Provisional Application No. 62/907,146, filed 27 Sep. 2019, the disclosure of which is hereby incorporated by reference as if written herein in its entirety.

Disclosed herein are new compounds and compositions and their application as pharmaceuticals for the treatment of disease. Methods of inhibition of RIPK1 in a human or animal subject are also provided for the treatment of diseases mediated by RIPK1 such as neurodegenerative disorders, inflammatory disorders, and cancer.

The role of Receptor Interacting Protein Kinase 1 (RIPK1) in the regulation of apoptotic or necroptotic cell death pathways has been reported, and its emerging role in the mediation coordinating the response to pro-inflammatory signaling in a number of cell types and contexts is emerging. RIPK1 consists of an N-terminal kinase domain, a RHIM (RIP homotypic interaction motif) domain, and a death domain, which collectively undergo extensive post-translational modification in response to signaling through various receptors such as tumor necrosis factor a receptors (TNFRs), toll-like receptors, NOD-like receptor, and others. RIPK1 has been most extensively studied in the context of TNFR1 signaling, which triggers its recruitment to the C-terminal domain of the receptor via the protein TRADD (TNF receptor associated death domain protein). There RIPK1 is ubiquitinated by the E3 ubiquitin ligases TNF receptor-associated factor 2 (TRAF2) or TRAF5 and the cellular inhibitor of apoptosis proteins (cIAPs) cIAP1 and cIAP2. This molecular assembly is known as complex 1. Cylindromatosis (CYLD) then mediates the deubiquitination of RIPK1 to allow assembly of complex lib, also known as the necrosome. The necrosome consists of the RIPK1 homolog RIPK3 and the pseudokinase MLKL. The assembly and function of the necrosome is inhibited by caspase 8 such that only when caspase 8 activity is blocked is the necrosome functional. In that context the necrosome causes necroptosis, an inflammatory form of programmed cell death in which membrane lysis causes the release of cellular contents into the extracellular space.

RIPK1 can also, in different contexts, regulate apoptosis and inflammation. When cIAPs are inhibited so that RIPK1 ubiquitination does not occur, RIPK1 participates in apoptosis. Ubiquitinated RIPK1 can also recruit NF-KB essential modulator (NEMO) and TAK1 binding protein 2 or 3 (TAB2/3), leading to activation of inhibitor of kappa B (IKB) kinase beta (IKK) and transforming growth factor beta (TGF)-activated kinase 1 (TAK1), which in turn promotes the NF-KB pro-inflammatory or pro-survival gene expression programs. Given its role in inflammation, RIPK1 has been implicated in many diseases featuring chronic and acute inflammatory signaling, including viral infections, sepsis, retinal degeneration, traumatic brain injury, ischemic stroke, intracerebral hemorrhage, amyotrophic lateral sclerosis, acute kidney injury, myocardial reperfusion injury, Alzheimer's disease, ulcerative colitis, osteoarthritis, and others. In animal models of these diseases, RIPK1 kinase inhibitors such as necrostatin-1 have shown to be effective, leading to the development of such molecules for clinical trials in a number of indications.

DETAILED DESCRIPTION

Provided herein is Embodiment 1, a compound of structural Formula (I):

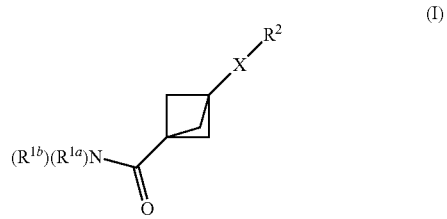

or a salt thereof, wherein:

X is alkylene and is optionally substituted with one or more $R^7$, or X is chosen from carbamoyl, carbonyl, and a bond;

$R^{1a}$ and $R^{1b}$ are independently chosen from H and alkyl, which is optionally substituted with one $R^3$, and which is optionally substituted with one or more $R^4$, or $R^{1a}$ and $R^{1b}$, together with the intervening nitrogen, combine to form heterocycloalkyl or heteroaryl, either of which is optionally substituted with one $R^3$, and either of which is optionally substituted with one or more $R^4$;

$R^2$ is chosen from hydrogen, hydroxy, cyano, and halo, or $R^2$ is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl)carbonyl, (cycloalkyl)carbonyl, (heterocycloalkyl)carbonyl, (aryl)carbonyl, (alkyl)amino, (cycloalkyl)amino, (heterocycloalkyl)amino, (aryl)amino, and (heteroaryl)amino, any of which is optionally substituted with one or more $R^5$;

$R^3$ is chosen from aryl, (aryl)oxy, heteroaryl, (heteroaryl)oxy, cycloalkyl, and heterocycloalkyl, any of which is optionally substituted with one or more $R^6$;

each $R^4$ is independently chosen from alkyl, halo, cyano, and hydroxy;

each $R^5$ is independently chosen from halo, cyano, amido, alkyl, alkoxy, cyanoalkyl, hydroxyalkyl, alkoxyalkyl, cycloalkyl, haloalkyl, oxo, $P(O)(CH_3)_2$, $SO_2CH_3$, aryl optionally substituted with one or more alkyl, and heteroaryl optionally substituted with one or more alkyl;

two $R^5$, together with the intervening atoms, optionally combine to form a cycloalkyl or heterocycloalkyl;

each $R^6$ is independently chosen from halo, alkyl, cycloalkyl, cyano, alkoxy, hydroxy, haloalkyl, hydroxyalkyl, and haloalkoxy; and each $R^7$ is independently chosen from alkyl, cyano, halo, and hydroxy.

Certain compounds disclosed herein possess useful RIPK1 inhibiting activity, and may be used in the treatment or prophylaxis of a disease or condition in which RIPK1 plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting RIPK1. Other embodiments provide methods for treating a RIPK1-mediated disorder in a patient in need of such treatment, comprising administering to said patient a therapeutically effective amount of a compound or composition as disclosed herein. Also provided is the use of certain compounds disclosed herein for use in the manufacture of a medicament for the treatment of a disease or condition ameliorated by the inhibition of RIPK1.

Also provided herein is Embodiment 2, a compound of structural Formula (Ia):

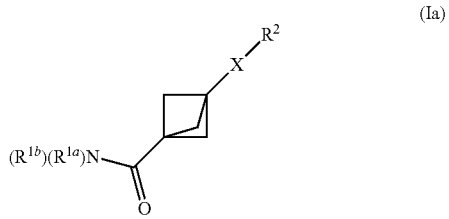

or a salt thereof, wherein:
X is alkylene and is optionally substituted with one or more $R^7$,
or X is chosen from carbamoyl, carbonyl, and a bond;
$R^{1a}$ and $R^{1b}$ are independently chosen from H and alkyl, which is optionally substituted with one $R^3$, and which is optionally substituted with one or more $R^4$,
or $R^{1a}$ and $R^{1b}$, together with the intervening nitrogen, combine to form heterocycloalkyl or heteroaryl, either of which is optionally substituted with one $R^3$, and either of which is optionally substituted with one or more $R^4$;
$R^2$ is chosen from hydrogen, hydroxy, cyano, and halo,
or $R^2$ is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl)carbonyl, (cycloalkyl)carbonyl, (heterocycloalkyl)carbonyl, (aryl)carbonyl, (alkyl)amino, (cycloalkyl)amino, (heterocycloalkyl)amino, (aryl)amino, and (heteroaryl)amino, any of which is optionally substituted with one or more $R^5$;
$R^3$ is chosen from aryl, (aryl)oxy, heteroaryl, (heteroaryl)oxy, cycloalkyl, and heterocycloalkyl, any of which is optionally substituted with one or more $R^6$;
each $R^4$ is independently chosen from alkyl, halo, cyano, and hydroxy;
each $R^5$ is independently chosen from halo, cyano, amido, alkyl, alkoxy, hydroxyalkyl, alkoxyalkyl, cycloalkyl, haloalkyl, oxo, $P(O)(CH_3)_2$, $SO_2CH_3$, aryl optionally substituted with one or more alkyl, and heteroaryl optionally substituted with one or more alkyl;
two $R^5$, together with the intervening atoms, optionally combine to form a cycloalkyl or heterocycloalkyl;
each $R^6$ is independently chosen from halo, alkyl, cyano, alkoxy, hydroxy, haloalkyl, and haloalkoxy; and
each $R^7$ is independently chosen from alkyl, cyano, halo, and hydroxy.

Also provided are the following embodiments:
Embodiment 3: in some embodiments, such as, the compound of Embodiment 1, each $R^4$ is independently chosen from methyl, halo, and cyano.
Embodiment 4: in some embodiments, such as, the compound of Embodiment 3, each $R^4$ is independently chosen from halo and cyano.
Embodiment 5: in some embodiments, such as, the compound of Embodiment 4, each $R^4$ is independently chosen from fluoro and cyano.

Embodiment 6: in some embodiments, such as, the compound of any one of Embodiments 1-5:
$R^{1a}$ is alkyl, which is optionally substituted with one $R^3$, and which is optionally substituted with one or more $R^4$; and
$R^{1b}$ is H.
Embodiment 7: in some embodiments, such as, the compound of Embodiment 6, $R^{1a}$ is alkyl, which is substituted with 1 $R^3$, and which is optionally substituted with one or more $R^4$.
Embodiment 8: in some embodiments, such as, the compound of either one of Embodiments 6 and 7, $R^{1a}$ is optionally substituted with 1, 2, or 3 $R^4$.
Embodiment 9: in some embodiments, such as, the compound of Embodiment 8, $R^{1a}$ is substituted with 1, 2, or 3 $R^4$.
Embodiment 10: in some embodiments, such as, the compound of Embodiment 9, $R^{1a}$ is substituted with 1 or 2 $R^4$.
Embodiment 11: in some embodiments, such as, the compound of Embodiment 9, $R^{1a}$ is substituted with 2 $R^4$.
Embodiment 12: in some embodiments, such as, the compound of Embodiment 9, $R^{1a}$ is substituted with 2 or 3 $R^4$.
Embodiment 13: in some embodiments, such as, the compound of Embodiment 9, $R^{1a}$ is substituted with 3 $R^4$.
Embodiment 14: in some embodiments, such as, the compound of Embodiment 8, $R^{1a}$ is optionally substituted with 1 or 2 $R^4$.
Embodiment 15: in some embodiments, such as, the compound of Embodiment 14, $R^{1a}$ is optionally substituted with 1 $R^4$.
Embodiment 16: in some embodiments, such as, the compound of Embodiment 14, $R^{1a}$ is substituted with 1 $R^4$.
Embodiment 17: in some embodiments, such as, the compound of any one of Embodiments 1-5, $R^{1a}$ and $R^{1b}$, together with the intervening nitrogen, combine to form heterocycloalkyl or heteroaryl, either of which is optionally substituted with one $R^3$, and either of which is optionally substituted with one or more $R^4$.
Embodiment 18: in some embodiments, such as, the compound of Embodiment 17, $R^{1a}$ and $R^{1b}$, together with the intervening nitrogen, combine to form heterocycloalkyl, which is optionally substituted with one $R^3$, and which is optionally substituted with one or more $R^4$.
Embodiment 19: in some embodiments, such as, the compound of Embodiment 18, the heterocycloalkyl formed by $R^{1a}$ and $R^{1b}$, together with the intervening nitrogen, has 5 or 6 members.
Embodiment 20: in some embodiments, such as, the compound of Embodiment 19, the heterocycloalkyl formed by $R^{1a}$ and $R^{1b}$, together with the intervening nitrogen, has 5 members.
Embodiment 21: in some embodiments, such as, the compound of Embodiment 20, the heterocycloalkyl formed by $R^{1a}$ and $R^{1b}$, together with the intervening nitrogen, is chosen from pyrazoline and pyrrolidine.
Embodiment 22: in some embodiments, such as, the compound of any one of Embodiments 18-21, the heterocycloalkyl formed by $R^{1a}$ and $R^{1b}$, together with the intervening nitrogen is substituted with 1 $R^3$, and which is optionally substituted with one or more $R^4$.
Embodiment 23: in some embodiments, such as, the compound of any one of Embodiments 18-22, the heterocycloalkyl formed by $R^{1a}$ and $R^{1b}$, together with the intervening nitrogen is optionally substituted with 1, 2, or 3 $R^4$.
Embodiment 24: in some embodiments, such as, the compound of Embodiment 23, the heterocycloalkyl formed by $R^{1a}$ and $R^{1b}$, together with the intervening nitrogen is substituted with 1, 2, or 3 $R^4$.

Embodiment 25: in some embodiments, such as, the compound of Embodiment 24, the heterocycloalkyl formed by $R^{1a}$ and $R^{1b}$, together with the intervening nitrogen is substituted with 1 or 2 $R^4$.

Embodiment 26: in some embodiments, such as, the compound of Embodiment 24, the heterocycloalkyl formed by $R^{1a}$ and $R^{1b}$, together with the intervening nitrogen is substituted with 2 $R^4$.

Embodiment 27: in some embodiments, such as, the compound of Embodiment 24, the heterocycloalkyl formed by $R^{1a}$ and $R^{1b}$, together with the intervening nitrogen is substituted with 2 or 3 $R^4$.

Embodiment 28: in some embodiments, such as, the compound of Embodiment 24, the heterocycloalkyl formed by $R^{1a}$ and $R^{1b}$, together with the intervening nitrogen is substituted with 3 $R^4$.

Embodiment 29: in some embodiments, such as, the compound of Embodiment 23, the heterocycloalkyl formed by $R^{1a}$ and $R^{1b}$, together with the intervening nitrogen is optionally substituted with 1 or 2 $R^4$.

Embodiment 30: in some embodiments, such as, the compound of Embodiment 29, the heterocycloalkyl formed by $R^{1a}$ and $R^{1b}$, together with the intervening nitrogen is optionally substituted with 1 $R^4$.

Embodiment 31: in some embodiments, such as, the compound of Embodiment 29, the heterocycloalkyl formed by $R^{1a}$ and $R^{1b}$, together with the intervening nitrogen is substituted with 1 $R^4$.

Embodiment 32: in some embodiments, such as, the compound of any one of Embodiments 9-13 and 24-28, at least one $R^4$ is halo.

Embodiment 33: in some embodiments, such as, the compound of any one of Embodiments 12, 13, 27, and 28, at least two $R^4$ are halo.

Embodiment 34: in some embodiments, such as, the compound of any one of Embodiments 1-33, $R^4$ is halo.

Embodiment 35: in some embodiments, such as, the compound of any one of Embodiments 9-13 and 24-28, at least one $R^4$ is fluoro.

Embodiment 36: in some embodiments, such as, the compound of any one of Embodiments 12, 13, 27, and 28, at least two $R^4$ are fluoro.

Embodiment 37: in some embodiments, such as, the compound of any one of Embodiments 1-36, $R^4$ is fluoro.

Embodiment 38: in some embodiments, such as, the compound of Embodiment 14, $R^{1a}$ is unsubstituted with an $R^4$.

Embodiment 39: in some embodiments, such as, the compound of Embodiment 29, the heterocycloalkyl formed by $R^{1a}$ and $R^{1b}$, together with the intervening nitrogen is unsubstituted with an $R^4$.

Embodiment 40: in some embodiments, such as, the compound of any one of Embodiments 22-39, the heterocycloalkyl formed by $R^{1a}$ and $R^{1b}$, together with the intervening nitrogen, is pyrazoline.

Embodiment 41: in some embodiments, such as, the compound of any one of Embodiments 22-39, the heterocycloalkyl formed by $R^{1a}$ and $R^{1b}$, together with the intervening nitrogen, is pyrrolidine.

Embodiment 42: in some embodiments, such as, the compound of Embodiment 22, the heterocycloalkyl formed by $R^{1a}$ and $R^{1b}$, together with the intervening nitrogen is

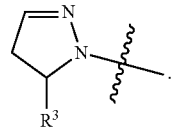

Embodiment 43: in some embodiments, such as, the compound of Embodiment 22, the heterocycloalkyl formed by $R^{1a}$ and $R^{1b}$, together with the intervening nitrogen is chosen from

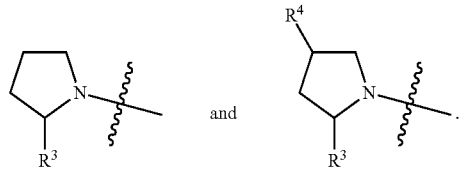

Embodiment 44: in some embodiments, such as, the compound of Embodiment 43, $R^4$ is halo.

Embodiment 45: in some embodiments, such as, the compound of Embodiment 43, $R^4$ is fluoro.

Embodiment 46: in some embodiments, such as, the compound of Embodiment 22, the heterocycloalkyl formed by $R^{1a}$ and $R^{1b}$, together with the intervening nitrogen is

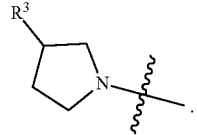

Embodiment 47: in some embodiments, such as, the compound of any one of Embodiments 1-46, each $R^6$ is independently chosen from halo, alkyl, cyano, alkoxy, hydroxy, haloalkyl, and haloalkoxy.

Embodiment 48: in some embodiments, such as, the compound of Embodiment 47, each $R^6$ is independently chosen from halo, methyl, cyano, methoxy, hydroxy, difluoromethyl, trifluoromethyl, and trifluoromethoxy.

Embodiment 49: in some embodiments, such as, the compound of Embodiment 48, each $R^6$ is independently chosen from halo, methyl, cyano, and methoxy.

Embodiment 50: in some embodiments, such as, the compound of any one of Embodiments 1-46, each $R^6$ is independently chosen from halo, $C_{1-6}$alkyl, $C_{3-7}$cycloalkyl, cyano, $C_{1-6}$alkoxy, hydroxy, $C_{1-6}$haloalkyl, $C_{1-6}$hydroxyalkyl, and $C_{1-6}$haloalkoxy.

Embodiment 51: in some embodiments, such as, the compound of Embodiment 50, each $R^6$ is independently chosen from halo, methyl, cyclopropyl, cyano, methoxy, hydroxy, difluoromethyl, trifluoromethyl, hydroxymethyl, and trifluoromethoxy.

Embodiment 52: in some embodiments, such as, the compound of Embodiment 51, each $R^6$ is independently chosen from halo, methyl, cyclopropyl, cyano, hydroxymethyl, and methoxy.

Embodiment 53: in some embodiments, such as, the compound of Embodiment 52, each $R^6$ is independently chosen from halo, methyl, and cyano.

Embodiment 54: in some embodiments, such as, the compound of Embodiment 53, each $R^6$ is independently chosen from halo and cyano.

Embodiment 55: in some embodiments, such as, the compound of any one of Embodiments 1-54, $R^3$ is optionally substituted with 1, 2, or 3 $R^6$.

Embodiment 56: in some embodiments, such as, the compound of Embodiment 55, $R^3$ is substituted with 1, 2, or 3 $R^6$.

Embodiment 57: in some embodiments, such as, the compound of Embodiment 56, $R^3$ is substituted with 1 or 2 $R^6$.

Embodiment 58: in some embodiments, such as, the compound of Embodiment 56, $R^3$ is substituted with 2 $R^6$.

Embodiment 59: in some embodiments, such as, the compound of Embodiment 56, $R^3$ is substituted with 2 or 3 $R^6$.

Embodiment 60: in some embodiments, such as, the compound of Embodiment 56, $R^3$ is substituted with 3 $R^6$.

Embodiment 61: in some embodiments, such as, the compound of any one of Embodiments 57-60, at least one $R^6$ is halo.

Embodiment 62: in some embodiments, such as, the compound of any one of Embodiments 57-60, at least one $R^6$ is fluoro.

Embodiment 63: in some embodiments, such as, the compound of either one of Embodiments 59 and 60, at least two $R^6$ are halo.

Embodiment 64: in some embodiments, such as, the compound of either one of Embodiments 59 and 60, at least two $R^6$ are fluoro.

Embodiment 65: in some embodiments, such as, the compound of Embodiment 55, $R^3$ is optionally substituted with 1 or 2 $R^6$.

Embodiment 66: in some embodiments, such as, the compound of Embodiment 65, $R^3$ is optionally substituted with 1 $R^6$.

Embodiment 67: in some embodiments, such as, the compound of Embodiment 65, $R^3$ is substituted with 1 $R^6$.

Embodiment 68: in some embodiments, such as, the compound of any one of Embodiments 1-67, $R^6$ is halo.

Embodiment 69: in some embodiments, such as, the compound of any one of Embodiments 1-67, $R^6$ is fluoro.

Embodiment 70: in some embodiments, such as, the compound of any one of Embodiments 1-46, $R^3$ is unsubstituted with an $R^6$.

Embodiment 71: in some embodiments, such as, the compound of any one of Embodiments 1-70, $R^3$ is chosen from aryl, (aryl)oxy, heteroaryl, and (heteroaryl)oxy.

Embodiment 72: in some embodiments, such as, the compound of Embodiment 71, $R^3$ is chosen from $C_{6-10}$aryl, ($C_{6-10}$aryl)oxy, 5-10-membered heteroaryl, and (5-10-membered heteroaryl)oxy.

Embodiment 73: in some embodiments, such as, the compound of Embodiment 72, $R^3$ is chosen from phenyl, phenoxy, pyridinyl, pyridazinyl, pyrimidinyl, pyrazinyl, (pyridinyl)oxy, (pyridazinyl)oxy, (pyrimidinyl)oxy, (pyrazinyl)oxy, thiazolyl, (thiazolyl)oxy, pyrazolyl, and (pyrazolyl)oxy.

Embodiment 74: in some embodiments, such as, the compound of Embodiment 72, $R^3$ is chosen from $C_{6-10}$aryl, ($C_{6-10}$aryl)oxy, 6-10-membered heteroaryl, and (6-10-membered heteroaryl)oxy.

Embodiment 75: in some embodiments, such as, the compound of Embodiment 74, $R^3$ is chosen from phenyl, phenoxy, pyridinyl, pyridazinyl, pyrimidinyl, pyrazinyl, (pyridinyl)oxy, (pyridazinyl)oxy, (pyrimidinyl)oxy, and (pyrazinyl)oxy.

Embodiment 76: in some embodiments, such as, the compound of Embodiment 75, $R^3$ is chosen from phenyl, phenoxy, pyridinyl, and (pyridinyl)oxy.

Embodiment 77: in some embodiments, such as, the compound of Embodiment 76, $R^3$ is chosen from phenyl, phenoxy, and pyridinyl.

Embodiment 78: in some embodiments, such as, the compound of Embodiment 55, $R^3$ is chosen from

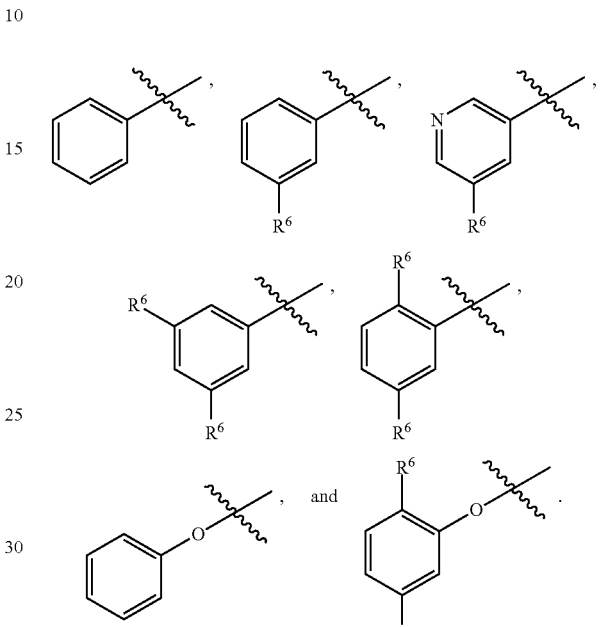

Embodiment 79: in some embodiments, such as, the compound of Embodiment 55, $R^3$ is chosen from

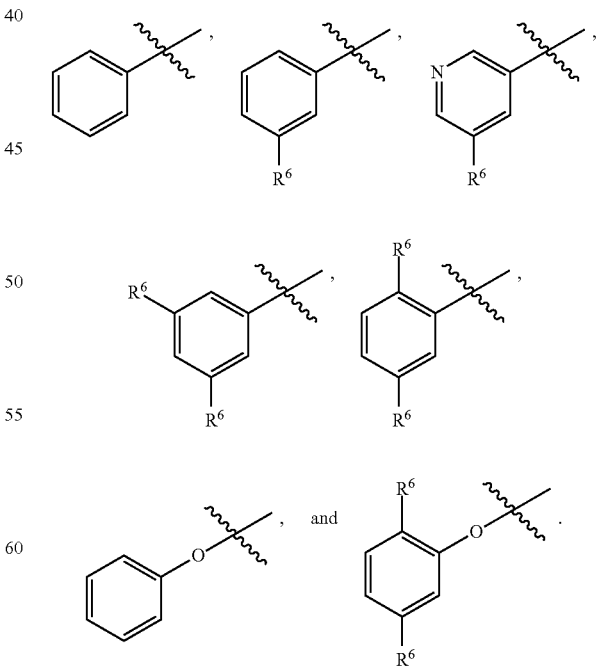

Embodiment 80: in some embodiments, such as, the compound of Embodiment 50, R³ is chosen from

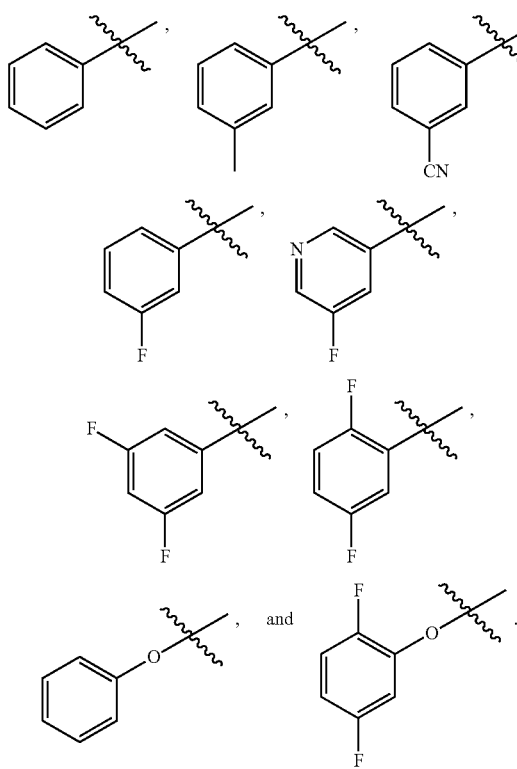

Embodiment 81: in some embodiments, such as, the compound of Embodiment 80, R³ is chosen from

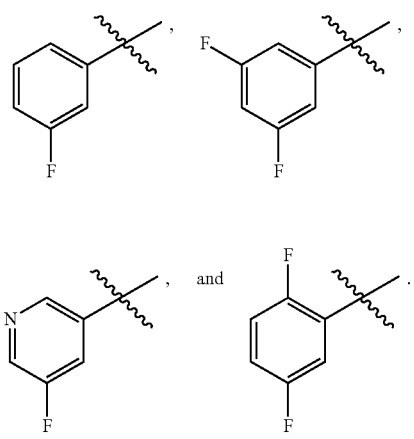

Embodiment 82: in some embodiments, such as, the compound of Embodiment 81, R³ is chosen from

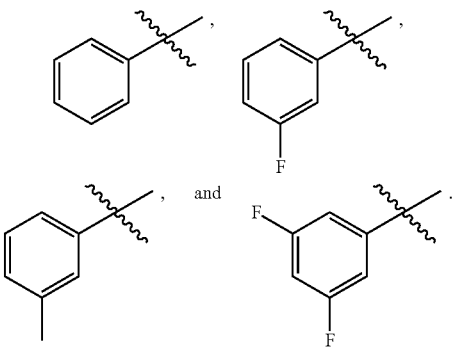

Embodiment 83: in some embodiments, such as, the compound of Embodiment 56, R³ is chosen from aryl and heteroaryl.

Embodiment 84: in some embodiments, such as, the compound of Embodiment 83, R³ is chosen from phenyl and pyridinyl.

Embodiment 85: in some embodiments, such as, the compound of Embodiment 84, R³ is phenyl.

Embodiment 86: in some embodiments, such as, the compound of Embodiment 56, R³ is chosen from (aryl)oxy and (heteroaryl)oxy.

Embodiment 87: in some embodiments, such as, the compound of Embodiment 86, R³ is phenoxy.

Embodiment 88: in some embodiments, such as, the compound of any one of Embodiments 83-87, R⁶ is halo.

Embodiment 89: in some embodiments, such as, the compound of any one of Embodiments 83-87, R⁶ is fluoro.

Also provided herein is Embodiment 90, the compound of Embodiment 1 having structural Formula (II):

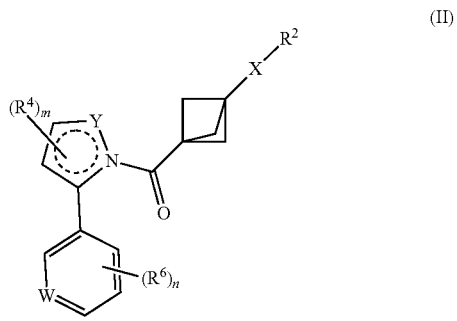

or a salt thereof, wherein:
m is chosen from 0, 1, and 2;
n is chosen from 0, 1, 2, and 3;
W is chosen from C(R$^{6a}$) and N;
X is alkylene and is optionally substituted with one or more R⁷,
or X is chosen from carbamoyl, carbonyl, and a bond;
Y is chosen from CH₂, CH, NH, and N;
Y and the intervening carbons and nitrogen combine to form heterocycloalkyl or heteroaryl;
R² is chosen from hydrogen, hydroxy, cyano, and halo,
or R² is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl)

carbonyl, (cycloalkyl)carbonyl, (heterocycloalkyl) carbonyl, (aryl)carbonyl, (alkyl)amino, (cycloalkyl) amino, (heterocycloalkyl)amino, (aryl)amino, and (heteroaryl)amino, any of which is optionally substituted with one or more $R^5$;

each $R^4$ is independently chosen from halo, cyano, and hydroxy;

each $R^5$ is independently chosen from halo, cyano, amido, alkyl, alkoxy, cyanoalkyl, hydroxyalkyl, alkoxyalkyl, cycloalkyl, haloalkyl, oxo, $P(O)(CH_3)_2$, $SO_2CH_3$, aryl optionally substituted with one or more alkyl, and heteroaryl optionally substituted with one or more alkyl;

two $R^5$, together with the intervening atoms, optionally combine to form a cycloalkyl or heterocycloalkyl;

each $R^6$ is independently chosen from halo, alkyl, cycloalkyl, cyano, alkoxy, hydroxy, haloalkyl, hydroxy alkyl, and haloalkoxy;

$R^{6a}$ is chosen from H, halo, alkyl, cyano, alkoxy, hydroxy, haloalkyl, hydroxyalkyl, and haloalkoxy; and each $R^7$ is independently chosen from alkyl, cyano, halo, and hydroxy.

Embodiment 91: in some embodiments, such as, the compound of Embodiment 90, m is chosen from 0 and 1.

Embodiment 92: in some embodiments, such as, the compound of Embodiment 91, m is 1.

Embodiment 93: in some embodiments, such as, the compound of Embodiment 91, m is 0.

Embodiment 94: in some embodiments, such as, the compound of any one of Embodiments 90-93, n is chosen from 0, 1, and 2.

Embodiment 95: in some embodiments, such as, the compound of Embodiment 94, n is chosen from 0 and 1.

Embodiment 96: in some embodiments, such as, the compound of Embodiment 94, n is chosen from 1 and 2.

Embodiment 97: in some embodiments, such as, the compound of Embodiment 95, n is 1.

Embodiment 98: in some embodiments, such as, the compound of any one of Embodiments 90-97, $R^{6a}$ is chosen from H, halo, alkyl, cyano, alkoxy, hydroxy, haloalkyl, and haloalkoxy.

Embodiment 99: in some embodiments, such as, the compound of Embodiment 98, $R^{6a}$ is chosen from H, fluoro, chloro, methyl, cyano, methoxy, hydroxy, difluoromethyl, trifluoromethyl, and trifluoromethoxy.

Embodiment 100: in some embodiments, such as, the compound of Embodiment 99, $R^{6a}$ is chosen from H, fluoro, methyl, cyano, and methoxy.

Embodiment 101: in some embodiments, such as, the compound of Embodiment 100, $R^{6a}$ is chosen from H and fluoro.

Embodiment 102: in some embodiments, such as, the compound of Embodiment 100, $R^{6a}$ is H.

Embodiment 103: in some embodiments, such as, the compound of any one of Embodiments 90-97, $R^{6a}$ is chosen from H, fluoro, chloro, methyl, cyclopropyl, cyano, methoxy, hydroxy, difluoromethyl, trifluoromethyl, hydroxymethyl, and trifluoromethoxy.

Embodiment 104: in some embodiments, such as, the compound of Embodiment 103, $R^{6a}$ is chosen from H, fluoro, methyl, cyclopropyl, cyano, hydroxymethyl, and methoxy.

Embodiment 105: in some embodiments, such as, the compound of any one of Embodiments 90-104, each $R^6$ is independently chosen from halo, alkyl, cyano, alkoxy, hydroxy, haloalkyl, and haloalkoxy.

Embodiment 106: in some embodiments, such as, the compound of Embodiment 105, each $R^6$ is independently chosen from fluoro, chloro, methyl, cyano, methoxy, hydroxy, difluoromethyl, trifluoromethyl, and trifluoromethoxy.

Embodiment 107: in some embodiments, such as, the compound of Embodiment 106, each $R^6$ is independently chosen from fluoro, methyl, cyano, and methoxy.

Embodiment 108: in some embodiments, such as, the compound of any one of Embodiments 90-104, each $R^6$ is independently chosen from halo, $C_{1-6}$alkyl, $C_{3-7}$cycloalkyl, cyano, $C_{1-6}$alkoxy, hydroxy, $C_{1-6}$haloalkyl, $C_{1-6}$hydroxyalkyl, and $C_{1-6}$haloalkoxy.

Embodiment 109: in some embodiments, such as, the compound of Embodiment 108, each $R^6$ is independently chosen from fluoro, chloro, methyl, cyclopropyl, cyano, methoxy, hydroxy, difluoromethyl, trifluoromethyl, hydroxymethyl, and trifluoromethoxy.

Embodiment 110: in some embodiments, such as, the compound of Embodiment 109, each $R^6$ is independently chosen from fluoro, methyl, cyclopropyl, cyano, hydroxymethyl, and methoxy.

Embodiment 111: in some embodiments, such as, the compound of Embodiment 95, n is 0.

Also provided herein is Embodiment 112, the compound of Embodiment 90 having structural Formula (III):

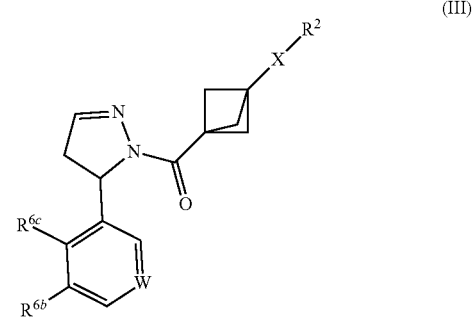

or a salt thereof, wherein:

W is chosen from $C(R^{6a})$ and N;

X is alkylene and is optionally substituted with one or more $R^7$, or X is chosen from carbamoyl, carbonyl, and a bond;

$R^2$ is chosen from hydrogen, hydroxy, cyano, and halo, or $R^2$ is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl) carbonyl, (cycloalkyl)carbonyl, (heterocycloalkyl) carbonyl, (aryl)carbonyl, (alkyl)amino, (cycloalkyl) amino, (heterocycloalkyl)amino, (aryl)amino, and (heteroaryl)amino, any of which is optionally substituted with one or more $R^5$;

each $R^5$ is independently chosen from halo, cyano, amido, alkyl, alkoxy, cyanoalkyl, hydroxyalkyl, alkoxyalkyl, cycloalkyl, haloalkyl, oxo, $P(O)(CH_3)_2$, $SO_2CH_3$, aryl optionally substituted with one or more alkyl, and heteroaryl optionally substituted with one or more alkyl;

two $R^5$, together with the intervening atoms, optionally combine to form a cycloalkyl or heterocycloalkyl;

$R^{6a}$, $R^{6b}$, and $R^{6c}$ are independently chosen from H, halo, alkyl, cycloalkyl, cyano, alkoxy, hydroxy, haloalkyl, hydroxyalkyl, and haloalkoxy; and each $R^7$ is independently chosen from alkyl, cyano, halo, and hydroxy.

Also provided herein is Embodiment 113: the compound of Embodiment 90 having structural Formula (IV):

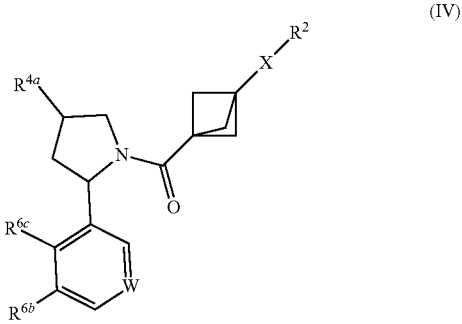

(IV)

or a salt thereof, wherein:
W is chosen from $C(R^{6a})$ and N;
X is alkylene and is optionally substituted with one or more $R^7$,
or X is chosen from carbamoyl, carbonyl, and a bond;
$R^2$ is chosen from hydrogen, hydroxy, cyano, and halo,
or $R^2$ is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl)carbonyl, (cycloalkyl)carbonyl, (heterocycloalkyl)carbonyl, (aryl)carbonyl, (alkyl)amino, (cycloalkyl)amino, (heterocycloalkyl)amino, (aryl)amino, and (heteroaryl)amino, any of which is optionally substituted with one or more $R^5$;
$R^{4a}$ is chosen from H, halo, cyano, and hydroxy;
each $R^5$ is independently chosen from halo, cyano, amido, alkyl, alkoxy, cyanoalkyl, hydroxyalkyl, alkoxyalkyl, cycloalkyl, haloalkyl, oxo, $P(O)(CH_3)_2$, $SO_2CH_3$, aryl optionally substituted with one or more alkyl, and heteroaryl optionally substituted with alkyl;
two $R^5$, together with the intervening atoms, optionally combine to form a cycloalkyl or heterocycloalkyl;
$R^{6a}$, $R^{6b}$, and $R^{6c}$ are independently chosen from H, halo, alkyl, cycloalkyl, cyano, alkoxy, hydroxy, haloalkyl, hydroxyalkyl, and haloalkoxy; and
each $R^7$ is independently chosen from alkyl, cyano, halo, and hydroxy.

Also provided herein is Embodiment 114: the compound of Embodiment 1 having structural Formula (V):

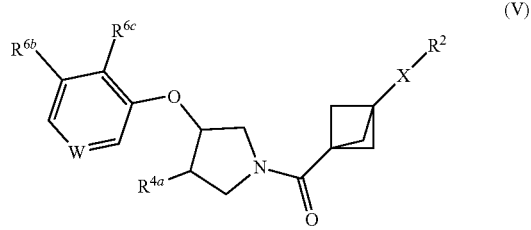

(V)

or a salt thereof, wherein:
W is chosen from $C(R^{6a})$ and N;
X is alkylene and is optionally substituted with one or more $R^7$,
or X is chosen from carbamoyl, carbonyl, and a bond;
$R^2$ is chosen from hydrogen, hydroxy, cyano, and halo,
or $R^2$ is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl)carbonyl, (cycloalkyl)carbonyl, (heterocycloalkyl)carbonyl, (aryl)carbonyl, (alkyl)amino, (cycloalkyl)amino, (heterocycloalkyl)amino, (aryl)amino, and (heteroaryl)amino, any of which is optionally substituted with one or more $R^5$;
$R^{4a}$ is chosen from H, halo, cyano, and hydroxy;
each $R^5$ is independently chosen from halo, cyano, amido, alkyl, alkoxy, cyanoalkyl, hydroxyalkyl, alkoxyalkyl, cycloalkyl, haloalkyl, oxo, $P(O)(CH_3)_2$, $SO_2CH_3$, aryl optionally substituted with one or more alkyl, and heteroaryl optionally substituted with alkyl;
two $R^5$, together with the intervening atoms, optionally combine to form a cycloalkyl or heterocycloalkyl;
$R^{6a}$, $R^{6b}$, and $R^{6c}$ are independently chosen from H, halo, alkyl, cycloalkyl, cyano, alkoxy, hydroxy, haloalkyl, hydroxyalkyl, and haloalkoxy; and
each $R^7$ is independently chosen from alkyl, cyano, halo, and hydroxy.

Embodiment 115: in some embodiments, such as, the compound of any one of Embodiments 112-114, $R^{6a}$, $R^{6b}$, and $R^{6c}$ are independently chosen from H, halo, $C_{1-6}$alkyl, cyano, $C_{1-6}$alkoxy, hydroxy, $C_{1-6}$haloalkyl, $C_{1-6}$hydroxyalkyl, and $C_{1-6}$haloalkoxy.

Embodiment 116: in some embodiments, such as, the compound of Embodiment 115, $R^{6a}$, $R^{6b}$, and $R^{6c}$ are independently chosen from H, fluoro, chloro, methyl, cyano, methoxy, hydroxy, difluoromethyl, trifluoromethyl, hydroxymethyl, and trifluoromethoxy.

Embodiment 117: in some embodiments, such as, the compound of Embodiment 116, $R^{6a}$, $R^{6b}$, and $R^{6c}$ are independently chosen from H, fluoro, methyl, cyano, hydroxymethyl, and methoxy.

Embodiment 118: in some embodiments, such as, the compound of Embodiment 117, $R^{6a}$, $R^{6b}$, and $R^{6c}$ are independently chosen from H, fluoro, methyl, cyano, and methoxy.

Embodiment 119: in some embodiments, such as, the compound of Embodiment 118, $R^{6a}$, $R^{6b}$, and $R^{6c}$ are independently chosen from H and fluoro.

Embodiment 120: in some embodiments, such as, the compound of any one of Embodiments 112-119, exactly one of $R^{6a}$, $R^{6b}$, and $R^{6c}$ is H.

Embodiment 121: in some embodiments, such as, the compound of Embodiment 120, $R^{6b}$ is H.

Embodiment 122: in some embodiments, such as, the compound of Embodiment 120, $R^{6C}$ is H.

Embodiment 123: in some embodiments, such as, the compound of any one of Embodiments 112-119, exactly two of $R^{6a}$, $R^{6b}$, and $R^{6c}$ are H.

Embodiment 124: in some embodiments, such as, the compound of any one of Embodiments 112-119, W is $C(R^{6a})$.

Embodiment 125: in some embodiments, such as, the compound of Embodiment 124, $R^{6a}$ is H.

Embodiment 126: in some embodiments, such as, the compound of any one of Embodiments 112-119, W is N.

Embodiment 127: in some embodiments, such as, the compound of either one of Embodiments 125 and 126, exactly one of $R^{6b}$ and $R^{6c}$ is H.

Embodiment 128: in some embodiments, such as, the compound of either one of Embodiments 125 and 126, $R^{6b}$ and $R^{6c}$ are H.

Embodiment 129: in some embodiments, such as, the compound of any one of Embodiments 112-128, $R^{4a}$ is chosen from H, halo, and cyano.

Embodiment 130: in some embodiments, such as, the compound of Embodiment 129, $R^{4a}$ is chosen from H and fluoro.

Embodiment 131: in some embodiments, such as, the compound of Embodiment 130, $R^{4a}$ is fluoro.

Embodiment 132: in some embodiments, such as, the compound of Embodiment 129, $R^{4a}$ is H.

Embodiment 133: in some embodiments, such as, the compound of any one of Embodiments 1-132, $R^2$ is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl)carbonyl, (cycloalkyl)carbonyl, (heterocycloalkyl)carbonyl, (aryl)carbonyl, (alkyl)amino, (cycloalkyl)amino, (heterocycloalkyl)amino, (aryl)amino, and (heteroaryl)amino, any of which is optionally substituted with 1, 2, or 3 $R^5$.

Embodiment 134: in some embodiments, such as, the compound of Embodiment 133:
each $R^5$ is independently chosen from halo, cyano, —CONH$_2$, —CONHCH$_3$, —CON(CH$_3$)$_2$, $C_{1-6}$alkyl, $C_{1-6}$alkoxy, hydroxy$C_{1-6}$alkyl, $C_{1-6}$alkoxy$C_{1-6}$alkyl, $C_{3-7}$cycloalkyl, $C_{1-6}$haloalkyl, oxo, P(O)(CH$_3$)$_2$, and SO$_2$CH$_3$; and
two $R^5$, together with the intervening atoms, optionally combine to form a cycloalkyl or heterocycloalkyl.

Embodiment 135: in some embodiments, such as, the compound of Embodiment 134:
each $R^5$ is independently chosen from fluoro, chloro, cyano, $C_{1-6}$alkyl, $C_{1-6}$alkoxy, hydroxy$C_{1-6}$alkyl, $C_{1-6}$alkoxy$C_{1-6}$alkyl, $C_{3-7}$cycloalkyl, and trifluoromethyl; and
two $R^5$, together with the intervening atoms, optionally combine to form a cycloalkyl or heterocycloalkyl.

Embodiment 136: in some embodiments, such as, the compound of Embodiment 135:
each $R^5$ is independently chosen from fluoro, cyano, methyl, methoxy, hydroxymethyl, methoxymethyl, cyclopropyl, and trifluoromethyl; and
two $R^5$, together with the intervening atoms, optionally combine to form a cycloalkyl or heterocycloalkyl.

Embodiment 137: in some embodiments, such as, the compound of Embodiment 133, each $R^5$ is independently chosen from halo, cyano, —CONH$_2$, —CONHCH$_3$, —CON(CH$_3$)$_2$, $C_{1-6}$alkyl, $C_{1-6}$alkoxy, hydroxy$C_{1-6}$alkyl, $C_{1-6}$alkoxy$C_{1-6}$alkyl, $C_{3-7}$cycloalkyl, $C_{1-6}$haloalkyl, oxo, P(O)(CH$_3$)$_2$, and SO$_2$CH$_3$.

Embodiment 138: in some embodiments, such as, the compound of Embodiment 137, each $R^5$ is independently chosen from fluoro, chloro, cyano, $C_{1-6}$alkyl, $C_{1-6}$alkoxy, hydroxy$C_{1-6}$alkyl, $C_{1-6}$alkoxy$C_{1-6}$alkyl, $C_{3-7}$cycloalkyl, and trifluoromethyl.

Embodiment 139: in some embodiments, such as, the compound of Embodiment 138, each $R^5$ is independently chosen from fluoro, cyano, methyl, methoxy, hydroxymethyl, methoxymethyl, cyclopropyl, and trifluoromethyl.

Embodiment 140: in some embodiments, such as, the compound of Embodiment 137, each $R^5$ is independently chosen from F, Cl, Br, CN, CONH$_2$, methyl, methoxy, P(O)(CH$_3$)$_2$, and (methyl)pyrazolyl.

Embodiment 141: in some embodiments, such as, the compound of Embodiment 140, each $R^5$ is independently chosen from F, methyl, CN, and methoxy.

Embodiment 142: in some embodiments, such as, the compound of Embodiment 141, each $R^5$ is independently chosen from F, methyl, and CN.

Embodiment 143: in some embodiments, such as, the compound of Embodiment 142, each $R^5$ is CN.

Embodiment 144: in some embodiments, such as, the compound of Embodiment 133, $R^5$ is heteroaryl optionally substituted with 1 or 2 alkyl.

Embodiment 145: in some embodiments, such as, the compound of Embodiment 144, $R^5$ is chosen from pyrrole, pyrazole, and imidazole, any of which is optionally substituted with 1 alkyl.

Embodiment 146: in some embodiments, such as, the compound of Embodiment 144, $R^5$ is chosen from pyridine, pyridazine, pyrimidine, and pyrazine, any of which is optionally substituted with 1 alkyl.

Embodiment 147: in some embodiments, such as, the compound of Embodiment 144, $R^5$ is heteroaryl optionally substituted with 1 methyl.

Embodiment 148: in some embodiments, such as, the compound of any one of Embodiments 133-147, $R^2$ is chosen from aryl, heteroaryl, (aryl)oxy, and (heteroaryl)oxy.

Embodiment 149: in some embodiments, such as, the compound of Embodiment 148, $R^2$ is chosen from aryl and heteroaryl.

Embodiment 150: in some embodiments, such as, the compound of Embodiment 148, $R^2$ is chosen from (aryl)oxy and (heteroaryl)oxy.

Embodiment 151: in some embodiments, such as, the compound of any one of Embodiments 133-147, $R^2$ is chosen from $C_{1-6}$alkyl, NH$_2$, NH($C_{1-6}$alkyl), N($C_{1-6}$alkyl)$_2$, $C_{3-7}$cycloalkyl, 3-7 membered heterocycloalkyl, $C_{6-10}$aryl, 5-10 membered heteroaryl, $C_{1-6}$alkoxy, ($C_{3-7}$cycloalkyl)oxy, (3-7 membered heterocycloalkyl)oxy, ($C_{6-10}$aryl)oxy, (5-10 membered heteroaryl)oxy, ($C_{1-6}$alkyl)carbonyl, ($C_{3-7}$cycloalkyl)carbonyl, (3-7 membered heterocycloalkyl)carbonyl, ($C_{6-10}$aryl)carbonyl, NH($C_{1-6}$alkyl), NH($C_{3-7}$cycloalkyl), NH(3-7 membered heterocycloalkyl), NH($C_{6-10}$aryl), and NH(5-10 membered heteroaryl).

Embodiment 152: in some embodiments, such as, the compound of Embodiment 151, $R^2$ is chosen from NH$_2$, NH($C_{1-6}$alkyl), N($C_{1-6}$alkyl)$_2$, NH($C_{3-7}$cycloalkyl), NH(3-7 membered heterocycloalkyl), NH($C_{6-10}$aryl), and NH(5-10 membered heteroaryl).

Embodiment 153: in some embodiments, such as, the compound of Embodiment 152, $R^2$ is chosen from NH$_2$, NH($C_{1-6}$alkyl), NH($C_{6-10}$aryl), and NH(5-10 membered heteroaryl).

Embodiment 154: in some embodiments, such as, the compound of Embodiment 152, $R^2$ is chosen from NH$_2$, NHCH$_3$, NH(phenyl), NH(pyrimidin-2-yl), and NH(pyrimidin-4-yl).

Embodiment 155: in some embodiments, such as, the compound of Embodiment 151, $R^2$ is 5-10 membered heteroaryl.

Embodiment 156: in some embodiments, such as, the compound of Embodiment 151, $R^2$ is chosen from pyrazol-1-yl, 1H-indazol-1-yl, 2H-indazol-2-yl, 1H-pyrazolo[3,4-c]pyridin-1-yl, imidazol-1-yl, benzo[d]imidazol-1-yl, 1H-1,2,3-triazol-1-yl, 2H-1,2,3-triazol-2-yl, 1H-benzo[d][1,2,3]triazol-1-yl, and 2H-benzo[d][1,2,3]triazol-2-yl.

Embodiment 157: in some embodiments, such as, the compound of Embodiment 151, $R^2$ is chosen from $C_{1-6}$alkoxy, ($C_{3-7}$cycloalkyl)oxy, (3-7 membered heterocycloalkyl)oxy, ($C_{6-10}$aryl)oxy, and (5-10 membered heteroaryl)oxy.

Embodiment 158: in some embodiments, such as, the compound of Embodiment 157, $R^2$ is chosen from $C_{1-6}$alkoxy, ($C_{3-7}$cycloalkyl)oxy, and (3-7 membered heterocycloalkyl)oxy.

Embodiment 159: in some embodiments, such as, the compound of Embodiment 157, $R^2$ is chosen from ($C_{6-10}$aryl)oxy, and (5-10 membered heteroaryl)oxy.

Embodiment 160: in some embodiments, such as, the compound of any one of Embodiments 133-159, $R^2$ is optionally substituted with 1 or 2 $R^5$.

Embodiment 161: in some embodiments, such as, the compound of Embodiment 160, $R^2$ is optionally substituted with 1 $R^5$.

Embodiment 162: in some embodiments, such as, the compound of Embodiment 161, $R^2$ is substituted with 1 $R^5$.

Embodiment 163: in some embodiments, such as, the compound of Embodiment 161, $R^2$ is unsubstituted with an $R^5$.

Embodiment 164: in some embodiments, such as, the compound of any one of Embodiments 133-147, $R^2$ is chosen from

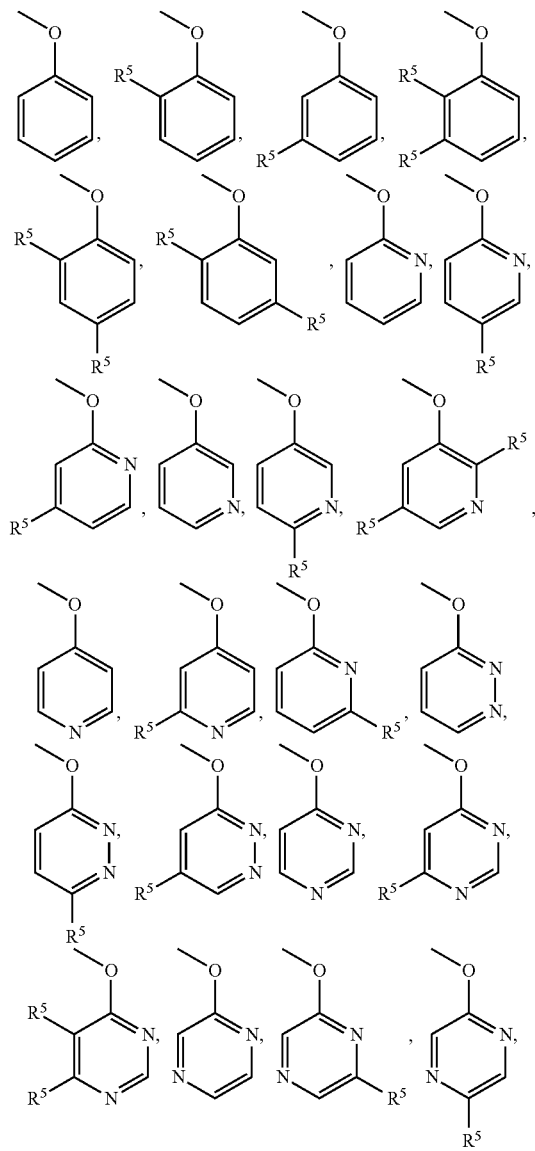

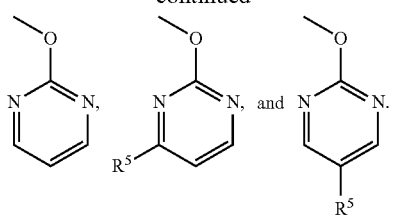

Embodiment 165: in some embodiments, such as, the compound of any one of Embodiments 133-147, $R^2$ is chosen from

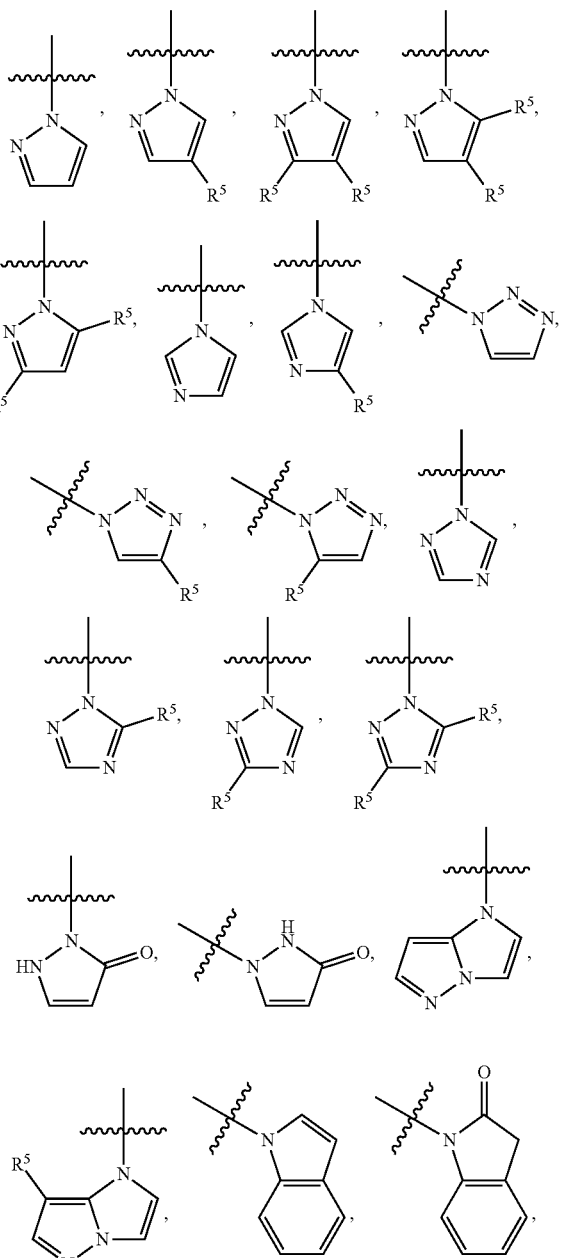

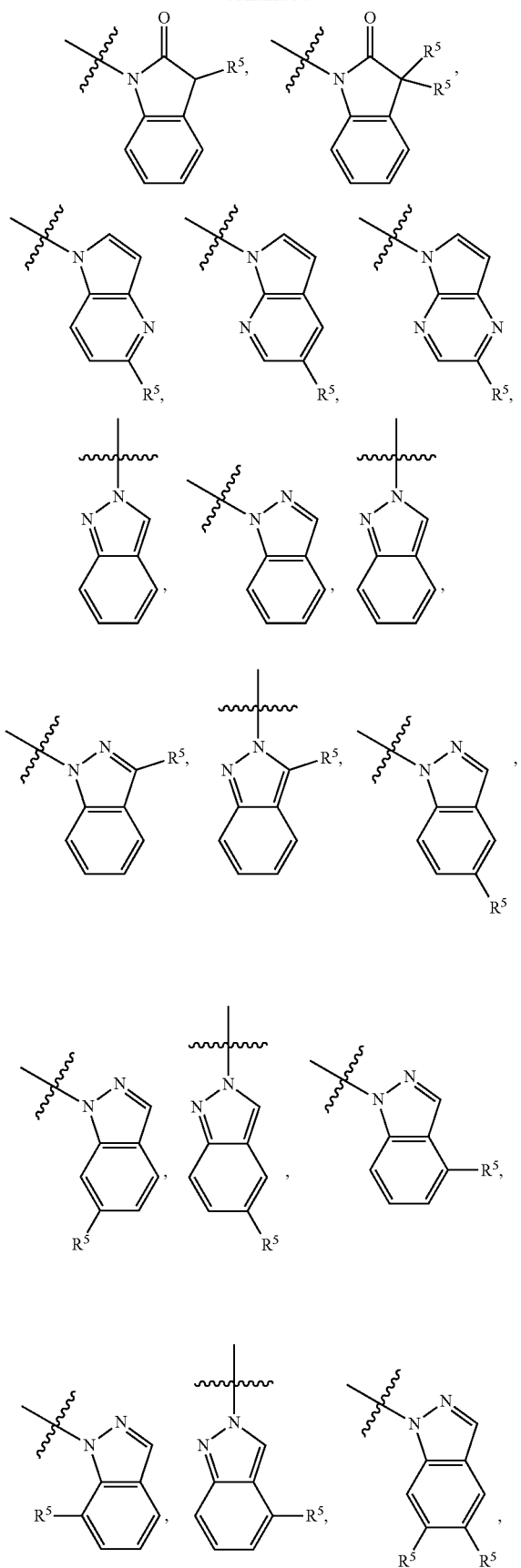
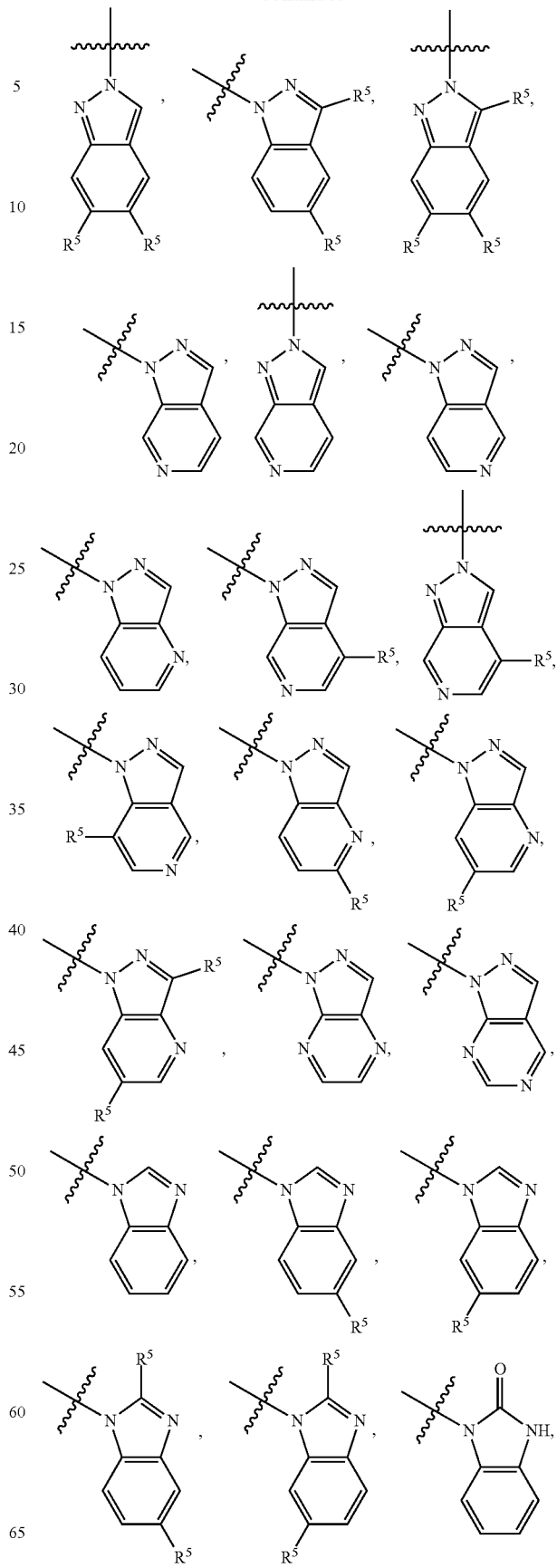

-continued

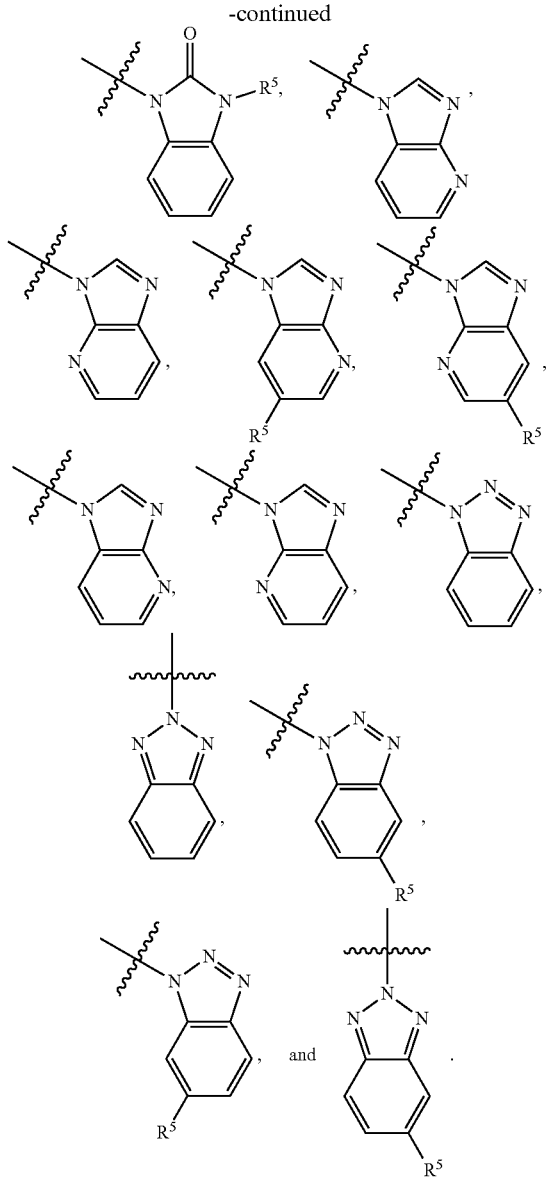

Embodiment 166: in some embodiments, such as, the compound of any one of Embodiments 1-132, $R^2$ is chosen from

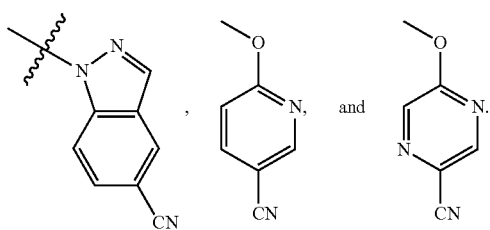

Embodiment 167: in some embodiments, such as, the compound of any one of Embodiments 1-132, $R^2$ is chosen from H, hydroxy, cyano, and halo.

Embodiment 168: in some embodiments, such as, the compound of Embodiment 167, $R^2$ is chosen from fluoro and chloro.

Embodiment 169: in some embodiments, such as, the compound of any one of Embodiments 133-168, each $R^7$ is independently chosen from $C_{1-6}$alkyl, cyano, halo, and hydroxy.

Embodiment 170: in some embodiments, such as, the compound of Embodiment 169, each $R^7$ is independently chosen from —$CH_3$, —$CH_2CH_3$, —$CH_2CH_2CH_3$, —$CH_2CH_2CH_2CH_3$, cyano, fluoro, chloro, and hydroxy.

Embodiment 171: in some embodiments, such as, the compound of Embodiment 170, each $R^7$ is independently chosen from $CH_3$, cyano, fluoro, chloro, and hydroxy.

Embodiment 172: in some embodiments, such as, the compound of any one of Embodiments 133-171, X is alkylene and is optionally substituted with 1 $R^7$.

Embodiment 173: in some embodiments, such as, the compound of Embodiment 172, X is $C_{1-6}$alkylene and is optionally substituted with 1 $R^7$.

Embodiment 174: in some embodiments, such as, the compound of Embodiment 172, X is alkylene and is unsubstituted with an $R^7$.

Embodiment 175: in some embodiments, such as, the compound of Embodiment 173, X is chosen from —$CH_2$— and —$CHR^7$—.

Embodiment 176: in some embodiments, such as, the compound of Embodiment 172, X is chosen from —$CH_2$—, —$CH(CH_3)$—, —$CHOH$—, and —$CHF$—.

Embodiment 177: in some embodiments, such as, the compound of Embodiment 176, X is —$CH_2$—.

Embodiment 178: in some embodiments, such as, the compound of any one of Embodiments 133-168, X is carbamoyl.

Embodiment 179: in some embodiments, such as, the compound of any one of Embodiments 133-168, X is carbonyl.

Also provided herein is Embodiment 180: the compound of Embodiment 90 having either structural Formula (VIa) or structural Formula (VIb):

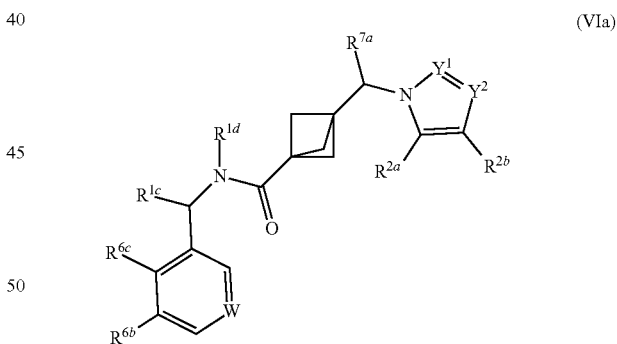

(VIa)

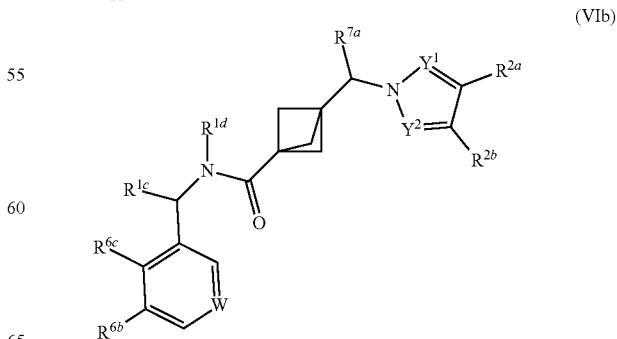

(VIb)

or a salt thereof, wherein:

W is chosen from $C(R^{6a})$ and N;

$Y^1$ and $Y^2$ are independently chosen from CH, $C(R^5)$, and N;

$R^{1c}$ and $R^{1d}$, together with the intervening carbon and nitrogen, combine to form a 5-membered heterocycloalkyl which is optionally substituted with one $R^4$;

$R^{2a}$ and $R^{2b}$ are independently chosen from H, hydroxy, cyano, halo, and alkyl, or $R^{2a}$ and $R^{2b}$ combine to form alkylene or heteroalkylene, either of which is optionally substituted with 1 or 2 $R^5$;

$R^4$ is chosen from halo, cyano, and hydroxy;

each $R^5$ is independently chosen from halo, cyano, amido, alkyl, alkoxy, cyanoalkyl, hydroxyalkyl, alkoxyalkyl, cycloalkyl, haloalkyl, oxo, $P(O)(CH_3)_2$, $SO_2CH_3$, aryl optionally substituted with one or more alkyl, and heteroaryl optionally substituted with alkyl;

two $R^5$, together with the intervening atoms, optionally combine to form a cycloalkyl or heterocycloalkyl;

$R^{6a}$, $R^{6b}$, and $R^{6c}$ are independently chosen from H, halo, alkyl, cycloalkyl, cyano, alkoxy, hydroxy, haloalkyl, hydroxyalkyl, and haloalkoxy; and $R^{7a}$ is chosen from H, alkyl, cyano, halo, and hydroxy.

Embodiment 181: in some embodiments, such as, the compound of Embodiment 180, $Y^1$ and $Y^2$ are independently chosen from CH, $C(CH_3)$, and N.

Embodiment 182: in some embodiments, such as, the compound of Embodiment 180, $Y^1$ and $Y^2$ are independently chosen from CH and N.

Embodiment 183: in some embodiments, such as, the compound of any one of Embodiments 180-182, $R^{2a}$ and $R^{2b}$ combine to form alkylene or heteroalkylene chosen from —$CH_2CH_2CH_2$—, —CH=CH—CH=CH—, —N=CH—CH=CH—, —CH=N—CH=CH—, —CH=CH—N=CH—, and —CH=CH—CH=N—, any of which is optionally substituted with 1 or 2 $R^5$.

Embodiment 184: in some embodiments, such as, the compound of Embodiment 183, $R^{2a}$ and $R^{2b}$ combine to form —CH=CH—CH=CH—, which is optionally substituted with 1 or 2 $R^5$.

Embodiment 185: in some embodiments, such as, the compound of any one of Embodiments 180-184, each $R^5$ is independently chosen from fluoro, chloro, cyano, $C_{1-6}$alkyl, $C_{1-6}$alkoxy, hydroxy$C_{1-6}$alkyl, $C_{1-6}$alkoxy$C_{1-6}$alkyl, $C_{3-7}$cycloalkyl, and trifluoromethyl.

Embodiment 186: in some embodiments, such as, the compound of Embodiment 185, each $R^5$ is independently chosen from fluoro, cyano, methyl, methoxy, hydroxymethyl, methoxymethyl, cyclopropyl, and trifluoromethyl.

Embodiment 187: in some embodiments, such as, the compound of any one of Embodiments 180-186, $R^{6a}$, $R^{6b}$, and $R^{6c}$ are independently chosen from H, halo, $C_{1-6}$alkyl, $C_{3-7}$cycloalkyl, cyano, $C_{1-6}$alkoxy, hydroxy, $C_{1-6}$haloalkyl, $C_{1-6}$hydroxyalkyl, and $C_{1-6}$haloalkoxy.

Embodiment 188: in some embodiments, such as, the compound of Embodiment 187, $R^{6a}$, $R^{6b}$, and $R^{6c}$ are independently chosen from H, fluoro, chloro, methyl, cyclopropyl, cyano, methoxy, hydroxy, difluoromethyl, trifluoromethyl, hydroxymethyl, and trifluoromethoxy.

Embodiment 189: in some embodiments, such as, the compound of Embodiment 188, $R^{6a}$, $R^{6b}$, and $R^{6c}$ are independently chosen from H, fluoro, methyl, cyclopropyl, cyano, hydroxymethyl, and methoxy.

Embodiment 190: in some embodiments, such as, the compound of Embodiment 189, $R^{6a}$, $R^{6b}$, and $R^{6c}$ are independently chosen from H, fluoro, methyl, cyano, and methoxy.

Embodiment 191: in some embodiments, such as, the compound of Embodiment 190, $R^{6a}$, $R^{6b}$, and $R^{6c}$ are independently chosen from H and fluoro.

Embodiment 192: in some embodiments, such as, the compound of any one of Embodiments 180-191, exactly one of $R^{6a}$, $R^{6b}$, and $R^{6c}$ is H.

Embodiment 193: in some embodiments, such as, the compound of Embodiment 120, $R^{6b}$ is H.

Embodiment 194: in some embodiments, such as, the compound of Embodiment 120, $R^{6C}$ is H.

Embodiment 195: in some embodiments, such as, the compound of any one of Embodiments 112-119, exactly two of $R^{6a}$, $R^{6b}$, and $R^{6c}$ are H.

Embodiment 196: in some embodiments, such as, the compound of any one of Embodiments 180-186, $R^{7a}$ is chosen from H, $C_{1-6}$alkyl, cyano, halo, and hydroxy.

Embodiment 197: in some embodiments, such as, the compound of Embodiment 196, $R^{7a}$ is chosen from H, —$CH_3$, —$CH_2CH_3$, —$CH_2CH_2CH_3$, —$CH_2CH_2CH_2H_3$, cyano, halo, and hydroxy.

Embodiment 198: in some embodiments, such as, the compound of Embodiment 197, $R^{7a}$ is chosen from H, —$CH_3$, —$CH_2CH_3$, —$CH_2CH_2CH_3$, —$CH_2CH_2CH_2H_3$, cyano, fluoro, chloro, and hydroxy.

Embodiment 199: in some embodiments, such as, the compound of Embodiment 198, $R^{7a}$ is chosen from H, chosen from $CH_3$, cyano, fluoro, chloro, and hydroxy.

Embodiment 200: in some embodiments, such as, the compound of Embodiment 199, $R^{7a}$ is chosen from H, $CH_3$, fluoro, and hydroxy.

Embodiment 201: in some embodiments, such as, the compound of Embodiment 200, $R^{7a}$ is chosen from H, chosen from fluoro and hydroxy.

Embodiment 202: in some embodiments, such as, the compound of Embodiment 201, $R^{7a}$ is chosen from H and fluoro.

Embodiment 203: in some embodiments, such as, the compound of Embodiment 202, $R^{7a}$ is H.

Also provided herein is Embodiment 204: the compound of Embodiment 90 having structural Formula (VII):

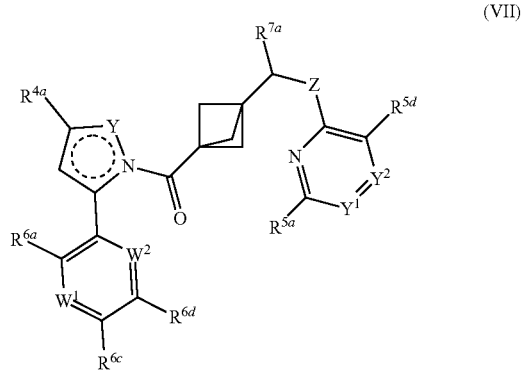

(VII)

or a salt thereof, wherein:

$W^1$ is chosen from $C(R^{6b})$ and N;

$W^2$ is chosen from $C(R^{6e})$ and N;

Y is chosen from $CH_2$, CH, NH, and N;

Y and the intervening carbons and nitrogen combine to form heterocycloalkyl;

$Y^1$ is chosen from $C(R^{5b})$ and N;

$Y^2$ is chosen from $C(R^{5c})$ and N;

Z is chosen from O, NH, and $N(CH_3)$;

$R^{1c}$ and $R^{1d}$, together with the intervening carbon and nitrogen, combine to form a 5-membered heterocycloalkyl which is optionally substituted with one $R^4$;

$R^{2a}$ and $R^{2b}$ are independently chosen from H, hydroxy, cyano, halo, and alkyl, or $R^{2a}$ and $R^{2b}$ combine to form alkylene or heteroalkylene, either of which is optionally substituted with 1 or 2 $R^5$;

$R^{4a}$ is chosen from H, halo, cyano, and hydroxy;

$R^{5a}$, $R^{5b}$, $R^{5c}$, and $R^{5d}$ are independently chosen from H, halo, cyano, amido, alkyl, alkoxy, cyanoalkyl, hydroxyalkyl, alkoxyalkyl, cycloalkyl, haloalkyl, $P(O)(CH_3)_2$, $SO_2CH_3$, aryl optionally substituted with one or more alkyl, and heteroaryl optionally substituted with alkyl;

$R^{6a}$, $R^{6b}$, $R^{6c}$, $R^{6d}$, and $R^{6e}$ are independently chosen from H, halo, alkyl, cycloalkyl, cyano, alkoxy, hydroxy, haloalkyl, hydroxyalkyl, and haloalkoxy; and $R^{7a}$ is chosen from H, alkyl, cyano, halo, and hydroxy.

Embodiment 205: in some embodiments, such as, the compound of Embodiment 204, the heterocycloalkyl formed by Y and the intervening carbons and nitrogen is chosen from pyrazoline and pyrrolidine.

Embodiment 206: in some embodiments, such as, the compound of either one of Embodiments 204 and 205, $R^{5a}$, $R^{5b}$, $R^{5c}$, and $R^{5d}$ are independently chosen from H, halo, cyano, $CONH_2$, $C_{1-6}$alkyl, $C_{1-6}$alkoxy, cyano$C_{1-6}$alkyl, hydroxy$C_{1-6}$alkyl, $C_{1-6}$alkoxy$C_{1-6}$alkyl, $C_{3-7}$cycloalkyl, halo$C_{1-6}$alkyl, $P(O)(CH_3)_2$, $SO_2CH_3$, and 5- to 7-membered heteroaryl optionally substituted with methyl.

Embodiment 207: in some embodiments, such as, the compound of Embodiment 206, $R^{5a}$, $R^{5b}$, $R^{5c}$, and $R^{5d}$ are independently chosen from H, halo, cyano, $CONH_2$, methyl, methoxy, and (methyl)pyrazolyl.

Embodiment 208: in some embodiments, such as, the compound of any one of Embodiments 204-207, at least one of $R^{5a}$ and $R^{5d}$ is H.

Embodiment 209: in some embodiments, such as, the compound of Embodiment 208, $R^{5a}$ and $R^{5d}$ are H.

Embodiment 210: in some embodiments, such as, the compound of any one of Embodiments 204-209, at most one of $Y^1$ and $Y^2$ is N.

Embodiment 211: in some embodiments, such as, the compound of any one of Embodiments 204-210, $Y^1$ is $C(R^{5b})$.

Embodiment 212: in some embodiments, such as, the compound of any one of Embodiments 204-211, $Y^2$ is $C(R^{5c})$.

Embodiment 213: in some embodiments, such as, the compound of any one of Embodiments 204-212, $R^{6a}$, $R^{6b}$, $R^{6c}$, $R^{6d}$, and $R^{6e}$ are independently chosen from H, halo, methyl, cyclopropyl, cyano, methoxy, hydroxy, halomethyl, hydroxymethyl and halomethoxy.

Embodiment 214: in some embodiments, such as, the compound of Embodiment 213, $R^{6a}$, $R^{6b}$, $R^{6c}$, $R^{6d}$, and $R^{6e}$ are independently chosen from H, halo, methyl, cyclopropyl, cyano, and hydroxymethyl.

Embodiment 215: in some embodiments, such as, the compound of Embodiment 214, $R^{6a}$, $R^{6b}$, $R^{6c}$, $R^{6d}$, and $R^{6e}$ are independently chosen from H, fluoro, and methyl.

Embodiment 216: in some embodiments, such as, the compound of any one of Embodiments 204-215, at least one of $R^{6a}$, $R^{6c}$, and $R^{6d}$ is H.

Embodiment 217: in some embodiments, such as, the compound of Embodiment 216, at least two of $R^{6a}$, $R^{6c}$, and $R^{6d}$ are H.

Embodiment 218: in some embodiments, such as, the compound of Embodiment 217, $R^{6a}$, $R^{6c}$, and $R^{6d}$ are H.

Embodiment 219: in some embodiments, such as, the compound of any one of Embodiments 204-218, at most one of $W^1$ and $W^2$ is N.

Embodiment 220: in some embodiments, such as, the compound of any one of Embodiments 204-219, $W^1$ is $C(R^{6b})$.

Embodiment 221: in some embodiments, such as, the compound of Embodiment 220, $W^1$ is chosen from CH and CF.

Embodiment 222: in some embodiments, such as, the compound of any one of Embodiments 204-221, $W^2$ is $C(R^{6e})$.

Embodiment 223: in some embodiments, such as, the compound of Embodiment 222, $W^2$ is chosen from CH and CF.

Embodiment 224: in some embodiments, the compound is chosen from:

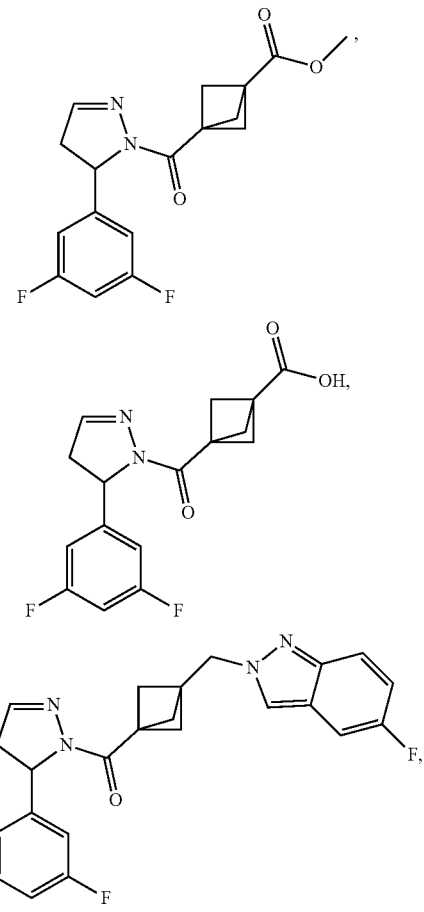

-continued
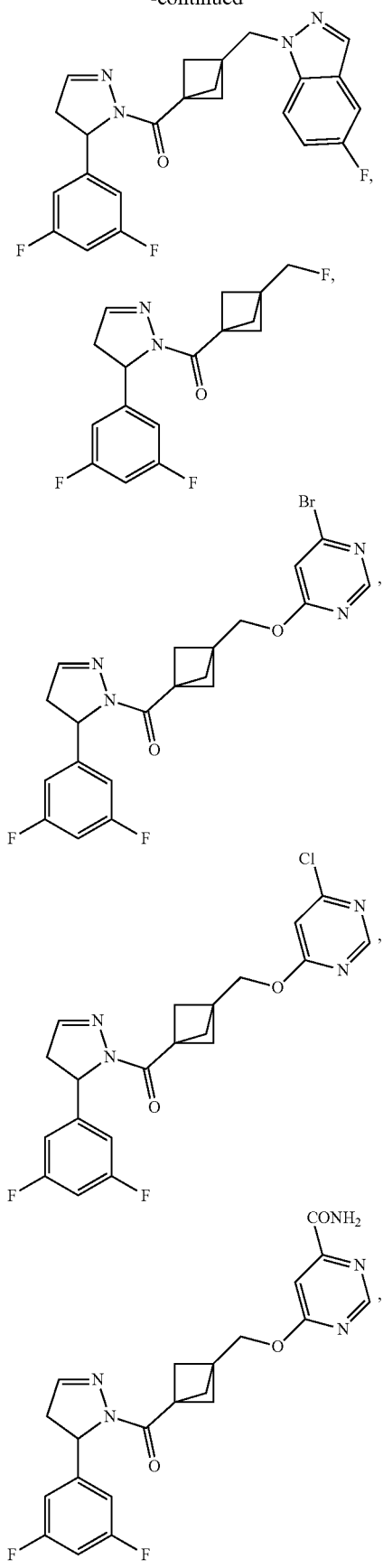
-continued
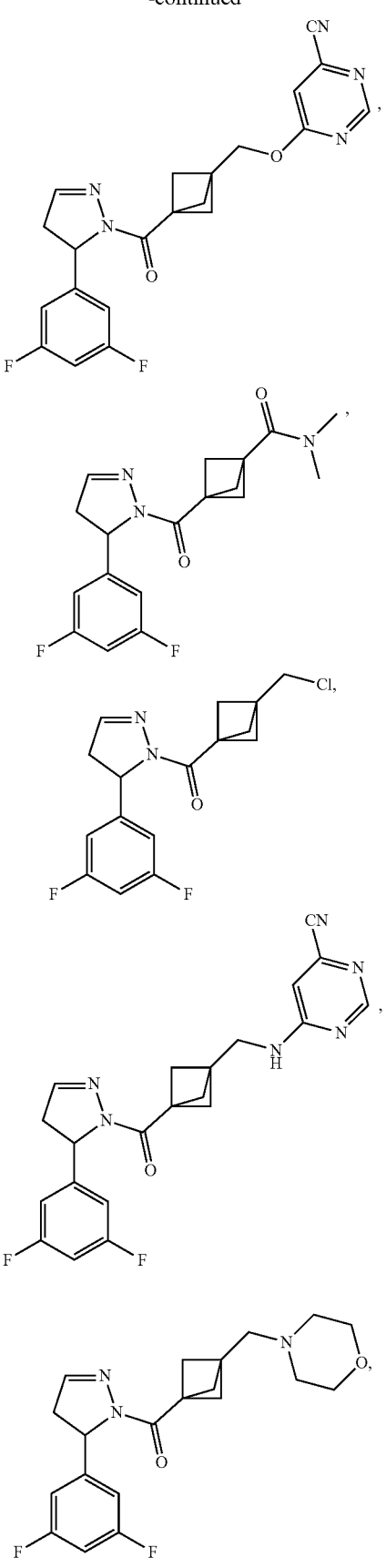

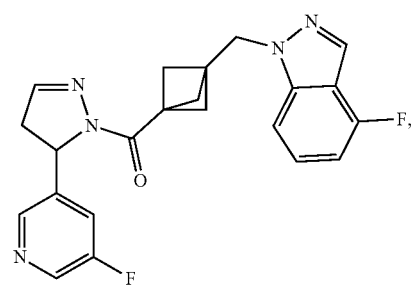
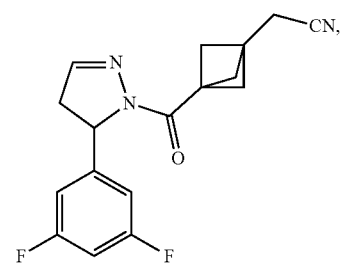
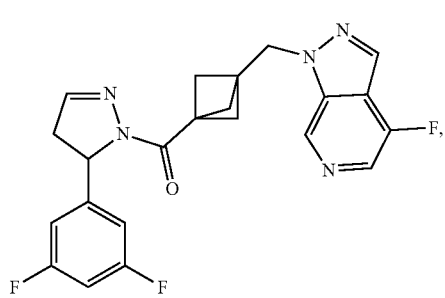
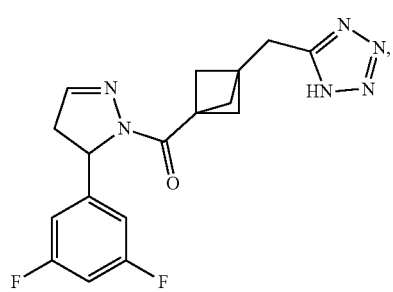
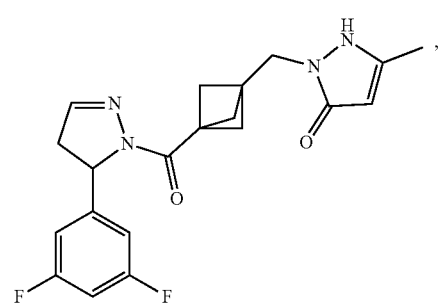
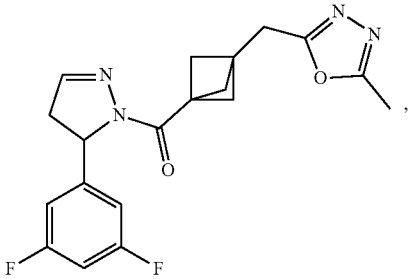
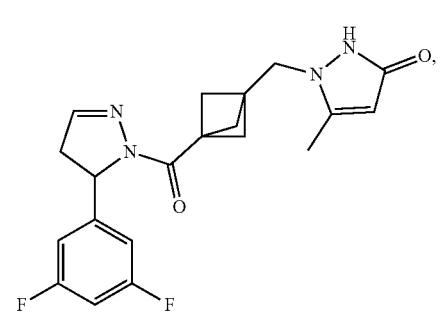
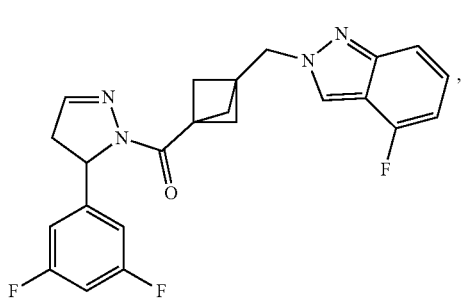
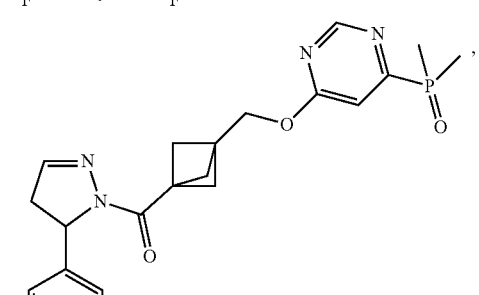
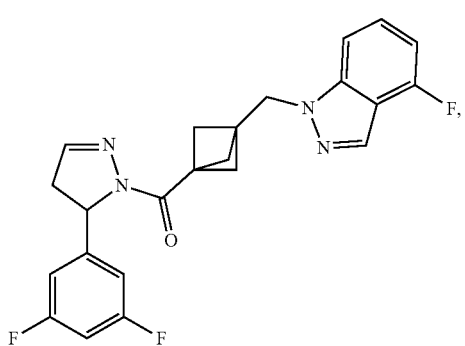

31
-continued
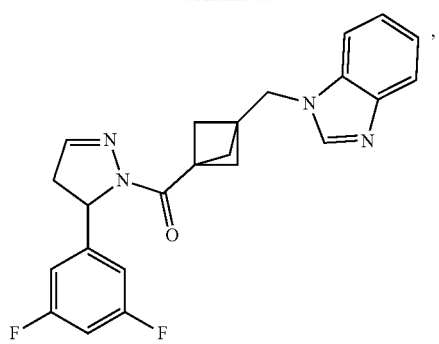
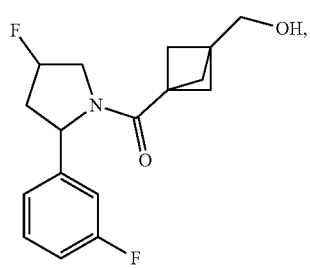
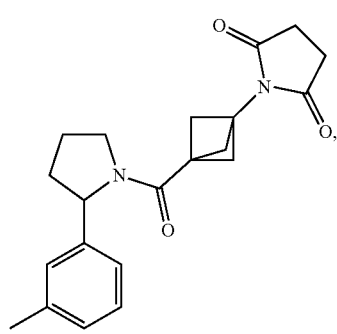
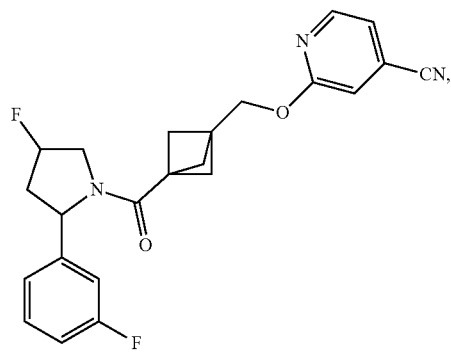
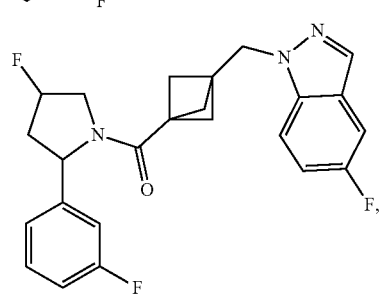
32
-continued
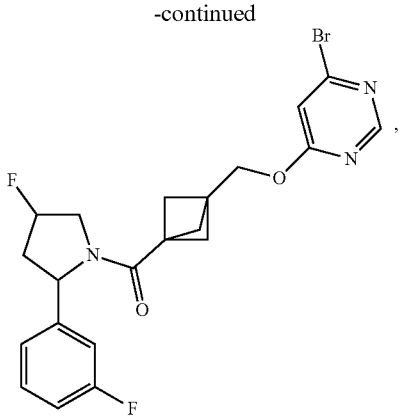
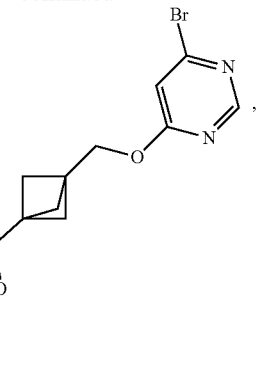

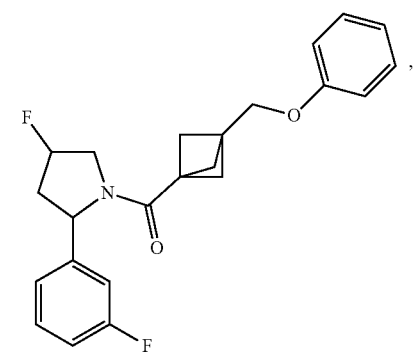
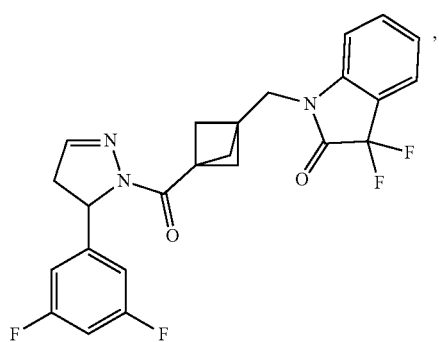
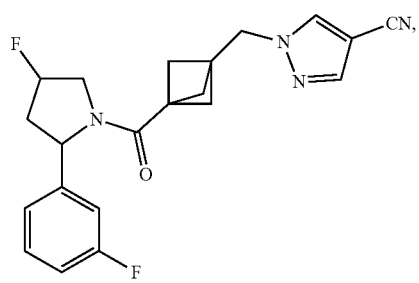
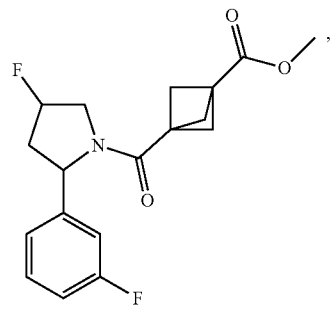
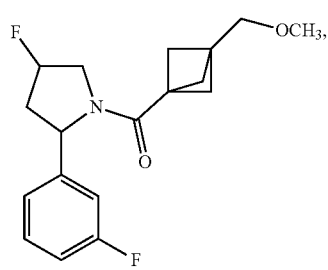
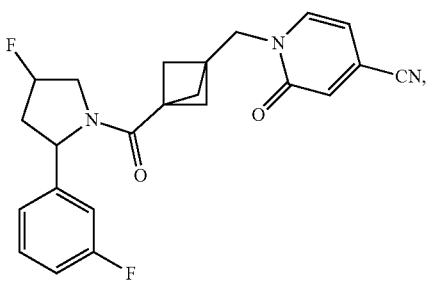
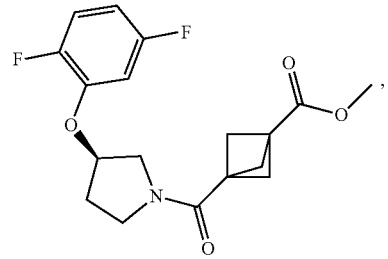
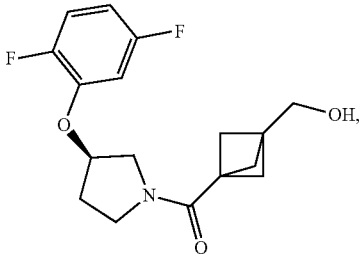
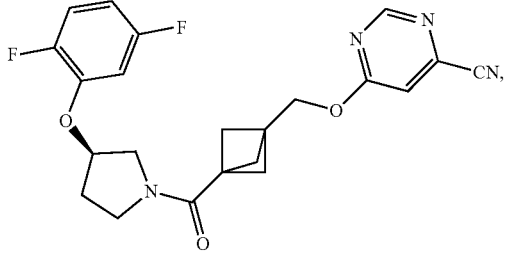
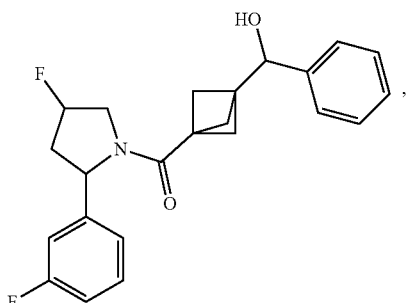
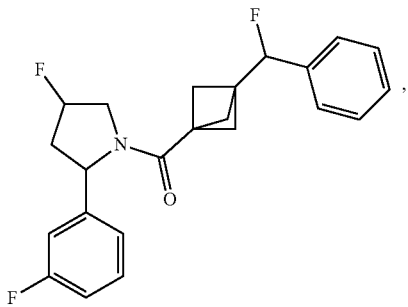

35
-continued
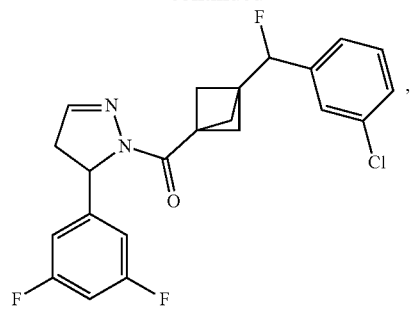
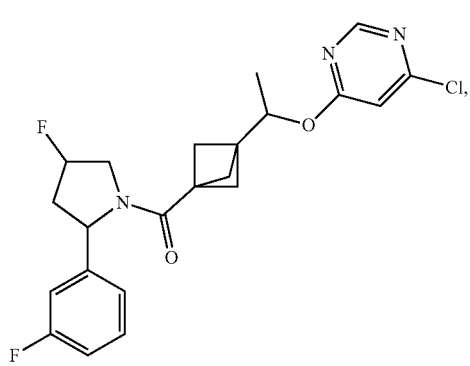
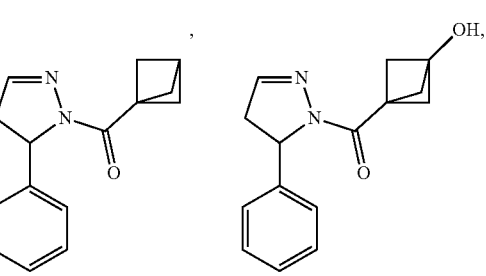
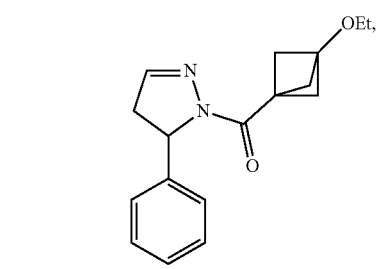
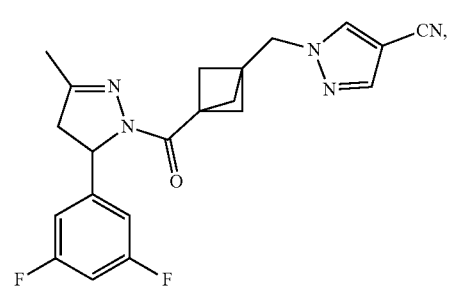
36
-continued
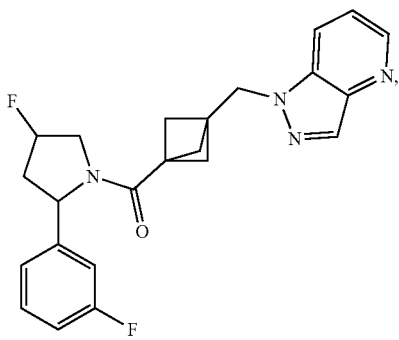
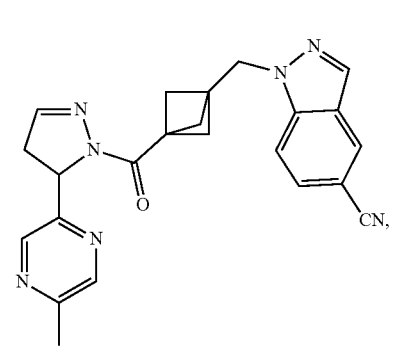
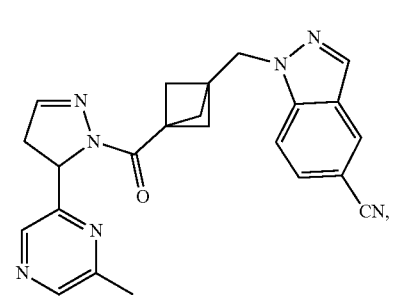

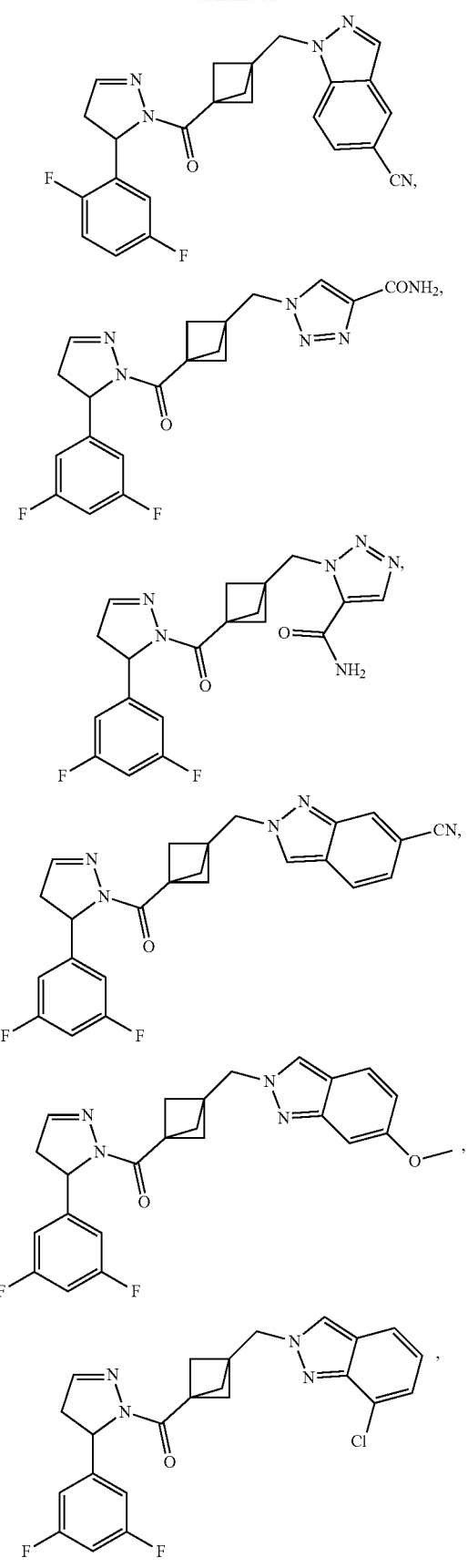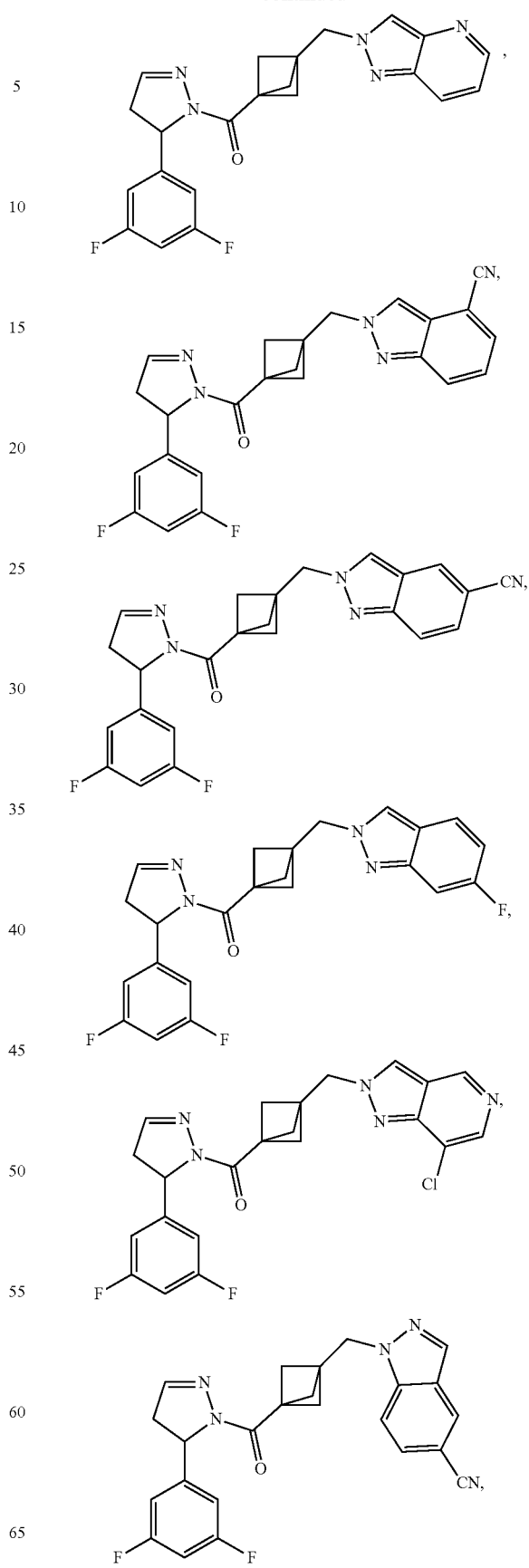

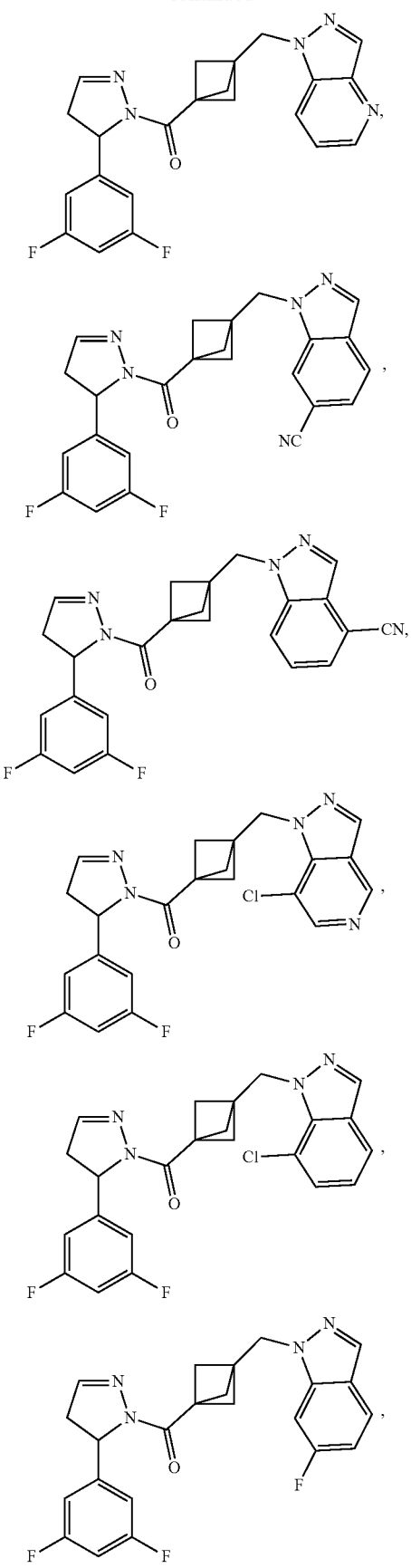
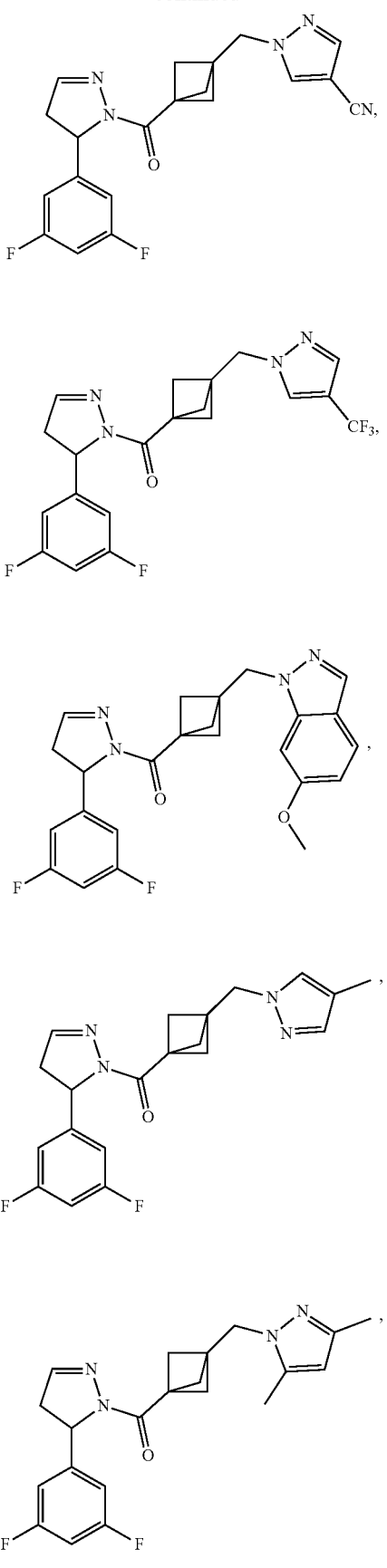

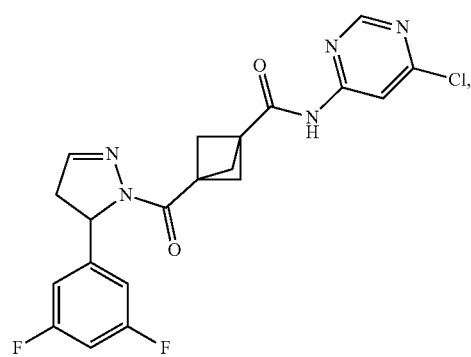
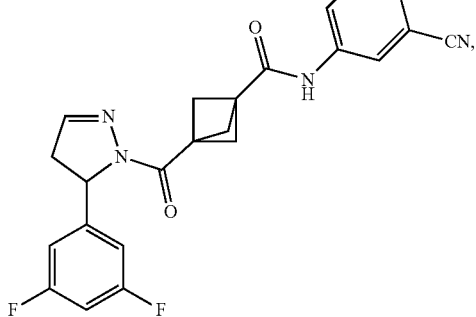
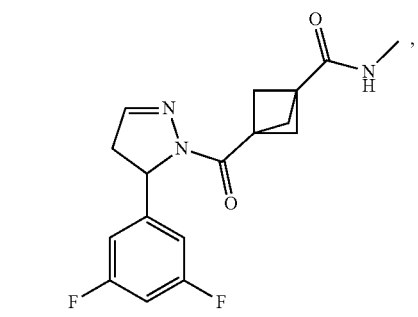
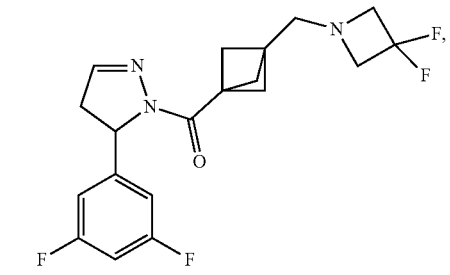
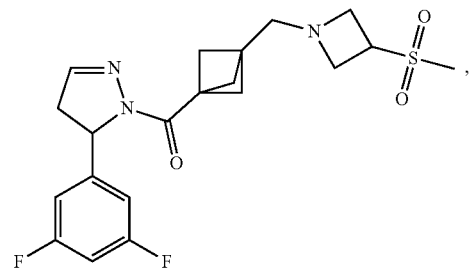
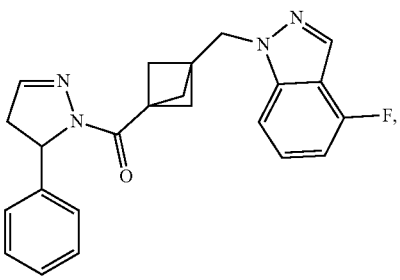
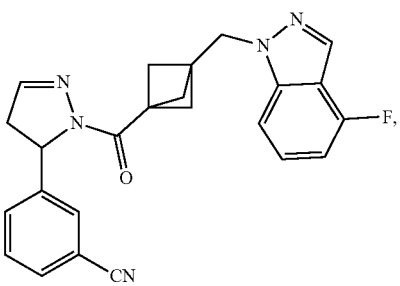
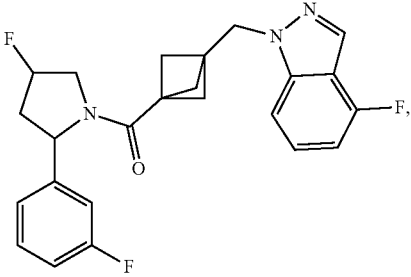
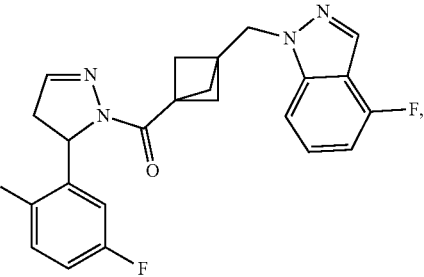
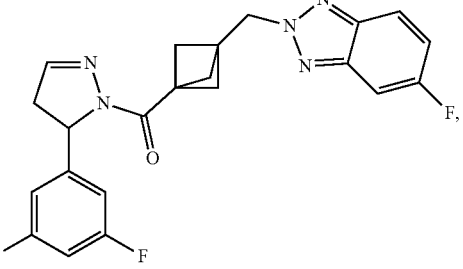
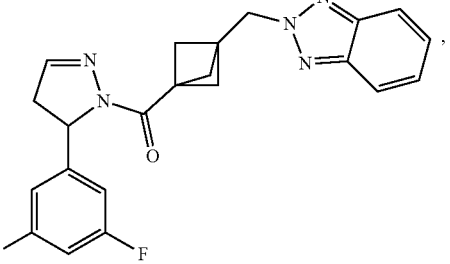

43
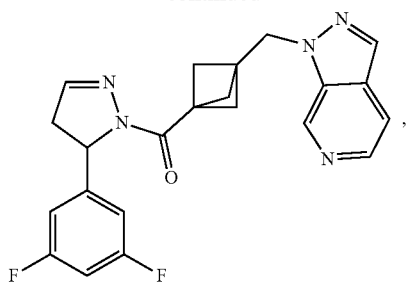
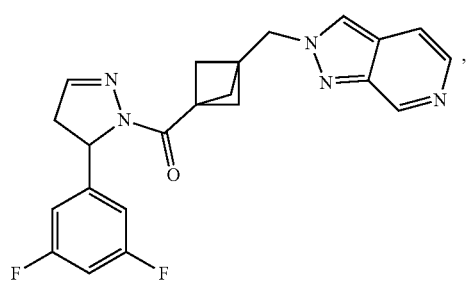
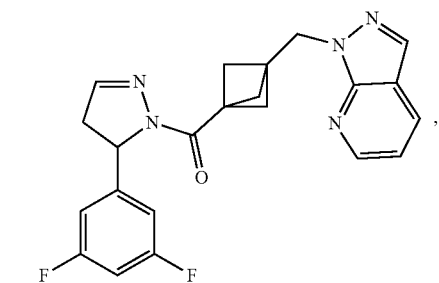
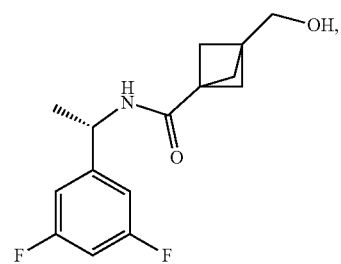
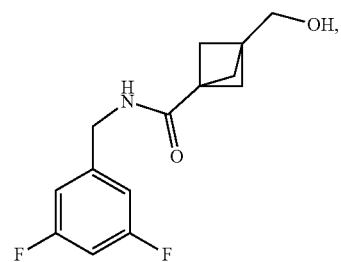
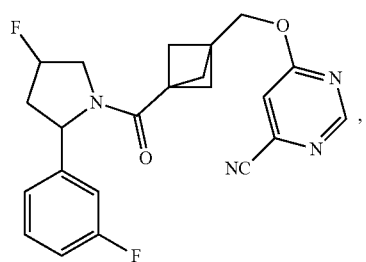
44
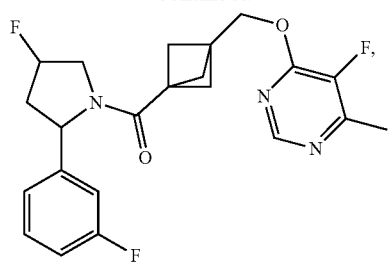
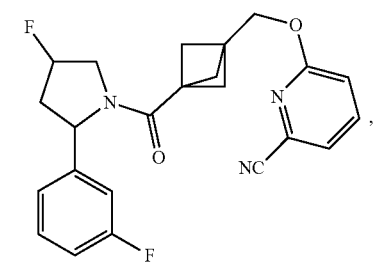
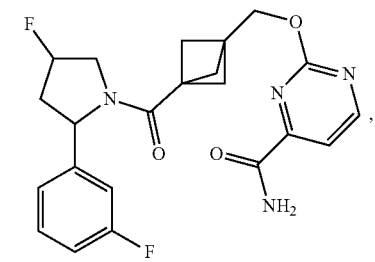
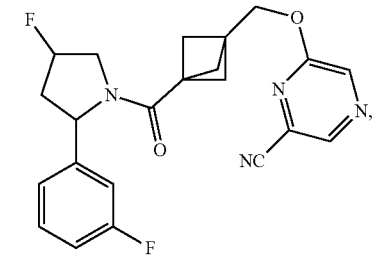
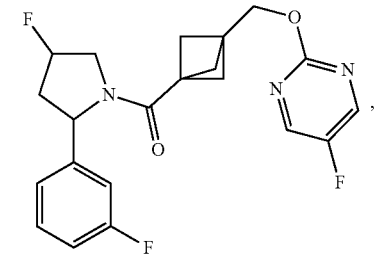
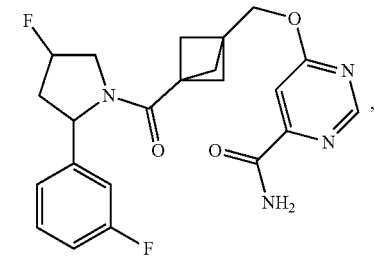

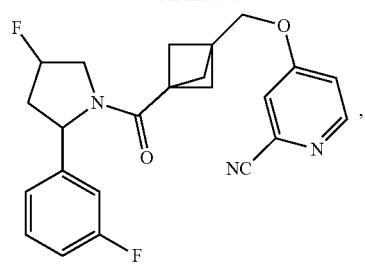
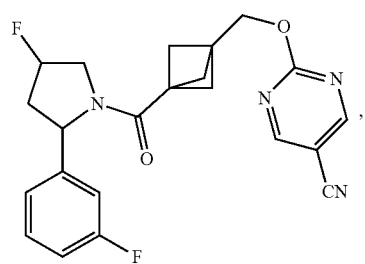
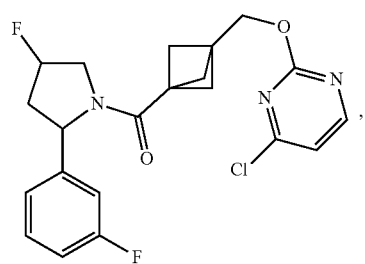
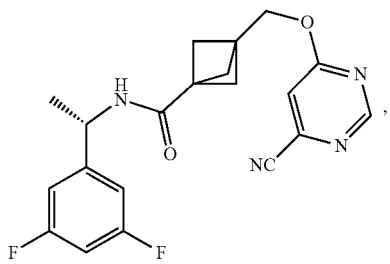
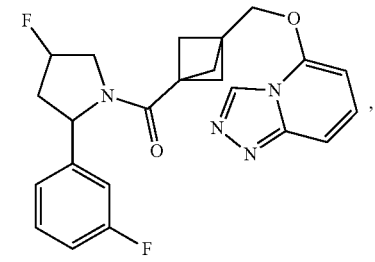
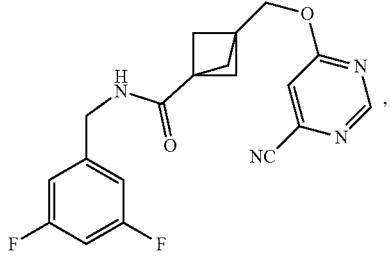
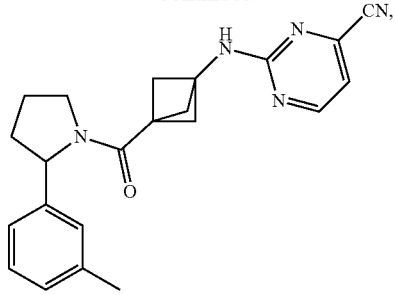
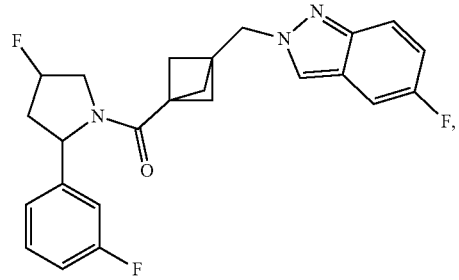
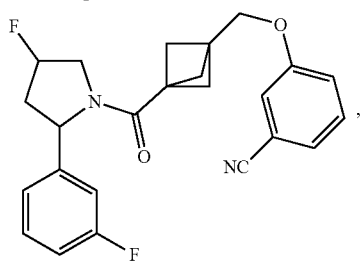
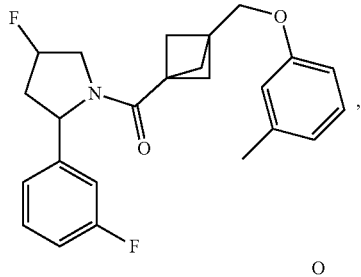
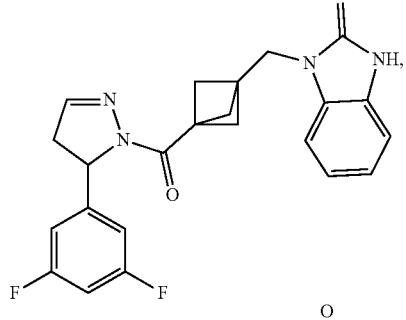
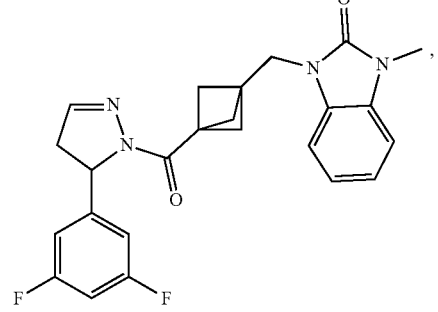

-continued
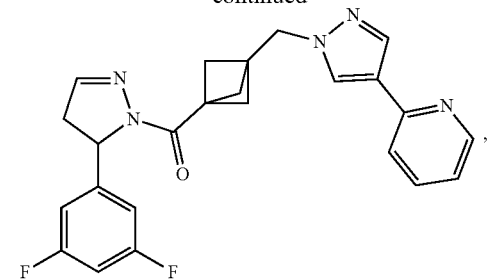
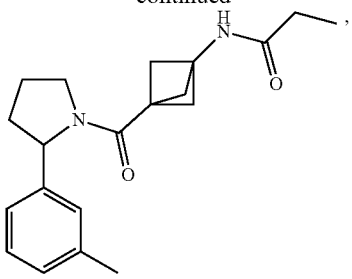

49
-continued
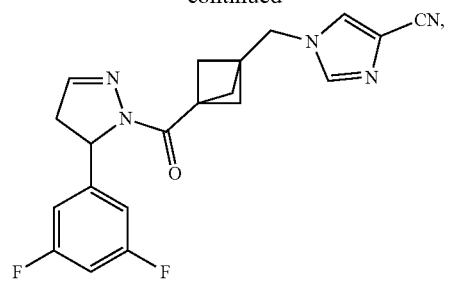
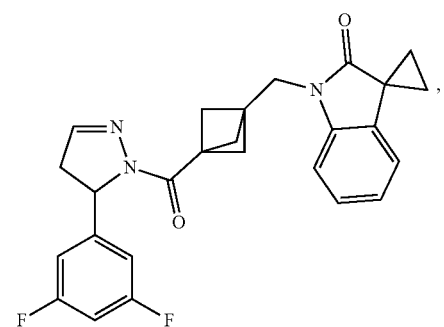
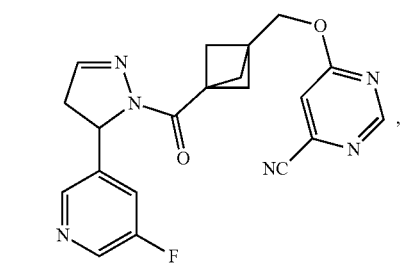
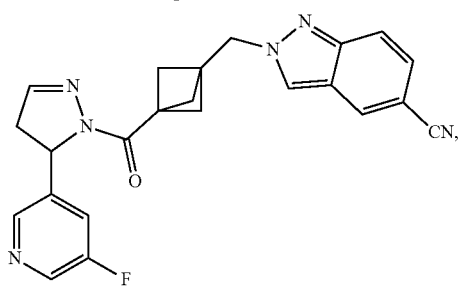
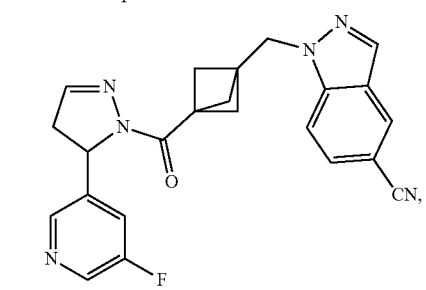
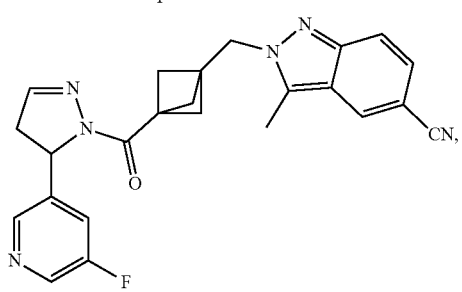
50
-continued
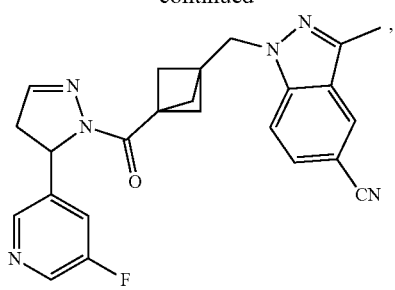
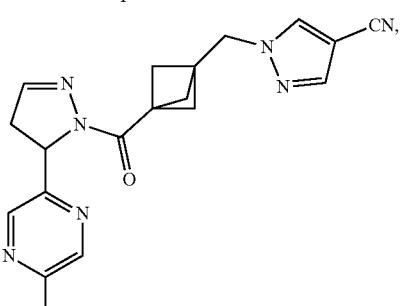
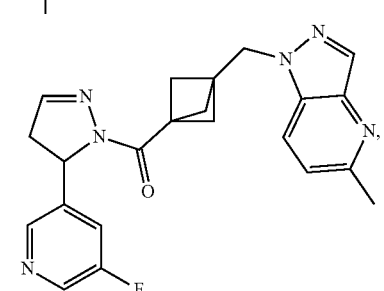
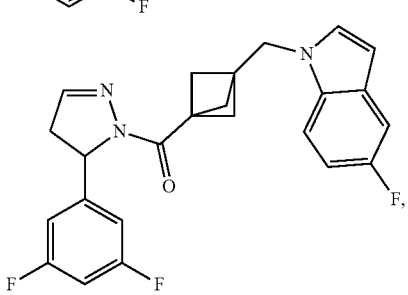
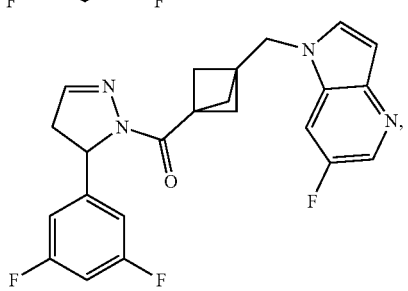
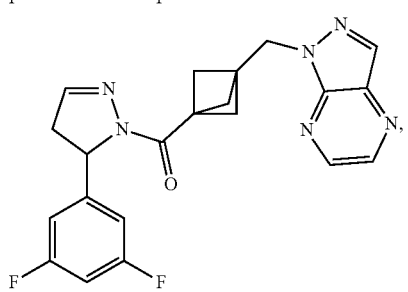

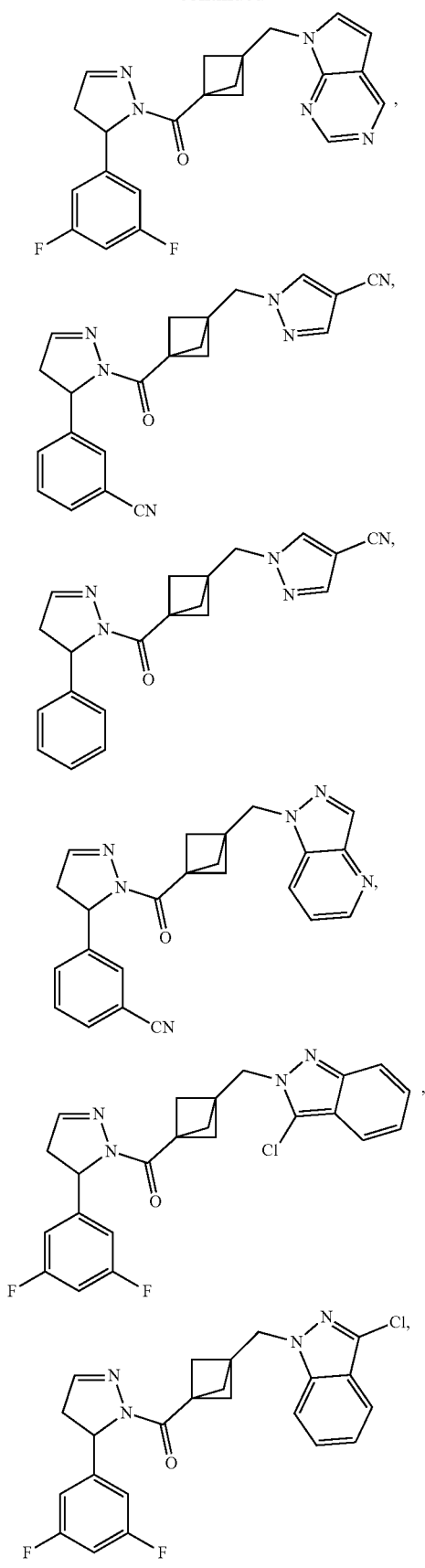
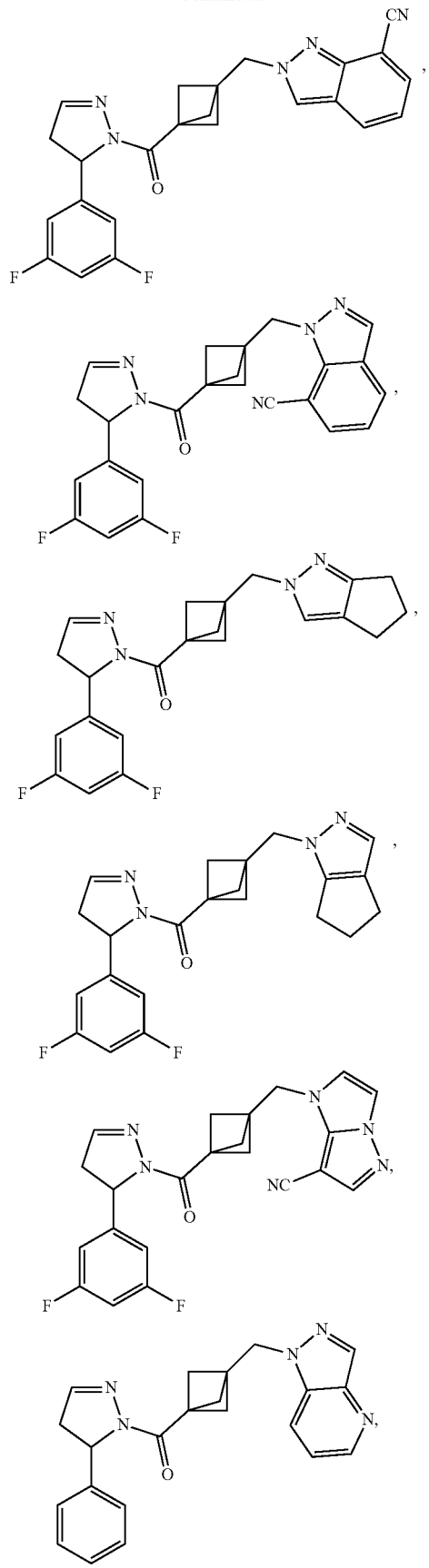

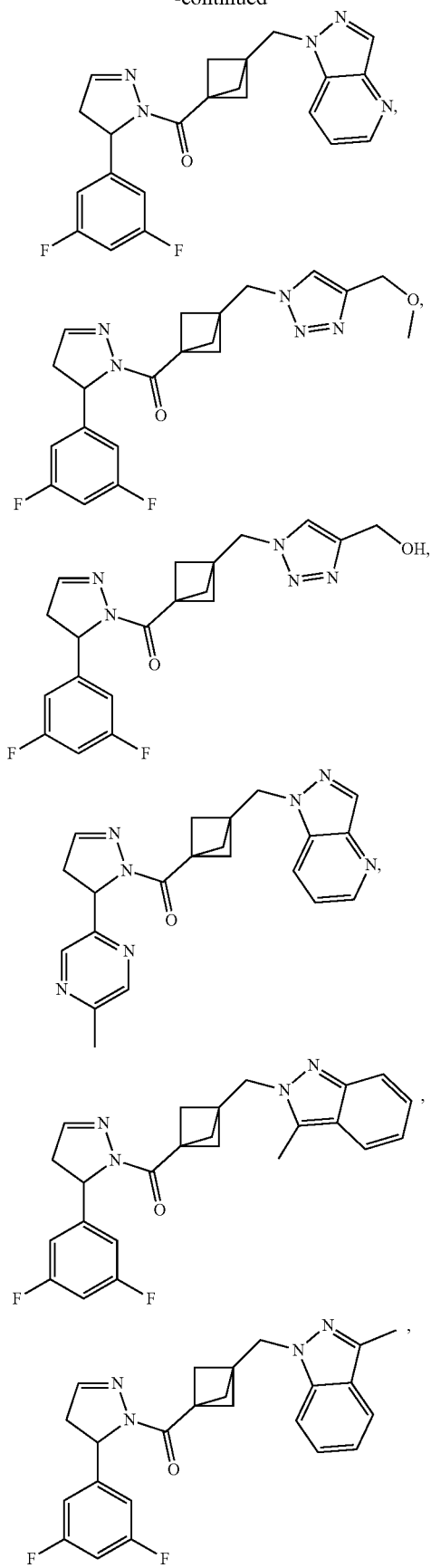
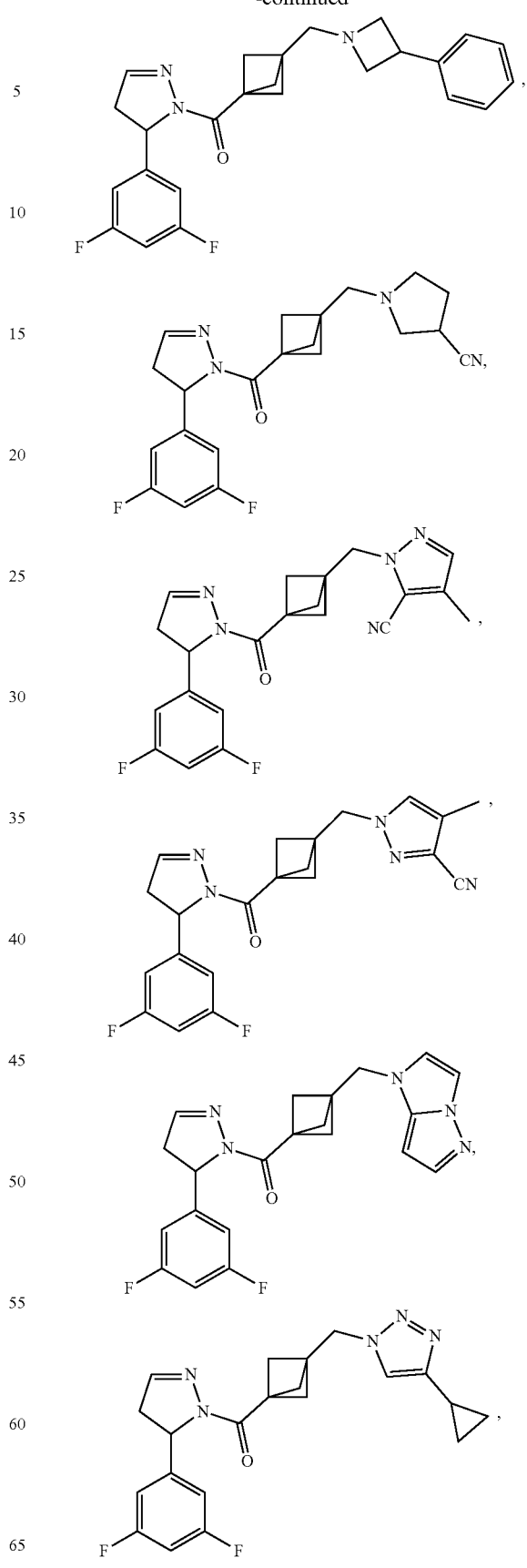

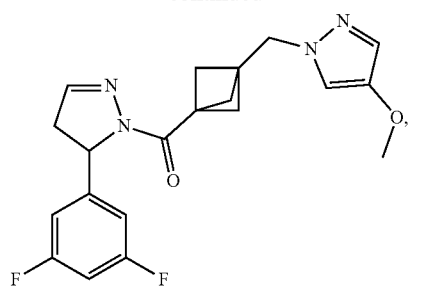
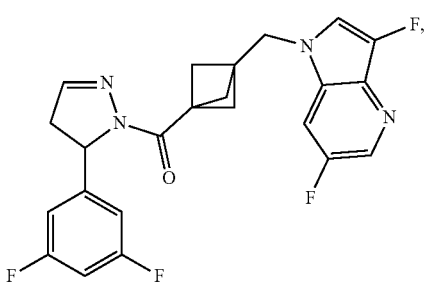
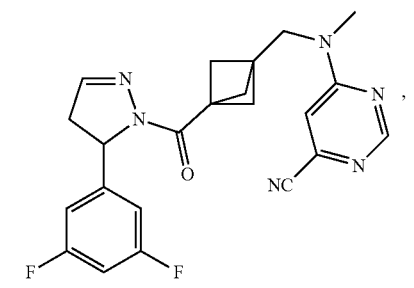
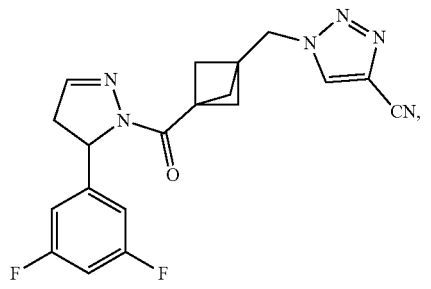
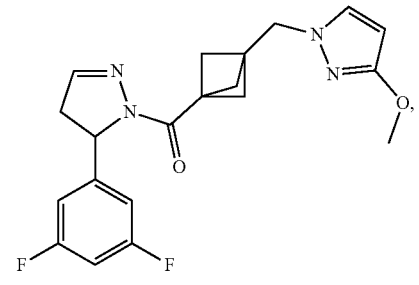
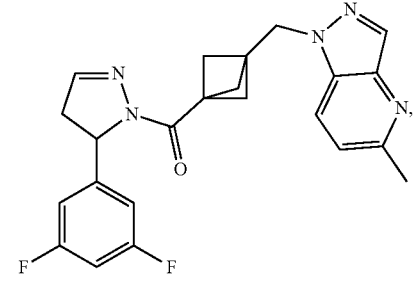
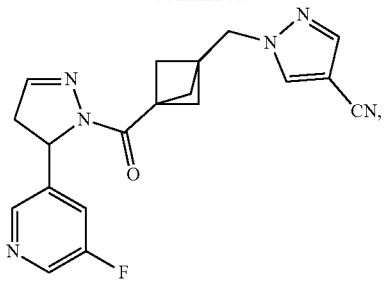
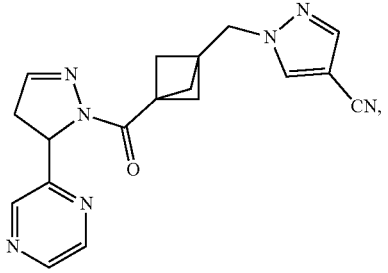
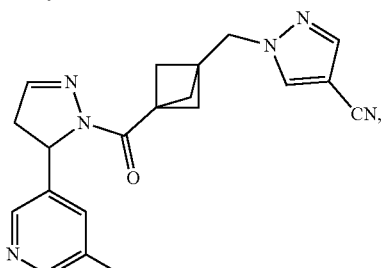
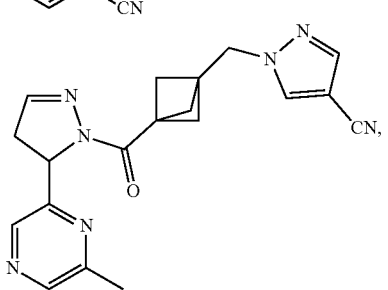
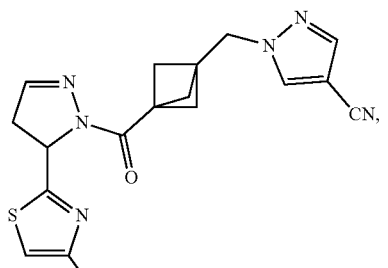
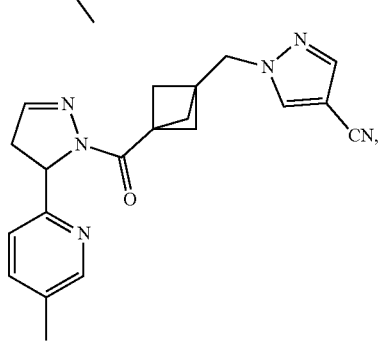

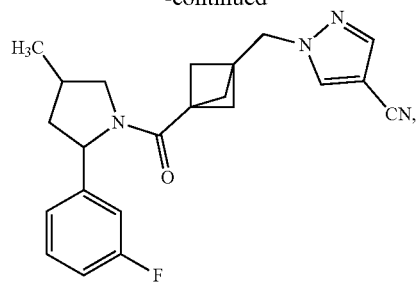
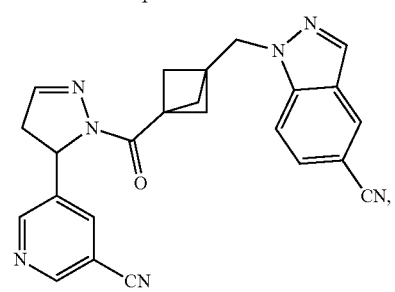
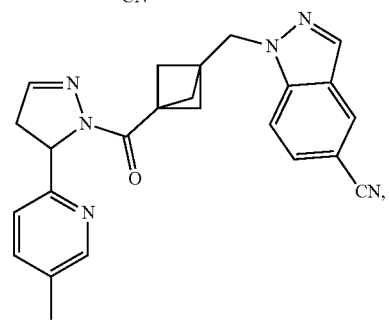
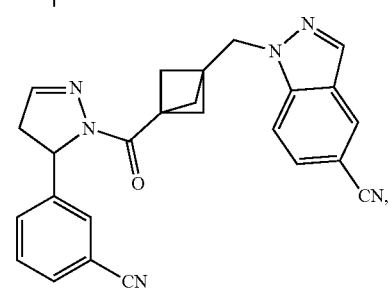
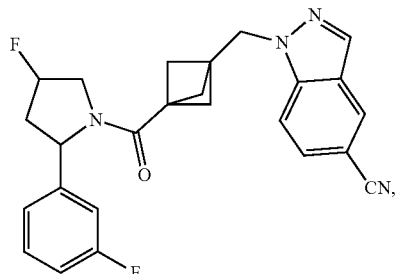
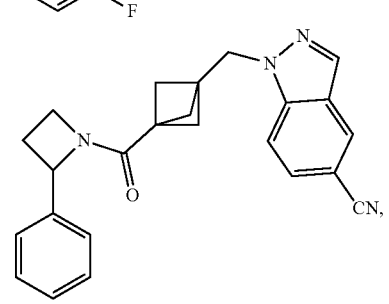
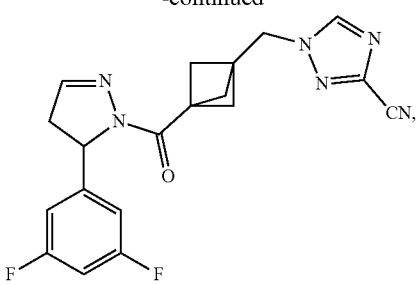
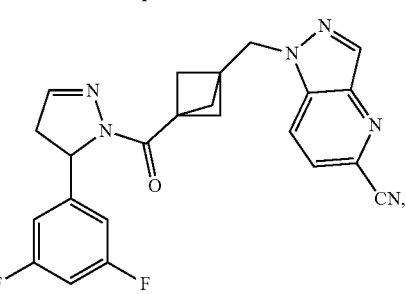
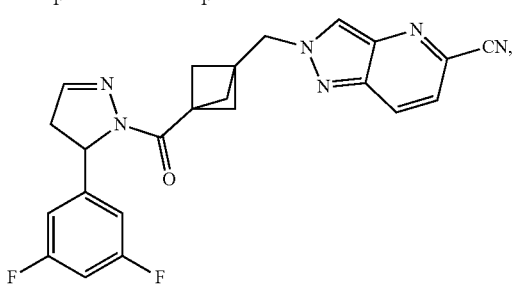
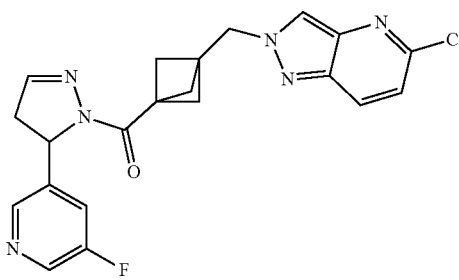
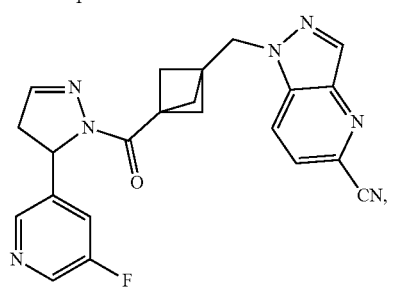
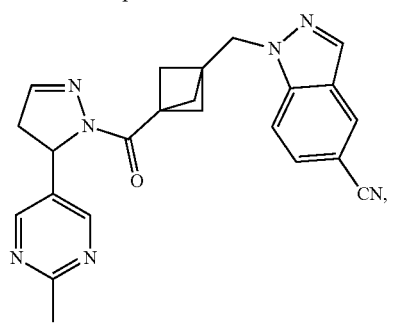

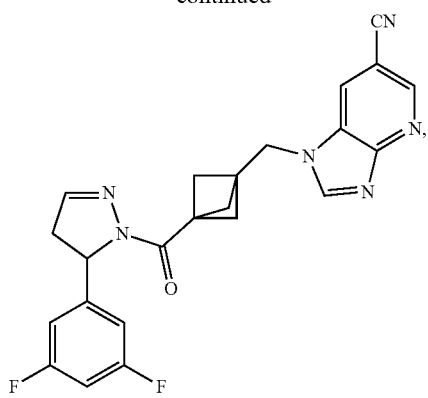
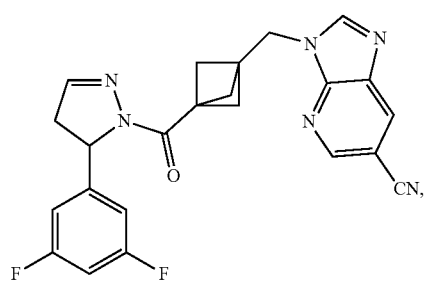
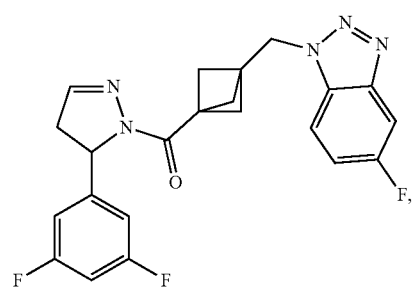
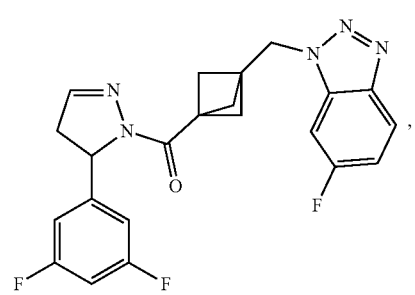
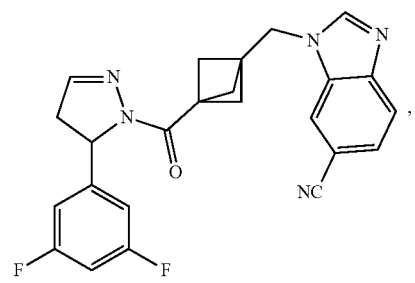
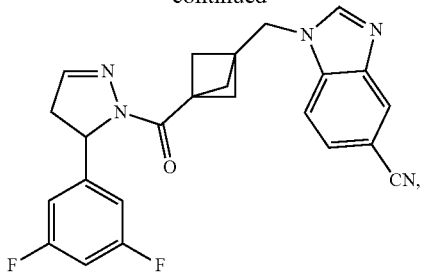
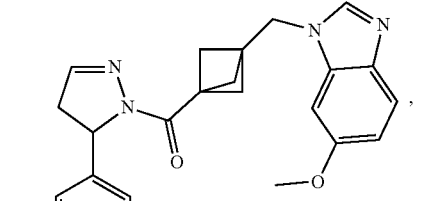
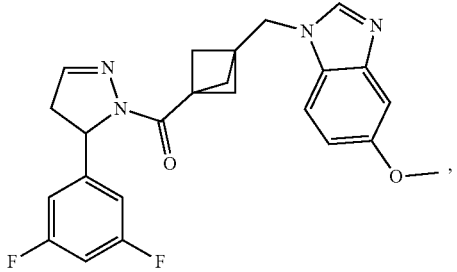
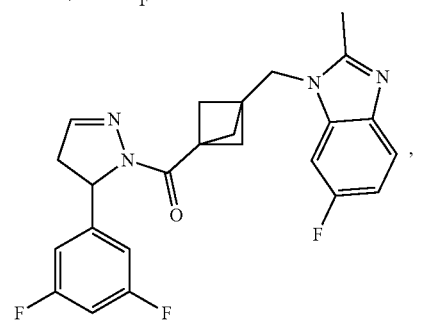
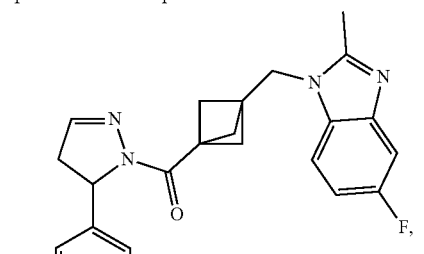
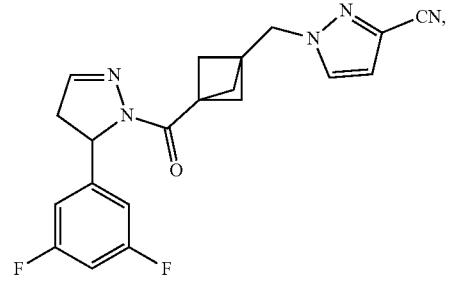

61
-continued
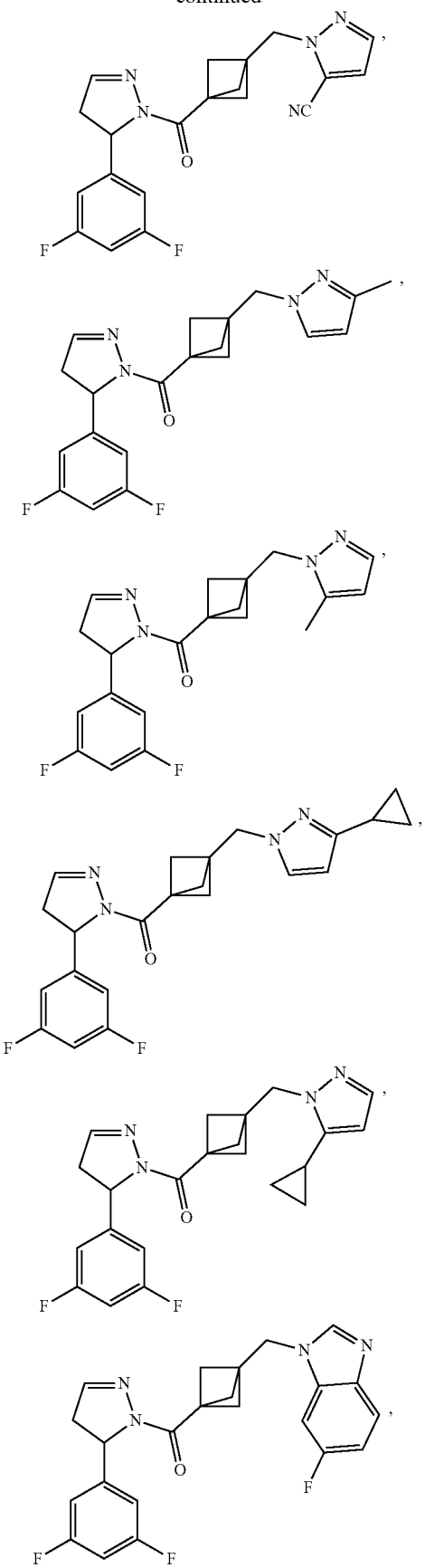
62
-continued
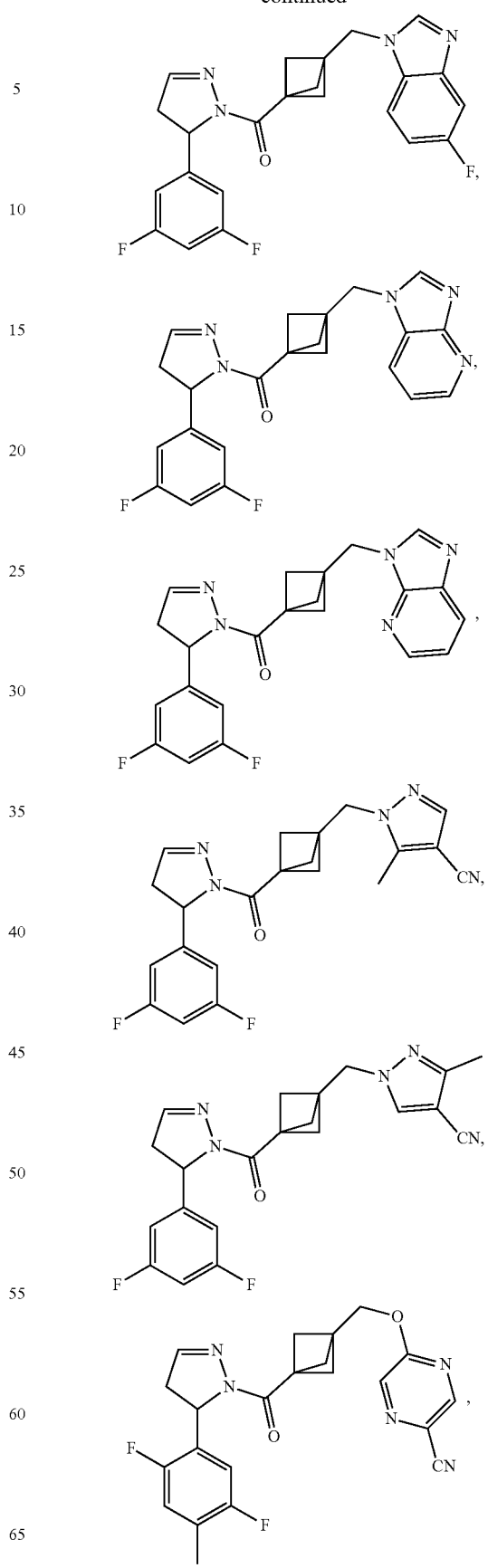

63
-continued
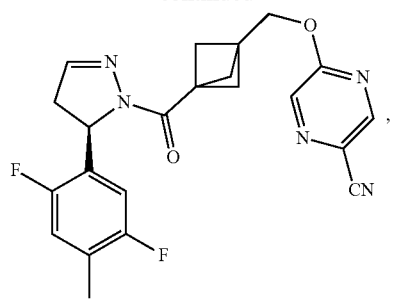
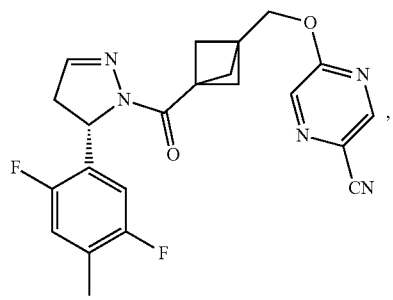
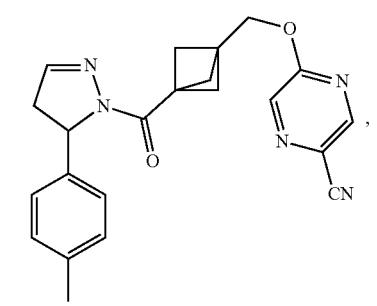
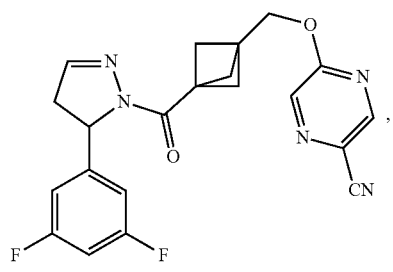
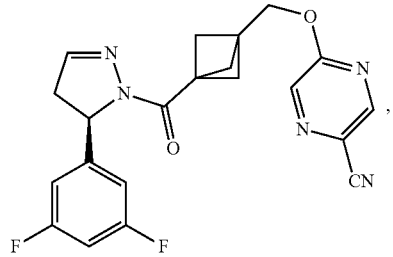
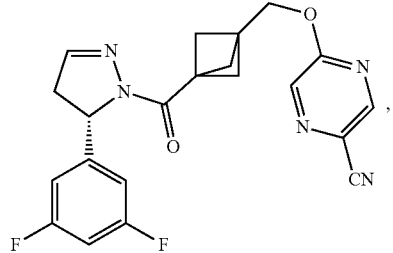
64
-continued
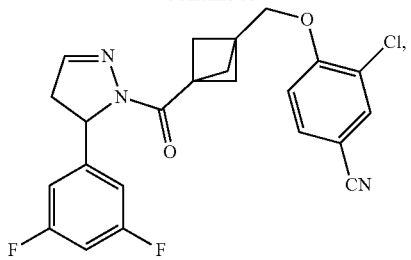
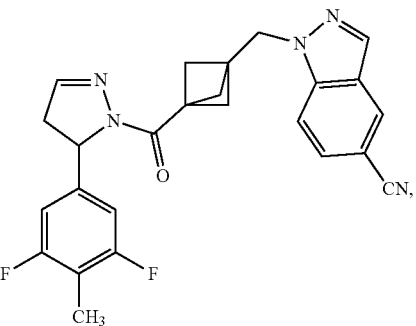
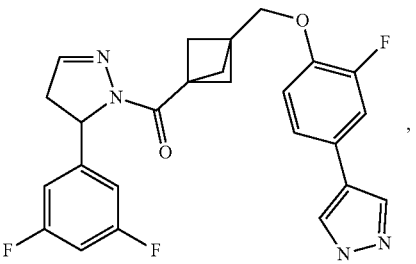
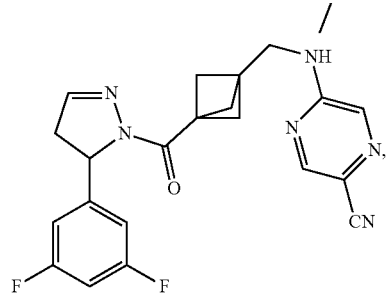
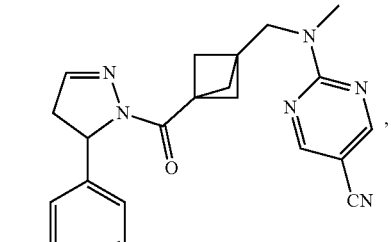
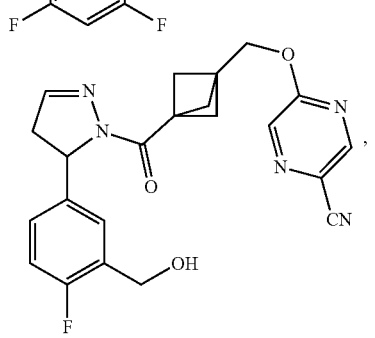

-continued
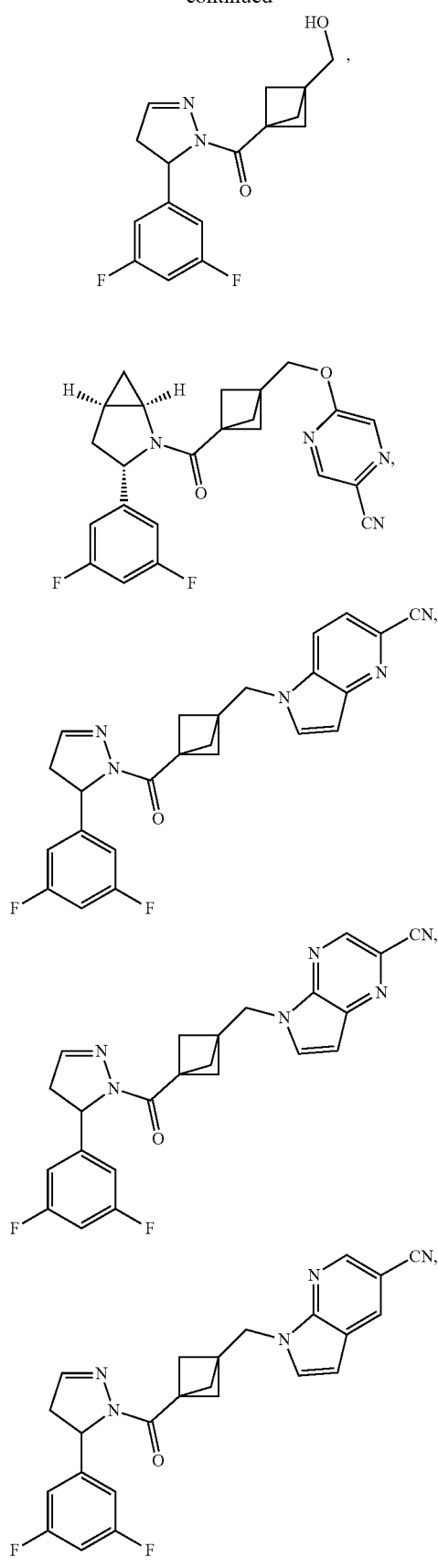
-continued
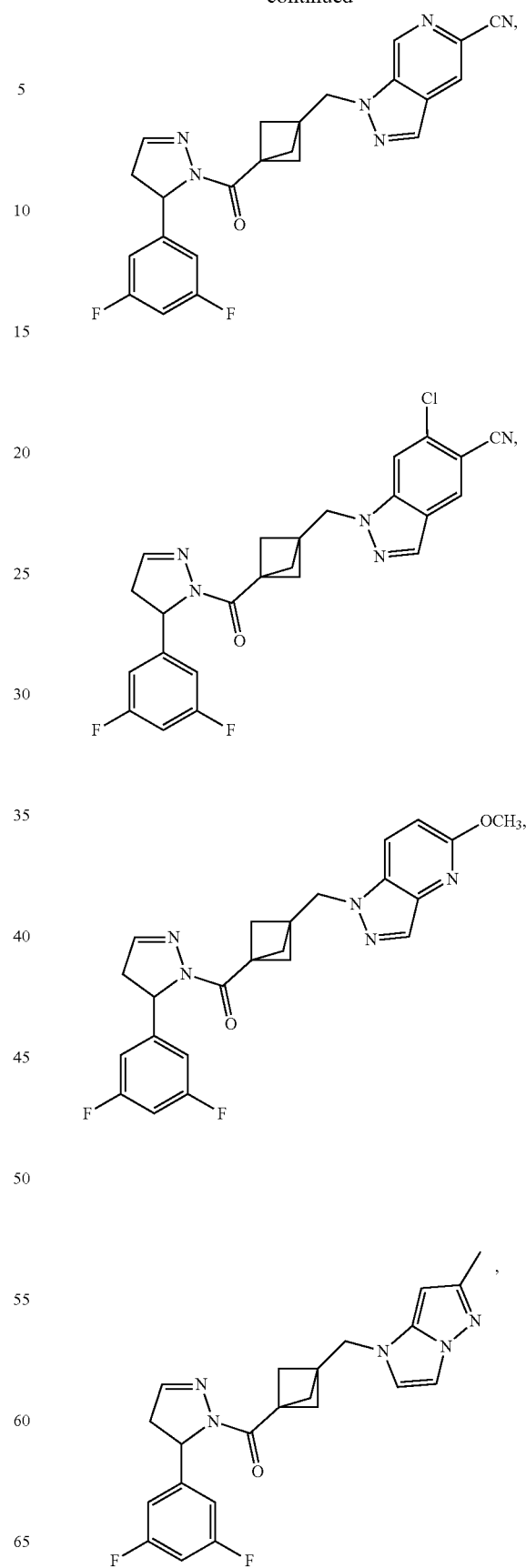

67
-continued
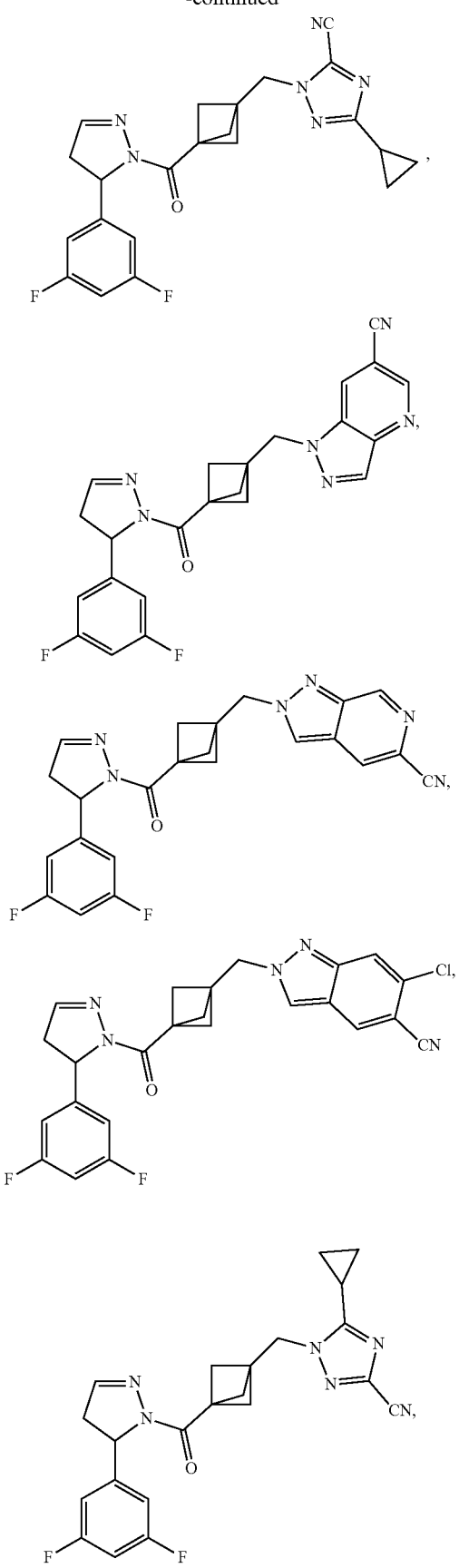
68
-continued
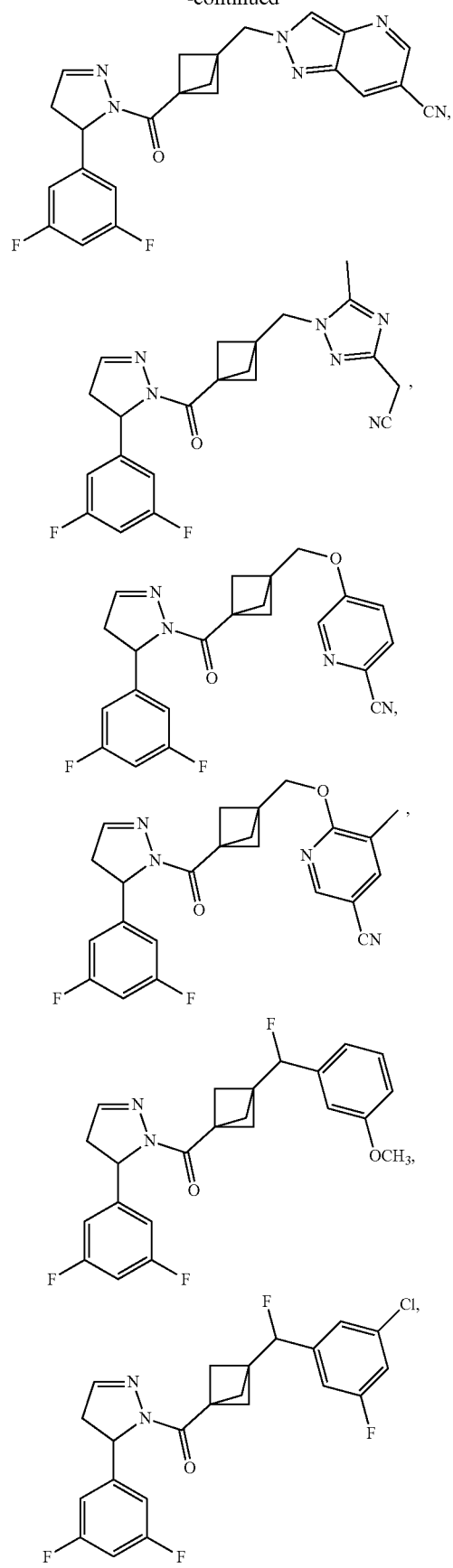

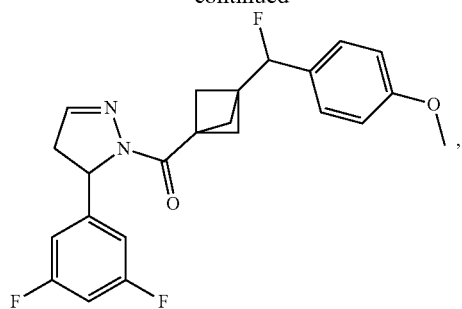
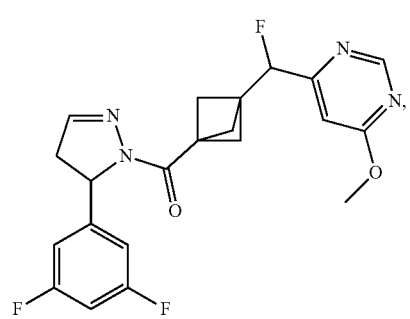
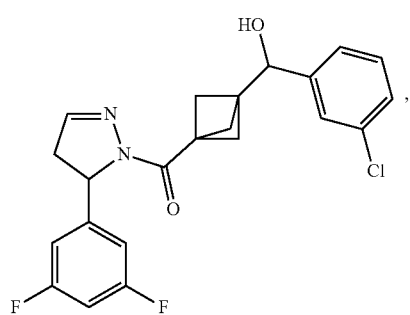
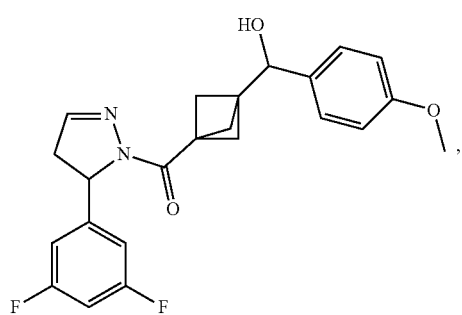
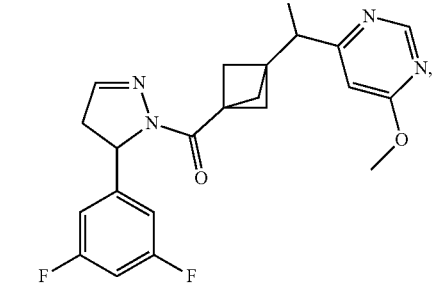
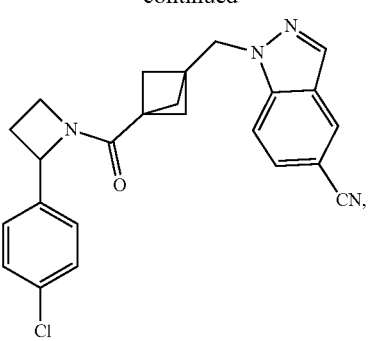
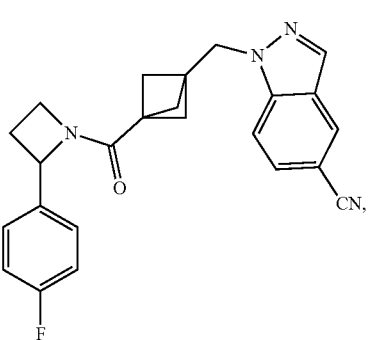
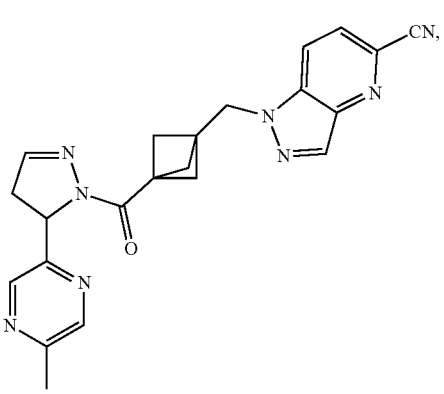
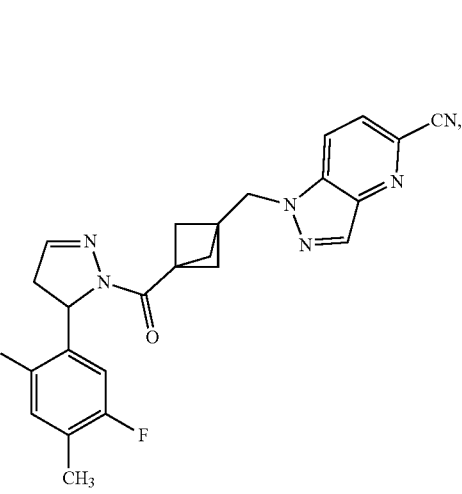

71
-continued
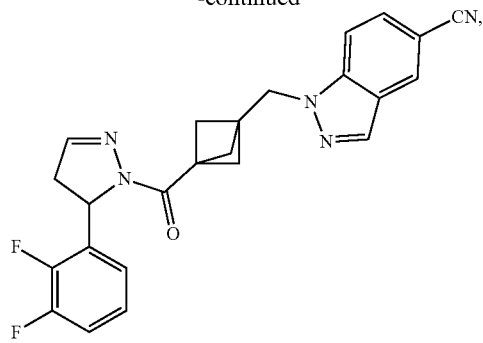
72
-continued
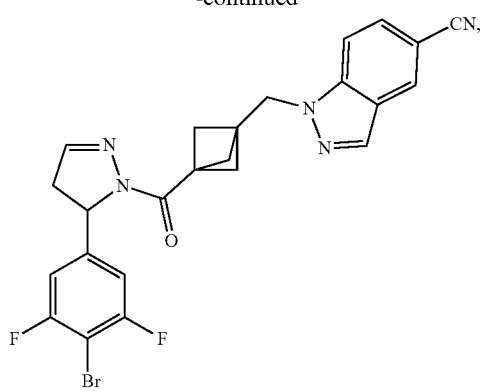

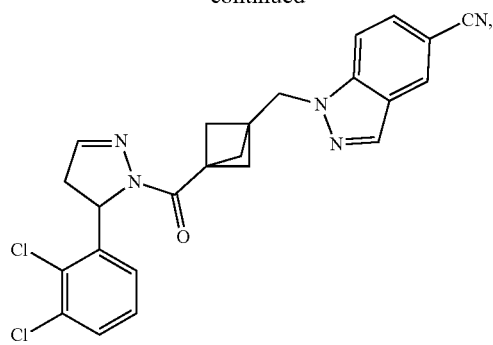

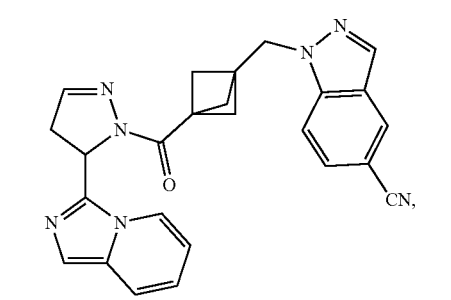
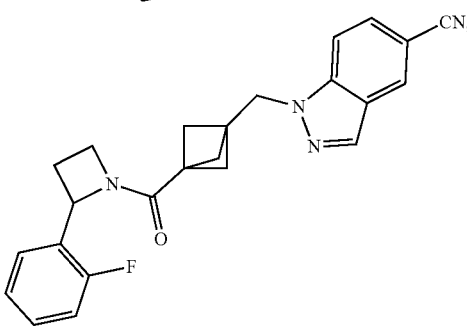
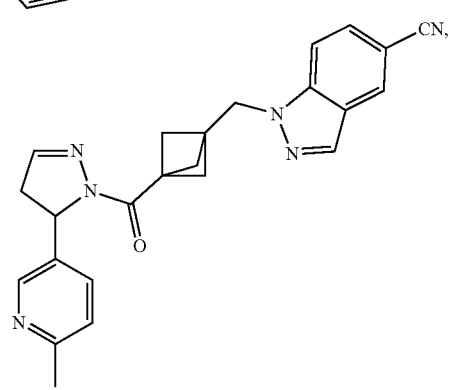
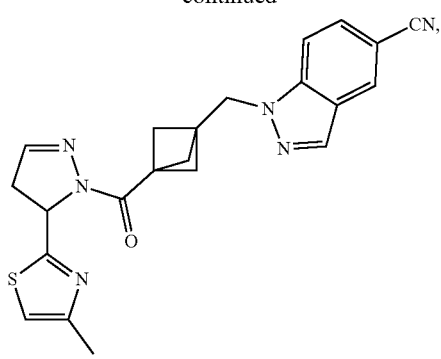
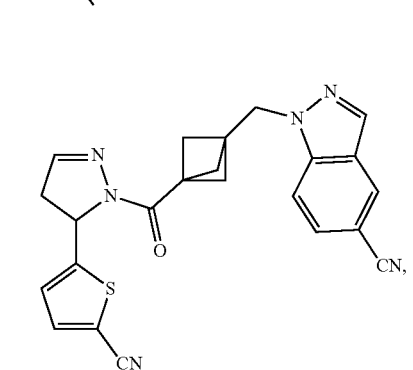
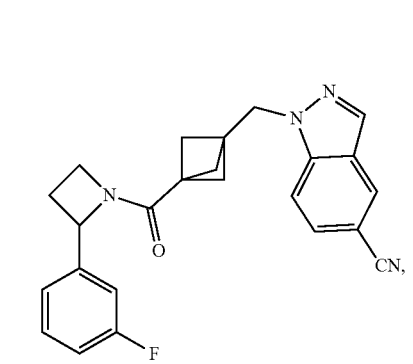
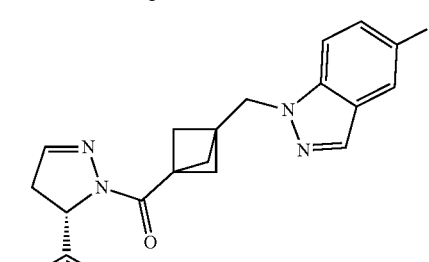
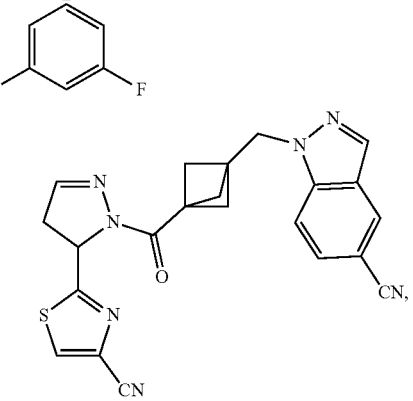

75
-continued
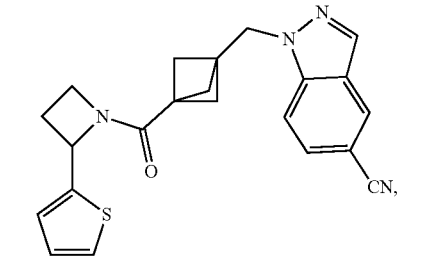
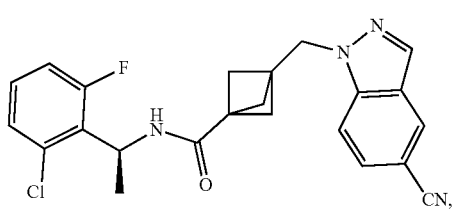
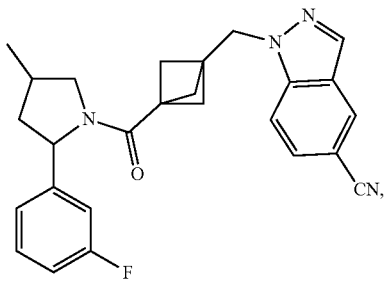
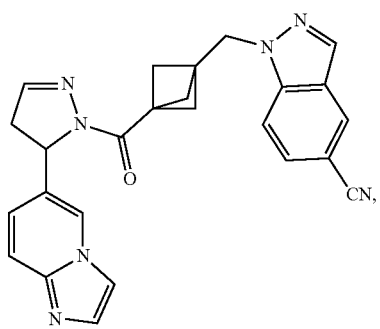
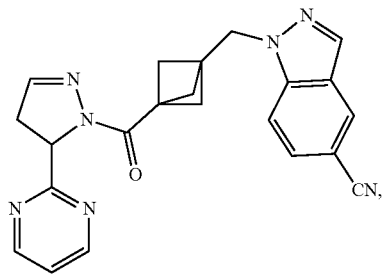
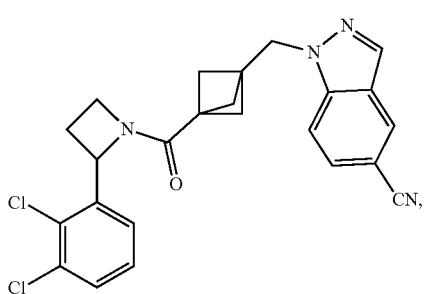
76
-continued
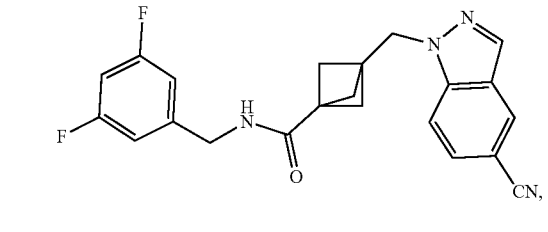
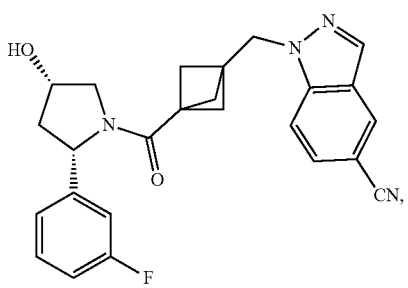
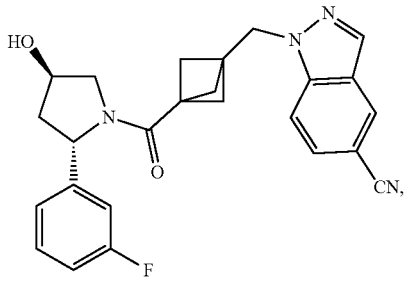
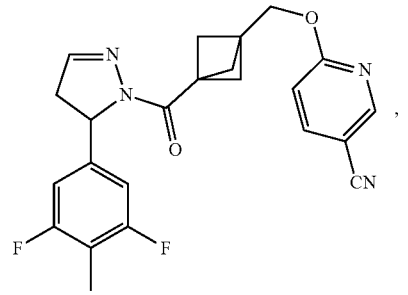
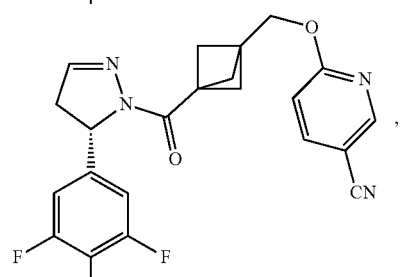
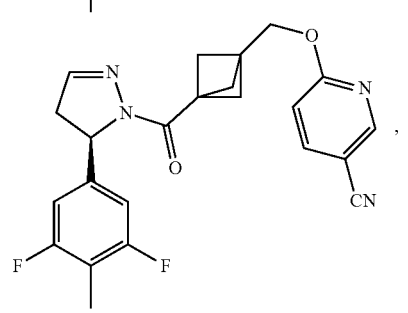

77
-continued
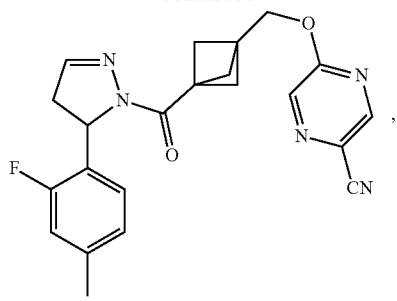,
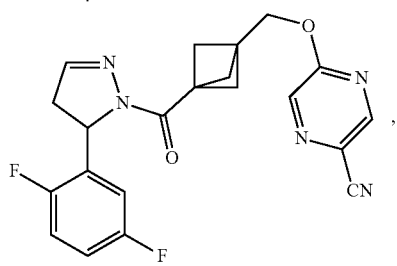,
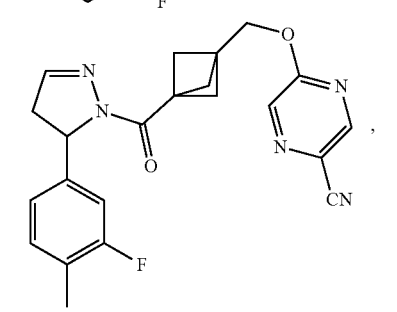,
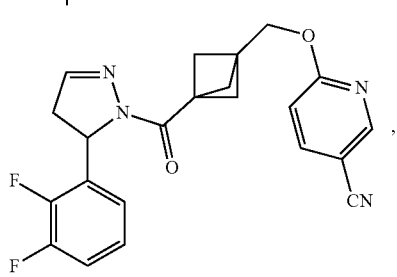,
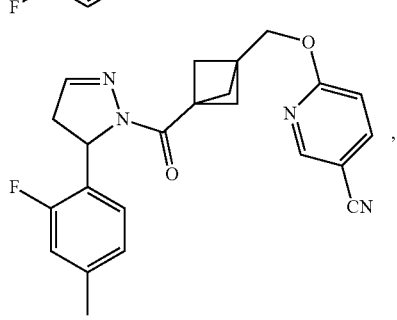,
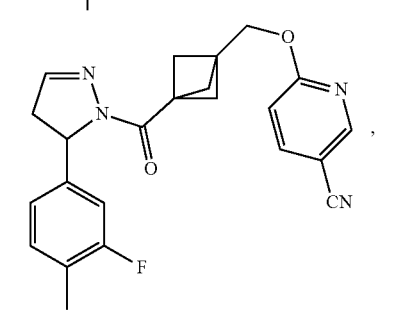,
78
-continued
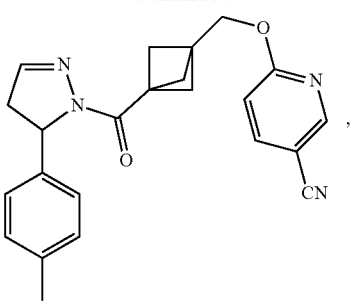,
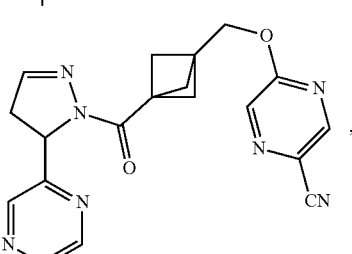,
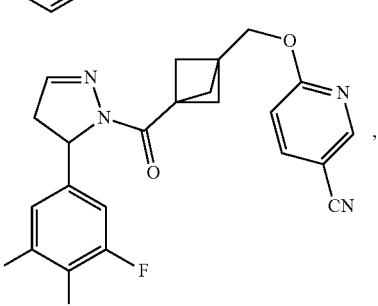,
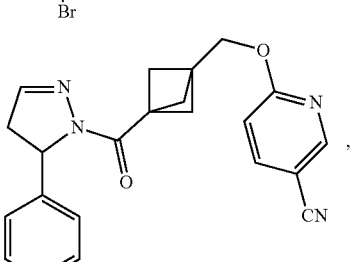,
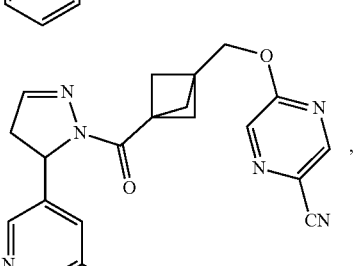,
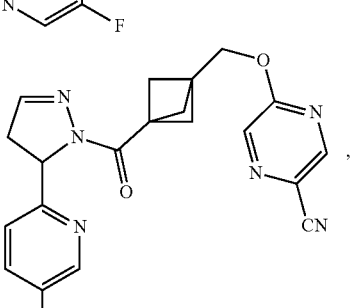,

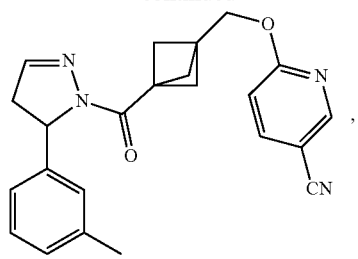,
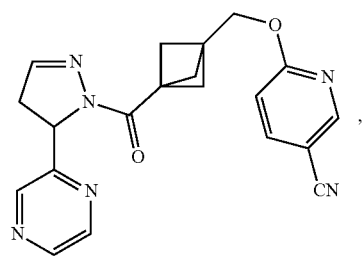,
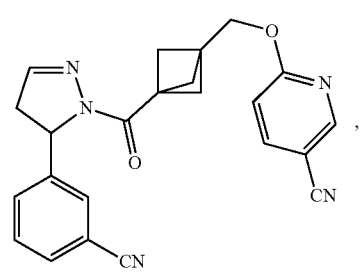,
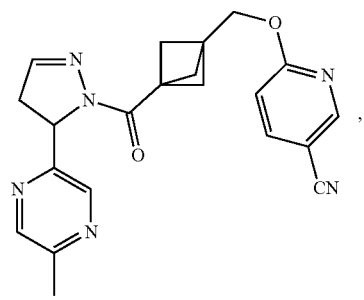,
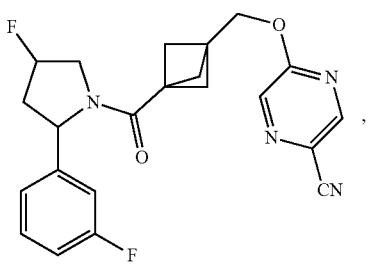,
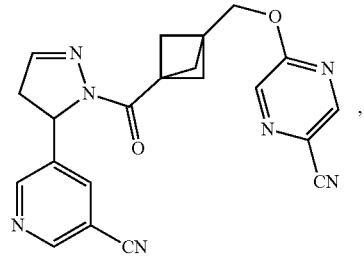,
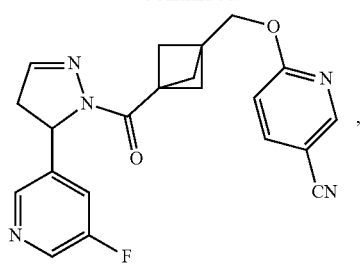,
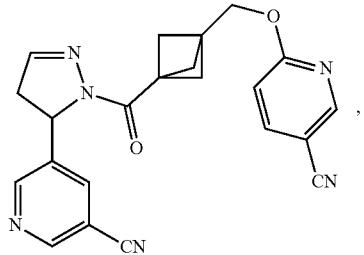,
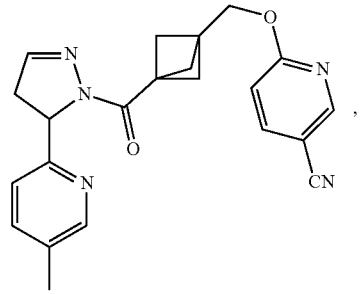,
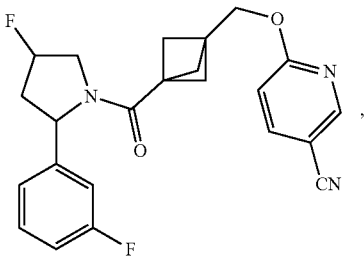,
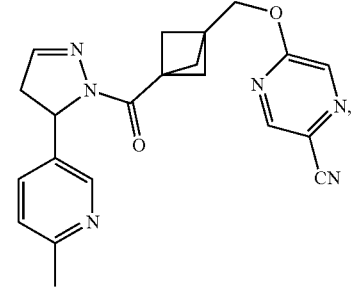,
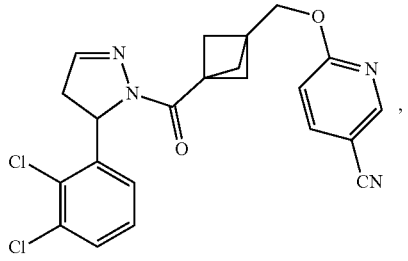,

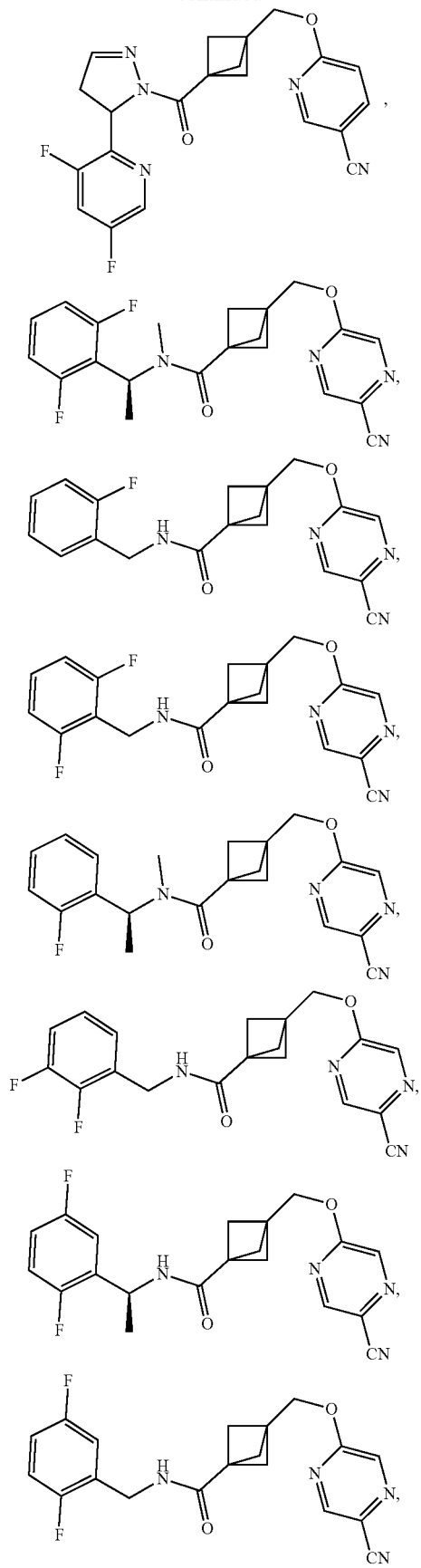
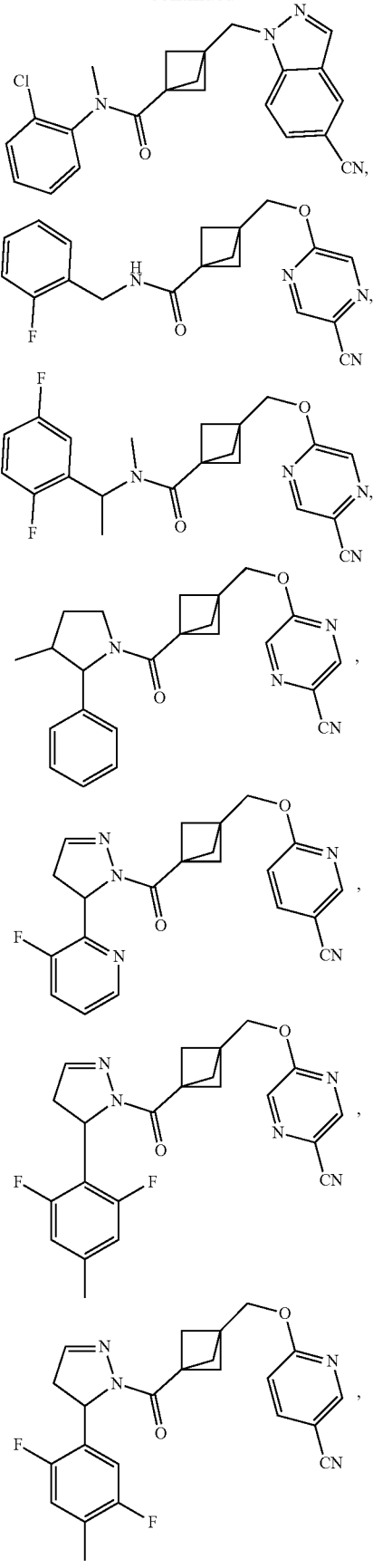

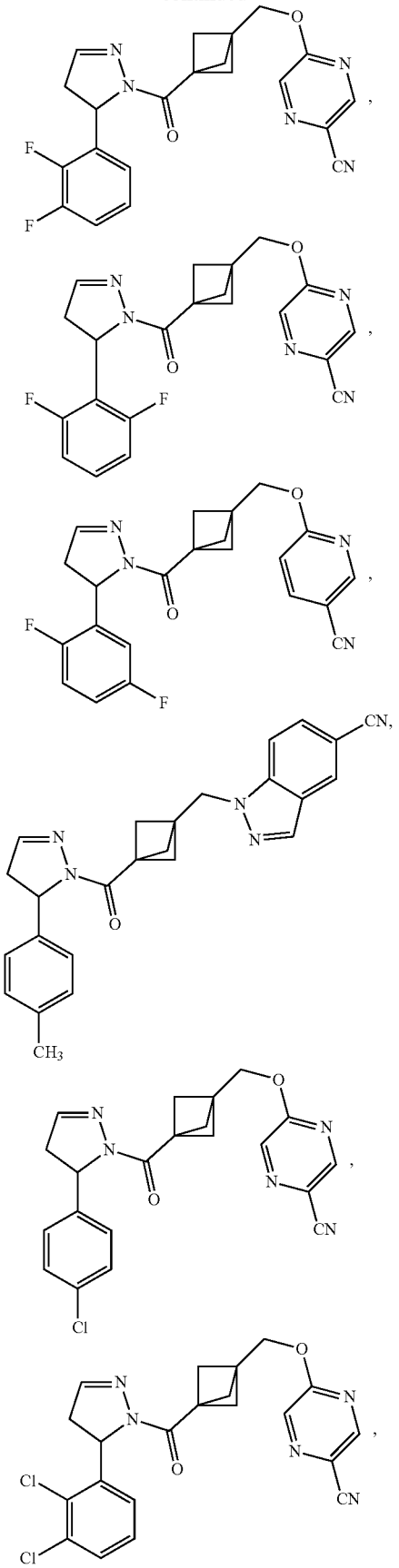 [SMILES: N#Cc1cnc(OCC23CC(C(=O)N4N=CCC4c4cccc(F)c4F)(C2)C3)cn1 ; N#Cc1cnc(OCC23CC(C(=O)N4N=CCC4c4c(F)cccc4F)(C2)C3)cn1 ; N#Cc1ccc(OCC23CC(C(=O)N4N=CCC4c4cc(F)ccc4F)(C2)C3)nc1 ; Cc1ccc(C2CC=NN2C(=O)C23CC(Cn4ncc5cc(C#N)ccc54)(C2)C3)cc1 ; N#Cc1cnc(OCC23CC(C(=O)N4N=CCC4c4ccc(Cl)cc4)(C2)C3)cn1 ; N#Cc1cnc(OCC23CC(C(=O)N4N=CCC4c4cccc(Cl)c4Cl)(C2)C3)cn1]
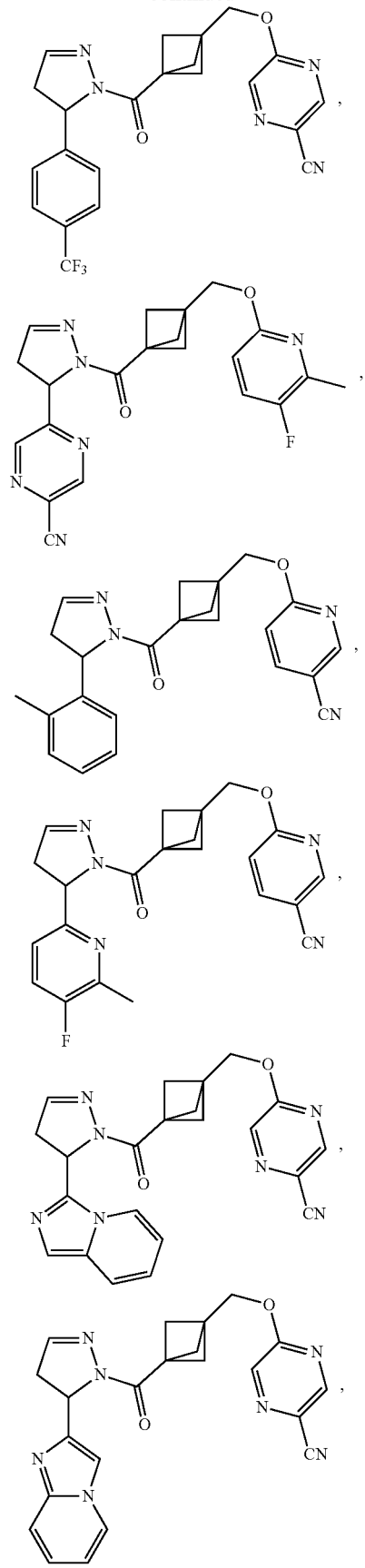

85
-continued
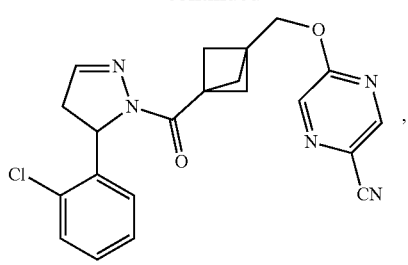,
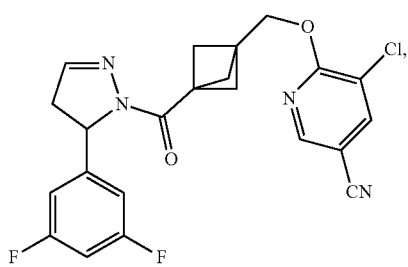
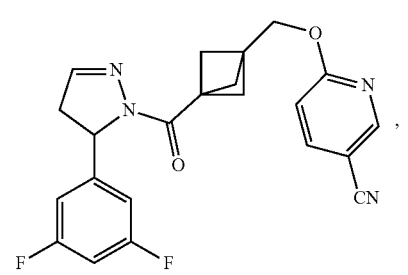,
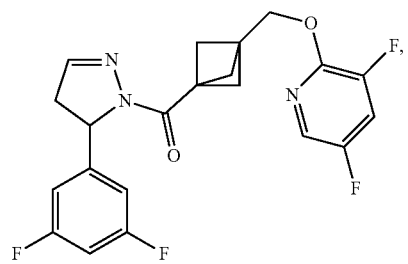
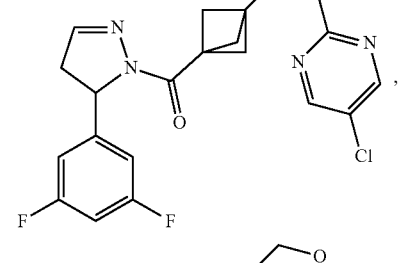,
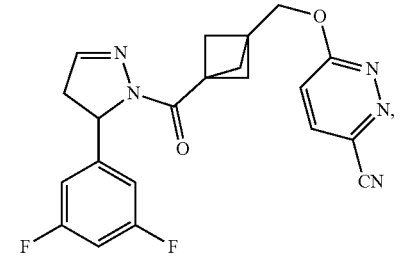
86
-continued
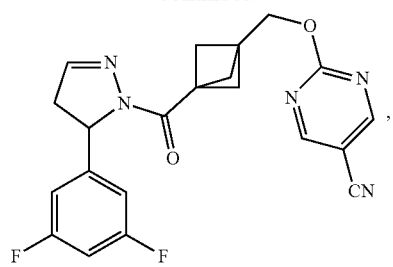,
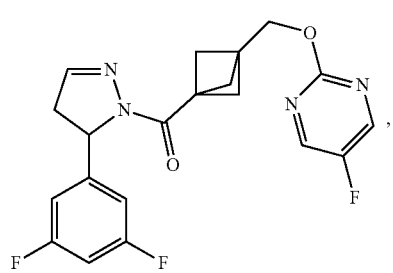,
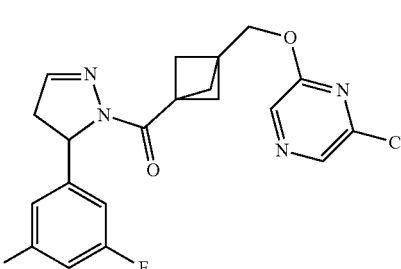
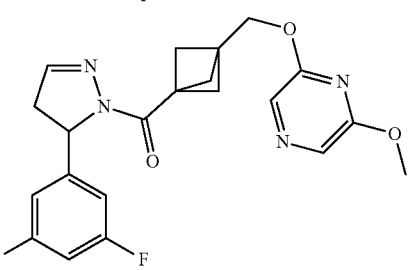,
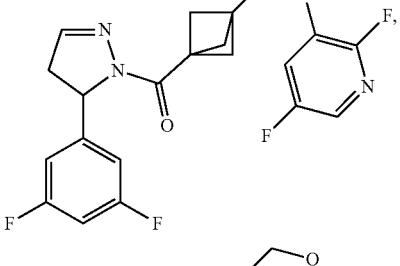,
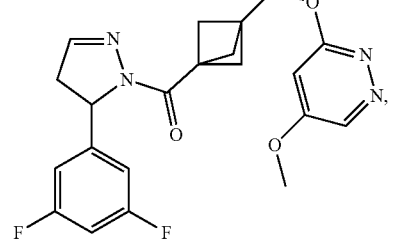, 87
-continued
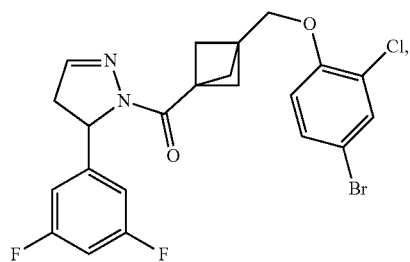
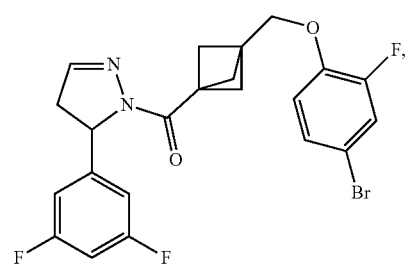
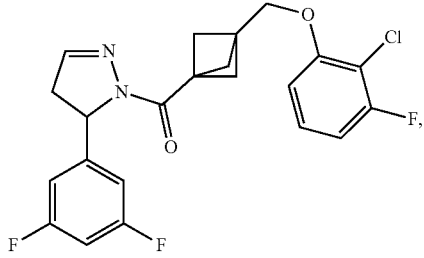
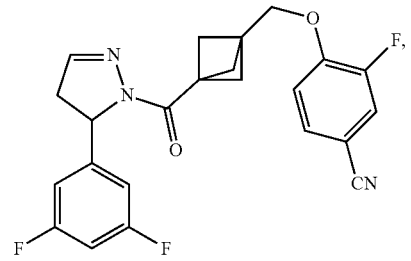
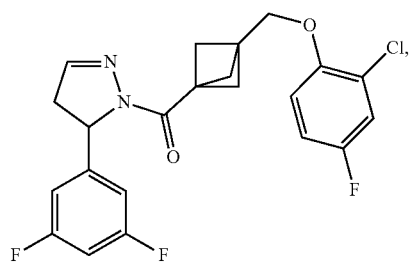
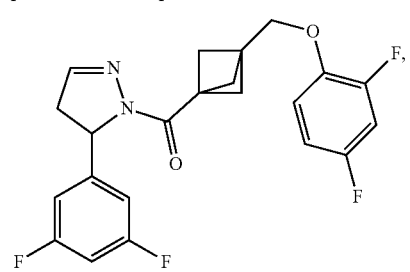
88
-continued
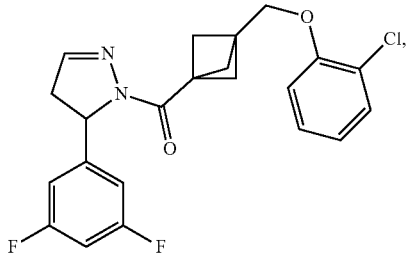
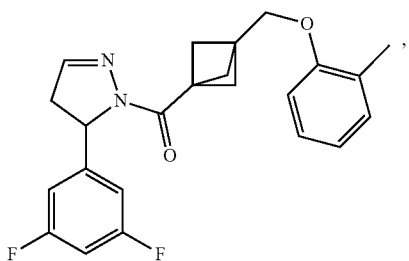
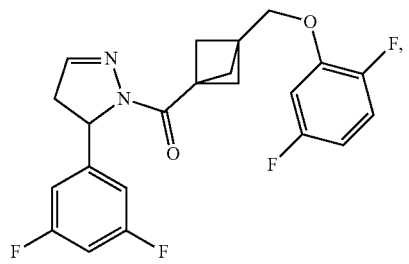
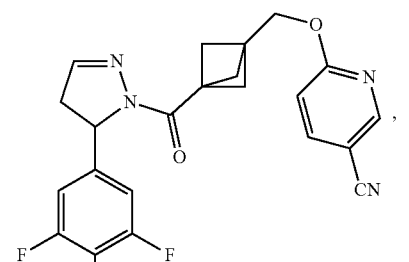
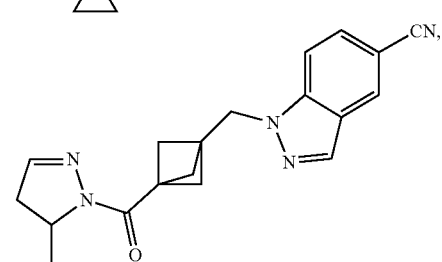
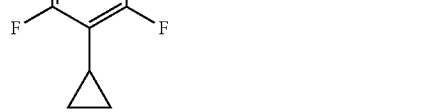

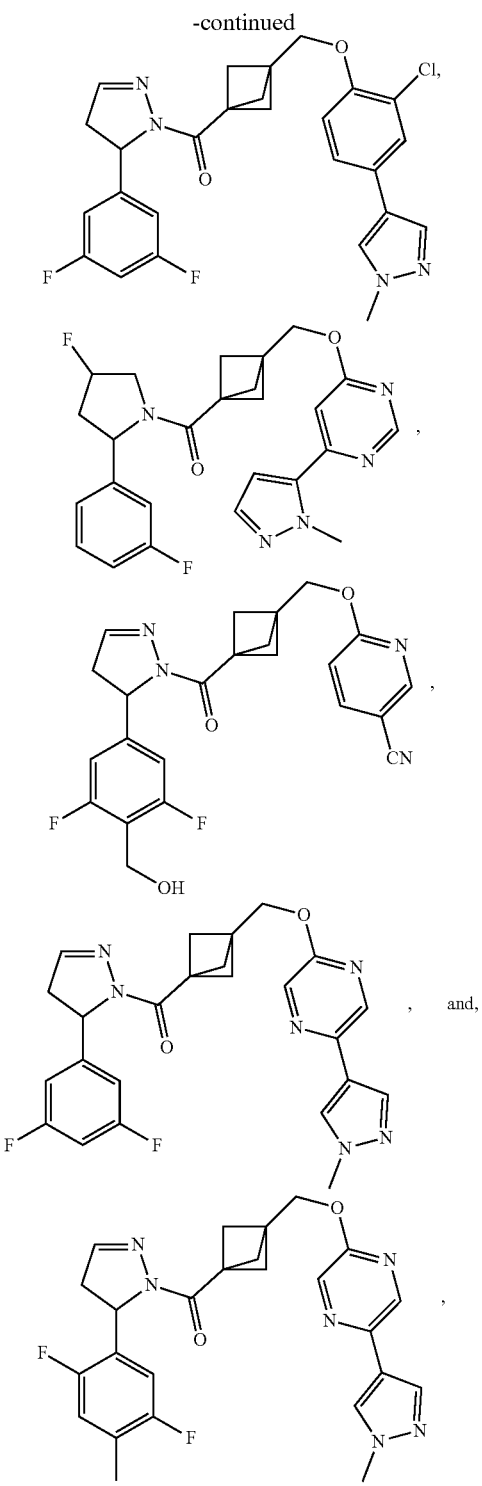

or a salt thereof.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

Also provided are methods of inhibiting at least one RIPK1 function comprising the step of contacting RIPK1 with a compound as described herein. The cell phenotype, cell proliferation, activity of RIPK1, change in biochemical output produced by active RIPK1, expression of RIPK1, or binding of RIPK1 with a natural binding partner may be monitored. Such methods may be modes of treatment of disease, biological assays, cellular assays, biochemical assays, or the like.

Also provided herein are methods of treatment of a RIPK1-mediated disease comprising the administration of a therapeutically effective amount of a compound as disclosed herein, or a salt thereof, to a patient in need thereof.

In certain embodiments, the disease is chosen from neurodegenerative disorders, inflammatory disorders, and cancer.

In certain embodiments, the disease is cancer. In certain embodiments, the cancer is treated by promoting an appropriate immune response to the tumor. In certain embodiments, the appropriate immune response to the tumor comprises, or results in, one or more of the following: an increase in the number or activity, or degree of tumor infiltration, of cytotoxic T-lymphocytes and/or natural killer cells;

an increase in the number or activity of M1 macrophages in the tumor microenvironment and/or a decrease in the in the number or activity of M2 macrophages in the tumor microenvironment;

a decrease in the number or activity of regulatory T cells; and a decrease in the number or activity of myeloid-derived suppressor cells.

Also provided herein is a compound as disclosed herein for use as a medicament.

Also provided herein is a compound as disclosed herein for use as a medicament for the treatment of a RIPK1-mediated disease.

Also provided is the use of a compound as disclosed herein as a medicament.

Also provided is the use of a compound as disclosed herein as a medicament for the treatment of a RIPK1-mediated disease.

Also provided is a compound as disclosed herein for use in the manufacture of a medicament for the treatment of a RIPK1-mediated disease.

Also provided is the use of a compound as disclosed herein for the treatment of a RIPK1-mediated disease.

Also provided herein is a method of inhibition of RIPK1 comprising contacting RIPK1 with a compound as disclosed herein, or a salt thereof.

Also provided herein is a method for achieving an effect in a patient comprising the administration of a therapeutically effective amount of a compound as disclosed herein, or a salt thereof, to a patient wherein the effect is chosen from cognition enhancement.

Also provided is a method of modulation of a RIPK1-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral administration.

In certain embodiments, the oral pharmaceutical composition is chosen from a tablet and a capsule.

Definitions

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups are optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like.

The term "alkylene," as used herein, alone or in combination, refers to a straight chain saturated or unsaturated hydrocarbon attached at two positions, such as methylene (—CH$_2$—), ethylene (—CH$_2$CH$_2$—), and propylene (—CH$_2$CH$_2$CH$_2$—). "Alkylene" thus consists of units chosen from —CH$_2$— and —CH=. Representative alkylenes include —CH$_2$—, —CH$_2$CH$_2$—, —CH=CH—, —CH$_2$CH$_2$CH$_2$—, —CH$_2$CH=CH—, and —CH=CH—CH=CH—. Alkylenes can be characterized by the count of atoms in the chain; thus, the representative alkylenes have 1, 2, 2, 3, 3, and 4 atoms, respectively.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, when alone, refer to an amino group as described below attached to the parent molecular moiety through a carbonyl group, or vice versa. The terms "amido" and "carbamoyl," as used herein, when in combination, refer to either of —C(O)NH— and —NHC(O)—. The term "C-amido" as used herein, alone or in combination, refers to a —C(O)N (RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino (CH$_3$C(O)NH—).

The term "amino," as used herein, alone or in combination, refers to —NRR' wherein R and R are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which is optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4=$ derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which is optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. In certain embodiments, said cycloalkyl will comprise a spirocycle ring system. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo[3.2.1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and one, two, or three heteroatoms chosen from N, O, and S, and wherein the N and S atoms may optionally be oxidized and the N heteroatom may optionally be quaternized. The heteroatom(s) may be placed at any interior position of the heteroalkyl group. Up to two heteroatoms may be consecutive, such as, for example, —CH$_2$—NH—OCH$_3$.

The term "heteroalkylene," as used herein, alone or in combination, refers to an alkylene in which either one or both of the following hold: (a) one or more —CH$_2$— groups is substituted with —NH— groups, and/or (b) one or more —CH= groups is substituted with —N= groups. Representative heteroalkylenes include —CH$_2$NH—, —CH=NH—, —NHCH$_2$CH$_2$—, —CH$_2$NHCH$_2$—, —NHCH=CH—, —NHCH$_2$CH$_2$CH$_2$—, —CH=CH—N=CH, and —CH=CH—CH=N—. As with alkylenes, heteroalkylenes can be characterized by the count of atoms in the chain; thus, the representative alkylenes have 2, 2, 3, 3, 3, 4, 4, and 4 atoms, respectively.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings wherein heteroaryl rings are fused with other heteroaryl rings wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridinyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member wherein each said heteroatom may be independently chosen from nitrogen, oxygen, and sulfur. In certain embodiments, said heterocycloalkyl will comprise a spirocycle ring system. In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-h]pyridinyl, benzothiazolyl, dihydroindolyl, dihy-dropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups is optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently chosen from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which is optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR' wherein R and R' are independently chosen from hydrogen and lower alkyl, either of which is optionally substituted.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "spirocycle ring system" refers to a polycyclic ring system comprising two rings such that a single atom is common to both rings.

The terms "sulfonate," "sulfonic acid," and "sulfonic," as used herein, alone or in combination, refer the —$SO_3H$ group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently chosen from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which is optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

A "cognitive disorder," as used herein refers to a mental health disorder in which loss of cognitive function is the primary symptom, and which primarily affects learning, memory, perception, and/or problem solving. Cognitive disorders include amnesia, dementia, and delirium. Causes may include damage to the memory portions of the brain, whether from trauma or chemotherapy.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"RIPK1 binder" is used herein to refer to a compound that exhibits an $K_d$ with respect to RIPK1 of no more than about 100 μM and more typically not more than about 50 μM, as measured in the RIPK1 binding assay described generally herein. The RIPK1 binding assay measures the $K_d$ (dissociation constant) for the binding of a compound with the active site of RIPK1. Certain compounds disclosed herein have been discovered to bind to RIPK1. In certain embodiments, compounds will exhibit an $K_d$ with respect to RIPK1 of no more than about 10 μM; in further embodiments, compounds will exhibit a $K_d$ with respect to RIPK1 of no more than about 1 μM; in yet further embodiments, compounds will exhibit a $K_d$ with respect to RIPK1 of not more than about 0.1 μM; in yet further embodiments, compounds will exhibit a $K_d$ with respect to RIPK1 of not more than about 10 nM, as measured in the RIPK1 assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound.

Salts and Polymorphs

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

Formulations

The formulations include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhaler or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Administration and Treatment

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for diabetes involving administration of one of the compounds described herein, increased therapeutic benefit may result by also providing the patient with another therapeutic agent for diabetes. In any case, regardless of the disease, disorder or condition being treated, the overall benefit experienced by the patient may simply be additive of the two therapeutic agents or the patient may experience a synergistic benefit.

Specific, non-limiting examples of possible combination therapies include use of certain compounds of the invention with: donepezil, rivastigmine, galantamine, and memantine. Further examples include anti-amyloid antibodies and vaccines, anti-Ab antibodies and vaccines, anti-tau antibodies and vaccines, β-secretase inhibitors, 5-HT4 agonists, 5-HT6 antagonists, 5-HT1a antagonists, α7 nicotinic receptor agonists, 5-HT3 receptor antagonists, PDE4 inhibitors, O-glycnacase inhibitors, and other medicines approved for the treatment of Alzheimer's disease. Further examples include metformin, minocycline, tissue plasminogen activator, and other therapies that improve neuronal survival.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating RIPK1-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of RIPK1-mediated disorders.

In a related aspect, certain embodiments provide methods for the treatment of cancer that comprise the coadministration of another therapeutic agent. In some embodiments, the other therapeutic agent is a checkpoint inhibitor. In some embodiments, the other therapeutic agent is chosen from an anti-PD1 inhibitor, an anti-PDL1 inhibitor, an anti-CTLA4 inhibitor, an anti-OX50 inhibitor, an anti-TIM3 inhibitor, and an anti-LAG3 inhibitor.

For use in cancer and neoplastic diseases a RIPK1 inhibitor may be optimally used together with one or more of the following non-limiting examples of anti-cancer agents:

1) inhibitors or modulators of a protein involved in one or more of the DNA damage repair (DDR) pathways such as:
   a. PARP1/2, including, but not limited to: olaparib, niraparib, rucaparib;
   b. checkpoint kinase 1 (CHK1), including, but not limited to: UCN-01, AZD7762, PF477736, SCH900776, MK-8776, LY2603618, V158411, and EXEL-9844;
   c. checkpoint kinase 2 (CHK2), including, but not limited to: PV1019, NSC 109555, and VRX0466617;
   d. dual CHK1/CHK2, including, but not limited to: XL-844, AZD7762, and PF-473336;
   e. WEE1, including, but not limited to: MK-1775 and PD0166285;
   f. ATM, including, but not limited to KU-55933,
   g. DNA-dependent protein kinase, including, but not limited to NU7441 and M3814; and
   h. Additional proteins involved in DDR;
2) Inhibitors or modulators of one or more immune checkpoints, including, but not limited to:
   a. PD-1 inhibitors such as nivolumab (OPDIVO), pembrolizumab (KEYTRUDA), pidilizumab (CT-011), and AMP-224 (AMPLIMMUNE);
   b. PD-L1 inhibitors such as Atezolizumab (TECENTRIQ), Avelumab (Bavencio), Durvalumab (Imfinzi), MPDL3280A (Tecentriq), BMS-936559, and MEDI4736;
   c. anti-CTLA-4 antibodies such as ipilimumab (YERVOY) and CP-675,206 (TREMELIMUMAB);
   d. inhibitors of T-cell immunoglobulin and mucin domain 3 (Tim-3);
   e. inhibitors of V-domain Ig suppressor of T cell activation (Vista);
   f. inhibitors of band T lymphocyte attenuator (BTLA);
   g. inhibitors of lymphocyte activation gene 3 (LAG3); and
   h. inhibitors of T cell immunoglobulin and immunoreceptor tyrosine-based inhibitory motif domain (TIGIT);
3) telomerase inhibitors or telomeric DNA binding compounds;
4) alkylating agents, including, but not limited to: chlorambucil (LEUKERAN), oxaliplatin (ELOXATIN), streptozocin (ZANOSAR), dacarbazine, ifosfamide, lomustine (CCNU), procarbazine (MATULAN), temozolomide (TEMODAR), and thiotepa;
5) DNA crosslinking agents, including, but not limited to: carmustine, chlorambucil (LEUKERAN), carboplatin (PARAPLATIN), cisplatin (PLATIN), busulfan (MYLERAN), melphalan (ALKERAN), mitomycin (MITOSOL), and cyclophosphamide (ENDOXAN);
6) anti-metabolites, including, but not limited to: cladribine (LEUSTATIN), cytarbine, (ARA-C), mercaptopurine (PURINETHOL), thioguanine, pentostatin (NIPENT), cytosine arabinoside (cytarabine, ARA-C), gemcitabine (GEMZAR), fluorouracil (5-FU, CARAC), capecitabine (XELODA), leucovorin (FUSILEV), methotrexate (RHEUMATREX), and raltitrexed;
7) antimitotic, which are often plant alkaloids and terpenoids, or derivatives thereof including but not limited to: taxanes such as docetaxel (TAXITERE), paclitaxel (ABRAXANE, TAXOL), vinca alkaloids such as vincristine (ONCOVIN), vinblastine, vindesine, and vinorelbine (NAVELBINE);
8) topoisomerase inhibitors, including, but not limited to: amacrine, camptothecin (CTP), genistein, irinotecan (CAMPTOSAR), topotecan (HYCAMTIN), doxorubicin (ADRIAMYCIN), daunorubicin (CERUBIDINE), epirubicin (ELLENCE), ICRF-193, teniposide (VTJ-MON), mitoxantrone (NOVANTRONE), and etoposide (EPOSIN);
9) DNA replication inhibitors, including, but not limited to: fludarabine (FLUDARA), aphidicolin, ganciclovir, and cidofovir;
10) ribonucleoside diphosphate reductase inhibitors, including, but not limited to: hydroxyurea;
11) transcription inhibitors, including, but not limited to: actinomycin D (dactinomycin, COSMEGEN) and plicamycin (mithramycin);
12) DNA cleaving agents, including, but not limited to: bleomycin (BLENOXANE), idarubicin,
13) cytotoxic antibiotics, including, but not limited to: actinomycin D (dactinomycin, COSMEGEN),
14) aromatase inhibitors, including, but not limited to: aminoglutethimide, anastrozole (ARIMIDEX), letrozole (FEMARA), vorozole (RIVIZOR), and exemestane (AROMASIN);
15) angiogenesis inhibitors, including, but not limited to: genistein, sunitinib (SUTENT), and bevacizumab (AVASTIN);
16) anti-steroids and anti-androgens, including, but not limited to: aminoglutethimide (CYTADREN), bicalutamide (CASODEX), cyproterone, flutamide (EULEXIN), nilutamide (NILANDRON);

17) tyrosine kinase inhibitors, including, but not limited to: imatinib (GLEEVEC), erlotinib (TARCEVA), lapatininb (TYKERB), sorafenib (NEXAVAR), and axitinib (INLYTA);
18) mTOR inhibitors, including, but not limited to: everolimus, temsirolimus (TORISEL), and sirolimus;
19) monoclonal antibodies, including, but not limited to: trastuzumab (HERCEPTIN) and rituximab (RITUXAN);
20) apoptosis inducers such as cordycepin;
21) protein synthesis inhibitors, including, but not limited to: clindamycin, chloramphenicol, streptomycin, anisomycin, and cycloheximide;
22) antidiabetics, including, but not limited to: metformin and phenformin;
23) antibiotics, including, but not limited to:
    a. tetracyclines, including, but not limited to: doxycydine;
    b. erythromycins, including, but not limited to: azithromycin;
    c. glycylglycines, including, but not limited to: tigecycline;
    d. antiphrastic, including, but not limited to: pyrvinium pamoate;
    e. beta-lactams, including, but not limited to the penicillins and cephalosporins;
    f. anthracycline antibiotics, including, but not limited to: daunorubicin and doxorubicin;
    g. other antibiotics, including, but not limited to: chloramphenicol, mitomycin C, and actinomycin;
24) antibody therapeutic agents, including, but not limited to: muromonab-CD3, infliximab (REMICADE), adalimumab (HUMIRA), omalizumab (XOLAIR), daclizumab (ZENAPAX), rituximab (RITUXAN), ibritumomab (ZEVALIN), tositumomab (BEXXAR), cetuximab (ERBITUX), trastuzumab (HERCEPTIN), ADCETRIS, alemtuzumab (CAMPATH-1H), Lym-1 (ONCOLYM), ipilimumab (YERVOY), vitaxin, bevacizumab (AVASTIN), and abciximab (REOPRO); and
25) other agents, such as *Bacillus* Calmette-Guérin (B-C-G) vaccine; buserelin (ETILAMIDE); chloroquine (ARALEN); clodronate, pamidronate, and other bisphosphonates; colchicine; demethoxyviridin; dichloroacetate; estramustine; filgrastim (NEUPOGEN); fludrocortisone (FLORINEF); goserelin (ZOLADEX); interferon; leucovorin; leuprolide (LUPRON); levamisole; lonidamine; mesna; metformin; mitotane (o,p'-DDD, LYSODREN); nocodazole; octreotide (SANDOSTATIN); perifosine; porfimer (particularly in combination with photo- and radiotherapy); suramin; tamoxifen; titanocene dichloride; tretinoin; anabolic steroids such as fluoxymesterone (HALOTESTIN); estrogens such as estradiol, diethylstilbestrol (DES), and dienestrol; progestins such as medroxyprogesterone acetate (MPA) and megestrol; and testosterone.

In certain embodiments, the compounds, compositions, and methods disclosed herein may be useful for the treatment of a disorder associated with an inflammatory component of cellular stress. In certain embodiments, the disorder is chosen from multiple sclerosis, Neimanm-Pick disease, Alzheimers disease, Parkinson's disease, amyotrophic lateral sclerosis, Lewy body dementia, frontotemporal dementia, glutamine expansion diseases such as Huntington's disease, Kennedy's disease, and spinocerebellar ataxia In certain embodiments, the compounds, compositions, and methods disclosed herein may be useful for the treatment of neuropathy. In certain embodiments, the neuropathy is chosen from diabetic neuropathy and chemotherapy induced neuropathy.

In certain embodiments, the compounds, compositions, and methods disclosed herein may be useful for the treatment of a retinal disease. In certain embodiments, the retinal disease is chosen from macular degeneration and retinitis.

In certain embodiments, the compounds, compositions, and methods disclosed herein may be useful for the treatment of an injury to the CNS. In certain embodiments, the injury is chosen from a traumatic brain injury and stroke.

In certain embodiments, the compounds, compositions, and methods disclosed herein may be useful for the treatment of an autoimmune disorder. In certain embodiments, the autoimmune disorder is chosen from ulcerative colitis, rheumatoid arthritis, psoriasis, lupus, inflammatory bowel disease.

In certain embodiments, the compounds, compositions, and methods disclosed herein may be useful for the treatment of viral infections.

In certain embodiments, the compounds, compositions, and methods disclosed herein may be useful for the treatment of sepsis.

In certain embodiments, the compounds, compositions, and methods disclosed herein may be useful for the treatment of retinal degeneration.

In certain embodiments, the compounds, compositions, and methods disclosed herein may be useful for the treatment of ischemic stroke.

In certain embodiments, the compounds, compositions, and methods disclosed herein may be useful for the treatment of intracerebral hemorrhage.

In certain embodiments, the compounds, compositions, and methods disclosed herein may be useful for the treatment of amyotrophic lateral sclerosis.

In certain embodiments, the compounds, compositions, and methods disclosed herein may be useful for the treatment of an acute kidney injury.

In certain embodiments, the compounds, compositions, and methods disclosed herein may be useful for the treatment of a myocardial reperfusion injury.

In certain embodiments, the compounds, compositions, and methods disclosed herein may be useful for the treatment of Alzheimer's disease.

In certain embodiments, the compounds, compositions, and methods disclosed herein may be useful for the treatment of ulcerative colitis.

In certain embodiments, the compounds, compositions, and methods disclosed herein may be useful for the treatment of osteoarthritis.

In certain embodiments, the compounds, compositions, and methods disclosed herein may be coadministered with another therapeutic agent.

Besides being useful for human treatment, certain compounds and formulations disclosed herein may also be useful for veterinary treatment of companion animals, exotic animals and farm animals, including mammals, rodents, and the like. More preferred animals include horses, dogs, and cats.

List of Abbreviations $Ac_2O$=acetic anhydride; AcCl=acetyl chloride; AcOH=acetic acid; AIBN=azobisisobutyronitrile; aq.=aqueous; BAST=bis(2-methoxyethyl)aminosulfur trifluoride; Bu=butyl; $Bu_3SnH$=tributyltin hydride;

CD₃OD=deuterated methanol; CDCl₃=deuterated chloroform; CDI=1,1'-carbonyldiimidazole; DAST=(diethylamino)sulfur trifluoride; dba=dibenzylideneacetone DBU=1,8-diazabicyclo[5.4.0]undec-7-ene; DCM=dichloromethane; DEAD=diethyl azodicarboxylate; DtBAD=di-t-butyl azodicarboxylate; DIBAL-H=di-isobutyl aluminium hydride; DIEA=DIPEA=N,N-diisopropylethylamine; DMAP=4-dimethylaminopyridine; DMF=N,N-dimethylformamide; DMSO-d₆=deuterated dimethyl sulfoxide; DMSO=dimethyl sulfoxide; DPPA=diphenylphosphoryl azide; dppf=1,1'-bis(diphenylphosphino)ferrocene; EDC.HCl=EDCl.HCl=1-ethyl-3-(3-dimethylaminopropyl)carbodiimide hydrochloride; Et=ethyl; Et₂O=diethyl ether; EtOAc=ethyl acetate; EtOH=ethanol; h=hour; HATU=2-(1H-7-azabenzotriazol-1-yl)-1,1,3,3-tetramethyl uranium hexafluorophosphate methanaminium; HMDS=hexamethyldisilazane; HOBT=1-hydroxybenzotriazole; iPr=i-Pr=isopropyl=2-propyl; iPrOH=i-PrOH=isopropanol; LAH=lithium aluminiumhydride; LDA=lithium diisopropyl amide; LiHMDS=Lithium bis(trimethylsilyl)amide; MeCN=acetonitrile; MeI=methyl iodide; MeOH=methanol; MP-carbonate resin=macroporous triethylammonium methylpolystyrene carbonate resin; MsCl=mesyl chloride; MTBE=methyl tert-butyl ether; n-BuLi=n-butyllithium; NaHMDS=Sodium bis(trimethylsilyl)amide; NaOEt=sodium ethoxide; NaOMe=sodium methoxide; NaOtBu=sodium t-butoxide; NBS=N-bromosuccinimide; NCS=N-chlorosuccinimide; NIS=N-iodosuccinimide; NMP=N-Methyl-2-pyrrolidone; Pd(Ph₃)₄=tetrakis(triphenylphosphine)palladium(O); Pd₂(dba)₃=tris(dibenzylideneacetone)dipalladium(O); PdCl₂(PPh₃)₂=bis(triphenylphosphine)palladium(II) dichloride; PG=protecting group; Ph=phenyl; prep-HPLC=preparative high-performance liquid chromatography; PMBCl=para-methoxybenzyl; PMBCl=para-methoxybenzyl chloride; PMBOH=para-methoxybenzyl alcohol; PyBop=(benzotriazol-1-yloxy)tripyrrolidinophosphonium hexafluorophosphate; Pyr=pyridine; RT=room temperature; RuPhos=2-dicyclohexylphosphino-2',6'-diisopropoxybiphenyl; sat.=saturated; ss=saturated solution; tBu=t-Bu=tert-butyl=1,1-dimethylethyl; TBAF=tetrabutylammonium fluoride; TBDPS=t-butyldiphenylsilyl; t-BuOH=tBuOH=tert-butanol; T₃P=Propylphosphonic Anhydride; TEA=Et₃N=triethylamine; TFA=trifluoroacetic acid; TFAA=trifluoroacetic anhydride; THF=tetrahydrofuran; TIPS=triisopropylsilyl; Tol=toluene; TsCl=tosyl chloride; Trt=trityl=(triphenyl)methyl; Xantphos=4,5-Bis(diphenylphosphino)-9,9-dimethylxanthene; XPhos=2-dicyclohexylphosphino-2',4',6'-triisopropylbiphenyl.

General Synthetic Methods for Preparing Compounds

The following schemes can be used to practice the present invention.

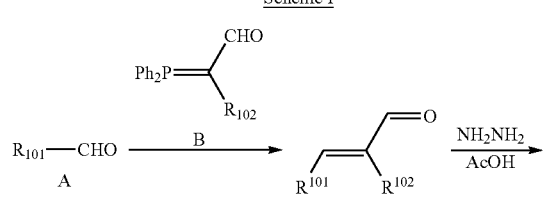

Scheme I

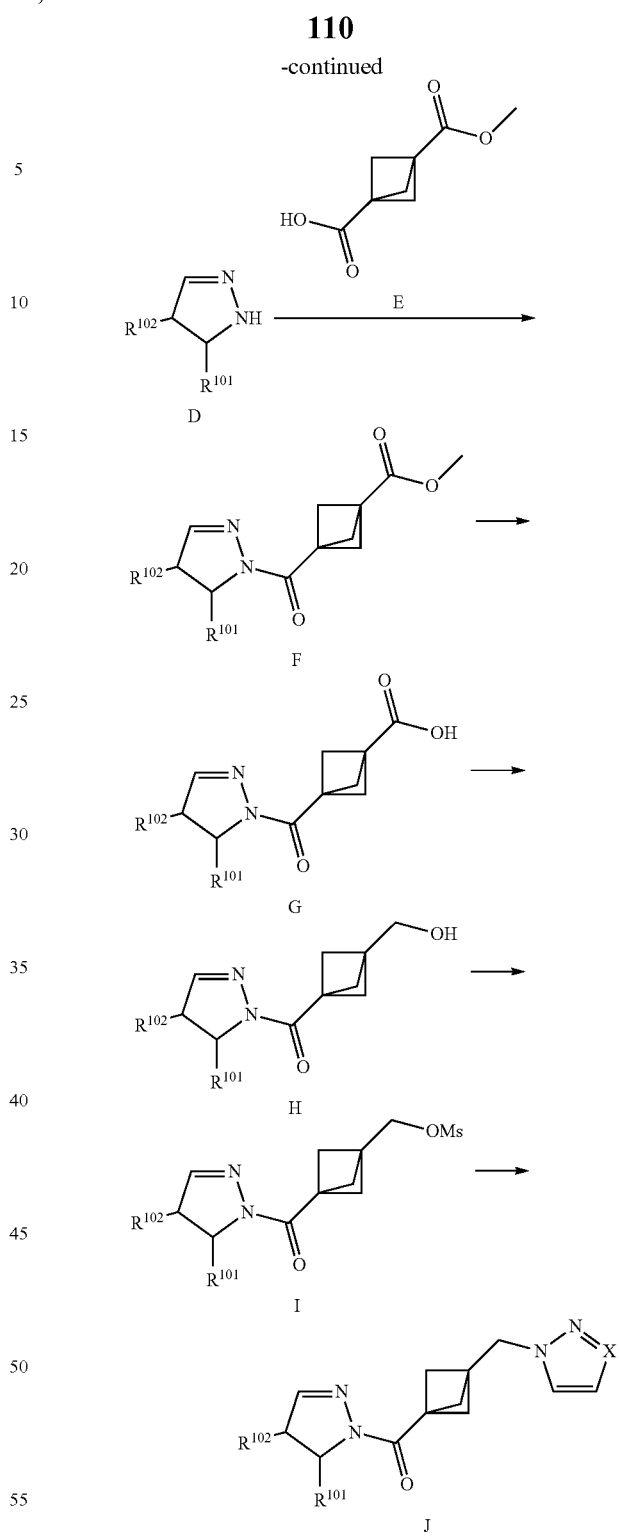

Certain examples disclosed herein can be synthesized by using the general synthetic procedure set forth in Scheme I.

The starting aldehyde (A) can be functionalized to acrolein derivative (C) through a Wittig type of reaction with a phosphorane reagent such as 2-(triphenyl-λ⁵-phosphaneylidene)acetaldehyde (B). Alternatively, the unsaturated carbonyl compounds can also be synthesized from (A) by an aldol condensation with an acetal aldehyde (not shown). In addition compounds such as (C) can be made through various transformations known to one skilled in the art and that are prevalent in the literature, including but not limited to modifications of aryl halides with alkene borane species via a Suzuki type reaction or with an alkene species via a Heck type reaction, any of which can be followed by subsequent modifications if necessary.

The unsaturated carbonyl intermediate (C) can be cyclized with hydrazine (neat, hydrate, or solution) in protic or aprotic solvents, with or without an acid such as acetic acid, and with or without heat or cooling, to form pyrazoline compound (D), also referred to as a dihydropyrazole.

The pyrazoline (D) can undergo coupling reactions with carboxylic acids such as 3-(methoxycarbonyl)bicyclo[1.1.1]pentane-1-carboxylic acid (E) using various coupling conditions like HATU or T₃P, or via the corresponding acid chloride (not shown, available via reaction with, e.g. (COCl)₂ or SOCl₂), to form amide (F).

Compound (F) may be a final compound, or may contain an orthogonally protected or functionalized moiety for further modification. For example, hydrolysis affords the carboxylic acid (G) which can be reduced to the alcohol (H), using standard conditions such as basic hydrolysis with LiOH and reduction with THF-Borane, respectively.

Compound (H) may be a final compound or may contain an orthogonally protected or functionalized moiety for further modification. For example, the primary alcohol of (H) can be converted to a leaving group with a sulfonyl chloride like mesyl or tosyl chloride. Not depicted in scheme 1 but very similarity, the alcohol of compound (H) can also be converted to a halide, such as a bromide directly, with Appel like reaction conditions using triphenyl phosphine (free or resin bound) and a bromine source like tetrabromomethane, and this alkyl bromide will be expected to react similarly as mesylate (I) or tosylate (not shown). In addition, the alcohol of compound (H) can be converted to the chloride or the fluoride using means known to those trained in the art.

Compound (I) can be subjected to nucleophilic substitution conditions, in solvents such as DMF, in the presence of bases such as Cs₂CO₃, to form products such as the N-substituted pyrazole (J), In addition, other substitution products can be made from amines, cyanides, azides, hydrazines, hydrazones, amidines, alcohols and other heterocycles not excluding or limiting to imidazoles, indazoles, benzimidazoles, benzotriazoles. By subsequent reactions of these products, such as azides and nitriles, further compounds, including but but not limited to pyrazoles, pyrimidines, triazoles and oxadiazoles may be obtained. Compound (I) can also be converted to compounds similar to compound (J) through nucleophilic substitutions, with other bases such as NaH and LiHMDS in solvents like THF or NMP.

Scheme II

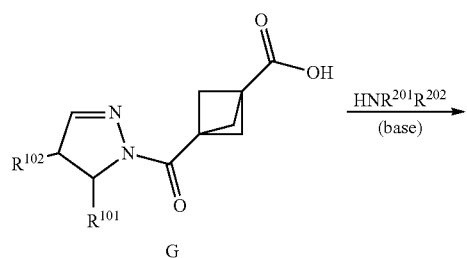

G $HNR^{201}R^{202}$
(base)

-continued

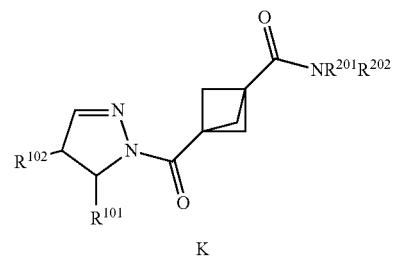

K

As shown in Scheme II, compound (G) can be coupled with amines via procedures disclosed in Scheme I for transformation of compound (D) to (F), or with a similar procedure known in the art, affording amide (K).

Scheme III

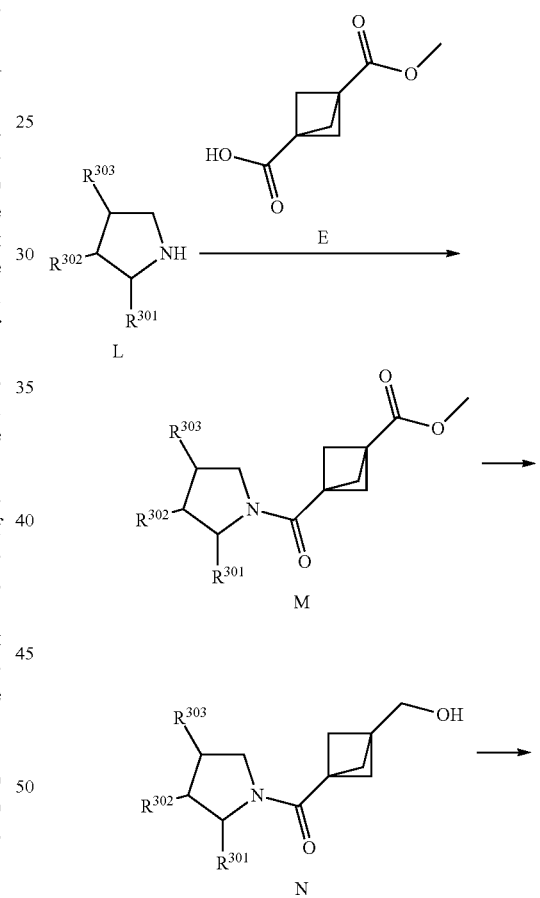

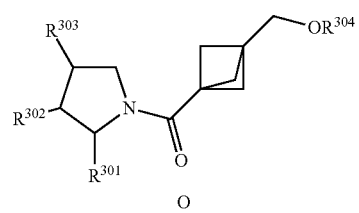

As shown in Scheme III, pyrrolidine compounds can be obtained through a reaction sequence similar to that disclosed in Scheme I. Pyrrolidine (L) can be coupled with carboxylic acids such as (E) via procedures disclosed in Scheme 1 for transformation of compound (D) to (F), or with a similar procedure known in the art, affording amide (M). The ester functionality of (M) can be reduced to alcohol (N), either directly or through the carboxylic acid (not shown), using reagents such as LiBH$_4$. Finally, primary alcohol (N) can be transformed via a displacement reaction to yield coupled product (O). Possible manipulations include but are not limited to: Mitsunobu coupling, nucleophilic aliphatic substitution and nucleophilic aromatic substitution of the alcohol, and nucleophilic aliphatic substitution of, e.g, a corresponding halide or sulfonate ester of the alcohol.

DAST being one of several examples. Other manipulations of the secondary alcohol of (Q) are well established in the art.

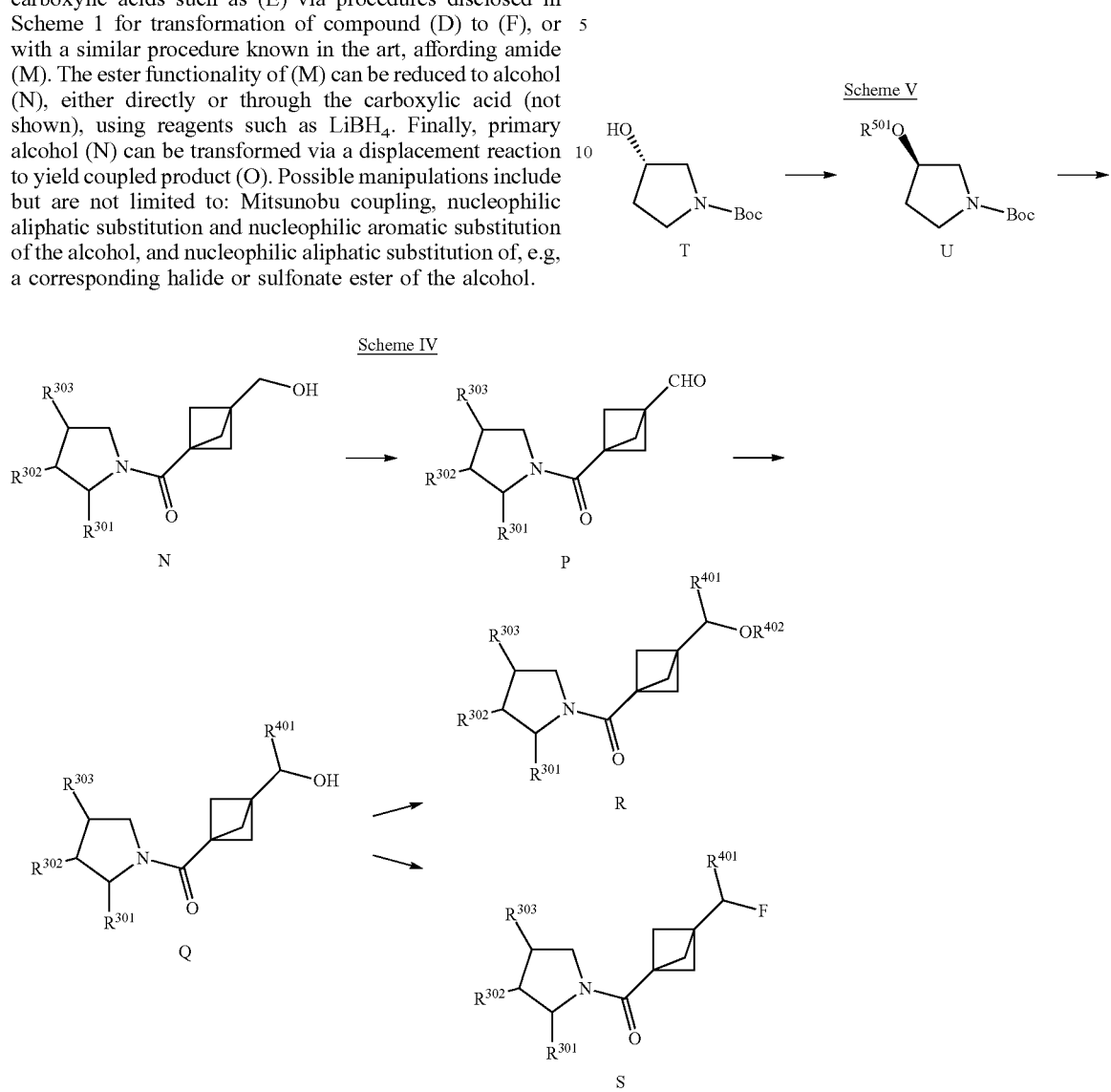

Compound (N) can be additionally modified as disclosed in scheme IV. In this instance the primary alcohol can be oxidized to provide aldehyde (P) with reactions and reagents common to the art, such as a Swern oxidation.

Compound (O) can be transformed further depending on orthogonal functional groups within the molecule. For example, as disclosed in this scheme, the aldehyde can be transformed to the alcohol (Q) through known reactions of the art, including but not limited to reaction with a Grignard reagent such as CH$_3$MgBr or PhMgBr.

Compound (Q) can be a final compound or can be transformed further depending on orthogonal functional groups within the molecule and, as in this scheme, can be transformed to the ether compound (R) through known reactions of the art and in the literature as as described in schemes I, II, and III.

Alternatively, compound (Q) can be converted to the fluoride using known reagents to the art and in the literature, -continued

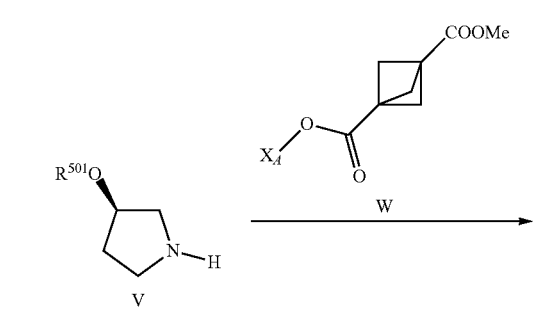

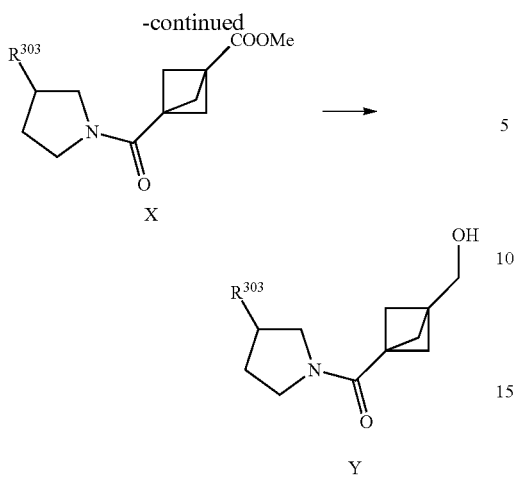

Certain compounds disclosed herein can be synthesized by using the general synthetic procedure set forth in Scheme V. Protected hydroxypyrrolidine T can be substituted using Mitsunobu chemistry to yield ether U. Deprotection provides secondary amine V, which can be coupled with activated ester W ($X_A$=activating group such as succinimide) to give amide X. Further functionalization, using procedures disclosed in the above Schemes are using techniques known in the art, will yield primary alcohol Y or other compounds.

The representative pyrazolines were synthesized similar to example 1 with noted exceptions. The corresponding pheylacrylaldehyde used to make the pyrazoline was also synthesized similar to that as described in example 1 or as described in example 207.

TABLE 1

Representative Pyrazoline (4,5-dihydro-1H-pyrazole) Intermediates.

| Structure/Formula | $^1$H NMR | Variations to reaction conditions | Purification details | First used in example |
|---|---|---|---|---|
| 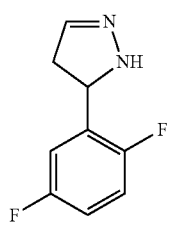 [SMILES: Fc1ccc(F)c(C2CC=NN2)c1] | (600 MHz, DMSO-d$_6$) δ 7.30 (d, J = 4.1 Hz, 1H), 7.13-7.07 (m, 1H), 7.06-7.00 (m, 2H), 6.73 (br-s, 1H), 4.64 (td, J = 10.6, 4.1 Hz, 1H), 3.07 (ddd, J = 16.9, 10.7, 1.7 Hz, 1H), 2.49-2.40 (m, 1H) | | | 1 |
| $C_{10}H_{10}F_2N_2$ | (300 MHz, CDCl$_3$) δ 6.95-6.85 (m, 1H), 6.81-6.64 (m, 2H), 5.39 (dd, J = 11.8, 4.7 Hz, 1H), 3.36 (dd, J = 18.3, 11.8 Hz, 1H), 3.06 (dd, J = 16.7, 10.5 Hz, 1H), 2.11 (s, 3H) | | | 47 |
| $C_9H_8F_2N_2$ | (500 MHz, CD$_3$OD) δ 7.24-7.19 (m, 1H), 7.12-7.06 (m, 1H), 7.03-6.97 (m, 1H), 6.87-6.84 (m, 1H), 4.95-4.89 (m, 1H), 3.27-3.15 (m, 1H), 2.64-2.54 (m, 1H). | | | 53 |

TABLE 1-continued

Representative Pyrazoline (4,5-dihydro-1H-pyrazole) Intermediates.

| Structure/ Formula | ¹H NMR | Variations to reaction conditions | Purification details | First used in example |
|---|---|---|---|---|
| 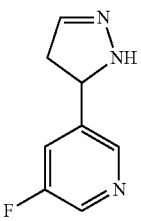 [SMILES: Fc1cncc(C2CC=NN2)c1]<br>$C_8H_8FN_3$ | (500 MHz, CD₃OD) δ 8.40-8.39 (m, 1H), 8.37-8.36 (m, 1H), 7.69-7.64 (m, 1H), 6.90-6.85 (m, 1H), 4.84-4.78 (m, 1H), 3.23 (ddd, J = 17.3, 10.8, 1.7 Hz, 1H), 2.66 (ddd, J = 17.3, 10.5, 1.6 Hz, 1H). | | | 14 |
| 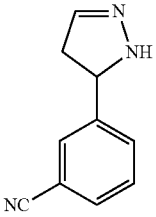 [SMILES: N#Cc1cccc(C2CC=NN2)c1]<br>$C_{10}H_9N_3$ | (500 MHz, CD₃OD) δ 7.74-7.71 (m, 1H), 7.69-7.66 (m, 1H), 7.64-7.61 (m, 1H), 7.54-7.49 (m, 1H), 6.87-6.84 (m, 1H), 4.81-4.73 (m, 1H), 3.20 (ddd, J = 17.3, 10.7, 1.7 Hz, 1H), 2.63 (ddd, J = 17.3, 10.4, 1.7 Hz, 1H). | | | 82 |
| 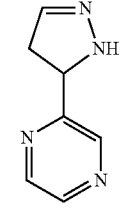<br>$C_7H_8N_4$ | (600 MHz, CDCl₃) δ 8.70 (d, J = 1.4 Hz, 1H), 8.56-8.47 (m, 2H), 6.86 (d, J = 1.7 Hz, 1H), 4.91 (dd, J = 11.1, 8.1 Hz, 1H), 3.27 (ddd, J = 17.2, 11.1, 1.6 Hz, 1H), 2.94 (ddd, J = 17.2, 8.1, 1.6 Hz, 1H). | | | 51 |
| 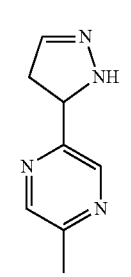<br>$C_8H_{10}N_4$ | (300 MHz, CDCl₃) δ 8.55 (d, J = 1.4 Hz, 1H), 8.40 (d, J = 1.4 Hz, 1H), 6.89-6.84 (m, 1H), 4.87 (dd, J = 11.0, 8.0 Hz, 1H), 3.24 (ddd, J = 17.2, 11.0, 1.6 Hz, 1H), 2.92 (ddd, J = 17.2, 8.1, 1.6 Hz, 1H), 2.57 (s, 3H). | | | 49 |
| 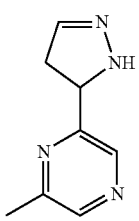<br>$C_8H_{10}N_4$ | (600 MHz, CDCl₃) δ 8.48 (s, 1H), 8.38 (s, 1H), 6.89-6.81 (m, 1H), 4.86 (dd, J = 11.1, 8.0 Hz, 1H), 3.25 (ddd, J = 17.2, 11.1, 1.6 Hz, 1H), 2.93 (ddd, J = 17.2, 8.0, 1.7 Hz, 1H), 2.56 (s, 3H). | | | 50 |

TABLE 1-continued

Representative Pyrazoline (4,5-dihydro-1H-pyrazole) Intermediates.

| Structure/ Formula | ¹H NMR | Variations to reaction conditions | Purification details | First used in example |
|---|---|---|---|---|
| 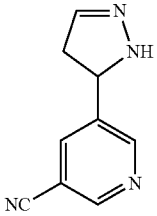 [SMILES: N#Cc1cncc(C2CC=NN2)c1]<br>$C_{10}H_9N_3$ | (600 MHz, CDCl₃) δ 8.81 (d, J = 2.0 Hz, 1H), 8.79 (d, J = 2.2 Hz, 1H), 8.07-8.03 (m, 1H), 6.88-6.84 (m, 1H), 5.93 (s, 1H), 4.86-4.80 (m, 1H), 3.25 (ddd, J = 17.1, 10.9, 1.7 Hz, 1H), 2.65 (ddd, J = 17.1, 10.4, 1.6 Hz, 1H). | | | 168 |
| 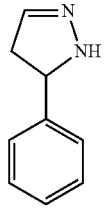 [SMILES: C1=NNC(c2ccccc2)C1]<br>$C_9H_{10}N_2$ | (600 MHz, DMSO-d₆) δ 7.77-7.53 (m, 5H), 6.77-6.72 (m, 1H), 4.72-4.62 (m, 1H), 3.09 (ddd, J = 17.0, 10.8, 1.7 Hz, 1H), 2.54-2.45 (m, 1H). | | | 44 |
| 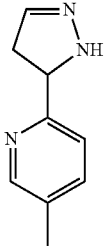<br>$C_9H_{11}N_3$ | (600 MHz, CDCl₃) δ 8.37 (s, 1H), 7.52-7.46 (m, 1H), 7.28-7.25 (m, 1H), 6.86-6.79 (m, 1H), 4.88-4.79 (m, 1H), 3.23-3.15 (m, 1H), 2.86 (ddd, J = 17.2, 7.7, 1.7 Hz, 1H), 2.32 (s, 3H). | | | 171 |
| 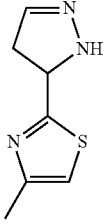<br>$C_7H_9N_3S$ | (600 MHz, DMSO-d₆) δ 7.52 (d, J = 4.8 Hz, 1H), 7.14 (s, 1H), 6.79 (s, 1H), 4.84 (td, J = 10.8, 4.9 Hz, 1H), 3.17 (ddd, J = 17.1, 11.3, 1.7 Hz, 1H), 2.66-2.58 (m, 1H), 2.32 (s, 3H). | | | 170 |
| 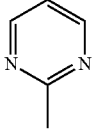<br>$C_8H_{10}N_4$ | (500 MHz, DMSO-d₆) δ 8.62 (s, 2H), 7.31 (d, J = 3.9 Hz, 1H), 6.84-6.77 (m, 1H), 4.62 (td, J = 10.5, 3.9 Hz, 1H), 3.08 (ddd, J = 16.9, 10.7, 1.7 Hz, 1H), 2.62-2.54 (m, 4H). | | | 183 |

TABLE 1-continued

Representative Pyrazoline (4,5-dihydro-1H-pyrazole) Intermediates.

| Structure/ Formula | ¹H NMR | Variations to reaction conditions | Purification details | First used in example |
|---|---|---|---|---|
| 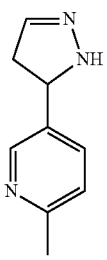<br>$C_9H_{11}N_3$ | (600 MHz, DMSO-$d_6$) δ 8.37 (d, J = 2.3 Hz, 1H), 7.60 (dd, J = 8.0, 2.4 Hz, 1H), 7.22 (d, J = 3.9 Hz, 1H), 7.22-7.18 (m, 1H), 6.75 (d, J = 1.8 Hz, 1H), 4.59 (td, J = 10.6, 3.9 Hz, 1H), 3.04 (ddd, J = 16.9, 10.7, 1.7 Hz, 1H), 2.48-2.45 (m, 1H), 2.43 (s, 3H). | AcOH-1.7 eq, H4N2-1.5 eq, EtOH, 80° C. | | 249 |
| 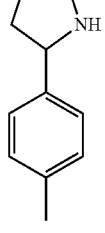<br>$C_{10}H_{12}N_2$ | (500 MHz, DMSO-$d_6$) δ 7.22-7.18 (m, 2H), 7.14-7.11 (m, 3H), 6.71 (d, J = 1.7 Hz, 1H), 4.54 (td, J = 10.7, 3.3 Hz, 1H), 3.00 (ddd, J = 16.8, 10.7, 1.7 Hz, 1H), 2.43 (ddd, J = 16.8, 10.6, 1.6 Hz, 1H), 2.27 (s, 3H). | AcOH-1.7 eq, H4N2-1.5 eq, EtOH, 80° C. | 0-60% iPrOH/ EtOAc soln | 198 |
| 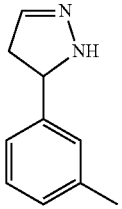<br>$C_{10}H_{12}N_2$ | (600 MHz, DMSO-$d_6$) δ 7.20 (t, J = 7.5 Hz, 1H), 7.15-7.12 (m, 2H), 7.10 (d, J = 7.7 Hz, 1H), 7.05 (d, J = 7.5 Hz, 1H), 6.71 (d, J = 1.8 Hz, 1H), 4.54 (td, J = 10.7, 3.4 Hz, 1H), 3.02 (ddd, J = 16.8, 10.7, 1.7 Hz, 1H), 2.45 (ddd, J = 16.8, 10.7, 1.6 Hz, 1H), 2.28 (s, 3H). | AcOH-1.7 eq, H4N2-1.5 eq, EtOH, 80° C. | | 243 |
| 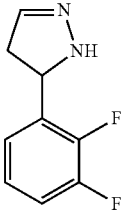 [SMILES: Fc1cccc(C2CC=NN2)c1F]<br>$C_9H_8F_2N_2$ | (600 MHz, DMSO-$d_6$) δ 7.35-7.30 (m, 1H), 7.27-7.23 (m, 2H), 7.21-7.16 (m, 1H), 6.76 (d, J = 1.7 Hz, 1H), 4.81 (td, J = 10.5, 4.0 Hz, 1H), 3.15-3.08 (m, 1H), 2.55-2.51 (m, 1H). | | 0-40% EtOAc/ iPrOH (5:1) | 237 |
| 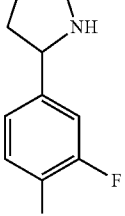<br>$C_9H_8F_2N_2$ | (600 MHz, DMSO-$d_6$) δ 7.55-7.41 (m, 1H), 7.43-7.29 (m, 2H), 7.26 (d, J = 4.0 Hz, 1H), 6.73 (d, J = 1.7 Hz, 1H), 4.61 (td, J = 10.7, 3.7 Hz, 1H), 3.05 (ddd, J = 16.9, 10.7, 1.7 Hz, 1H), 2.49-2.44 (m, 1H). | AcOH-1.7 eq, H4N2-1.5 eq, EtOH, 80° C. | 0-40% EtOAc/ iPrOH (5:1) | 242 |

TABLE 1-continued

Representative Pyrazoline (4,5-dihydro-1H-pyrazole) Intermediates.

| Structure/ Formula | ¹H NMR | Variations to reaction conditions | Purification details | First used in example |
|---|---|---|---|---|
| 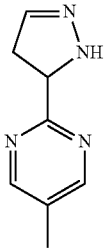<br>$C_7H_8N_4$ | (600 MHz, DMSO-$d_6$) δ 8.79 (d, J = 4.8 Hz, 2H), 7.42 (t, J = 4.9 Hz, 1H), 7.15 (s, 1H), 6.74 (s, 1H), 4.73 (ddd, J = 11.2, 6.4, 2.6 Hz, 1H), 3.13 (ddd, J = 17.1, 6.4, 1.7 Hz, 1H), 3.04 (ddd, J = 17.2, 11.1 Hz, 1H). | AcOH-1.7 eq, H4N2-1.5 eq, EtOH, 80° C. | 0-100% DCM/ MeOH (10:1) | 259 |
| 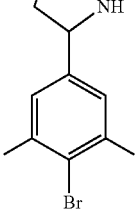<br>$C_9H_7BrF_2N_2$ | (600 MHz, DMSO-$d_6$) δ 7.32 (d, J = 4.1 Hz, 1H), 7.24-7.21 (m, 2H), 6.73 (d, J = 1.7 Hz, 1H), 4.64 (td, J = 10.6, 4.1 Hz, 1H), 3.08 (ddd, J = 17.0, 10.9, 1.7 Hz, 1H), 2.49-2.45 (m, 1H). | AcOH-1.7 eq, H4N2-1.5 eq, EtOH, 80° C. | 0-40% EtOAc/ iPrOH (5:1) | 203 |
| 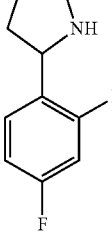<br>$C_9H_8F_2N_2$ | (600 MHz, DMSO-$d_6$) δ 7.50-7.43 (m, 1H), 7.24-7.17 (m, 2H), 7.06 (td, J = 8.6, 2.7 Hz, 1H), 6.75 (d, J = 1.8 Hz, 1H), 4.75 (td, J = 10.6, 3.9 Hz, 1H), 3.11-3.04 (m, 1H), 2.46 (dd, J = 17.0, 10.2 Hz, 1H). | AcOH-1.7 eq, H4N2-1.5 eq, EtOH, 80° C. | 0-40% EtOAc/ iPrOH (5:1) | 240 |
| 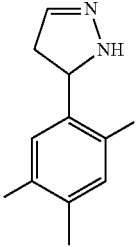<br>$C_{10}H_{10}F_2N_2$ | (600 MHz, DMSO-$d_6$) δ 7.21 (d, J = 4.0 Hz, 1H), 7.17-7.10 (m, 2H), 6.74 (d, J = 1.8 Hz, 1H), 4.73 (td, J = 10.5, 3.9 Hz, 1H), 3.07 (ddd, J = 17.0, 11.1, 1.6 Hz, 1H), 2.46 (dd, J = 17.0, 10.0 Hz, 1H), 2.20 (d, J = 1.9 Hz, 3H). | AcOH-1.7 eq, H4N2-1.5 eq, EtOH, 80° C. | 0-40% EtOAc/ iPrOH (5:1) | 236 |
| 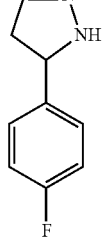<br>$C_9H_9FN_2$ | (600 MHz, DMSO-$d_6$) δ 7.88-7.74 (m, 1H), 7.40-7.34 (m, 2H), 7.30-7.23 (m, 2H), 6.72 (s, 1H), 4.60 (td, J = 10.7, 4.0 Hz, 1H), 3.03 (ddd, J = 16.6, 10.7, 1.6 Hz, 1H), 2.44 (dd, J = 17.0, 10.7 Hz, 1H). | AcOH-1.7 eq, H4N2-1.5 eq, EtOH, 80° C. | 0-40% EtOAc/ iPrOH (5:1) | 244 |

TABLE 1-continued

Representative Pyrazoline (4,5-dihydro-1H-pyrazole) Intermediates.

| Structure/ Formula | $^1$H NMR | Variations to reaction conditions | Purification details | First used in example |
|---|---|---|---|---|
| C$_9$H$_8$Cl$_2$N$_2$ | (600 MHz, DMSO-d$_6$) δ 7.53 (ddd, J = 21.0, 7.9, 1.6 Hz, 2H), 7.37 (t, J = 7.9 Hz, 1H), 7.30 (d, J = 4.0 Hz, 1H), 6.71 (d, J = 1.7 Hz, 1H), 4.89 (td, J = 10.4, 4.0 Hz, 1H), 3.22 (ddd, J = 17.1, 11.0, 1.7 Hz, 1H), 2.40-2.32 (m, 1H). | AcOH-1.7 eq, H4N2-1.5 eq, EtOH, 80° C. | 0-30% EtOAc/ iPrOH (5:1) | 245 |
| C$_{10}$H$_{10}$N$_4$ | (500 MHz, CDCl$_3$) δ 8.03-7.93 (m, 1H), 7.55-7.41 (m, 1H), 7.36 (d, J = 0.9 Hz, 1H), 7.03-6.89 (m, 1H), 6.76-6.69 (m, 1H), 6.61-6.52 (m, 1H), 5.99 (s, 1H), 5.27 (t, J = 10.3 Hz, 1H), 3.17 (dd, J = 10.3, 1.6 Hz, 2H). | AcOH-1.7 eq, H4N2-1.5 eq, EtOH, 80° C. | | 247 |
| C$_8$H$_7$F$_2$N$_3$ | (500 MHz, DMSO-d$_6$) δ 8.45 (d, J = 2.4 Hz, 1H), 7.97-7.89 (m, 1H), 7.13 (d, J = 3.2 Hz, 1H), 6.77 (d, J = 2.1 Hz, 1H), 4.94-4.85 (m, 1H), 3.11-2.95 (m, 2H). | AcOH-0.3 eq, H4N2-5 eq, tBuOH, 80° C. | | 291 |
| C$_9$H$_{10}$FN$_3$ | (500 MHz, DMSO-d$_6$) δ 7.64-7.57 (m, 1H), 7.31 (dd, J = 8.5, 3.8 Hz, 1H), 7.25 (d, J = 3.9 Hz, 1H), 6.73 (d, J = 2.1 Hz, 1H), 4.64 (td, J = 1H), 3.05 (ddd, J = 17.1, 11.1, 1.7 Hz, 1H), 2.75-2.67 (m, 1H), 2.43 (d, J = 3.0 Hz, 3H). | AcOH-0.3 eq, H4N2-5 eq, iPrOH, 80° C. | | 315 |
| C$_{10}$H$_{12}$N$_2$ | (500 MHz, DMSO-d$_6$) δ 7.42-7.37 (m, 1H), 7.20-7.10 (m, 4H), 6.70 (s, 1H), 4.75 (td, J = 10.6, 3.8 Hz, 1H), 3.11 (ddd, J = 16.8, 10.8, 1.7 Hz, 1H), 2.45-2.37 (m, 1H), 2.28 (s, 3H). | AcOH-0.3 eq, H4N2-5 eq, tBuOH, 80° C. | | 314 |

TABLE 1-continued

Representative Pyrazoline (4,5-dihydro-1H-pyrazole) Intermediates.

| Structure/<br>Formula | ¹H NMR | Variations to<br>reaction<br>conditions | Purification<br>details | First<br>used in<br>example |
|---|---|---|---|---|
| $C_9H_8F_2N_2$ (2,6-difluorophenyl pyrazoline) | (500 MHz, DMSO-$d_6$) δ 7.41-7.30 (m, 1H), 7.08-7.03 (m, 2H), 7.01-6.92 (m, 1H), 6.79 (d, J = 1.8 Hz, 1H), 4.94-4.85 (m, 1H), 3.11-3.01 (m, 1H), 2.80-2.71 (m, 1H). | AcOH-<br>0.3 eq, H4N2-<br>5 eq, tBuOH,<br>80° C. | | 307 |
| $C_{10}H_9F_3N_2$ (4-trifluoromethylphenyl pyrazoline) | (500 MHz, DMSO-$d_6$) δ 7.69 (d, J = 8.1 Hz, 2H), 7.55 (d, J = 8.1 Hz, 2H), 7.33 (d, J = 4.0 Hz, 1H), 6.75 (d, J = 1.7 Hz, 1H), 4.70 (td, J = 10.7, 3.9 Hz, 1H), 3.11 (ddd, J = 16.9, 10.9, 1.7 Hz, 1H), 2.49-2.44 (m, 1H). | AcOH-<br>0.3 eq, H4N2-<br>5 eq, tBuOH,<br>80° C. | | 307 |
| $C_9H_9ClN_2$ (4-chlorophenyl pyrazoline) | (600 MHz, DMSO-$d_6$) δ 7.40-7.34 (m, 2H), 7.36-7.30 (m, 2H), 7.30-7.23 (m, 1H), 5.76 (s, 1H), 4.60 (td, J = 10.7, 3.9 Hz, 1H), 3.05 (ddd, J = 16.8, 10.7, 1.6 Hz, 1H), 2.45-2.38 (m, 1H). | AcOH-<br>0.3 eq, H4N2-<br>5 eq, tBuOH,<br>80° C. | | 311 |
| $C_{10}H_{10}N_4$ (imidazo[1,2-a]pyridinyl pyrazoline) | (500 MHz, DMSO-$d_6$) δ 8.48 (dt, J = 6.8, 1.2 Hz, 1H), 7.81 (s, 1H), 7.50-7.43 (m, 1H), 7.20 (ddd, J = 9.0, 6.7, 1.3 Hz, 1H), 7.07-7.02 (m, 1H), 6.85 (td, J = 6.8, 1.2 Hz, 1H), 6.79-6.75 (m, 1H), 4.75-4.67 (m, 1H), 3.00 (ddd, J = 16.8, 10.7, 1.6 Hz, 1H), 2.80 (ddd, J = 16.8, 8.6, 1.7 Hz, 1H). | AcOH-<br>0.3 eq, H4N2-<br>5 eq, tBuOH,<br>80° C. | | 258 |
| $C_{10}H_{10}F_2N_2$ (2,6-difluoro-4-methylphenyl pyrazoline) | (600 MHz, DMSO-$d_6$) δ 7.02 (d, J = 4.9 Hz, 1H), 6.89 (d, J = 9.4 Hz, 2H), 6.77 (s, 1H), 4.90-4.79 (m, 1H), 3.02 (dd, J = 17.1, 12.1 Hz, 1H), 2.72 (dd, J = 17.2, 10.1 Hz, 1H), 2.36 (d, J = 1.8 Hz, 3H). | AcOH-<br>0.3 eq, H4N2-<br>5 eq, tBuOH,<br>80° C. | | 304 |

TABLE 1-continued

Representative Pyrazoline (4,5-dihydro-1H-pyrazole) Intermediates.

| Structure/ Formula | ¹H NMR | Variations to reaction conditions | Purification details | First used in example |
|---|---|---|---|---|
| $C_9H_9ClN_2$ | (500 MHz, DMSO-$d_6$) δ 7.55 (dd, J = 7.6, 1.8 Hz, 1H), 7.44 (dd, J = 7.8, 1.4 Hz, 1H), 7.42-7.24 (m, 3H), 6.72 (d, J = 1.7 Hz, 1H), 4.87 (td, J = 10.5, 3.9 Hz, 1H), 3.19 (ddd, J = 17.0, 10.9, 1.7 Hz, 1H), 2.41-2.30 (m, 1H). | AcOH-0.9 eq, H4N2-2.5 eq, tBuOH, 80° C. | | 318 |
| $C_{16}H_{24}F_2N_2OSi$ | (300 MHz, DMSO-$d_6$) δ 7.17 (m, 2H), 7.05 (m, 1H), 6.59-6.53 (m, 1H), 4.65 (s, 3H), 4.59-4.57 (m, 1H), 0.80 (s, 6H), −0.01 (d, J = 7.6 Hz, 9H). | AcOH-0.3 eq, H4N2-2.5 eq, tBuOH, 8080° C. | (0-40%) EtOAc in hexanes | |
| $C_{16}H_{25}FN_2O_2Si$ | (600 MHz, DMSO-$d_6$) δ 7.29-7.22 (m, 2H), 7.13-7.05 (m, 2H), 6.65 (s, 1H), 4.72-4.69 (m, 1H), 4.66 (s, 2H), 3.00 (dd, J = 16.9, 10.9 Hz, 1H), 2.39-2.32 (m, 1H), 0.82 (s, 9H), 0.02 (s, 6H). | AcOH-0.3 eq, H4N2-2.5 eq, tBuOH, 8080° C. | (0-40%) EtOAc in hexanes | 344 |
| $C_{16}H_{25}FN_2O_2Si$ | (600 MHz, DMSO) δ 7.44-7.39 (m, 1H), 7.28-7.23 (m, 1H), 7.18 (d, J = 4.0 Hz, 1H), 7.14-7.05 (m, 1H), 6.71 (s, 1H), 4.72 (s, 2H), 4.59 (td, J = 10.7, 3.9 Hz, 1H), 3.04 (ddd, J = 17.0, 10.8, 1.7 Hz, 1H), 2.46-2.36 (m, 1H), 0.93-0.85 (m, 9H), 0.12-0.04 (m, 6H). | | | 207 |
| $C_7H_6N_4S$ | (500 MHz, DMSO) δ 8.76 (s, 1H), 7.73 (d, J = 5.4 Hz, 1H), 6.84 (s, 1H), 4.94 (ddd, J = 11.6, 10.1, 5.4 Hz, 1H), 3.27 (ddd, J = 17.5, 11.6, 1.7 Hz, 1H), 2.74-2.62 (m, 1H). | | | 254 |

TABLE 1-continued

Representative Pyrazoline (4,5-dihydro-1H-pyrazole) Intermediates.

| Structure/ Formula | ¹H NMR | Variations to reaction conditions | Purification details | First used in example |
|---|---|---|---|---|
| $C_8H_7N_3S$ | (600 MHz, DMSO) δ 7.84 (d, J = 3.8 Hz, 1H), 7.61-7.56 (m, 1H), 7.17 (d, J = 3.8 Hz, 1H), 6.81 (s, 1H), 4.98-4.89 (m, 1H), 3.17 (ddd, J = 17.0, 10.9, 1.7 Hz, 1H), 2.56-2.51 (m, 1H). | | | 251 |
| $C_{26}H_{28}F_2N_2OSi$ | LCMS (ES+) $C_{26}H_{28}N_2F_2OSi$ requires: 450, found 451 [M + H]⁺ | | | 343 |
| $C_8H_8FN_3$ | LCMS (ES+) $C_8H_8FN_3$ requires: 165, found 166 [M + H]⁺. | | | 303 |
| $C_{10}H_{11}FN_2$ | (500 MHz, CDCl₃) δ 7.30 (t, J = 7.9 Hz, 1H), 6.95-6.92 (m, 1H), 6.88-6.83 (m, 2H), 5.01-4.95 (m, 1H), 3.19-3.11 (m, 1H), 2.69-2.60 (m, 1H), 2.33 (s, 3H). | | | 238 |
| $C_{10}H_{11}FN_2$ | (500 MHz, CDCl₃) δ 7.16-7.10 (m, 1H), 7.03-6.95 (m, 2H), 6.85-6.78 (m, 1H), 4.72-4.64 (m, 1H), 3.17-3.07 (m, 1H), 2.73-2.54 (m, 1H), 2.27-2.24 (m, 3H). | | | 239 |

TABLE 1-continued

Representative Pyrazoline (4,5-dihydro-1H-pyrazole) Intermediates.

| Structure/Formula | $^1$H NMR | Variations to reaction conditions | Purification details | First used in example |
|---|---|---|---|---|
| ![structure] $C_9H_{10}FN_3$ | (600 MHz, CDCl$_3$) δ8.25 (d, J = 1.6 Hz, 1H), 7.42-7.37 (m, 1H), 6.85 (d, J = 1.7 Hz, 1H), 4.79-4.73 (m, 1H), 3.22-3.14 (m, 1H), 2.71-2.62 (m, 1H), 2.53-2.49 (m, 3H). | | | 246 |

The invention is further illustrated by the following examples.

Example 1

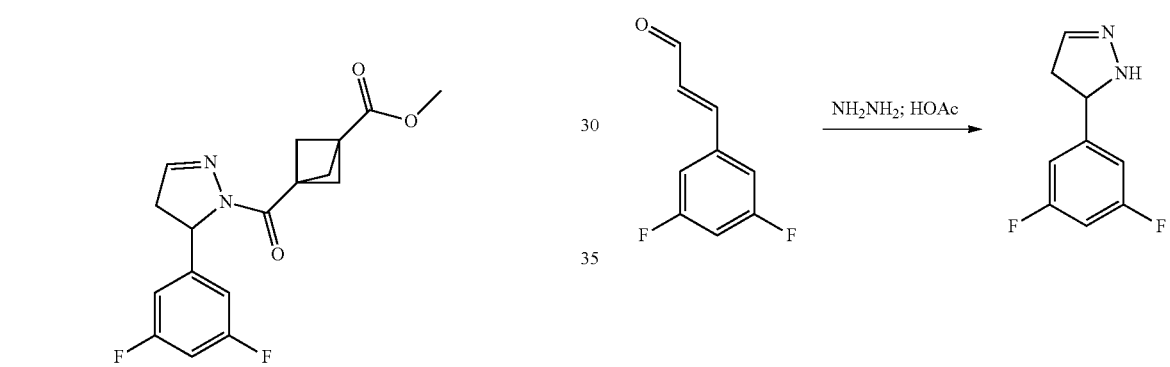

Methyl 3-(5-(3,5-difluorophenyl)-4,5-dihydro-1H-pyrazole-1-carbonyl)bicyclo[1.1.1]pentane-1-carboxylate

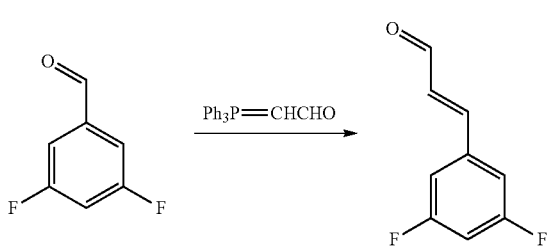

(E)-3-(3,5-difluorophenyl)acrylaldehyde

A solution of 3,5-difluorobenzaldehyde (4 g, 28 mmol) and 2-(triphenyl-λ$^5$-phosphaneylidene)acetaldehyde (8.5 g, 28 mmol) in THF (15 ml) was refluxed overnight. The reaction was concentrated, and the residue was adsorbed onto silica gel and purified via flash chromatography (0-30%, EtOAc in hexanes) to give the title compound (3.2 g, 19 mmol, 68% yield) as a yellow solid. $^1$H NMR (300 MHz, CDCl$_3$) δ 9.73 (d, J=7.5 Hz, 1H), 7.39 (d, J=16.0 Hz, 1H), 7.15-7.04 (m, 2H), 6.96-6.84 (m, 1H), 6.68 (dd, J=16.0, 7.5 Hz, 1H).

5-(3,5-difluorophenyl)-4,5-dihydro-1H-pyrazole

To a solution of hydrazine hydrate (0.91 ml, 18 mmol) in ethanol (19 ml) stirred at 0° C. was added HOAc (1.1 ml, 20 mmol). The solution was then heated to 45° C. and the product from the previous step was added portion wise. The vessel was sealed and stirred at 90° C. overnight. The reaction was concentrated and the residue was adsorbed onto silica gel and purified via flash chromatography (20-60%, EtOAc:MeOH (4:1) in hexanes) to give the title compound (2 g, 10 mmol, 71% yield) as a yellow oil.

$^1$H NMR (600 MHz, DMSO-d$_6$) δ 7.30 (d, J=4.1 Hz, 1H), 7.13-7.07 (m, 1H), 7.06-7.00 (m, 2H), 6.73 (br-s, 1H), 4.64 (td, J=10.6, 4.1 Hz, 1H), 3.07 (ddd, J=16.9, 10.7, 1.7 Hz, 1H), 2.49-2.40 (m, 1H).

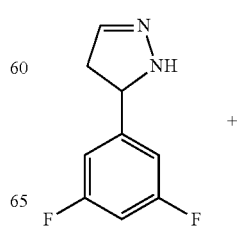 +

135

-continued

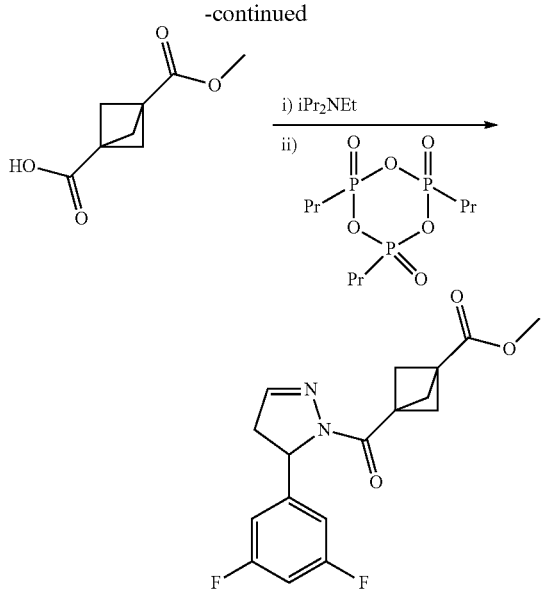

Methyl 3-(5-(3,5-difluorophenyl)-4,5-dihydro-1H-pyrazole-1-carbonyl)-bicyclo[1.1.1]pentane-1-carboxylate (Example 1)

To a solution of the product from the previous step (1.1 g, 6.0 mmol) and 3-(methoxycarbonyl)bicyclo[1.1.1]pentane-1-carboxylic acid (1.1 g, 6.6 mmol) in DMF (20 ml) was added iPr$_2$NEt (3.1 ml, 18 mmol) and the reaction was stirred for 5 min. 2,4,6-Tripropyl-1,3,5,2,4,6-trioxatriphosphinane 2,4,6-trioxide (10 ml, 18 mmol, 50% in EtOAc) was then added and the reaction was stirred overnight. The reaction was diluted in EtOAc and washed with H$_2$O and brine. The organic layers were dried, concentrated, and filtered. The residue was adsorbed onto silica gel and purified via flash chromatography (20-65%, EtOAc in hexanes) to give the title compound (1.8 g, 5.3 mmol, 88% yield) as an off-white solid.

MS (ES$^+$) C$_{17}$H$_{16}$F$_2$N$_2$O$_3$ requires: 334, found: 335 [M+H]$^+$.

$^1$H NMR (600 MHz, DMSO-d$_6$) δ 7.25 (m, 1H), 7.13 (m, 1H), 6.85-6.80 (m, 2H), 5.33 (dd, J=11.9, 4.9 Hz, 1H), 3.62 (s, 3H), 3.43 (ddd, J=19.0, 11.9, 1.6 Hz, 1H), 2.72 (ddd, J=19.0, 5.0, 1.6 Hz, 1H), 2.31 (s, 6H).

Example 2

136

3-(5-(3,5-Difluorophenyl)-4,5-dihydro-1H-pyrazole-1-carbonyl)-bicyclo[1.1.1]pentane-1-carboxylic acid

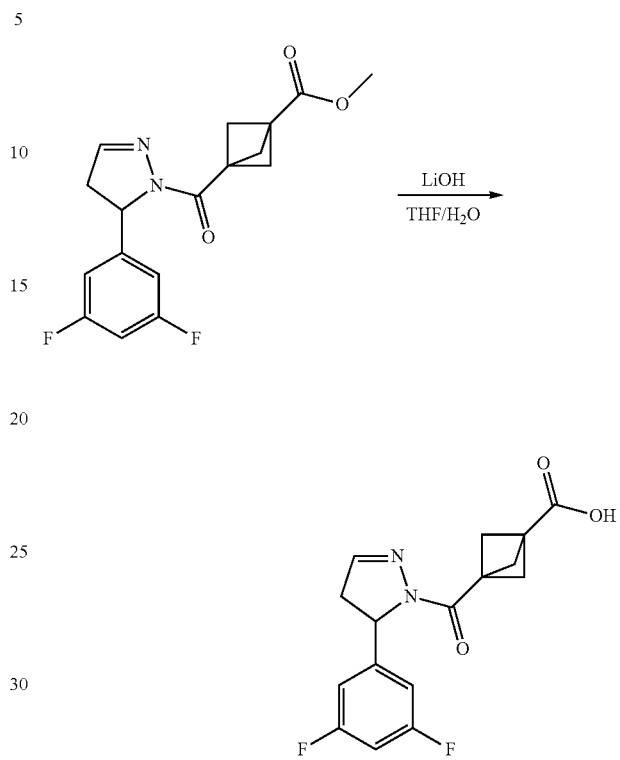

To a solution of methyl 3-(5-(3,5-difluorophenyl)-4,5-dihydro-1H-pyrazole-1-carbonyl)bicyclo[1.1.1]pentane-1-carboxylate (Example 1, 0.55 g, 1.6 mmol) in THF (6.5 ml) and H$_2$O (1.6 ml) was added LiOH (83 mg, 3.4 mmol) at rt, and the mixture was vigorously stirred until completion, as determined by LCMS. The reaction was cooled to 0° C. and the reaction was quenched with 1M HCl (3.2 ml, 3.2 mmol, 1M) and stirred for at least 15 min. Then mixture was diluted with EtOAc and H$_2$O and extracted with EtOAc twice. The combined organic layers were dried and concentrated to give the title compound (0.52 g, 1.6 mmol, 99% yield) as a yellow solid. The product was used as is without further purification. MS (ES$^+$) C$_{16}$H$_{14}$F$_2$N$_2$O$_3$ requires: 320, found: 321 [M+H]$^+$.

Examples 3 and 4

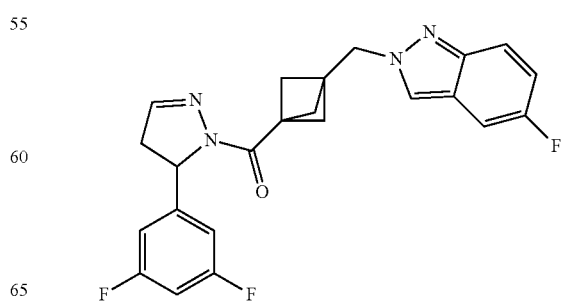

(5-(3,5-Difluorophenyl)-4,5-dihydro-1H-pyrazol-1-yl)(3-((5-fluoro-2H-indazol-2-yl)methyl)bicyclo[1.1.1]pentan-1-yl)methanone (3) and

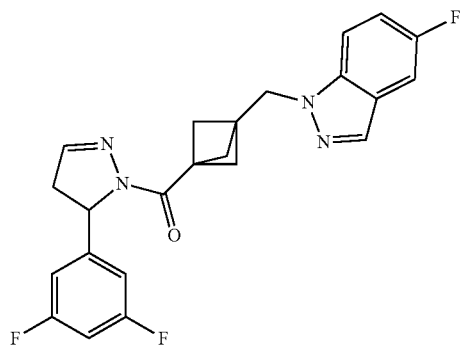 [SMILES: O=C(N1N=CCC1c1cc(F)cc(F)c1)C12CC(Cn3ncc4cc(F)ccc43)(C1)C2]

(5-(3,5-Difluorophenyl)-4,5-dihydro-1H-pyrazol-1-yl)(3-((5-fluoro-1H-indazol-1-yl)methyl)bicyclo[1.1.1]pentan-1-yl)methanone (4)

MS (ES$^+$) C$_{16}$H$_{16}$F$_2$N$_2$O$_2$ requires: 306, found: 307 [M+H]$^+$.

$^1$H NMR (500 MHz, CD$_3$OD) δ 7.12 (m, 1H), 6.83 (m, 1H), 6.77-6.71 (m, 2H), 5.35 (dd, J=11.8, 4.8 Hz, 1H), 3.54 (s, 2H), 3.45 (ddd, J=19.0, 11.8, 1.6 Hz, 1H), 2.74 (ddd, J=18.9, 4.8, 1.8 Hz, 1H), 2.07 (s, 6H).

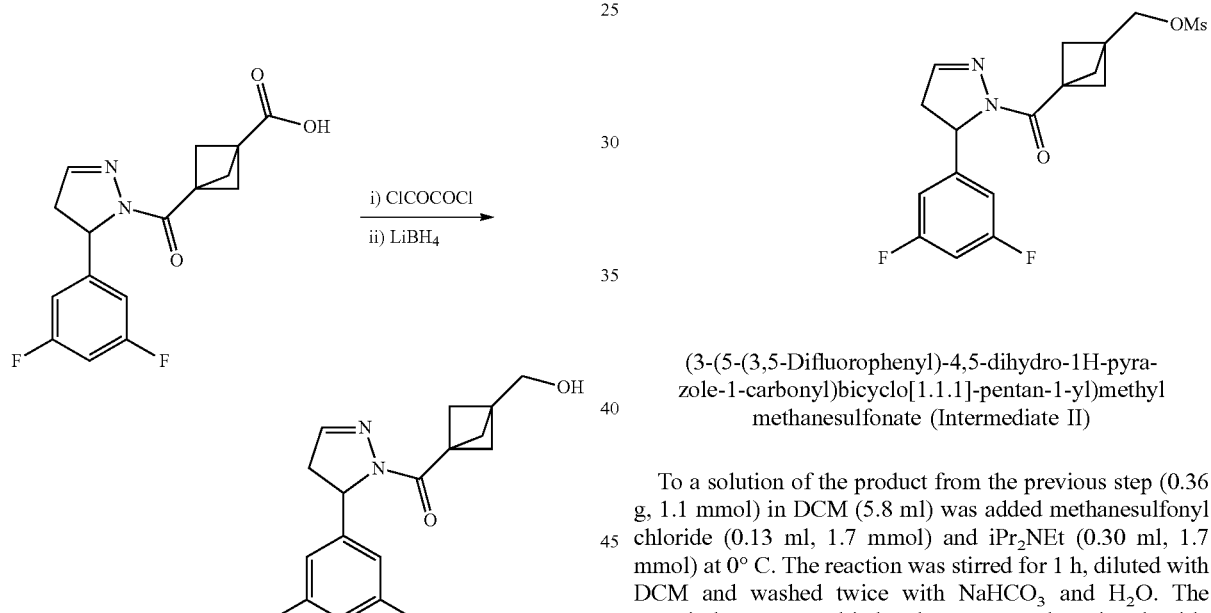

(5-(3,5-Difluorophenyl)-4,5-dihydro-1H-pyrazol-1-yl)(3-(hydroxymethyl)-bicyclo[1.1.1]pentan-1-yl)methanone (Intermediate I)

To a solution of the Example 2 compound (0.57 mg, 1.7 mmol) in THF (5.9 ml) was added 3 drops of DMF and oxalyl chloride (0.16 ml, 1.9 mmol) at 0° C. The reaction was monitored for complete consumption of acid. The mixture was concentrated and redissolved in THF (5.9 ml). LiBH$_4$ (86 mg, 3.9 mmol) was then added at 0° C., and the solution was stirred for 15 min. Saturated NH$_4$Cl was added, the residue was partitioned between EtOAc and H$_2$O, and the aqueous phase was extracted with EtOAc. The combined organic layers were dried and concentrated. The residue was adsorbed onto silica gel and purified via flash chromatography (20-100%, EtOAc in hexanes) to give the title compound (0.24 g, 0.78 mmol, 43% yield) as a yellow solid.

(3-(5-(3,5-Difluorophenyl)-4,5-dihydro-1H-pyrazole-1-carbonyl)bicyclo[1.1.1]-pentan-1-yl)methyl methanesulfonate (Intermediate II)

To a solution of the product from the previous step (0.36 g, 1.1 mmol) in DCM (5.8 ml) was added methanesulfonyl chloride (0.13 ml, 1.7 mmol) and iPr$_2$NEt (0.30 ml, 1.7 mmol) at 0° C. The reaction was stirred for 1 h, diluted with DCM and washed twice with NaHCO$_3$ and H$_2$O. The organic layers were dried and concentrated to give the title compound as a yellow amorphous solid. The product was used as is without further purification. MS (ES$^+$) C$_{17}$H$_{18}$F$_2$N$_2$O$_4$S requires: 384, found: 385 [M+H]$^+$.

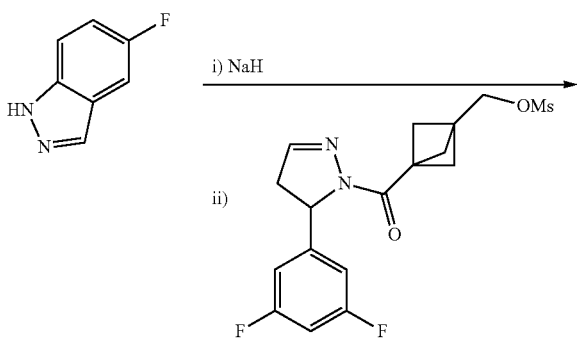

-continued

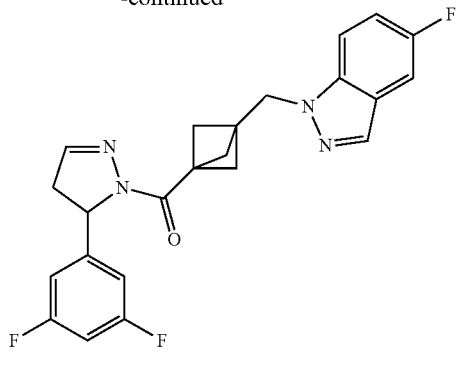

(5-(3,5-Difluorophenyl)-4,5-dihydro-1H-pyrazol-1-yl)(3-((5-fluoro-2H-indazol-2-yl)methyl)bicyclo[1.1.1]pentan-1-yl)methanone (Example 3) and (5-(3,5-difluorophenyl)-4,5-dihydro-1H-pyrazol-1-yl)(3-((5-fluoro-1H-indazol-1-yl)methyl)bicyclo[1.1.1]pentan-1-yl)methanone (Example 4)

To a solution of 5-fluoro-1H-indazole (14 mg, 0.10 mmol) in DMF (0.15 ml) was added NaH (60% dispersion in mineral oil, 4.1 mg, 0.10 mmol) at 0° C. and the reaction was stirred until no more bubbling occurred. Then a solution of the product from the previous step (20 mg, 0.05 mmol) in DMF (0.15 ml) was added at 0° C. and the reaction was stirred for 5 minutes at 0° C. The reaction was warmed to rt, heated and stirred at 65° C. 1 h. The reaction was diluted in MeOH and purified by mass-triggered preparative HPFC (Mobile phase: A=0.1% TFA/H$_2$O, B=0.1% TFA/MeCN; Gradient: B=10-90%; 12 min; Column: C18) to give two compounds.

The first eluting product, Example 3 (2.2 mg, 5.2 μmol, 9% yield) was assigned as the isomer shown, based on elution order.

MS (ES$^+$) C$_{23}$H$_{19}$F$_3$N$_4$O requires: 424, found: 425 [M+H]$^+$.

$^1$H NMR (500 MHz, CD$_3$OD) δ 8.17 (d, J=0.9 Hz, 1H), 7.66-7.60 (m, 1H), 7.35-7.30 (m, 1H), 7.16-7.10 (m, 1H), 7.09-7.06 (m, 1H), 6.85-6.78 (m, 1H), 6.75-6.68 (m, 2H), 5.31 (dd, J=11.8, 4.9 Hz, 1H), 4.56 (s, 2H), 3.41 (ddd, J=19.1, 11.8, 1.6 Hz, 1H), 2.71 (ddd, J=19.1, 4.9, 1.8 Hz, 1H), 2.07 (s, 6H).

The second eluting product, Example 4 (1.6 mg, 3.7 μmol, 7% yield) was assigned as the isomer shown, based on elution order.

MS (ES$^+$) C$_{23}$H$_{19}$F$_3$N$_4$O requires: 424, found: 425 [M+H]$^+$.

$^1$H NMR (500 MHz, CD$_3$OD) δ 7.99 (d, J=0.9 Hz, 1H), 7.60-7.53 (m, 1H), 7.44-7.39 (m, 1H), 7.25-7.19 (m, 1H), 7.07-7.04 (m, 1H), 6.84-6.77 (m, 1H), 6.73-6.66 (m, 2H), 5.29 (dd, J=11.8, 4.8 Hz, 1H), 4.55 (s, 2H), 3.40 (ddd, J=19.1, 11.8, 1.7 Hz, 1H), 2.69 (ddd, J=19.0, 4.8, 1.8 Hz, 1H), 2.00 (s, 6H).

Example 5

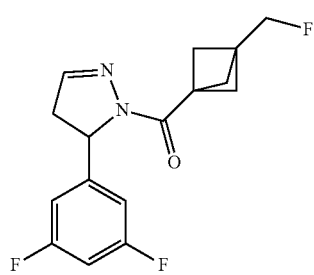 [SMILES: O=C(N1N=CCC1c1cc(F)cc(F)c1)C12CC(CF)(C1)C2]

(5-(3,5-Difluorophenyl)-4,5-dihydro-1H-pyrazol-1-yl)(3-(fluoromethyl)-bicyclo[1.1.1]pentan-1-yl)methanone To a solution of Intermediate I (38 mg, 0.12 mmol) in DCM (0.20 ml) at −78° C. was added DAST (16 μl, 0.12 mmol), and the mixture was allowed to stir and warm to RT overnight. The reaction mixture was then diluted in DCM, washed with saturated NaHCO$_3$ solution, dried, concentrated, and purified by mass-triggered preparative HPLC (Mobile phase: A=0.1% TFA/H$_2$O, B=0.1% TFA/MeCN; Gradient: B=10-90%; 12 min; Column: C18) to give the title compound (1 mg, 3.2 μmol, 2% yield) as an amorphous solid.

MS (ES$^+$) C$_{16}$H$_{15}$F$_3$N$_2$O requires: 308, found: 309 [M+H]$^+$.

$^1$H NMR (500 MHz, CDCl$_3$) δ 6.95-6.93 (m, 1H), 6.72-6.66 (m, 3H), 5.31 (dd, J=11.9, 5.0 Hz, 1H), 4.40 (d, J=47.6 Hz, 2H), 3.37 (ddd, J=18.7, 12.0, 1.7 Hz, 1H), 2.73 (ddd, J=18.8, 5.0, 1.8 Hz, 1H), 2.18 (s, 6H).

Example 6

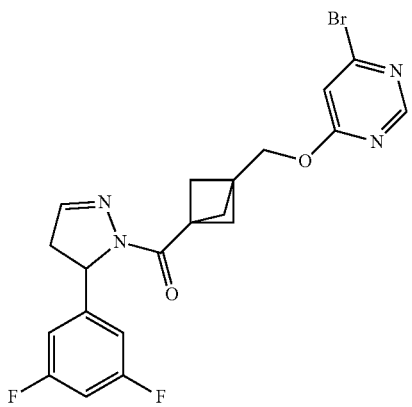 [SMILES: O=C(N1N=CCC1c1cc(F)cc(F)c1)C12CC(COc3cc(Cl)ncn3)(C1)C2]

(3-(((6-Bromopyrimidin-4-yl)oxy)methyl)bicyclo[1.1.1]pentan-1-yl)(5-(3,5-difluorophenyl)-4,5-dihydro-1H-pyrazol-1-yl)methanone

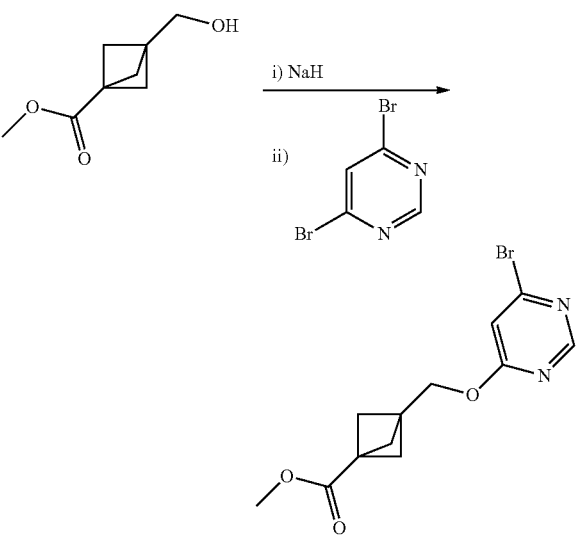

Methyl 3-(((6-bromopyrimidin-4-yl)oxy)methyl)bicyclo[1.1.1]pentane-1-carboxylate To a solution of methyl 3-(hydroxymethyl)bicyclo[1.1.1]pentane-1-carboxylate (0.13 g, 0.89 mmol) in THF (4.4 ml) at 0° C. was added NaH in one portion, and the mixture was stirred at 0° C. for 15 min. 4,6-Dibromopyrimidine (0.31 g, 1.3 mmol) was then added and reaction was stirred at 0° C. for 5 min and then warmed to RT. More NaH and 4,6-dibromo-pyrimidine was added at 0° C. and the reaction was allowed to proceed overnight. The reaction was cooled to 0° C., H$_2$O was added, and the resulting mixture was diluted and extracted with EtOAc. The combined organic layers were dried concentrated, and purified by flash chromatography to give the title compound (60 mg, 0.19 mmol, 21% yield) as a colorless oil. $^1$H NMR (600 MHz, DMSO-d$_6$) δ 8.60 (d, J=0.9 Hz, 1H), 7.35 (d, J=1.0 Hz, 1H), 4.43 (s, 2H), 3.60 (s, 3H), 1.99 (s, 6H).

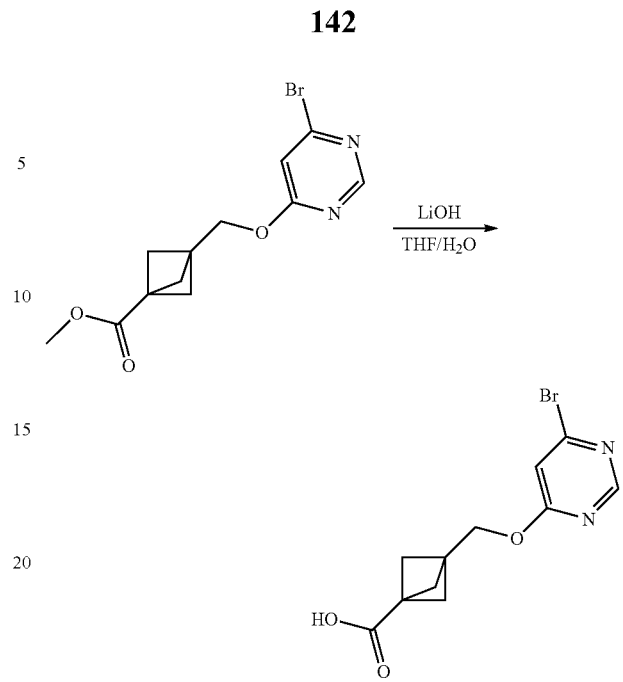

3-(((6-Bromopyrimidin-4-yl)oxy)methyl)bicyclo[1.1.1]pentane-1-carboxylic acid (Intermediate III)

To a solution of the product from the previous step (60 mg, 0.19 mmol) in THF (0.76 ml) was added H$_2$O (0.19 ml) and LiOH·H$_2$O (4.5 mg, 0.19 mmol) and the solution was stirred at 0° C. for 10 minutes and then warmed to RT. Once all starting material was consumed (determined by TLC), the reaction was cooled to 0° C. and 1M HCl (0.38 ml, 0.38 mmol) was added until pH was below 3. The solution was concentrated to obtain the title compound (57 mg, 0.19 mmol, 100% yield) as a white solid which was used without further purification. MS (ES$^+$) C$_{11}$H$_{11}$BrN$_2$O$_3$ requires: 298, found: 299 [M+H]$^+$.

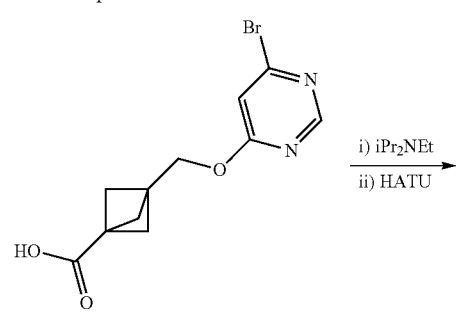

143
-continued

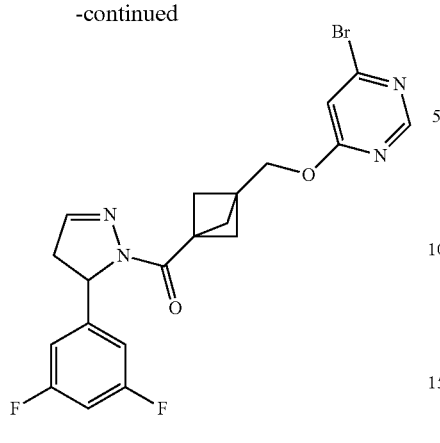

Step 3: (3-(((6-Bromopyrimidin-4-yl)oxy)methyl) bicyclo[1.1.1]pentan-1-yl)(5-(3,5-difluorophenyl)-4, 5-dihydro-1H-pyrazol-1-yl)methanone (Example 6)

To a flask containing Intermediate III (57 mg, 0.19 mmol) in DMF (0.63 ml) was added iPr$_2$NEt (73 µl, 0.42 mmol) and 5-(3,5-difluorophenyl)-4,5-dihydro-1H-pyrazole (55 mg, 0.30 mmol), and the mixture was stirred at 0° C. for 5 min. To the solution was added HATU (95 mg, 0.24 mmol) and the reaction was stirred at RT overnight. The solution was diluted in EtOAc and H$_2$O, partitioned, and the organic phase was washed with H$_2$O and brine. The aqueous phases were combined and extracted with EtOAc twice. The organic layers were combined, dried, concentrated, adsorbed onto silica gel, and purified via flash chromatography (10-25%, EtOAc in hexanes) to give the title compound (29 mg, 0.06 mmol, 32% yield) as a yellow solid.

MS (ES$^+$) C$_{20}$H$_{17}$BrF$_2$N$_4$O$_2$ requires: 462, found: 463 [M+H]$^+$.

$^1$H NMR (300 MHz, CD$_3$OD) δ 8.50 (d, J=0.9 Hz, 1H), 7.17 (d, J=0.9 Hz, 1H), 7.15-7.11 (m, 1H), 6.88-6.79 (m, 1H), 6.79-6.71 (m, 2H), 5.35 (dd, J=11.8, 4.8 Hz, 1H), 4.47 (s, 2H), 3.45 (ddd, J=19.0, 11.8, 1.6 Hz, 1H), 2.75 (ddd, J=19.0, 4.9, 1.8 Hz, 1H), 2.17 (s, 6H).

Example 7

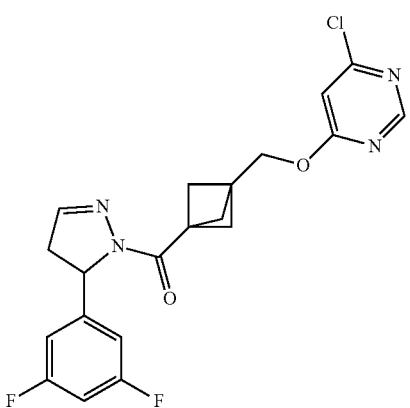

144

(3-(((6-Chloropyrimidin-4-yl)oxy)methyl)bicyclo [1.1.1]pentan-1-yl)(5-(3,5-difluorophenyl)-4,5-di-hydro-1H-pyrazol-1-yl)methanone

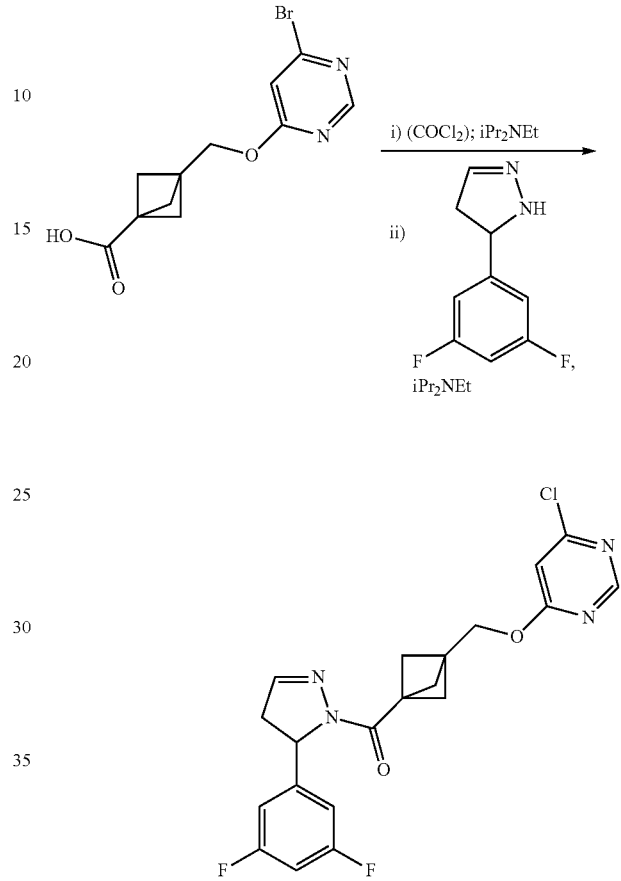

To a solution of Intermediate III (40 mg, 0.13 mmol) in THF (0.66 ml) was added iPr$_2$NEt (82 µl, 0.46 mmol) and one drop of DMF. The reaction was then cooled to 0° C. Oxalyl chloride (50 mg, 0.40 mmol) was then added dropwise and stirred in the ice bath for 15 min. The flask was then warmed to RT and monitored by LCMS for consumption of the acid. The solution was then concentrated, redissolved in THF (0.50 ml), cooled to 0° C., iPr$_2$NEt (1.0 eq) and then a solution of 5-(3,5-difluorophenyl)-4,5-dihydro-1H-pyrazole (18 µl, 0.14 mmol) in THF was then added dropwise. The reaction was stirred for 72 h. The reaction was then diluted in EtOAc and H$_2$O and let stir for 5 min. The organic layers was removed and the aqueous layer was extracted with EtOAc. The organic layers were combined, dried with MgSO$_4$, and concentrated. The residue was adsorbed onto silica gel and purified via flash chromatography (20-70%, EtOAc in hexanes) to give the title compound (52 mg, 0.12 mmol, 93% yield) as an orange solid.

MS (ES$^+$) C$_{20}$H$_{17}$ClF$_2$N$_4$O$_2$ required: 418, found: 419 [M+H]$^+$.

$^1$H NMR (500 MHz, CDCl$_3$) δ 8.55 (d, J=0.9 Hz, 1H), 6.95-6.93 (m, 1H), 6.80 (d, J=0.9 Hz, 1H), 6.72-6.64 (m, 3H), 5.31 (dd, J=11.9, 4.9 Hz, 1H), 4.44 (s, 2H), 3.37 (ddd, J=18.7, 11.9, 1.7 Hz, 1H), 2.73 (ddd, J=18.8, 5.0, 1.8 Hz, 1H), 2.18 (s, 6H).

Example 8

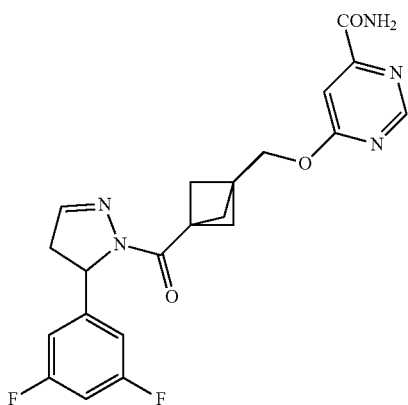 [SMILES: NC(=O)c1cc(OCC23CC(C(=O)N4N=CCC4c4cc(F)cc(F)c4)(C2)C3)ncn1]

6-((3-(5-(3,5-Difluorophenyl)-4,5-dihydro-1H-pyrazole-1-carbonyl)bicyclo[1.1.1]pentan-1-yl)methoxy)pyrimidine-4-carboxamide

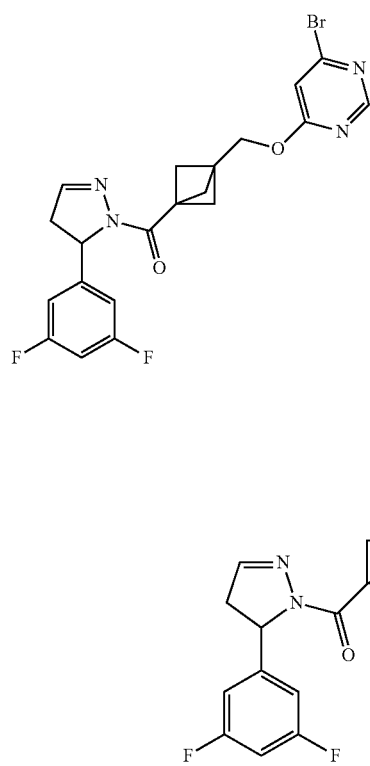

A solution of the Example 6 compound (18 mg, 0.03 mmol), $Zn(CN)_2$ (5.4 mg, 0.04 mmol), $Pd(PPh_3)_4$ (4.4 mg, 3.8 μmol), in degassed DMF (0.25 ml) was heated to 90° C. overnight. The reaction was stopped by cooling to RT and then molecular sieves were added, and 0.2 eq. of $Pd(PPh_3)_4$ and $Zn(CN)_2$ was added. The reaction was stirred at 90° C. overnight. The reaction was filtered and purified by mass-triggered preparative HPLC (Mobile phase: A=0.1% TFA/H$_2$O, B=0.1% TFA/MeCN; Gradient: B=10-90%; 12 min; Column: C18) to give the title compound (1 mg, 2.5 μmol, 6% yield) as an orange oil.

MS (ES+) $C_{21}H_{19}F_2N_5O_3$ requires: 427, found: 428 [M+H]+.

$^1$H NMR (500 MHz, CD$_3$OD) δ 8.77 (d, J=1.0 Hz, 1H), 7.42 (d, J=1.1 Hz, 1H), 7.15-7.11 (m, 1H), 6.86-6.79 (m, 1H), 6.78-6.71 (m, 2H), 5.38-5.32 (m, 1H), 4.51 (s, 2H), 3.45 (ddd, J=19.0, 11.8, 1.6 Hz, 1H), 2.74 (ddd, J=19.0, 4.8, 1.8 Hz, 1H), 2.18 (s, 6H).

Example 9

6-((3-(5-(3,5-Difluorophenyl)-4,5-dihydro-1H-pyrazole-1-carbonyl)bicyclo[1.1.1]pentan-1-yl)methoxy)pyrimidine-4-carbonitrile

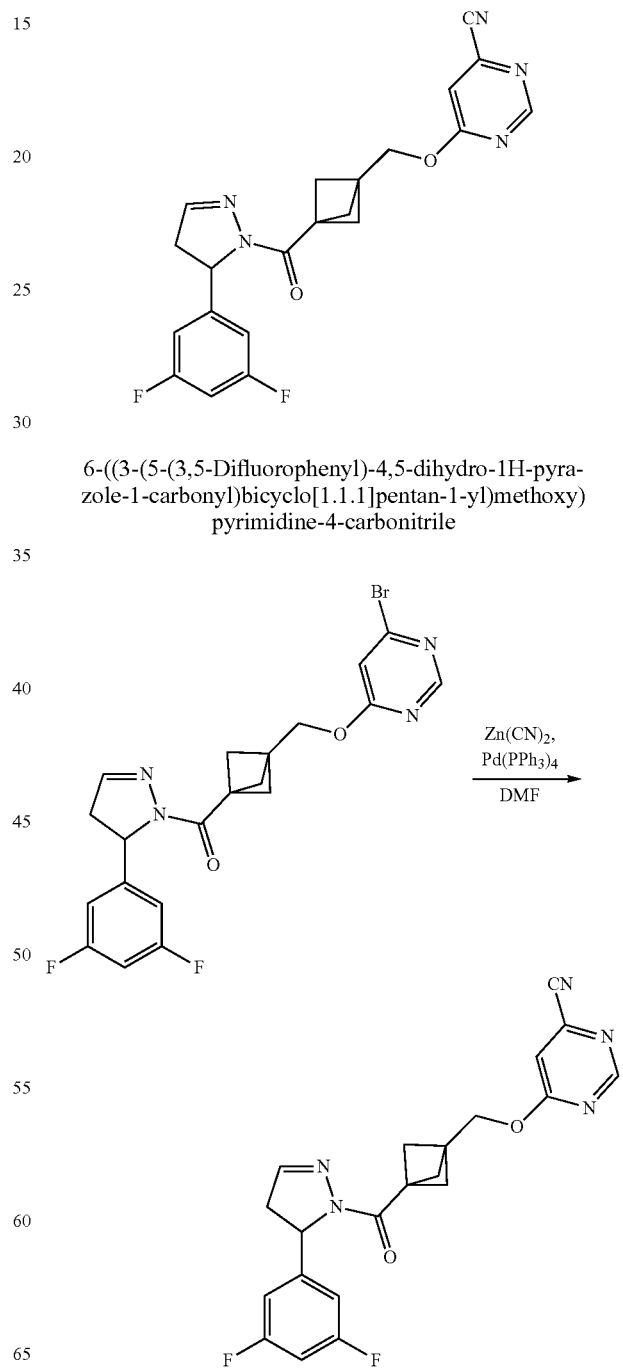

To a flask containing the Example 6 compound (30 mg, 0.06 mmol), Zn(CN)$_2$ (10 mg, 0.08 mmol), and Pd(PPh$_3$)$_4$ (7.4 mg, 6.4 µmol) was added DMF (0.32 ml) and the reaction was degassed and stirred at 110° C. for 24 h. The mixture was diluted with EtOAc and washed with H$_2$O, and the aqueous layer was extracted with EtOAc. The combined organic layers were washed with brine, dried, and concentrated. The residue was adsorbed onto silica gel and purified via flash chromatography (0-100% EtOAc, in hexanes) to give the title compound (1 mg, 2.4 µmol, 3.7% yield) as a colorless solid.

MS (ES$^+$) C$_{21}$H$_{17}$F$_2$N$_5$O$_2$ requires: 409, found: 410 [M+H]$^+$.

$^1$H NMR (500 MHz, CD$_3$OD) δ 8.77 (d, J=1.0 Hz, 1H), 7.42 (d, J=1.1 Hz, 1H), 7.15-7.11 (m, 1H), 6.86-6.79 (m, 1H), 6.78-6.70 (m, 2H), 5.35 (dd, J=11.8, 4.8 Hz, 1H), 4.51 (s, 2H), 3.45 (ddd, J=19.0, 11.8, 1.6 Hz, 1H), 2.74 (ddd, J=19.0, 4.8, 1.8 Hz, 1H), 2.18 (s, 6H).

Example 10

To a solution containing the Example 2 compound (12 mg, 0.03 mmol), iPr$_2$NEt (19 µl, 0.11 mmol) and one drop of DMF in THF (0.15 ml) at RT was added oxalyl chloride (9.6 µl, 0.11 mmol) and stirred for 30 min. The reaction was concentrated and redissolved in THF (0.15 ml). To the solution was added dimethylamine hydrochloride (7.6 mg, 0.09 mmol) and iPr$_2$NEt (19 µl, 0.11 mmol), and the mixture was stirred overnight. The residue was purified by mass-triggered preparative HPLC (Mobile phase: A=0.1% TFA/H$_2$O, B=0.1% TFA/MeCN; Gradient: B=10-90%; 12 min; Column: C18) to give the title compound (2.6 mg, 7.4 µmol, 19% yield) as a colorless amorphous material.

MS (ES$^+$) C$_{18}$H$_{19}$F$_2$N$_3$O$_2$ requires: 347, found: 348 [M+H]$^+$.

$^1$H NMR (600 MHz, CD$_3$OD) δ 7.27-7.21 (m, 1H), 6.95-6.87 (m, 1H), 6.86-6.78 (m, 2H), 5.42 (dd, J=11.8, 4.7 Hz, 1H), 3.58-3.48 (m, 1H), 3.21 (s, 3H), 2.99 (s, 3H), 2.87-2.79 (m, 1H), 2.57 (s, 6H).

Example 11

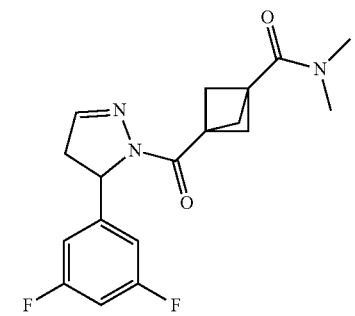

3-(5-(3,5-Difluorophenyl)-4,5-dihydro-1H-pyrazole-1-carbonyl)-N,N-dimethylbicyclo[1.1.1]pentane-1-carboxamide

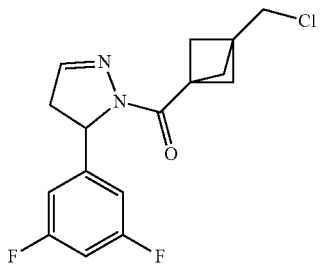 [SMILES: O=C(N1N=CCC1c1cc(F)cc(F)c1)C12CC(CCl)(C1)C2]

(3-(Chloromethyl)bicyclo[1.1.1]pentan-1-yl)(5-(3,5-difluorophenyl)-4,5-dihydro-1H-pyrazol-1-yl)methanone

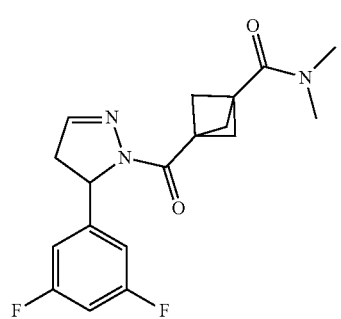

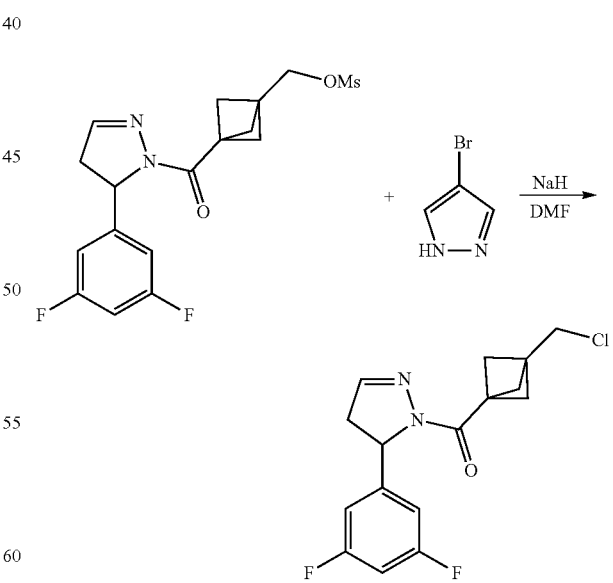

To a cooled 0° C. solution of 4-bromo-1H-pyrazole (38 mg, 0.26 mmol) and Intermediate II (50 mg, 0.13 mmol) in DMF (0.65 mL) was added NaH (60% mineral dispersion, 10 mg, 0.26 mmol), and the reaction was slowly warmed to RT. The reaction was then stirred at 65° C. for 1 h. The reaction was then concentrated, adsorbed onto silica gel, and purified via flash chromatography (0-100%, EtOAc in hexanes) to give the title compound (35 mg, 0.10 mmol, 83% yield) as a white solid.

MS (ES+) $C_{16}H_{15}ClF_2N_2O$ requires: 324, found: 325 [M+H]+.

$^1$H NMR (500 MHz, CD$_3$OD) δ 7.16-7.11 (m, 1H), 6.87-6.78 (m, 1H), 6.78-6.71 (m, 2H), 5.35 (dd, J=11.8, 4.8 Hz, 1H), 3.61 (s, 2H), 3.45 (ddd, J=19.0, 11.8, 1.6 Hz, 1H), 2.75 (ddd, J=19.0, 4.9, 1.8 Hz, 1H), 2.12 (s, 6H).

Example 12

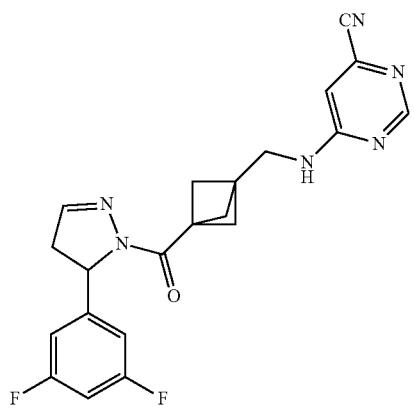 [SMILES: N#Cc1cc(NCC23CC(C(=O)N4N=CCC4c4cc(F)cc(F)c4)(C2)C3)ncn1]

6-(((3-(5-(3,5-Difluorophenyl)-4,5-dihydro-1H-pyrazole-1-carbonyl)bicyclo[1.1.1]pentan-1-yl)methyl)amino)pyrimidine-4-carbonitrile

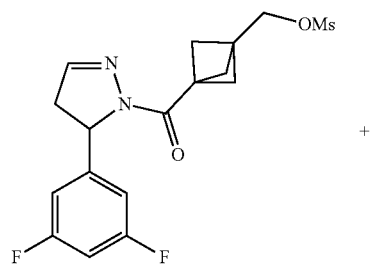

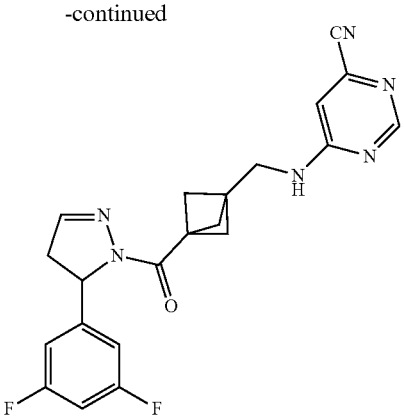

To a solution of Intermediate II (31 mg, 0.081 mmol) and 6-aminopyrimidine-4-carbonitrile (19 mg, 0.16 mmol) in DMF (0.40 ml) was added Cs$_2$CO$_3$ (52 mg, 0.16 mmol), and the mixture was stirred at RT until completion. The reaction was then purified by mass-triggered preparative HPLC (Mobile phase: A=0.1% TFA/H$_2$O, B=0.1% TFA/MeCN; Gradient: B=10-90%; 12 min; Column: C18) to give the title compound (5.2 mg, 0.01 mmol, 15% yield) as a white solid.

MS (ES+) $C_{21}H_{18}F_2N_6O$ requires: 408, found: 409 [M+H]+.

$^1$H NMR (500 MHz, CD$_3$OD) δ 8.46-8.38 (m, 1H), 7.16-7.08 (m, 1H), 6.93-6.88 (m, 1H), 6.85-6.79 (m, 1H), 6.76-6.70 (m, 2H), 5.34 (dd, J=11.8, 4.8 Hz, 1H), 3.58 (s, 2H), 3.47-3.40 (m, 1H), 2.77-2.70 (m, 1H), 2.09 (s, 6H).

Example 13

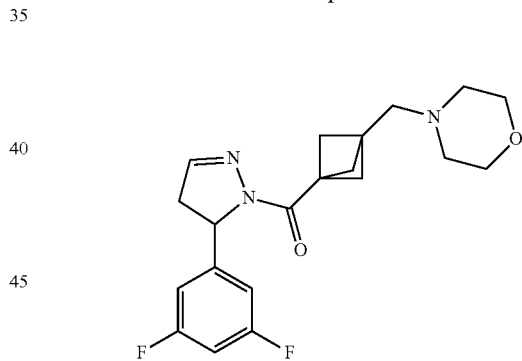

(5-(3,5-Difluorophenyl)-4,5-dihydro-1H-pyrazol-1-yl)(3-(morpholinomethyl)bicyclo[1.1.1]pentan-1-yl)methanone

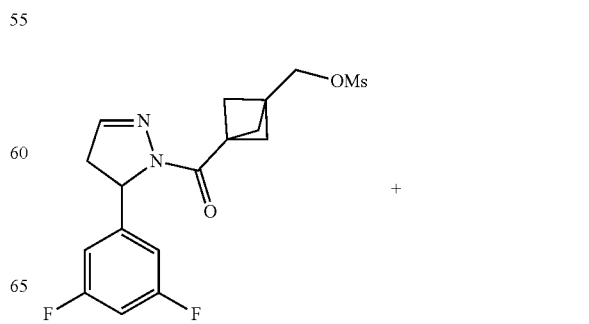

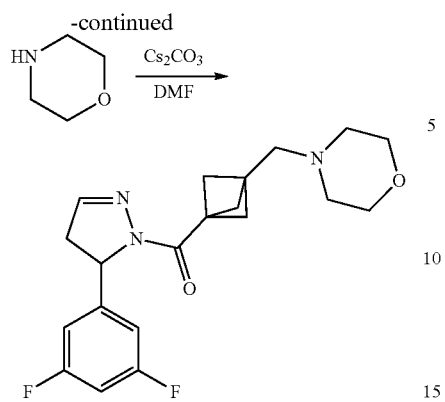
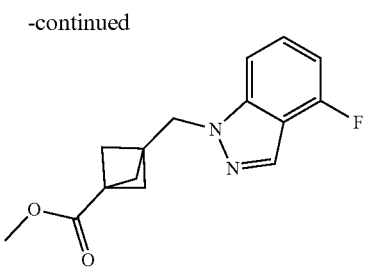

Methyl 3-((4-fluoro-1H-indazol-1-yl)methyl)bicyclo[1.1.1]pentane-1-carboxylate

To a solution of Intermediate II (20 mg, 0.05 mmol) and morpholine (5.4 µl, 0.06 mmol) in DMF (0.26 ml) was added $Cs_2CO_3$ (33 mg, 0.10 mmol) and the reaction was stirred at 45° C. overnight. The reaction mixture was filtered and purified by mass-triggered preparative HPLC (Mobile phase: A=0.1% TFA/$H_2O$, B=0.1% TFA/MeCN; Gradient: B=10-90%; 12 min; Column: C18) to give the title compound (4.9 mg, 0.01 mmol, 25% yield) as a white solid.

MS (ES$^+$) $C_{20}H_{23}F_2N_3O_2$ requires: 375, found: 376 [M+H]$^+$.

$^1$H NMR (500 MHz, CDCl$_3$) δ 6.99-6.94 (m, 1H), 6.74-6.61 (m, 3H), 5.28 (dd, J=11.9, 5.0 Hz, 1H), 4.04-3.94 (m, 4H), 3.67-3.58 (m, 2H), 3.38 (ddd, J=18.8, 11.9, 1.6 Hz, 1H), 3.21 (s, 2H), 2.97-2.86 (m, 2H), 2.74 (ddd, J=18.8, 4.9, 1.7 Hz, 1H), 2.33 (s, 6H).

To a solution of 4-fluoro-1H-indazole (0.26 g, 1.9 mmol) in DMF (3.2 ml) was added NaH (84 mg, 2.1 mmol) at 0° C., and the mixture was stirred until no more bubbling occurred. Then methyl 3-(bromomethyl)bicyclo[1.1.1]pentane-1-carboxylate (0.35 g, 1.6 mmol) in a solution of DMF (3.2 ml) was added to the reaction dropwise. The mixture was then stirred at 0° C. for 10 min, warmed to RT and stirred for 1 h. The reaction was quenched at 0° C. with sat NH$_4$Cl solution, then diluted with EtOAc. The organic layers were washed with H$_2$O twice and then brine. The combined organic layers were dried and concentrated. The residue was adsorbed onto silica gel and purified via flash chromatography (0-100%, EtOAc in hexanes) to give the title compound (0.12 g, 0.43 mmol, 26% yield) as the first eluting compound. Assignment as the 1-alkylated indazole isomer shown above was based on NMR comparison to Example 22. $^1$H NMR (600 MHz, CDCl$_3$) δ 8.06 (d, J=0.9 Hz, 1H), 7.33-7.27 (m, 1H), 7.13 (d, J=8.4 Hz, 1H), 6.78 (dd, J=9.9, 7.7 Hz, 1H), 4.49 (s, 2H), 3.62 (s, 3H), 1.96 (s, 6H).

Example 14

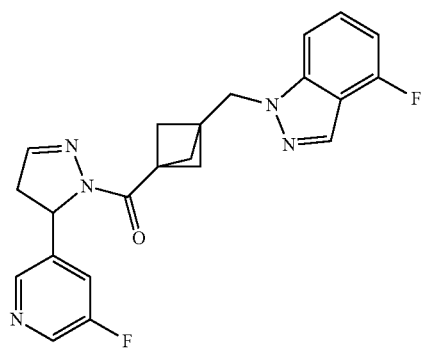 [SMILES: O=C(N1N=CCC1c1cncc(F)c1)C12CC(Cn3ncc4c(F)cccc43)(C1)C2]

(3-((4-Fluoro-1H-indazol-1-yl)methyl)bicyclo[1.1.1]pentan-1-yl)(5-(5-fluoropyridin-3-yl)-4,5-dihydro-1H-pyrazol-1-yl)methanone

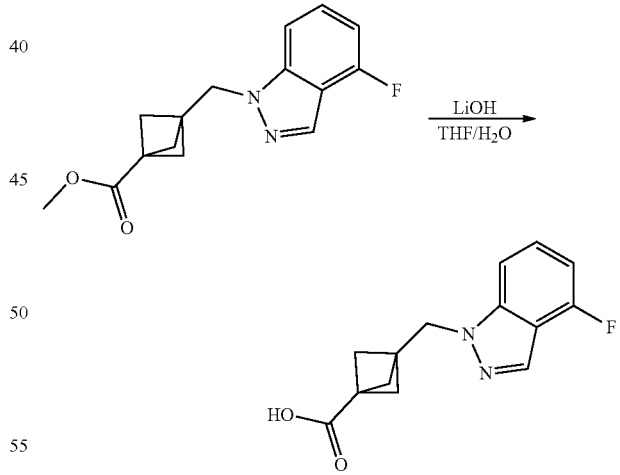

3-((4-Fluoro-1H-indazol-1-yl)methyl)bicyclo[1.1.1]pentane-1-carboxylic acid

To a solution of the product from the previous step (0.11 g, 0.40 mmol) in THF (1.0 ml) and H$_2$O (0.26 ml) was added LiOH (20 mg, 0.84 mmol). The mixture was stirred for 2 h at 0° C. and then warmed to RT. The reaction was quenched with 1 M HCl (0.40 ml, 0.40 mmol) and then the mixture was concentrated and azeotroped with MeCN to give the

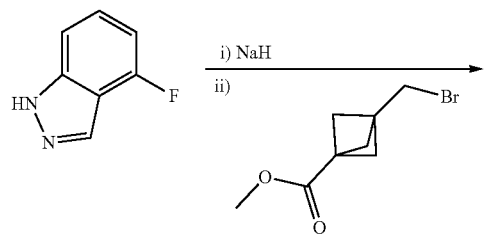

title compound (0.14 g, 0.53 mmol, 134% yield) as a white solid. The product was used without further purification. MS (ES⁺) $C_{14}H_{13}FN_2O_2$ requires: 260, found: 261 [M+H]⁺.

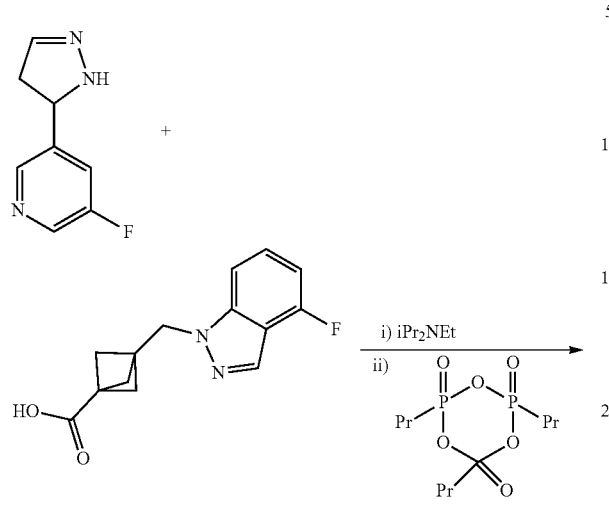

(3-((4-Fluoro-1H-indazol-1-yl)methyl)bicyclo[1.1.1]pentan-1-yl)(5-(5-fluoropyridin-3-yl)-4,5-dihydro-1H-pyrazol-1-yl)methanone (Example 14)

To a solution of the product from the previous step (20 mg, 0.07 mmol) and 3-(4,5-dihydro-1H-pyrazol-5-yl)-5-fluoropyridine (12 mg, 0.077 mmol) in DMF (0.25 ml) was added iPr₂NEt (40 µl, 0.23 mmol) and the reaction was stirred for 10 minutes. 2,4,6-Tripropyl-1,3,5,2,4,6-trioxatriphosphinane 2,4,6-trioxide (0.13 ml, 0.23 mmol, 50% solution in EtOAc) was then added, and the reaction was stirred overnight. The mixture was purified by mass-triggered preparative HPLC (Mobile phase: A=0.1% TFA/H₂O, B=0.1% TFA/MeCN; Gradient: B=10-90%; 12 min; Column: C18) to give the title compound (13 mg, 0.03 mmol, 42% yield) as a yellow oil.

MS (ES⁺) $C_{22}H_{19}F_2N_5O$ requires: 407, found: 408 [M+H]⁺.

¹H NMR (500 MHz, CDCl₃) δ 8.55-8.50 (m, 1H), 8.51-8.46 (m, 1H), 8.16 (d, J=0.9 Hz, 1H), 7.62-7.56 (m, 1H), 7.41-7.33 (m, 1H), 7.17 (d, J=8.4 Hz, 1H), 7.05-6.98 (m, 1H), 6.87-6.80 (m, 1H), 5.45 (dd, J=12.0, 5.3 Hz, 1H), 4.57 (s, 2H), 3.49 (ddd, J=19.1, 12.0, 1.7 Hz, 1H), 2.83 (ddd, J=19.1, 5.4, 1.8 Hz, 1H). 2.07 (s, 6H).

Example 15

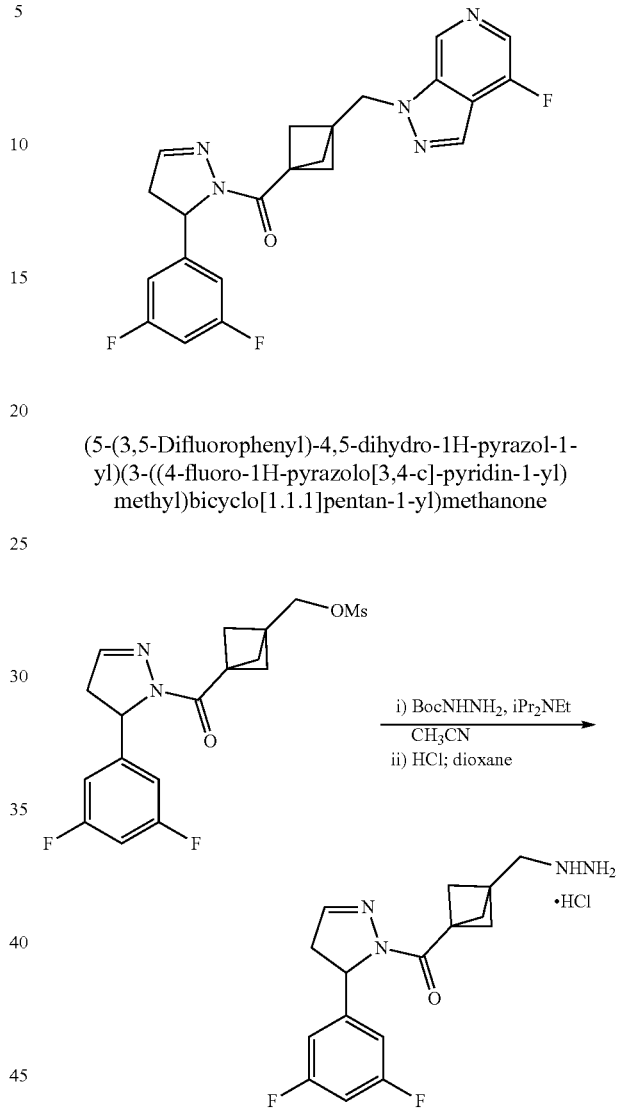

(5-(3,5-Difluorophenyl)-4,5-dihydro-1H-pyrazol-1-yl)(3-((4-fluoro-1H-pyrazolo[3,4-c]-pyridin-1-yl)methyl)bicyclo[1.1.1]pentan-1-yl)methanone (5-(3,5-difluorophenyl)-4,5-dihydro-1H-pyrazol-1-yl)(3-(hydrazineylmethyl)-bicyclo[1.1.1]pentan-1-yl)methanone hydrochloride (Intermediate IV)

To a solution of Intermediate II (80 mg, 0.20 mmol) in CH₃CN (0.20 ml) was added tert-butyl hydrazinecarboxylate (55 mg, 0.41 mmol) and iPr₂NEt (54 µl, 0.31 mmol). The reaction was stirred at 65° C. overnight. The reaction was then stirred at 85° C. for 1 h. The reaction was diluted with DCM, washed with H₂O and brine. The organic layer was dried and concentrated. The crude oil was then dissolved in 4M HCl in dioxane (0.41 ml), and the mixture was stirred overnight. The mixture was concentrated to give the title compound (90 mg, 0.25 mmol, 121% yield) as an orange solid that was used without further purification. MS (ES⁺) $C_{16}H_{18}F_2N_4O$ requires: 320, found: 321 [M+H]⁺.

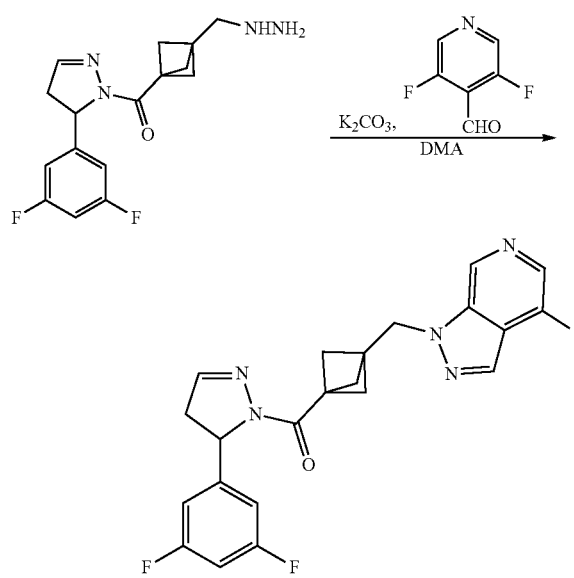 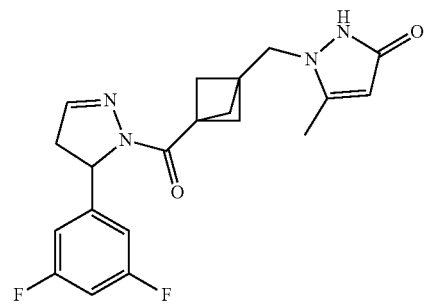

156

2-((3-(5-(3,5-difluorophenyl)-4,5-dihydro-1H-pyrazole-1-carbonyl)-bicyclo[1.1.1]pentan-1-yl)methyl)-5-methyl-1,2-dihydro-3H-pyrazol-3-one (16a) and

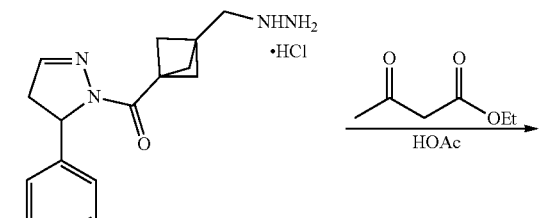

1-((3-(5-(3,5-difluorophenyl)-4,5-dihydro-1H-pyrazole-1-carbonyl)-bicyclo[1.1.1]pentan-1-yl)methyl)-5-methyl-1,2-dihydro-3H-pyrazol-3-one (16b)

(5-(3,5-Difluorophenyl)-4,5-dihydro-1H-pyrazol-1-yl)(3-((4-fluoro-1H-pyrazolo[3,4-c]pyridin-1-yl)methyl)bicyclo[1.1.1]pentan-1-yl)methanone (Example 15)

To a solution of the product from the previous step (40 mg, 0.12 mmol) and 3,5-difluoroisonicotinaldehyde (16 mg, 0.11 mmol) in DMA (0.22 ml) was added K₂CO₃ (39 mg, 0.28 mmol) and the reaction was stirred at 120° C. overnight. The reaction mixture was filtered and purified by mass-triggered preparative HPLC (Mobile phase: A=0.1% TFA/H₂O, B=0.1% TFA/MeCN; Gradient: B=10-90%; 12 min; Column: C18) to give the title compound (0.8 mg, 1.8 μmol, 1.6% yield) as an orange solid.

MS (ES⁺) $C_{22}H_{18}F_3N_5O$ requires: 425, found: 426 [M+H]⁺.

¹H NMR (500 MHz, CDCl₃) δ 8.97 (d, J=1.4 Hz, 1H), 8.28 (d, J=0.8 Hz, 1H), 8.19 (d, J=2.1 Hz, 1H), 6.90-6.88 (m, 1H), 6.71-6.64 (m, 1H), 6.64-6.59 (m, 2H), 5.26 (dd, J=11.9, 4.9 Hz, 1H), 4.70 (s, 2H), 3.33 (ddd, J=18.8, 11.9, 1.7 Hz, 1H), 2.70 (ddd, J=18.3, 4.7, 1.5 Hz, 1H), 2.10 (s, 6H).

Example 16

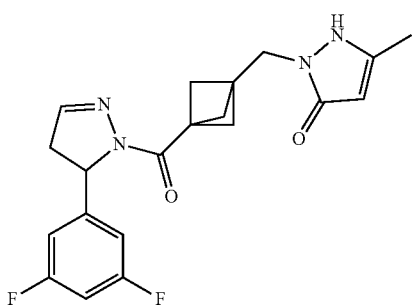 [SMILES: Cc1cc(=O)n(CC23CC(C(=O)N4N=CCC4c4cc(F)cc(F)c4)(C2)C3)[nH]1]

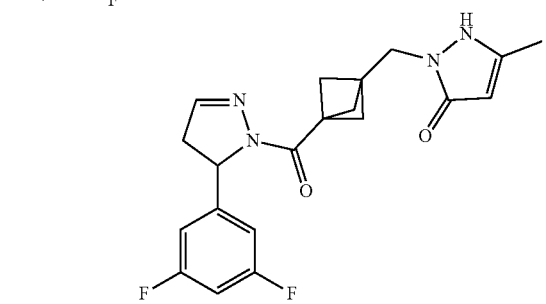

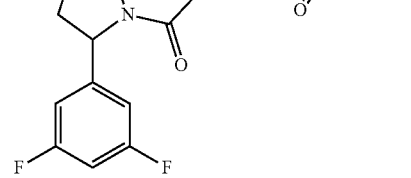

To a solution of Intermediate IV (93 mg, 0.26 mmol) in glacial AcOH (1.3 ml) was added ethyl 3-oxobutanoate (33 μl, 0.26 mmol), and the resulting solution was stirred at 100° C. for 24 h. The solvent was evaporated and the residue was purified by mass-triggered preparative HPLC (Mobile phase: A=0.1% TFA/H₂O, B=0.1% TFA/MeCN; Gradient: B=10-90%; 12 min; Column: C18) to give mixture of the title compounds as an off-white solid (8.1 mg, 0.021 mmol, 8% yield). MS (ES+) C20H20F2N4O2 requires: 386, found: 387 [M+H]+.

Example 17

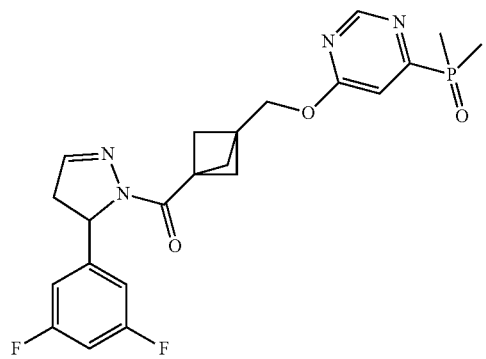 [SMILES: CP(C)(=O)c1cc(OCC23CC(C(=O)N4N=CCC4c4cc(F)cc(F)c4)(C2)C3)ncn1]

(5-(3,5-Difluorophenyl)-4,5-dihydro-1H-pyrazol-1-yl)(3-(((6-(dimethylphosphoryl)pyrimidin-4-yl)oxy)methyl)bicyclo[1.1.1]pentan-1-yl)methanone

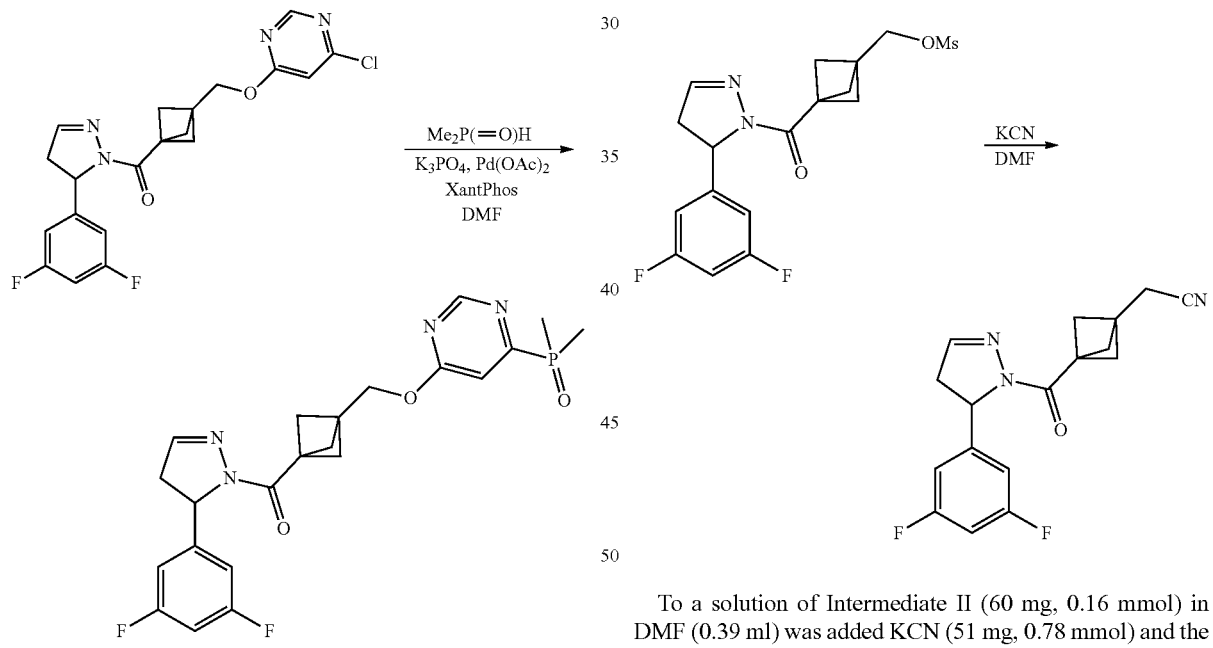

To a solution of the Example 7 compound (12 mg, 0.02 mmol) and dimethylphosphine oxide (3.4 mg, 0.04 mmol) in DMF (53 μl) was added K3PO4 (7.4 mg, 0.03 mmol), Pd(OAc)2 (0.65 mg, 2.9 μmol) and XantPhos (1.6 mg, 2.9 6 μmol). The reaction was purged with N2 and stirred at 120° C. overnight. The reaction was filtered through a CELITE® plug and purified by mass-triggered preparative HPLC (Mobile phase: A=0.1% TFA/H2O, B=0.1% TFA/MeCN; Gradient: B=10-90%; 12 min; Column: C18) to give the title compound (0.4 mg, 0.86 μmol, 3.0% yield) as an amorphous solid.

MS (ES+) C22H23F2N4O3P requires: 460, found: 461 [M+H]+.

1H NMR (500 MHz, CD3OD) δ 8.85 (d, J=1.3 Hz, 1H), 7.43-7.36 (m, 1H), 7.15-7.11 (m, 1H), 6.89-6.79 (m, 1H), 6.78-6.70 (m, 2H), 5.35 (dd, J=11.8, 4.8 Hz, 1H), 4.52 (s, 2H), 3.48-3.41 (m, 1H), 2.74 (ddd, J=19.0, 4.9, 1.8 Hz, 1H), 2.18 (s, 6H), 1.81 (s, 3H), 1.78 (s, 3H).

Example 18

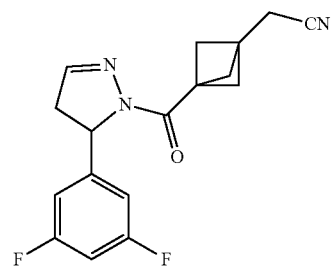

2-(3-(5-(3,5-Difluorophenyl)-4,5-dihydro-1H-pyrazole-1-carbonyl)-bicyclo[1.1.1]pentan-1-yl)acetonitrile To a solution of Intermediate II (60 mg, 0.16 mmol) in DMF (0.39 ml) was added KCN (51 mg, 0.78 mmol) and the resulting mixture was stirred at 65° C. overnight. The reaction was diluted with DCM and washed with H2O (2x) and brine. The aqueous layers were extracted with DCM. The combined organics were dried over MgSO4 and concentrated to give the title compound (40 mg, 0.12 mmol, 82% yield) as a light brown solid that was not further purified.

MS (ES+) C17H15F2N3O requires: 315, found: 316 [M+H]+.

1H NMR (DMSO-d6) δ: 7.20-7.27 (m, 1H), 7.04-7.17 (m, 1H), 6.74-6.87 (m, 2H), 5.25-5.40 (m, 1H), 3.38-3.49 (m, 1H), 2.80-2.90 (m, 2H), 2.66-2.77 (m, 1H), 2.02-2.12 (m, 6H).

Example 19

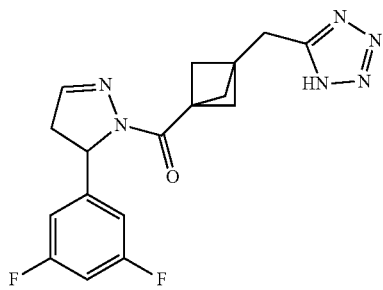 [SMILES: O=C(N1N=CCC1c1cc(F)cc(F)c1)C12CC(Cc3nnn[nH]3)(C1)C2]

(3-((1H-tetrazol-5-yl)methyl)bicyclo[1.1.1]pentan-1-yl)(5-(3,5-difluorophenyl)-4,5-dihydro-1H-pyrazol-1-yl)methanone

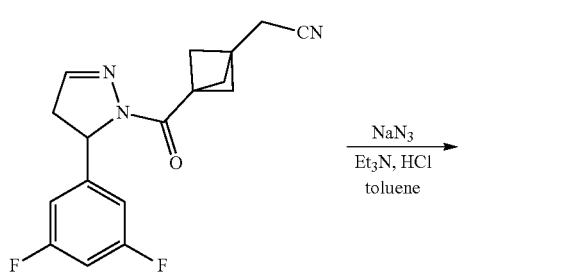

To a solution of the Example 18 compound (36 mg, 0.11 mmol) in toluene (0.40 ml) were added Et$_3$N (32 μl, 0.23 mmol), HCl (4M in dioxane, 57 μl, 0.23 mmol), and NaN$_3$ (15 mg, 0.23 mmol), and the resulting mixture was stirred at 120° C. overnight. To the reaction was added toluene (0.40 ml), and NaN$_3$ (15 mg), Et$_3$N (32 μl) and HCl (4M in dioxane, 57 μl) and the mixture was heated at 120° C. for an additional 7 h. The reaction was diluted with EtOAc, washed with aq. HCl (0.25 M), followed by brine, dried over MgSO$_4$, and concentrated to give the title compound (34 mg, 0.10 mmol, 83% yield) as an off white solid. MS (ES$^+$) C$_{17}$H$_{16}$F$_2$N$_6$O requires: 358, found: 359 [M+H]$^+$.

Example 20

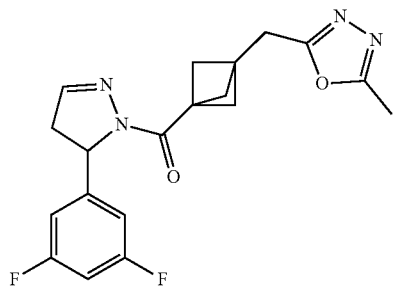 [SMILES: Cc1nnc(CC23CC(C(=O)N4N=CCC4c4cc(F)cc(F)c4)(C2)C3)o1]

(5-(3,5-Difluorophenyl)-4,5-dihydro-1H-pyrazol-1-yl)(3-((5-methyl-1,3,4-oxadiazol-2-yl)methyl)bicyclo[1.1.1]pentan-1-yl)methanone A solution of the Example 19 compound (34 mg, 0.095 mmol) in Ac$_2$O (0.60 ml, 6.4 mmol) was stirred at 150° C. overnight. The reaction was diluted with EtOAc and washed with sat'd NaHCO$_3$ and brine. The aqueous layers were extracted with EtOAc. The combined organics were dried over MgSO$_4$ and concentrated. The residue was purified by mass-triggered preparative HPLC (Mobile phase: A=0.1% TFA/H$_2$O, B=0.1% TFA/MeCN; Gradient: B=10-90%; 12 min; Column: C18) to give the title compound (2.1 mg, 5.64 μmol, 4.94% yield) as a yellow amorphous material semi-solid.

MS (ES$^+$) C$_{19}$H$_{18}$F$_2$N$_4$O$_2$ requires: 372, found: 373 [M+H]$^+$.

$^1$H NMR (DMSO-d$_6$) δ: 7.19-7.23 (m, 1H), 7.08-7.16 (m, 1H), 6.75-6.83 (m, 2H), 5.23-5.40 (m, 1H), 3.41 (ddd, J=18.9, 12.1, 1.4 Hz, 1H), 3.03-3.12 (m, 2H), 2.69 (ddd, J=18.9, 4.9, 1.8 Hz, 1H), 2.43-2.48 (m, 3H), 2.02-2.07 (m, 6H).

Examples 21 and 22

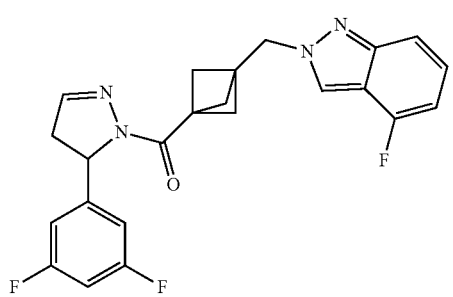 [SMILES: O=C(N1N=CCC1c1cc(F)cc(F)c1)C12CC(Cn3cc4c(F)cccc4n3)(C1)C2]

(5-(3,5-Difluorophenyl)-4,5-dihydro-1H-pyrazol-1-yl)(3-((4-fluoro-2H-indazol-2-yl)methyl)bicyclo[1.1.1]pentan-1-yl)methanone (Example 21) and

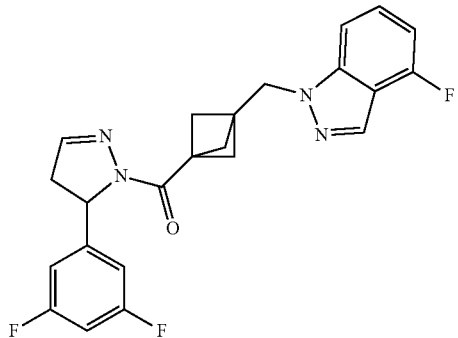 [SMILES: O=C(N1N=CCC1c1cc(F)cc(F)c1)C12CC(Cn3ncc4c(F)cccc43)(C1)C2]

(5-(3,5-Difluorophenyl)-4,5-dihydro-1H-pyrazol-1-yl)(3-((4-fluoro-1H-indazol-1-yl)methyl)bicyclo[1.1.1]pentan-1-yl)methanone (Example 22)

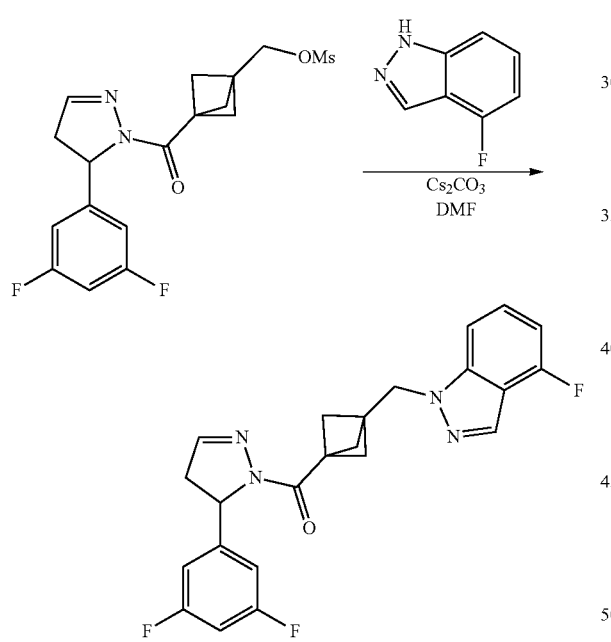

To a suspension of Intermediate II (20 mg, 0.052 mmol) in DMF (0.26 ml) were added 4-fluoro-1H-indazole (14 mg, 0.10 mmol) and $Cs_2CO_3$ (34 mg, 0.10 mmol) and the resulting mixture was stirred at RT overnight. The reaction mixture was acidified with TFA and filtered through a syringe filter. The filtrate was purified by mass-triggered preparative HPLC (Mobile phase: A=0.1% TFA/$H_2O$, B=0.1% TFA/MeCN; Gradient: B=50-90%; 12 min; Column: C18) to give two compounds.

The first eluting product, Example 21 was a brown solid (4.4 mg, 8.17 μmol, 16% yield) assigned as the TFA salt of the isomer shown, based on elution order and ROESY NMR analysis.

MS (ES$^+$) $C_{23}H_{19}F_3N_4O$ requires: 424, found: 425 [M+H]$^+$.

$^1$H NMR (500 MHz, CDCl$_3$) δ 7.97-7.94 (m, 1H), 7.52-7.47 (m, 1H), 7.23-7.17 (m, 1H), 6.90-6.87 (m, 1H), 6.74-6.65 (m, 2H), 6.65-6.61 (m, 2H), 5.27 (dd, J=11.9, 4.9 Hz, 1H), 4.55 (s, 2H), 3.33 (ddd, J=18.8, 11.9, 1.6 Hz, 1H), 2.69 (ddd, J=18.8, 4.9, 1.8 Hz, 1H), 2.14 (s, 6H).

The second eluting product, Example 22, was a brown solid (6.3 mg, 0.012 mmol, 22% yield) assigned as the TFA salt of the isomer shown, based on elution order.

MS (ES$^+$) $C_{23}H_{19}F_3N_4O$ requires: 424, found: 425 [M+H]

$^1$H NMR (500 MHz, CDCl$_3$) δ 8.09-8.03 (m, 1H), 7.32-7.27 (m, 1H), 7.17-7.13 (m, 1H), 6.88-6.84 (m, 1H), 6.80-6.75 (m, 1H), 6.69-6.64 (m, 1H), 6.63-6.58 (m, 2H), 5.26 (dd, J=11.9, 4.9 Hz, 1H), 4.52 (s, 2H), 3.31 (ddd, J=18.8, 12.0, 1.6 Hz, 1H), 2.68 (ddd, J=18.8, 5.0, 1.8 Hz, 1H), 2.07 (s, 6H).

Example 23

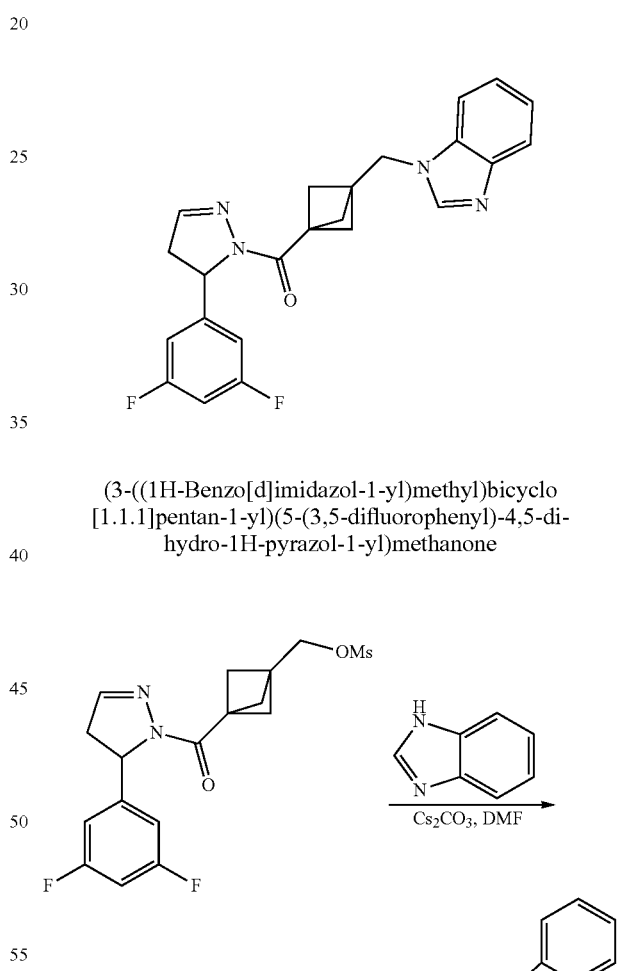

(3-((1H-Benzo[d]imidazol-1-yl)methyl)bicyclo[1.1.1]pentan-1-yl)(5-(3,5-difluorophenyl)-4,5-dihydro-1H-pyrazol-1-yl)methanone

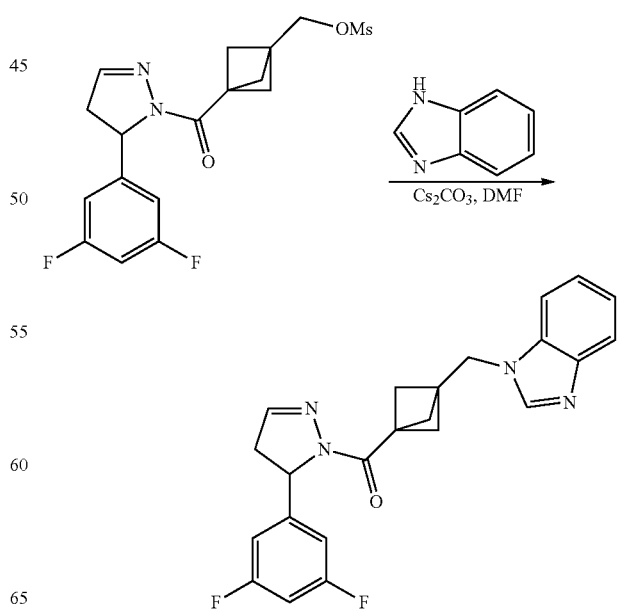

To a suspension of Intermediate II (20 mg, 0.052 mmol) in DMF (0.26 ml) were added 1H-benzo[d]imidazole (12 mg, 0.10 mmol) and Cs$_2$CO$_3$ (34 mg, 0.10 mmol) and the resulting mixture was stirred at 25° C. for 3 h. The reaction mixture was filtered through a syringe filter, and the filtrate was purified by mass-triggered preparative HPLC (Mobile phase: A=0.1% TFA/H$_2$O, B=0.1% TFA/MeCN; Gradient: B=10-90%; 12 min; Column: C18) to give the title compound as a TFA salt (17 mg, 0.032 mmol, 62% yield) as a white solid.

MS (ES$^+$) C$_{23}$H$_{20}$F$_2$N$_4$O requires: 406, found: 407 [M+H]$^+$.

$^1$H NMR (600 MHz, DMSO-d$_6$) δ 9.21 (s, 1H), 7.91 (d, J=8.0 Hz, 1H), 7.83 (d, J=7.8 Hz, 1H), 7.61-7.45 (m, 2H), 7.15 (s, 1H), 7.13-7.07 (m, 1H), 6.76 (d, J=7.4 Hz, 2H), 5.33-5.24 (m, 1H), 4.64 (s, 2H), 3B (1 m, 1H, under H$_2$O peak, implied) 2.72-2.61 (m, 1H), 1.99 (s, 6H).

Example 24

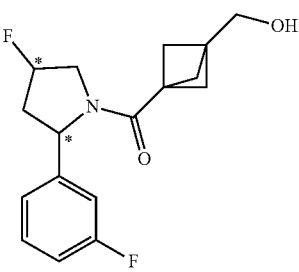 [SMILES: O=C(N1CC(F)CC1c1cccc(F)c1)C12CC(CO)(C1)C2]

(4-Fluoro-2-(3-fluorophenyl)pyrrolidin-1-yl)(3-(hydroxymethyl)bicyclo[1.1.1]pentan-1-yl)methanone

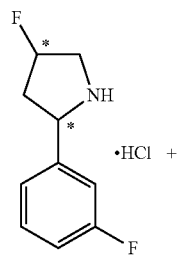

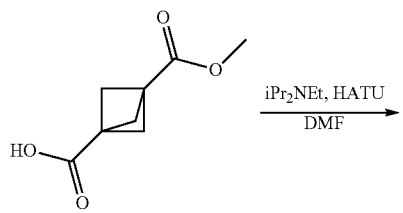

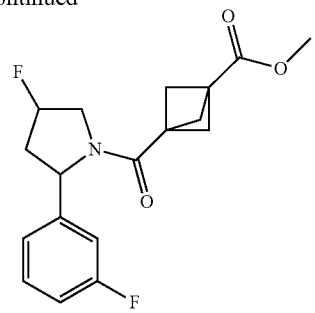

Methyl 3-(4-fluoro-2-(3-fluorophenyl)pyrrolidine-1-carbonyl)bicyclo[1.1.1]-pentane-1-carboxylate To a solution of 4-fluoro-2-(3-fluorophenyl)pyrrolidine hydrochloride (1.5 g, 6.8 mmol, mixture of diasteromers due to relative stereochemistry at starred chiral centers) in DMF (34 ml) were added 3-(methoxycarbonyl)bicyclo[1.1.1]pentane-1-carboxylic acid (1.2 g, 6.8 mmol), iPr$_2$NEt (3.6 ml, 20 mmol) and HATU (3.9 g, 10 mmol) and the resulting mixture was stirred at 25° C. overnight. The volatiles were removed under reduced pressure. The reaction mixture was diluted with EtOAc, washed with saturated NaHCO$_3$ and saturated NaCl, dried over Na$_2$SO$_4$, and concentrated under reduced pressure. The residue was adsorbed onto silica gel and purified via flash chromatography (0-100%, EtOAc in hexanes) to give the title compound as an orange foam solid. MS (ES$^+$) C$_{18}$H$_{19}$F$_2$NO$_3$ requires: 335, found: 336 [M+H]$^+$.

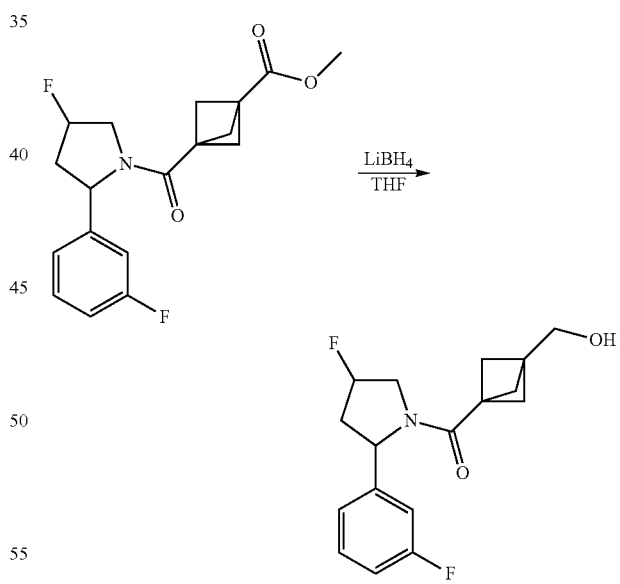

(4-Fluoro-2-(3-fluorophenyl)pyrrolidin-1-yl)(3-(hydroxymethyl)bicyclo[1.1.1]-pentan-1-yl)methanone (Example 24)

To a suspension of the product from the previous step (0.81 g, 2.4 mmol) in THF (4.0 ml) was added LiBH$_4$ (79 mg, 3.6 mmol), and the resulting mixture was stirred at 0° C. for 3 h. An additional 1.5 eq. of LiBH$_4$ was added at 0° C. and the reaction mixture was stirred for 6 h. The reaction mixture was quenched with the addition of 1 M HCl. The reaction mixture was diluted with EtOAc and washed with H₂O. The layers were separated, and the organic layer was washed with saturated NaCl, dried over Na₂SO₄, and concentrated under reduced pressure. The residue was adsorbed onto silica gel and purified via flash chromatography (0-100% DCM in (10:1:0.1 DCM:MeOH:NH₄OH) to give the title compound (0.54 g, 1.8 mmol, 73% yield) as a white solid.

MS (ES⁺) $C_{17}H_{19}F_2NO_2$ requires: 307, found: 308 [M+H]⁺.

¹H NMR (600 MHz, DMSO-d₆) δ 7.41-7.24 (m, 1H), 7.09-6.81 (m, 3H), 5.48-5.08 (m, 2H), 4.63-4.34 (m, 1H), 4.15-3.65 (m, 2H), 3.23-3.14 (m, 2H), 2.77-2.42 (m, 1H), 2.33-2.06 (m, 1H), 1.95 (s, 3H), 1.70-1.49 (m, 3H).

Example 25

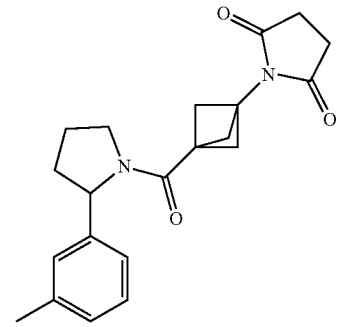 [SMILES: Cc1cccc(C2CCCN2C(=O)C23CC(N4C(=O)CCC4=O)(C2)C3)c1]

1-(3-(2-(m-Tolyl)pyrrolidine-1-carbonyl)bicyclo[1.1.1]pentan-1-yl)pyrrolidine-2,5-dione

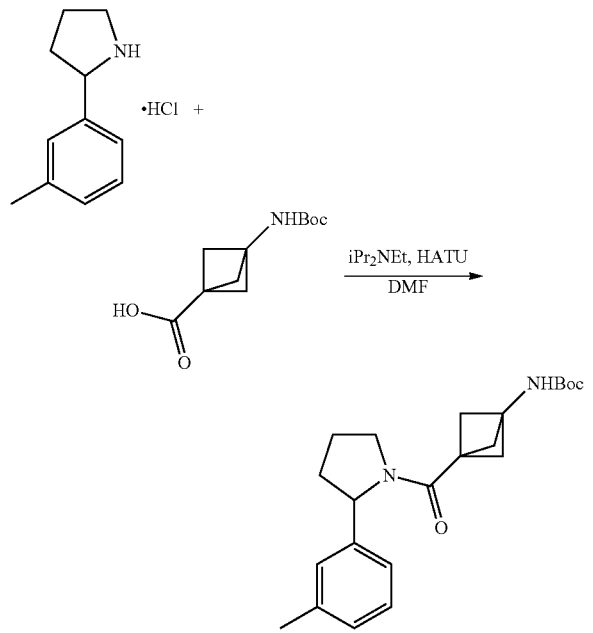

tert-Butyl (3-(2-(m-tolyl)pyrrolidine-1-carbonyl)bicyclo[1.1.1]pentan-1-yl)carbamate Synthesis of the title compound was accomplished from 3-((tert-butoxycarbonyl)-amino)bicyclo[1.1.1]pentane-1-carboxylic acid and 2-(m-tolyl)pyrrolidine using a procedure similar to that described for Example 24.

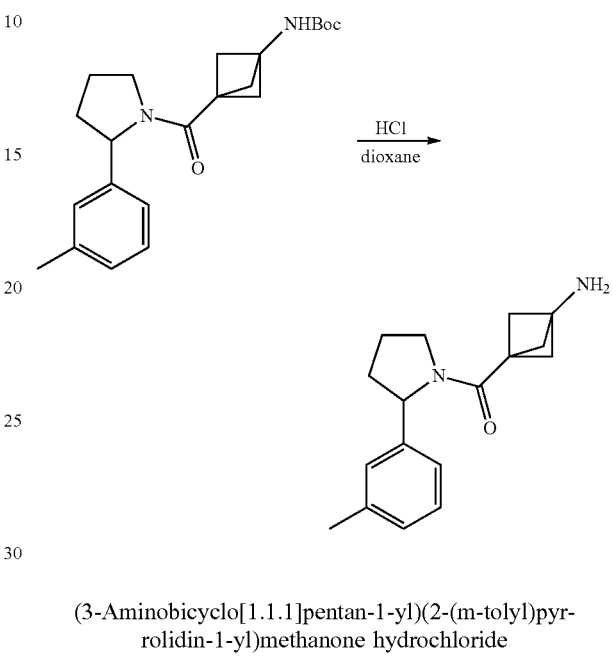

(3-Aminobicyclo[1.1.1]pentan-1-yl)(2-(m-tolyl)pyrrolidin-1-yl)methanone hydrochloride To a solution of the product from the previous step (0.13 g, 0.34 mmol) in MeOH (0.69 ml) was added dropwise 4 M HCl in dioxane (0.86 ml, 3.4 mmol) at 0° C. and the resulting mixture was stirred and allowed to warm to RT slowly. The volatiles were removed under reduced pressure to give the title compound as a grey solid. MS (ES⁺) $C_{17}H_{22}N_2O$ requires: 270, found: 271 [M+H]⁺.

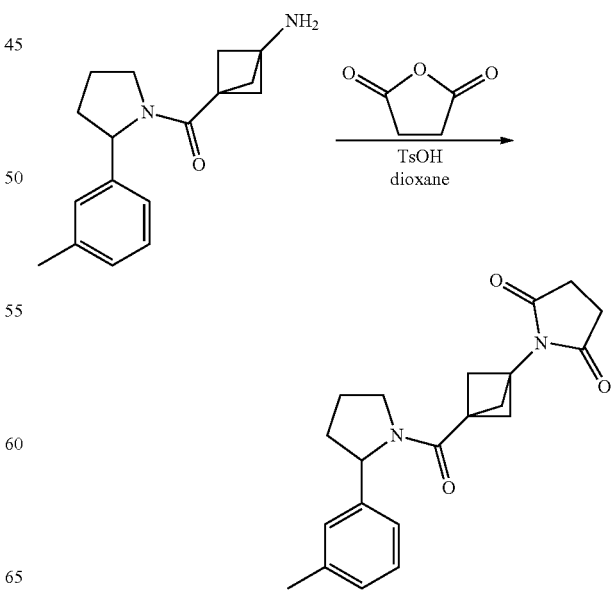

1-(3-(2-(m-Tolyl)pyrrolidine-1-carbonyl)bicyclo[1.1.1]pentan-1-yl)pyrrolidine-2,5-dione (Example 25)

To a solution of the product from the previous step (20 mg, 0.074 mmol) in dioxane (0.74 ml) was added succinic anhydride (8.1 mg, 0.081 mmol) and p-toluenesulfonic acid (1.4 mg, 7.4 µmol) and the resulting mixture was stirred at 80° C. for 6 h. The reaction mixture was concentrated under reduced pressure and the residue was purified by mass-triggered preparative HPLC (Mobile phase: A=0.1% TFA/H$_2$O, B=0.1% TFA/MeCN; Gradient: B=20-60%; 12 min; Column: C18) to give the title compound (2.4 mg, 6.8 µmol, 9% yield) as a white solid.

MS (ES$^+$) C$_{21}$H$_{24}$N$_2$O$_3$ requires: 352, found: 353 [M+H]$^+$.

$^1$H NMR (600 MHz, DMSO-d$_6$) δ 7.20 (dt, J=45.7, 7.6 Hz, 1H), 7.03 (dd, J=38.8, 7.5 Hz, 1H), 6.96-6.84 (m, 2H), 5.23-4.98 (m, 1H), 3.83 (td, J=9.0, 3.6 Hz, 1H), 3.49-3.42 (m, 1H), 2.58 (s, 2H), 2.53 (s, 3H), 2.47 (s, 2H), 2.36-2.07 (m, 7H), 1.94-1.74 (m, 2H), 1.69-1.52 (m, 1H).

Example 26

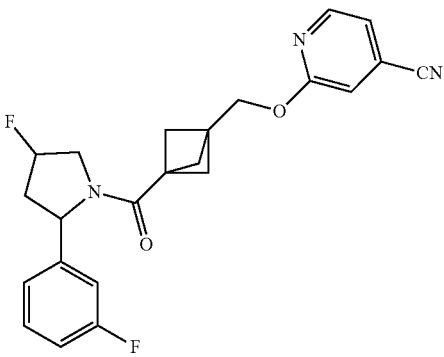 [SMILES: N#Cc1ccnc(OCC23CC(C(=O)N4CC(F)CC4c4cccc(F)c4)(C2)C3)c1]

2-((3-(4-Fluoro-2-(3-fluorophenyl)pyrrolidine-1-carbonyl)-bicyclo[1.1.1]pentan-1-yl)methoxy)isonicotinonitrile

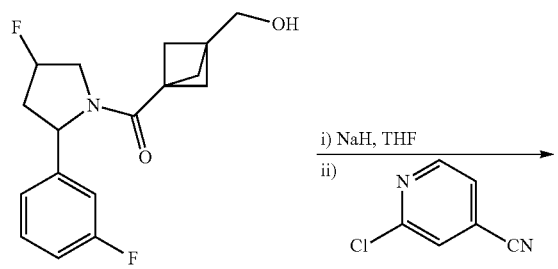

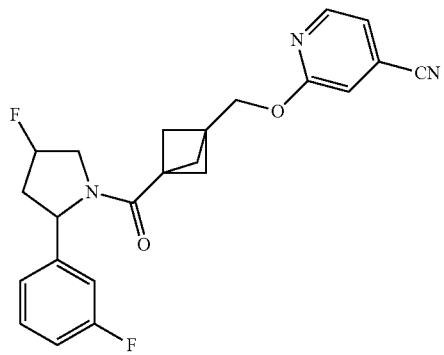

To a cooled 0° C. solution of the Example 24 compound (80 mg, 0.26 mmol) in THF (1.301 ml) was added NaH (60% mineral oil dispersion, 11 mg, 0.29 mmol). The resulting mixture was stirred at 0° C. for 0.5 h and 2-chloroisonicotinonitrile (43.3 mg, 0.312 mmol) was added. The reaction mixture was allowed to warm to RT overnight. The reaction mixture was diluted with EtOAc and washed with H$_2$O. The layers were separated, and the organic layer was washed with saturated NaCl, dried over Na$_2$SO$_4$, and concentrated under reduced pressure. The residue was adsorbed onto silica gel and purified via flash chromatography (0-100% DCM in (9:1:0.1 DCM:MeOH:NH$_4$OH). The product eluted in the void volume and was impure. The residue was repurified by mass-triggered preparative HPLC (Mobile phase: A=0.1% TFA/H$_2$O, B=0.1% TFA/MeCN; Gradient: B=40-80%; 20 min; Column: C18) to give the title compound (29.8 mg, 0.073 mmol, 28.0% yield) as a white solid.

MS (ES$^+$) C$_{23}$H$_{21}$F$_2$N$_3$O$_2$ requires: 409, found: 410 [M+H]$^+$.

$^1$H NMR (500 MHz, CDCl$_3$) δ 8.32-8.12 (m, 1H), 7.37-7.20 (m, 1H), 7.12-6.83 (m, 5H), 5.49-5.16 (m, 2H), 4.49-4.20 (m, 2H), 4.20-3.87 (m, 2H), 2.68-2.26 (m, 2H), 2.19 (s, 3H), 1.93-1.77 (m, 3H).

Example 27

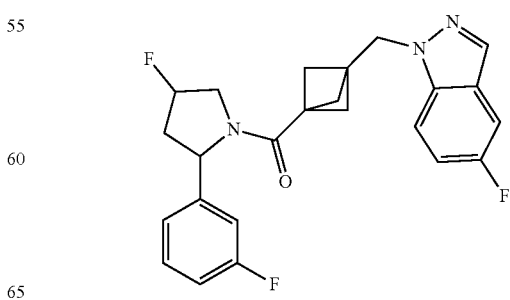

(3-((5-Fluoro-1H-indazol-1-yl)methyl)bicyclo[1.1.1]pentan-1-yl)(4-fluoro-2-(3-fluorophenyl)pyrrolidin-1-yl)methanone

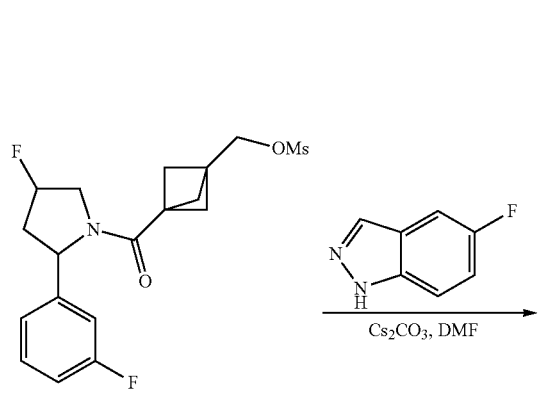

To a suspension of 3-(4-fluoro-2-(3-fluorophenyl)pyrrolidine-1-carbonyl)bicyclo-[1.1.1]pentan-1-yl)methyl methanesulfonate (40 mg, 0.10 mmol) in DMF (0.50 ml) were added 5-fluoro-1H-indazole (15 mg, 0.11 mmol) and Cs$_2$CO$_3$ (67 mg, 0.21 mmol). The resulting mixture was stirred at 25° C. for 4 h then 40° C. overnight. The volatiles were removed under reduced pressure. The residue was purified by mass-triggered preparative HPLC (Mobile phase: A=0.1% TFA/H$_2$O, B=0.1% TFA/MeCN; Gradient: B=30-70%; 20 min; Column: C18) to give the title compound as a TFA salt (21 mg, 0.040 mmol, 38% yield) as a white solid. The 1-N indazole isomer structure was confirmed by ROESY NMR and was the second product to elute.

MS (ES$^+$) C$_{24}$H$_{22}$F$_3$N$_3$O requires: 425, found: 426 [M+H]$^+$.

$^1$H NMR (500 MHz, DMSO-d$_6$) δ 8.10-7.93 (m, 1H), 7.74-7.56 (m, 1H), 7.56-7.47 (m, 1H), 7.36-7.19 (m, 2H), 7.04-6.82 (m, 3H), 5.41-5.12 (m, 2H), 4.64-4.37 (m, 2H), 4.08-3.64 (m, 2H), 2.69-2.34 (m, 1H), 2.27-2.01 (m, 1H), 1.97-1.88 (m, 3H), 1.63-1.47 (m, 3H).

Example 28

(3-((((6-Bromopyrimidin-4-yl)oxy)methyl)bicyclo[1.1.1]pentan-1-yl)(4-fluoro-2-(3-fluorophenyl)pyrrolidin-1-yl)methanone

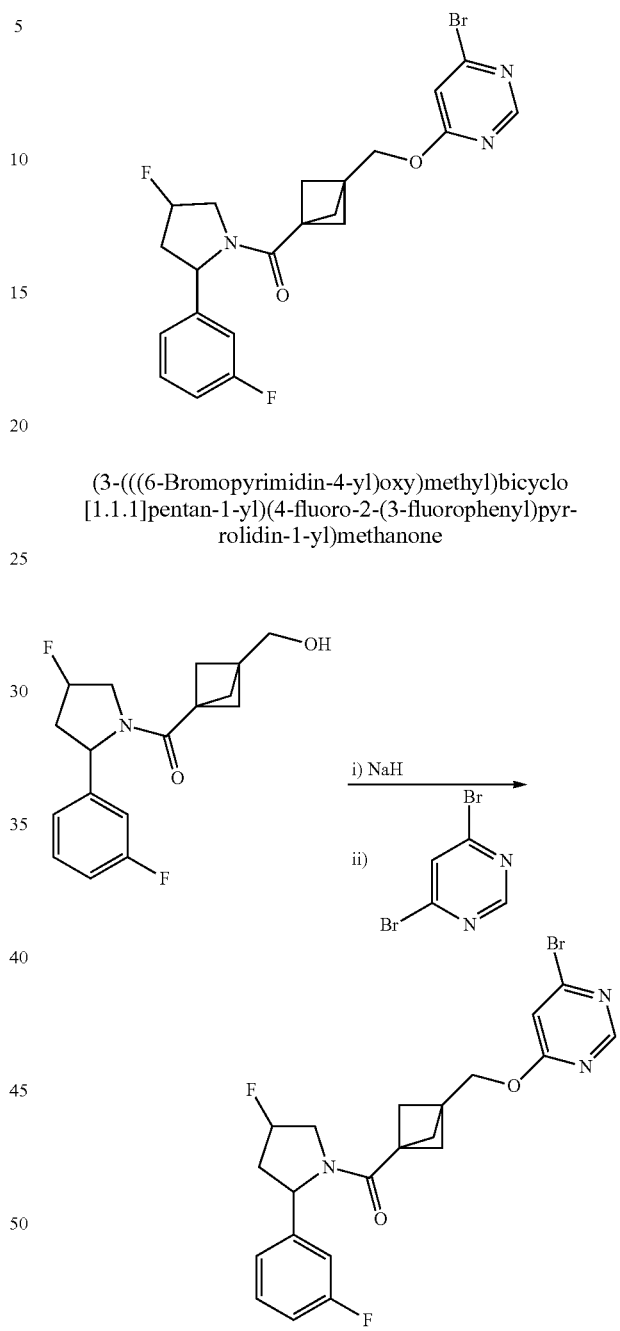

To a cooled 0° C. solution of the Example 24 compound (29 mg, 0.095 mmol) in THF (0.47 ml) under N$_2$ was added NaH (60% mineral oil dispersion, 4.2 mg, 0.10 mmol). The resulting mixture was stirred at 0° C. for 0.5 h, 4,6-dibromopyrimidine (27 mg, 0.11 mmol) was added and the reaction mixture was stirred and allowed to warm to RT overnight. The reaction mixture was stirred at 40° C. for 5 h. The reaction mixture was cooled to 0° C., additional NaH (60% mineral oil dispersion 4.2 mg, 0.10 mmol) was added under an N$_2$ atmosphere, stirred at 0° C. for 15 min, and additional 4,6-dibromopyrimidine (27 mg, 0.11 mmol) was added at 0° C. The reaction mixture was allowed to warm to RT, followed by stirring at 40° C. overnight. The reaction mixture was diluted with EtOAc, H₂O was added, and the layers were separated. The aqueous phase was extracted with EtOAc, and the combined organic layers were washed with H₂O, dried over Na₂SO₄, concentrated under reduced pressure, and purified by flash chromatography (0-50 9:1:0.1) DCM:MeOH:NH₄OH in DCM) to give the title compound (22 mg, 0.047 mmol, 50% yield) as a yellow solid.

MS (ES⁺) $C_{21}H_{20}BrF_2N_3O_2$ requires: 463/465, found: 464/466 [M+H]⁺.

¹H NMR (600 MHz, DMSO-d₆) δ 8.65-8.51 (m, 1H), 7.45-7.23 (m, 2H), 7.09-6.85 (m, 3H), 5.46-5.17 (m, 2H), 4.51-4.25 (m, 2H), 4.13-3.73 (m, 2H), 2.33-2.20 (m, 1H), 2.16-1.97 (m, 4H), 1.80-1.61 (m, 3H).

Examples 29 and 30

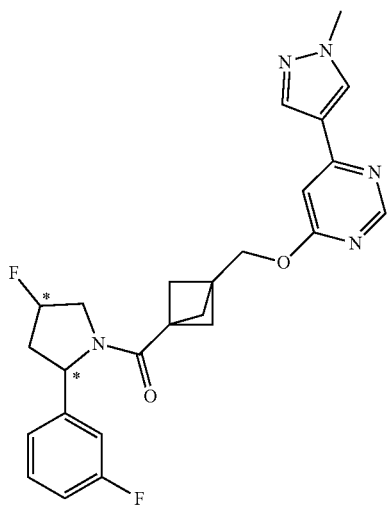 [SMILES: Cn1cc(-c2cc(OCC34CC(C(=O)N5CC(F)CC5c5cccc(F)c5)(C3)C4)ncn2)cn1]

(4-Fluoro-2-(3-fluorophenyl)pyrrolidin-1-yl)(3-(((6-(1-methyl-1H-pyrazol-4-yl)pyrimidin-4-yl)oxy)methyl)bicyclo[1.1.1]pentan-1-yl)methanone

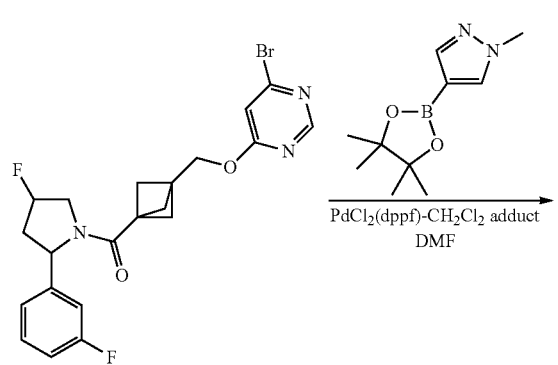

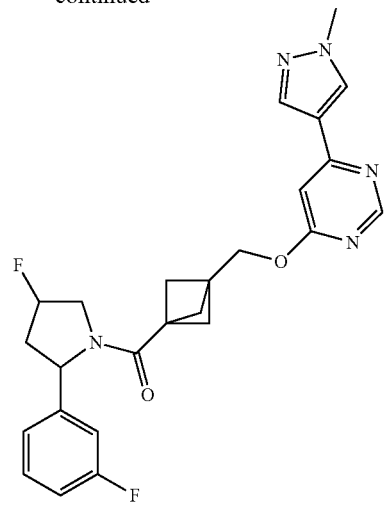

A solution of 1-methyl-4-(4,4,5,5-tetramethyl-1,3,2-dioxaborolan-2-yl)-1H-pyrazole (11 mg, 0.053 mmol), Na₂CO₃ (40 μl, 0.081 mmol) and the Example 28 compound (19 mg, 0.040 mmol) in DMF (0.4 ml) was purged with N₂, PdCl₂(dppf)-CH₂Cl₁₋₂ Adduct (3 mg, 4.0 μmol) was added, the mixture was purged with N₂ again, and the reaction mixture was stirred at 70° C. overnight. The reaction mixture was diluted with EtOAc and washed with saturated NaHCO₃. The layers were separated, and the organic layer was washed with saturated NaCl, dried over Na₂SO₄, concentrated under reduced pressure, and purified by flash chromatography (0-100% 9:1:0.1 DCM:MeOH:NH₄OH in DCM) to give the title compound (4.2 mg, 9.0 μmol, 22% yield) as two diastereomeric products, as white solids.

Example 29

MS (ES⁺) $C_{25}H_{25}F_2N_5O_2$ requires: 465, found: 466 [M+H]⁺.

¹H NMR (600 MHz, DMSO-d₆) δ 8.70-8.08 (m, 2H), 7.68-7.25 (m, 2H), 7.21-6.85 (m, 4H), 5.52-5.13 (m, 2H), 4.13-3.69 (m, 7H), 2.16-2.04 (m, 3H), 1.86-1.46 (m, 2H), 1.29-1.05 (m, 3H).

Example 30

MS (ES⁺) $C_{25}H_{25}F_2N_5O_2$ requires: 465, found: 465.

Example 31

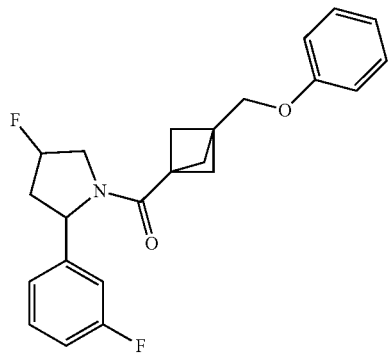 [SMILES: O=C(N1CC(F)CC1c1cccc(F)c1)C12CC(COc3ccccc3)(C1)C2]

173

(4-Fluoro-2-(3-fluorophenyl)pyrrolidin-1-yl) (3-(phenoxymethyl)-bicyclo[1.1.1]pentan-1-yl)methanone

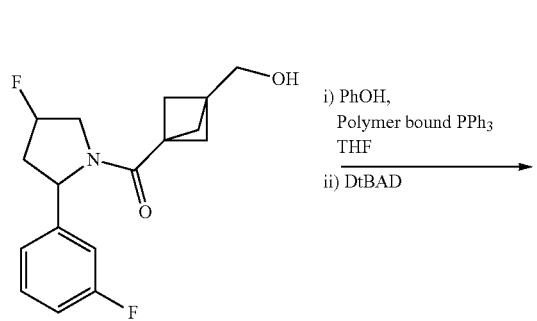

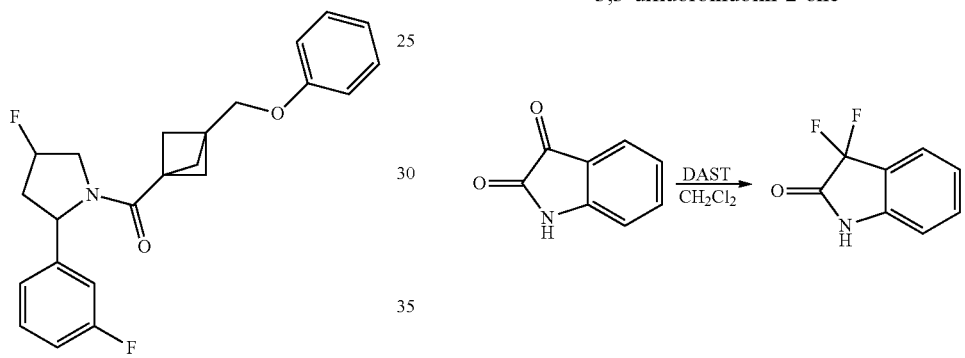

To a solution of the Example 24 compound (20 mg, 0.065 mmol) in THF (0.32 ml) were added phenol (8.0 mg, 0.085 mmol) and polymer bound PPh$_3$ (3 mmol/g, 43 mg, 0.13 mmol) and the resulting mixture was stirred at 25° C. for 10 min. DtBAD (19 mg, 0.085 mmol) was added and the reaction mixture was stirred at 25° C. overnight. The reaction mixture was filtered through CELITE®, and the filtrate was concentrated under reduced pressure. The residue was purified by flash chromatography (0-100% EtOAc in hexanes). The crude product was repurified by mass-triggered preparative HPLC (Mobile phase: A=0.1% TFA/H$_2$O, B=0.1% TFA/MeCN; Gradient: B=10-90%; 12 min; Column: C18) to give the title compound (13 mg, 0.033 mmol, 51% yield) as an orange solid.

MS (ES$^+$) C$_{23}$H$_{23}$F$_2$NO$_2$ requires: 383, found: 384 [M+H]$^+$.

$^1$H NMR (600 MHz, DMSO-d$_6$) δ 7.43-7.31 (m, 1H), 7.31-7.21 (m, 2H), 7.09-6.81 (m, 6H), 5.50-5.19 (m, 2H), 4.14-3.75 (m, 4H), 2.75-2.55 (m, 1H), 2.33-2.05 (m, 4H), 1.83-1.67 (m, 3H).

174

Example 32

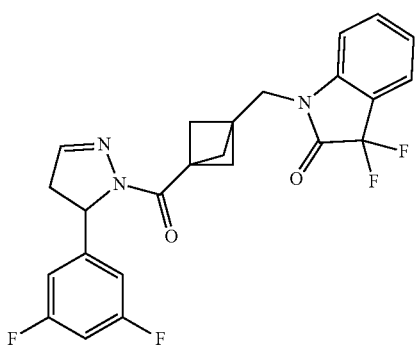 [SMILES: O=C(N1N=CCC1c1cc(F)cc(F)c1)C12CC(CN3C(=O)C(F)(F)c4ccccc43)(C1)C2]

1-((3-(5-(3,5-Difluorophenyl)-4,5-dihydro-1H-pyrazole-1-carbonyl)-bicyclo[1.1.1]pentan-1-yl)methyl)-3,3-difluoroindolin-2-one 3,3-Difluoroindolin-2-one To a cooled −78° C. suspension of indoline-2,3-dione (30 mg, 0.20 mmol) in DCM (1.3 ml) was added DAST (67 μl, 0.51 mmol), and the resulting mixture was stirred at −78° C. for 10 min then allowed to warm to RT overnight. The reaction was quenched with saturated NaHCO$_3$, diluted with DCM and H$_2$O, and the organic layer was separated, dried over MgSO$_4$, concentrated under reduced pressure, and purified by flash chromatography (0-50% EtOAc in hexanes) to give the title compound (24 mg, 0.14 mmol, 69% yield) as a yellow solid.: $^1$H NMR (500 MHz, CDCl$_3$) δ 7.78 (s, 1H), 7.56 (d, J=7.3 Hz, 1H), 7.49-7.41 (m, 1H), 7.20-7.14 (m, 1H), 6.93 (d, J=7.9 Hz, 1H).

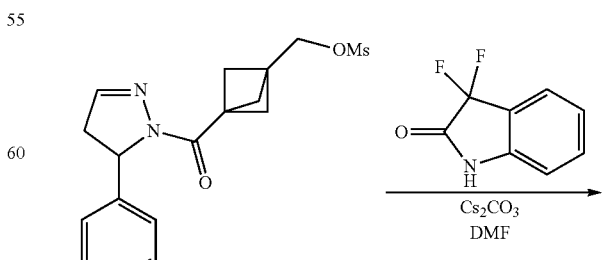

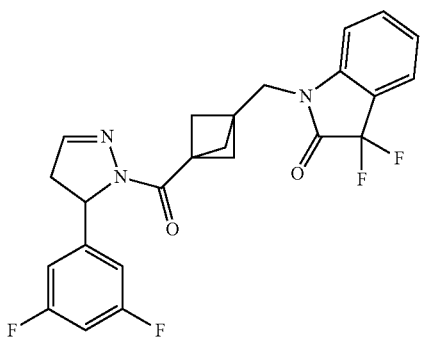

1-((3-(5-(3,5-Difluorophenyl)-4,5-dihydro-1H-pyrazole-1-carbonyl)bicyclo[1.1.1]-pentan-1-yl)methyl)-3,3-difluoroindolin-2-one (Example 32)

To a solution of Intermediate II (20 mg, 0.052 mmol) in DMF (0.26 ml) were added 3,3-difluoroindolin-2-one (9.7 mg, 0.057 mmol) and $Cs_2CO_3$ (17 mg, 0.052 mmol) and the resulting mixture was stirred at 25° C. for overnight. The reaction mixture was acidified with TFA, filtered through a syringe filter, and purified by mass-triggered preparative HPLC (Mobile phase: A=0.1% TFA/$H_2O$, B=0.1% TFA/MeCN; Gradient: B=40-80%; 12 min; Column: C18) to give the title compound (13 mg, 0.028 mmol, 53% yield) as a white solid.

MS (ES+) $C_{24}H_{19}F_4N_3O_2$ requires: 457, found: 458 [M+H]+.

1H NMR (500 MHz, CDCl3) δ 7.58-7.52 (m, 1H), 7.51-7.43 (m, 1H), 7.20-7.13 (m, 1H), 6.93-6.85 (m, 2H), 6.71-6.64 (m, 1H), 6.64-6.59 (m, 2H), 5.32-5.21 (m, 1H), 3.83 (d, J=2.2 Hz, 2H), 3.40-3.28 (m, 1H), 2.75-2.65 (m, 1H), 2.15 (s, 6H).

Example 33

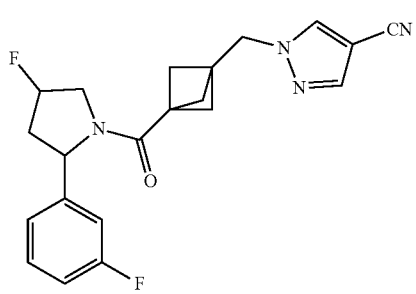 [SMILES: N#Cc1cnn(CC23CC(C(=O)N4CC(F)CC4c4cccc(F)c4)(C2)C3)c1]

1-((3-(4-Fluoro-2-(3-fluorophenyl)pyrrolidine-1-carbonyl)-bicyclo[1.1.1]pentan-1-yl)methyl)-1H-pyrazole-4-carbonitrile

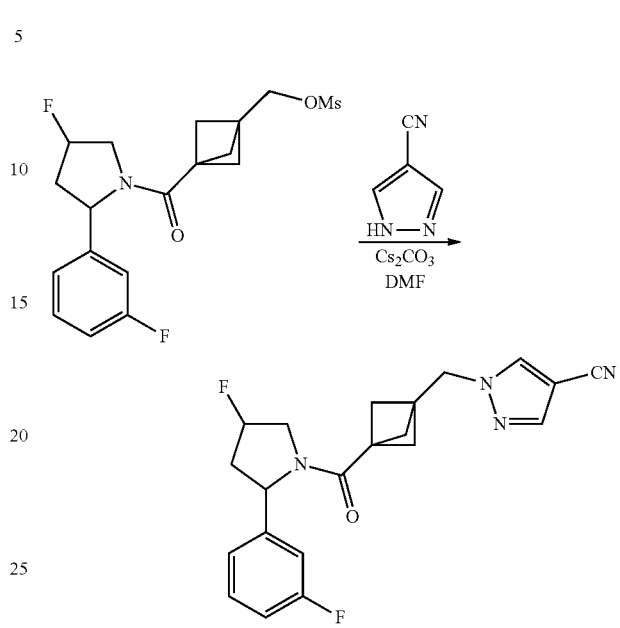

To a suspension of (3-(4-fluoro-2-(3-fluorophenyl)pyrrolidine-1-carbonyl)-bicyclo[1.1.1]pentan-1-yl)methyl methanesulfonate (20 mg, 0.052 mmol) in DMF (0.50 ml) were added 1H-pyrazole-4-carbonitrile (9.6 mg, 0.10 mmol) and $Cs_2CO_3$ (34 mg, 0.10 mmol). The resulting mixture was stirred at 25° C. for 4 h and then at 40° C. overnight. The volatiles were removed under reduced pressure. The residue was purified by mass-triggered preparative HPLC (Mobile phase: A=0.1% TFA/$H_2O$, B=0.1% TFA/MeCN; Gradient: B=30-70%; 20 min; Column: C18) to give the title compound (9.1 mg, 0.024 mmol, 46% yield) as a white solid.

MS (ES+) $C_{21}H_{20}F_2N_4O$ requires: 382, found: 383 [M+H]+.

1H NMR (600 MHz, DMSO-d6) δ 8.63-8.38 (m, 1H), 8.15-7.95 (m, 1H), 7.44-7.23 (m, 1H), 7.08-6.85 (m, 3H), 5.45-5.14 (m, 2H), 4.39-4.13 (m, 2H), 4.07-3.70 (m, 2H), 2.78-2.53 (m, 1H), 2.24-2.02 (m, 1H), 1.97 (d, J=4.1 Hz, 3H), 1.69-1.47 (m, 3H).

Example 34

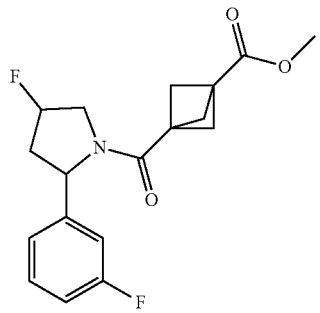

177

Methyl 3-(4-fluoro-2-(3-fluorophenyl)pyrrolidine-1-carbonyl)-bicyclo[1.1.1]pentane-1-carboxylate

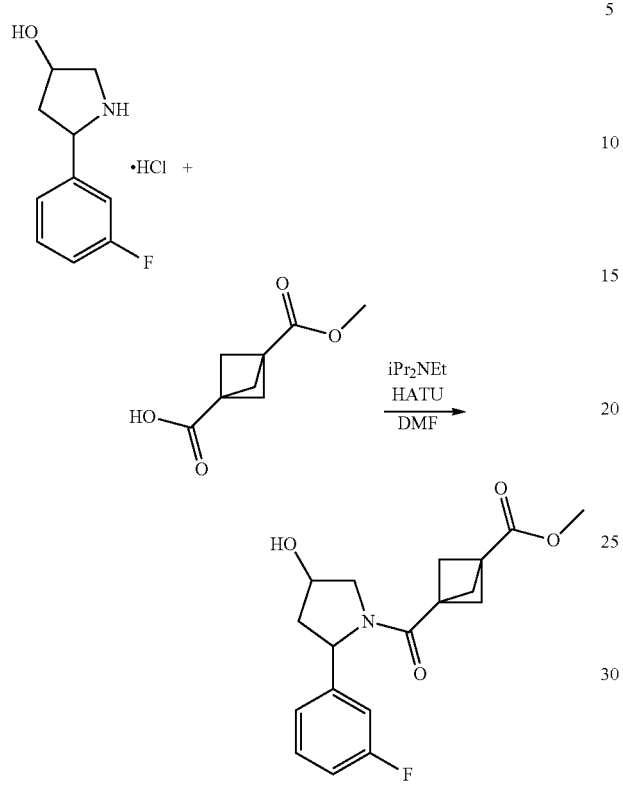

Methyl 3-(2-(3-fluorophenyl)-4-hydroxypyrrolidine-1-carbonyl)bicyclo[1.1.1]-pentane-1-carboxylate To a vial of 3-(methoxycarbonyl)bicyclo[1.1.1]pentane-1-carboxylic acid (0.50 g, 2.9 mmol) in DMF (11.5 ml) was added 5-(3-fluorophenyl)pyrrolidin-3-ol hydrochloride (0.70 g, 3.2 mmol), iPr$_2$NEt (1.5 ml, 8.8 mmol), and HATU (1.7 g, 4.4 mmol). The resulting mixture was stirred at RT overnight. The reaction mixture was diluted with EtOAc and washed with H$_2$O and saturated NaCl, dried over Na$_2$SO$_4$, concentrated under reduced pressure, purified by flash chromatography (0-100%, EtOAc in hexanes) to give the title compound (0.58 g, 1.7 mmol, 59% yield) as an orange foam solid. MS (ES$^+$) C$_{18}$H$_{20}$FNO$_4$ requires: 333, found: 334 [M+H]$^+$.

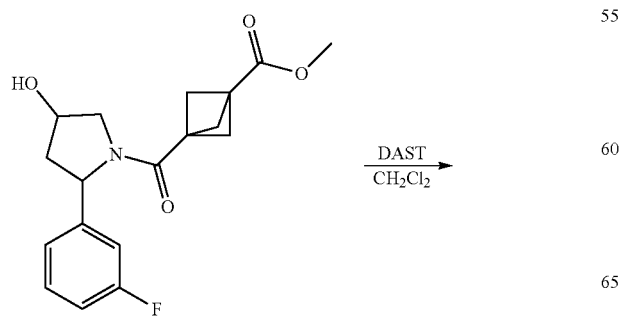

178

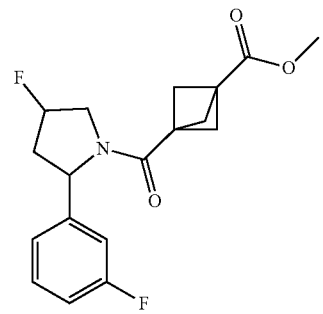 [SMILES: COC(=O)C12CC(C(=O)N3CC(F)CC3c3cccc(F)c3)(C1)C2]

Methyl 3-(4-fluoro-2-(3-fluorophenyl)pyrrolidine-1-carbonyl)bicyclo[1.1.1]-pentane-1-carboxylate (Example 34)

To a solution of the product from the previous step (0.58 g, 1.7 mmol) in DCM (2.5 ml) at −78° C. was added DAST (0.46 ml, 3.5 mmol) and the resulting mixture was stirred at −78° C. for 0.5 h then allowed to reach RT. The reaction mixture was added dropwise to a solution of saturated NaHCO$_3$ held at 0° C., and the layers were separated. The aqueous phase was extracted with DCM (×2), and the combined organic layers were dried over anhydrous Na$_2$SO$_4$ and concentrated under reduced pressure. The residue was purified by flash chromatography (0-100%, EtOAc in Hexanes) to give the title compound (0.19 g, 0.57 mmol, 32% yield) as a white solid.

MS (ES$^+$) C$_{18}$H$_{19}$F$_2$NO$_3$ requires: 335, found: 336 [M+H]$^+$.

$^1$H NMR (600 MHz, CDCl$_3$) δ 7.48-7.25 (m, 1H), 7.16-6.88 (m, 3H), 5.49-5.15 (m, 2H), 4.17-3.75 (m, 2H), 3.66-3.50 (m, 3H), 2.76-2.52 (m, 1H), 2.35 (s, 4H), 2.03-1.84 (m, 3H).

Example 35

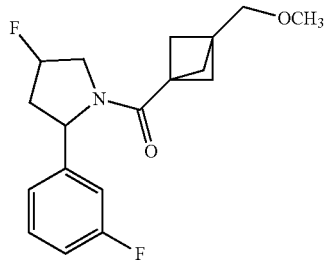 [SMILES: COCC12CC(C(=O)N3CC(F)CC3c3cccc(F)c3)(C1)C2]

(4-Fluoro-2-(3-fluorophenyl)pyrrolidin-1-yl) (3-(methoxymethyl)-bicyclo[1.1.1]pentan-1-yl)methanone 1-((3-(4-Fluoro-2-(3-fluorophenyl)pyrrolidine-1-carbonyl)bicyclo[1.1.1]pentan-1-yl)methyl)-2-oxo-1,2-dihydropyridine-4-carbonitrile

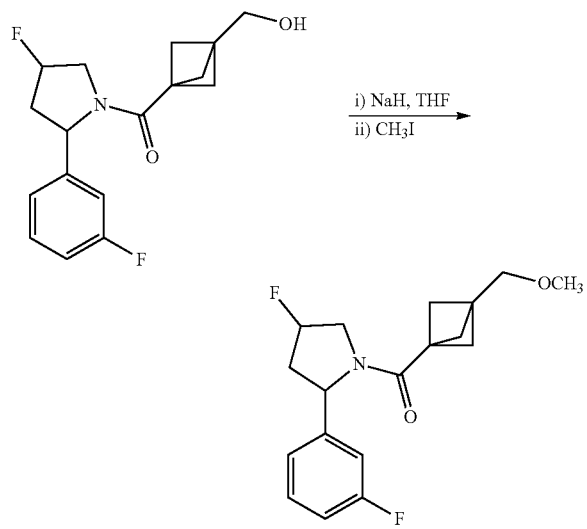

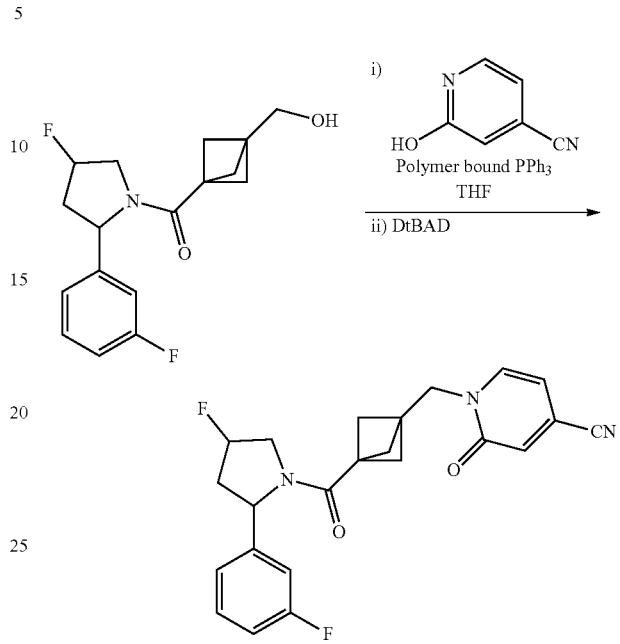

To a cooled 0° C. solution of the Example 24 compound (15 mg, 0.049 mmol) in THF (0.24 ml) under an N₂ environment was added NaH (60% mineral oil dispersion, 2.1 mg, 0.054 mmol) and the resulting mixture was stirred at 0° C. for 0.5 h. To the reaction was added MeI (3.7 µl, 0.059 mmol), stirred at 0° C. for 0.5 h, allowed to warm to RT overnight. To the reaction was added additional MeI (3.7 µl, 0.059 mmol), and stirring was continued at 40° C. for 3 h. The volatiles were removed under reduced pressure and the residue was purified by mass-triggered preparative HPLC (Mobile phase: A=0.1% TFA/H₂O, B=0.1% TFA/MeCN; Gradient: B=50-90%; 12 min; Column: C18) to give the title compound (5.6 mg, 0.017 mmol, 36% yield) as a brown oil.

MS (ES⁺) $C_{18}H_{21}F_2NO_2$ requires: 321, found: 322 [M+H]⁺.

¹H NMR (600 MHz, DMSO-d₆) δ 7.43-7.22 (m, 1H), 7.11-6.81 (m, 3H), 5.51-5.17 (m, 2H), 4.22-3.73 (m, 2H), 3.27-3.25 (m, 2H), 3.18-3.10 (m, 3H), 2.76-2.54 (m, 1H), 2.32-2.06 (m, 1H), 2.02 (s, 3H), 1.71-1.56 (m, 3H).

To a solution of the Example 24 compound (20 mg, 0.065 mmol) in THF (0.32 ml) were added 2-hydroxyisonicotinonitrile (7.8 mg, 0.085 mmol) and polymer bound PPh₃ (3 mmol/g) L-08 (43 mg, 0.13 mmol) and the resulting mixture was stirred at 25° C. for 10 min. DtBAD (19 mg, 0.085 mmol) was added and the reaction mixture was stirred at 25° C. overnight. The reaction mixture was filtered through CELITE®, and the filtrate was concentrated under reduced pressure. The residue was purified by mass-triggered preparative HPLC (Mobile phase: A=0.1% TFA/H₂O, B=0.1% TFA/MeCN; Gradient: B=50-90%; 20 min; Column: C18) to give the title compound (6 mg, 0.015 mmol, 22% yield) as an off-white solid.

MS (ES⁺) $C_{23}H_{21}F_2N_3O_2$ requires: 409, found: 410 [M+H]⁺.

¹H NMR (600 MHz, CDCl₃) δ 7.40-7.12 (m, 2H), 7.01-6.77 (m, 3H), 6.33-6.08 (m, 2H), 5.45-5.07 (m, 2H), 4.26-3.74 (m, 4H), 2.66-2.21 (m, 2H), 2.13 (s, 3H), 1.86-1.70 (m, 3H).

Example 36

Example 37

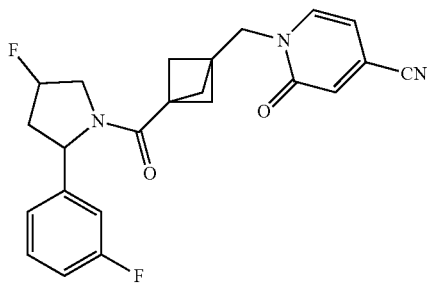 [SMILES: N#Cc1ccn(CC23CC(C(=O)N4CC(F)CC4c4cccc(F)c4)(C2)C3)c(=O)c1]

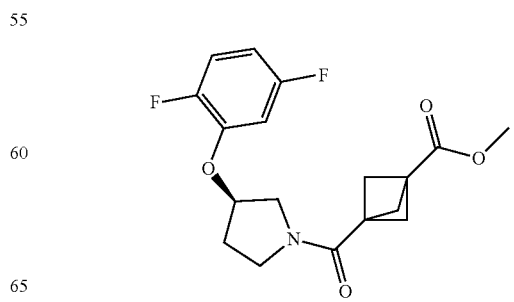

Methyl (R)-3-(3-(2,5-difluorophenoxy)pyrrolidine-1-carbonyl)-bicyclo[1.1.1]pentane-1-carboxylate

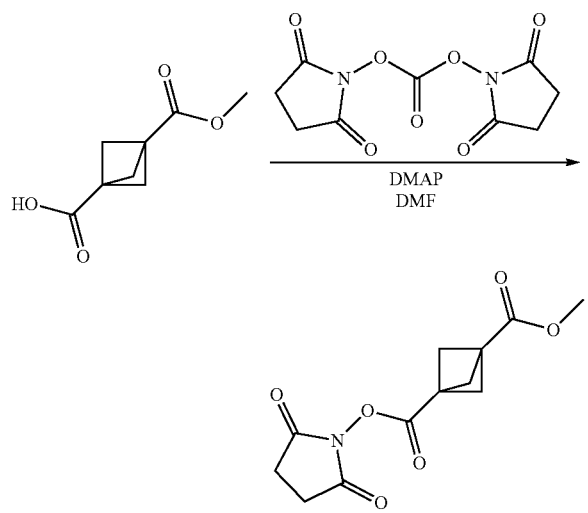

1-(2,5-Dioxopyrrolidin-1-yl) 3-methyl bicyclo[1.1.1]pentane-1,3-dicarboxylate To a suspension of 3-(methoxycarbonyl)bicyclo[1.1.1]pentane-1-carboxylic acid (4.5 g, 26 mmol) in DMF (26 ml), was added bis(2,5-dioxopyrrolidin-1-yl) carbonate (8.1 g, 32 mmol), and DMAP (0.065 g, 0.53 mmol) and the resulting mixture was stirred at RT for 48 h. The reaction mixture was poured over 100 mL ice water and stirred for 15 min. The solid that had formed was removed by filtration and washed with 0.1 M HCl (45 mL), 0.1 M NaOH (45 mL), $H_2O$ (100 mL), and hexanes (100 mL). The solid was further dried in the lyophilizer to give the title compound (6.0 g, 22 mmol, 85% yield) as a white solid. MS (ES+) $C_{12}H_{13}NO_6$ requires: 267, found: 290 $[M+Na]^+$.

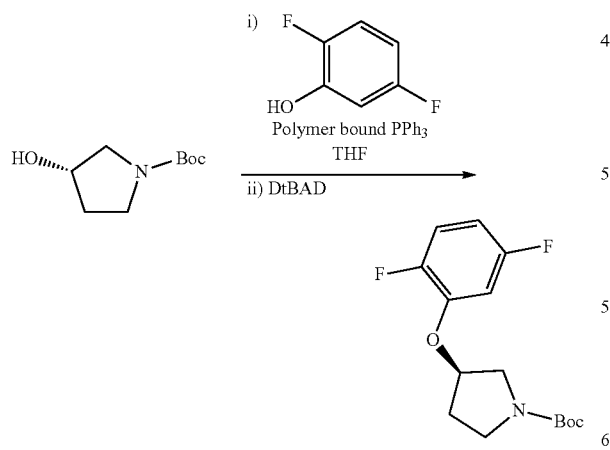

tert-Butyl (R)-3-(2,5-difluorophenoxy)pyrrolidine-1-carboxylate

To a solution of tert-butyl (S)-3-hydroxypyrrolidine-1-carboxylate (0.15 g, 0.80 mmol) in THF (4.0 ml) were added 2,5-difluorophenol (0.13 mg, 1.0 mmol) and polymer bound $PPh_3$ (3 mmol/g) L-08 (0.53 g, 1.6 mmol) and the resulting mixture was stirred at RT for 10 min. DtBAD (0.24 g, 1.0 mmol) was added and the reaction mixture was stirred at RT overnight. The reaction mixture was filtered through CELITE®, the filtrate was concentrated, and the residue was adsorbed onto silica gel and purified by flash chromatography (0-30%, EtOAc in hexanes) to give the title compound (0.22 g, 0.72 mmol, 90% yield) as a white solid. MS (ES$^+$) $C_{15}H_{19}F_2NO_3$ requires: 299, found: 322 $[M+Na]^+$.

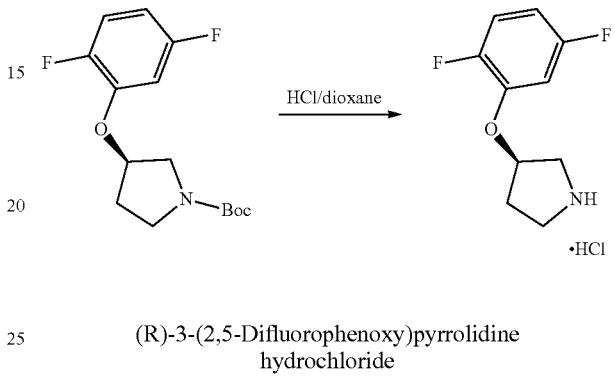

(R)-3-(2,5-Difluorophenoxy)pyrrolidine hydrochloride

To a cooled 0° C. solution of the product from the previous step (210 mg, 0.72 mmol) in dioxane (3.6 ml) was added 4M HCl in dioxane (0.90 ml, 3.6 mmol). The resulting mixture was stirred at 0° C. for 0.5 h and allowed to warm to RT overnight. The volatiles were removed under reduced pressure to give the title compound (160 mg, 0.69 mmol, 96% yield) as a white solid. MS (ES$^+$) $C_{10}H_{11}F_2NO$ requires: 199, found: 200 $[M+H]^+$.

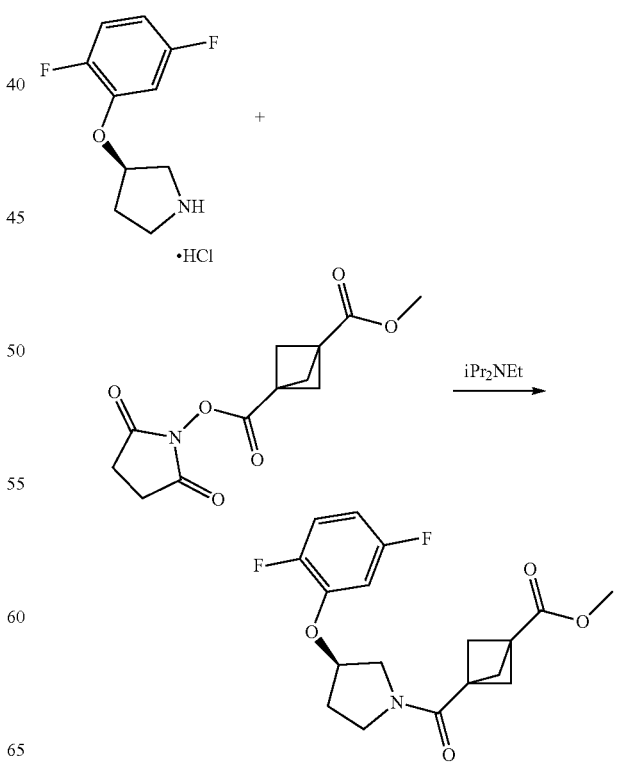

Methyl (R)-3-(3-(2,5-difluorophenoxy)pyrrolidine-1-carbonyl)bicyclo[1.1.1]-pentane-1-carboxylate (Example 37)

To a solution of the product from the previous step (0.12 g, 0.51 mmol) in DMF (5 mL) were added 1-(2,5-dioxopyrrolidin-1-yl) 3-methyl bicyclo[1.1.1]pentane-1,3-dicarboxylate (0.15 g, 0.56 mmol) and iPr$_2$NEt (0.44 mL, 2.5 mmol) and the resulting mixture was stirred at RT for 24 h. The volatiles were removed under reduced pressure. The reaction mixture was diluted with EtOAc and washed with saturated NaHCO$_3$ and saturated NaCl, dried over Na$_2$SO$_4$, concentrated under reduced pressure, and purified by flash chromatography (0-100%, EtOAc in hexanes) to give the title compound (0.14 g, 0.40 mmol, 79% yield) as an off-white solid.

MS (ES+) C$_{18}$H$_{19}$F$_2$NO$_4$ requires: 351, found: 352 [M+H]$^+$.

$^1$H NMR (600 MHz, DMSO-d$_6$) δ 7.33-7.16 (m, 2H), 6.87-6.75 (m, 1H), 5.19-5.02 (m, 1H), 3.89-3.68 (m, 1H), 3.61 (d, J=6.8 Hz, 3H), 3.60-3.50 (m, 3H), 2.33-2.24 (m, 6H), 2.24-2.14 (m, 1H), 2.12-1.98 (m, 1H).

Example 38

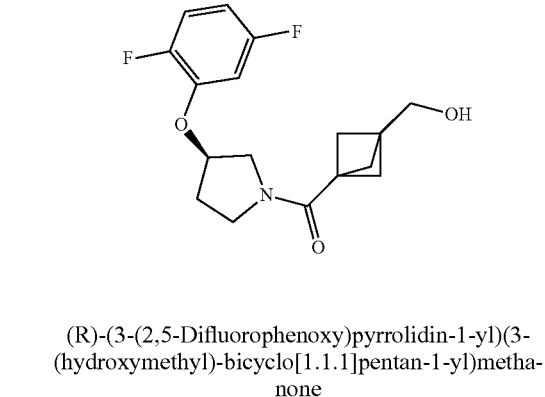

(R)-(3-(2,5-Difluorophenoxy)pyrrolidin-1-yl)(3-(hydroxymethyl)-bicyclo[1.1.1]pentan-1-yl)methanone

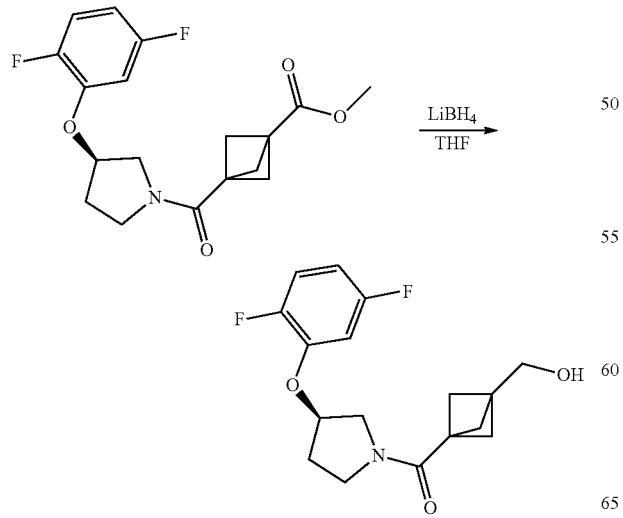

To a cooled 0° C. solution of the Example 37 compound (0.14 g, 0.39 mmol) in THF (0.66 ml) was added LiBH$_4$ (13 mg, 0.59 mmol). The resulting mixture was stirred at 0° C. for 3 h. To the reaction was added additional LiBH$_4$ (13 mg, 0.59 mmol) and the mixture was stirred at 0° C. for 3 h. The reaction was quenched with the addition of 1 M HCl (2 mL). The reaction mixture was diluted with EtOAc, washed with H$_2$O followed by saturated NaCl, dried over Na$_2$SO$_4$, concentrated under reduced pressure, and purified by flash chromatography (0-50%, 9:1:0.1 DCM:MeOH:NH$_4$OH in DCM) to give the title compound (97 mg, 0.30 mmol, 75% yield) as an off-white solid.

MS (ES$^+$) C$_{17}$H$_{19}$F$_2$NO$_3$ requires: 323, found: 324 [M+H]$^+$.

$^1$H NMR (600 MHz, DMSO-d$_6$) δ 7.37-7.14 (m, 2H), 6.91-6.69 (m, 1H), 5.11 (d, J=55.8 Hz, 1H), 4.67-4.43 (m, 1H), 3.88-3.69 (m, 1H), 3.62-3.52 (m, 2H), 3.44-3.37 (m, 1H), 3.27-3.03 (m, 2H), 2.30-1.99 (m, 1H), 1.97-1.74 (m, 7H).

Example 39

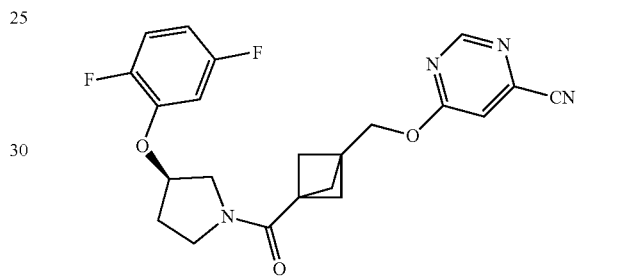

(R)-6-((3-(3-(2,5-difluorophenoxy)pyrrolidine-1-carbonyl)-bicyclo[1.1.1]pentan-1-yl)methoxy)pyrimidine-4-carbonitrile

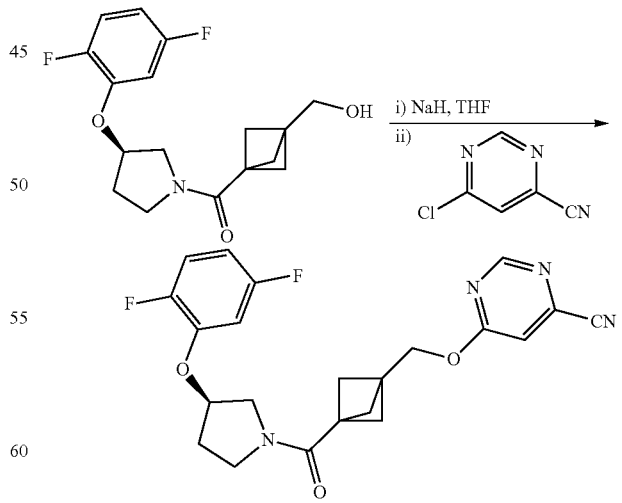

To a cooled 0° C. solution of the Example 38 compound (20 mg, 0.062 mmol) in THF (0.30 ml) was added NaH (60% mineral oil dispersion, 1.6 mg, 0.068 mmol) and the resulting mixture was stirred at 0° C. for 15 min. To the reaction was added 6-chloropyrimidine-4-carbonitrile (10 mg, 0.074 mmol), and the mixture was stirred at RT for 4 h. The volatiles were removed under reduced pressure and the residue was purified by mass-triggered preparative HPLC (Mobile phase: A=0.1% TFA/H$_2$O, B=0.1% TFA/MeCN; Gradient: B=50-90%; 12 min; Column: C18) to give the title compound (8.3 mg, 0.019 mmol, 31% yield) as an off-white solid.

MS (ES$^+$) C$_{22}$H$_{20}$F$_2$N$_4$O$_3$ requires: 426, found: 427 [M+H]$^+$.

$^1$H NMR (600 MHz, DMSO-d$_6$) δ 8.95-8.89 (m, 1H), 7.77-7.68 (m, 1H), 7.31-7.23 (m, 1H), 7.23-7.14 (m, 1H), 6.86-6.78 (m, 1H), 5.20-5.02 (m, 1H), 4.56-4.40 (m, 2H), 3.89-3.65 (m, 1H), 3.60-3.51 (m, 2H), 3.34 (td, J=10.9, 7.5 Hz, 1H), 2.27-2.12 (m, 1H), 2.12-1.93 (m, 7H).

Example 40

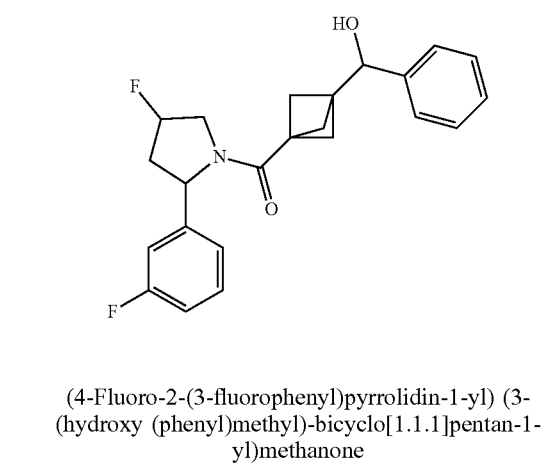

(4-Fluoro-2-(3-fluorophenyl)pyrrolidin-1-yl) (3-(hydroxy (phenyl)methyl)-bicyclo[1.1.1]pentan-1-yl)methanone

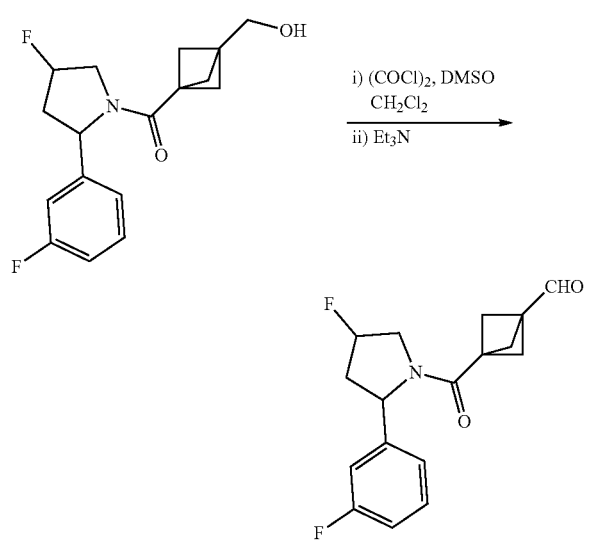

3-(4-Fluoro-2-(3-fluorophenyl)pyrrolidine-1-carbonyl)bicyclo[1.1.1]pentane-1-carbaldehyde To a solution of oxalyl chloride (71 µl, 0.81 mmol) in DCM (4.5 ml) was added DMSO (0.11 ml, 1.6 mmol) and the resulting mixture was stirred at −78° C. for 10 min. A solution of the Example 24 compound (50 mg, 0.16 mmol) in DCM (0.9 ml) was added followed by TEA (0.57 ml, 4.1 mmol). The resulting mixture was stirred for 1 hr at −78° C. and then allowed to reach RT. The solution was poured into saturated NaHCO$_3$, and the layers were separated. The aqueous phase was extracted with DCM (3×), the combined organic layers were washed with saturated NaCl, dried over Na$_2$SO$_4$, and concentrated under reduced pressure. The product was carried on to the next step without purification.

MS (ES$^+$) C$_{17}$H$_{17}$F$_2$NO$_2$ requires: 305, found: 306 [M+H]$^+$.

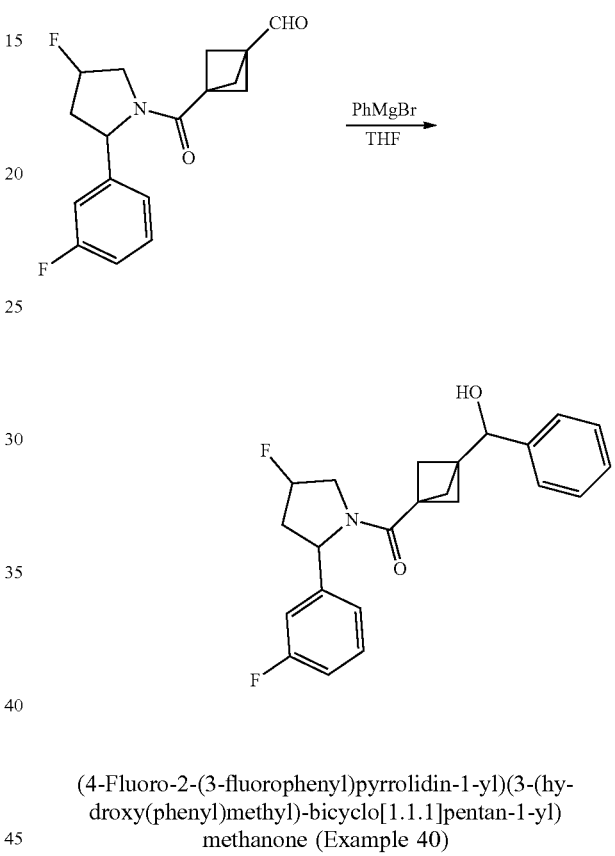

(4-Fluoro-2-(3-fluorophenyl)pyrrolidin-1-yl)(3-(hydroxy(phenyl)methyl)-bicyclo[1.1.1]pentan-1-yl) methanone (Example 40)

To a solution of the product from the previous step (25 mg, 0.082 mmol) in THF (0.5) at 0° C. were added phenylmagnesium bromide (55 µl of a 3.0 M solution in Et$_2$O; 0.16 mmol) and the resulting mixture was stirred at 0° C. for 30 min then allowed to reach RT. Saturated NH$_4$Cl was added, and the layers were separated. The aqueous phase was extracted with EtOAc (3×), the combined organic layers were washed with saturated NaCl, dried over Na$_2$SO$_4$, concentrated under reduced pressure, and purified by mass-triggered preparative HPLC (Mobile phase: A=0.1% TFA/H$_2$O, B=0.1% TFA/MeCN; Gradient: B=40-80%; 12 min; Column: C18) to give the title compound (6.5 mg, 0.017 mmol, 21% yield) as a white powder.

MS (ES$^+$) C$_{23}$H$_{23}$F$_2$NO$_2$ requires: 383, found: 384 [M+H]$^+$.

$^1$H NMR (600 MHz, DMSO-d$_6$) δ 7.47-7.14 (m, 5H), 7.13-7.81 (m, 4H), 5.42-5.12 (m, 2H), 4.62-4.36 (m, 1H), 4.0-3.85 (m, 3H), 2.41-2.15 (m, 2H), 2.13-1.93 (m, 1H), 1.89-1.58 (m, 3H), 1.56-1.37 (m, 2H).

Example 41

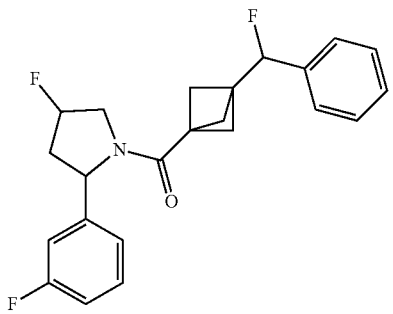 [SMILES: O=C(N1CC(F)CC1c1cccc(F)c1)C12CC(C(F)c3ccccc3)(C1)C2]

(3-(Fluoro(phenyl)methyl)bicyclo[1.1.1]pentan-1-yl)-(4-fluoro-2-(3-fluorophenyl)pyrrolidin-1-yl)methanone

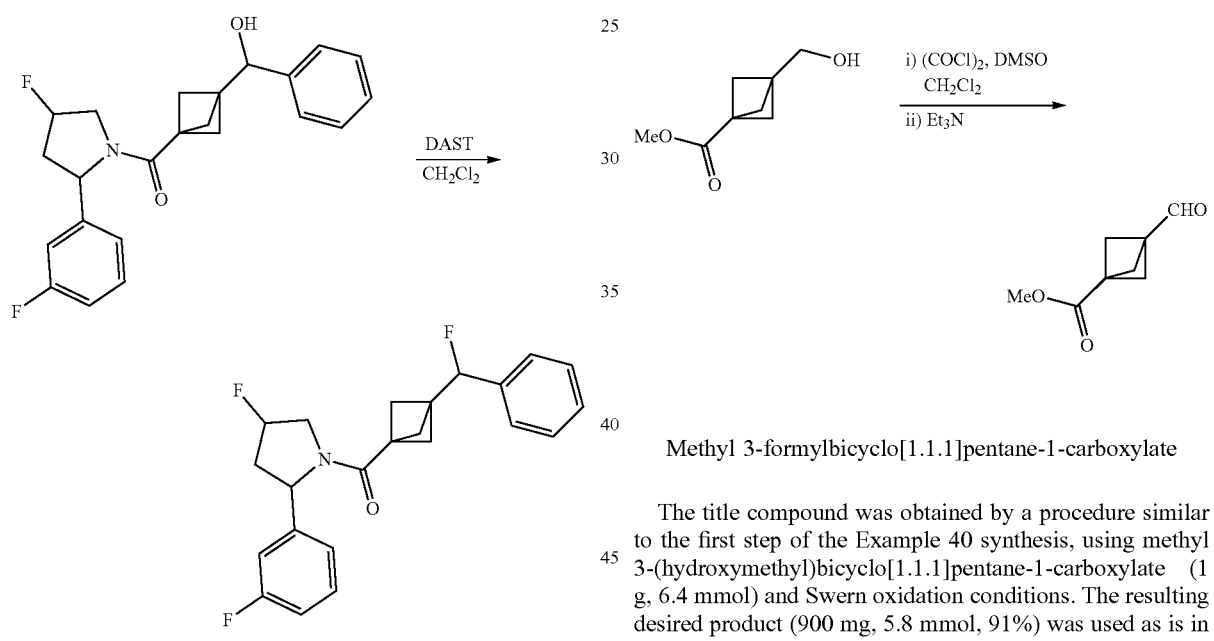

To a solution of the Example 40 compound (20 mg, 0.052 mmol) in DCM (0.5 ml) at 0° C. was added DAST (8.27 μl, 0.063 mmol) and the resulting mixture was stirred at 0° C. for 1 h then allowed to reach RT. The mixture was cooled to 0° C., saturated NaHCO₃ was added, and the layers were separated. The aqueous phase was extracted with DCM (3×), and the combined organic layers were concentrated under reduced pressure and purified by mass-triggered preparative HPLC (Mobile phase: A=0.1% TFA/H₂O, B=0.1% TFA/MeCN; Gradient: B=40-80%; 12 min; Column: C18) to give the title compound (2.0 mg, 5.5 μmol, 10% yield) as a pale yellow amorphous material.

MS (ES⁺) $C_{23}H_{22}F_3NO$ requires: 385, found: 386 [M+H]⁺.

¹H NMR (600 MHz, CDCl₃) δ 7.41-7.18 (m, 5H), 7.10 (s, 1H), 7.00-6.80 (m, 3H), 5.50-5.14 (m, 2H), 4.16-3.85 (m, 2H), 2.64-2.38 (m, 2H), 2.35-2.28 (m, 1H), 2.15-2.03 (m, 3H), 1.85-1.65 (m, 3H).

Example 42

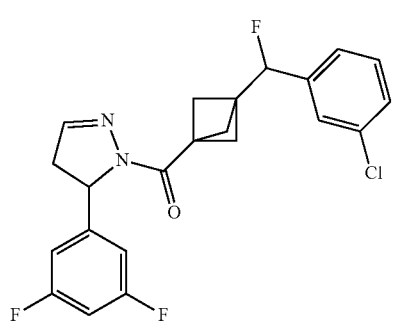 [SMILES: O=C(N1N=CCC1c1cc(F)cc(F)c1)C12CC(C(F)c3cccc(Cl)c3)(C1)C2]

(3-((3-chlorophenyl)fluoromethyl)bicyclo[1.1.1]pentan-1-yl)(5-(3,5-difluorophenyl)-4,5-dihydro-1H-pyrazol-1-yl)methanone Methyl 3-formylbicyclo[1.1.1]pentane-1-carboxylate The title compound was obtained by a procedure similar to the first step of the Example 40 synthesis, using methyl 3-(hydroxymethyl)bicyclo[1.1.1]pentane-1-carboxylate (1 g, 6.4 mmol) and Swern oxidation conditions. The resulting desired product (900 mg, 5.8 mmol, 91%) was used as is in the next step.

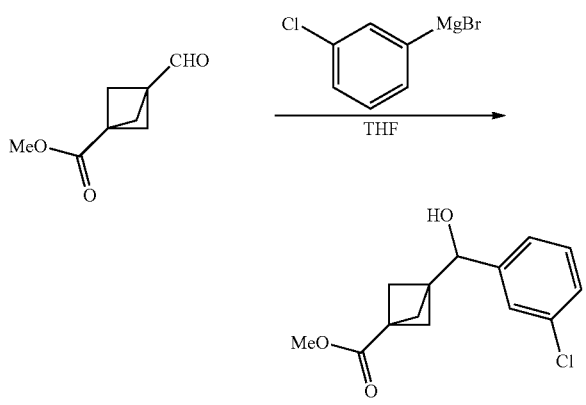

Methyl 3-((3-chlorophenyl)(hydroxy)methyl)bicy-clo-[1.11]-pentane-1-carboxylate The title compound was obtained by a procedure similar to the second step of the Example 40 synthesis, using methyl 3-formylbicyclo[1.1.1]pentane-1-carboxylate (100 mg, 0.65 mmol) and (3-chlorophenyl)magnesium bromide (2.6 mL, 1.3 mmol) and the desired product (114 mg, 0.43 mmol, 66%) a pale yellow liquid was used as is in the next step. MS (ES$^+$) C$_{14}$H$_{15}$ClO$_3$ requires: 266, found: 267 [M+H]$^+$

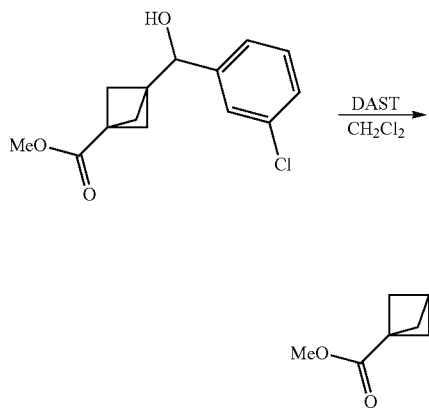

Methyl 3-((3-chlorophenyl)fluoromethyl)bicyclo [1.1.1]pentane-1-carboxylate

The title compound was obtained by a procedure similar to the synthesis of Example 41 from Example 40, using methyl 3-((3-chlorophenyl)(hydroxy)methyl)bicyclo[1.1.1]pentane-1-carboxylate (100 mg, 0.36 mmol) and DAST followed by flash chromatography to give the desired product (80 mg, 0.30 mmol, 79%). MS (ES$^+$) C$_{14}$H$_{14}$ClFO$_2$ requires: 268, found: 269 [M+H]$^+$.

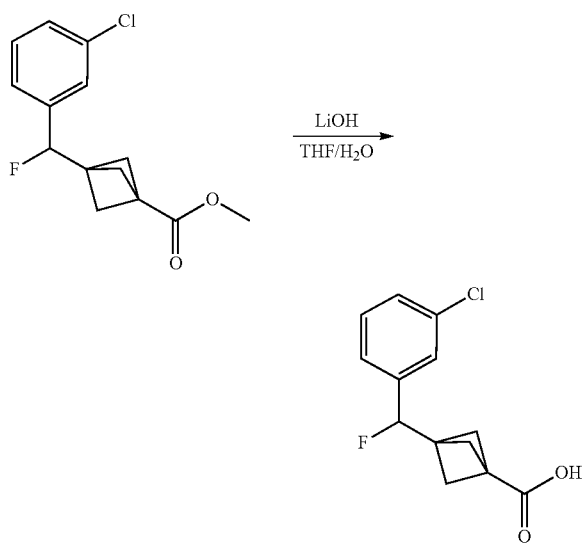

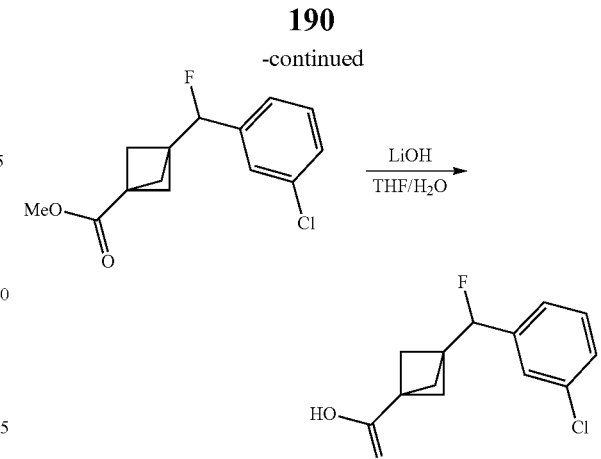

3-((3-Chlorophenyl)fluoromethyl)bicyclo[1.1.1]pentane-1-carboxylic acid

The title compound was synthesized similar to Example 14 from methyl 3-((3-chlorophenyl)-fluoromethyl)bicyclo [1.1.1]pentane-1-carboxylate (80 mg, 0.30 mmol) and LiOH, and was used as is in the next step. MS (ES$^+$) C$_{13}$H$_{12}$ClFO$_2$ requires: 254, found: 255 [M+H]$^+$.

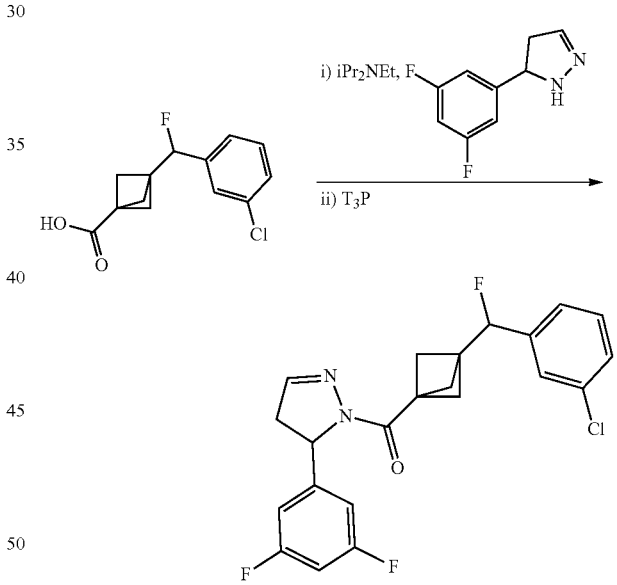

(3-((3-Chlorophenyl)fluoromethyl)bicyclo[1.1.1] pentan-1-yl)(5-(3,5-difluorophenyl)-4,5-dihydro-1H-pyrazol-1-yl)methanone The title compound was synthesized similar to Example 14 from 5-(3,5-difluorophenyl)-4,5-dihydro-1H-pyrazole (77 mg, 0.42 mmol) and 3-((3-chlorophenyl)fluoromethyl) bicyclo[1.1.1]pentane-1-carboxylic acid (90 mg, 0.35 mmol) using T$_3$P (50% wt in EtOAc) and iPr$_2$NEt in DMF to give the desired product (6.7 mg, 0.02 mmol, 5%) as a orange amorphous material. MS (ES$^+$) C$_{22}$H$_8$ClF$_3$N$_2$O requires: 418, found: 419 [M+H]$^+$.

Example 43

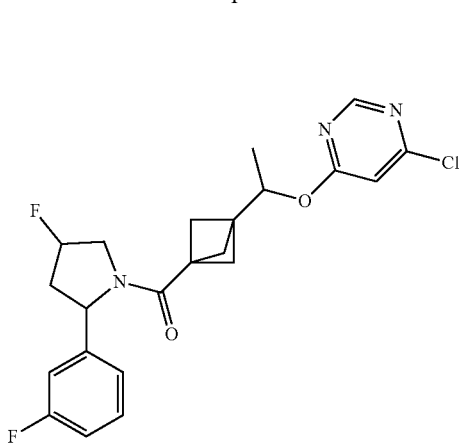

(3-(1-((6-Chloropyrimidin-4-yl)oxy)ethyl)bicyclo[1.1.1]pentan-1-yl)(4-fluoro-2-(3-fluorophenyl)pyrrolidin-1-yl)methanone

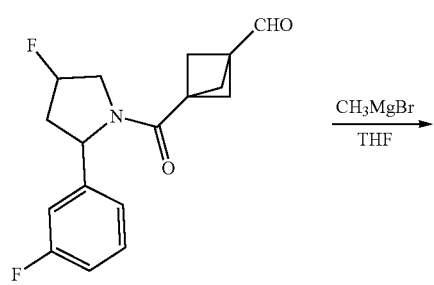

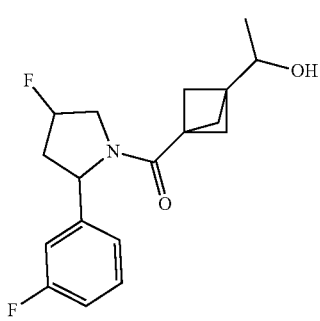

(4-Fluoro-2-(3-fluorophenyl)pyrrolidin-1-yl)(3-(1-hydroxyethyl)bicyclo[1.1.1]-pentan-1-yl)methanone Synthesis of the title compound was accomplished from 3-(4-fluoro-2-(3-fluorophenyl)pyrrolidine-1-carbonyl)bicyclo[1.1.1]pentane-1-carbaldehyde and methylmagnesium bromide using a procedure similar to that described for Example 40.

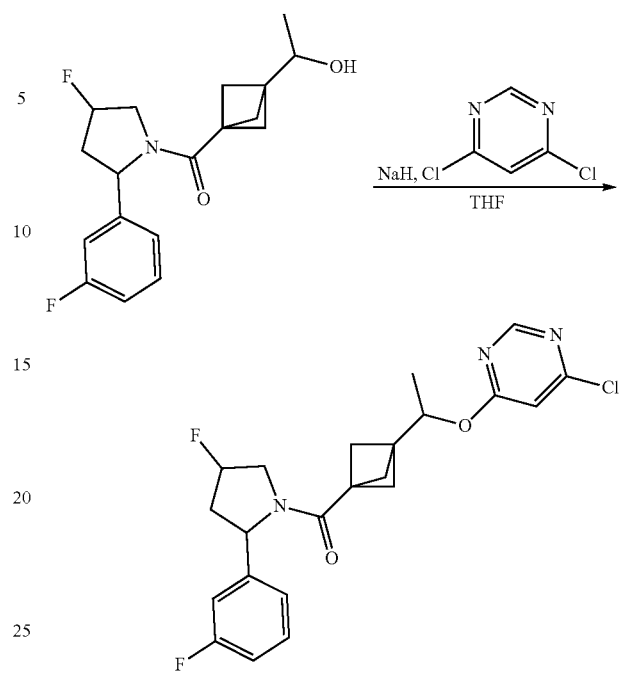

(3-(1-((6-Chloropyrimidin-4-yl)oxy)ethyl)bicyclo[1.1.1]pentan-1-yl)(4-fluoro-2-(3-fluorophenyl)pyrrolidin-1-yl)methanone (Example 43)

To a solution of the product from the previous step (20 mg, 0.062 mmol) in THF (0.5 ml) at 0° C. was added 4,6-dichloropyridine (9.55 mg, 0.068 mmol) and NaH (60% dispersion in mineral oil, 5.0 mg, 0.12 mmol) and the resulting mixture was stirred at 0° C. for 1 h. The reaction mixture at 0° C. was quenched with 1M HCl, warmed to RT, and purified by mass-triggered preparative HPLC (Mobile phase: A=0.1% TFA/H$_2$O, B=0.1% TFA/MeCN; Gradient: B=40-80%; 12 min; Column: C18) to give the title compound (2.0 mg, 5.0 μmol, 8% yield) as a white solid.

MS (ES$^+$) C$_{22}$H$_{22}$ClF$_2$N$_3$O$_2$ requires: 433, found: 434 [M+H]$^+$.

$^1$H NMR (600 MHz, DMSO-d$_6$) δ 8.70-8.54 (m, 1H), 7.45-6.8 (m, 5H), 5.45-5.15 (m, 3H), 4.11-3.71 (m, 2H), 2.40-2.18 (m, 2H), 2.16-1.91 (m, 4H), 1.73-1.55 (m, 2H), 1.30-1.03 (m, 3H).

Example 44

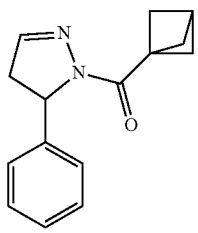 [SMILES: O=C(N1N=CCC1c1ccccc1)C12CC(C1)C2]

Bicyclo[1.1.1]pentan-1-yl(5-phenyl-4,5-dihydro-1H-pyrazol-1-yl)methanone

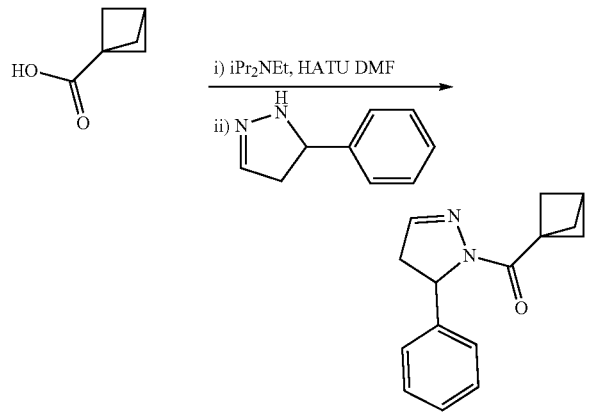

To a stirring solution of bicyclo[1.1.1]pentane-1-carboxylic acid (17 mg, 0.15 mmol) in DMF (0.5 ml) was added iPr₂NEt (0.048 ml, 0.27 mmol), then in 10 min HATU (78 mg, 0.205 mmol), then in 15 min 5-phenyl-4,5-dihydro-1H-pyrazole (20 mg, 0.137 mmol). The reaction was stirred for 2 h at RT. Saturated NaHCO₃ was then added, and the layers were separated. The aqueous phase was extracted with EtOAc (3×) and the combined organic layers were concentrated under reduced pressure. The residue was purified by mass-triggered preparative HPLC (Mobile phase: A=0.1% TFA/H₂O, B=0.1% TFA/MeCN; Gradient: B=30-70%; 20 min; Column: C18) to give the title compound (7 mg, 0.027 mmol, 20% yield) as a yellow amorphous material. MS (ES⁺) $C_{15}H_{16}N_2O$ requires: 240, found: 241 [M+H]⁺.

Example 45

(3-Hydroxybicyclo[1.1.1]pentan-1-yl)(5-phenyl-4,5-dihydro-1H-pyrazol-1-yl)methanone

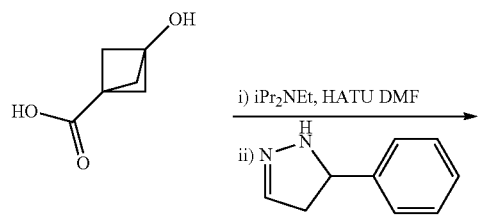

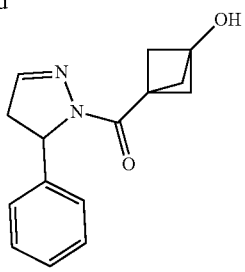

The procedure used to obtain the Example 44 compound was applied to 3-hydroxy-bicyclo[1.1.1]pentane-1-carboxylic acid (48 mg, 0.38 mmol) and 5-phenyl-4,5-dihydro-1H-pyrazole (50 mg, 0.34 mmol) to give the title compound (32 mg, 0.13 mmol, 36% yield) as an off-white powder.

MS (ES⁺) $C_{15}H_{16}N_2O_2$ requires: 256, found: 257 [M+H]⁺.

¹H NMR (600 MHz, DMSO-d₆) δ 7.37-7.29 (m, 2H), 7.28-7.22 (m, 1H), 7.21-7.16 (m, 1H), 7.11-7.04 (m, 2H), 6.61-6.25 (m, 1H), 5.30 (dd, J=11.9, 4.5 Hz, 1H), 3.49-3.38 (m, 1H), 2.71-2.58 (m, 1H), 2.10 (s, 6H).

Example 46

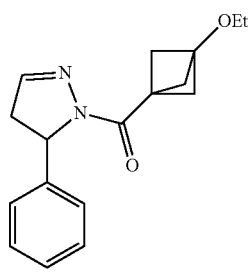

(3-Ethoxybicyclo[1.1.1]pentan-1-yl)(5-phenyl-4,5-dihydro-1H-pyrazol-1-yl)methanone

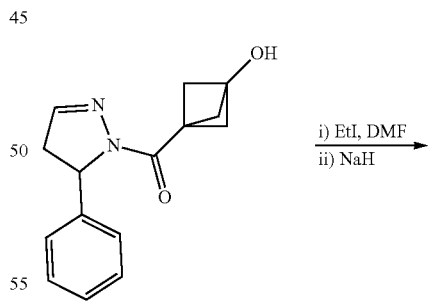

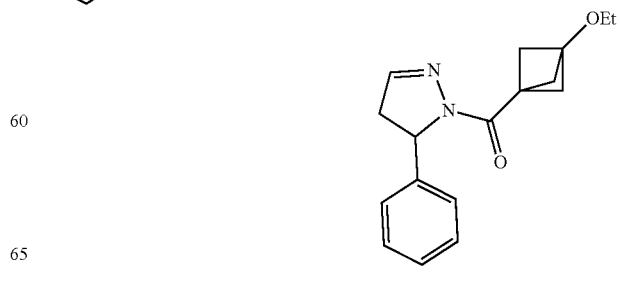

To a solution of the Example 45 compound (10 mg, 0.039 mmol) in DMF (0.3 ml) was added iodoethane (6.7 mg, 0.043 mmol) and the solution was cooled to −78° C. NaH (60% dispersion in mineral oil, 1.7 mg, 0.043 mmol) was then added, and the resulting mixture was stirred at −78° C. for 1 h. The reaction at −78° C. was quenched with TFA, warmed to RT, and purified by mass-triggered preparative HPFC (Mobile phase: A=0.1% TFA/H$_2$O, B=0.1% TFA/MeCN; Gradient: B=30-70%; 12 min; Column: C18) to give the title compound (1.8 mg, 6.3 μmol, 16% yield) as a pale yellow liquid.

MS (ES$^+$) C$_{17}$H$_{20}$N$_2$O$_2$ requires: 284, found: 285 [M+H]$^+$.

$^1$H NMR (600 MHz, DMSO-d$_6$) δ 7.36-7.30 (m, 2H), 7.28-7.21 (m, 2H), 7.17-7.07 (m, 2H), 5.32 (dd, J=11.8, 4.7 Hz, 1H), 3.51-3.42 (m, 3H), 2.69-2.60 (m, 1H), 2.17 (s, 6H), 1.12 (t, J=7.0 Hz, 3H).

Example 47

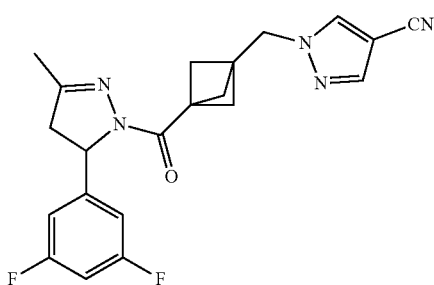

1-((3-(5-(3,5-difluorophenyl)-3-methyl-4,5-dihydro-1H-pyrazole-1-carbonyl)-bicyclo[1.1.1]pentan-1-yl)methyl)-1H-pyrazole-4-carbonitrile

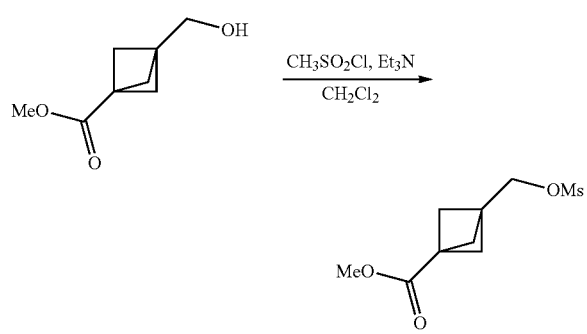

Ethyl 3-(((methylsulfonyl)oxy)methyl)bicyclo[1.1.1]pentane-1-carboxylate (Intermediate V)

To a solution of methyl 3-(hydroxymethyl)bicyclo [1.1.1]pentane-1-carboxylate (0.99 g, 6.3 mmol) in DCM (21 ml) at 0° C. was added Et$_3$N (1.9 ml, 14 mmol), followed by the dropwise addition methanesulfonyl chloride (0.59 ml, 7.6 mmol), and the resulting mixture was stirred at 0° C. for 5 min, then at rt for 3.5 h. The reaction was diluted with DCM and ice/0.1M HCl mixture. The layers were separated, and the organic layer was washed with H$_2$O and brine. The aqueous layers were back-extracted with DCM, and the combined organic layers were dried over MgSO$_4$ and concentrated to give the title compound (1.3 g, 5.1 mmol, 92% yield) as a clear oil. MS (ES$^+$) C$_9$H$_{14}$O$_5$S requires: 234, found: 235 [M+H]$^+$.

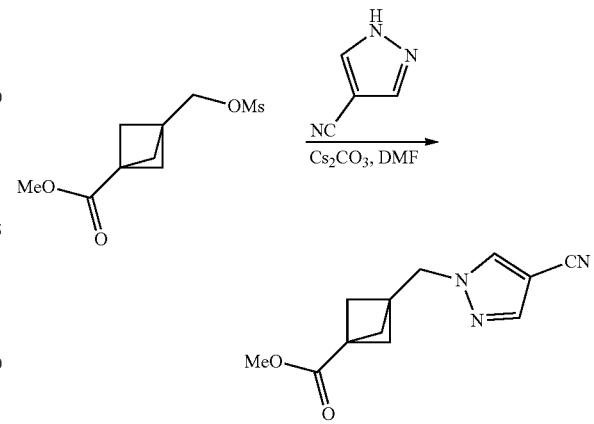

Methyl 3-((4-cyano-1H-pyrazol-1-yl)methyl)bicyclo [1.1.1]pentane-1-carboxylate

To a solution of Intermediate V (120 mg, 0.51 mmol) in DMF (2.5 ml) was added 1H-pyrazole-4-carbonitrile (52 mg, 0.56 mmol) and Cs$_2$CO$_3$ (250 mg, 0.77 mmol), and the resulting mixture was stirred at rt overnight. The reaction was diluted with EtOAc and washed successively with H$_2$O and brine. Each aqueous layer was back-extracted with EtOAc (2×). The combined organic layers were dried over MgSO$_4$ and concentrated to give the title compound (110 mg, 0.47 mmol, 93% yield). MS (ES$^+$) C$_{12}$H$_{13}$N$_3$O$_2$ requires: 231, found: 232 [M+H]$^+$.

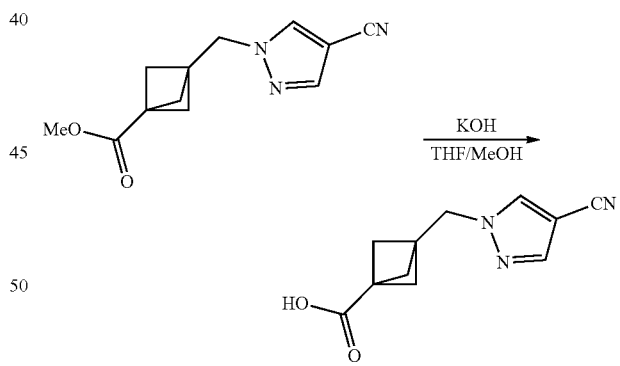

3-((4-Cyano-1H-pyrazol-1-yl)methyl)bicyclo[1.1.1]pentane-1-carboxylic acid

To a solution of the product from the previous step (103 mg, 0.45 mmol) in THF (2 ml) and MeOH (2 ml) was added KOH (50.0 mg, 0.89 mmol), and the resulting mixture was stirred at rt overnight. To the reaction solution was added additional KOH (25.0 mg, 0.45 mmol), and the mixture was stirred for an additional 7 h. The reaction was diluted with H$_2$O and washed with EtOAc. The aqueous layer was acidified with 1M HCl and extracted with EtOAc (3×). The combined organic layers were washed with brine, dried over MgSO₄, and concentrated to give the title compound (70 mg, 0.32 mmol, 72% yield) as a white solid. MS (ES⁺) C₁₁H₁₁N₃O₂ requires: 217, found: 218 [M+H]⁺.

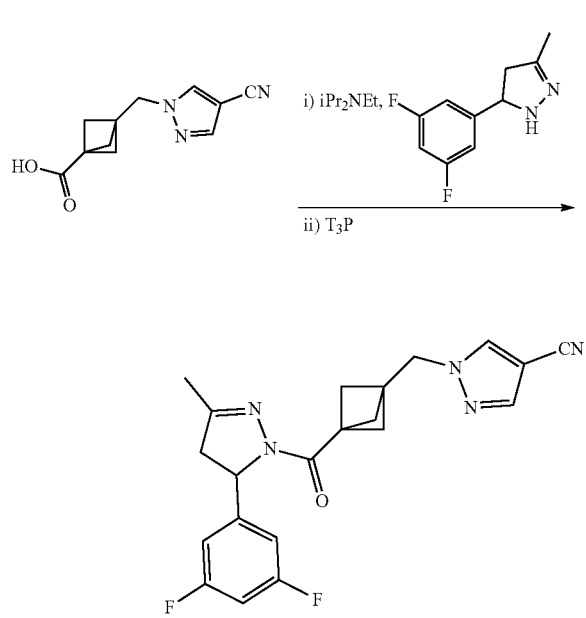

1-((3-(5-(3,5-Difluorophenyl)-3-methyl-4,5-dihydro-1H-pyrazole-1-carbonyl)-bicyclo[1.1.1]pentan-1-yl)methyl)-1H-pyrazole-4-carbonitrile To a solution of the product from the previous step (15 mg, 0.069 mmol) and 5-(3,5-difluorophenyl)-3-methyl-4,5-dihydro-1H-pyrazole (16 mg, 0.083 mmol) in DMF (345 µl) was added iPr₂NEt (36 µl, 0.21 mmol), and the reaction stirred for 10 minutes. T₃P (123 µl, 0.21 mmol) was then added and the mixture was stirred for 48 h. The reaction was diluted with MeOH and purified by mass-triggered preparative HPLC (Mobile phase: A=0.1% TFA/H₂O, B=0.1% TFA/MeCN; Gradient: B=10-90%; 12 min; Column: C18) to give the title compound (3.2 mg, 8.09 µmol, 11% yield). MS (ES⁺) C₂₁H₁₉F₂N₅O requires: 395, found: 396 [M+H]⁺.

Example 48

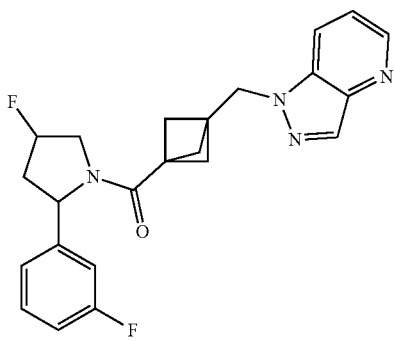 [SMILES: O=C(N1CC(F)CC1c1cccc(F)c1)C12CC(Cn3ncc4ncccc43)(C1)C2]

(3-((1H-pyrazolo[4,3-b]pyridin-1-yl)methyl)bicyclo[1.1.1]pentan-1-yl)-(4-fluoro-2-(3-fluorophenyl)pyrrolidin-1-yl)methanone

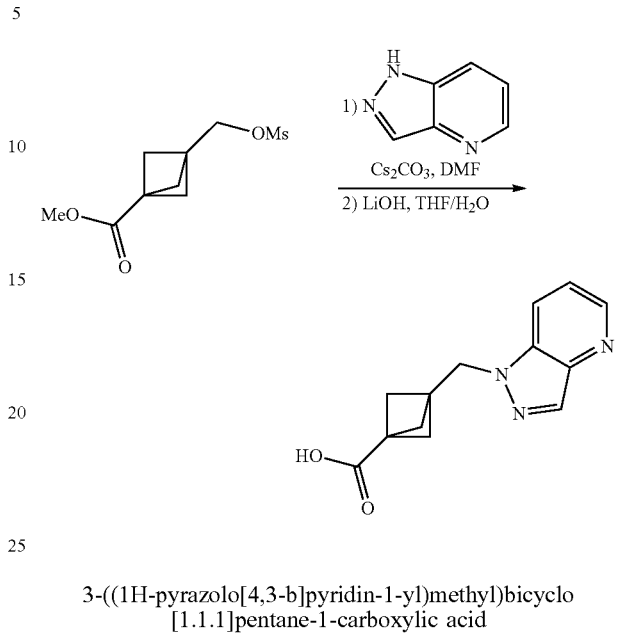

3-((1H-pyrazolo[4,3-b]pyridin-1-yl)methyl)bicyclo[1.1.1]pentane-1-carboxylic acid The title compound was obtained by a procedure similar to that described for Example 47, using Intermediate V (300 mg, 1.28 mmol) and 1H-pyrazolo[4,3-b]pyridine (168 mg, 1.4 mmol) with Cs₂CO₃ in DMF, purification by flash chromatography, followed by hydrolysis with LiOH in THF/H₂O to give the title compound (132 mg, 0.54 mmol, 42% yield, two steps) as a white solid. MS (ES⁺) C₁₃H₁₃N₃O₂ requires: 243, found: 244 [M+H]⁺.

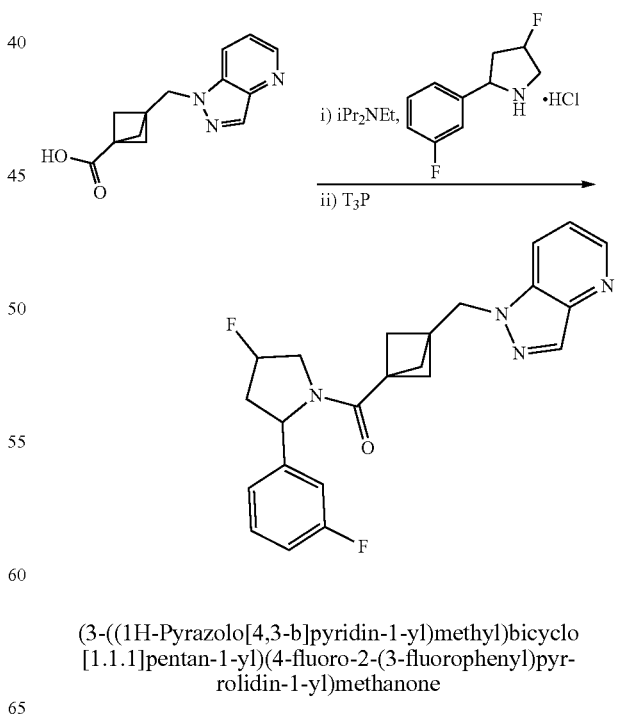

(3-((1H-Pyrazolo[4,3-b]pyridin-1-yl)methyl)bicyclo[1.1.1]pentan-1-yl)(4-fluoro-2-(3-fluorophenyl)pyrrolidin-1-yl)methanone To a suspension of the product from the previous step (20 mg, 0.082 mmol) in EtOAc (411 µl) were added 4-fluoro- 2-(3-fluorophenyl)-pyrrolidine hydrochloride (19.87 mg, 0.090 mmol), pyridine (20 µl, 0.25 mmol), and T₃P (98 µl, 0.16 mmol), and the resulting mixture was stirred at 60° C. overnight. H₂O was added, and the layers were separated. The aqueous phase was extracted with EtOAc (3×) and the combined organic layers were concentrated under reduced pressure. The residue was purified by mass-triggered preparative HPLC (Mobile phase: A=0.1% TFA/H₂O, B=0.1% TFA/MeCN; Gradient: B=10-90%; 12 min; Column: C18) to give the title compound as a TFA salt (23 mg, 0.045 mmol, 54% yield) as a off-white solid. MS (ES⁺) $C_{23}H_{22}F_2N_4O$ requires: 408, found: 409 [M+H]⁺.

Example 49

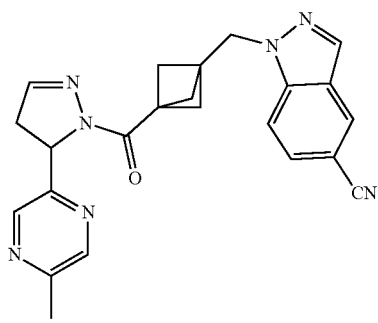 [SMILES: Cc1cnc(C2CC=NN2C(=O)C23CC(Cn4ncc5cc(C#N)ccc54)(C2)C3)cn1]

1-((3-(5-(5-Methylpyrazin-2-yl)-4,5-dihydro-1H-pyrazole-1-carbonyl)-bicyclo[1.1.1]pentan-1-yl) methyl)-1H-indazole-5-carbonitrile

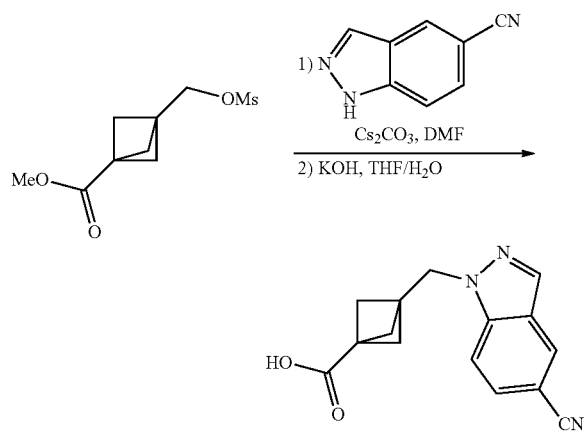

3-((5-Cyano-1H-indazol-1-yl)methyl)bicyclo[1.1.1] pentane-1-carboxylic acid

The title compound was obtained by a procedure similar to that described for Example 47, using Intermediate V (600 mg, 2.6 mmol) and 1H-indazole-5-carbonitrile (403 mg, 2.8 mmol) with Cs₂CO₃ in DMF, purification by flash chromotography, and then hydrolysis with KOH in THF/MeOH to give the title compound (295 mg, 1.1 mmol, 42% yield, 2 steps) as a white solid. MS (ES+) $C_{15}H_{13}N_3O_2$ requires: 267, found: 268 [M+H]⁺.

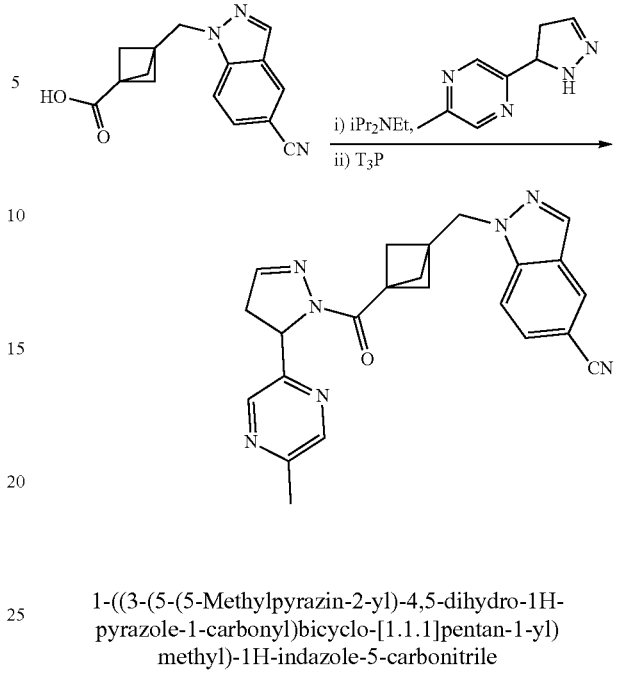

1-((3-(5-(5-Methylpyrazin-2-yl)-4,5-dihydro-1H-pyrazole-1-carbonyl)bicyclo-[1.1.1]pentan-1-yl) methyl)-1H-indazole-5-carbonitrile To a solution of the product from the previous step (10 mg, 0.03 mmol) and 2-(4,5-dihydro-1H-pyrazol-5-yl)-5-methylpyrazine (6.1 mg, 0.03 mmol) in DMF (0.10 mL) was added iPr₂NEt (120 µF, 0.11 mmol), and the reaction was stirred at RT for 3 min. T₃P (50% wt in EtOAc, 22 µF, 0.03 mmol) was then added, and the mixture was stirred overnight. The reaction was diluted in 1% TFA in MeOH and purified by mass-triggered preparative HPLC (Mobile phase: A=0.1% TFA/H₂O, B=0.1% TFA/MeCN; Gradient: B=30-70%; 20 min; Column: C18) to give the title compound as a TFA salt (5.8 mg, 0.01 mmol, 38% yield) yellow viscous oil.

MS (ES⁺) $C_{23}H_{21}N_7O$ requires: 411 found: 412 [M+H]⁺.

¹H NMR (600 MHz, Chloroform-d) δ 8.51-8.48 (m, 1H), 8.45-8.41 (m, 1H), 8.15-8.13 (m, 1H), 8.13-8.10 (m, 1H), 7.59-7.54 (m, 1H), 7.47-7.42 (m, 1H), 6.96-6.93 (m, 1H), 5.42 (dd, J=11.8, 5.6 Hz, 1H), 4.54 (s, 2H), 3.30 (ddd, J=18.7, 11.8, 1.6 Hz, 1H), 3.06 (ddd, J=18.7, 5.6, 1.8 Hz, 1H), 2.56 (s, 3H), 2.04 (s, 6H).

Example 50

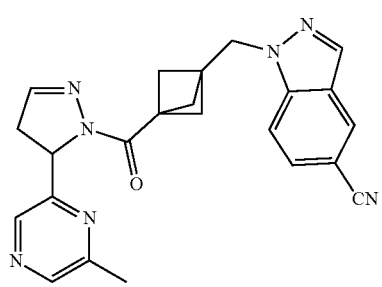 [SMILES: Cc1cncc(C2CC=NN2C(=O)C23CC(Cn4ncc5cc(C#N)ccc54)(C2)C3)n1]

201

1-((3-(5-(6-methylpyrazin-2-yl)-4,5-dihydro-1H-pyrazole-1-carbonyl)bicyclo[1.1.1]pentan-1-yl)methyl)-1H-indazole-5-carbonitrile The title compound was obtained by a procedure similar to that used for Example 49.

MS (ES+) $C_{23}H_{21}N_7O$ requires: 411 found: 412 [M+H]$^+$.

$^1$H NMR (600 MHz, DMSO-d$_6$) δ 8.42-8.40 (m, 1H), 8.40 (s, 1H), 8.28-8.27 (m, 1H), 8.26 (s, 1H), 7.90-7.85 (m, 1H), 7.74-7.69 (m, 1H), 7.17-7.13 (m, 1H), 5.33 (dd, J=11.9, 5.5 Hz, 1H), 4.63 (s, 2H), 3.33 (ddd, J=18.8, 12.0, 1.7 Hz, 1H), 2.85 (ddd, J=18.8, 5.5, 1.8 Hz, 1H), 2.42 (s, 3H), 1.88 (s, 6H).

Example 51

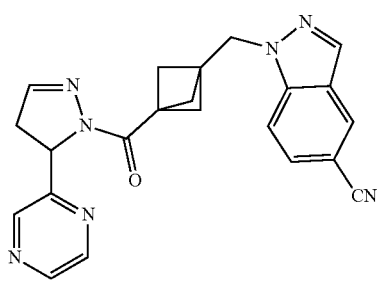 [SMILES: N#Cc1ccc2c(cnn2CC23CC(C(=O)N4N=CCC4c4cnccn4)(C2)C3)c1]

1-((3-(5-(pyrazin-2-yl)-4,5-dihydro-1H-pyrazole-1-carbonyl)bicyclo[1.1.1]pentan-1-yl)methyl)-1H-indazole-5-carbonitrile The title compound was obtained by a procedure similar to that used for Example 49.

MS (ES+) $C_{22}H_{19}N_7O$ requires: 397 found: 398 [M+H]$^+$.

$^1$H NMR (600 MHz, Chloroform-d) δ 8.63-8.61 (m, 1H), 8.60-8.58 (m, 1H), 8.51-8.48 (m, 1H), 8.15-8.14 (m, 1H), 8.13-8.12 (m, 1H), 7.59-7.56 (m, 1H), 7.47-7.43 (m, 1H), 6.98-6.95 (m, 1H), 5.46 (dd, J=11.8, 5.5 Hz, 1H), 4.55 (s, 2H), 3.33 (ddd, J=18.7, 11.8, 1.6 Hz, 1H), 3.10 (ddd, J=18.7, 5.6, 1.8 Hz, 1H), 2.05 (s, 6H).

Example 52

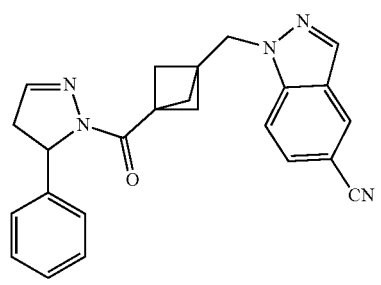 [SMILES: N#Cc1ccc2c(cnn2CC23CC(C(=O)N4N=CCC4c4ccccc4)(C2)C3)c1]

202

1-((3-(5-phenyl-4,5-dihydro-1H-pyrazole-1-carbonyl)-bicyclo[1.1.1]pentan-1-yl)methyl)-1H-indazole-5-carbonitrile The title compound was obtained by a procedure similar to that used for Example 49.

MS (ES+) $C_{24}H_{21}N_5O$ requires: 395 found: 396 [M+H]$^+$.

$^1$H NMR (600 MHz, Chloroform-d) δ 8.14 (t, J=1.1 Hz, 1H), 8.10 (d, J=1.0 Hz, 1H), 7.59-7.54 (m, 1H), 7.48-7.43 (m, 1H), 7.29-7.26 (m, 2H), 7.24-7.19 (m, 1H), 7.10-7.08 (m, 1H), 7.08-7.07 (m, 1H), 6.88-6.84 (m, 1H), 5.30 (dd, J=11.8, 4.8 Hz, 1H), 4.54 (s, 2H), 3.31 (ddd, J=18.8, 11.8, 1.6 Hz, 1H), 2.72 (ddd, J=18.8, 4.8, 1.8 Hz, 1H), 2.06 (s, 6H).

Example 53

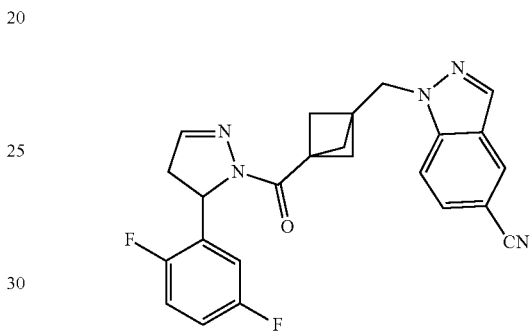

1-((3-(5-(2,5-difluorophenyl)-4,5-dihydro-1H-pyrazole-1-carbonyl)-bicyclo[1.1.1]pentan-1-yl)methyl)-1H-indazole-5-carbonitrile The title compound was obtained by a procedure similar to that used for Example 49.

MS (ES+) $C_{24}H_{19}F_2N_5O$ requires: 431 found: 432 [M+H]$^+$.

$^1$H NMR (600 MHz, Chloroform-d) δ 8.16-8.13 (m, 1H), 8.11-8.11 (m, 1H), 7.60-7.55 (m, 1H), 7.48-7.44 (m, 1H), 7.01-6.94 (m, 1H), 6.92-6.85 (m, 2H), 6.68-6.62 (m, 1H), 5.47 (dd, J=12.0, 5.2 Hz, 1H), 4.56 (s, 2H), 3.33 (ddd, J=18.8, 12.0, 1.6 Hz, 1H), 2.70 (dddd, J=18.8, 5.3, 1.8, 0.9 Hz, 1H), 2.08 (s, 6H).

Example 54

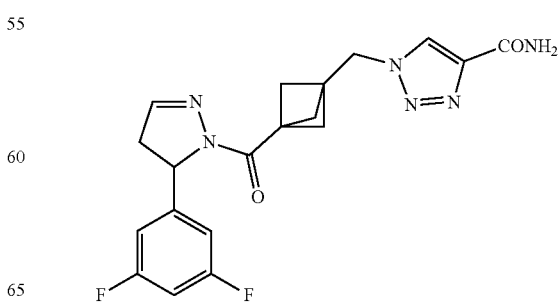

1-((3-(5-(3,5-difluorophenyl)-4,5-dihydro-1H-pyrazole-1-carbonyl)-bicyclo[1.1.1]pentan-1-yl)methyl)-1H-1,2,3-triazole-4-carboxamide

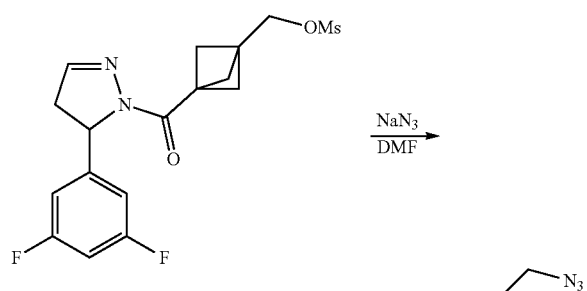

(3-(Azidomethyl)bicyclo[1.1.1]pentan-1-yl)(5-(3,5-difluorophenyl)-4,5-dihydro-1H-pyrazol-1-yl)methanone To a suspension of Intermediate II (40 mg, 0.10 mmol) in DMF (520 μl) was added NaN$_3$ (20 mg, 0.31 mmol), and the resulting mixture was stirred at 80° C. for 2.5 h. The reaction mixture was diluted with EtOAc, H$_2$O was added, and the layers were separated. The aqueous phase was extracted with EtOAc, and the combined organic layers were washed with saturated NaCl, dried over MgSO$_4$, and concentrated under reduced pressure to give the title compound (36 mg, 0.11 mmol, 104% yield) as a yellow oil. The residue was carried forward without further purification. MS (ES$^+$) C$_{16}$H$_{15}$F$_2$N$_5$O requires: 331, found: 332 [M+H]$^+$.

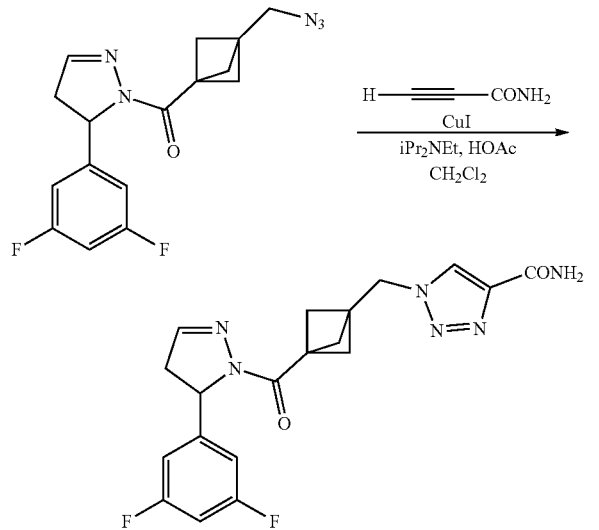

1-((3-(5-(3,5-Difluorophenyl)-4,5-dihydro-1H-pyrazole-1-carbonyl)bicyclo[1.1.1]-pentan-1-yl)methyl)-1H-1,2,3-triazole-4-carboxamide To a solution of the product from the previous step (9 mg, 0.027 mmol) in DCM (150 μl) were added an aliquot (100 μl) from a DCM solution of AcOH and iPr$_2$NEt (40 μmol/ml), propiolamide (1.9 mg, 0.027 mmol), and copper(I) iodide (0.26 mg, 1.4 μmol) and the resulting mixture was stirred at rt overnight. The reaction mixture turned yellow overnight. The volatiles were removed under reduced pressure. The residue was purified by mass-triggered preparative HPLC (Mobile phase: A=0.1% TFA/H$_2$O, B=0.1% TFA/MeCN; Gradient: B=10-90%; 12 min; Column: C18) to give the title compound (5.9 mg, 0.015 mmol, 54% yield) as a white solid. MS (ES$^+$) C$_{19}$H$_{18}$F$_2$N$_6$O$_2$ requires: 400, found: 401 [M+H]$^+$.

Example 55

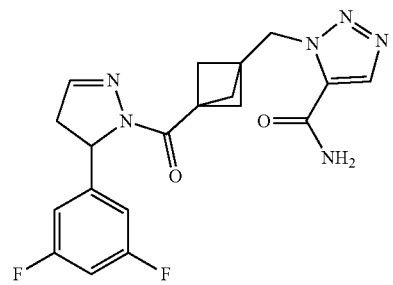 [SMILES: NC(=O)c1cnnn1CC12CC(C(=O)N3N=CCC3c3cc(F)cc(F)c3)(C1)C2]

1-((3-(5-(3,5-difluorophenyl)-4,5-dihydro-1H-pyrazole-1-carbonyl)-bicyclo[1.1.1]pentan-1-yl)methyl)-1H-1,2,3-triazole-5-carboxamide

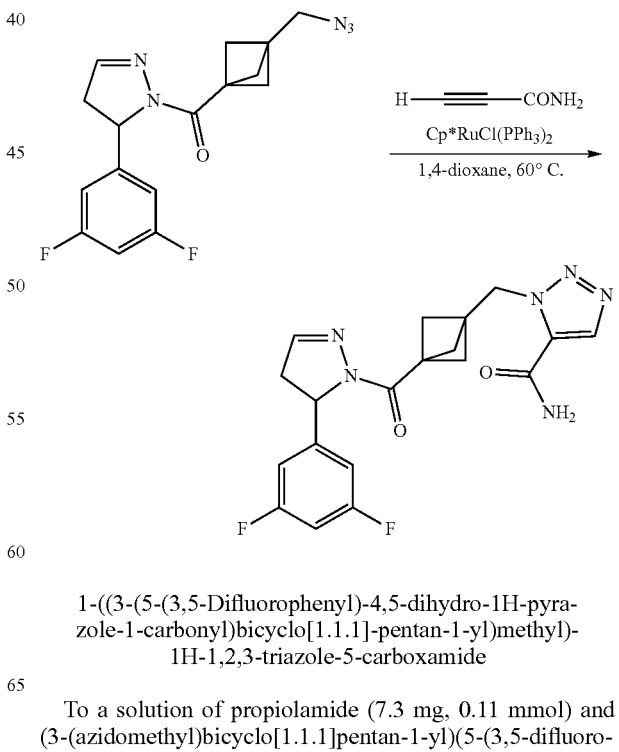

1-((3-(5-(3,5-Difluorophenyl)-4,5-dihydro-1H-pyrazole-1-carbonyl)bicyclo[1.1.1]-pentan-1-yl)methyl)-1H-1,2,3-triazole-5-carboxamide To a solution of propiolamide (7.3 mg, 0.11 mmol) and (3-(azidomethyl)bicyclo[1.1.1]pentan-1-yl)(5-(3,5-difluorophenyl)-4,5-dihydro-1H-pyrazol-1-yl)methanone (32 mg, 0.096 mmol) in 1,4-dioxane (362 µl) was added Cp*RuCl (PPh$_3$)$_2$ (1.3 mg, 3.8 µmol) and the resulting mixture was stirred at 60° C. for 48 hrs. The combined mixture was concentrated under reduced pressure. The residue was purified by mass-triggered preparative HPLC (Mobile phase: A=0.1% TFA/H$_2$O, B=0.1% TFA/MeCN; Gradient: B=20- 60%; 20 min; Column: C18) to give the title compound product as an off-white solid (9.0 mg, 0.015 mmol, 18.37% yield). MS (ES$^+$) C$_{19}$H$_{18}$F$_2$N$_6$O$_2$ requires: 400, found: 401 [M+H]$^+$. The isolated material is a 2:1 mixture (determined by NMR) of the desired head-to-head cycloaddition product 55 and the head-to-tail cycloaddition product 54. MS (ES$^+$) C$_{19}$H$_{18}$F$_2$N$_6$O$_2$ requires: 400, found: 401 [M+H]$^+$.

TABLE 2

Examples 56-183.

| Ex. No | Structure | Name | MS$^{(a)}$ | Proc. Ex. No.$^{(b)}$ |
|---|---|---|---|---|
| 56 | 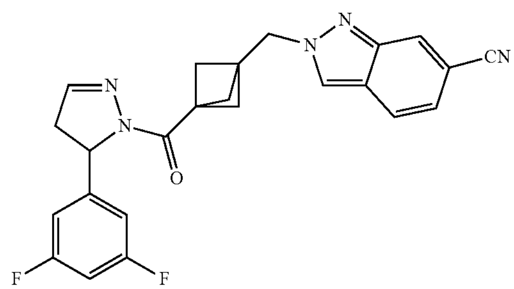 [SMILES: N#Cc1ccc2cn(CC34CC(C(=O)N5N=CCC5c5cc(F)cc(F)c5)(C3)C4)nc2c1] | 2-((3-(5-(3,5-difluorophenyl)-4,5-dihydro-1H-pyrazole-1-carbonyl)bicyclo[1.1.1]-pentan-1-yl)methyl)-2H-indazole-6-carbonitrile | 431/432 | 3 |
| 57 | 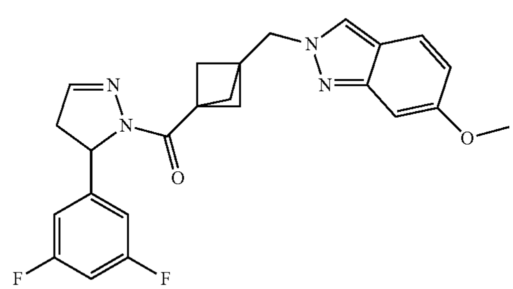 [SMILES: COc1ccc2cn(CC34CC(C(=O)N5N=CCC5c5cc(F)cc(F)c5)(C3)C4)nc2c1] | (5-(3,5-difluorophenyl)-4,5-dihydro-1H-pyrazol-1-yl)(3-((6-methoxy-2H-indazol-2-yl)methyl)bicyclo[1.1.1]-pentan-1-yl)methanone | 436/437 | 3 |
| 58 | 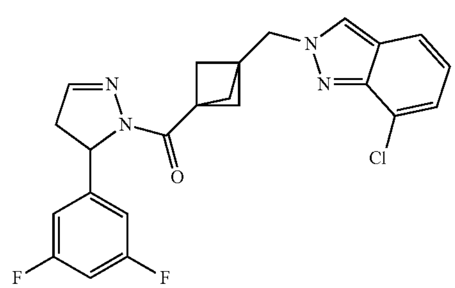 [SMILES: O=C(N1N=CCC1c1cc(F)cc(F)c1)C12CC(Cn3cc4cccc(Cl)c4n3)(C1)C2] | (3-((7-chloro-2H-indazol-2-yl)methyl)bicyclo[1.1.1]-pentan-1-yl)(5-(3,5-difluorophenyl)-4,5-dihydro-1H-pyrazol-1-yl)methanone | 440/441 | 3 |
| 59 | 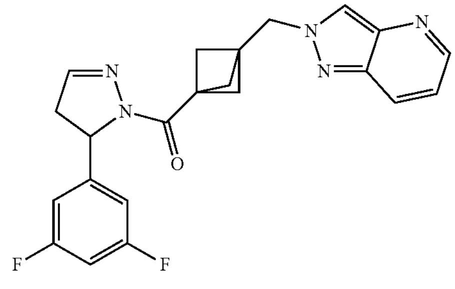 [SMILES: O=C(N1N=CCC1c1cc(F)cc(F)c1)C12CC(Cn3cc4ncccc4n3)(C1)C2] | (3-((2H-pyrazolo[4,3-b]-pyridin-2-yl)methyl)bicyclo-[1.1.1]pentan-1-yl)(5-(3,5-difluorophenyl)-4,5-dihydro-1H-pyrazol-1-yl)methanone | 407/408 | 3 |

TABLE 2-continued

Examples 56-183.

| Ex. No | Structure | Name | MS(a) | Proc. Ex. No.(b) |
|---|---|---|---|---|
| 60 | 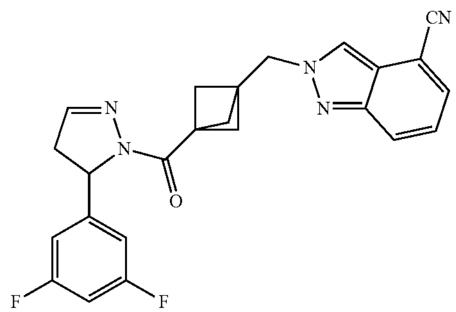 [SMILES: N#Cc1cccc2nn(CC34CC(C(=O)N5N=CCC5c5cc(F)cc(F)c5)(C3)C4)cc12] | 2-((3-(5-(3,5-difluorophenyl)-4,5-dihydro-1H-pyrazole-1-carbonyl)bicyclo[1.1.1]-pentan-1-yl)methyl)-2H-indazole-4-carbonitrile | 431/432 | 3 |
| 61 | 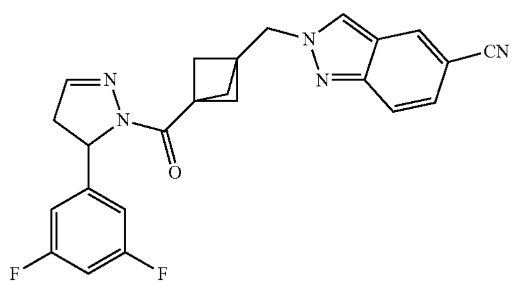 [SMILES: N#Cc1ccc2nn(CC34CC(C(=O)N5N=CCC5c5cc(F)cc(F)c5)(C3)C4)cc2c1] | 2-((3-(5-(3,5-difluorophenyl)-4,5-dihydro-1H-pyrazole-1-carbonyl)bicyclo[1.1.1]-pentan-1-yl)methyl)-2H-indazole-5-carbonitrile | 431/432 | 3 |
| 62 | 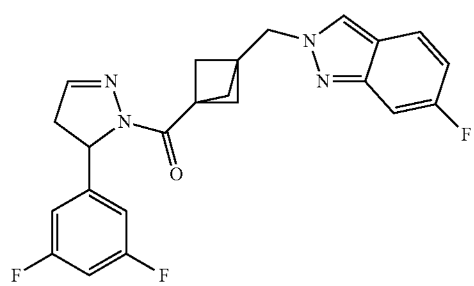 [SMILES: O=C(N1N=CCC1c1cc(F)cc(F)c1)C12CC(Cn3cc4ccc(F)cc4n3)(C1)C2] | (5-(3,5-difluorophenyl)-4,5-dihydro-1H-pyrazol-1-yl)(3-((6-fluoro-2H-indazol-2-yl)methyl)bicyclo[1.1.1]-pentan-1-yl)methanone | 424/425 | 3 |
| 63 | 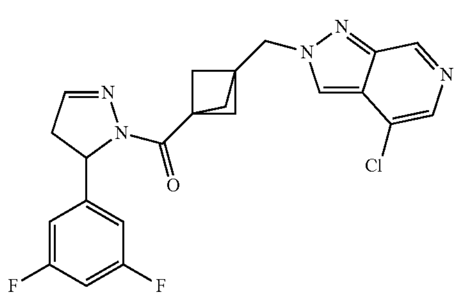 [SMILES: O=C(N1N=CCC1c1cc(F)cc(F)c1)C12CC(Cn3cc4c(Cl)cncc4n3)(C1)C2] | (3-((7-chloro-2H-pyrazolo-[4,3-c]pyridin-2-yl)methyl)-bicyclo[1.1.1]pentan-1-yl)(5-(3,5-difluorophenyl)-4,5-dihydro-1H-pyrazol-1-yl)-methanone | 441/442 | 3 |
| 64 | 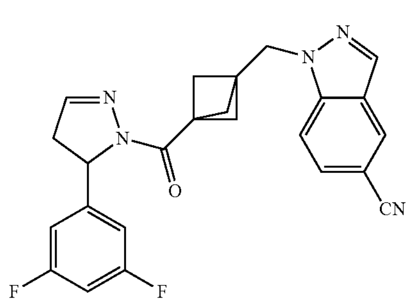 [SMILES: N#Cc1ccc2c(cnn2CC23CC(C(=O)N4N=CCC4c4cc(F)cc(F)c4)(C2)C3)c1] | 1-((3-(5-(3,5-difluorophenyl)-4,5-dihydro-1H-pyrazole-1-carbonyl)bicyclo[1.1.1]-pentan-1-yl)methyl)-1H-indazole-5-carbonitrile | 431/432 | 4 |

TABLE 2-continued

Examples 56-183.

| Ex. No | Structure | Name | MS(a) | Proc. Ex. No.(b) |
|---|---|---|---|---|
| 65 | 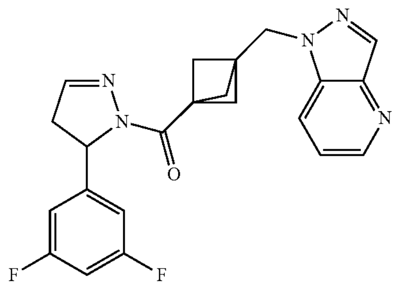 [SMILES: O=C(N1N=CCC1c1cc(F)cc(F)c1)C12CC(Cn3ncc4ncccc43)(C1)C2] | (3-((1H-pyrazolo[4,3-b]-pyridin-1-yl)methyl)bicyclo-[1.1.1]pentan-1-yl)(5-(3,5-difluorophenyl)-4,5-dihydro-1H-pyrazol-1-yl)methanone | 407/ 408 | 4 |
| 66 | 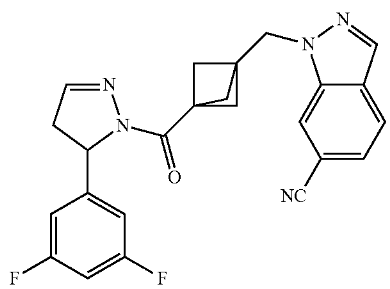 [SMILES: N#Cc1ccc2cnn(CC34CC(C(=O)N5N=CCC5c5cc(F)cc(F)c5)(C3)C4)c2c1] | 1-((3-(5-(3,5-difluorophenyl)-4,5-dihydro-1H-pyrazole-1-carbonyl)bicyclo[1.1.1]-pentan-1-yl)methyl)-1H-indazole-6-carbonitrile | 431/ 432 | 4 |
| 67 | 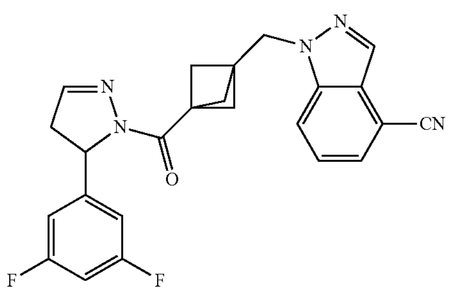 [SMILES: N#Cc1cccc2c1cnn2CC12CC(C(=O)N3N=CCC3c3cc(F)cc(F)c3)(C1)C2] | 1-((3-(5-(3,5-difluorophenyl)-4,5-dihydro-1H-pyrazole-1-carbonyl)bicyclo[1.1.1]-pentan-1-yl)methyl)-1H-indazole-4-carbonitrile | 431/ 432 | 4 |
| 68 | 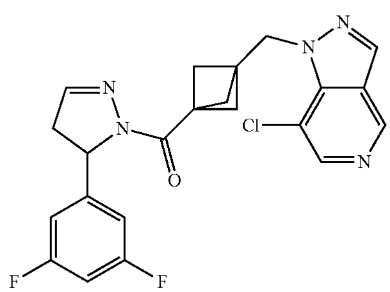 | (3-((7-chloro-1H-pyrazolo-[4,3-c]pyridin-1-yl)methyl)-bicyclo[1.1.1]pentan-1-yl)(5-(3,5-difluorophenyl)-4,5-dihydro-1H-pyrazol-1-yl)methanone | 441/ 442 | 4 |
| 69 | 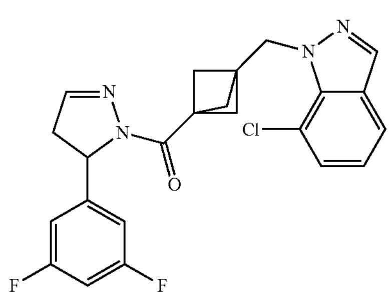 [SMILES: O=C(N1N=CCC1c1cc(F)cc(F)c1)C12CC(Cn3ncc4cccc(Cl)c43)(C1)C2] | (3-((7-chloro-1H-indazol-1-yl)methyl)bicyclo[1.1.1]-pentan-1-yl)(5-(3,5-difluoro-phenyl)-4,5-dihydro-1H-pyrazol-1-yl)methanone | 440/ 441 | 4 |

TABLE 2-continued

Examples 56-183.

| Ex. No | Structure | Name | MS(a) | Proc. Ex. No.(b) |
|---|---|---|---|---|
| 70 | 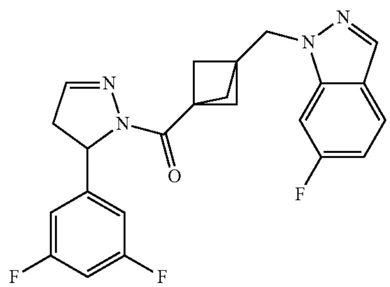 [SMILES: O=C(N1N=CCC1c1cc(F)cc(F)c1)C12CC(Cn3ncc4ccc(F)cc43)(C1)C2] | (5-(3,5-difluorophenyl)-4,5-dihydro-1H-pyrazol-1-yl)(3-((6-fluoro-1H-indazol-1-yl)methyl)bicyclo[1.1.1]pentan-1-yl)methanone | 424/425 | 4 |
| 71 | 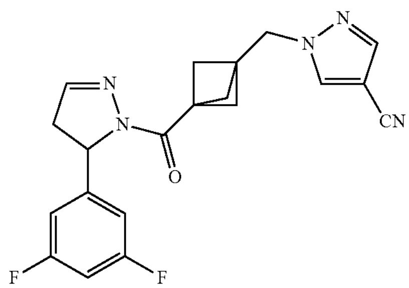 [SMILES: N#Cc1cnn(CC23CC(C(=O)N4N=CCC4c4cc(F)cc(F)c4)(C2)C3)c1] | 1-((3-(5-(3,5-difluorophenyl)-4,5-dihydro-1H-pyrazole-1-carbonyl)bicyclo[1.1.1]-pentan-1-yl)methyl)-1H-pyrazole-4-carbonitrile | 381/382 | 4 |
| 72 | 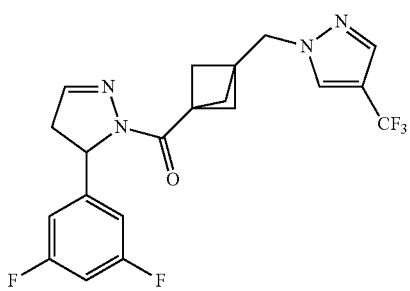 [SMILES: O=C(N1N=CCC1c1cc(F)cc(F)c1)C12CC(Cn3cc(C(F)(F)F)cn3)(C1)C2] | (5-(3,5-difluorophenyl)-4,5-dihydro-1H-pyrazol-1-yl)(3-((4-(trifluoromethyl)-1H-pyrazol-1-yl)methyl)bicyclo-[1.1.1]pentan-1-yl)methanone | 424/425 | 4 |
| 73 | 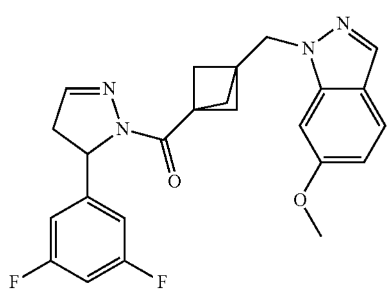 [SMILES: COc1ccc2cnn(CC34CC(C(=O)N5N=CCC5c5cc(F)cc(F)c5)(C3)C4)c2c1] | (5-(3,5-difluorophenyl)-4,5-dihydro-1H-pyrazol-1-yl)(3-((6-methoxy-1H-indazol-1-yl)methyl)bicyclo[1.1.1]-pentan-1-yl)methanone | 436/437 | 4 |
| 74 | 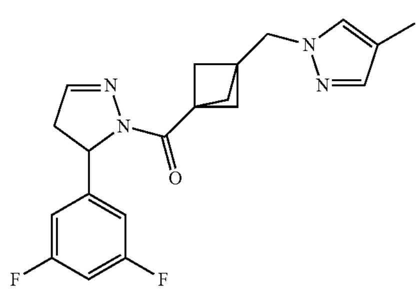 [SMILES: Cc1cnn(CC23CC(C(=O)N4N=CCC4c4cc(F)cc(F)c4)(C2)C3)c1] | (5-(3,5-difluorophenyl)-4,5-dihydro-1H-pyrazol-1-yl)(3-((4-methyl-1H-pyrazol-1-yl)methyl)bicyclo[1.1.1]pentan-1-yl)methanone | 370/371 | 4 |

TABLE 2-continued

Examples 56-183.

| Ex. No | Structure | Name | MS[a] | Proc. Ex. No.[b] |
|---|---|---|---|---|
| 75 | 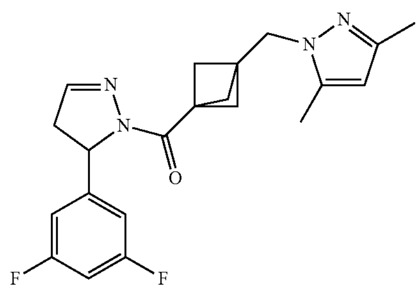 [SMILES: Cc1cc(C)n(CC23CC(C(=O)N4N=CCC4c4cc(F)cc(F)c4)(C2)C3)n1] | (5-(3,5-difluorophenyl)-4,5-dihydro-1H-pyrazol-1-yl)(3-((3,5-dimethyl-1H-pyrazol-1-yl)methyl)bicyclo[1.1.1]-pentan-1-yl)methanone | 384/385 | 4 |
| 76 | 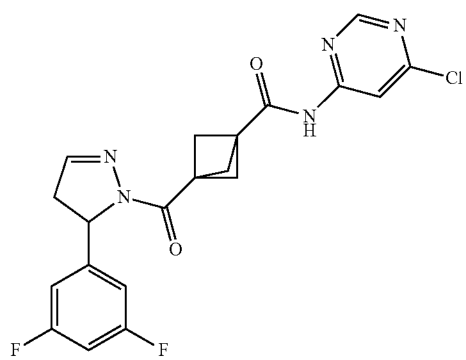 [SMILES: O=C(Nc1cc(Cl)ncn1)C12CC(C(=O)N3N=CCC3c3cc(F)cc(F)c3)(C1)C2] | N-(6-chloropyrimidin-4-yl)-3-(5-(3,5-difluorophenyl)-4,5-dihydro-1H-pyrazole-1-carbonyl)bicyclo[1.1.1]-pentane-1-carboxamide | 431/432 | 10 |
| 77 | 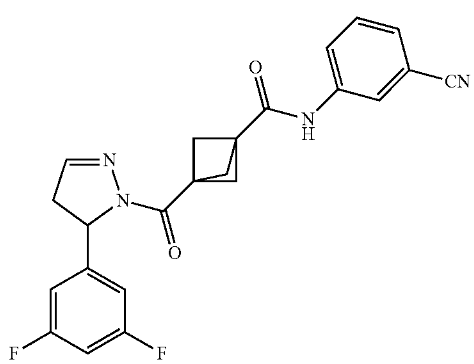 [SMILES: N#Cc1cccc(NC(=O)C23CC(C(=O)N4N=CCC4c4cc(F)cc(F)c4)(C2)C3)c1] | N-(3-cyanophenyl)-3-(5-(3,5-difluorophenyl)-4,5-dihydro-1H-pyrazole-1-carbonyl)-bicyclo[1.1.1]pentane-1-carboxamide | 420/421 | 10 |
| 78 | 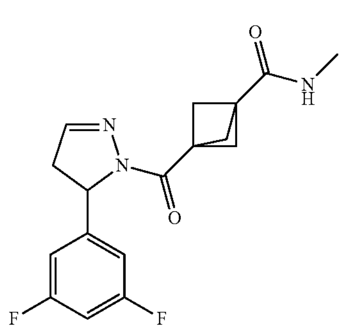 [SMILES: CNC(=O)C12CC(C(=O)N3N=CCC3c3cc(F)cc(F)c3)(C1)C2] | 3-(5-(3,5-difluorophenyl)-4,5-dihydro-1H-pyrazole-1-carbonyl)-N-methylbicyclo-[1.1.1]pentane-1-carboxamide | 333/334 | 10 |

TABLE 2-continued

Examples 56-183.

| Ex. No | Structure | Name | MS[a] | Proc. Ex. No.[b] |
|---|---|---|---|---|
| 79 | 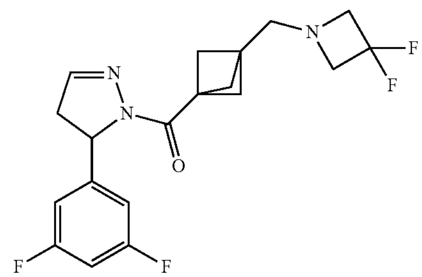 [SMILES: O=C(N1N=CCC1c1cc(F)cc(F)c1)C12CC(CN3CC(F)(F)C3)(C1)C2] | (3-((3,3-difluoroazetidin-1-yl)methyl)bicyclo[1.1.1]-pentan-1-yl)(5-(3,5-difluorophenyl)-4,5-dihydro-1H-pyrazol-1-yl)methanone | 381/382 | 13 |
| 80 | 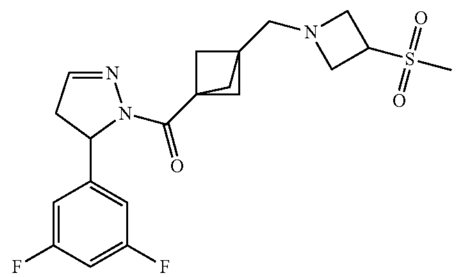 [SMILES: CS(=O)(=O)C1CN(CC23CC(C(=O)N4N=CCC4c4cc(F)cc(F)c4)(C2)C3)C1] | (5-(3,5-difluorophenyl)-4,5-dihydro-1H-pyrazol-1-yl)(3-((3-(methylsulfonyl)azetidin-1-yl)methyl)bicyclo[1.1.1]-pentan-1-yl)methanone | 423/424 | 13 |
| 81 | 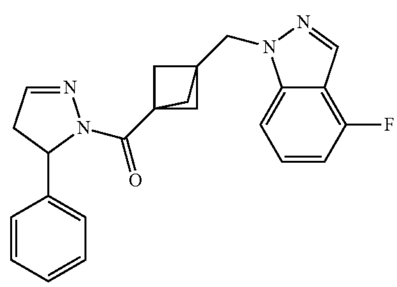 [SMILES: O=C(N1N=CCC1c1ccccc1)C12CC(Cn3ncc4c(F)cccc43)(C1)C2] | (3-((4-fluoro-1H-indazol-1-yl)methyl)bicyclo[1.1.1]-pentan-1-yl)(5-phenyl-4,5-dihydro-1H-pyrazol-1-yl)-methanone | 388/389 | 14 |
| 82 | 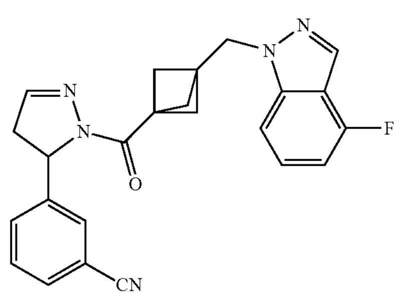 [SMILES: N#Cc1cccc(C2CC=NN2C(=O)C23CC(Cn4ncc5c(F)cccc54)(C2)C3)c1] | 3-(1-(3-((4-fluoro-1H-indazol-1-yl)methyl)bicyclo-[1.1.1]pentane-1-carbonyl)-4,5-dihydro-1H-pyrazol-5-yl)benzonitrile | 413/414 | 14 |
| 83 | 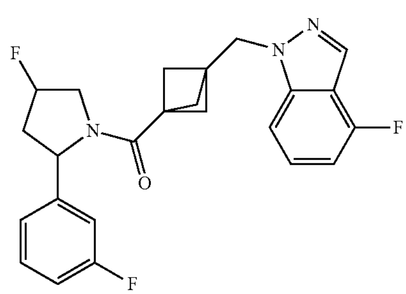 [SMILES: O=C(N1CC(F)CC1c1cccc(F)c1)C12CC(Cn3ncc4c(F)cccc43)(C1)C2] | (3-((4-fluoro-1H-indazol-1-yl)methyl)bicyclo[1.1.1]-pentan-1-yl)(4-fluoro-2-(3-fluorophenyl)pyrrolidin-1-yl)methanone | 425/426 | 14 |

TABLE 2-continued

Examples 56-183.

| Ex. No | Structure | Name | MS(a) | Proc. Ex. No.(b) |
|---|---|---|---|---|
| 84 | 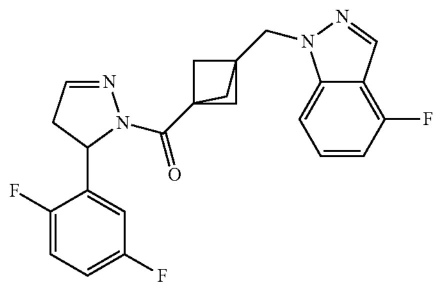 [SMILES: O=C(N1N=CCC1c1cc(F)ccc1F)C12CC(Cn3ncc4c(F)cccc43)(C1)C2] | (5-(2,5-difluorophenyl)-4,5-dihydro-1H-pyrazol-1-yl)(3-((4-fluoro-1H-indazol-1-yl)-methyl)bicyclo[1.1.1]pentan-1-yl)methanone | 424/424 | 14 |
| 85 | 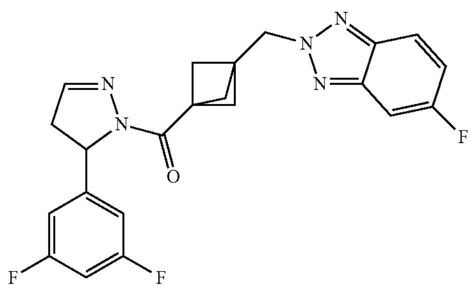 [SMILES: O=C(N1N=CCC1c1cc(F)cc(F)c1)C12CC(Cn3nc4ccc(F)cc4n3)(C1)C2] | (5-(3,5-difluorophenyl)-4,5-dihydro-1H-pyrazol-1-yl)(3-((5-fluoro-2H-benzo[d]-[1,2,3]triazol-2-yl)methyl)-bicyclo[1.1.1]pentan-1-yl)-methanone | 425/426 | 22 |
| 86 | 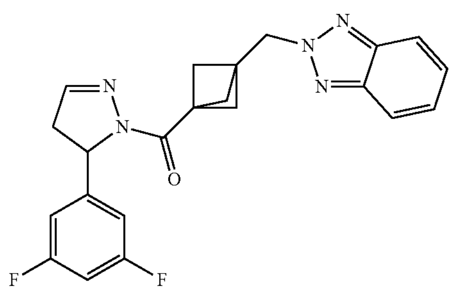 [SMILES: O=C(N1N=CCC1c1cc(F)cc(F)c1)C12CC(Cn3nc4ccccc4n3)(C1)C2] | (3-((2H-benzo[d][1,2,3]-triazol-2-yl)methyl)bicyclo-[1.1.1]pentan-1-yl)(5-(3,5-difluorophenyl)-4,5-dihydro-1H-pyrazol-1-yl)methanone | 407/408 | 22 |
| 87 | 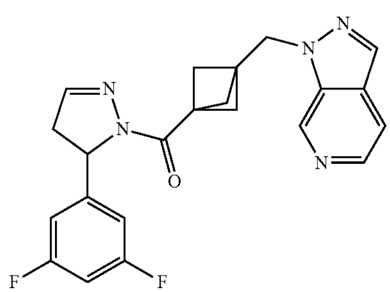 [SMILES: O=C(N1N=CCC1c1cc(F)cc(F)c1)C12CC(Cn3ncc4ccncc43)(C1)C2] | (3-((1H-pyrazolo[3,4-c]-pyridin-1-yl)methyl)bicyclo-[1.1.1]pentan-1-yl)(5-(3,5-difluorophenyl)-4,5-dihydro-1H-pyrazol-1-yl)methanone | 407/408 | 22 |
| 88 | 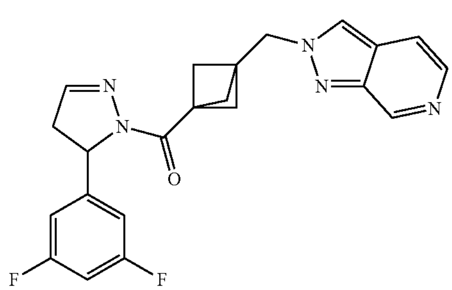 [SMILES: O=C(N1N=CCC1c1cc(F)cc(F)c1)C12CC(Cn3cc4ccncc4n3)(C1)C2] | (3-((2H-pyrazolo[3,4-c]-pyridin-2-yl)methyl)bicyclo-[1.1.1]pentan-1-yl)(5-(3,5-difluorophenyl)-4,5-dihydro-1H-pyrazol-1-yl)methanone | 407/408 | 22 |

TABLE 2-continued

Examples 56-183.

| Ex. No | Structure | Name | MS[a] | Proc. Ex. No.[b] |
|---|---|---|---|---|
| 89 | 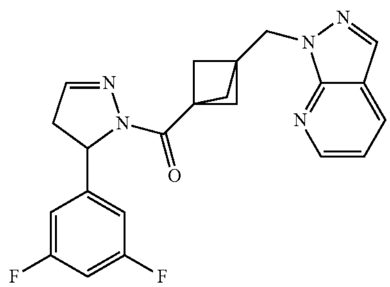 [SMILES: O=C(N1N=CCC1c1cc(F)cc(F)c1)C12CC(Cn3ncc4cccnc43)(C1)C2] | (3-((1H-pyrazolo[3,4-b]-pyridin-1-yl)methyl)bicyclo-[1.1.1]pentan-1-yl)(5-(3,5-difluorophenyl)-4,5-dihydro-1H-pyrazol-1-yl)methanone | 407/ 408 | 22 |
| 90 | 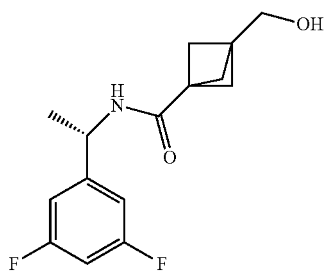 [SMILES: C[C@H](NC(=O)C12CC(CO)(C1)C2)c1cc(F)cc(F)c1] | (S)-N-(1-(3,5-difluoro-phenyl)ethyl)-3-(hydroxymethyl)-bicyclo[1.1.1]pentane-1-carboxamide | 281/ 282 | 24 |
| 91 | 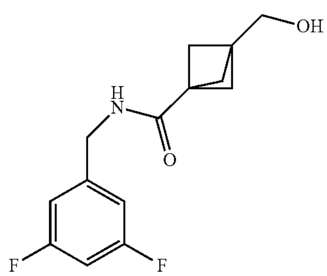 [SMILES: O=C(NCc1cc(F)cc(F)c1)C12CC(CO)(C1)C2] | N-(3,5-difluorobenzyl)-3-(hydroxymethyl)bicyclo-[1.1.1]pentane-1-carboxamide | 267/ 268 | 24 |
| 92 | 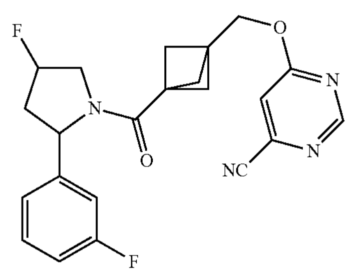 | 6-((3-(4-fluoro-2-(3-fluorophenyl)pyrrolidine-1-carbonyl)bicyclo[1.1.1]-pentan-1-yl)methoxy)-pyrimidine-4-carbonitrile | 410/ 411 | 26 |
| 93 | 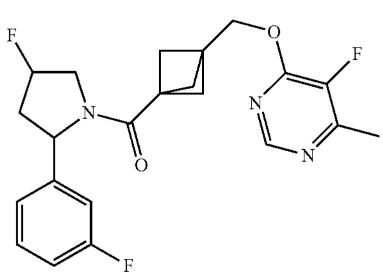 [SMILES: Cc1ncnc(OCC23CC(C(=O)N4CC(F)CC4c4cccc(F)c4)(C2)C3)c1F] | (4-fluoro-2-(3-fluorophenyl)-pyrrolidin-1-yl)(3-(((5-fluoro-6-methylpyrimidin-4-yl)oxy)methyl)bicyclo[1.1.1]-pentan-1-yl)methanone | 417/ 418 | 26 |

TABLE 2-continued

Examples 56-183.

| Ex. No | Structure | Name | MS$^{(a)}$ | Proc. Ex. No.$^{(b)}$ |
|---|---|---|---|---|
| 94 | 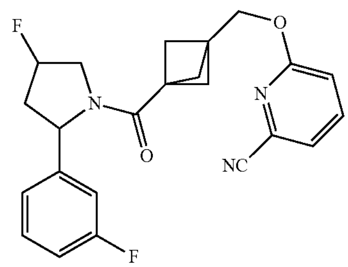 | 6-((3-(4-fluoro-2-(3-fluoro-phenyl)pyrrolidine-1-carbonyl)bicyclo[1.1.1]-pentan-1-yl)methoxy)-picolinonitrile | 409/410 | 26 |
| 95 | 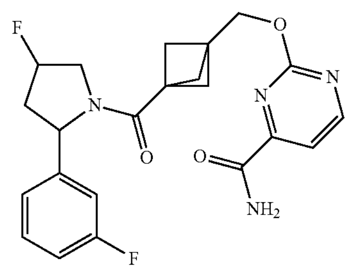 [SMILES: NC(=O)c1ccnc(OCC23CC(C(=O)N4CC(F)CC4c4cccc(F)c4)(C2)C3)n1] | 2-((3-(4-fluoro-2-(3-fluoro-phenyl)pyrrolidine-1-carbonyl)bicyclo[1.1.1]-pentan-1-yl)methoxy)-pyrimidine-4-carboxamide | 428/429 | 26 |
| 96 | 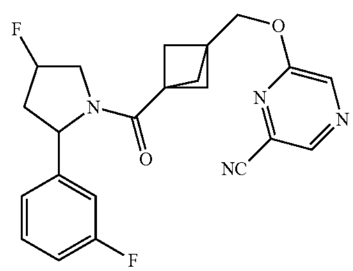 [SMILES: N#Cc1cncc(OCC23CC(C(=O)N4CC(F)CC4c4cccc(F)c4)(C2)C3)n1] | 6-((3-(4-fluoro-2-(3-fluoro-phenyl)pyrrolidine-1-carbonyl)bicyclo[1.1.1]-pentan-1-yl)methoxy)-pyrazine-2-carbonitrile | 410/411 | 26 |
| 97 | 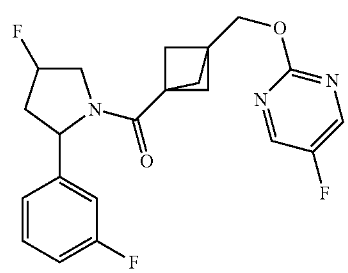 [SMILES: O=C(N1CC(F)CC1c1cccc(F)c1)C12CC(COc3ncc(F)cn3)(C1)C2] | (4-fluoro-2-(3-fluorophenyl)-pyrrolidin-1-yl)(3-(((5-fluoropyrimidin-2-yl)oxy)-methyl)bicyclo[1.1.1]pentan-1-yl)methanone | 403/404 | 26 |
| 98 | 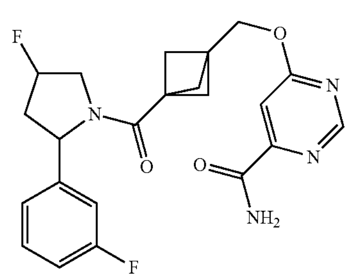 [SMILES: NC(=O)c1cc(OCC23CC(C(=O)N4CC(F)CC4c4cccc(F)c4)(C2)C3)ncn1] | 6-((3-(4-fluoro-2-(3-fluorophenyl)pyrrolidine-1-carbonyl)bicyclo[1.1.1]-pentan-1-yl)methoxy)-pyrimidine-4-carboxamide | 428/429 | 26 |

TABLE 2-continued

Examples 56-183.

| Ex. No | Structure | Name | MS(a) | Proc. Ex. No.(b) |
|---|---|---|---|---|
| 99 | 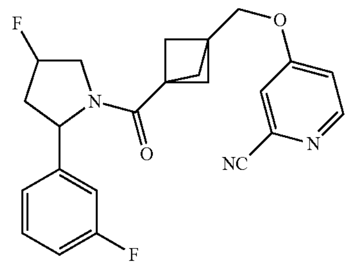 [SMILES: N#Cc1cc(OCC23CC(C(=O)N4CC(F)CC4c4cccc(F)c4)(C2)C3)ccn1] | 4-((3-(4-fluoro-2-(3-fluorophenyl)pyrrolidine-1-carbonyl)bicyclo[1.1.1]-pentan-1-yl)methoxy)-picolinonitrile | 409/410 | 26 |
| 100 | 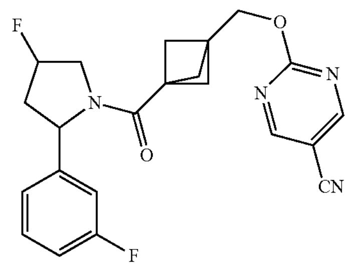 [SMILES: N#Cc1cnc(OCC23CC(C(=O)N4CC(F)CC4c4cccc(F)c4)(C2)C3)nc1] | 2-((3-(4-fluoro-2-(3-fluorophenyl)pyrrolidine-1-carbonyl)bicyclo[1.1.1]-pentan-1-yl)methoxy)-pyrimidine-5-carbonitrile | 410/411 | 26 |
| 101 | 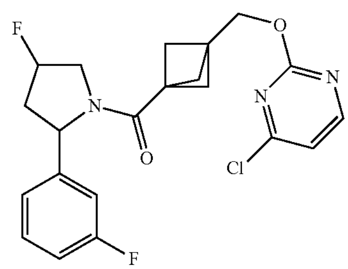 [SMILES: O=C(N1CC(F)CC1c1cccc(F)c1)C12CC(COc3nccc(Cl)n3)(C1)C2] | (3-(((4-chloropyrimidin-2-yl)oxy)methyl)bicyclo[1.1.1]-pentan-1-yl)(4-fluoro-2-(3-fluorophenyl)pyrrolidin-1-yl)methanone | 419/420 | 26 |
| 102 | 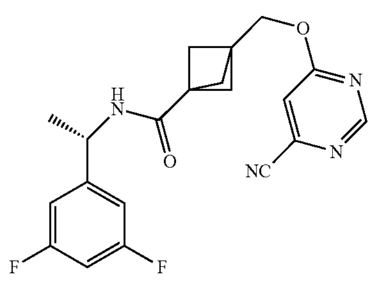 [SMILES: C[C@H](NC(=O)C12CC(COc3cc(C#N)ncn3)(C1)C2)c1cc(F)cc(F)c1] | (S)-3-(((6-cyanopyrimidin-4-yl)oxy)methyl)-N-(1-(3,5-difluorophenyl)ethyl)-bicyclo[1.1.1]pentane-1-carboxamide | 384/385 | 26 |
| 103 | 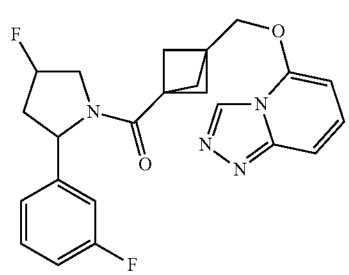 [SMILES: O=C(N1CC(F)CC1c1cccc(F)c1)C12CC(COc3cccc4nncn34)(C1)C2] | (3-(([1,2,4]triazolo[4,3-a]-pyridin-5-yloxy)methyl)-bicyclo[1.1.1]pentan-1-yl)(4-fluoro-2-(3-fluorophenyl)-pyrrolidin-1-yl)methanone | 424/425 | 26 |

TABLE 2-continued

Examples 56-183.

| Ex. No | Structure | Name | MS[a] | Proc. Ex. No.[b] |
|---|---|---|---|---|
| 104 | 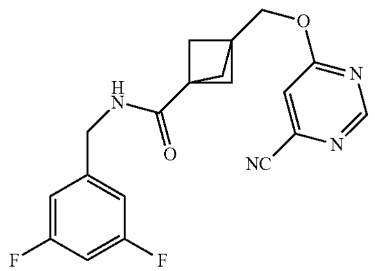 [SMILES: N#Cc1cc(OCC23CC(C(=O)NCc4cc(F)cc(F)c4)(C2)C3)ncn1] | 3-(((6-cyanopyrimidin-4-yl)oxy)methyl)-N-(3,5-difluorobenzyl)bicyclo-[1.1.1]pentane-1-carboxamide | 370/371 | 26 |
| 105 | 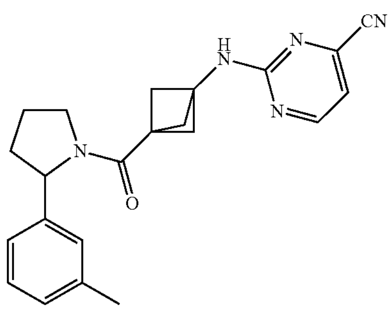 [SMILES: Cc1cccc(C2CCCN2C(=O)C23CC(Nc4nccc(C#N)n4)(C2)C3)c1] | 2-((3-(2-(m-tolyl)pyrrolidine-1-carbonyl)bicyclo[1.1.1]-pentan-1-yl)amino)-pyrimidine-4-carbonitrile | 373/374 | 26 |
| 106 | 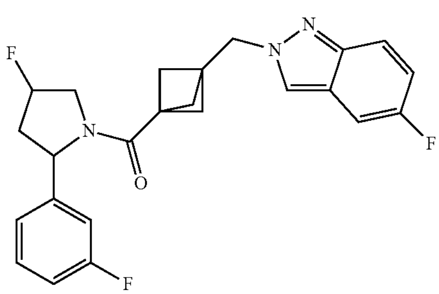 [SMILES: O=C(N1CC(F)CC1c1cccc(F)c1)C12CC(Cn3cc4cc(F)ccc4n3)(C1)C2] | (4-fluoro-2-(3-fluorophenyl)-pyrrolidin-1-yl)(3-((5-fluoro-2H-indazol-2-yl)methyl)-bicyclo[1.1.1]pentan-1-yl)methanone | 425/426 | 27 |
| 107 | 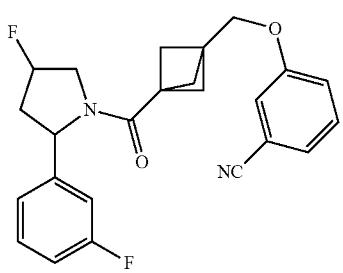 [SMILES: N#Cc1cccc(OCC23CC(C(=O)N4CC(F)CC4c4cccc(F)c4)(C2)C3)c1] | 3-((3-(4-fluoro-2-(3-fluoro-phenyl)pyrrolidine-1-carbonyl)bicyclo[1.1.1]-pentan-1-yl)methoxy)-benzonitrile | 408/409 | 31 |
| 108 | 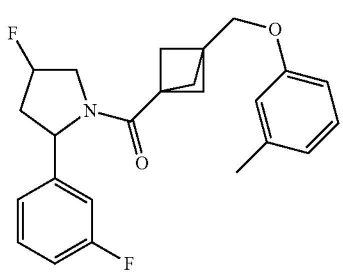 [SMILES: Cc1cccc(OCC23CC(C(=O)N4CC(F)CC4c4cccc(F)c4)(C2)C3)c1] | (4-fluoro-2-(3-fluorophenyl)-pyrrolidin-1-yl)(3-((m-tolyloxy)methyl)bicyclo-[1.1.1]pentan-1-yl)methanone | 397/398 | 31 |

TABLE 2-continued

Examples 56-183.

| Ex. No | Structure | Name | MS[a] | Proc. Ex. No.[b] |
|---|---|---|---|---|
| 109 | 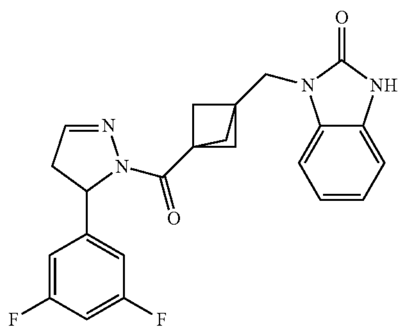 [SMILES: O=C(N1N=CCC1c1cc(F)cc(F)c1)C12CC(Cn3c(=O)[nH]c4ccccc43)(C1)C2] | 1-((3-(5-(3,5-difluorophenyl)-4,5-dihydro-1H-pyrazole-1-carbonyl)bicyclo[1.1.1]-pentan-1-yl)methyl)-1,3-dihydro-2H-benzo[d]-imidazol-2-one | 422/423 | 32 |
| 110 | 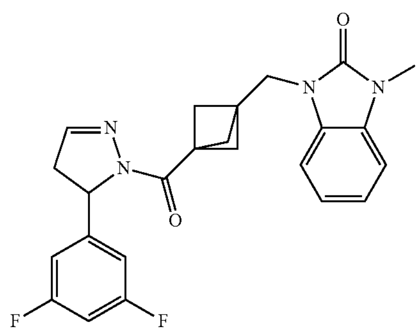 [SMILES: Cn1c(=O)n(CC23CC(C(=O)N4N=CCC4c4cc(F)cc(F)c4)(C2)C3)c2ccccc21] | 1-((3-(5-(3,5-difluorophenyl)-4,5-dihydro-1H-pyrazole-1-carbonyl)bicyclo[1.1.1]-pentan-1-yl)methyl)-3-methyl-1,3-dihydro-2H-benzo[d]imidazol-2-one | 436/437 | 32 |
| 111 | 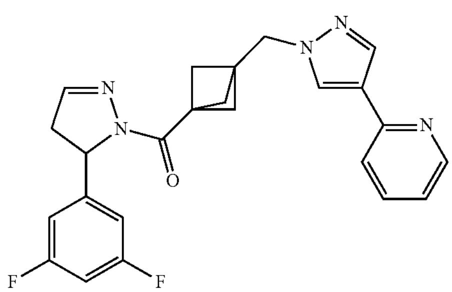 [SMILES: O=C(N1N=CCC1c1cc(F)cc(F)c1)C12CC(Cn3cc(-c4ccccn4)cn3)(C1)C2] | (5-(3,5-difluorophenyl)-4,5-dihydro-1H-pyrazol-1-yl)(3-((4-(pyridin-2-yl)-1H-pyrazol-1-yl)methyl)-bicyclo[1.1.1]pentan-1-yl)methanone | 433/434 | 33 |
| 112 | 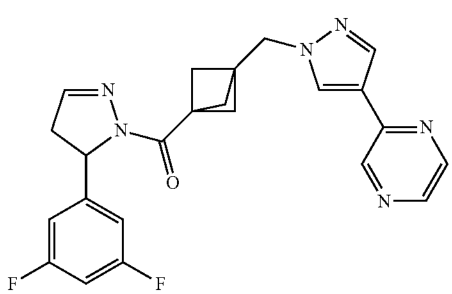 [SMILES: O=C(N1N=CCC1c1cc(F)cc(F)c1)C12CC(Cn3cc(-c4cnccn4)cn3)(C1)C2] | (5-(3,5-difluorophenyl)-4,5-dihydro-1H-pyrazol-1-yl)(3-((4-(pyrazin-2-yl)-1H-pyrazol-1-yl)methyl)-bicyclo[1.1.1]pentan-1-yl)-methanone | 434/435 | 33 |
| 113 | 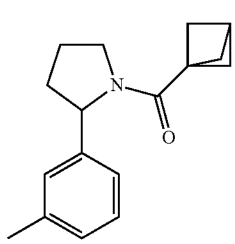 [SMILES: Cc1cccc(C2CCCN2C(=O)C23CC(C2)C3)c1] | bicyclo[1.1.1]pentan-1-yl(2-(m-tolyl)pyrrolidin-1-yl)methanone | 255/256 | 44 |

TABLE 2-continued

Examples 56-183.

| Ex. No | Structure | Name | MS(a) | Proc. Ex. No.(b) |
|---|---|---|---|---|
| 114 | 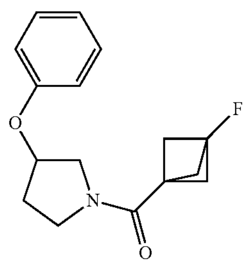 [SMILES: O=C(N1CCC(Oc2ccccc2)C1)C12CC(F)(C1)C2] | (3-fluorobicyclo[1.1.1]-pentan-1-yl)(3-phenoxypyrrolidin-1-yl)methanone | 275/276 | 44 |
| 115 | 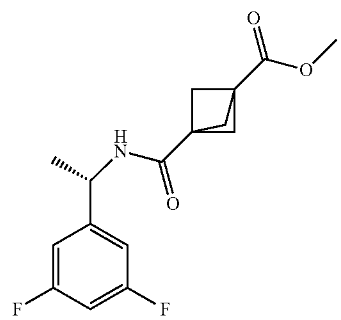 [SMILES: COC(=O)C12CC(C(=O)N[C@@H](C)c3cc(F)cc(F)c3)(C1)C2] | methyl (S)-3-((1-(3,5-difluorophenyl)ethyl)-carbamoyl)bicyclo[1.1.1]-pentane-1-carboxylate | 309/310 | 44 |
| 116 | 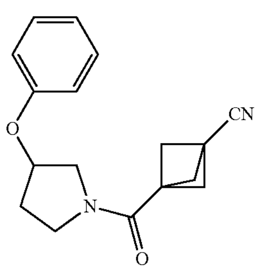 [SMILES: N#CC12CC(C(=O)N3CCC(Oc4ccccc4)C3)(C1)C2] | 3-(3-phenoxypyrrolidine-1-carbonyl)bicyclo[1.1.1]-pentane-1-carbonitrile | 282/283 | 44 |
| 117 | 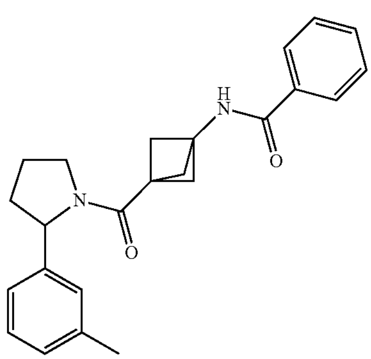 [SMILES: Cc1cccc(C2CCCN2C(=O)C23CC(NC(=O)c4ccccc4)(C2)C3)c1] | N-(3-(2-(m-tolyl)pyrrolidine-1-carbonyl)bicyclo[1.1.1]-pentan-1-yl)benzamide | 374/375 | 44 |
| 118 | 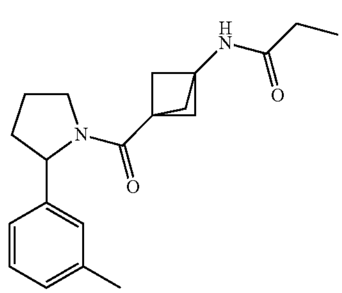 [SMILES: CCC(=O)NC12CC(C(=O)N3CCCC3c3cccc(C)c3)(C1)C2] | N-(3-(2-(m-tolyl)pyrrolidine-1-carbonyl)bicyclo[1.1.1]-pentan-1-yl)propionamide | 326/327 | 44 |

TABLE 2-continued

Examples 56-183.

| Ex. No | Structure | Name | MS(a) | Proc. Ex. No.(b) |
|---|---|---|---|---|
| 119 | 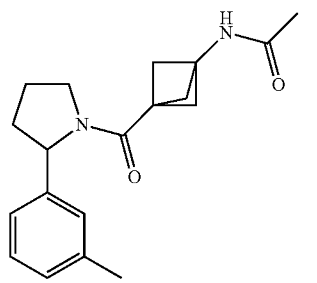 [SMILES: CC(=O)NC12CC(C(=O)N3CCCC3c3cccc(C)c3)(C1)C2] | N-(3-(2-(m-tolyl)pyrrolidine-1-carbonyl)bicyclo[1.1.1]-pentan-1-yl)acetamide | 312/313 | 44 |
| 120 | 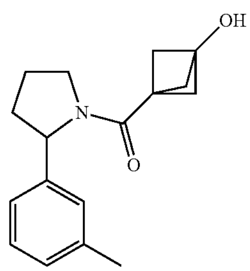 [SMILES: Cc1cccc(C2CCCN2C(=O)C23CC(O)(C2)C3)c1] | (3-hydroxybicyclo[1.1.1]-pentan-1-yl)(2-(m-tolyl)-pyrrolidin-1-yl)methanone | 271/272 | 44 |
| 121 | 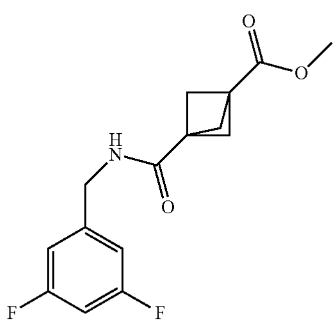 [SMILES: COC(=O)C12CC(C(=O)NCc3cc(F)cc(F)c3)(C1)C2] | methyl 3-((3,5-difluoro-benzyl)carbamoyl)-bicyclo[1.1.1]pentane-1-carboxylate | 295/296 | 44 |
| 122 | 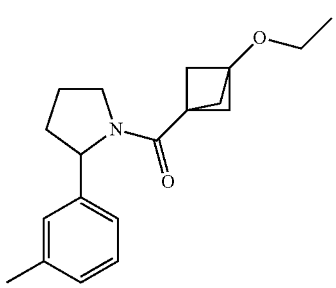 [SMILES: CCOC12CC(C(=O)N3CCCC3c3cccc(C)c3)(C1)C2] | (3-ethoxybicyclo[1.1.1]-pentan-1-yl)(2-(m-tolyl)-pyrrolidin-1-yl)methanone | 299/300 | 46 |
| 123 | 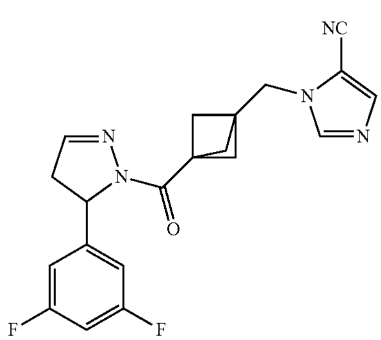 [SMILES: N#Cc1cncn1CC12CC(C(=O)N3N=CCC3c3cc(F)cc(F)c3)(C1)C2] | 1-((3-(5-(3,5-difluorophenyl)-4,5-dihydro-1H-pyrazole-1-carbonyl)bicyclo[1.1.1]-pentan-1-yl)methyl)-1H-imidazole-5-carbonitrile | 381/382 | 23 |

TABLE 2-continued

Examples 56-183.

| Ex. No | Structure | Name | MS[a] | Proc. Ex. No.[b] |
|---|---|---|---|---|
| 124 | 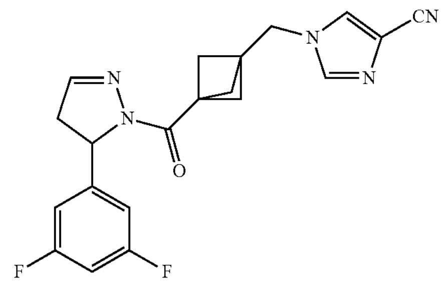 [SMILES: N#Cc1cn(CC23CC(C(=O)N4N=CCC4c4cc(F)cc(F)c4)(C2)C3)cn1] | 1-((3-(5-(3,5-difluorophenyl)-4,5-dihydro-1H-pyrazole-1-carbonyl)bicyclo[1.1.1]pentan-1-yl)methyl)-1H-imidazole-4-carbonitrile | 381/382 | 23 |
| 125 | 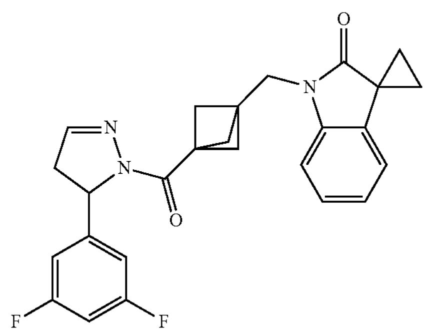 [SMILES: O=C(N1N=CCC1c1cc(F)cc(F)c1)C12CC(CN3C(=O)C4(CC4)c4ccccc43)(C1)C2] | 1'-((3-(5-(3,5-difluorophenyl)-4,5-dihydro-1H-pyrazole-1-carbonyl)-bicyclo[1.1.1]pentan-1-yl)methyl)-spiro[cyclopropane-1,3'-indolin]-2'-one | 447/448 | 32 |
| 126 | 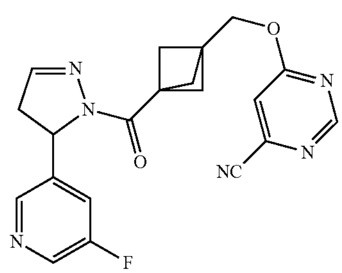 [SMILES: N#Cc1cc(OCC23CC(C(=O)N4N=CCC4c4cncc(F)c4)(C2)C3)ncn1] | 6-((3-(5-(5-fluoropyridin-3-yl)-4,5-dihydro-1H-pyrazole-1-carbonyl)bicyclo[1.1.1]pentan-1-yl)-methoxy)pyrimidine-4-carbonitrile | 392/393 | 39 |
| 127 | 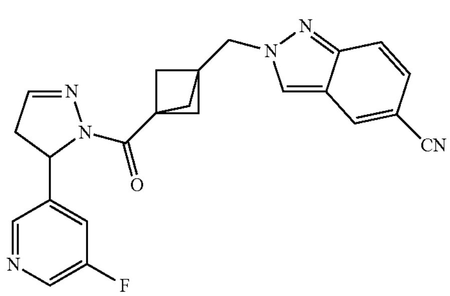 [SMILES: N#Cc1ccc2nn(CC34CC(C(=O)N5N=CCC5c5cncc(F)c5)(C3)C4)cc2c1] | 2-((3-(5-(5-fluoropyridin-3-yl)-4,5-dihydro-1H-pyrazole-1-carbonyl)bicyclo[1.1.1]pentan-1-yl)methyl)-2H-indazole-5-carbonitrile | 414/415 | 3 |
| 128 | 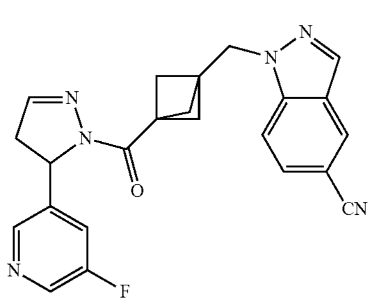 [SMILES: N#Cc1ccc2c(cnn2CC23CC(C(=O)N4N=CCC4c4cncc(F)c4)(C2)C3)c1] | 1-((3-(5-(5-fluoropyridin-3-yl)-4,5-dihydro-1H-pyrazole-1-carbonyl)bicyclo[1.1.1]pentan-1-yl)methyl)-1H-indazole-5-carbonitrile | 414/415 | 4 |

TABLE 2-continued

Examples 56-183.

| Ex. No | Structure | Name | MS(a) | Proc. Ex. No.(b) |
|---|---|---|---|---|
| 129 | 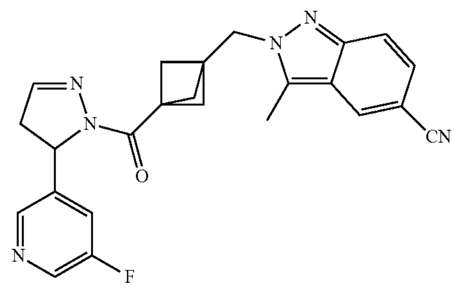 [SMILES: Cc1c2cc(C#N)ccc2nn1CC12CC(C(=O)N3N=CCC3c3cncc(F)c3)(C1)C2] | 2-((3-(5-(5-fluoropyridin-3-yl)-4,5-dihydro-1H-pyrazole-1-carbonyl)bicyclo[1.1.1]-pentan-1-yl)methyl)-3-methyl-2H-indazole-5-carbonitrile | 428/ 429 | 3 |
| 130 | 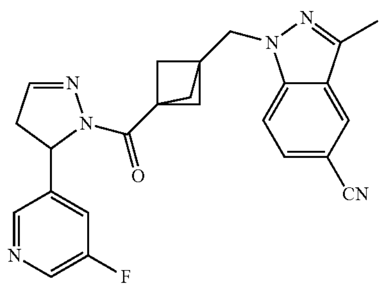 [SMILES: Cc1nn(CC23CC(C(=O)N4N=CCC4c4cncc(F)c4)(C2)C3)c2ccc(C#N)cc12] | 1-((3-(5-(5-fluoropyridin-3-yl)-4,5-dihydro-1H-pyrazole-1-carbonyl)bicyclo[1.1.1]-pentan-1-yl)methyl)-3-methyl-1H-indazole-5-carbonitrile | 428/ 429 | 4 |
| 131 | 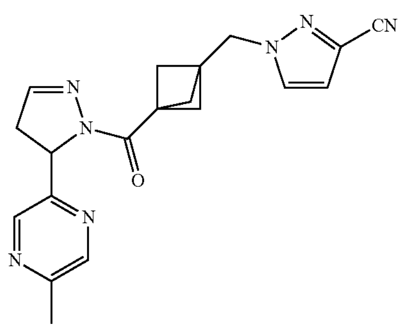 [SMILES: Cc1cnc(C2CC=NN2C(=O)C23CC(Cn4ccc(C#N)n4)(C2)C3)cn1] | 1-((3-(5-(5-methylpyrazin-2-yl)-4,5-dihydro-1H-pyrazole-1-carbonyl)bicyclo[1.1.1]-pentan-1-yl)methyl)-1H-pyrazole-4-carbonitrile | 361/ 362 | 47 |
| 132 | 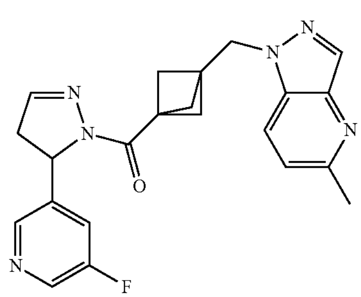 [SMILES: Cc1ccc2c(cnn2CC23CC(C(=O)N4N=CCC4c4cncc(F)c4)(C2)C3)n1] | (5-(5-fluoropyridin-3-yl)-4,5-dihydro-1H-pyrazol-1-yl)(3-((5-methyl-1H-pyrazolo[4,3-b]pyridin-1-yl)methyl)-bicyclo[1.1.1]pentan-1-yl)methanone | 404/ 405 | 4 |
| 133 | 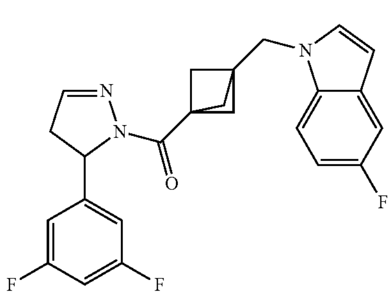 [SMILES: O=C(N1N=CCC1c1cc(F)cc(F)c1)C12CC(Cn3ccc4cc(F)ccc43)(C1)C2] | (5-(3,5-difluorophenyl)-4,5-dihydro-1H-pyrazol-1-yl)(3-((5-fluoro-1H-indol-1-yl)-methyl)bicyclo[1.1.1]pentan-1-yl)methanone | 423/ 424 | 4 |

TABLE 2-continued

Examples 56-183.

| Ex. No | Structure | Name | MS(a) | Proc. Ex. No.(b) |
|---|---|---|---|---|
| 134 | 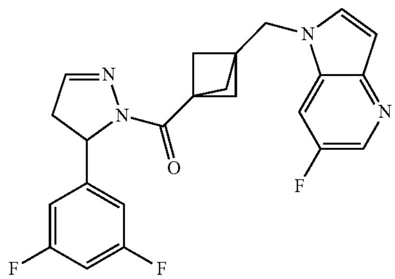 [SMILES: O=C(N1N=CCC1c1cc(F)cc(F)c1)C12CC(Cn3ccc4ncc(F)cc43)(C1)C2] | (5-(3,5-difluorophenyl)-4,5-dihydro-1H-pyrazol-1-yl)(3-((6-fluoro-1H-pyrrolo[3,2-b]pyridin-1-yl)methyl)bicyclo[1.1.1]pentan-1-yl)methanone | 424/425 | 4 |
| 135 | 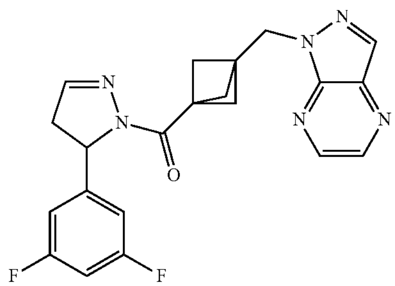 [SMILES: O=C(N1N=CCC1c1cc(F)cc(F)c1)C12CC(Cn3ncc4nccnc43)(C1)C2] | (3-((1H-pyrazolo[3,4-b]pyrazin-1-yl)methyl)bicyclo[1.1.1]pentan-1-yl)(5-(3,5-difluorophenyl)-4,5-dihydro-1H-pyrazol-1-yl)methanone | 408/409 | 4 |
| 136 | 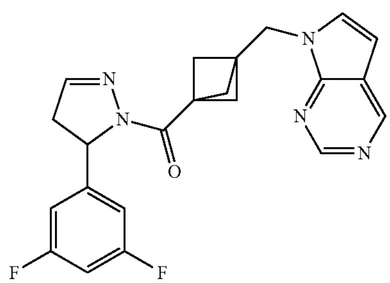 [SMILES: O=C(N1N=CCC1c1cc(F)cc(F)c1)C12CC(Cn3ccc4cncnc43)(C1)C2] | (3-((7H-pyrrolo[2,3-d]pyrimidin-7-yl)methyl)bicyclo[1.1.1]pentan-1-yl)(5-(3,5-difluorophenyl)-4,5-dihydro-1H-pyrazol-1-yl)methanone | 407/408 | 4 |
| 137 | 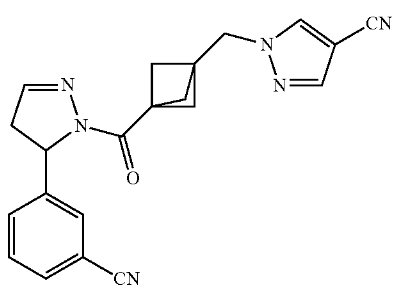 [SMILES: N#Cc1cccc(C2CC=NN2C(=O)C23CC(Cn4cc(C#N)cn4)(C2)C3)c1] | 1-((3-(5-(3-cyanophenyl)-4,5-dihydro-1H-pyrazole-1-carbonyl)bicyclo[1.1.1]pentan-1-yl)methyl)-1H-pyrazole-4-carbonitrile | 370/371 | 47 |
| 138 | 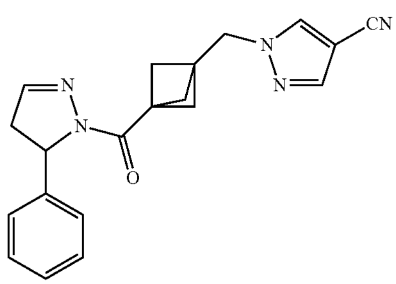 [SMILES: N#Cc1cnn(CC23CC(C(=O)N4N=CCC4c4ccccc4)(C2)C3)c1] | 1-((3-(5-phenyl-4,5-dihydro-1H-pyrazole-1-carbonyl)bicyclo[1.1.1]pentan-1-yl)methyl)-1H-pyrazole-4-carbonitrile | 345/346 | 47 |

TABLE 2-continued

Examples 56-183.

| Ex. No | Structure | Name | MS(a) | Proc. Ex. No.(b) |
|---|---|---|---|---|
| 139 | 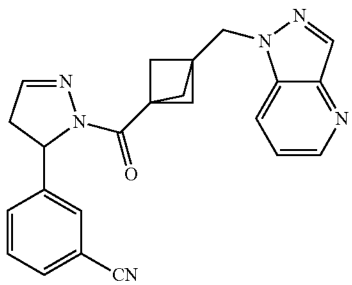 [SMILES: N#Cc1cccc(C2CC=NN2C(=O)C23CC(Cn4ncc5ncccc54)(C2)C3)c1] | 3-(1-(3-((1H-pyrazolo[4,3-b]-pyridin-1-yl)methyl)bicyclo-[1.1.1]pentane-1-carbonyl)-4,5-dihydro-1H-pyrazol-5-yl)benzonitrile | 396/ 397 | 48 |
| 140 | 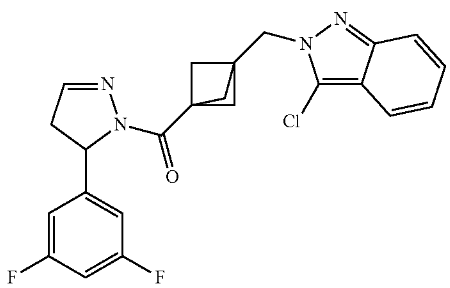 [SMILES: O=C(N1N=CCC1c1cc(F)cc(F)c1)C12CC(Cn3nc4ccccc4c3Cl)(C1)C2] | (3-((3-chloro-2H-indazol-2-yl)methyl)bicyclo[1.1.1]-pentan-1-yl)(5-(3,5-difluorophenyl)-4,5-dihydro-1H-pyrazol-1-yl)methanone | 440/ 441 | 3 |
| 141 | 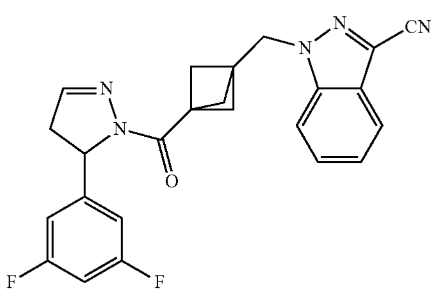 [SMILES: N#Cc1nn(CC23CC(C(=O)N4N=CCC4c4cc(F)cc(F)c4)(C2)C3)c2ccccc12] | (3-((3-chloro-1H-indazol-1-yl)methyl)bicyclo[1.1.1]-pentan-1-yl)(5-(3,5-difluorophenyl)-4,5-dihydro-1H-pyrazol-1-yl)methanone | 440/ 441 | 4 |
| 142 | 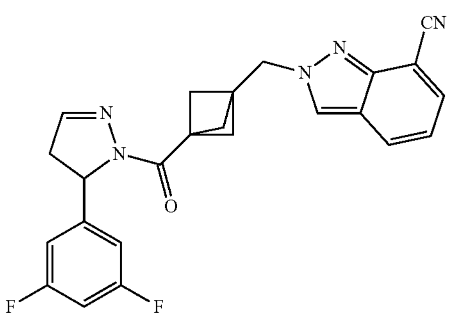 [SMILES: N#Cc1cccc2cn(CC34CC(C(=O)N5N=CCC5c5cc(F)cc(F)c5)(C3)C4)nc12] | 2-((3-(5-(3,5-difluorophenyl)-4,5-dihydro-1H-pyrazole-1-carbonyl)bicyclo[1.1.1]pentan-1-yl)methyl)-2H-indazole-7-carbonitrile | 431/ 432 | 3 |
| 143 | 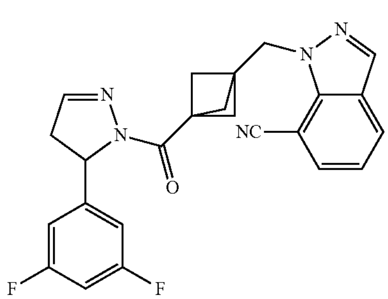 | 1-((3-(5-(3,5-difluorophenyl)-4,5-dihydro-1H-pyrazole-1-carbonyl)bicyclo[1.1.1]-pentan-1-yl)methyl)-1H-indazole-7-carbonitrile | 431/ 432 | 4 |

TABLE 2-continued

Examples 56-183.

| Ex. No | Structure | Name | MS[a] | Proc. Ex. No.[b] |
|---|---|---|---|---|
| 144 | 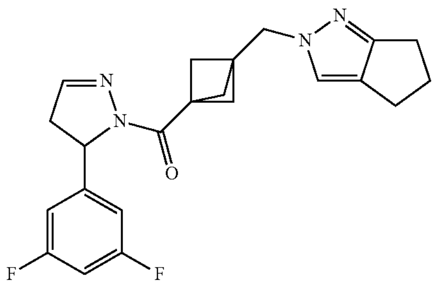 [SMILES: O=C(N1N=CCC1c1cc(F)cc(F)c1)C12CC(Cn3cc4c(n3)CCC4)(C1)C2] | (5-(3,5-difluorophenyl)-4,5-dihydro-1H-pyrazol-1-yl)(3-((5,6-dihydrocyclopenta[c]-pyrazol-2(4H)-yl)methyl)-bicyclo[1.1.1]pentan-1-yl)methanone | 396/397 | 3 |
| 145 | 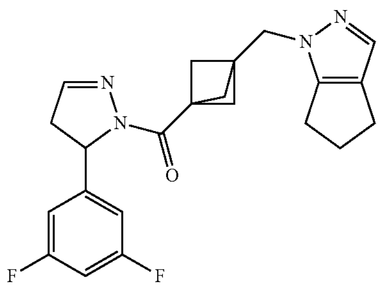 [SMILES: O=C(N1N=CCC1c1cc(F)cc(F)c1)C12CC(Cn3ncc4c3CCC4)(C1)C2] | (5-(3,5-difluorophenyl)-4,5-dihydro-1H-pyrazol-1-yl)(3-((5,6-dihydrocyclopenta[c]-pyrazol-1(4H)-yl)methyl)-bicyclo[1.1.1]pentan-1-yl)methanone | 396/397 | 4 |
| 146 | 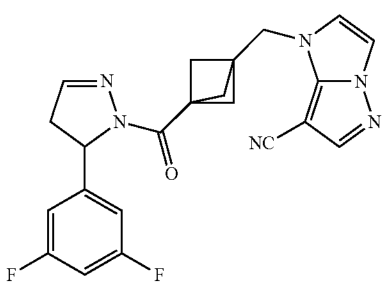 [SMILES: N#Cc1cnn2ccn(CC34CC(C(=O)N5N=CCC5c5cc(F)cc(F)c5)(C3)C4)c12] | 1-((3-(5-(3,5-difluorophenyl)-4,5-dihydro-1H-pyrazole-1-carbonyl)bicyclo[1.1.1]-pentan-1-yl)methyl)-1H-imidazo[1,2-b]pyrazole-7-carbonitrile | 420/421 | 3 |
| 147 | 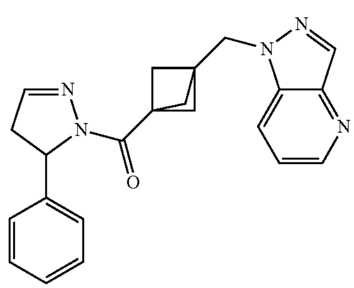 [SMILES: O=C(N1N=CCC1c1ccccc1)C12CC(Cn3ncc4ncccc43)(C1)C2] | (3-((1H-pyrazolo[4,3-b]-pyridin-1-yl)methyl)-bicyclo[1.1.1]pentan-1-yl)(5-phenyl-4,5-dihydro-1H-pyrazol-1-yl)methanone | 371/372 | 48 |
| 148 | 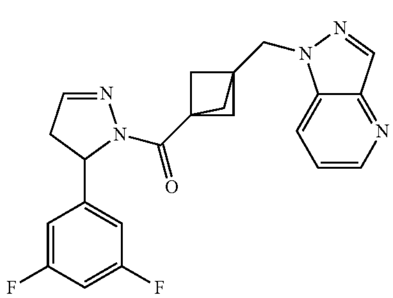 | (3-((1H-pyrazolo[4,3-b]-pyridin-1-yl)methyl)bicyclo-[1.1.1]pentan-1-yl)(5-(3,5-difluorophenyl)-4,5-dihydro-1H-pyrazol-1-yl)methanone | 421/422 | 48 |

TABLE 2-continued

Examples 56-183.

| Ex. No | Structure | Name | MS[a] | Proc. Ex. No.[b] |
|---|---|---|---|---|
| 149 | 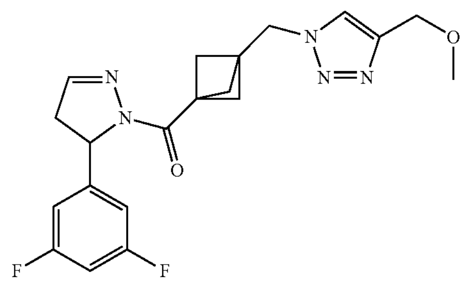 [SMILES: COCc1cn(CC23CC(C(=O)N4N=CCC4c4cc(F)cc(F)c4)(C2)C3)nn1] | (5-(3,5-difluorophenyl)-4,5-dihydro-1H-pyrazol-1-yl)(3-((4-(methoxymethyl)-1H-1,2,3-triazol-1-yl)methyl)-bicyclo[1.1.1]pentan-1-yl)methanone | 401/402 | 54 |
| 150 | 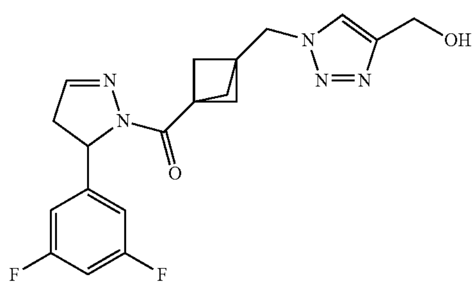 [SMILES: O=C(N1N=CCC1c1cc(F)cc(F)c1)C12CC(Cn3cc(CO)nn3)(C1)C2] | (5-(3,5-difluorophenyl)-4,5-dihydro-1H-pyrazol-1-yl)(3-((4-(hydroxymethyl)-1H-1,2,3-triazol-1-yl)methyl)-bicyclo[1.1.1]pentan-1-yl)methanone | 387/388 | 54 |
| 151 | 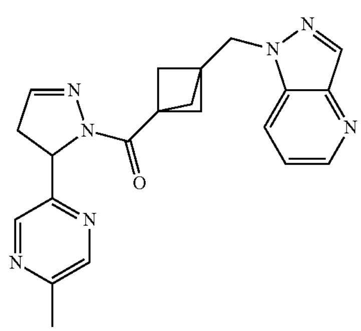 [SMILES: Cc1cnc(C2CC=NN2C(=O)C23CC(Cn4ncc5ncccc54)(C2)C3)cn1] | (3-((1H-pyrazolo[4,3-b]-pyridin-1-yl)methyl)bicyclo-[1.1.1]pentan-1-yl)(5-(5-methylpyrazin-2-yl)-4,5-dihydro-1H-pyrazol-1-yl)methanone | 387/388 | 48 |
| 152 | 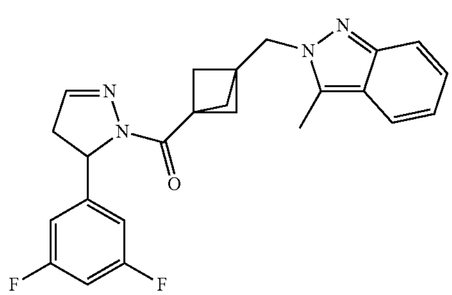 [SMILES: Cc1c2ccccc2nn1CC12CC(C(=O)N3N=CCC3c3cc(F)cc(F)c3)(C1)C2] | (5-(3,5-difluorophenyl)-4,5-dihydro-1H-pyrazol-1-yl)(3-((3-methyl-2H-indazol-2-yl)-methyl)bicyclo[1.1.1]pentan-1-yl)methanone | 420/421 | 3 |
| 153 | 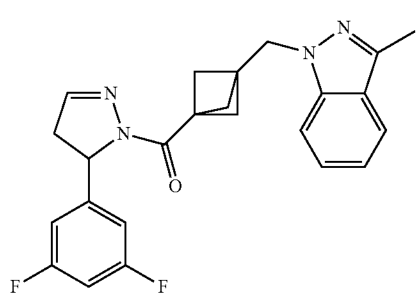 [SMILES: Cc1nn(CC23CC(C(=O)N4N=CCC4c4cc(F)cc(F)c4)(C2)C3)c2ccccc12] | (5-(3,5-difluorophenyl)-4,5-dihydro-1H-pyrazol-1-yl)(3-((3-methyl-1H-indazol-1-yl)-methyl)bicyclo[1.1.1]pentan-1-yl)methanone | 420/421 | 4 |

TABLE 2-continued

Examples 56-183.

| Ex. No | Structure | Name | MS(a) | Proc. Ex. No.(b) |
|---|---|---|---|---|
| 154 | 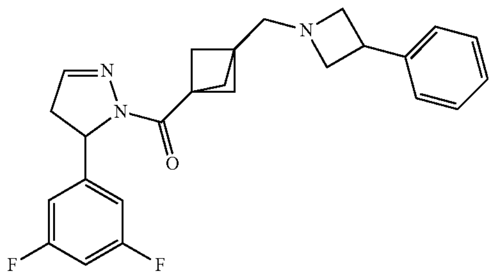 [SMILES: O=C(N1N=CCC1c1cc(F)cc(F)c1)C12CC(CN3CC(c4ccccc4)C3)(C1)C2] | (5-(3,5-difluorophenyl)-4,5-dihydro-1H-pyrazol-1-yl)(3-((3-phenylazetidin-1-yl)methyl)bicyclo[1.1.1]pentan-1-yl)methanone | 421/422 | 13 |
| 155 | 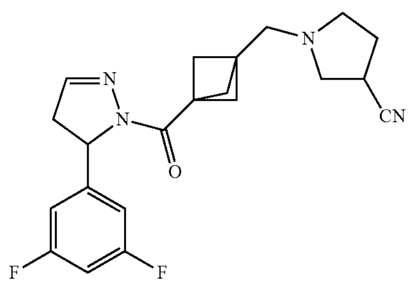 [SMILES: N#CC1CCN(CC23CC(C(=O)N4N=CCC4c4cc(F)cc(F)c4)(C2)C3)C1] | 1-((3-(5-(3,5-difluorophenyl)-4,5-dihydro-1H-pyrazole-1-carbonyl)bicyclo[1.1.1]pentan-1-yl)methyl)pyrrolidine-3-carbonitrile | 384/385 | 13 |
| 156 | 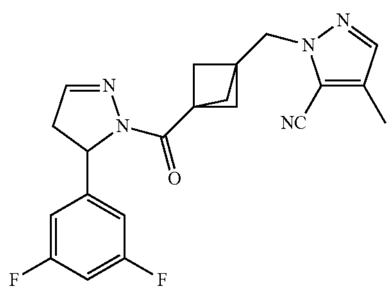 [SMILES: Cc1cnn(CC23CC(C(=O)N4N=CCC4c4cc(F)cc(F)c4)(C2)C3)c1C#N] | 1-((3-(5-(3,5-difluorophenyl)-4,5-dihydro-1H-pyrazole-1-carbonyl)bicyclo[1.1.1]pentan-1-yl)methyl)-4-methyl-1H-pyrazole-5-carbonitrile | 395/396 | 3 |
| 157 | 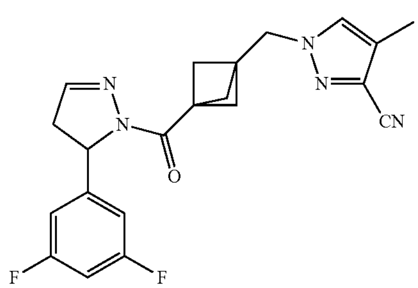 [SMILES: Cc1cn(CC23CC(C(=O)N4N=CCC4c4cc(F)cc(F)c4)(C2)C3)nc1C#N] | 1-((3-(5-(3,5-difluorophenyl)-4,5-dihydro-1H-pyrazole-1-carbonyl)bicyclo[1.1.1]pentan-1-yl)methyl)-4-methyl-1H-pyrazole-3-carbonitrile | 395/396 | 4 |
| 158 | 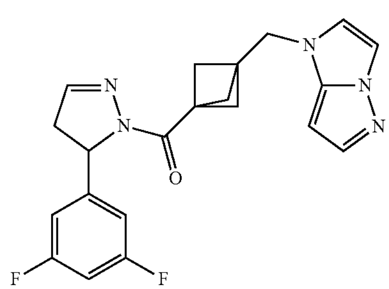 [SMILES: O=C(N1N=CCC1c1cc(F)cc(F)c1)C12CC(Cn3ccn4nccc34)(C1)C2] | (3-((1H-imidazo[1,2-b]pyrazol-1-yl)methyl)bicyclo[1.1.1]pentan-1-yl)(5-(3,5-difluorophenyl)-4,5-dihydro-1H-pyrazol-1-yl)methanone | 395/396 | 3 |

TABLE 2-continued

Examples 56-183.

| Ex. No | Structure | Name | MS(a) | Proc. Ex. No.(b) |
|---|---|---|---|---|
| 159 | 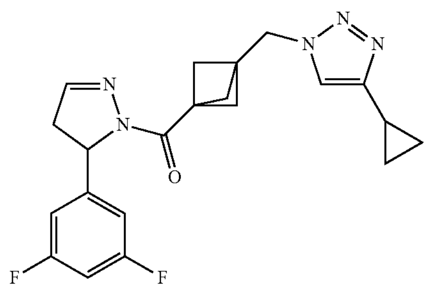 [SMILES: O=C(N1N=CCC1c1cc(F)cc(F)c1)C12CC(Cn3cc(C4CC4)nn3)(C1)C2] | (3-((4-cyclopropyl-1H-1,2,3-triazol-1-yl)methyl)bicyclo-[1.1.1]pentan-1-yl)(5-(3,5-difluorophenyl)-4,5-dihydro-1H-pyrazol-1-yl)methanone | 397/398 | 54 |
| 160 | 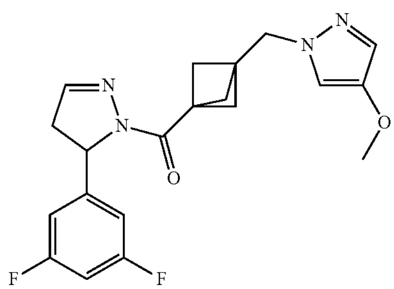 [SMILES: COc1cnn(CC23CC(C(=O)N4N=CCC4c4cc(F)cc(F)c4)(C2)C3)c1] | (5-(3,5-difluorophenyl)-4,5-dihydro-1H-pyrazol-1-yl)(3-((4-methoxy-1H-pyrazol-1-yl)methyl)bicyclo[1.1.1]-pentan-1-yl)methanone | 386/387 | 4 |
| 161 | 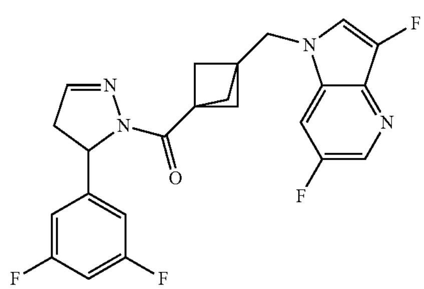 [SMILES: O=C(N1N=CCC1c1cc(F)cc(F)c1)C12CC(Cn3cc(F)c4ncc(F)cc43)(C1)C2] | (3-((3,6-difluoro-1H-pyrrolo-[3,2-b]pyridin-1-yl)methyl)-bicyclo[1.1.1]pentan-1-yl)(5-(3,5-difluorophenyl)-4,5-dihydro-1H-pyrazol-1-yl)methanone | 442/433 | 4 |
| 162 | 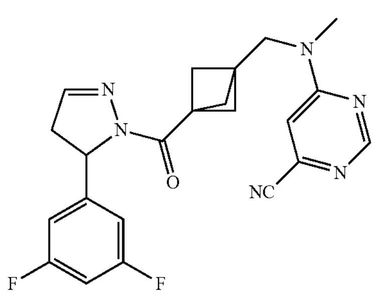 [SMILES: CN(CC12CC(C(=O)N3N=CCC3c3cc(F)cc(F)c3)(C1)C2)c1cc(C#N)ncn1] | 6-(((3-(5-(3,5-difluorophenyl)-4,5-dihydro-1H-pyrazole-1-carbonyl)-bicyclo[1.1.1]pentan-1-yl)methyl)(methyl)amino)pyrimidine-4-carbonitrile | 422/423 | 26 |
| 163 | 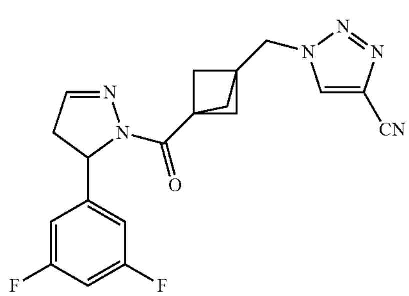 [SMILES: N#Cc1cn(CC23CC(C(=O)N4N=CCC4c4cc(F)cc(F)c4)(C2)C3)nn1] | 1-((3-(5-(3,5-difluorophenyl)-4,5-dihydro-1H-pyrazole-1-carbonyl)bicyclo[1.1.1]-pentan-1-yl)methyl)-1H-1,2,3-triazole-4-carbonitrile | 382/383 | 54 |

TABLE 2-continued

Examples 56-183.

| Ex. No | Structure | Name | MS(a) | Proc. Ex. No.(b) |
|---|---|---|---|---|
| 164 | 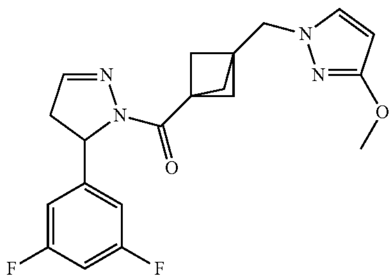 [SMILES: COc1ccn(CC23CC(C(=O)N4N=CCC4c4cc(F)cc(F)c4)(C2)C3)n1] | (5-(3,5-difluorophenyl)-4,5-dihydro-1H-pyrazol-1-yl)(3-((3-methoxy-1H-pyrazol-1-yl)methyl)bicyclo[1.1.1]-pentan-1-yl)methanone | 386/387 | 4 |
| 165 | 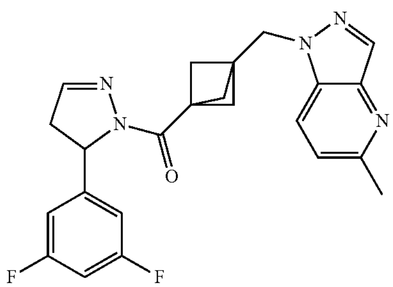 [SMILES: Cc1ccc2c(cnn2CC23CC(C(=O)N4N=CCC4c4cc(F)cc(F)c4)(C2)C3)n1] | (5-(3,5-difluorophenyl)-4,5-dihydro-1H-pyrazol-1-yl)(3-((5-methyl-1H-pyrazolo[4,3-b]pyridin-1-yl)methyl)-bicyclo[1.1.1]pentan-1-yl)methanone | 421/422 | 4 |
| 166 | 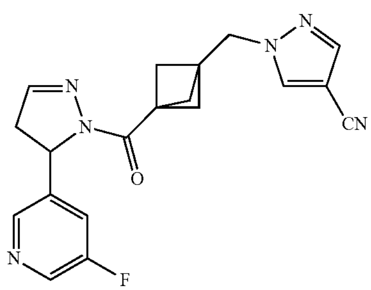 [SMILES: N#Cc1cnn(CC23CC(C(=O)N4N=CCC4c4cncc(F)c4)(C2)C3)c1] | 1-((3-(5-(5-fluoropyridin-3-yl)-4,5-dihydro-1H-pyrazole-1-carbonyl)bicyclo[1.1.1]-pentan-1-yl)methyl)-1H-pyrazole-4-carbonitrile | 364/365 | 47 |
| 167 | 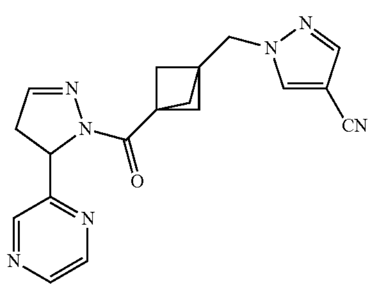 [SMILES: N#Cc1cnn(CC23CC(C(=O)N4N=CCC4c4cnccn4)(C2)C3)c1] | 1-((3-(5-(pyrazin-2-yl)-4,5-dihydro-1H-pyrazole-1-carbonyl)bicyclo[1.1.1]-pentan-1-yl)methyl)-1H-pyrazole-4-carbonitrile | 347/348 | 47 |
| 168 | 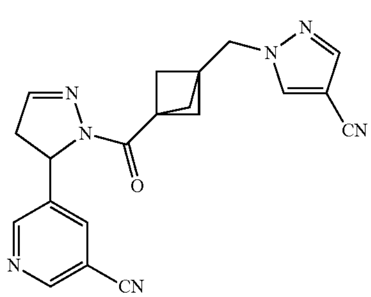 [SMILES: N#Cc1cncc(C2CC=NN2C(=O)C23CC(Cn4cc(C#N)cn4)(C2)C3)c1] | 5-(1-(3-((4-cyano-1H-pyrazol-1-yl)methyl)-bicyclo[1.1.1]pentane-1-carbonyl)-4,5-dihydro-1H-pyrazol-5-yl)nicotinonitrile | 371/372 | 47 |

TABLE 2-continued

Examples 56-183.

| Ex. No | Structure | Name | MS[a] | Proc. Ex. No.[b] |
|---|---|---|---|---|
| 169 | 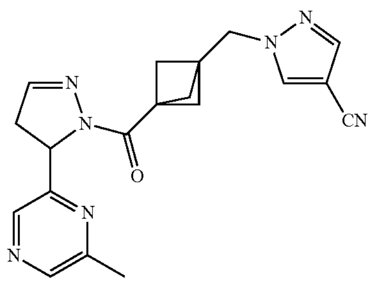 [SMILES: Cc1cncc(C2CC=NN2C(=O)C23CC(Cn4cc(C#N)cn4)(C2)C3)n1] | 1-((3-(5-(6-methylpyrazin-2-yl)-4,5-dihydro-1H-pyrazole-1-carbonyl)bicyclo[1.1.1]-pentan-1-yl)methyl)-1H-pyrazole-4-carbonitrile | 361/ 362 | 47 |
| 170 | 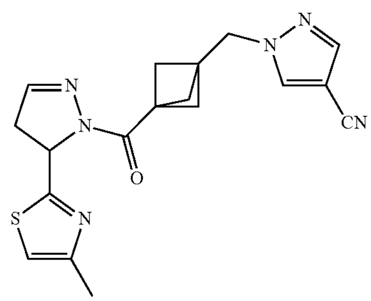 [SMILES: Cc1csc(C2CC=NN2C(=O)C23CC(Cn4cc(C#N)cn4)(C2)C3)n1] | 1-((3-(5-(4-methylthiazol-2-yl)-4,5-dihydro-1H-pyrazole-1-carbonyl)bicyclo[1.1.1]-pentan-1-yl)methyl)-1H-pyrazole-4-carbonitrile | 366/ 367 | 47 |
| 171 | 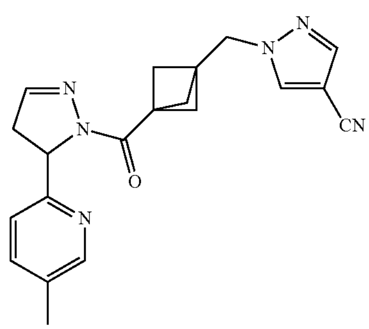 [SMILES: Cc1ccc(C2CC=NN2C(=O)C23CC(Cn4cc(C#N)cn4)(C2)C3)nc1] | 1-((3-(5-(5-methylpyridin-2-yl)-4,5-dihydro-1H-pyrazole-1-carbonyl)bicyclo[1.1.1]-pentan-1-yl)methyl)-1H-pyrazole-4-carbonitiile | 360/ 361 | 47 |
| 172 | 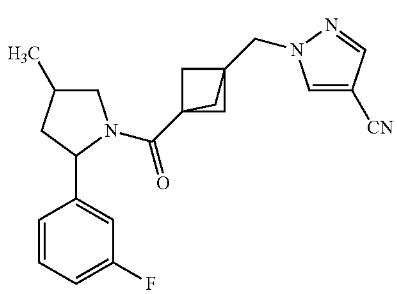 [SMILES: CC1CC(c2cccc(F)c2)N(C(=O)C23CC(Cn4cc(C#N)cn4)(C2)C3)C1] | 1-((3-(2-(3-fluorophenyl)-4-methylpyrrolidine-1-carbonyl)bicyclo[1.1.1]-pentan-1-yl)methyl)-1H-pyrazole-4-carbonitrile | 378/ 379 | 49 |
| 173 | 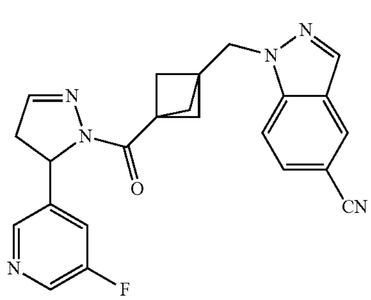 [SMILES: N#Cc1ccc2c(cnn2CC23CC(C(=O)N4N=CCC4c4cncc(F)c4)(C2)C3)c1] | 1-((3-(5-(5-cyanopyridin-3-yl)-4,5-dihydro-1H-pyrazole-1-carbonyl)bicyclo[1.1.1]-pentan-1-yl)methyl)-1H-indazole-5-carbonitrile | 421/ 422 | 49 |

TABLE 2-continued

Examples 56-183.

| Ex. No | Structure | Name | MS(a) | Proc. Ex. No.(b) |
|---|---|---|---|---|
| 174 | 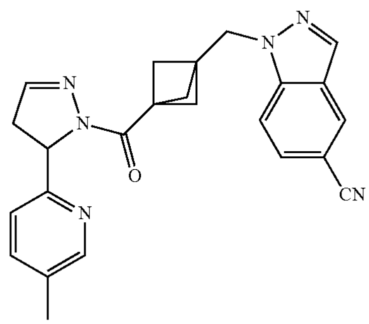 [SMILES: Cc1ccc(C2CC=NN2C(=O)C23CC(Cn4ncc5cc(C#N)ccc54)(C2)C3)nc1] | 1-((3-(5-(5-methylpyridin-2-yl)-4,5-dihydro-1H-pyrazole-1-carbonyl)bicyclo[1.1.1]-pentan-1-yl)methyl)-1H-indazole-5-carbonitrile | 410/411 | 49 |
| 175 | 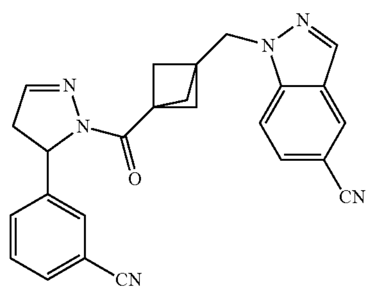 [SMILES: N#Cc1cccc(C2CC=NN2C(=O)C23CC(Cn4ncc5cc(C#N)ccc54)(C2)C3)c1] | 1-((3-(5-(3-cyanophenyl)-4,5-dihydro-1H-pyrazole-1-carbonyl)bicyclo[1.1.1]-pentan-1-yl)methyl)-1H-indazole-5-carbonitrile | 420/421 | 49 |
| 176 | 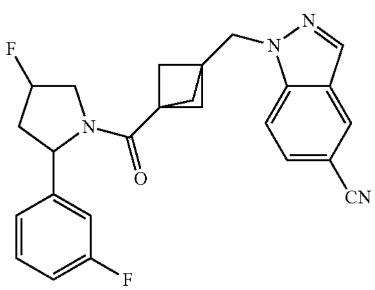 [SMILES: N#Cc1ccc2c(cnn2CC23CC(C(=O)N4CC(F)CC4c4cccc(F)c4)(C2)C3)c1] | 1-((3-(4-fluoro-2-(3-fluorophenyl)pyrrolidine-1-carbonyl)bicyclo[1.1.1]-pentan-1-yl)methyl)-1H-indazole-5-carbonitrile | 432/433 | 49 |
| 177 | 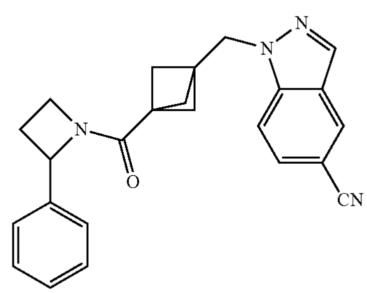 [SMILES: N#Cc1ccc2c(cnn2CC23CC(C(=O)N4CCC4c4ccccc4)(C2)C3)c1] | 1-((3-(2-phenylazetidine-1-carbonyl)bicyclo[1.1.1]-pentan-1-yl)methyl)-1H-indazole-5-carbonitrile | 382/383 | 49 |
| 178 | 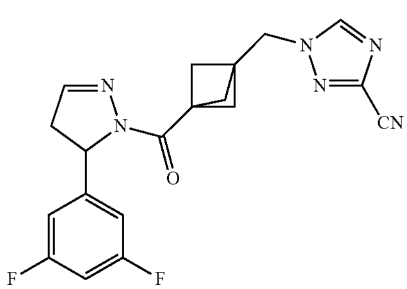 [SMILES: N#Cc1ncn(CC23CC(C(=O)N4N=CCC4c4cc(F)cc(F)c4)(C2)C3)n1] | 1-((3-(5-(3,5-difluorophenyl)-4,5-dihydro-1H-pyrazole-1-carbonyl)bicyclo[1.1.1]-pentan-1-yl)methyl)-1H-1,2,4-triazole-3-carbonitrile | 382/383 | 3 |

TABLE 2-continued

Examples 56-183.

| Ex. No | Structure | Name | MS[a] | Proc. Ex. No.[b] |
|---|---|---|---|---|
| 179 | 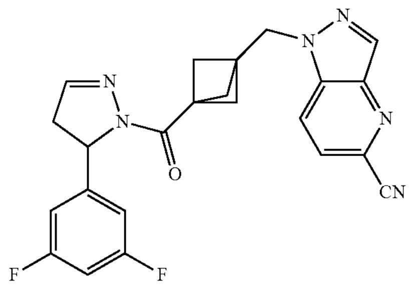 [SMILES: N#Cc1ccc2c(cnn2CC23CC(C(=O)N4N=CCC4c4cc(F)cc(F)c4)(C2)C3)n1] | 1-((3-(5-(3-fluorophenyl)-4,5-dihydro-1H-pyrazole-1-carbonyl)bicyclo[1.1.1]-pentan-1-yl)methyl)-1H-pyrazolo[4,3-b]pyridine-5-carbonitrile | 432/433 | 4 |
| 180 | 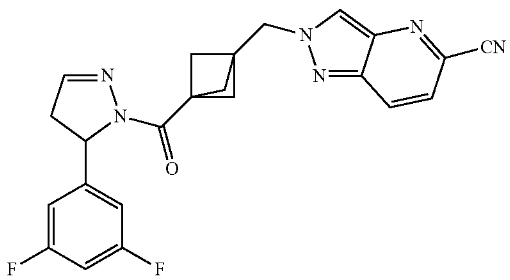 | 2-((3-(5-(3,5-difluorophenyl)-4,5-dihydro-1H-pyrazole-1-carbonyl)bicyclo[1.1.1]-pentan-1-yl)methyl)-2H-pyrazolo[4,3-b]pyridine-5-carbonitrile | 432/433 | 3 |
| 181 | 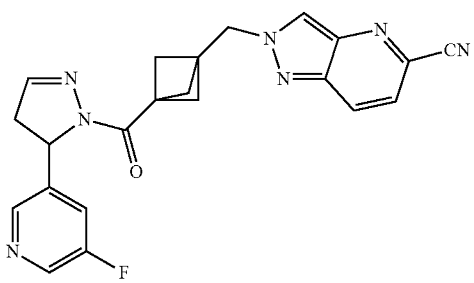 [SMILES: N#Cc1ccc2nn(CC34CC(C(=O)N5N=CCC5c5cncc(F)c5)(C3)C4)cc2n1] | 2-((3-(5-(5-fluoropyridin-3-yl)-4,5-dihydro-1H-pyrazole-1-carbonyl)bicyclo[1.1.1]-pentan-1-yl)methyl)-2H-pyrazolo[4,3-b]pyridine-5-carbonitrile | 415/416 | 3 |
| 182 | 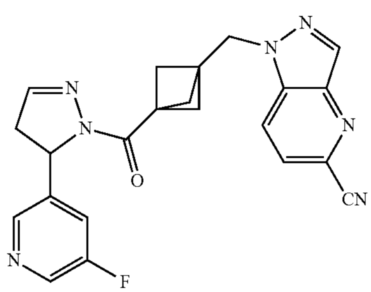 [SMILES: N#Cc1ccc2c(cnn2CC23CC(C(=O)N4N=CCC4c4cncc(F)c4)(C2)C3)n1] | 1-((3-(5-(5-fluoropyridin-3-yl)-4,5-dihydro-1H-pyrazole-1-carbonyl)bicyclo[1.1.1]-pentan-1-yl)methyl)-1H-pyrazolo[4,3-b]pyridine-5-carbonitrile | 415/416 | 4 |
| 183 | 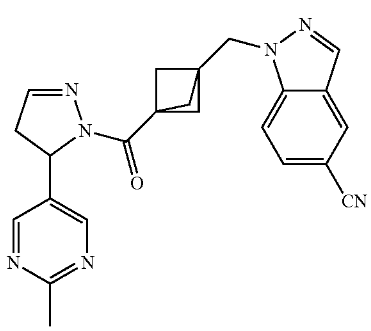 [SMILES: Cc1ncc(C2CC=NN2C(=O)C23CC(Cn4ncc5cc(C#N)ccc54)(C2)C3)cn1] | 1-((3-(5-(2-methylpyrimidin-5-yl)-4,5-dihydro-1H-pyrazole-1-carbonyl)-bicyclo[1.1.1]pentan-1-yl)methyl)-1H-indazole-5-carbonitrile | 411/412 | 49 |

[a] MS is reported as exact mass/observed MS+
[b] synthesis is similar to procedure used for the cited example The compound disclosed in Table 3 was formed as a single regioisomerically pure compound; assignment as either of the two regioisomeric structures has not been established.

TABLE 3

Example 184.

| Ex. No | Structure | Name | MS | Proc. Ex. No. |
|---|---|---|---|---|
| 184 | 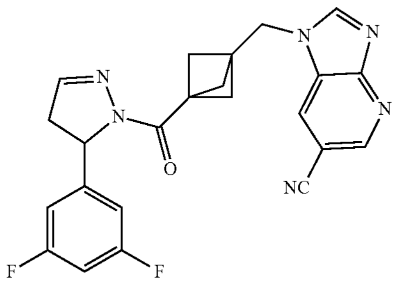 [SMILES: N#Cc1cnc2ncn(CC34CC(C(=O)N5N=CCC5c5cc(F)cc(F)c5)(C3)C4)c2c1] | 1-((3-(5-(3,5-difluorophenyl)-4,5-dihydro-1H-pyrazole-1-carbonyl)bicyclo[1.1.1]-pentan-1-yl)methyl)-1H-imidazo[4,5-b]pyridine-6-carbonitrile | 432/433 | 23 |
| | | 3-((3-(5-(3,5-difluorophenyl)-4,5-dihydro-1H-pyrazole-1-carbonyl)bicyclo[1.1.1]pentan-1-yl)methyl)-3H-imidazo[4,5-b]pyridine-6-carbonitrile | | |

The compounds disclosed in Table 4 were formed as regioisomeric mixtures.

TABLE 4

Examples 185-194.

| Ex. No | Structure | Name | MS[a] | Proc. Ex. No.[b] |
|---|---|---|---|---|
| 185 | 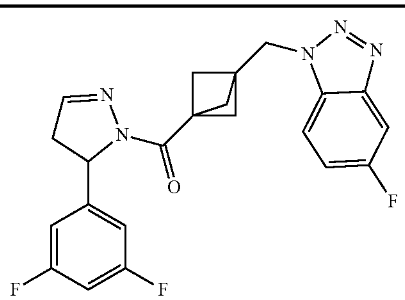 | (5-(3,5-difluorophenyl)-4,5-dihydro-1H-pyrazol-1-yl)(3-((5-fluoro-1H-benzo[d]-[1,2,3]triazol-1-yl)methyl)-bicyclo[1.1.1]pentan-1-yl)methanone | 425/426 | 22 |
| | | (5-(3,5-difluorophenyl)-4,5-dihydro-1H-pyrazol-1-yl)(3-((6-fluoro-1H-benzo[d]-[1,2,3]triazol-1-yl)methyl)-bicyclo[1.1.1]pentan-1-yl)methanone | | |

TABLE 4-continued

Examples 185-194.

| Ex. No | Structure | Name | MS(a) | Proc. Ex. No.(b) |
|---|---|---|---|---|
| 186 | 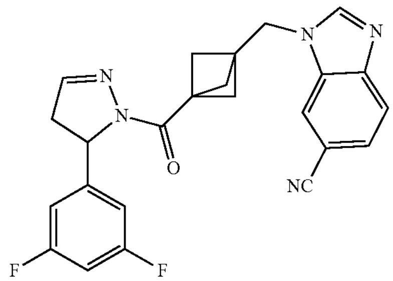 | 1-((3-(5-(3,5-difluorophenyl)-4,5-dihydro-1H-pyrazole-1-carbonyl)bicyclo[1.1.1]-pentan-1-yl)methyl)-1H-benzo[d]imidazole-6-carbonitrile | 431/ 432 | 23 |
|  | | 1-((3-(5-(3,5-difluorophenyl)-4,5-dihydro-1H-pyrazole-1-carbonyl)bicyclo[1.1.1]-pentan-1-yl)methyl)-1H-benzo[d]imidazole-5-carbonitrile | | |
| 187 | 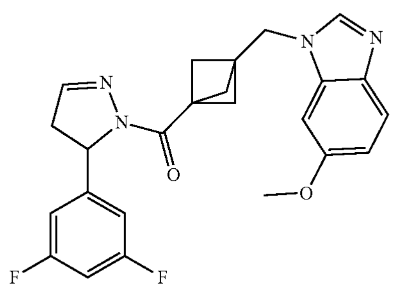 [SMILES: COc1ccc2ncn(CC34CC(C(=O)N5N=CCC5c5cc(F)cc(F)c5)(C3)C4)c2c1] | (5-(3,5-difluorophenyl)-4,5-dihydro-1H-pyrazol-1-yl)(3-((6-methoxy-1H-benzo[d]-imidazol-1-yl)methyl)-bicyclo[1.1.1]pentan-1-yl)-methanone | 436/ 438 | 23 |
|  | | (5-(3,5-difluorophenyl)-4,5-dihydro-1H-pyrazol-1-yl)(3-((5-methoxy-1H-benzo[d]-imidazol-1-yl)methyl)-bicyclo[1.1.1]pentan-1-yl)-methanone | | |
| 188 | 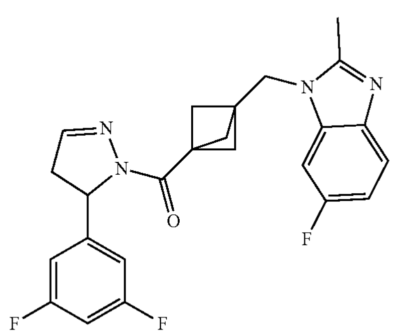 [SMILES: Cc1nc2ccc(F)cc2n1CC12CC(C(=O)N3N=CCC3c3cc(F)cc(F)c3)(C1)C2] | (5-(3,5-difluorophenyl)-4,5-dihydro-1H-pyrazol-1-yl)(3-((6-fluoro-2-methyl-1H-benzo[d]imidazol-1-yl)-methyl)bicyclo[1.1.1]pentan-1-yl)methanone | 438/ 439 | 23 |

TABLE 4-continued

Examples 185-194.

| Ex. No | Structure | Name | MS[a] | Proc. Ex. No.[b] |
|---|---|---|---|---|
| | | (5-(3,5-difluorophenyl)-4,5-dihydro-1H-pyrazol-1-yl)(3-((5-fluoro-2-methyl-1H-benzo[d]imidazol-1-yl)methyl)bicyclo[1.1.1]pentan-1-yl)methanone | | |
| 189 | 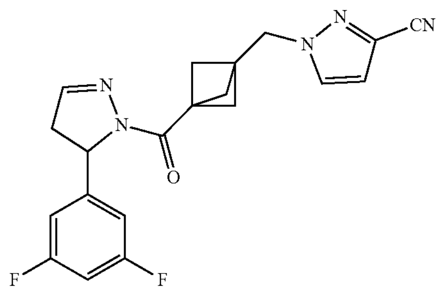 [SMILES: N#Cc1ccn(CC23CC(C(=O)N4N=CCC4c4cc(F)cc(F)c4)(C2)C3)n1] | 1-((3-(5-(3,5-difluorophenyl)-4,5-dihydro-1H-pyrazole-1-carbonyl)bicyclo[1.1.1]-pentan-1-yl)methyl)-1H-pyrazole-3-carbonitrile | 381/382 | 33 |
| | | 1-((3-(5-(3,5-difluorophenyl)-4,5-dihydro-1H-pyrazole-1-carbonyl)bicyclo[1.1.1]-pentan-1-yl)methyl)-1H-pyrazole-5-carbonitrile | | |
| 190 | 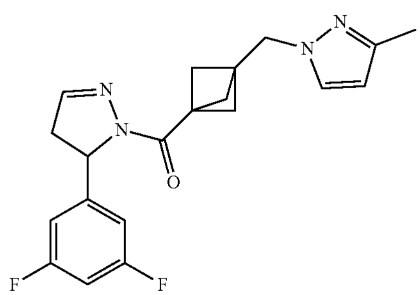 [SMILES: Cc1ccn(CC23CC(C(=O)N4N=CCC4c4cc(F)cc(F)c4)(C2)C3)n1] | (5-(3,5-difluorophenyl)-4,5-dihydro-1H-pyrazol-1-yl)(3-((3-methyl-1H-pyrazol-1-yl)methyl)bicyclo[1.1.1]-pentan-1-yl)methanone | 370/371 | 33 |
| | | (5-(3,5-difluorophenyl)-4,5-dihydro-1H-pyrazol-1-yl)(3-((5-methyl-1H-pyrazol-1-yl)methyl)bicyclo[1.1.1]-pentan-1-yl)methanone | | |

TABLE 4-continued

Examples 185-194.

| Ex. No | Structure | Name | MS(a) | Proc. Ex. No.(b) |
|---|---|---|---|---|
| 191 | 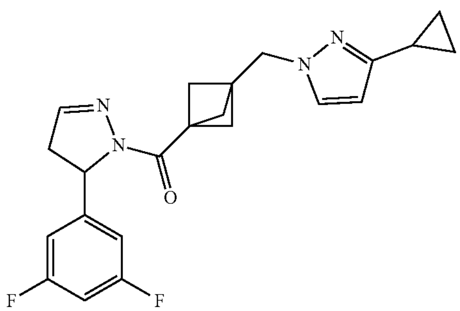 [SMILES: O=C(N1N=CCC1c1cc(F)cc(F)c1)C12CC(Cn3ccc(C4CC4)n3)(C1)C2] | (3-((3-cyclopropyl-1H-pyrazol-1-yl)methyl)-bicyclo[1.1.1]pentan-1-yl)(5-(3,5-difluorophenyl)-4,5-dihydro-1H-pyrazol-1-yl)methanone | 396/397 | 33 |
|  | | (3-((5-cyclopropyl-1H-pyrazol-1-yl)methyl)-bicyclo[1.1.1]pentan-1-yl)(5-(3,5-difluorophenyl)-4,5-dihydro-1H-pyrazol-1-yl)methanone | | |
| 192 | 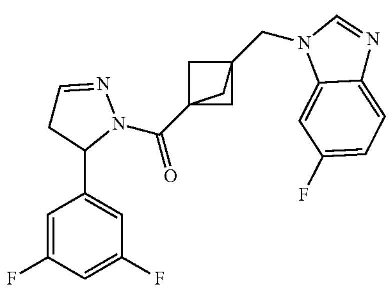 [SMILES: O=C(N1N=CCC1c1cc(F)cc(F)c1)C12CC(Cn3cnc4ccc(F)cc43)(C1)C2] | (5-(3,5-difluorophenyl)-4,5-dihydro-1H-pyrazol-1-yl)(3-((6-fluoro-1H-benzo[d]-imidazol-1-yl)methyl)-bicyclo[1.1.1]pentan-1-yl)methanone | 424/425 | 4 |
|  | | (5-(3,5-difluorophenyl)-4,5-dihydro-1H-pyrazol-1-yl)(3-((5-fluoro-1H-benzo[d]-imidazol-1-yl)methyl)-bicyclo[1.1.1]pentan-1-yl)methanone | | |
| 193 | 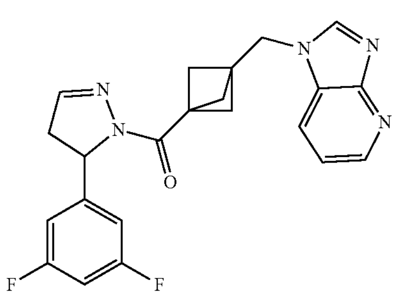 [SMILES: O=C(N1N=CCC1c1cc(F)cc(F)c1)C12CC(Cn3cnc4ncccc43)(C1)C2] | (3-((1H-imidazo[4,5-b]-pyridin-1-yl)methyl)-bicyclo[1.1.1]pentan-1-yl)(5-(3,5-difluorophenyl)-4,5-dihydro-1H-pyrazol-1-yl)methanone | 408/409 | 23 |

TABLE 4-continued

Examples 185-194.

| Ex. No | Structure | Name | MS[a] | Proc. Ex. No.[b] |
|---|---|---|---|---|
|  |  | (3-((3H-imidazol[4,5-b]pyridin-3-yl)methyl)-bicyclo[1.1.1]pentan-1-yl)(5-(3,5-difluorophenyl)-4,5-dihydro-1H-pyrazol-1-yl)methanone |  |  |
| 194 | 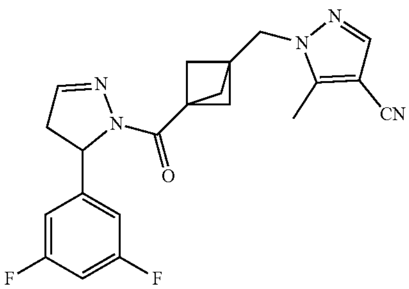 [SMILES: Cc1c(C#N)cnn1CC12CC(C(=O)N3N=CCC3c3cc(F)cc(F)c3)(C1)C2] | 1-((3-(5-(3,5-difluorophenyl)-4,5-dihydro-1H-pyrazole-1-carbonyl)bicyclo[1.1.1]-pentan-1-yl)methyl)-5-methyl-1H-pyrazole-4-carbonitrile | 395/ 396 | 3/4 |
|  |  | 1-((3-(5-(3,5-difluorophenyl)-4,5-dihydro-1H-pyrazole-1-carbonyl)bicyclo[1.1.1]-pentan-1-yl)methyl)-3-methyl-1H-pyrazole-4-carbonitrile |  |  |

[a]MS is reported as exact mass/observed MS⁺
[b]synthesis is similar to procedure used for the cited example

Example 195

5-((3-(5-(2,5-Difluoro-4-methylphenyl)-4,5-dihydro-1H-pyrazole-1-carbonyl)bicyclo[1.1.1]pentan-1-yl)methoxy)pyrazine-2-carbonitrile 1-(tert-Butyl) 3-methyl bicyclo[1.1.1]pentane-1,3-dicarboxylate To a flask containing 3-(methoxycarbonyl)bicyclo[1.1.1]pentane-1-carboxylic acid (24.7 g, 145 mmol), DMAP (5.32 g, 43.5 mmol) and Boc₂O (67.4 ml, 290 mmol) was added tBuOH (97 ml), and the mixture was stirred at rt. The reaction was vented under a stream of N₂, and after the evolution of gas abated, the reaction was stirred for 3 d, by which time material solidified. The reaction was diluted with CH₂Cl₂ and concentrated, then diluted with Et₂O (100 ml) and washed with aqueous citric acid (250 ml, 10%), aqueous NaOH (250 ml, 0.1 M), and brine. Each aqueous layer was extracted with the same Et₂O (2×125 ml). The organic layers were combined, dried over MgSO₄, and concentrated, and residual tBuOH was azeotroped from CH₂Cl₂/Hexanes to give the title compound (42.7 g, 181 mmol, 125% yield) as a white waxy solid that contained 11 mole % tBuOH, and the title compound 96% pure. The material was carried on to the next step without further purification.

¹H NMR (500 MHz, DMSO-d₆) δ 3.61 (s, 3H), 2.19 (s, 6H), 1.40 (s, 9H).

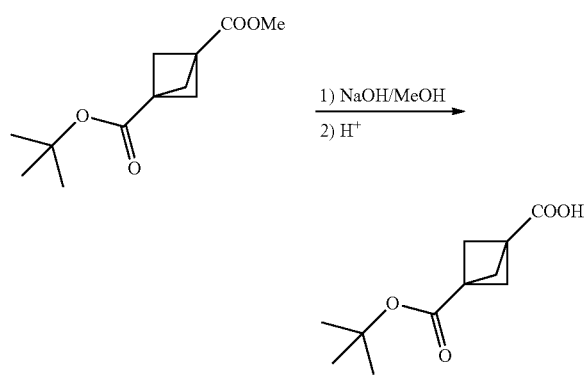

3-(tert-Butoxycarbonyl)bicyclo[1.1.1]pentane-1-carboxylic acid

To a solution of the product from the previous step (13.3 g, 58.8 mmol) in MeOH (147 ml) was added NaOH (64.7 ml, 64.7 mmol), and the resulting mixture was stirred at rt until complete consumption of starting material was achieved. The reaction mixture was partially concentrated, diluted with water, and wash with E₂O. The aqueous layer acidified with citric acid to pH 3. The resulting precipitate was filtered and washed with water. Additional precipitate that formed in filtrate was filtered over the first precipitate. Additional solid that formed in the second filtrate was filtered over the mixture of the first and second precipitates. The final combined solid was washed with more water and hexanes to give the title compound (8.94 g, 42.1 mmol, 71% yield).

MS (ES⁻) C₁₁H₁₆O₄ requires: 212, found: 211 [M–H]⁻.

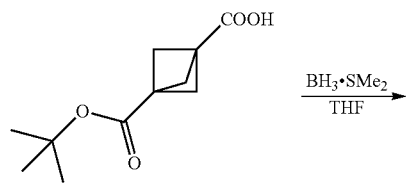

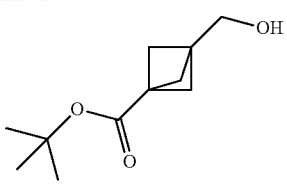

tert-Butyl 3-(hydroxymethyl)bicyclo[1.1.1]pentane-1-carboxylate

To a cooled 0° C. solution of the product from the previous step (25.5 g, 120 mmol) in THF (240 ml) was added BH₃·SMe₂ (2M in THF, 66 ml, 130 mmol) dropwise and the resulting mixture was stirred at 0° C., allowed to warm to rt and stirred for 2 d. The reaction mixture was then cooled to 0° C. and water (11 mL) added dropwise, during which period gas was evolved, followed by solid K₂CO₃ (~30 g). The reaction mixture was partially concentrated, diluted with water and extracted with EtOAc (2×300 ml). Each organic layer was washed with brine, combined, dried over MgSO₄, and concentrated to give the title compound (24 g, 121 mmol, 101% yield) as a clear liquid that hardened over time to a partial opaque solid.

¹H NMR (600 MHz, DMSO-d₆) δ 4.49 (t, J=5.6 Hz, 1H), 3.31 (d, J=5.6 Hz, 2H), 1.74 (s, 6H), 1.34 (s, 9H).

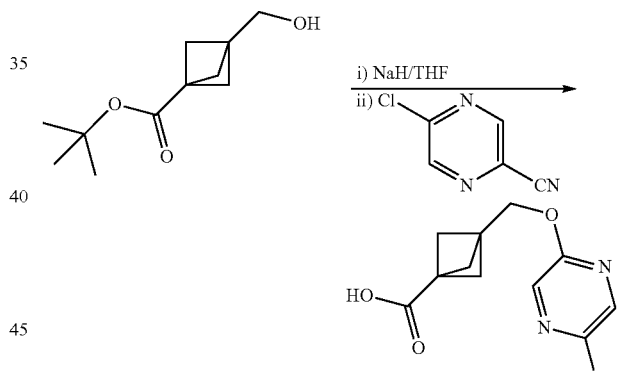

tert-Butyl 3-(((5-cyanopyrazin-2-yl)oxy)methyl)bicyclo[1.1.1]pentane-1-carboxylate To a cooled 0° C. suspension of the product from the previous step (2.66 g, 13.4 mmol) in THF (33.5 ml) was added NaH (0.590 g, 14.8 mmol, 60% dispersion in mineral oil) and reaction was stirred at 0° C. for 15 min. To the reaction was added dropwise 5-chloropyrazine-2-carbonitrile (2.43 g, 17.4 mmol) in THF (33.5 ml). The mixture was stirred at 0° C., and allowed to warmed to rt overnight. The reaction was poured into mixture of ice and saturated NH₄Cl and stirred until the ice melted. The mixture was extracted with EtOAc (3×50 ml). Each organic layer was washed with the same brine, combined, dried over MgSO₄, concentrated, and purified by flash chromatography on silica gel; eluent (0 to 20% 8:2 EtOAc:IPA in hexanes) to give the title compound (2.92 g, 9.69 mmol, 72% yield) as a white solid.

MS (ES⁺) $C_{16}H_{19}N_3O_3$ requires: 301, found: 302[M+H]⁺.

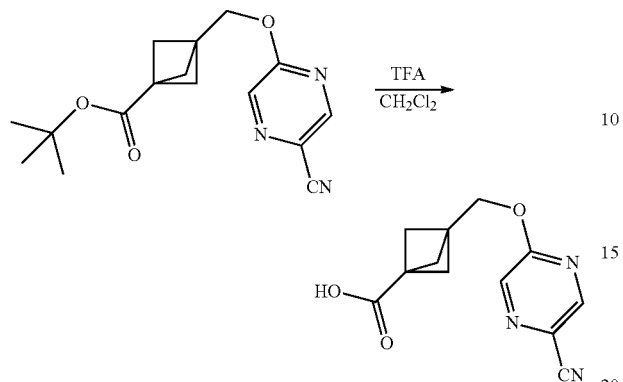

3-(((5-cyanopyrazin-2-yl)oxy)methyl)bicyclo[1.1.1]pentane-1-carboxylic acid

To a solution of the product from the previous step (1.18 g, 3.92 mmol) in $CH_2Cl_2$ (12 ml) cooled at 0° C. was added TFA (4.0 ml, 52 mmol), and the resulting mixture was stirred and allowed to warm to rt. After 4 h the reaction was concentrated, and residual solvent was azeotroped with toluene and $CH_2Cl_2$/Hexanes. The residue was diluted with EtOAc and water, and the phases were separated. The aqueous layer was extracted with EtOAc (3×). Each organic layer was washed with the same brine, combined, dried over $MgSO_4$, and concentrated to give the title compound (0.84 g, 3.43 mmol, 87% yield).

MS (ES⁻) $C_{12}H_{11}N_3O_3$ requires: 245, found: 244 [M−H]⁻.

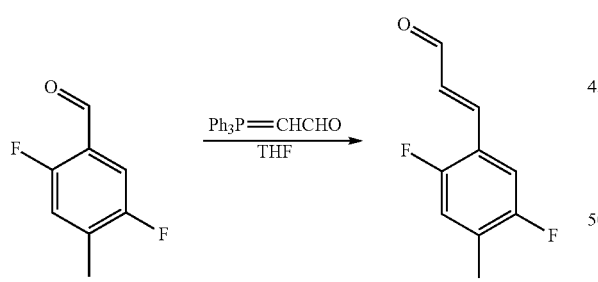

(E)-3-(2,5-Difluoro-4-methylphenyl)acrylaldehyde

To a flask containing 2,5-difluoro-4-methylbenzaldehyde (1 g, 6.4 mmol) in THF (3 mL) was added 2-(triphenyl-λ⁵-phosphaneylidene)acetaldehyde (1.9 g, 6.4 mmol), and the reaction was heated at 80° C. overnight. The reaction turned dark brown. The reaction was then adsorbed onto silica gel and purified by flash chromatography (0-15% EtOAc in hexanes) to give the title compound (406.5 mg, 2.231 mmol, 34.8% yield) as a yellow solid.

MS (ES⁺) $C_{10}H_8F_2O$ requires: 182, found: 183 [M+H]⁺.

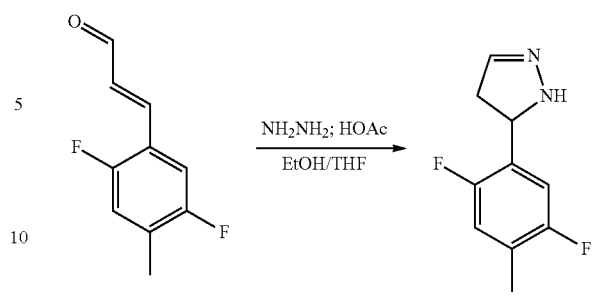

5-(2,5-Difluoro-4-methylphenyl)-4,5-dihydro-1H-pyrazole

To a solution of hydrazine hydrate (205 µl, 3.35 mmol) in ethanol (3570 µl) at 0° C. was added HOAc (217 µl, 3.79 mmol) dropwise over 5 min. The reaction was heated to 45° C., and to the reaction mixture was added a solution of the product from the previous step (406.5 mg, 2.231 mmol) in THF (893 µl). The reaction vessel was then sealed and stirred at 90° C. overnight. The reaction mixture became yellow. The reaction was cooled, absorbed onto silica gel, and purified by flash chromatography on silica gel; eluent (0-40% EtOAc:iPrOH (4:1) in hexanes) to give the title compound (355 mg, 1.81 mmol, 81% yield) as a yellow oil.

MS (ES⁺) $C_{10}H_{10}F_2N_2$ requires: 196, found: 197 [M+H]⁺.

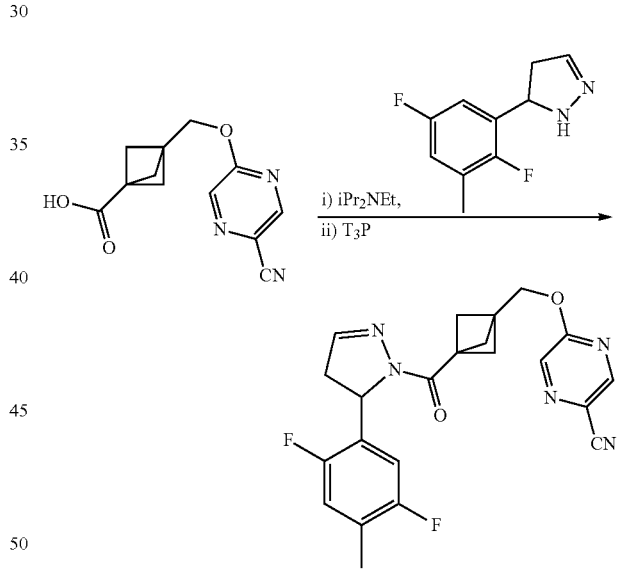

5-((3-(5-(2,5-Difluoro-4-methylphenyl)-4,5-dihydro-1H-pyrazole-1-carbonyl)bicyclo[1.1.1]pentan-1-yl)methoxy)pyrazine-2-carbonitrile To a solution of 3-(((5-cyanopyrazin-2-yl)oxy)methyl)bicyclo[1.1.1]pentane-1-carboxylic acid in DMF (2.0 mL) were added the product from the previous step (84 mg, 0.43 mmol), iPr₂NEt (213 µl, 1.22 mmol) and T3P (50% in EtOAc, 728 µl, 1.22 mmol) and the resulting mixture was stirred at rt overnight. The reaction mixture was diluted with water and saturated $NaHCO_3$ and extracted twice with EtOAc. The combined organic layers were washed with brine, dried over $MgSO_4$, concentrated, and purified twice by flash chromatography on silica gel, eluent (0-20% 80:20

EA:IPA in hexanes 25 min), followed by mass-triggered preparative HPLC (Mobile phase: A=0.1% TFA/H2O, B=0.1% TFA/MeCN; Gradient: B=10-90%; 20 min; Column: C18). The collected fractions were combined, concentrated, diluted with EtOAc, and made basic with saturated NaHCO$_3$. The phases were separated, and organic phase was washed with H$_2$O, then brine. The aqueous layers were extracted once with EtOAc. The combined organic layers were dried over MgSO$_4$, and concentrated to give (15.9 mg, 0.038 mmol, 9.21% yield) as a white solid.

MS (ES$^+$) C$_{22}$H$_{19}$F$_2$N$_5$O$_2$ requires:423, found: 424 [M+H]$^+$.

$^1$H NMR (500 MHz, DMSO-d$_6$) δ 8.83 (d, J=1.3 Hz, 1H), 8.50 (d, J=1.3 Hz, 1H), 7.27-7.21 (m, 1H), 7.17 (dd, J=10.5, 6.1 Hz, 1H), 6.74 (dd, J=9.7, 6.2 Hz, 1H), 5.36 (dd, J=12.1, 5.2 Hz, 1H), 4.49 (s, 2H), 3.43 (ddd, J=18.9, 12.1, 1.6 Hz, 1H), 2.70 (ddd, J=18.8, 5.3, 1.8 Hz, 1H), 2.25-2.16 (m, 3H), 2.07 (s, 6H).

Example 196

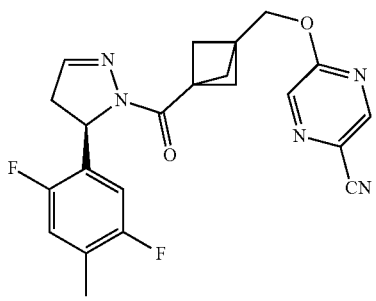 [SMILES: Cc1cc(F)c([C@H]2CC=NN2C(=O)C23CC(COc4cnc(C#N)cn4)(C2)C3)cc1F]

(R)-5-((3-(5-(2,5-difluoro-4-methylphenyl)-4,5-dihydro-1H-pyrazole-1-carbonyl)bicyclo[1.1.1]pentan-1-yl)methoxy)pyrazine-2-carbonitrile and Example 197

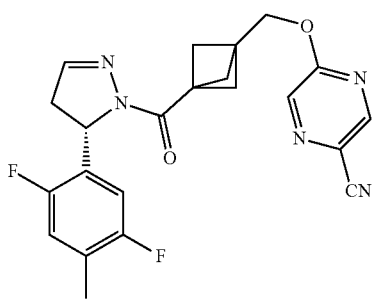 [SMILES: Cc1cc(F)c([C@@H]2CC=NN2C(=O)C23CC(COc4cnc(C#N)cn4)(C2)C3)cc1F]

(S)-5-((3-(5-(2,5-difluoro-4-methylphenyl)-4,5-dihydro-1H-pyrazole-1-carbonyl)bicyclo[1.1.1]pentan-1-yl)methoxy)pyrazine-2-carbonitrile Example 196: The title compound was obtained by SFC purification of Example 195 using the following conditions: DAICEL CHIRALPAK AD (250 mm*30 mm, 10 um); mobile phase: B: 0.1% NH$_3$·H$_2$O MEOH; B %: 60%-60%, gradient time(min): 4.5; 100; flow rate (mL/min): 70. The elution was concentrated (ACN was added after concentrated first time) to give the title compound as the first eluting and less potent isomer. The compound was assigned as the (R) enantiomer due to the observed potency, and consideration of the known binding mode of similar molecules for which RIPK1 protein-inhibitor co-crystal structures have been obtained.

MS (ES$^+$) C$_{22}$H$_{19}$F$_2$N$_5$O$_2$ requires:423, found: 424 [M+H]$^+$.

$^1$H NMR (400 MHz, CDCl$_3$) δ=8.44 (d, J=1.4 Hz, 1H), 8.30 (d, J=1.4 Hz, 1H), 6.95 (t, J=1.6 Hz, 1H), 6.87 (dd, J=6.1, 10.0 Hz, 1H), 6.67 (dd, J=6.1, 9.4 Hz, 1H), 5.48 (dd, J=5.2, 12.0 Hz, 1H), 4.47 (s, 2H), 3.37 (ddd, J=1.5, 12.0, 18.7 Hz, 1H), 2.74 (ddd, J=0.9, 5.2, 18.7 Hz, 1H), 2.22 (d, J=1.8 Hz, 3H), 2.20 (s, 6H).

Example 197: The title compound was obtained by SFC purification of Example 195 as described for example 196 as the second eluting and more potent isomer. The compound was assigned as the (S) enantiomer due to the observed potency, and consideration of the known binding mode of similar molecules for which the RIPK1 protein-inhibitor co-crystal structures have been obtained.

MS (ES$^+$) C$_{22}$H$_{19}$F$_2$N$_5$O$_2$ requires:423, found: 424 [M+H]$^+$.

$^1$H NMR (400 MHz, CDCl$_3$) δ=8.44 (d, J=1.4 Hz, 1H), 8.30 (d, J=1.3 Hz, 1H), 6.95 (t, J=1.6 Hz, 1H), 6.90-6.84 (m, 1H), 6.70-6.65 (m, 1H), 5.52-5.44 (m, 1H), 4.47 (s, 2H), 3.44-3.31 (m, 1H), 2.80-2.70 (m, 1H), 2.23-2.21 (m, 3H), 2.20 (s, 6H).

Example 198

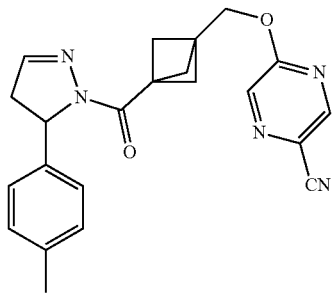 [SMILES: Cc1ccc(C2CC=NN2C(=O)C23CC(COc4cnc(C#N)cn4)(C2)C3)cc1]

5-((3-(5-(p-Tolyl)-4,5-dihydro-1H-pyrazole-1-carbonyl)bicyclo[1.1.1]pentan-1-yl)methoxy)pyrazine-2-carbonitrile

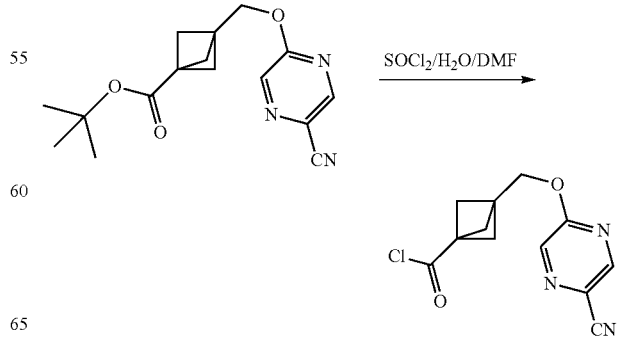

3-(((5-Cyanopyrazin-2-yl)oxy)methyl)bicyclo[1.1.1]pentane-1-carbonyl chloride To a solution of tert-butyl 3-(((5-cyanopyrazin-2-yl)oxy)methyl)bicyclo[1.1.1]-pentane-1-carboxylate (100 mg, 0.332 mmol) in SOCl$_2$ (240 µl, 3.3 mmol) was added H$_2$O (6.0 µl, 0.33 mmol), and the resulting mixture was stirred at rt for 2 h. To the reaction was added DMF (1.3 µl, 0.017 mmol), and the reaction stirred at rt for 3 h. The reaction was concentrated, and residual solvent was azeotroped with toluene and CH$_2$Cl$_2$/Hexanes to give the title compound as a white semi-solid. An aliquot in MeOH analyzed by LCMS gives the methyl ester, MS (ES$^+$) C$_{13}$H$_{13}$N$_3$O$_3$ requires: 259, found 260 [M+H]$^+$. The material was taken to the next step without further purification.

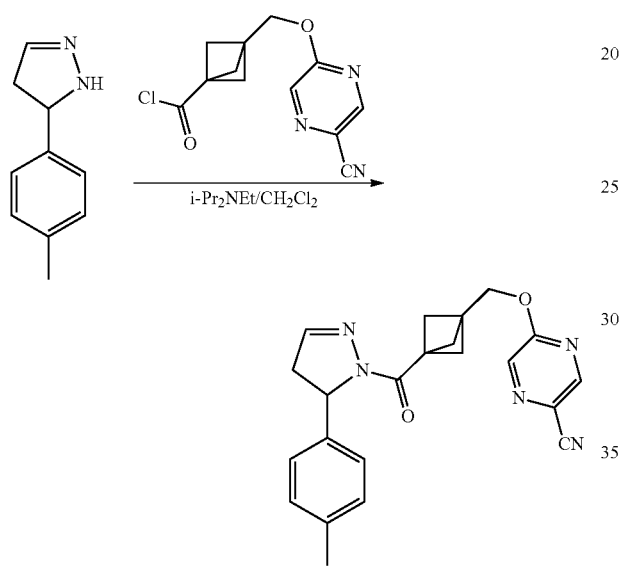

5-((3-(5-(p-tolyl)-4,5-dihydro-1H-pyrazole-1-carbonyl)bicyclo[1.1.1]pentan-1-yl)methoxy)pyrazine-2-carbonitrile An aliquot from a solution of the product from the previous step (22 mg, 0.083 mmol) in CH$_2$Cl$_2$ (200 µL) was dripped into a solution of 5-(p-tolyl)-4,5-dihydro-1H-pyrazole (14.70 mg, 0.092 mmol) and iPr$_2$NEt (72.9 µL, 0.417 mmol) dissolved in CH$_2$Cl$_2$ (200 µL) and cooled in an ice bath, with stirring under N$_2$. The resulting mixture was stirred at 0° C. for 30 min then at rt overnight. The reaction was loaded directly onto a dry 12 RediSep® column and purified by flash chromatography on silica gel; eluent (0 to 20% of EtOAc:IPA(4:1) in hexanes) to give the title compound (13 mg, 0.034 mmol, 40% yield) as a light yellow semi-solid.

MS (ES$^+$) C$_{22}$H$_{21}$N$_5$O$_2$ requires: 387, found: 388 [M+H]$^+$.

$^1$H NMR (500 MHz, DMSO-d$_6$) δ 8.83 (d, J=1.3 Hz, 1H), 8.50 (d, J=1.3 Hz, 1H), 7.24-7.18 (m, 1H), 7.12 (d, J=7.7 Hz, 2H), 7.01-6.94 (m, 2H), 5.25 (dd, J=11.8, 4.5 Hz, 1H), 4.49 (s, 2H), 3.47-3.37 (m, 1H), 2.62 (ddd, J=18.9, 4.6, 1.8 Hz, 1H), 2.26 (s, 3H), 2.07 (s, 6H).

Example 199

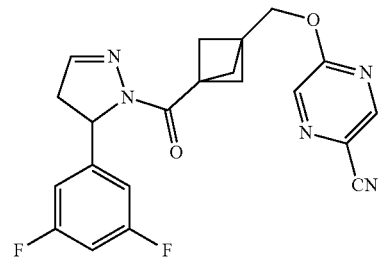 [SMILES: N#Cc1cnc(OCC23CC(C(=O)N4N=CCC4c4cc(F)cc(F)c4)(C2)C3)cn1]

5-((3-(5-(3,5-difluorophenyl)-4,5-dihydro-1H-pyrazole-1-carbonyl)bicyclo[1.1.1]pentan-1-yl)methoxy)pyrazine-2-carbonitrile

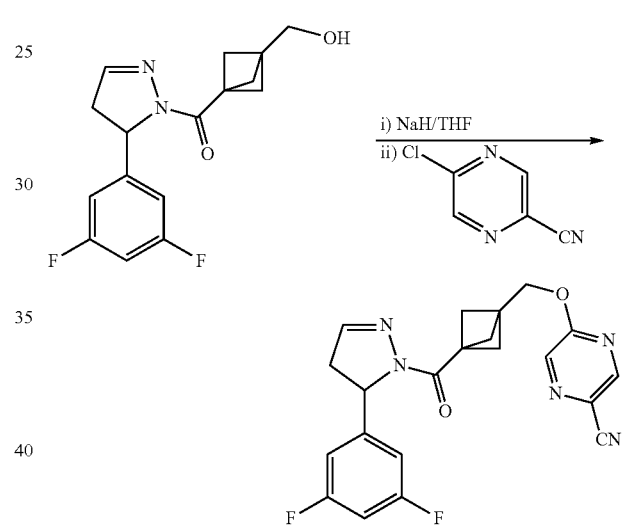

To a cooled 0° C. suspension of (5-(3,5-difluorophenyl)-4,5-dihydro-1H-pyrazol-1-yl)(3-(hydroxymethyl)bicyclo[1.1.1]pentan-1-yl)methanone (990 mg, 3.23 mmol) in THF (8 mL) was added NaH (dispersion in mineral oil, 60%) (142 mg, 3.56 mmol), and the reaction was stirred at 0° C. for 15 min. To the reaction was added dropwise 5-chloropyrazine-2-carbonitrile (586 mg, 4.20 mmol) in THF (8 mL), and the mixture was stirred at 0° C. and then allowed to warm to rt overnight. The reaction was poured into a mixture of ice and saturated NH$_4$Cl and stirred until the ice melted. The mixture was extracted with EtOAc (3×50 ml). Each organic layer was washed with the same brine, combined, dried over MgSO$_4$, concentrated, and purified by flash chromatography on silica gel; eluent (0 to 20% 8:2 EtOAc:IPA in hexanes) to give the title compound (1060 mg, 2.59 mmol, 80% yield) as a white solid.

(ES$^+$) C$_{21}$H$_{17}$F$_2$N$_5$O$_2$ requires: 409, found: 4104 [M+H]$^+$.

$^1$H NMR (600 MHz, DMSO-d$_6$) δ 8.83 (d, J=1.3 Hz, 1H), 8.50 (d, J=1.3 Hz, 1H), 7.21 (d, J=1.6 Hz, 1H), 7.16-7.09 (m, 1H), 6.84-6.76 (m, 2H), 5.33 (dd, J=11.9, 4.9 Hz, 1H), 4.49 (s, 2H), 3.47-3.37 (m, 1H), 2.75-2.67 (m, 1H), 2.09 (s, 6H).

Example 200

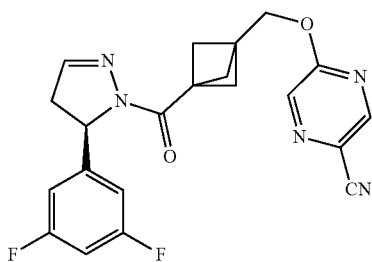 [SMILES: N#Cc1cnc(OCC23CC(C(=O)N4N=CC[C@@H]4c4cc(F)cc(F)c4)(C2)C3)cn1]

(R)-5-((3-(5-(3,5-difluorophenyl)-4,5-dihydro-1H-pyrazole-1-carbonyl)bicyclo[1.1.1]pentan-1-yl)methoxy)pyrazine-2-carbonitrile and Example 201

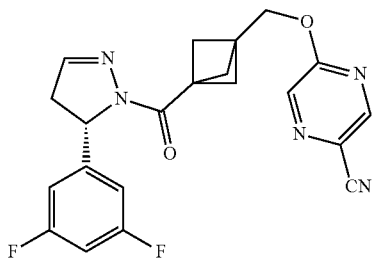 [SMILES: N#Cc1cnc(OCC23CC(C(=O)N4N=CC[C@H]4c4cc(F)cc(F)c4)(C2)C3)cn1]

(S)-5-((3-(5-(3,5-difluorophenyl)-4,5-dihydro-1H-pyrazole-1-carbonyl)bicyclo[1.1.1]pentan-1-yl)methoxy)pyrazine-2-carbonitrile Example 200: The title compound was obtained by SFC purification of Example 199 as the first eluting and less potent isomer. The compound was assigned as the (R) enantiomer due to the observed potency, and consideration of the known binding mode of similar molecules for which RIPK1 protein-inhibitor co-crystal structures have been obtained.

Example 201: The title compound was obtained by SFC purification of Example 199 as the second eluting and more potent isomer. The compound was assigned as the (S) enantiomer due to the observed potency, and consideration of the known binding mode of similar molecules for which RIPK1 protein-inhibitor co-crystal structures have been obtained.

(ES+) $C_{21}H_{17}F_2N_5O_2$ requires: 409, found: 4104 [M+H]+.

$^1$H NMR (600 MHz, DMSO-$d_6$) δ 8.83 (d, J=1.3 Hz, 1H), 8.50 (d, J=1.3 Hz, 1H), 7.21 (d, J=1.8 Hz, 1H), 7.18-7.09 (m, 1H), 6.84-6.76 (m, 2H), 5.33 (dd, J=11.9, 4.9 Hz, 1H), 4.49 (s, 2H), 3.41 (ddd, J=19.0, 11.9, 1.6 Hz, 1H), 2.70 (ddd, J=18.9, 4.9, 1.7 Hz, 1H), 2.09 (s, 6H).

Example 202

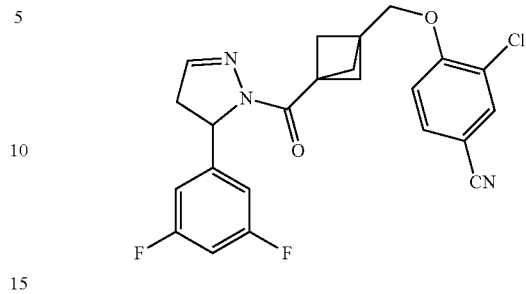

3-Chloro-4-((3-(5-(3,5-difluorophenyl)-4,5-dihydro-1H-pyrazole-1-carbonyl)bicyclo[1.1.1]pentan-1-yl)methoxy)benzonitrile

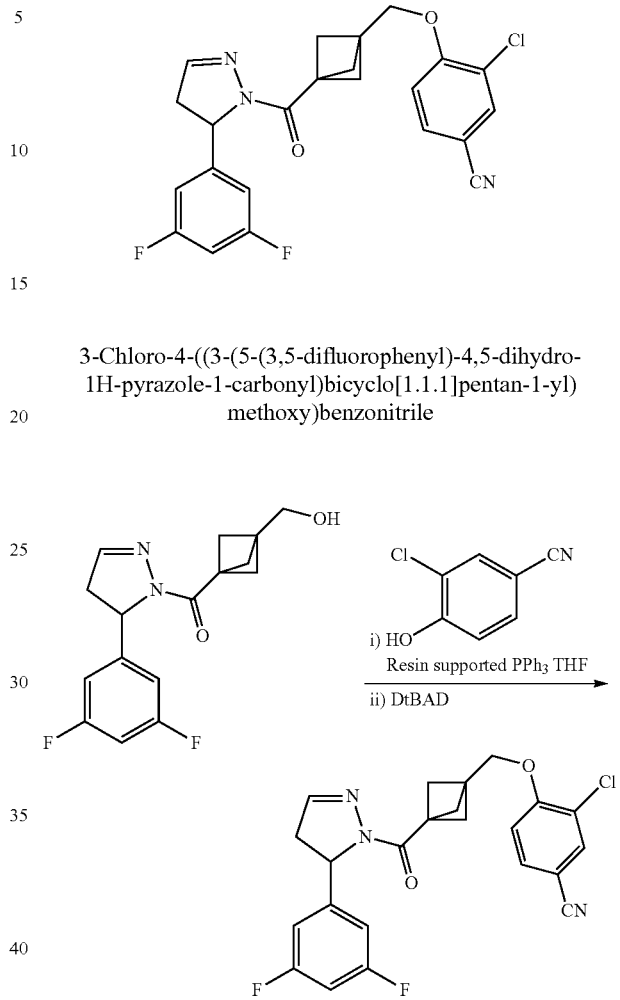

To a solution of (5-(3,5-difluorophenyl)-4,5-dihydro-1H-pyrazol-1-yl)(3-(hydroxymethyl)bicyclo[1.1.1]pentan-1-yl)methanone (20 mg, 0.065 mmol) in THF (320 μl) were added 3-chloro-4-hydroxybenzonitrile (13 mg, 0.085 mmol) and resin-supported PPh$_3$ (0.3 mmol/g, 44 mg, 0.13 mmol), and the resulting mixture was stirred at rt for 10 min. To the reaction was added DtBAD (20 mg, 0.085 mmol) and the reaction stirred at rt overnight. To the reaction was added CELITE®, and the mixture was diluted with CH$_2$Cl$_2$, filtered over a bed of CELITE®, and rinsed with CH$_2$Cl$_2$. To the filtrate was added TFA (50 uL), and the reaction mixture was concentrated. The residue was dissolved in DMSO (200 ul) and filtered, and the precipitate was rinsed with MeOH (2×150 ul). The combined organic solution was purified by mass-triggered preparative HPLC (Mobile phase: A=0.1% TFA/H$_2$O, B=0.1% TFA/MeCN; Gradient: B=10-90%; 12 min; Column: C18) to give the title compound (0.8 mg, 1.840 μmol, 2.8% yield) as a white solid.

MS (ES+) $C_{23}H_{18}ClF_2N_3O_2$ requires: 441, found: 442 [M+H]+.

$^1$H NMR (600 MHz, DMSO-$d_6$) δ 8.03 (d, J=2.2 Hz, 1H), 7.81 (dd, J=8.7, 2.2 Hz, 1H), 7.33 (d, J=8.7 Hz, 1H), 7.23 (t, J=1.7 Hz, 1H), 7.13 (tt, J=9.3, 2.3 Hz, 1H), 6.86-6.78 (m,

2H), 5.34 (dd, J=12.0, 4.9 Hz, 1H), 4.28 (s, 2H), 3.43 (ddd, J=18.7, 11.9, 1.6 Hz, 1H), 2.71 (ddd, J=19.0, 4.9, 1.8 Hz, 1H), 2.11 (s, 6H).

Example 203

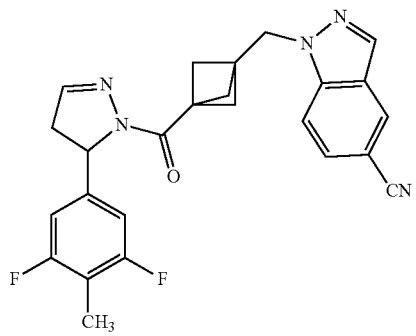 [SMILES: Cc1c(F)cc(C2CC=NN2C(=O)C23CC(Cn4ncc5cc(C#N)ccc54)(C2)C3)cc1F]

1-((3-(5-(3,5-Difluoro-4-methylphenyl)-4,5-dihydro-1H-pyrazole-1-carbonyl)bicyclo[1.1.1]pentan-1-yl)methyl)-1H-indazole-5-carbonitrile

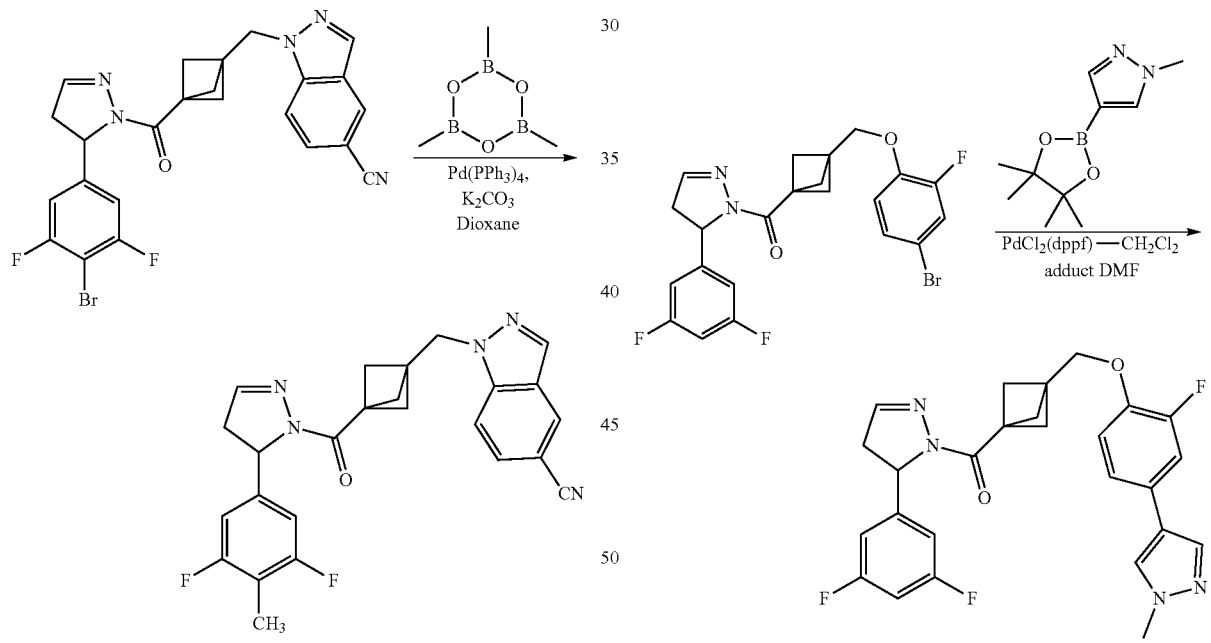

To a vial equipped with a stir bar, and containing 2,4,6-trimethyl-1,3,5,2,4,6-trioxatriborinane (4.2 mg, 0.033 mmol), K₂CO₃ (5.8 mg, 0.042 mmol), and Pd(PPh₃)₄ (1.6 mg, 1.4 µmol) was added a solution of 1-((3-(5-(4-bromo-3,5-difluorophenyl)-4,5-dihydro-1H-pyrazole-1-carbonyl)bicyclo[1.1.1]pentan-1-yl)methyl)-1H-indazole-5-carbonitrile (Example 241, 14 mg, 0.028 mmol) in N₂-degassed dioxane (50 µl). The reaction mixture was degassed with N₂, sealed, and then heated at 100° C. overnight. The reaction mixture was allowed to cool to rt, diluted with 10% TFA in MeOH (300 µL), and filtered through a cotton plug. The residue was purified by mass-triggered preparative HPLC (Mobile phase: A=0.1% TFA/H₂O, B=0.1% TFA/MeCN;

Gradient: B=10-90%; 12 min; Column: C18) to give the title compound (2.6 mg, 5.8 µmol, 20% yield) as a white solid.

MS (ES⁺) C₂₅H₂₁F₂N₅O requires: 445 found: 446 [M+H]⁺.

Example 204

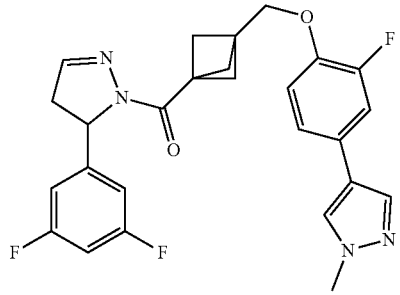 [SMILES: Cn1cc(-c2ccc(OCC34CC(C(=O)N5N=CCC5c5cc(F)cc(F)c5)(C3)C4)c(F)c2)cn1]

(5-(3,5-Difluorophenyl)-4,5-dihydro-1H-pyrazol-1-yl)(3-((2-fluoro-4-(1-methyl-1H-pyrazol-4-yl)phenoxy)methyl)bicyclo[1.1.1]pentan-1-yl)methanone To a solution of (3-((4-bromo-2-fluorophenoxy)methyl)bicyclo[1.1.1]pentan-1-yl)(5-(3,5-difluorophenyl)-4,5-dihydro-1H-pyrazol-1-yl)methanone (Example 331, 4.1 mg, 8.6 µmol) in N₂-degassed DMF (86 µl) in a vial was added 1-methyl-4-(4,4,5,5-tetramethyl-1,3,2-dioxaborolan-2-yl)-1H-pyrazole (2.3 mg, 0.011 mmol), and Na₂CO₃ (2M, 8.6 µl, 0.017 mmol), and the resulting mixture was stirred and purged with N₂. To this mixture was added PdCl₂(dppf)-CH₂Cl₁₋₂ adduct (1 mg, 0.9 µmol). The vial was sealed and stirred at 80° C. overnight. The reaction mixture was allowed to cool to rt. The residue was purified by mass-triggered preparative HPLC (Mobile phase: A=0.1% TFA/

H₂O, B=0.1% TFA/MeCN; Gradient: B=10-90%; 12 min; Column: C18) to give the title compound (1.6 mg, 3.33 µmol, 38% yield) as a white solid.

MS (ES⁺) C₂₆H₂₃F₃N₄O₂ requires: 480, found: 481 [M+H]⁺.

Example 205

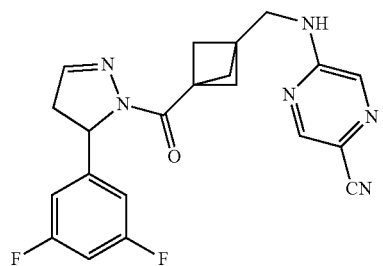 [SMILES: N#Cc1cnc(NCC23CC(C(=O)N4N=CCC4c4cc(F)cc(F)c4)(C2)C3)cn1]

5-(((3-(5-(3,5-Difluorophenyl)-4,5-dihydro-1H-pyrazole-1-carbonyl)bicyclo[1.1.1]pentan-1-yl)methyl)amino)pyrazine-2-carbonitrile

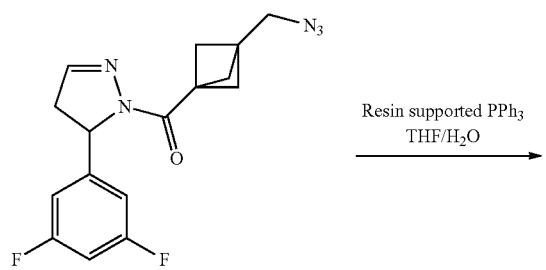

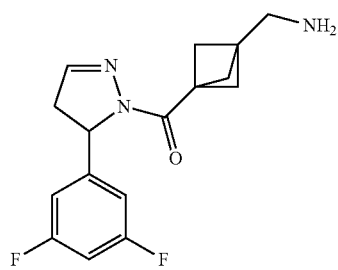

(3-(Aminomethyl)bicyclo[1.1.1]pentan-1-yl)(5-(3,5-difluorophenyl)-4,5-dihydro-1H-pyrazol-1-yl)methanone To a solution of (3-(azidomethyl)bicyclo[1.1.1]pentan-1-yl)(5-(3,5-difluorophenyl)-4,5-dihydro-1H-pyrazol-1-yl)methanone (140 mg, 0.42 mmol) in THF (2 ml) and H₂O (10 µl) was added resin-supported PPh₃ (0.3 mmol/g, 210 mg, 0.63 mmol) and the resulting mixture was stirred at rt for 3 d. To the mixture was added CH₂Cl₂ and CELITE®, and the mixture was filtered through a plug of CELITE®. The filtrate was concentrated to give 132 mg (0.432 mmol, 102% yield) as a white solid.

MS (ES⁺) C₁₆H₁₇F₂N₃O requires: 305, found: 306 [M+H]⁺.

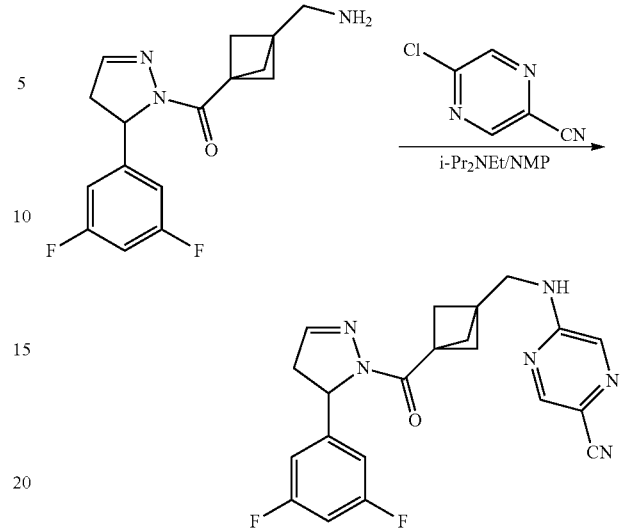

5-(((3-(5-(3,5-difluorophenyl)-4,5-dihydro-1H-pyrazole-1-carbonyl)bicyclo-[1.1.1]pentan-1-yl)methyl)amino)pyrazine-2-carbonitrile A microwave vial was charged with the product from the previous step (21 mg, 0.069 mmol), 5-chloropyrazine-2-carbonitrile (14 mg, 0.10 mmol), iPr₂NEt (48 µl, 0.28 mmol), and NMP (344 µl). The vial was sealed and the reaction mixture was heated at 150° C. in a microwave reactor for 30 min. The reaction mixture was diluted with EtOAc (4 mL), H₂O (4 mL) was added, and the layers were separated. The aqueous phase was extracted with EtOAc (2×3 mL), and the combined organic layers were washed with saturated NaCl, dried over MgSO₄, filtered and concentrated under reduced pressure. The residue was purified by flash chromatography on silica gel; eluent (0-50% EA:IPA 4:1 in hexanes) to give (13.9 mg, 0.034 mmol, 49% yield) as a white solid.

MS (ES⁺) C₂₁H₁₈F₂N₆O requires: 408, found: 409 [M+H]⁺.

Example 206

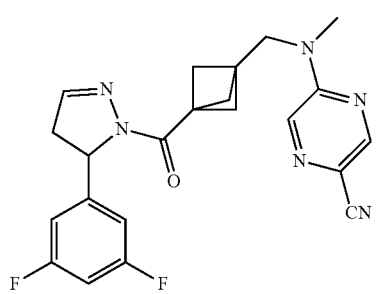 [SMILES: CN(CC12CC(C(=O)N3N=CCC3c3cc(F)cc(F)c3)(C1)C2)c1cnc(C#N)cn1]

281

5-(((3-(5-(3,5-Difluorophenyl)-4,5-dihydro-1H-pyrazole-1-carbonyl)bicyclo[1.1.1]pentan-1-yl)methyl)(methyl)amino)pyrazine-2-carbonitrile

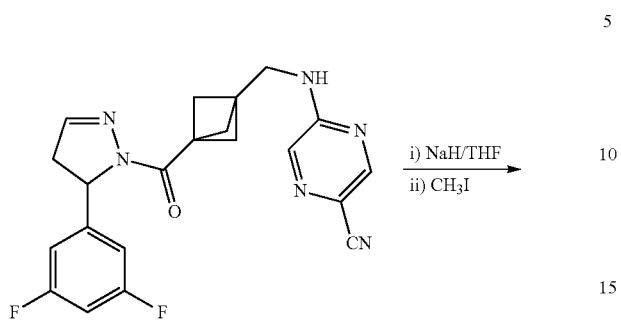

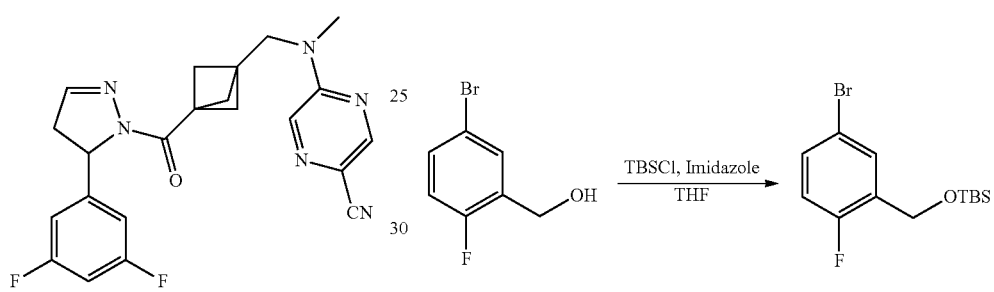

To a solution of 5-(((3-(5-(3,5-difluorophenyl)-4,5-dihydro-1H-pyrazole-1-carbonyl)bicyclo[1.1.1]pentan-1-yl)methyl)amino)pyrazine-2-carbonitrile (Example 205, 12 mg, 0.029 mmol) in THF (500 μL) at 0° C. was added NaH (4 mg, 0.09 mmol, 60% mineral oil dispersion), and the mixture was stirred for 10 min. To the reaction mixture was added MeI (2 μL, 0.032 mmol), and the reaction mixture was stirred in an ice bath and allowed to warm to rt over 2 h. The reaction was cooled again in the ice bath, additional MeI (2 μL, 0.032 mmol) was added, and the reaction allowed to warm to rt. The reaction was quenched with saturated NH$_4$Cl and extracted with EtOAc (2×). The combined organic layers were washed with saturated NaCl, dried over MgSO$_4$, concentrated under reduced pressure, and purified by flash chromatography on silica gel; eluent (0-50% EA:IPA 4:1 in hexanes) to give (9.0 mg, 0.021 mmol, 74% yield) as a white solid.

MS (ES$^+$) C$_{22}$H$_{20}$F$_2$N$_6$O requires: 422, found: 423 [M+H]$^+$.

$^1$H NMR (600 MHz, DMSO-d$_6$) δ 8.53 (s, 1H), 8.27 (s, 1H), 7.20-7.16 (m, 1H), 7.11 (tt, J=9.3, 2.4 Hz, 1H), 6.83-6.72 (m, 2H), 5.31 (dd, J=12.0, 4.9 Hz, 1H), 3.79 (s, 2H), 3.45-3.34 (m, 1H), 3.16 (s, 3H), 2.68 (ddd, J=18.9, 4.9, 1.8 Hz, 1H), 2.01 (s, 6H).

Example 207

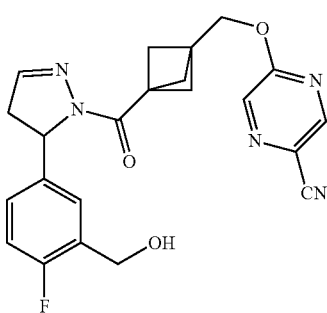 [SMILES: N#Cc1cnc(OCC23CC(C(=O)N4N=CCC4c4ccc(F)c(CO)c4)(C2)C3)cn1]

5-((3-(5-(4-Fluoro-3-(hydroxymethyl)phenyl)-4,5-dihydro-1H-pyrazole-1-carbonyl)bicyclo[1.1.1]pentan-1-yl)methoxy)pyrazine-2-carbonitrile ((5-Bromo-2-fluorobenzyl)oxy)(tert-butyl)dimethylsilane To a solution of (5-bromo-2-fluorophenyl)methanol (5.0 g, 24 mmol) in THF (120 ml) were added tert-butylchlorodimethylsilane (4.4 g, 29 mmol) and imidazole (4.2 g, 61 mmol), and the resulting mixture was stirred overnight. The reaction mixture was dilute with ice water (300 ml) and extracted with EtOAc (150 ml/3×). Each organic layer was washed with aqueous citric acid (~10%) and brine. The organic layers were combined, dried over MgSO$_4$, and concentrated to give the title compound (7.6 g, 23 mmol, 98% yield) as an opaque liquid.

$^1$H NMR (300 MHz, DMSO-d$_6$) δ 7.48 (dd, J=6.4, 2.1, 1.3 Hz, 1H), 7.45-7.38 (m, 1H), 7.09 (dd, J=9.9, 8.7 Hz, 1H), 4.64 (s, 2H), 0.80 (s, 9H), 0.00 (s, 6H).

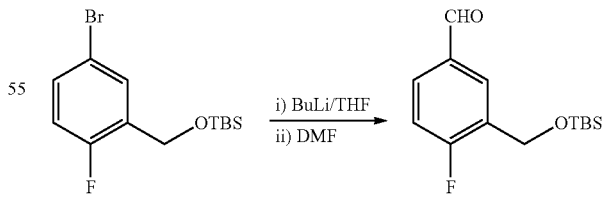

3-(((tert-Butyldimethylsilyl)oxy)methyl)-4-fluorobenzaldehyde

To a solution of the product from the previous step (1.0 g, 3.1 mmol) in THF (31 ml) at −78° C. was added BuLi (2.5M in hexanes, 1.4 ml, 3.5 mmol), and the mixture was stirred in the bath for 25 min. To the reaction was added DMF (1.3 ml, 17 mmol), and the mixture was stirred at −78° C. 1 h. The reaction was removed from the bath and diluted with $CH_2Cl_2$ and saturated $NaHCO_3$. The layers were separated. The aqueous phase was extracted once with $CH_2Cl_2$. The combined organic layers were washed with the same brine, combined, dried over $MgSO_4$, concentrated, and purified by flash chromatography on silica gel; eluent (0-15% EtOAc in hexanes) to give the title compound (0.48 g, 1.8 mmol, 57% yield) as a clear oil.

$^1$H NMR (300 MHz, DMSO-$d_6$) δ 9.88 (s, 1H), 7.95-7.88 (m, 1H), 7.85-7.78 (m, 1H), 7.37-7.28 (m, 1H), 4.71 (s, 2H), 0.80 (s, 9H), 0.00 (s, 6H).

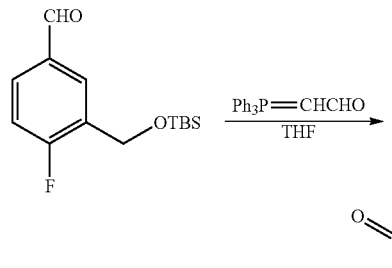

(E)-3-(3-(((tert-Butyldimethylsilyl)oxy)methyl)-4-fluorophenyl)acrylaldehyde

To a solution of the product from the previous step (0.48 g, 1.788 mmol) in THF (1.788 ml) was added 2-(triphenyl-λ$^5$-phosphaneylidene)acetaldehyde (0.544 g, 1.788 mmol), and the resulting mixture was stirred at 75° C. overnight. The reaction was adsorbed onto silica gel and purified by flash chromatography on silica gel; eluent (0-20% EtOAc in Hexanes) to give the title compound (0.2 g, 0.679 mmol, 38% yield) as a clear oil.

$^1$H NMR (600 MHz, DMSO-$d_6$) δ 9.56 (d, J=7.8 Hz, 1H), 7.73-7.63 (m, 3H), 7.23-7.15 (m, 1H), 6.67 (dd, J=15.9, 7.7 Hz, 1H), 4.67 (s, 2H), 0.80 (s, 9H), 0.00 (d, J=1.4 Hz, 6H).

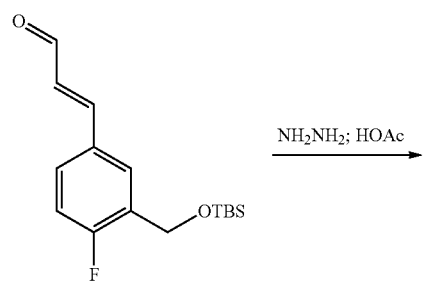

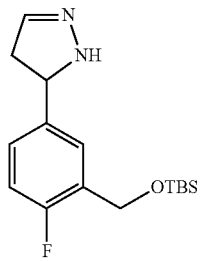

5-(3-(((tert-Butyldimethylsilyl)oxy)methyl)-4-fluorophenyl)-4,5-dihydro-1H-pyrazole To a solution of the product from the previous step (0.2 g, 0.7 mmol) in tBuOH (2 ml) was added hydrazine hydrate (0.20 ml, 3.4 mmol) in HOAc (0.012 ml, 0.20 mmol). The reaction vessel was then sealed and heated at 80° C. overnight. The volatiles were removed under reduced pressure. The residue was adsorbed onto silica gel and purified by flash chromatography; eluent (0-40% EA in hexanes to give (133.2 mg, 0.432 mmol, 64% yield) as a yellow liquid.

MS (ES$^+$) $C_{16}H_{25}FN_2OSi$ requires: 308, found: 309 [M+H]$^+$.

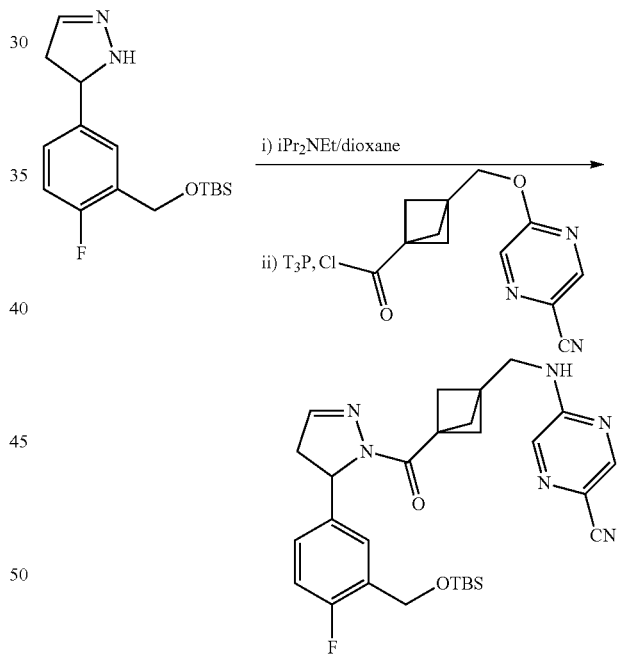

5-((3-(5-(3-(((tert-Butyldimethylsilyl)oxy)methyl)-4-fluorophenyl)-4,5-dihydro-1H-pyrazole-1-carbonyl)bicyclo[1.1.1]pentan-1-yl)methoxy)pyrazine-2-carbonitrile To a solution of the product from the previous step (214 μL, 0.214 mmol) in dioxane (800 μL) was added iPr$_2$NEt (143 μL, 0.823 mmol). To the reaction mixture was added a solution of 3-(((5-cyanopyrazin-2-yl)oxy)methyl)bicyclo[1.1.1]pentane-1-carbonyl chloride (330 μL, 0.165 mmol) in Dioxane/$CH_2Cl_2$ and T3P (50% in EtOAc, 98 μL, 0.17 mmol), and the reaction was stirred at rt overnight under $N_2$.

The reaction was diluted with EtOAc and washed with water and brine. The aqueous layers were extracted with EtOAc (2×). The organic layers were combined, dried over MgSO₄, concentrated, and purified by flash chromatography (0-50% EtAOc in hexanes) to give the title compound (33.9 mg, 0.063 mmol, 38% yield) as a yellow solid.

MS (ES+) $C_{28}H_{34}FN_5O_3Si$ requires: 535, found: 536 [M+H]+.

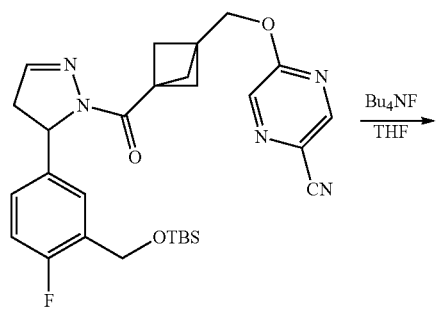

Example 208

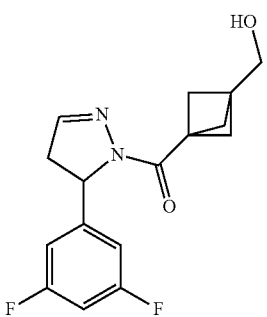 [SMILES: O=C(N1N=CCC1c1cc(F)cc(F)c1)C12CC(CO)(C1)C2]

(5-(3,5-Difluorophenyl)-4,5-dihydro-1H-pyrazol-1-yl)(3-(hydroxymethyl)bicyclo[1.1.1]pentan-1-yl)methanone This compound is identical to Intermediate I, described in the synthesis of Examples 3 and 4.

Example 209

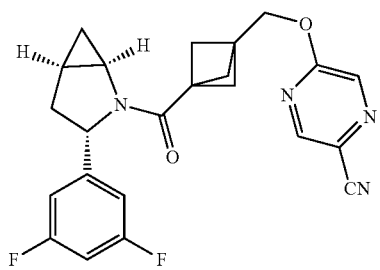 [SMILES: N#Cc1cnc(OCC23CC(C(=O)N4[C@@H]5C[C@@H]5C[C@H]4c4cc(F)cc(F)c4)(C2)C3)cn1]

5-((3-((1R,3S,5R)-3-(3,5-difluorophenyl)-2-azabicyclo[3.1.0]hexane-2-carbonyl)bicyclo[1.1.1]pentan-1-yl)methoxy)pyrazine-2-carbonitrile

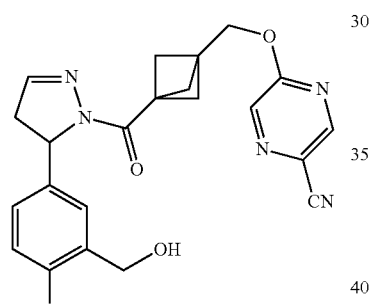

5-((3-(5-(4-Fluoro-3-(hydroxymethyl)phenyl)-4,5-dihydro-1H-pyrazole-1-carbonyl)bicyclo[1.1.1]pentan-1-yl)methoxy)pyrazine-2-carbonitrile To a solution of the product from the previous step (30 mg, 0.056 mmol) in THF (280 µl) at 0° C. was added TBAF (1M in THF, 84 µl, 0.084 mmol), and the resulting mixture was stirred and allowed to warm to rt overnight. The mixture was concentrated and purified by flash chromatography on silica gel; eluent (0 to 100% EtOAc in Hexanes) to give the title compound (8 mg, 0.02 mmol, 33% yield) as a white solid.

MS (ES⁺) $C_{22}H_{20}FN_5O_3$ requires: 421, found: 422[M+H]⁺. ¹H NMR (600 MHz, DMSO-d₆) δ 8.83 (s, 1H), 8.50 (s, 1H), 7.24-7.18 (m, 2H), 7.10-7.05 (m, 1H), 7.02-6.97 (m, 1H), 5.30 (dd, J=11.8, 4.6 Hz, 1H), 5.27 (t, J=5.6 Hz, 1H), 4.51 (d, J=5.6 Hz, 2H), 4.49 (s, 2H), 3.42 (dd, J=18.9, 11.8 Hz, 1H), 2.62 (dd, J=18.8, 4.4 Hz, 1H), 2.07 (s, 6H).

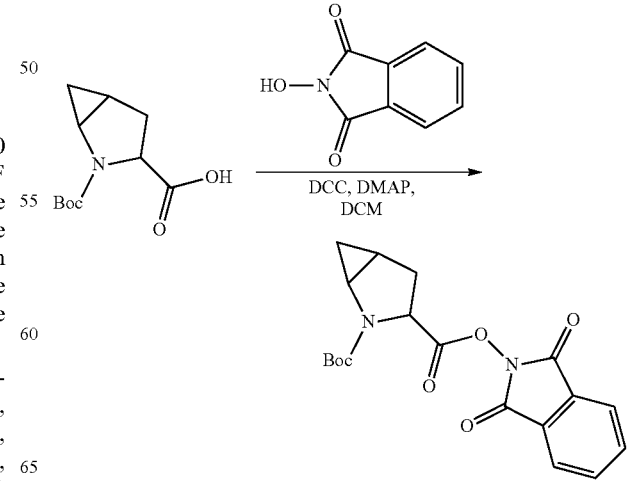

2-(Tert-Butyl) 3-(1,3-dioxoisoindolin-2-yl) 2-azabicyclo[3.1.0]hexane-2,3-dicarboxylate A round-bottom flask was charged with 2-(tert-butoxycarbonyl)-2-azabicyclo[3.1.0]hexane-3-carboxylic acid (1.8 g, 7.9 mmol, 1 eq), DMAP (97 mg, 79 umol, 0.1 eq) and 2-hydroxyisoindoline-1,3-dione (1.29 g, 7.92 mmol, 1 eq). DCM (30 mL) was added and the mixture was stirred vigorously. Then DCC (1.80 g, 8.71 mmol, 1.76 mL, 1.1 eq) was added, and the mixture was stirred at 20° C. for 3 h. The mixture was diluted with H$_2$O (100 mL) and extracted with EtOAc (100 mL×2). The combined organic layers were concentrated as a yellow oil which was purified by column chromatography on silica (PE:EA=1:1) to afford the title compound (2.8 g, 6.8 mmol, 86% yield, 91% purity) as a white solid. In separate reactions, both available diastereomers produced the desired product with assumed retention of chirality.

MS(ES$^+$) C$_{19}$H$_{20}$N$_2$O$_6$ requires:372, found 273 [M+H−Boc]$^+$.

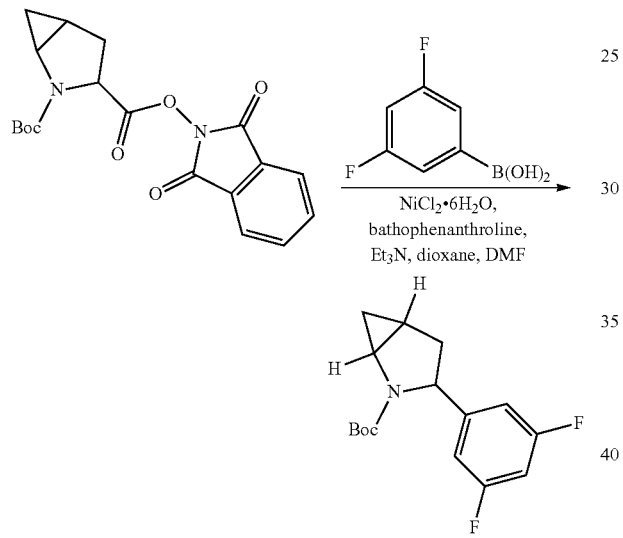

Tert-Butyl 3-(3,5-difluorophenyl)-2-azabicyclo[3.1.0]hexane-2-carboxylate

To a solution of 2-(tert-butyl) 3-(1,3-dioxoisoindolin-2-yl) 2-azabicyclo[3.1.0]hexane-2,3-dicarboxylate (2.8 g, 7.52 mmol, 1 eq) in dioxane (150 mL) was added (3,5-difluorophenyl)boronic acid (3.56 g, 22.6 mmol, 3 eq). The mixture was stirred at 20° C. for 5 min. Then to the mixture was added Et$_3$N (7.61 g, 75.2 mmol, 10.5 mL, 10 eq) and the solution was stirred at 20° C. for 5 min. Then a solution of NiCl$_2$·6H$_2$O (357 mg, 1.50 mmol, 0.2 eq) and bathophenanthroline (500 mg, 1.50 mmol, 0.2 eq) in DMF (15 mL) was added to the mixture, the tube was immediately placed in a preheated 75° C. oil bath for 12 h under stirring. The mixture was concentrated in vacuum and diluted with H$_2$O (100 mL), then extracted with EtOAc (100 mL×2). The combined organic layer was concentrated as a yellow oil which was purified by prep-HPLC (column: Waters Xbridge C18 150×50 mm×10 μm; mobile phase: [water (0.05% NH$_4$OH V/V)-ACN]; B %: 52%-82%, 11 min) and freeze-dried to title compound (313 mg, 1.06 mmol, 14% yield) as a yellow solid. In separate reactions, each diastereomers produced the desired product with assumed inversion of chirality at the 3 carbon. MS(ES$^+$) C$_{16}$H$_{19}$NO$_2$F$_2$ requires: 295, found 240 [M+H−tBu]$^+$.

$^1$H NMR (400 MHz, METHANOL-d$_4$) δ=6.92-6.72 (m, 3H), 4.70-4.50 (m, 1H), 3.52 (t, J=4.9 Hz, 1H), 2.51 (dd, J$_1$=13.4 Hz, J$_2$=8.8 Hz, 1H), 2.15-1.98 (m, 1H), 1.72-1.63 (m, 1H), 1.48-1.08 (m, 9H), 0.90-0.82 (m, 1H), 0.60-0.51 (m, 1H).

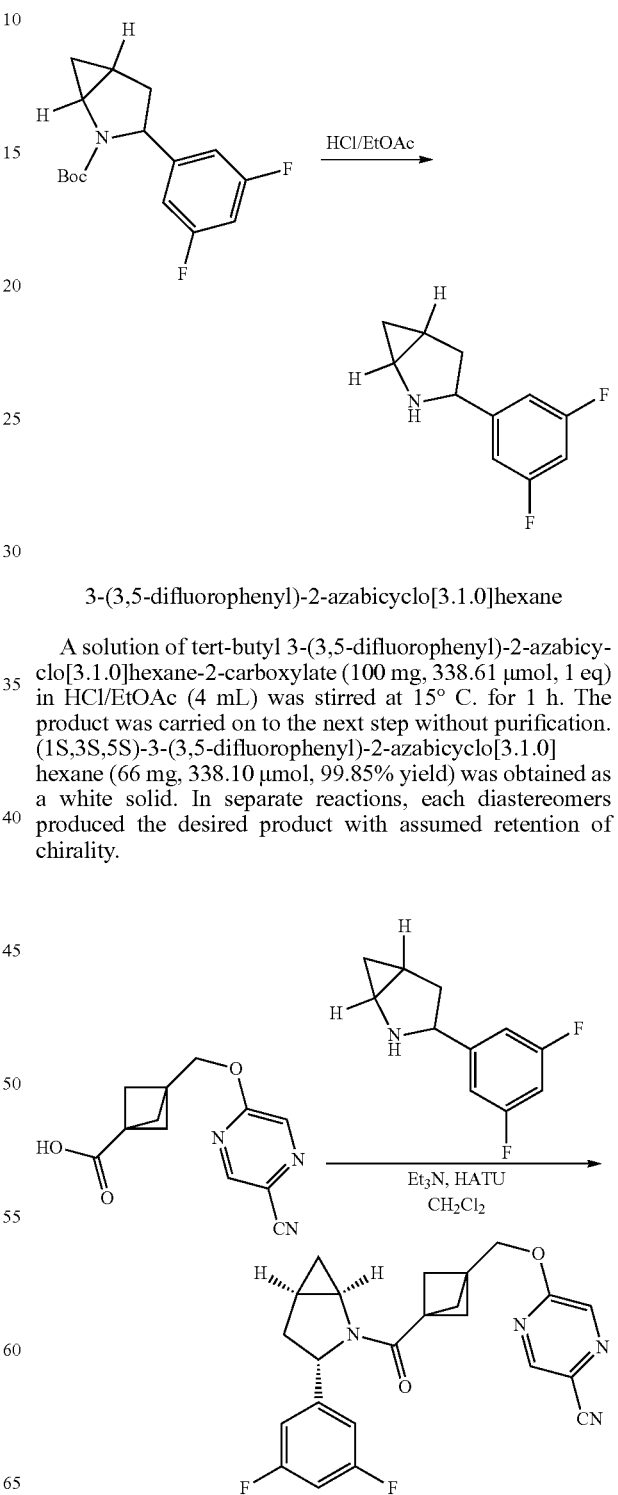

3-(3,5-difluorophenyl)-2-azabicyclo[3.1.0]hexane

A solution of tert-butyl 3-(3,5-difluorophenyl)-2-azabicyclo[3.1.0]hexane-2-carboxylate (100 mg, 338.61 μmol, 1 eq) in HCl/EtOAc (4 mL) was stirred at 15° C. for 1 h. The product was carried on to the next step without purification. (1S,3S,5S)-3-(3,5-difluorophenyl)-2-azabicyclo[3.1.0]hexane (66 mg, 338.10 μmol, 99.85% yield) was obtained as a white solid. In separate reactions, each diastereomers produced the desired product with assumed retention of chirality.

5-((3-((1R,3S,5R)-3-(3,5-difluorophenyl)-2-azabicyclo[3.1.0]hexane-2-carbonyl)bicyclo[1.1.1]pentan-1-yl)methoxy)pyrazine-2-carbonitrile To a solution of (1R,3S,5R)-3-(3,5-difluorophenyl)-2-azabicyclo[3.1.0]hexane (13 mg, 0.067 mmol) in CH$_2$Cl$_2$ (333 μl) were added 3-(((5-cyanopyrazin-2-yl)oxy)methyl)bicyclo[1.1.1]pentane-1-carboxylic acid (18 mg, 0.073 mmol), TEA (18 μl, 0.13 mmol) and HATU (25 mg, 0.67 mmol) and the resulting mixture was stirred at 25° C. for 16 h. The volatiles were removed under reduced pressure. The residue was purified via silica gel chromatography; eluent (0-100% EtOAc in hexanes) to give the title compound (8 mg, 0.019 mmol, 28% yield) as a tan solid. In separate reactions, each diastereomer was carried through to the final compound and tested. The one described here in gave the observed potency and the proposed orientation of the diastereomer was interpreted from 2012D NMR experiments of the final compound. The exact structure was not confirmed. The other diastereomer (conformation not determined) was greater than 10,000 nM.

MS (ES$^+$) C$_{23}$H$_{20}$F$_2$N$_4$O$_2$ requires: 422, found: 421 [M+H]$^+$.

$^1$H NMR (500 MHz, DMSO-d$_6$) δ 8.82 (d, J=1.3 Hz, 1H), 8.48 (d, J=1.3 Hz, 1H), 7.09-7.01 (m, 1H), 6.93-6.85 (m, 2H), 5.03-4.99 (m, 1H), 4.49 (s, 2H), 3.68-3.61 (m, 1H), 2.31-2.22 (m, 1H), 2.11 (s, 6H), 2.02-1.92 (m, 1H), 1.87-1.79 (m, 1H), 1.06-0.98 (m, 1H), 0.61-0.54 (m, 1H).

TABLE 5

Examples 210-345.

| Ex. No | Structure | Name | MS$^{(a)}$ | Proc. Ex. No.$^{(b)}$ |
|---|---|---|---|---|
| 210 | 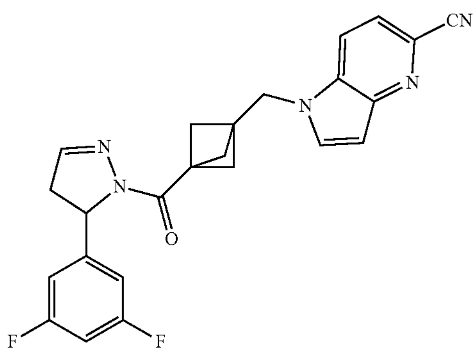 [SMILES: N#Cc1ccc2c(ccn2CC23CC(C(=O)N4N=CCC4c4cc(F)cc(F)c4)(C2)C3)n1] | 1-((3-(5-(3,5-difluorophenyl)-4,5-dihydro-1H-pyrazole-1-carbonyl)bicyclo[1.1.1]pentan-1-yl)methyl)-1H-pyrrolo[3,2-b]pyridine-5-carbonitrile | 431/432 | 21/22 |
| 211 | 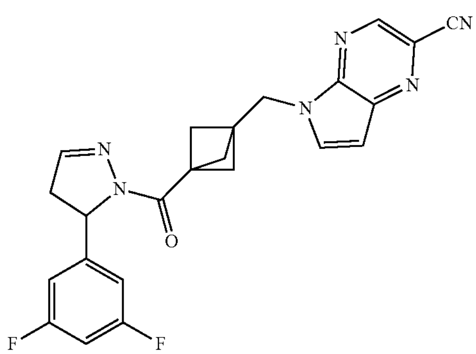 | 5-((3-(5-(3,5-difluorophenyl)-4,5-dihydro-1H-pyrazole-1-carbonyl)bicyclo[1.1.1]pentan-1-yl)methyl)-5H-pyrrolo[2,3-b]pyrazine-2-carbonitrile | 432/433 | 21/22 |
| 212 | 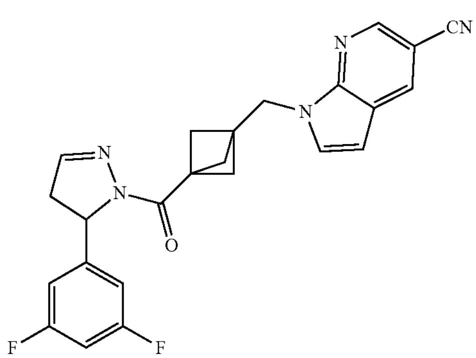 [SMILES: N#Cc1cnc2c(ccn2CC23CC(C(=O)N4N=CCC4c4cc(F)cc(F)c4)(C2)C3)c1] | 1-((3-(5-(3,5-difluorophenyl)-4,5-dihydro-1H-pyrazole-1-carbonyl)bicyclo[1.1.1]pentan-1-yl)methyl)-1H-pyrrolo[2,3-b]pyridine-5-carbonitrile | 431/432 | 21/22 |

TABLE 5-continued

Examples 210-345.

| Ex. No | Structure | Name | MS[a] | Proc. Ex. No.[b] |
|---|---|---|---|---|
| 213 | 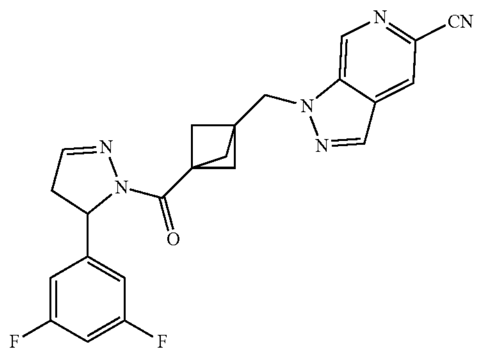 [SMILES: N#Cc1cc2cnn(CC34CC(C(=O)N5N=CCC5c5cc(F)cc(F)c5)(C3)C4)c2cn1] | 1-((3-(5-(3,5-difluorophenyl)-4,5-dihydro-1H-pyrazole-1-carbonyl)bicyclo[1.1.1]pentan-1-yl)methyl)-1H-pyrazolo[3,4-c]pyridine-5-carbonitrile | 432/433 | 21/22 |
| 214 | 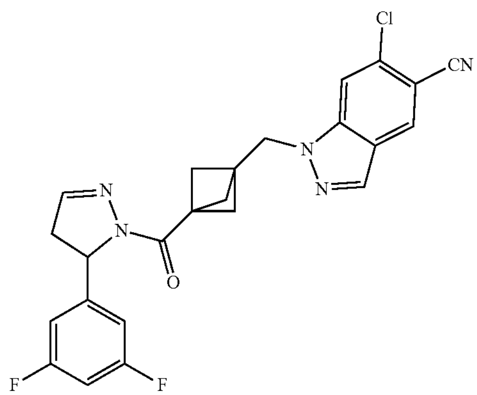 [SMILES: N#Cc1cc2cnn(CC34CC(C(=O)N5N=CCC5c5cc(F)cc(F)c5)(C3)C4)c2cc1Cl] | 6-chloro-1-((3-(5-(3,5-difluorophenyl)-4,5-dihydro-1H-pyrazole-1-carbonyl)-bicyclo[1.1.1]pentan-1-yl)-methyl)-1H-indazole-5-carbonitrile | 465/466 | 21/22 |
| 215 | 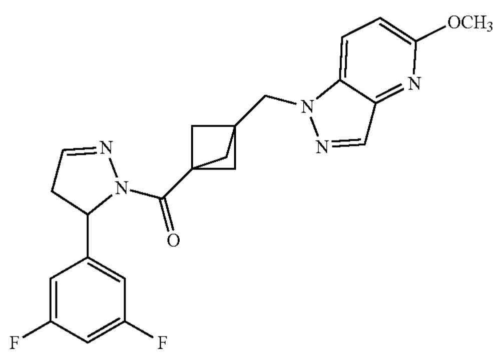 [SMILES: COc1ccc2c(cnn2CC23CC(C(=O)N4N=CCC4c4cc(F)cc(F)c4)(C2)C3)n1] | (5-(3,5-difluorophenyl)-4,5-dihydro-1H-pyrazol-1-yl)(3-((5-methoxy-1H-pyrazolo[4,3-b]pyridin-1-yl)methyl)bicyclo-[1.1.1]pentan-1-yl)methanone | 437/438 | 21/22 |
| 216 | 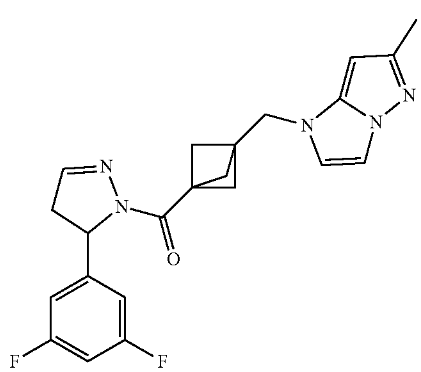 [SMILES: Cc1cc2n(CC34CC(C(=O)N5N=CCC5c5cc(F)cc(F)c5)(C3)C4)ccn2n1] | (5-(3,5-difluorophenyl)-4,5-dihydro-1H-pyrazol-1-yl)(3-((6-methyl-1H-imidazo[1,2-b]pyrazol-1-yl)methyl)bicyclo-[1.1.1]pentan-1-yl)methanone | 409/410 | 21/22 |

TABLE 5-continued

Examples 210-345.

| Ex. No | Structure | Name | MS(a) | Proc. Ex. No.(b) |
|---|---|---|---|---|
| 217 | 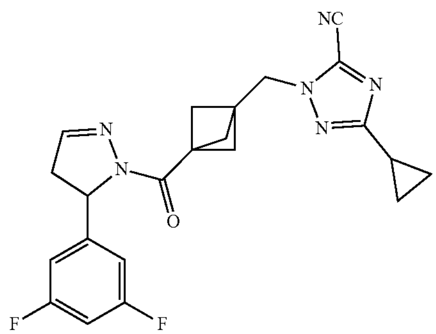 [SMILES: N#Cc1nc(C2CC2)nn1CC12CC(C(=O)N3N=CCC3c3cc(F)cc(F)c3)(C1)C2] | 3-cyclopropyl-1-((3-(5-(3,5-difluorophenyl)-4,5-dihydro-1H-pyrazole-1-carbonyl)-bicyclo[1.1.1]pentan-1-yl)-methyl)-1H-1,2,4-triazole-5-carbonitrile | 422/ 423 | 21/22 |
| 218 | 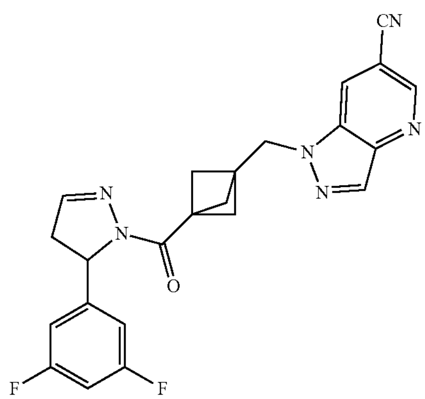 [SMILES: N#Cc1cnc2cnn(CC34CC(C(=O)N5N=CCC5c5cc(F)cc(F)c5)(C3)C4)c2c1] | 1-((3-(5-(3,5-difluorophenyl)-4,5-dihydro-1H-pyrazole-1-carbonyl)bicyclo[1.1.1]pentan-1-yl)methyl)-1H-pyrazolo[4,3-b]pyridine-6-carbonitrile | 432/ 433 | 21/22 |
| 219 | 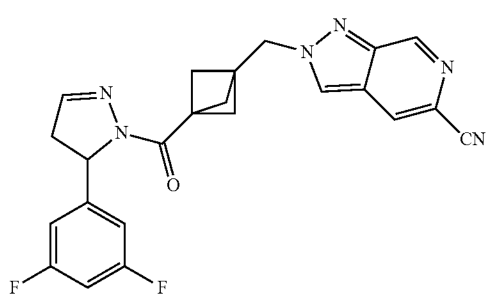 [SMILES: N#Cc1cc2cn(CC34CC(C(=O)N5N=CCC5c5cc(F)cc(F)c5)(C3)C4)nc2cn1] | 2-((3-(5-(3,5-difluorophenyl)-4,5-dihydro-1H-pyrazole-1-carbonyl)bicyclo[1.1.1]pentan-1-yl)methyl)-2H-pyrazolo[3,4-c]pyridine-5-carbonitrile | 432/ 433 | 21/22 |
| 220 | 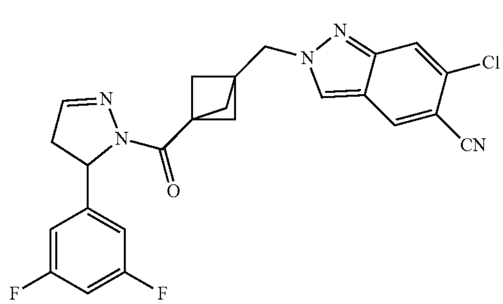 [SMILES: N#Cc1cc2cn(CC34CC(C(=O)N5N=CCC5c5cc(F)cc(F)c5)(C3)C4)nc2cc1Cl] | 6-chloro-2-((3-(5-(3,5-difluorophenyl)-4,5-dihydro-1H-pyrazole-1-carbonyl)-bicyclo[1.1.1]pentan-1-yl)-methyl)-2H-indazole-5-carbonitrile | 465/ 466 | 21/22 |

TABLE 5-continued

Examples 210-345.

| Ex. No | Structure | Name | MS$^{(a)}$ | Proc. Ex. No.$^{(b)}$ |
|---|---|---|---|---|
| 221 | 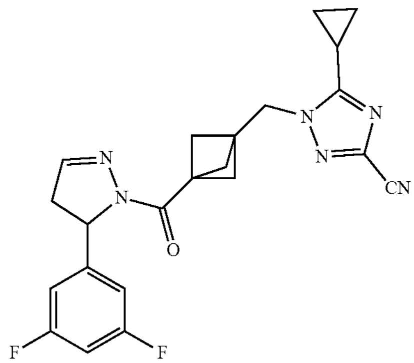 [SMILES: N#Cc1nc(C2CC2)n(CC23CC(C(=O)N4N=CCC4c4cc(F)cc(F)c4)(C2)C3)n1] | 5-cyclopropyl-1-((3-(5-(3,5-difluorophenyl)-4,5-dihydro-1H-pyrazole-1-carbonyl)-bicyclo[1.1.1]pentan-1-yl)-methyl)-1H-1,2,4-triazole-3-carbonitrile | 422/ 423 | 21/22 |
| 222 | 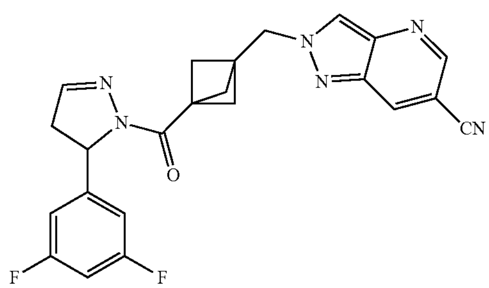 [SMILES: N#Cc1cnc2cn(CC34CC(C(=O)N5N=CCC5c5cc(F)cc(F)c5)(C3)C4)nc2c1] | 2-((3-(5-(3,5-difluorophenyl)-4,5-dihydro-1H-pyrazole-1-carbonyl)bicyclo[1.1.1]pentan-1-yl)methyl)-2H-pyrazolo[4,3-b]pyridine-6-carbonitrile | 432/ 433 | 21/22 |
| 223 | 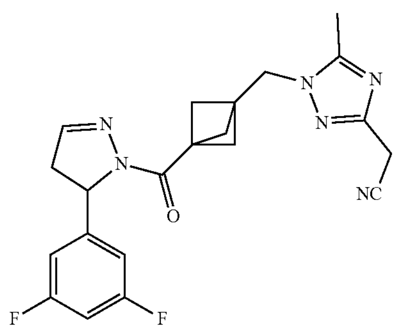 [SMILES: Cc1nc(CC#N)nn1CC12CC(C(=O)N3N=CCC3c3cc(F)cc(F)c3)(C1)C2] | 2-(1-((3-(5-(3,5-difluoro-phenyl)-4,5-dihydro-1H-pyrazole-1-carbonyl)bicyclo-[1.1.1]pentan-1-yl)methyl)-5-methyl-1H-1,2,4-triazol-3-yl)acetonitrile | 410/ 411 | 21/22 |
| 224 | 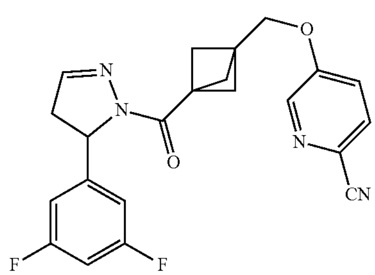 [SMILES: N#Cc1ccc(OCC23CC(C(=O)N4N=CCC4c4cc(F)cc(F)c4)(C2)C3)cn1] | 5-((3-(5-(3,5-difluorophenyl)-4,5-dihydro-1H-pyrazole-1-carbonyl)bicyclo[1.1.1]pentan-1-yl)methoxy)picolinonitrile | 408/ 409 | 26 |
| 225 | 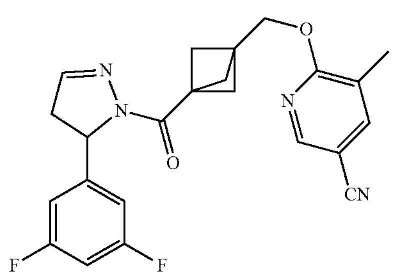 [SMILES: Cc1cc(C#N)cnc1OCC12CC(C(=O)N3N=CCC3c3cc(F)cc(F)c3)(C1)C2] | 6-((3-(5-(3,5-difluorophenyl)-4,5-dihydro-1H-pyrazole-1-carbonyl)bicyclo[1.1.1]pentan-1-yl)methoxy)-5-methyl-nicotinonitrile | 422/ 423 | 26 |

TABLE 5-continued

Examples 210-345.

| Ex. No | Structure | Name | MS[a] | Proc. Ex. No.[b] |
|---|---|---|---|---|
| 226 | 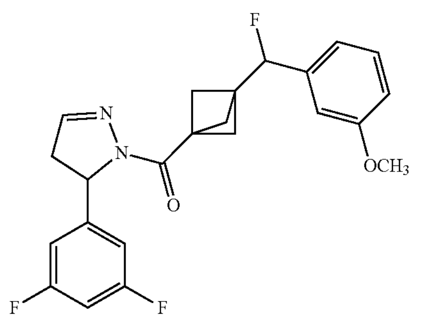 [SMILES: COc1cccc(C(F)C23CC(C(=O)N4N=CCC4c4cc(F)cc(F)c4)(C2)C3)c1] | (5-(3,5-difluorophenyl)-4,5-dihydro-1H-pyrazol-1-yl)(3-(fluoro(3-methoxyphenyl)-methyl)bicyclo[1.1.1]pentan-1-yl)methanone | 414/ 415 | 26 |
| 227 | 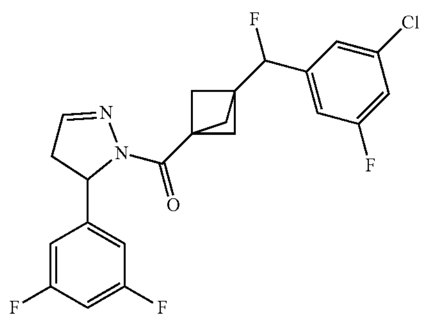 [SMILES: O=C(N1N=CCC1c1cc(F)cc(F)c1)C12CC(C(F)c3cc(F)cc(Cl)c3)(C1)C2] | (3-((3-chloro-5-fluorophenyl-)fluoromethyl)bicyclo[1.1.1]-pentan-1-yl)(5-(3,5-difluoro-phenyl)-4,5-dihydro-1H-pyrazol-1-yl)methanone | 436/ 437 | Exemplified, 42 |
| 228 | 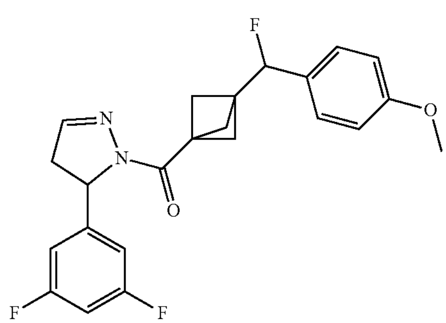 [SMILES: COc1ccc(C(F)C23CC(C(=O)N4N=CCC4c4cc(F)cc(F)c4)(C2)C3)cc1] | (5-(3,5-difluorophenyl)-4,5-dihydro-1H-pyrazol-1-yl)(3-(fluoro(4-methoxyphenyl)-methyl)bicyclo[1.1.1]pentan-1-yl)methanone | 414/ 415 | 42 |
| 229 | 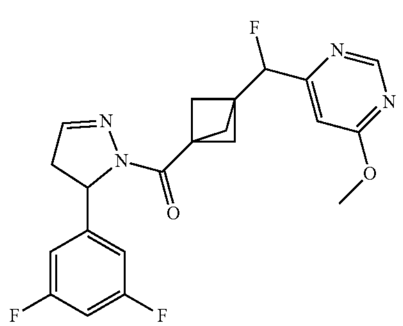 [SMILES: COc1cc(C(F)C23CC(C(=O)N4N=CCC4c4cc(F)cc(F)c4)(C2)C3)ncn1] | (5-(3,5-difluorophenyl)-4,5-dihydro-1H-pyrazol-1-yl)(3-(fluoro(6-methoxypyrimidin-4-yl)methyl)bicyclo[1.1.1]-pentan-1-yl)methanone | 416/ 417 | 42 |

TABLE 5-continued

Examples 210-345.

| Ex. No | Structure | Name | MS(a) | Proc. Ex. No.(b) |
|---|---|---|---|---|
| 230 | 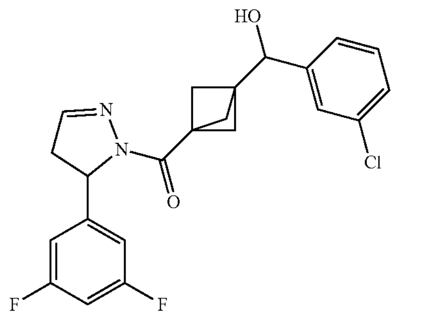 [SMILES: O=C(N1N=CCC1c1cc(F)cc(F)c1)C12CC(C(O)c3cccc(Cl)c3)(C1)C2] | (3((3-chlorophenyl)-(hydroxy)methyl)bicyclo-[1.1.1]pentan-1-yl)(5-(3,5-difluorophenyl)-4,5-dihydro-1H-pyrazol-1-yl)methanone | 416/417 | 42 |
| 231 | 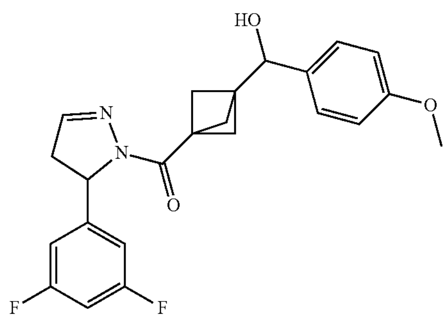 [SMILES: COc1ccc(C(O)C23CC(C(=O)N4N=CCC4c4cc(F)cc(F)c4)(C2)C3)cc1] | (5-(3,5-difluorophenyl)-4,5-dihydro-1H-pyrazol-1-yl)(3-(hydroxy(4-methoxyphenyl)-methyl)bicyclo[1.1.1]pentan-1-yl)methanone | 413/414 | 42 |
| 232 | 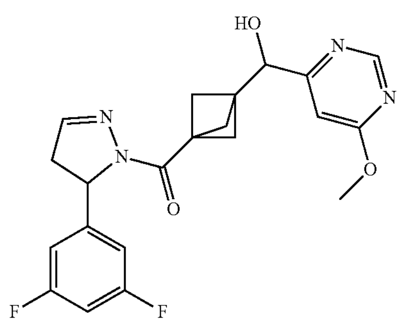 [SMILES: COc1cc(C(O)C23CC(C(=O)N4N=CCC4c4cc(F)cc(F)c4)(C2)C3)ncn1] | (5-(3,5-difluorophenyl)-4,5-dihydro-1H-pyrazol-1-yl)(3-(hydroxy(6-methoxy-pyrimidin-4-yl)methyl)-bicyclo[1.1.1]pentan-1-yl)-methanone | 414/415 | 42 |
| 233 | 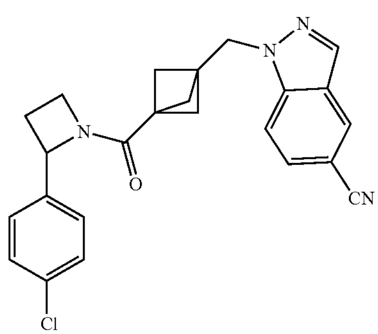 [SMILES: N#Cc1ccc2c(cnn2CC23CC(C(=O)N4CCC4c4ccc(Cl)cc4)(C2)C3)c1] | 1-((3-(2-(4-chlorophenyl)-azetidine-1-carbonyl)bicyclo-[1.1.1]pentan-1-yl)methyl)-1H-indazole-5-carbonitrile | 416/417 | 49 |

TABLE 5-continued

Examples 210-345.

| Ex. No | Structure | Name | MS[a] | Proc. Ex. No.[b] |
|---|---|---|---|---|
| 234 | 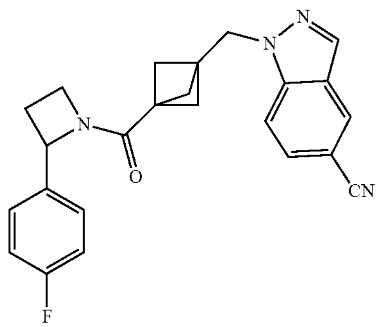 [SMILES: N#Cc1ccc2c(cnn2CC23CC(C(=O)N4CCC4c4ccc(F)cc4)(C2)C3)c1] | 1-((3-(2-(4-fluorophenyl)-azetidine-1-carbonyl)bicyclo-[1.1.1]pentan-1-yl)methyl)-1H-indazole-5-carbonitrile | 400/401 | 49 |
| 235 | 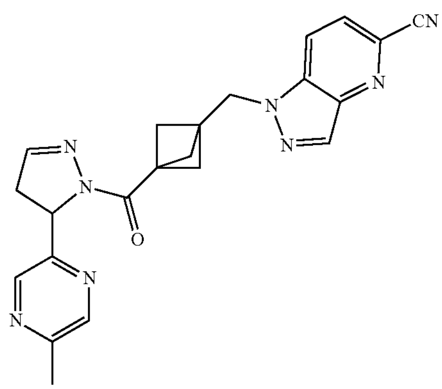 [SMILES: Cc1cnc(C2CC=NN2C(=O)C23CC(Cn4ncc5nc(C#N)ccc54)(C2)C3)cn1] | 1-((3-(5-(5-methylpyrazin-2-yl)-4,5-dihydro-1H-pyrazole-1-carbonyl)bicyclo[1.1.1]-pentan-1-yl)methyl)-1H-pyrazolo[4,3-b]pyridine-5-carbonitrile | 412/413 | 49 |
| 236 | 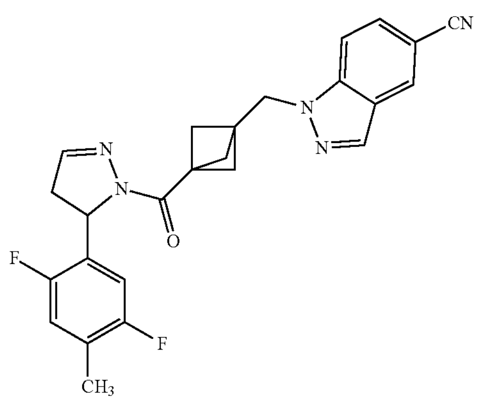 [SMILES: Cc1cc(F)c(C2CC=NN2C(=O)C23CC(Cn4ncc5cc(C#N)ccc54)(C2)C3)cc1F] | 1-((3-(5-(2,5-difluoro-4-methylphenyl)-4,5-dihydro-1H-pyrazole-1-carbonyl)-bicyclo[1.1.1]pentan-1-yl)-methyl)-1H-indazole-5-carbonitrile | 445/446 | 49 |
| 237 | 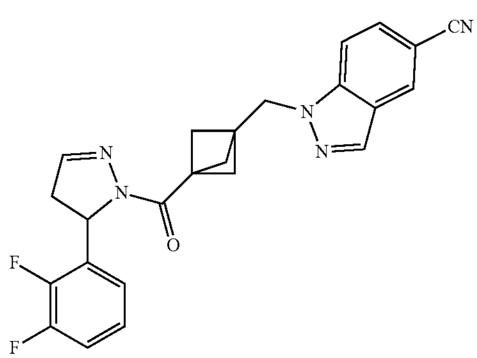 [SMILES: N#Cc1ccc2c(cnn2CC23CC(C(=O)N4N=CCC4c4cccc(F)c4F)(C2)C3)c1] | 1-((3-(5-(2,3-difluorophenyl)-4,5-dihydro-1H-pyrazole-1-carbonyl)bicyclo[1.1.1]pentan-1-yl)methyl)-1H-indazole-5-carbonitrile | 431/432 | 49 |

TABLE 5-continued

Examples 210-345.

| Ex. No | Structure | Name | MS[a] | Proc. Ex. No.[b] |
|---|---|---|---|---|
| 238 | 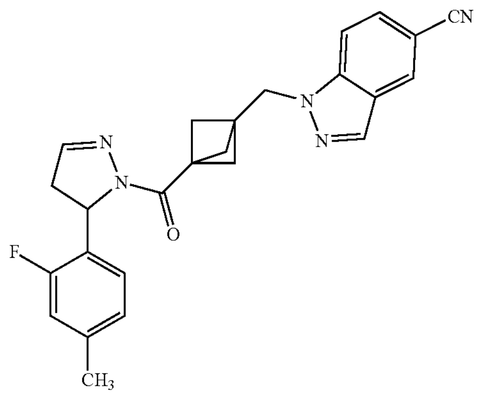 [SMILES: Cc1ccc(C2CC=NN2C(=O)C23CC(Cn4ncc5cc(C#N)ccc54)(C2)C3)c(F)c1] | 1-((3-(5-(2-fluoro-4-methyl-phenyl)-4,5-dihydro-1H-pyrazole-1-carbonyl)bicyclo-[1.1.1]pentan-1-yl)methyl)-1H-indazole-5-carbonitrile | 427/428 | 49 |
| 239 | 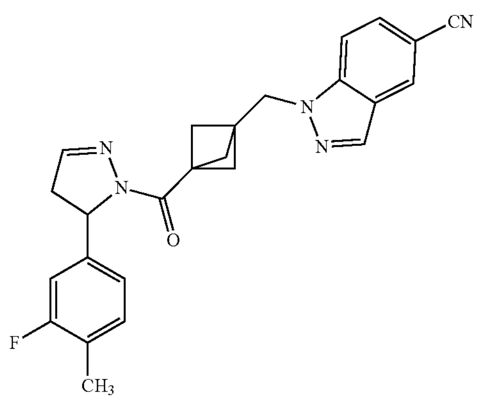 [SMILES: Cc1ccc(C2CC=NN2C(=O)C23CC(Cn4ncc5cc(C#N)ccc54)(C2)C3)cc1F] | 1-((3-(5-(3-fluoro-4-methyl-phenyl)-4,5-dihydro-1H-pyrazole-1-carbonyl)bicyclo-[1.1.1]pentan-1-yl)methyl)-1H-indazole-5-carbonitrile | 427/428 | 49 |
| 240 | 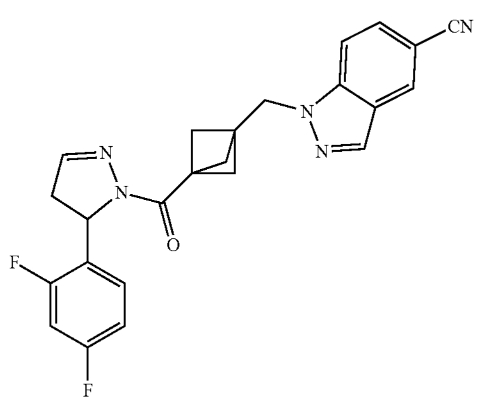 [SMILES: N#Cc1ccc2c(cnn2CC23CC(C(=O)N4N=CCC4c4ccc(F)cc4F)(C2)C3)c1] | 1-((3-(5-(2,4-difluorophenyl)-4,5-dihydro-1H-pyrazole-1-carbonyl)bicyclo[1.1.1]pentan-1-yl)methyl)-1H-indazole-5-carbonitrile | 431/432 | 49 |

TABLE 5-continued

Examples 210-345.

| Ex. No | Structure | Name | MS[a] | Proc. Ex. No.[b] |
|---|---|---|---|---|
| 241 | 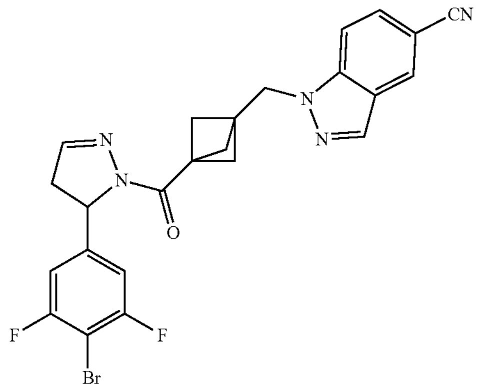 [SMILES: N#Cc1ccc2c(cnn2CC23CC(C(=O)N4N=CCC4c4cc(F)c(Br)c(F)c4)(C2)C3)c1] | 1-((3-(5-(4-bromo-3,5-difluorophenyl)-4,5-dihydro-1H-pyrazole-1-carbonyl)-bicyclo[1.1.1]pentan-1-yl)-methyl)-1H-indazole-5-carbonitrile | 509/ 510, 512 | 49 |
| 242 | 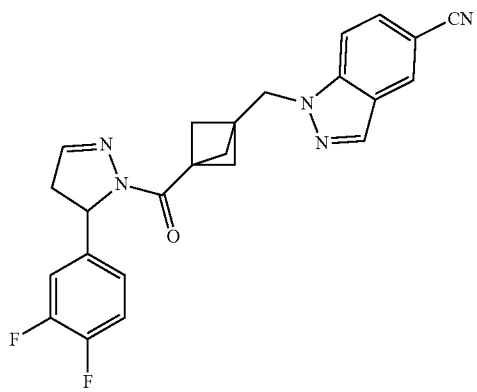 [SMILES: N#Cc1ccc2c(cnn2CC23CC(C(=O)N4N=CCC4c4ccc(F)c(F)c4)(C2)C3)c1] | 1-((3-(5-(3,4-difluorophenyl)-4,5-dihydro-1H-pyrazole-1-carbonyl)bicyclo[1.1.1]pentan-1-yl)methyl)-1H-indazole-5-carbonitrile | 431/ 431 | 49 |
| 243 | 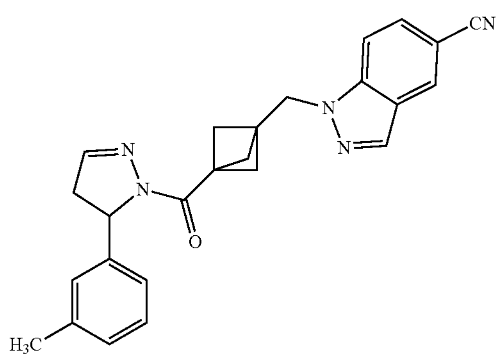 [SMILES: Cc1cccc(C2CC=NN2C(=O)C23CC(Cn4ncc5cc(C#N)ccc54)(C2)C3)c1] | 1-((3-(5-(m-tolyl)-4,5-dihydro-1H-pyrazole-1-carbonyl)-bicyclo[1.1.1]pentan-1-yl)-methyl)-1H-indazole-5-carbonitrile | 409/ 410 | 49 |
| 244 | 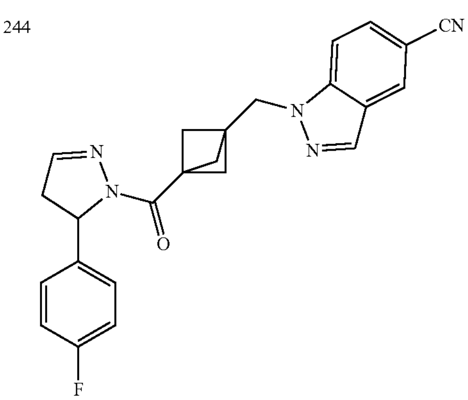 | 1-((3-(5-(4-fluorophenyl)-4,5-dihydro-1H-pyrazole-1-carbonyl)bicyclo[1.1.1]pentan-1-yl)methyl)-1H-indazole-5-carbonitrile | 413/ 414 | 49 |

TABLE 5-continued

Examples 210-345.

| Ex. No | Structure | Name | MS(a) | Proc. Ex. No.(b) |
|---|---|---|---|---|
| 245 | 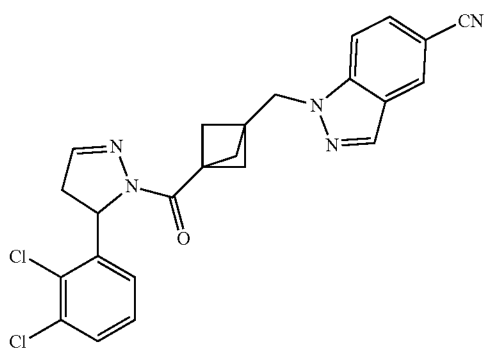 [SMILES: N#Cc1ccc2c(cnn2CC23CC(C(=O)N4N=CCC4c4cccc(Cl)c4Cl)(C2)C3)c1] | 1-((3-(5-(2,3-dichlorophenyl)-4,5-dihydro-1H-pyrazole-1-carbonyl)bicyclo[1.1.1]pentan-1-yl)methyl)-1H-indazole-5-carbonitrile | 463/464 | 49 |
| 246 | 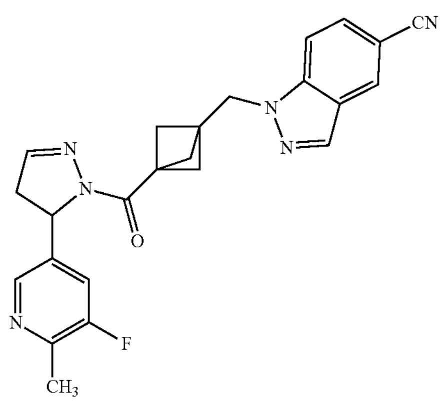 [SMILES: Cc1ncc(C2CC=NN2C(=O)C23CC(Cn4ncc5cc(C#N)ccc54)(C2)C3)cc1F] | 1-((3-(5-(5-fluoro-6-methyl-pyridin-3-yl)-4,5-dihydro-1H-pyrazole-1-carbonyl)bicyclo[1.1.1]pentan-1-yl)methyl)-1H-indazole-5-carbonitrile | 428/429 | 49 |
| 247 | 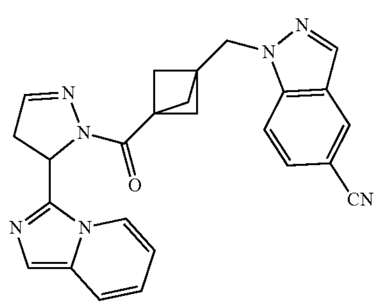 [SMILES: N#Cc1ccc2c(cnn2CC23CC(C(=O)N4N=CCC4c4ncc5ccccn45)(C2)C3)c1] | 1-((3-(5-(imidazo[1,5-a]pyridin-3-yl)-4,5-dihydro-1H-pyrazole-1-carbonyl)bicyclo[1.1.1]pentan-1-yl)methyl)-1H-indazole-5-carbonitrile | 435/436 | 49 |
| 248 | 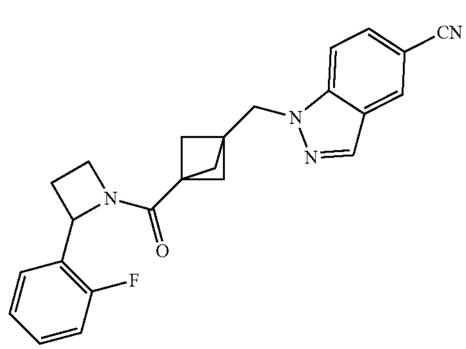 [SMILES: N#Cc1ccc2c(cnn2CC23CC(C(=O)N4CCC4c4ccccc4F)(C2)C3)c1] | 1-((3-(2-(2-fluorophenyl)-azetidine-1-carbonyl)bicyclo[1.1.1]pentan-1-yl)methyl)-1H-indazole-5-carbonitrile | 400/401 | 49 |

TABLE 5-continued

Examples 210-345.

| Ex. No | Structure | Name | MS(a) | Proc. Ex. No.(b) |
|---|---|---|---|---|
| 249 | 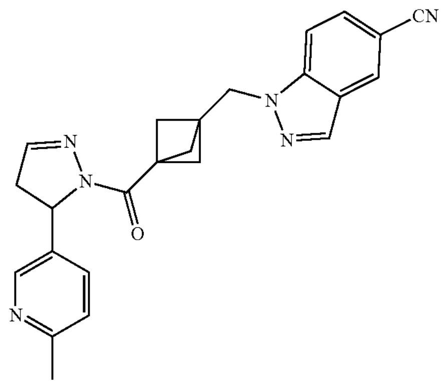 [SMILES: Cc1ccc(C2CC=NN2C(=O)C23CC(Cn4ncc5cc(C#N)ccc54)(C2)C3)cn1] | 1-((3-(5-(6-methylpyridin-3-yl)-4,5-dihydro-1H-pyrazole-1-carbonyl)bicyclo[1.1.1]-pentan-1-yl)methyl)-1H-indazole-5-carbonitrile | 410/ 411 | 49 |
| 250 | 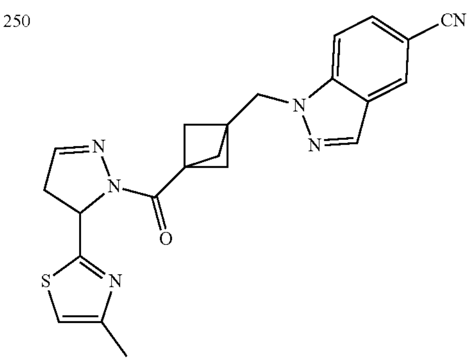 | 1-((3-(5-(4-methylthiazol-2-yl)-4,5-dihydro-1H-pyrazole-1-carbonyl)bicyclo[1.1.1]-pentan-1-yl)methyl)-1H-indazole-5-carbonitrile | 416/ 417 | 49 |
| 251 | 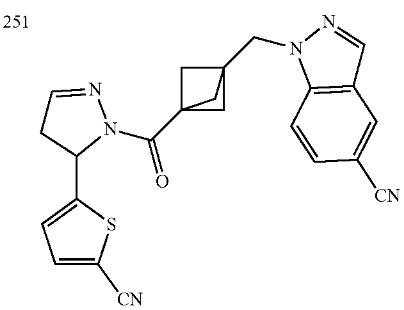 | 1-((3-(5-(5-cyanothiophen-2-yl)-4,5-dihydro-1H-pyrazole-1-carbonyl)bicyclo[1.1.1]-pentan-1-yl)methyl)-1H-indazole-5-carbonitrile | 426/ 427 | 49 |
| 252 | 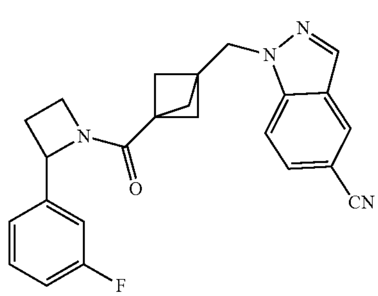 [SMILES: N#Cc1ccc2c(cnn2CC23CC(C(=O)N4CCC4c4cccc(F)c4)(C2)C3)c1] | 1-((3-(2-(3-fluorophenyl)-azetidine-1-carbonyl)bicyclo-[1.1.1]pentan-1-yl)methyl)-1H-indazole-5-carbonitrile | 400/ 401 | 49 |

TABLE 5-continued

Examples 210-345.

| Ex. No | Structure | Name | MS[a] | Proc. Ex. No.[b] |
|---|---|---|---|---|
| 253 | 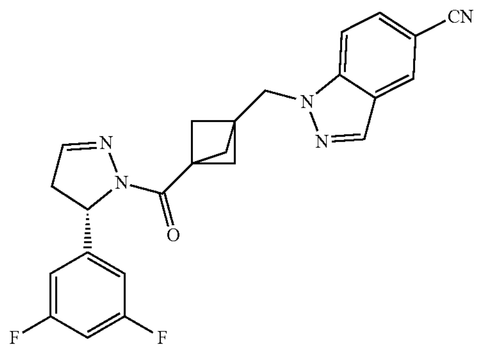 [SMILES: N#Cc1ccc2c(cnn2CC23CC(C(=O)N4N=CC[C@H]4c4cc(F)cc(F)c4)(C2)C3)c1] | (S)-1-((3-(5-(3,5-difluoro-phenyl)-4,5-dihydro-1H-pyrazole-1-carbonyl)bicyclo-[1.1.1]pentan-1-yl)methyl)-1H-indazole-5-carbonitrile | 432/433 | 49 |
| 254 | 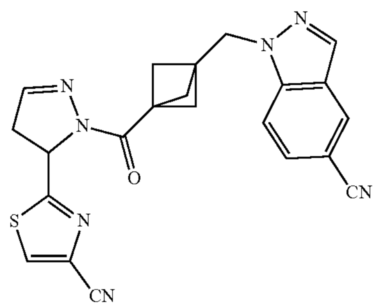 [SMILES: N#Cc1ccc2c(cnn2CC23CC(C(=O)N4N=CCC4c4nc(C#N)cs4)(C2)C3)c1] | 2-(1-(3-((5-cyano-1H-indazol-1-yl)methyl)bicyclo[1.1.1]-pentane-1-carbonyl)-4,5-dihydro-1H-pyrazol-5-yl)-thiazole-4-carbonitrile | 427/428 | 49 |
| 255 | 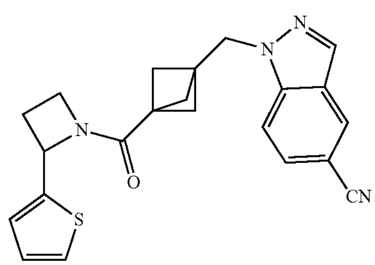 [SMILES: N#Cc1ccc2c(cnn2CC23CC(C(=O)N4CCC4c4cccs4)(C2)C3)c1] | 1-((3-(2-(thiophen-2-yl)-azetidine-1-carbonyl)bicyclo-[1.1.1]pentan-1-yl)methyl)-1H-indazole-5-carbonitrile | 388/389 | 49 |
| 256 | 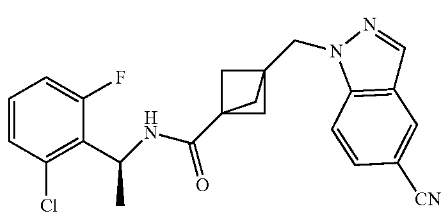 [SMILES: C[C@H](NC(=O)C12CC(Cn3ncc4cc(C#N)ccc43)(C1)C2)c1c(F)cccc1Cl] | (S)-N-(1-(2-chloro-6-fluoro-phenyl)ethyl)-3-((5-cyano-1H-indazol-1-yl)methyl)bicyclo-[1.1.1]pentane-1-carboxamide | 422/423 | 49 |
| 257 | 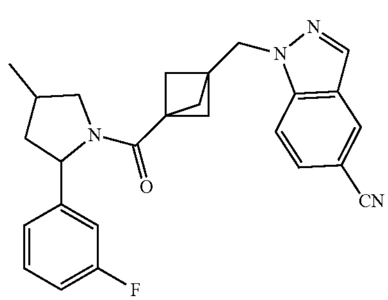 [SMILES: CC1CC(c2cccc(F)c2)N(C(=O)C23CC(Cn4ncc5cc(C#N)ccc54)(C2)C3)C1] | 1-((3-(2-(3-fluorophenyl)-4-methylpyrrolidine-1-carbonyl)-bicyclo[1.1.1]pentan-1-yl)-methyl)-1H-indazole-5-carbonitrile | 428/429 | 49 |

TABLE 5-continued

Examples 210-345.

| Ex. No | Structure | Name | MS[a] | Proc. Ex. No.[b] |
|---|---|---|---|---|
| 258 | 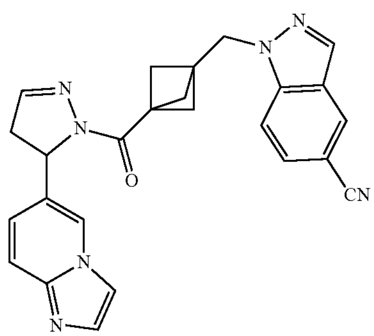 [SMILES: N#Cc1ccc2c(cnn2CC23CC(C(=O)N4N=CCC4c4ccc5nccn5c4)(C2)C3)c1] | 1-((3-(5-(imidazo[1,2-a]-pyridin-6-yl)-4,5-dihydro-1H-pyrazole-1-carbonyl)bicyclo-[1.1.1]pentan-1-yl)methyl)-1H-indazole-5-carbonitrile | 435/436 | 49 |
| 259 | 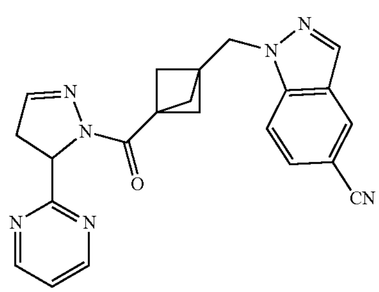 [SMILES: N#Cc1ccc2c(cnn2CC23CC(C(=O)N4N=CCC4c4ncccn4)(C2)C3)c1] | 1-((3-(5-(pyrimidin-2-yl)-4,5-dihydro-1H-pyrazole-1-carbonyl)bicyclo[1.1.1]pentan-1-yl)methyl)-1H-indazole-5-carbonitrile | 397/398 | 49 |
| 260 | 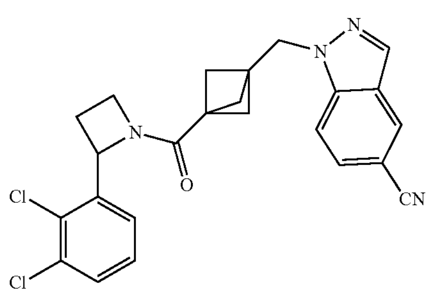 [SMILES: N#Cc1ccc2c(cnn2CC23CC(C(=O)N4CCC4c4cccc(Cl)c4Cl)(C2)C3)c1] | 1-((3-(2-(2,3-dichlorophenyl)-azetidine-1-carbonyl)bicyclo-[1.1.1]pentan-1-yl)methyl)-1H-indazole-5-carbonitrile | 450/451 | 49 |
| 261 | 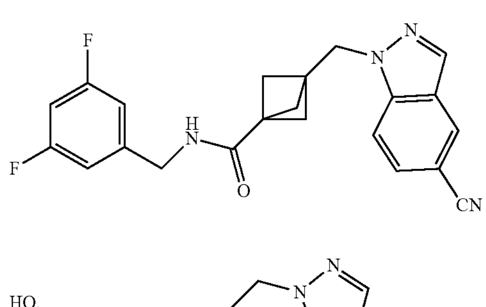 | 3-((5-cyano-1H-indazol-1-yl)methyl)-N-(3,5-difluoro-benzyl)bicyclo[1.1.1]pentane-1-carboxamide | 392/393 | 49 |
| 262 | 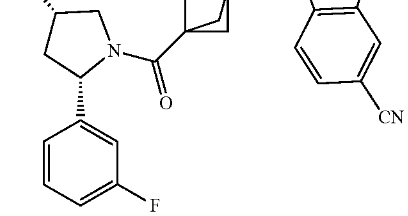 | 1-((3-((2S,4S)-2-(3-fluoro-phenyl)-4-hydroxypyrrolidine-1-carbonyl)bicyclo[1.1.1-pentan-1-yl)methyl)-1H-indazole-5-carbonitrile | 430/431 | 49, first eluting isomer. |

TABLE 5-continued

Examples 210-345.

| Ex. No | Structure | Name | MS(a) | Proc. Ex. No.(b) |
|---|---|---|---|---|
| 263 | 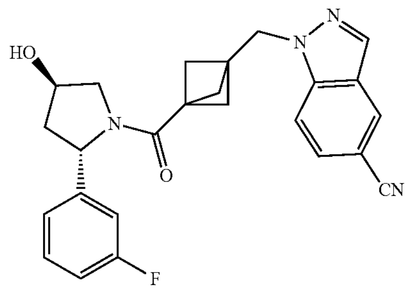 [SMILES: N#Cc1ccc2c(cnn2CC23CC(C(=O)N4C[C@H](O)C[C@H]4c4cccc(F)c4)(C2)C3)c1] | 1-((3-((2S,4R)-2-(3-fluorophenyl)-4-hydroxypyrrolidine-1-carbonyl)bicyclo[1.1.1]-pentan-1-yl)methyl)-1H-indazole-5-carbonitrile | 430/431 | 49, second eluting isomer. |
| 264 | 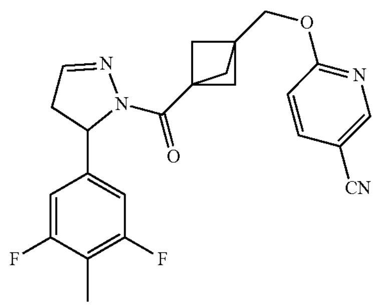 [SMILES: Cc1c(F)cc(C2CC=NN2C(=O)C23CC(COc4ccc(C#N)cn4)(C2)C3)cc1F] | 6-((3-(5-(3,5-difluoro-4-methylphenyl)-4,5-dihydro-1H-pyrazole-1-carbonyl)-bicyclo[1.1.1]pentan-1-yl)-methoxy)nicotinonitrile | 422/423 | 203 |
| 265 | 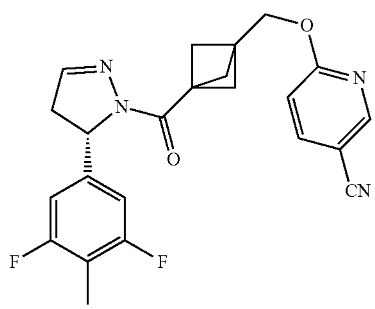 [SMILES: Cc1c(F)cc([C@@H]2CC=NN2C(=O)C23CC(COc4ccc(C#N)cn4)(C2)C3)cc1F] | (S)-6-((3-(5-(3,5-difluoro-4-methylphenyl)-4,5-dihydro-1H-pyrazole-1-carbonyl)-bicyclo[1.1.1]pentan-1-yl)-methoxy)nicotinonitrile | 422/423 | 197 |
| 266 | 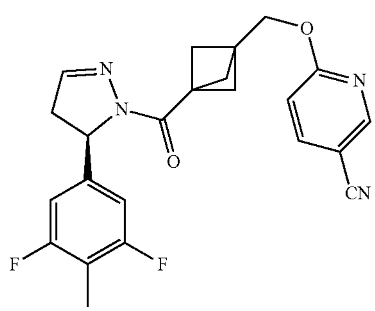 [SMILES: Cc1c(F)cc([C@H]2CC=NN2C(=O)C23CC(COc4ccc(C#N)cn4)(C2)C3)cc1F] | (R)-6-((3-(5-(3,5-difluoro-4-methylphenyl)-4,5-dihydro-1H-pyrazole-1-carbonyl)-bicyclo[1.1.1]pentan-1-yl)-methoxy)nicotinonitrile | 405/406 | SFC |
| 267 | 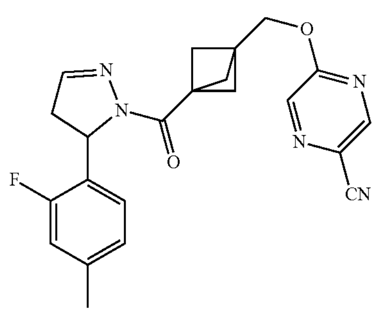 [SMILES: Cc1ccc(C2CC=NN2C(=O)C23CC(COc4cnc(C#N)cn4)(C2)C3)c(F)c1] | 5-((3-(5-(2-fluoro-4-methylphenyl)-4,5-dihydro-1H-pyrazole-1-carbonyl)bicyclo-[1.1.1]pentan-1-yl)methoxy)-pyrazine-2-carbonitrile | 422/423 | 195 |

TABLE 5-continued

Examples 210-345.

| Ex. No | Structure | Name | MS(a) | Proc. Ex. No.(b) |
|---|---|---|---|---|
| 268 | 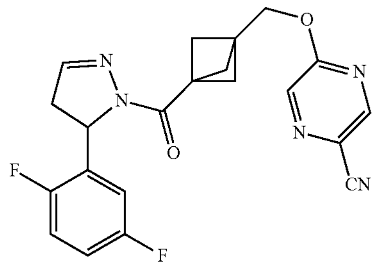 [SMILES: N#Cc1cnc(OCC23CC(C(=O)N4N=CCC4c4cc(F)ccc4F)(C2)C3)cn1] | 5-((3-(5-(2,5-difluorophenyl)-4,5-dihydro-1H-pyrazole-1-carbonyl)bicyclo[1.1.1]pentan-1-yl)methoxy)pyrazine-2-carbonitrile | 409/410 | 195 |
| 269 | 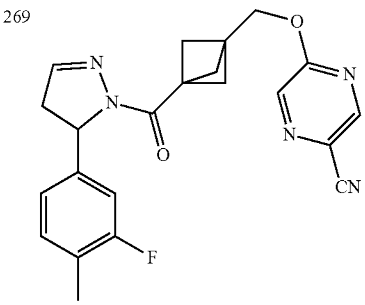 | 5-((3-(5-(3-fluoro-4-methylphenyl)-4,5-dihydro-1H-pyrazole-1-carbonyl)bicyclo-[1.1.1]pentan-1-yl)-methoxy)pyrazine-2-carbonitrile | 405/406 | 195 |
| 270 | 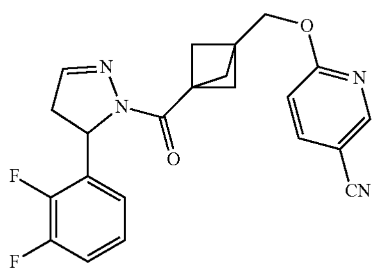 [SMILES: N#Cc1ccc(OCC23CC(C(=O)N4N=CCC4c4cccc(F)c4F)(C2)C3)nc1] | 6-((3-(5-(2,3-difluorophenyl)-4,5-dihydro-1H-pyrazole-1-carbonyl)bicyclo[1.1.1]pentan-1-yl)methoxy)nicotinonitrile | 408/409 | 195 |
| 271 | 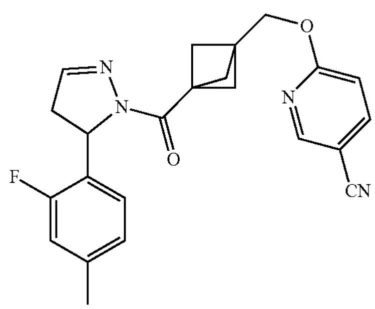 [SMILES: Cc1ccc(C2CC=NN2C(=O)C23CC(COc4ccc(C#N)cn4)(C2)C3)c(F)c1] | 6-((3-(5-(2-fluoro-4-methylphenyl)-4,5-dihydro-1H-pyrazole-1-carbonyl)bicyclo-[1.1.1]pentan-1-yl)methoxy)-nicotinonitrile | 404/405 | 195 |
| 272 | 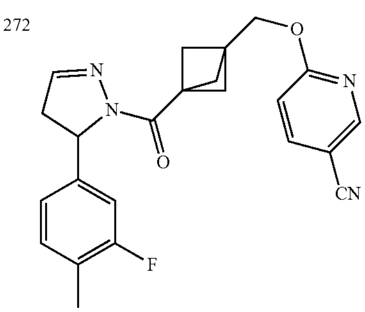 | 6-((3-(5-(3-fluoro-4-methylphenyl)-4,5-dihydro-1H-pyrazole-1-carbonyl)bicyclo-[1.1.1]pentan-1-yl)-methoxy)nicotinonitrile | 404/405 | 195 |

TABLE 5-continued

Examples 210-345.

| Ex. No | Structure | Name | MS(a) | Proc. Ex. No.(b) |
|---|---|---|---|---|
| 273 | 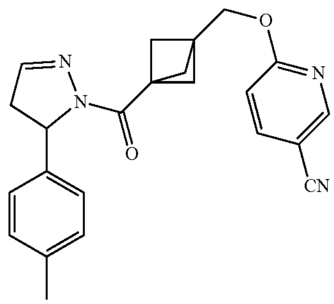 [SMILES: Cc1ccc(C2CC=NN2C(=O)C23CC(COc4ccc(C#N)cn4)(C2)C3)cc1] | 6-((3-(5-(p-tolyl)-4,5-dihydro-1H-pyrazole-1-carbonyl)-bicyclo[1.1.1]pentan-1-yl)-methoxy)nicotinonitrile | 386/ 387 | 195 |
| 274 | 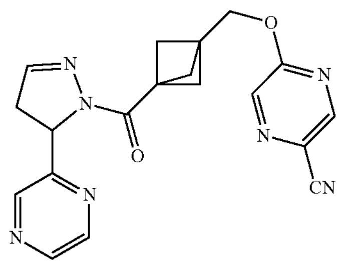 [SMILES: N#Cc1cnc(OCC23CC(C(=O)N4N=CCC4c4cnccn4)(C2)C3)cn1] | 5-((3-(5-(pyrazin-2-yl)-4,5-dihydro-1H-pyrazole-1-carbonyl)bicyclo[1.1.1]pentan-1-yl)methoxy)pyrazine-2-carbonitrile | 375/ 376 | 195 |
| 275 | 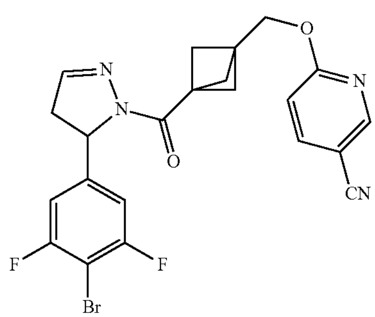 [SMILES: N#Cc1ccc(OCC23CC(C(=O)N4N=CCC4c4cc(F)c(Br)c(F)c4)(C2)C3)nc1] | 6-((3-(5-(4-bromo-3,5-difluorophenyl)-4,5-dihydro-1H-pyrazole-1-carbonyl)-bicyclo[1.1.1]pentan-1-yl)-methoxy)nicotinonitrile | 486/ 487 | 195 |
| 276 | 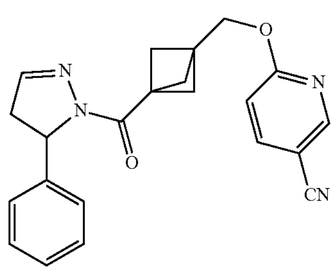 [SMILES: N#Cc1ccc(OCC23CC(C(=O)N4N=CCC4c4ccccc4)(C2)C3)nc1] | 6-((3-(5-phenyl-4,5-dihydro-1H-pyrazole-1-carbonyl)-bicyclo[1.1.1]pentan-1-yl)-methoxy)nicotinonitrile | 372/ 373 | 195 |
| 277 | 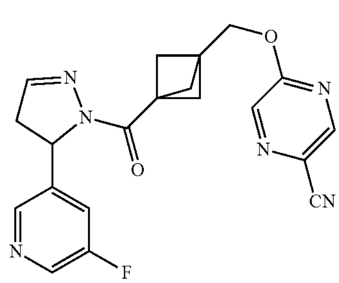 [SMILES: N#Cc1cnc(OCC23CC(C(=O)N4N=CCC4c4cncc(F)c4)(C2)C3)cn1] | 5-((3-(5-(5-fluoropyridin-3-yl)-4,5-dihydro-1H-pyrazole-1-carbonyl)bicyclo[1.1.1]-pentan-1-yl)methoxy)pyrazine-2-carbonitrile | 392/ 393 | 195 |

TABLE 5-continued

Examples 210-345.

| Ex. No | Structure | Name | MS[a] | Proc. Ex. No.[b] |
|---|---|---|---|---|
| 278 | 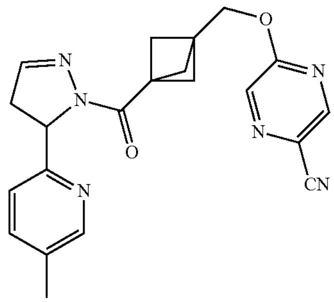 [SMILES: Cc1ccc(C2CC=NN2C(=O)C23CC(COc4cnc(C#N)cn4)(C2)C3)nc1] | 5-((3-(5-(5-methylpyridin-2-yl)-4,5-dihydro-1H-pyrazole-1-carbonyl)bicyclo[1.1.1]-pentan-1-yl)methoxy)pyrazine-2-carbonitrile | 388/ 389 | 195 |
| 279 | 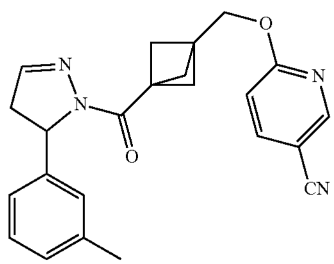 [SMILES: Cc1cccc(C2CC=NN2C(=O)C23CC(COc4ccc(C#N)cn4)(C2)C3)c1] | 6-((3-(5-(m-tolyl)-4,5-dihydro-1H-pyrazole-1-carbonyl)-bicyclo[1.1.1]pentan-1-yl)-methoxy)nicotinonitrile | 386/ 387 | 195 |
| 280 | 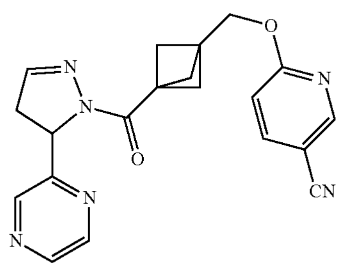 | 6-((3-(5-(pyrazin-2-yl)-4,5-dihydro-1H-pyrazole-1-carbonyl)bicyclo[1.1.1]pentan-1-yl)methoxy)nicotinonitrile | 374/ 375 | 195 |
| 281 | 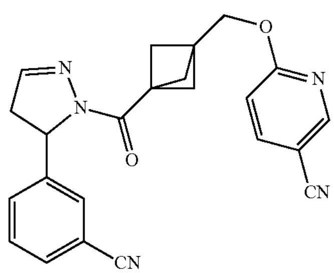 [SMILES: N#Cc1ccc(OCC23CC(C(=O)N4N=CCC4c4cccc(C#N)c4)(C2)C3)nc1] | 6-((3-(5-(3-cyanophenyl)-4,5-dihydro-1H-pyrazole-1-carbonyl)bicyclo[1.1.1]pentan-1-yl)methoxy)nicotinonitrile | 397/ 398 | 195 |
| 282 | 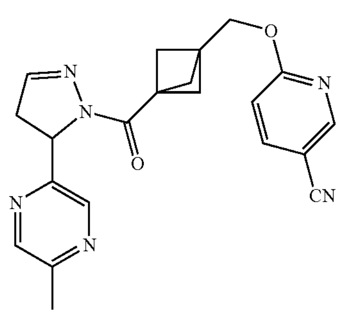 [SMILES: Cc1cnc(C2CC=NN2C(=O)C23CC(COc4ccc(C#N)cn4)(C2)C3)cn1] | 6-((3-(5-(5-methylpyrazin-2-yl)-4,5-dihydro-1H-pyrazole-1-carbonyl)bicyclo[1.1.1]-pentan-1-yl)methoxy)-nicotinonitrile | 388/ 389 | 195 |

TABLE 5-continued

Examples 210-345.

| Ex. No | Structure | Name | MS[a] | Proc. Ex. No.[b] |
|---|---|---|---|---|
| 283 | 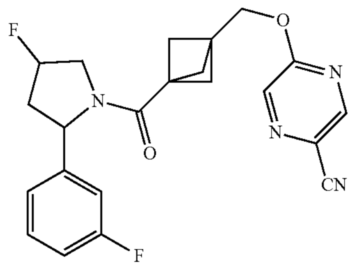 [SMILES: N#Cc1cnc(OCC23CC(C(=O)N4CC(F)CC4c4cccc(F)c4)(C2)C3)cn1] | 5-((3-(5-(3-fluorophenyl)-4,5-dihydro-1H-pyrazole-1-carbonyl)bicyclo[1.1.1]pentan-1-yl)methoxy)pyrazine-2-carbonitrile | 410/411 | 195 |
| 284 | 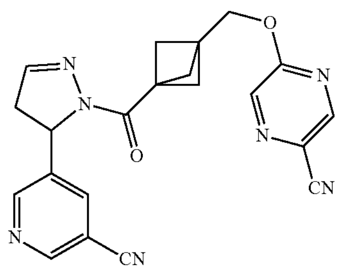 | 5-((3-(5-(5-cyanopyridin-3-yl)-4,5-dihydro-1H-pyrazole-1-carbonyl)bicyclo[1.1.1]pentan-1-yl)methoxy)pyrazine-2-carbonitrile | 399/400 | 195 |
| 285 | 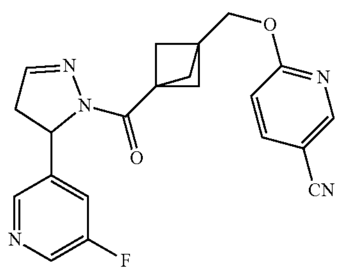 | 6-((3-(5-(5-fluoropyridin-3-yl)-4,5-dihydro-1H-pyrazole-1-carbonyl)bicyclo[1.1.1]-pentan-1-yl)methoxy)-nicotinonitrile | 391/392 | 195 |
| 286 | 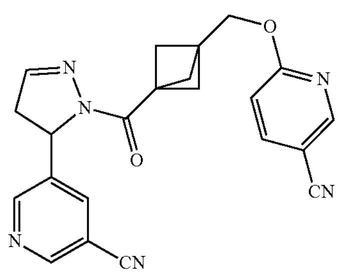 [SMILES: N#Cc1ccc(OCC23CC(C(=O)N4N=CCC4c4cncc(C#N)c4)(C2)C3)nc1] | 5-(1-(3-(((5-cyanopyridin-2-yl)oxy)methyl)bicyclo[1.1.1]-pentane-1-carbonyl)-4,5-dihydro-1H-pyrazol-5-yl)-nicotinonitrile | 398/399 | 195 |
| 287 | 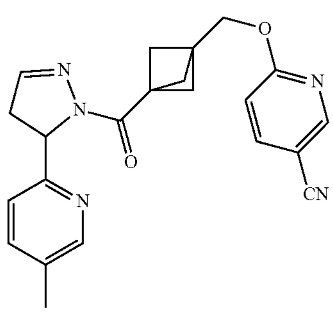 [SMILES: Cc1ccc(C2CC=NN2C(=O)C23CC(COc4ccc(C#N)cn4)(C2)C3)nc1] | 6-(1-(3-(((5-methylpyridin-2-yl)oxy)methyl)bicyclo[1.1.1]-pentane-1-carbonyl)-4,5-dihydro-1H-pyrazol-5-yl)-nicotinonitrile | 387/388 | 195 |

TABLE 5-continued

Examples 210-345.

| Ex. No | Structure | Name | MS(a) | Proc. Ex. No.(b) |
|---|---|---|---|---|
| 288 | 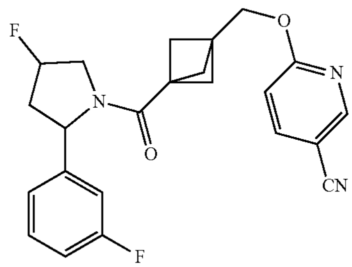 [SMILES: N#Cc1ccc(OCC23CC(C(=O)N4CC(F)CC4c4cccc(F)c4)(C2)C3)nc1] | 6-((3-(4-fluoro-2-(3-fluoro-phenyl)pyrrolidine-1-carbonyl)bicyclo[1.1.1]pentan-1-yl)methoxy)nicotinonitrile | 409/410 | 195 |
| 289 | 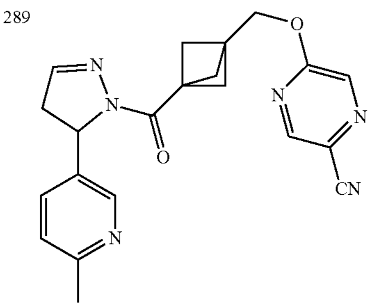 | 5-((3-(5-(6-methylpyridin-3-yl)-4,5-dihydro-1H-pyrazole-1-carbonyl)bicyclo[1.1.1]-pentan-1-yl)methoxy)pyrazine-2-carbonitrile | 388/389 | 195 |
| 290 | 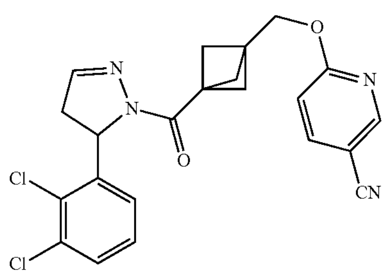 [SMILES: N#Cc1ccc(OCC23CC(C(=O)N4N=CCC4c4cccc(Cl)c4Cl)(C2)C3)nc1] | 6-((3-(5-(2,3-dichlorophenyl)-4,5-dihydro-1H-pyrazole-1-carbonyl)bicyclo[1.1.1]pentan-1-yl)methoxy)nicotinonitrile | 440/441 | 195 |
| 291 | 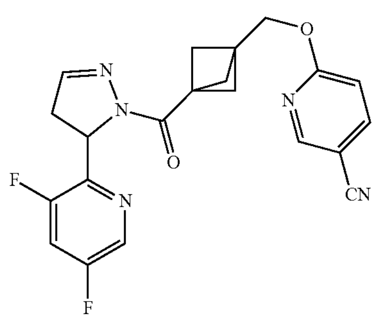 [SMILES: N#Cc1ccc(OCC23CC(C(=O)N4N=CCC4c4ncc(F)cc4F)(C2)C3)nc1] | 6-((3-(5-(3,5-difluoropyridin-2-yl)-4,5-dihydro-1H-pyrazole-1-carbonyl)bicyclo-[1.1.1]pentan-1-yl)methoxy)-nicotinonitrile | 409/410 | 195 |
| 292 | 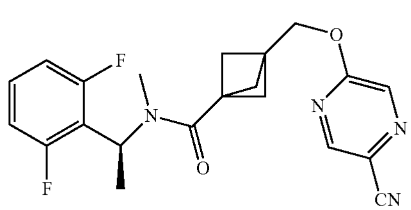 [SMILES: C[C@@H](c1c(F)cccc1F)N(C)C(=O)C12CC(COc3cnc(C#N)cn3)(C1)C2] | (S)-3-(((5-cyanopyrazin-2-yl)oxy)methyl)-N-(1-(2,6-difluorophenyl)ethyl)-N-methylbicyclo[1.1.1]pentane-1-carboxamide | 398/399 | 195 |

TABLE 5-continued

Examples 210-345.

| Ex. No | Structure | Name | MS[a] | Proc. Ex. No.[b] |
|---|---|---|---|---|
| 293 | 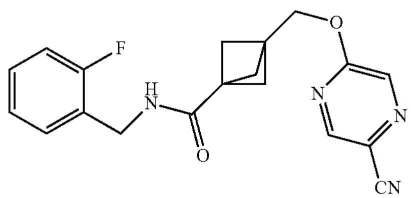 [SMILES: N#Cc1cnc(OCC23CC(C(=O)NCc4ccccc4F)(C2)C3)cn1] | 3-(((5-cyanopyrazin-2-yl)oxy)-methyl)-N-(2-fluorobenzyl)-bicyclo[1.1.1]pentane-1-carboxamide | 366/ 367 | 195 |
| 294 | 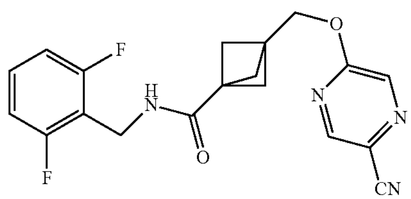 [SMILES: N#Cc1cnc(OCC23CC(C(=O)NCc4c(F)cccc4F)(C2)C3)cn1] | 3-(((5-cyanopyrazin-2-yl)oxy)-methyl)-N-(2,6-difluoro-benzyl)bicyclo[1.1.1]pentane-1-carboxamide | 370/ 371 | 195 |
| 295 | 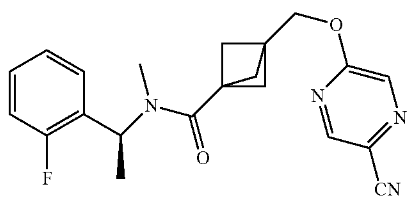 [SMILES: C[C@@H](c1ccccc1F)N(C)C(=O)C12CC(COc3cnc(C#N)cn3)(C1)C2] | (S)-3-(((5-cyanopyrazin-2-yl)oxy)methyl)-N-(1-(2-fluoro-phenyl)ethyl)-N-methyl-bicyclo[1.1.1]pentane-1-carboxamide | 380/ 381 | 195 |
| 296 | 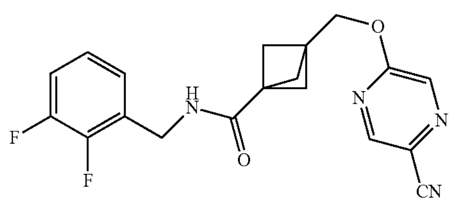 [SMILES: N#Cc1cnc(OCC23CC(C(=O)NCc4cccc(F)c4F)(C2)C3)cn1] | 3-(((5-cyanopyrazin-2-yl)-oxy)methyl)-N-(2,3-difluoro-benzyl)bicyclo[1.1.1]pentane-1-carboxamide | 370/ 371 | 195 |
| 297 | 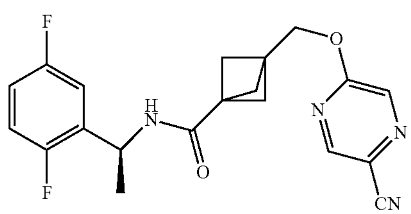 [SMILES: C[C@H](NC(=O)C12CC(COc3cnc(C#N)cn3)(C1)C2)c1cc(F)ccc1F] | (S)-3-(((5-cyanopyrazin-2-yl)-oxy)methyl)-N-(1-(2,5-difluorophenyl)ethyl)bicyclo-[1.1.1]pentane-1-carboxamide | 384/ 385 | 195 |
| 298 | 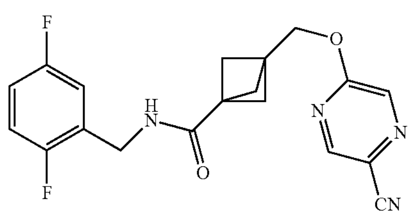 [SMILES: N#Cc1cnc(OCC23CC(C(=O)NCc4cc(F)ccc4F)(C2)C3)cn1] | 3-(((5-cyanopyrazin-2-yl)oxy)-methyl)-N-(2,5-difluoro-benzyl)bicyclo[1.1.1]pentane-1-carboxamide | 370/ 371 | 195 |
| 299 | 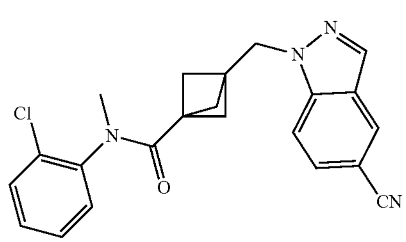 [SMILES: CN(C(=O)C12CC(Cn3ncc4cc(C#N)ccc43)(C1)C2)c1ccccc1Cl] | N-(2-chlorophenyl)-3-((5-cyano-1H-indazol-1-yl)-methyl)-N-methylbicyclo-[1.1.1]pentane-1-carboxamide | 390/ 391 | 195 |

TABLE 5-continued

Examples 210-345.

| Ex. No | Structure | Name | MS[a] | Proc. Ex. No.[b] |
|---|---|---|---|---|
| 300 | 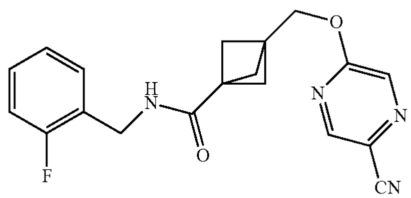 [SMILES: N#Cc1cnc(OCC23CC(C(=O)NCc4ccccc4F)(C2)C3)cn1] | 3-(((5-cyanopyrazin-2-yl)-oxy)methyl)-N-(2-fluoro-benzyl)bicyclo[1.1.1]pentane-1-carboxamide | 352/ 353 | 195 |
| 301 | 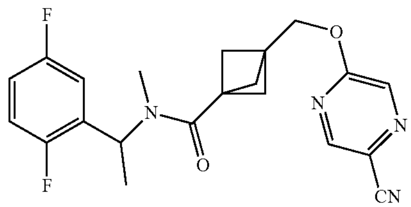 [SMILES: CC(c1cc(F)ccc1F)N(C)C(=O)C12CC(COc3cnc(C#N)cn3)(C1)C2] | 3-(((5-cyanopyrazin-2-yl)oxy)-methyl)-N-(1-(2,5-difluoro-phenyl)ethyl)-N-methyl-bicyclo[1.1.1]pentane-1-carboxamide | 398/ 399 | 195 |
| 302 | 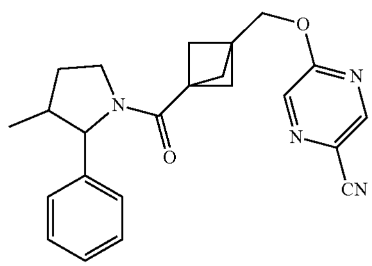 [SMILES: CC1CCN(C(=O)C23CC(COc4cnc(C#N)cn4)(C2)C3)C1c1ccccc1] | 5-((3-(3-methyl-2-phenyl-pyrrolidine-1-carbonyl)-bicyclo[1.1.1]pentan-1-yl)-methoxy)pyrazine-2-carbonitrile | 388/ 389 | 195 |
| 303 | 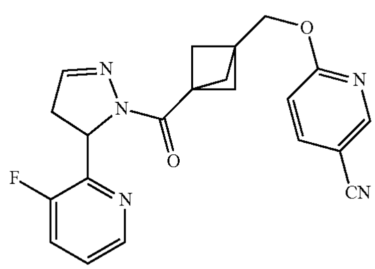 [SMILES: N#Cc1ccc(OCC23CC(C(=O)N4N=CCC4c4ncccc4F)(C2)C3)nc1] | 6-((3-(5-(3-fluoropyridin-2-yl)-4,5-dihydro-1H-pyrazole-1-carbonyl)bicyclo[1.1.1]-pentan-1-yl)methoxy)-nicotinonitrile | 391/ 392 | 195 |
| 304 | 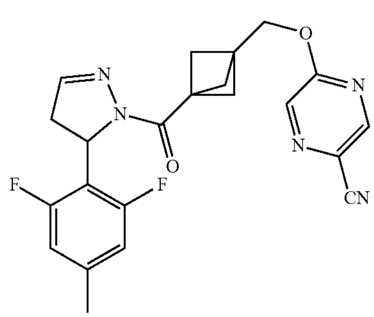 [SMILES: Cc1cc(F)c(C2CC=NN2C(=O)C23CC(COc4cnc(C#N)cn4)(C2)C3)c(F)c1] | 5-((3-(5-(2,6-difluoro-4-methylphenyl)-4,5-dihydro-1H-pyrazole-1-carbonyl)-bicyclo[1.1.1]pentan-1-yl)-methoxy)pyrazine-2-carbonitrile | 423/ 424 | 198 |

TABLE 5-continued

Examples 210-345.

| Ex. No | Structure | Name | MS[a] | Proc. Ex. No.[b] |
|---|---|---|---|---|
| 305 | 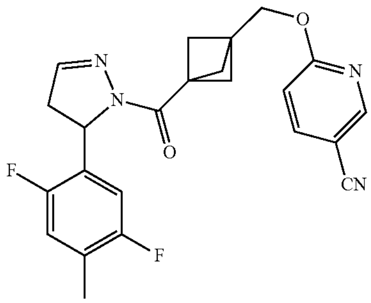 [SMILES: Cc1cc(F)c(C2CC=NN2C(=O)C23CC(COc4ccc(C#N)cn4)(C2)C3)cc1F] | 6-((3-(5-(2,5-difluoro-4-methylphenyl)-4,5-dihydro-1H-pyrazole-1-carbonyl)-bicyclo[1.1.1]pentan-1-yl)-methoxy)nicotinonitrile | 422/423 | 198 |
| 306 | 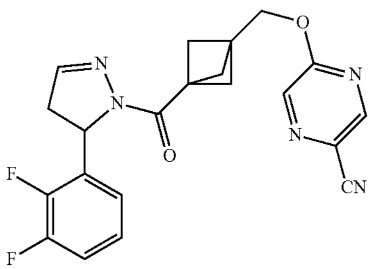 [SMILES: N#Cc1cnc(OCC23CC(C(=O)N4N=CCC4c4cccc(F)c4F)(C2)C3)cn1] | 5-((3-(5-(2,3-difluorophenyl)-4,5-dihydro-1H-pyrazole-1-carbonyl)bicyclo[1.1.1]pentan-1-yl)methoxy)pyrazine-2-carbonitrile | 409/410 | 198 |
| 307 | 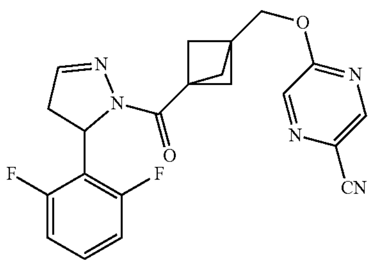 [SMILES: N#Cc1cnc(OCC23CC(C(=O)N4N=CCC4c4c(F)cccc4F)(C2)C3)cn1] | 5-((3-(5-(2,6-difluorophenyl)-4,5-dihydro-1H-pyrazole-1-carbonyl)bicyclo[1.1.1]pentan-1-yl)methoxy)pyrazine-2-carbonitrile | 409/410 | 198 |
| 308 | 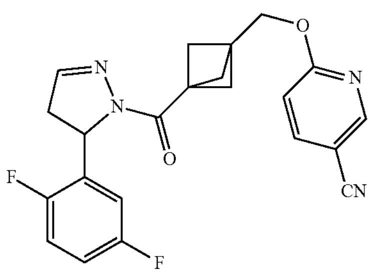 [SMILES: N#Cc1ccc(OCC23CC(C(=O)N4N=CCC4c4cc(F)ccc4F)(C2)C3)nc1] | 6-((3-(5-(2,5-difluorophenyl)-4,5-dihydro-1H-pyrazole-1-carbonyl)bicyclo[1.1.1]pentan-1-yl)methoxy)nicotinonitrile | 408/409 | 198 |
| 309 | 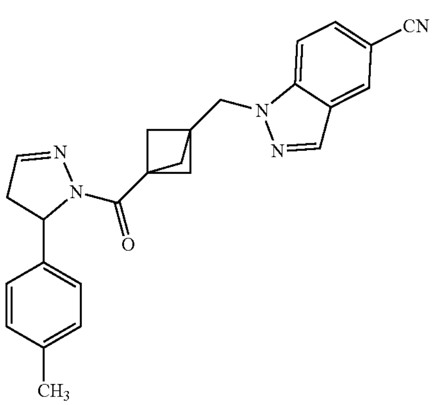 [SMILES: Cc1ccc(C2CC=NN2C(=O)C23CC(Cn4ncc5cc(C#N)ccc54)(C2)C3)cc1] | 1-((3-(5-(p-tolyl)-4,5-dihydro-1H-pyrazole-1-carbonyl)-bicyclo[1.1.1]pentan-1-yl)-methyl)-1H-indazole-5-carbonitrile | 409/410 | 198 |

TABLE 5-continued

Examples 210-345.

| Ex. No | Structure | Name | MS(a) | Proc. Ex. No.(b) |
|---|---|---|---|---|
| 310 | 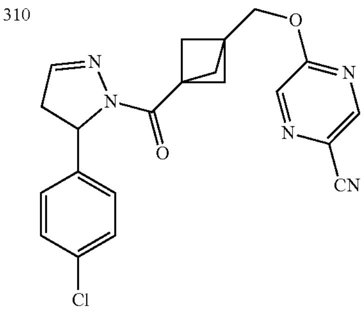 | 5-((3-(5-(4-chlorophenyl)-4,5-dihydro-1H-pyrazole-1-carbonyl)bicyclo[1.1.1]pentan-1-yl)methoxy)pyrazine-2-carbonitrile | 407/ 408 | 198 |
| 311 | 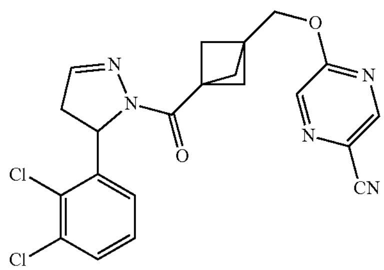 [SMILES: N#Cc1cnc(OCC23CC(C(=O)N4N=CCC4c4cccc(Cl)c4Cl)(C2)C3)cn1] | 5-((3-(5-(2,3-dichlorophenyl)-4,5-dihydro-1H-pyrazole-1-carbonyl)bicyclo[1.1.1]pentan-1-yl)methoxy)pyrazine-2-carbonitrile | 441/ 442 | 198 |
| 312 | 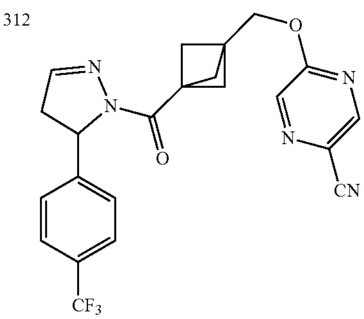 | 5-((3-(5-(4-(trifluoromethyl)-phenyl)-4,5-dihydro-1H-pyrazole-1-carbonyl)bicyclo-[1.1.1]pentan-1-yl)methoxy)-pyrazine-2-carbonitrile | 441/ 442 | 198 |
| 313 | 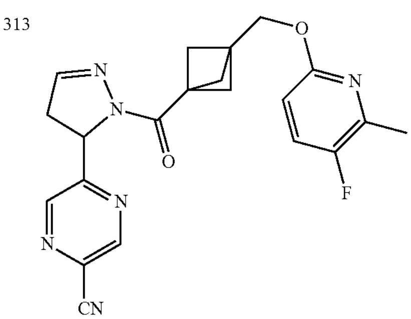 | 5-(1-(3-(((5-fluoro-6-methylpyridin-2-yl)oxy)-methyl)bicyclo[1.1.1]pentane-1-carbonyl)-4,5-dihydro-1H-pyrazol-5-yl)pyrazine-2-carbonitrile | 406/ 407 | 198 |
| 314 | 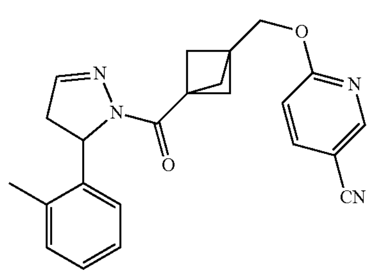 [SMILES: Cc1ccccc1C1CC=NN1C(=O)C12CC(COc3ccc(C#N)cn3)(C1)C2] | 6-((3-(5-(o-tolyl)-4,5-dihydro-1H-pyrazole-1-carbonyl)-bicyclo[1.1.1]pentan-1-yl)-methoxy)nicotinonitrile | 386/ 387 | 198 |

TABLE 5-continued

Examples 210-345.

| Ex. No | Structure | Name | MS[a] | Proc. Ex. No.[b] |
|---|---|---|---|---|
| 315 | 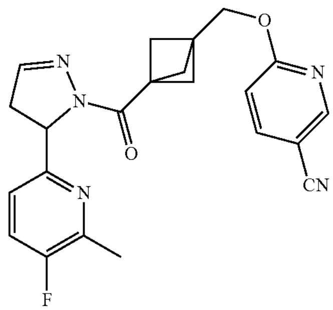 [SMILES: Cc1nc(C2CC=NN2C(=O)C23CC(COc4ccc(C#N)cn4)(C2)C3)ccc1F] | 6-((3-(5-(5-fluoro-6-methyl-pyridin-2-yl)-4,5-dihydro-1H-pyrazole-1-carbonyl)bicyclo-[1.1.1]pentan-1-yl)methoxy)-nicotinonitrile | 405/ 406 | 198 |
| 316 | 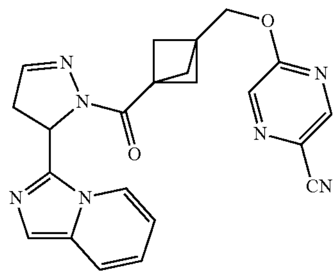 [SMILES: N#Cc1cnc(OCC23CC(C(=O)N4N=CCC4c4ncc5ccccn45)(C2)C3)cn1] | 5-((3-(5-(imidazo[1,5-a]-pyridin-3-yl)-4,5-dihydro-1H-pyrazole-1-carbonyl)bicyclo-[1.1.1]pentan-1-yl)methoxy)-pyrazine-2-carbonitrile | 413/ 414 | 198 |
| 317 | 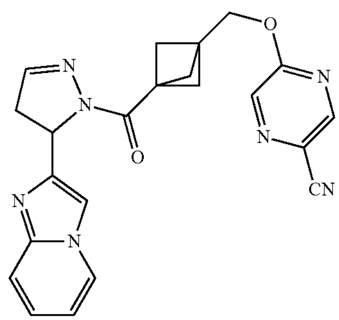 [SMILES: N#Cc1cnc(OCC23CC(C(=O)N4N=CCC4c4cn5ccccc5n4)(C2)C3)cn1] | 5-((3-(5-(imidazo[1,2-a]-pyridin-2-yl)-4,5-dihydro-1H-pyrazole-1-carbonyl)bicyclo-[1.1.1]pentan-1-yl)methoxy)-pyrazine-2-carbonitrile | 413/ 414 | 198 |
| 318 | 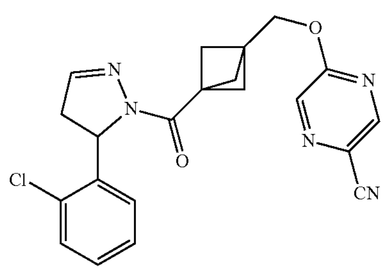 [SMILES: N#Cc1cnc(OCC23CC(C(=O)N4N=CCC4c4ccccc4Cl)(C2)C3)cn1] | 5-((3-(5-(2-chlorophenyl)-4,5-dihydro-1H-pyrazole-1-carbonyl)bicyclo[1.1.1]pentan-1-yl)methoxy)pyrazine-2-carbonitrile | 407/ 408 | 198 |
| 319 | 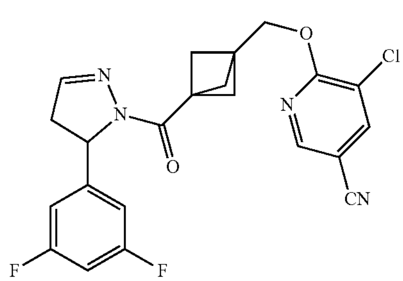 [SMILES: N#Cc1cnc(OCC23CC(C(=O)N4N=CCC4c4cc(F)cc(F)c4)(C2)C3)c(Cl)c1] | 5-chloro-6-((3-(5-(3,5-difluorophenyl)-4,5-dihydro-1H-pyrazole-1-carbonyl)-bicyclo[1.1.1]pentan-1-yl)-methoxy)nicotinonitrile | 442/ 443 | 199 |

US 11,753,381 B2

TABLE 5-continued

Examples 210-345.

| Ex. No | Structure | Name | MS$^{(a)}$ | Proc. Ex. No.$^{(b)}$ |
|---|---|---|---|---|
| 320 | 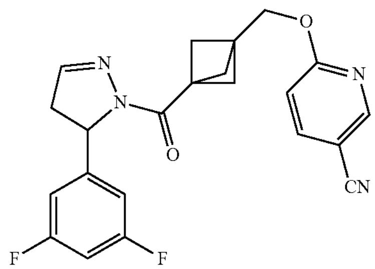 [SMILES: N#Cc1ccc(OCC23CC(C(=O)N4N=CCC4c4cc(F)cc(F)c4)(C2)C3)nc1] | 6-((3-(5-(3,5-difluorophenyl)-4,5-dihydro-1H-pyrazole-1-carbonyl)bicyclo[1.1.1]pentan-1-yl)methoxy)nicotinonitrile | 408/ 409 | 199 |
| 321 | 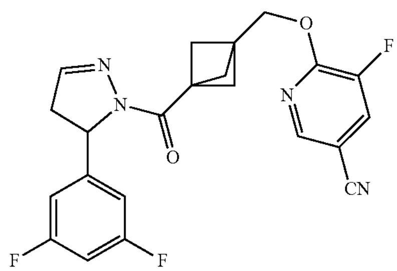 [SMILES: N#Cc1cnc(OCC23CC(C(=O)N4N=CCC4c4cc(F)cc(F)c4)(C2)C3)c(F)c1] | (5-(3,5-difluorophenyl)-4,5-dihydro-1H-pyrazol-1-yl)(3-(((3,5-difluoropyridin-2-yl)oxy)methyl)bicyclo[1.1.1]-pentan-1-yl)methanone | 419/ 420 | 199 |
| 322 | 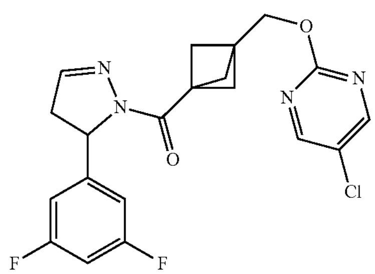 | (3-(((5-chloropyrimidin-2-yl)oxy)methyl)bicyclo[1.1.1]-pentan-1-yl)(5-(3,5-difluorophenyl)-4,5-dihydro-1H-pyrazol-1-yl)methanone | 418/ 419 | 199 |
| 323 | 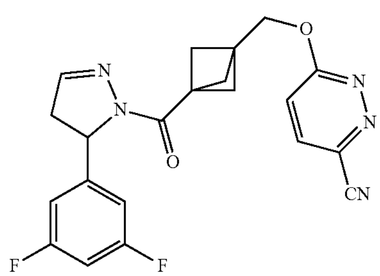 [SMILES: N#Cc1ccc(OCC23CC(C(=O)N4N=CCC4c4cc(F)cc(F)c4)(C2)C3)nn1] | 6-((3-(5-(3,5-difluorophenyl)-4,5-dihydro-1H-pyrazole-1-carbonyl)bicyclo[1.1.1]pentan-1-yl)methoxy)pyridazine-3-carbonitrile | 409/ 410 | 199 |
| 324 | 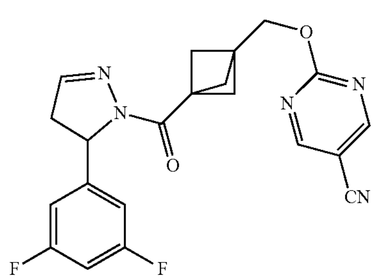 [SMILES: N#Cc1cnc(OCC23CC(C(=O)N4N=CCC4c4cc(F)cc(F)c4)(C2)C3)nc1] | 2-((3-(5-(3,5-difluorophenyl)-4,5-dihydro-1H-pyrazole-1-carbonyl)bicyclo[1.1.1]pentan-1-yl)methoxy)pyrimidine-5-carbonitrile | 409/ 410 | 199 |

TABLE 5-continued

Examples 210-345.

| Ex. No | Structure | Name | MS(a) | Proc. Ex. No.(b) |
|---|---|---|---|---|
| 325 | 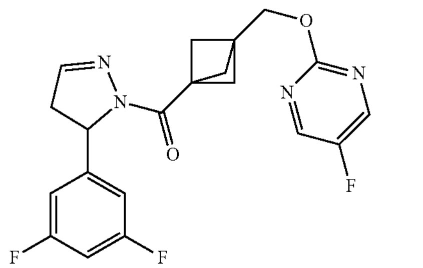 | (5-(3,5-difluorophenyl)-4,5-dihydro-1H-pyrazol-1-yl)(3-(((5-fluoropyrimidin-2-yl)oxy)methyl)bicyclo[1.1.1]-pentan-1-yl)methanone | 402/403 | 199 |
| 326 | 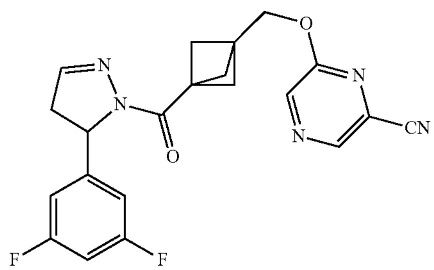 [SMILES: N#Cc1cncc(OCC23CC(C(=O)N4N=CCC4c4cc(F)cc(F)c4)(C2)C3)n1] | 5-((3-(5-(3,5-difluorophenyl)-4,5-dihydro-1H-pyrazole-1-carbonyl)bicyclo[1.1.1]pentan-1-yl)methoxy)pyrazine-2-carbonitrile | 409/410 | 199 |
| 327 | 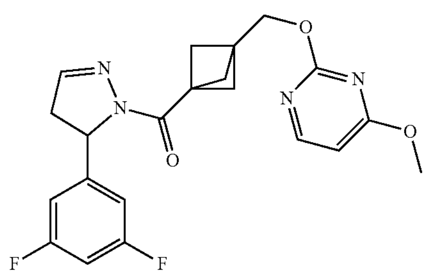 [SMILES: COc1ccnc(OCC23CC(C(=O)N4N=CCC4c4cc(F)cc(F)c4)(C2)C3)n1] | (5-(3,5-difluorophenyl)-4,5-dihydro-1H-pyrazol-1-yl)(3-(((4-methoxypyrimidin-2-yl)oxy)methyl)bicyclo[1.1.1]-pentan-1-yl)methanone | 414/415 | 199 |
| 328 | 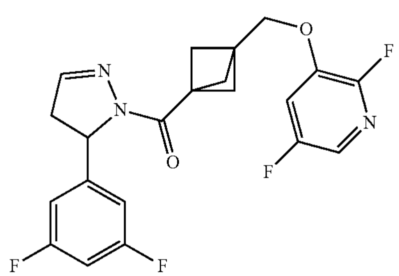 [SMILES: O=C(N1N=CCC1c1cc(F)cc(F)c1)C12CC(COc3cc(F)cnc3F)(C1)C2] | (5-(3,5-difluorophenyl)-4,5-dihydro-1H-pyrazol-1-yl)(3-(((2,5-difluoropyridin-3-yl)oxy)methyl)bicyclo[1.1.1]-pentan-1-yl)methanone | 419/420 | 199 |
| 329 | 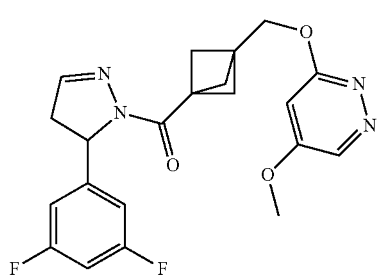 [SMILES: COc1cnnc(OCC23CC(C(=O)N4N=CCC4c4cc(F)cc(F)c4)(C2)C3)c1] | (5-(3,5-difluorophenyl)-4,5-dihydro-1H-pyrazol-1-yl)(3-(((5-methoxypyridazin-3-yl)oxy)methyl)bicyclo[1.1.1]-pentan-1-yl)methanone | 414/415 | 199 |

TABLE 5-continued

Examples 210-345.

| Ex. No | Structure | Name | MS(a) | Proc. Ex. No.(b) |
|---|---|---|---|---|
| 330 | 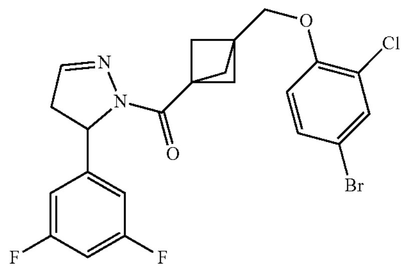 [SMILES: O=C(N1N=CCC1c1cc(F)cc(F)c1)C12CC(COc3ccc(Br)cc3Cl)(C1)C2] | (3-((4-bromo-2-chloro-phenoxy)methyl)bicyclo-[1.1.1]pentan-1-yl)(5-(3,5-difluorophenyl)-4,5-dihydro-1H-pyrazol-1-yl)methanone | 494/ 495, 497 | 202 |
| 331 | 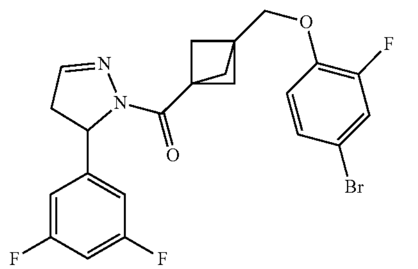 [SMILES: O=C(N1N=CCC1c1cc(F)cc(F)c1)C12CC(COc3ccc(Br)cc3F)(C1)C2] | (3-((4-bromo-2-fluoro-phenoxy)methyl)bicyclo-[1.1.1]pentan-1-yl)(5-(3,5-difluorophenyl)-4,5-dihydro-1H-pyrazol-1-yl)methanone | 478/ 479 | 202 |
| 332 | 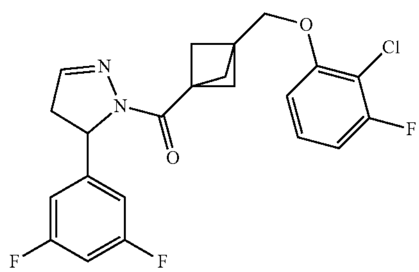 [SMILES: O=C(N1N=CCC1c1cc(F)cc(F)c1)C12CC(COc3cccc(F)c3Cl)(C1)C2] | (3-((2-chloro-3-fluoro-phenoxy)methyl)bicyclo-[1.1.1]pentan-1-yl)(5-(3,5-difluorophenyl)-4,5-dihydro-1H-pyrazol-1-yl)methanone | 434/ 435 | 202 |
| 333 | 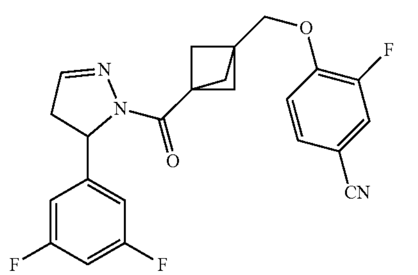 [SMILES: N#Cc1ccc(OCC23CC(C(=O)N4N=CCC4c4cc(F)cc(F)c4)(C2)C3)c(F)c1] | 4-((3-(5-(3,5-difluorophenyl)-4,5-dihydro-1H-pyrazole-1-carbonyl)bicyclo[1.1.1]pentan-1-yl)methoxy)-3-fluoro-benzonitrile | 425/ 426 | 202 |
| 334 | 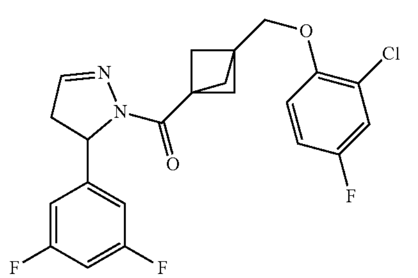 [SMILES: O=C(N1N=CCC1c1cc(F)cc(F)c1)C12CC(COc3ccc(F)cc3Cl)(C1)C2] | (3-((2-chloro-4-fluoro-phenoxy)methyl)bicyclo-[1.1.1]pentan-1-yl)(5-(3,5-difluorophenyl)-4,5-dihydro-1H-pyrazol-1-yl)methanone | 434/ 435 | 202 |

TABLE 5-continued

Examples 210-345.

| Ex. No | Structure | Name | MS(a) | Proc. Ex. No.(b) |
|---|---|---|---|---|
| 335 | 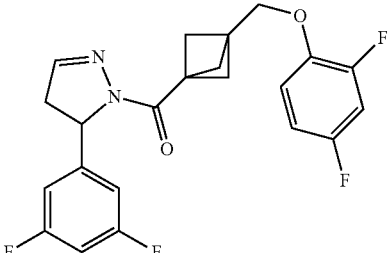 | (3-((2,4-difluorophenoxy)-methyl)bicyclo[1.1.1]pentan-1-yl)(5-(3,5-difluorophenyl)-4,5-dihydro-1H-pyrazol-1-yl)methanone | 418/ 419 | 202 |
| 336 | 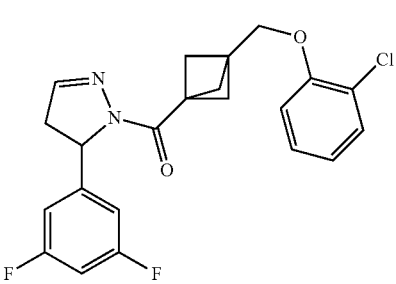 [SMILES: O=C(N1N=CCC1c1cc(F)cc(F)c1)C12CC(COc3ccccc3Cl)(C1)C2] | (3-((2-chlorophenoxy)methyl)-bicyclo[1.1.1]pentan-1-yl)(5-(3,5-difluorophenyl)-4,5-dihydro-1H-pyrazol-1-yl)-methanone | 416/ 417 | 202 |
| 337 | 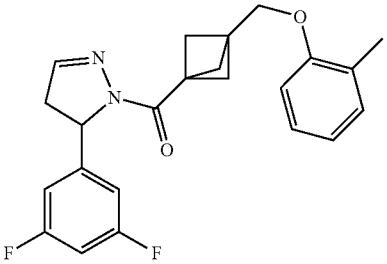 [SMILES: Cc1ccccc1OCC12CC(C(=O)N3N=CCC3c3cc(F)cc(F)c3)(C1)C2] | (5-(3,5-difluorophenyl)-4,5-dihydro-1H-pyrazol-1-yl)(3-((o-tolyloxy)methyl)bicyclo-[1.1.1]pentan-1-yl)methanone | 396/ 397 | 202 |
| 338 | 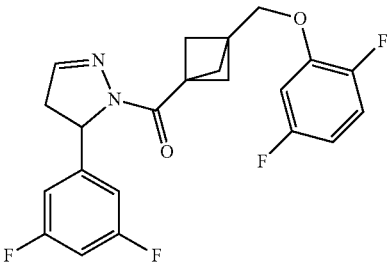 [SMILES: O=C(N1N=CCC1c1cc(F)cc(F)c1)C12CC(COc3cc(F)ccc3F)(C1)C2] | (3-((2,5-difluorophenoxy)-methyl)bicyclo[1.1.1]pentan-1-yl)(5-(3,5-difluorophenyl)-4,5-dihydro-1H-pyrazol-1-yl)methanone | 418/ 419 | 202 |
| 339 | 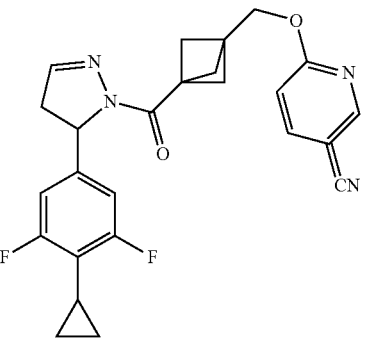 | 6-((3-(5-(4-cyclopropyl-3,5-difluorophenyl)-4,5-dihydro-1H-pyrazole-1-carbonyl)-bicyclo[1.1.1]pentan-1-yl)-methoxy)nicotinonitrile | 448/ 449 | 203 |

TABLE 5-continued

Examples 210-345.

| Ex. No | Structure | Name | MS[a] | Proc. Ex. No.[b] |
|---|---|---|---|---|
| 340 | 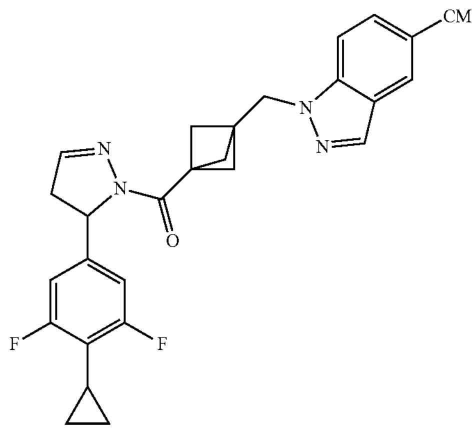 | 1-((3-(5-(4-cyclopropyl-3,5-difluorophenyl)-4,5-dihydro-1H-pyrazole-1-carbonyl)-bicyclo[1.1.1]pentan-1-yl)-methyl)-1H-indazole-5-carbonitrile | 471/ 472 | 203 |
| 341 | 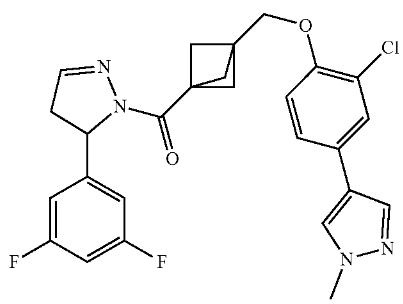 [SMILES: Cn1cc(-c2ccc(OCC34CC(C(=O)N5N=CCC5c5cc(F)cc(F)c5)(C3)C4)c(Cl)c2)cn1] | (3-((2-chloro-4-(1-methyl-1H-pyrazol-4-yl)phenoxy)methyl)-bicyclo[1.1.1]pentan-1-yl)(5-(3,5-difluorophenyl)-4,5-dihydro-1H-pyrazol-1-yl)-methanone | 496/ 497 | 204 |
| 342 | 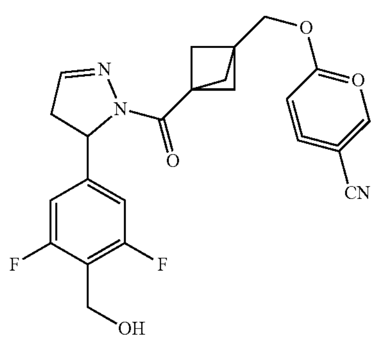 | 6-((3-(5-(3,5-difluoro-4-(hydroxymethyl)phenyl)-4,5-dihydro-1H-pyrazole-1-carbonyl)bicyclo[1.1.1]pentan-1-yl)methoxy)nicotinonitrile | 438/ 439 | 207 |
| 343 | 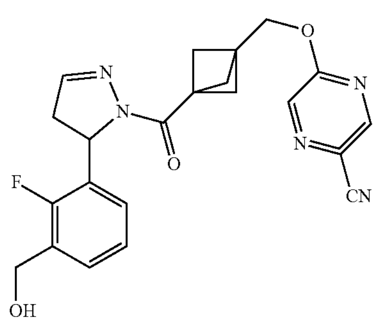 | 5-((3-(5-(2-fluoro-3-(hydroxymethyl)phenyl)-4,5-dihydro-1H-pyrazole-1-carbonyl)bicyclo[1.1.1]pentan-1-yl)methoxy)pyrazine-2-carbonitrile | $C_{22}H_{20}F$ $N_5O_3$ 421.16/ 422 | |

TABLE 5-continued

Examples 210-345.

| Ex. No | Structure | Name | MS[a] | Proc. Ex. No.[b] |
|---|---|---|---|---|
| 344 | 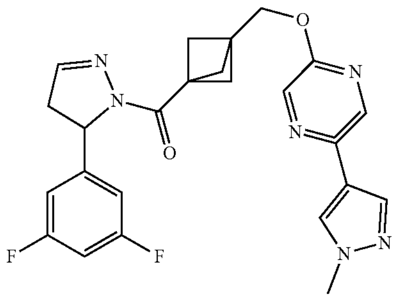 | (5-(3,5-difluorophenyl)-4,5-dihydro-1H-pyrazol-1-yl)(3-(((5-(1-methyl-1H-pyrazol-4-yl)pyrazin-2-yl)oxy)methyl)-bicyclo[1.1.1]pentan-1-yl)methanone | $C_{24}H_{22}F_2N_6O_2$ 464.18 | 204 |
| 345 | 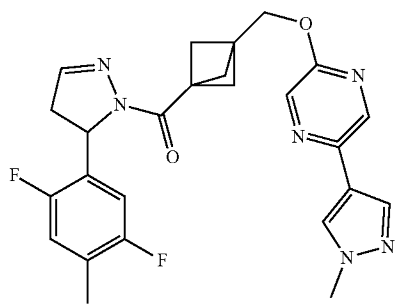 | (5-(2,5-difluoro-4-methylphenyl)-4,5-dihydro-1H-pyrazol-1-yl)(3-(((5-(1-methyl-1H-pyrazol-4-yl)pyrazin-2-yl)oxy)methyl)bicyclo[1.1.1]pentan-1-yl)methanone | $C_{25}H_{24}F_2N_6O_2$ 478.19 | 204 |

[a]MS is reported as exact mass/observed MS+
[b]synthesis is similar to procedure used for the cited example

TABLE 6

Selected $^1$H NMR data.

| Ex. No. | $^1$H NMR (600 MHz, DMSO-$d_6$) |
|---|---|
| 226 | δ 7.33 (t, J = 7.9 Hz, 1H), 7.18 (d, J = 1.9 Hz, 1H), 7.15-7.08 (m, 1H), 6.96-6.90 (m, 1H), 6.83 (d, J = 7.6 Hz, 1H), 6.81-6.77 (m, 3H), 5.61-5.51 (m, 1H), 5.31 (dd, J = 11.9, 4.9 Hz, 1H), 3.76 (s, 3H), 3.42-3.35 (m, 1H), 2.75-2.64 (m, 1H), 2.05-1.89 (m, 6H). |
| 227 | δ 7.48-7.43 (m, 1H), 7.21-7.15 (m, 2H), 7.11 (t, J = 9.2 Hz, 2H), 6.81-6.76 (m, 2H), 5.74-5.63 (m, 1H), 5.31 (dd, 7 = 11.9, 4.9 Hz, 1H), 3.44-3.38 (m, 1H), 2.72-2.65 (m, 1H), 2.01-1.92 (m, 6H). |
| 228 | δ 7.16-7.10 (m, 4H), 6.92-6.85 (m, 2H), 6.76 (dt, J = 8.4, 2.0 Hz, 2H), 5.32-5.27 (m, 1H), 4.52 (s, 1H), 3.74 (s, 3H), 2.70-2.61 (m, 1H), 1.92-1.81 (m, 4H), 1.81-1.73 (m, 3H). |
| 233 | δ 8.40 (d, J = 16.5 Hz, 1H), 8.29-8.17 (m, 1H), 7.88 (d, J = 8.7 Hz, 1H), 7.76-7.69 (m, 1H), 7.40-7.32 (m, 2H), 7.29-7.22 (m, 2H), 5.41-5.15 (m, 1H), 4.64-4.42 (m, 2H), 4.18 (t, J = 7.8 Hz, 1H), 3.95-3.83 (m, 1H), 2.69 (s, 1H), 1.85 (s, 5H), 1.47-1.34 (m, 2H). |
| 234 | δ 8.44-8.37 (m, 1H), 8.29-8.18 (m, 1H), 7.91-7.69 (m, 2H), 7.33-7.25 (m, 2H), 7.17-7.08 (m, 2H), 5.40-5.15 (m, 1H), 4.63-4.41 (m, 2H), 4.22-4.13 (m, 1H), 3.95-3.83 (m, 1H), 2.69-2.58 (m, 1H), 2.01-1.90 (m, 1H), 1.85 (s, 4H), 1.47-1.43 (m, 1H), 1.38-1.33 (m, 1H). |
| 235 | δ 8.55 (s, 1H), 8.47-8.41 (m, 2H), 8.37 (s, 1H), 7.98 (d, J = 8.7 Hz, 1H), 7.15 (d, J = 2.0 Hz, 1H), 5.37-5.31 (m, 1H), 4.68 (s, 2H), 3.35-3.28 (m, 1H), 2.88-2.81 (m, 1H), 2.44 (s, 3H), 1.87 (s, 6H). |

The following compounds can generally be made using the methods described above. It is expected that these compounds when made will have activity similar to those that have been made in the examples disclosed herein.

| Structure | Name | Formula/ Exact Mass, amu |
|---|---|---|
| | (5-(3,5-difluorophenyl)-4,5-dihydro-1H-pyrazol-1-yl)(3-((pyrazin-2-yloxy)methyl)bicyclo[1.1.1]pentan-1-yl)methanone | $C_{20}H_{18}F_2N_4O_2$ 384.14 |
| 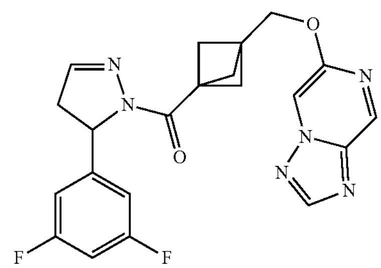 [SMILES: O=C(N1N=CCC1c1cc(F)cc(F)c1)C12CC(COc3cn4ncnc4cn3)(C1)C2] | (3-(([1,2,4]triazolo[1,5-a]pyrazin-6-yloxy)methyl)bicyclo[1.1.1]pentan-1-yl)(5-(3,5-difluorophenyl)-4,5-dihydro-1H-pyrazol-1-yl)methanone | $C_{21}H_{18}F_2N_6O_2$ 424.15 |
| | (5-(3,5-difluorophenyl)-4,5-dihydro-1H-pyrazol-1-yl)(3-((pyrazin-2-yloxy)methyl)bicyclo[1.1.1]pentan-1-yl)methanone | $C_{20}H_{18}F_2N_4O_2$ 384.14 |
| | (5-(3,5-difluorophenyl)-4,5-dihydro-1H-pyrazol-1-yl)(3-((imidazo[1,2-a]pyrazin-6-yloxy)methyl)-bicyclo[1.1.1]pentan-1-yl)methanone | $C_{22}H_{19}F_2N_5O_2$ 423.15 |
| 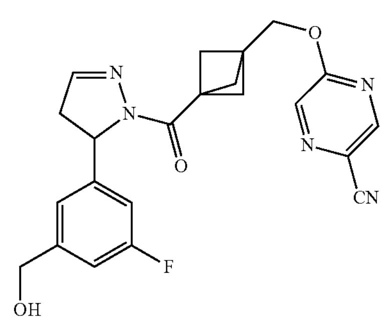 [SMILES: N#Cc1cnc(OCC23CC(C(=O)N4N=CCC4c4cc(F)cc(CO)c4)(C2)C3)cn1] | 5-((3-(5-(3-fluoro-5-(hydroxymethyl)phenyl)-4,5-dihydro-1H-pyrazole-1-carbonyl)-bicyclo[1.1.1]pentan-1-yl)methoxy)-pyrazine-2-carbonitrile | $C_{22}H_{20}FN_5O_3$ 421.16 |

| Structure | Name | Formula/ Exact Mass, amu |
|---|---|---|
| 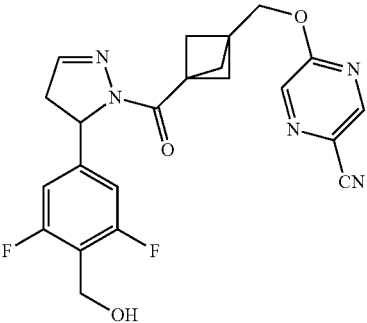 [SMILES: N#Cc1cnc(OCC23CC(C(=O)N4N=CCC4c4cc(F)c(CO)c(F)c4)(C2)C3)cn1] | 5-((3-(5-(3,5-difluoro-4-(hydroxymethyl)phenyl)-4,5-dihydro-1H-pyrazole-1-carbonyl)-bicyclo[1.1.1]pentan-1-yl)-methoxy)pyrazine-2-carbonitrile | $C_{22}H_{19}F_2N_5O_3$ 439.15 |
| 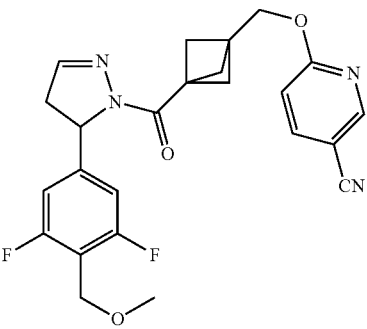 [SMILES: COCc1c(F)cc(C2CC=NN2C(=O)C23CC(COc4ccc(C#N)cn4)(C2)C3)cc1F] | 6-((3-(5-(3,5-difluoro-4-(methoxymethyl)phenyl)-4,5-dihydro-1H-pyrazole-1-carbonyl)-bicyclo[1.1.1]pentan-1-yl)-methoxy)nicotinonitrile | $C_{24}H_{22}F_2N_4O_3$ 452.17 |
| 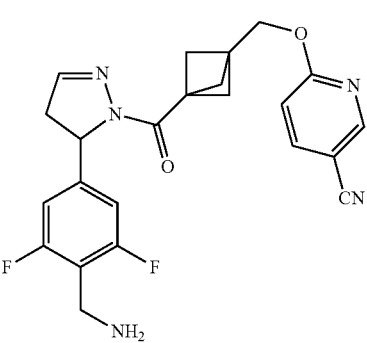 [SMILES: N#Cc1ccc(OCC23CC(C(=O)N4N=CCC4c4cc(F)c(CN)c(F)c4)(C2)C3)nc1] | 6-((3-(5-(4-(aminomethyl)-3,5-difluorophenyl)-4,5-dihydro-1H-pyrazole-1-carbonyl)-bicyclo[1.1.1]pentan-1-yl)-methoxy)nicotinonitrile | $C_{23}H_{21}F_2N_5O_2$ 437.17 |
| 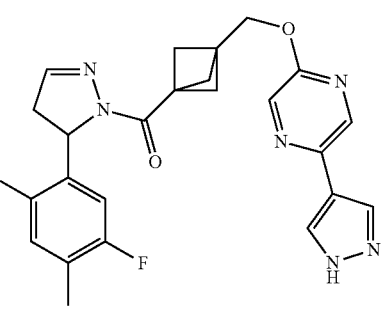 | 3-(((5-(1H-pyrazol-4-yl)pyrazin-2-yl)oxy)methyl)bicyclo[1.1.1]pentan-1-yl)(5-(2,5-difluoro-4-methylphenyl)-4,5-dihydro-1H-pyrazol-1-yl)methanone | $C_{24}H_{22}F_2N_6O_2$ 464.18 |

-continued

| Structure | Name | Formula/ Exact Mass, amu |
|---|---|---|
| 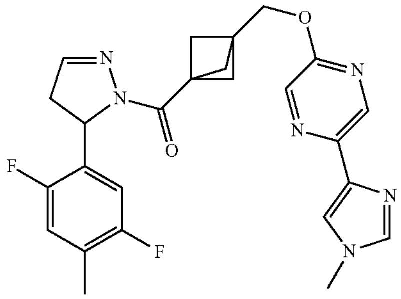 [SMILES: Cc1cc(F)c(C2CC=NN2C(=O)C23CC(COc4cnc(-c5cn(C)cn5)cn4)(C2)C3)cc1F] | (5-(2,5-difluoro-4-methylphenyl)-4,5-dihydro-1H-pyrazol-1-yl)(3-(((5-(1-methyl-1H-imidazol-4-yl)pyrazin-2-yl)oxy)methyl)bicyclo[1.1.1]pentan-1-yl)methanone | $C_{25}H_{24}F_2N_6O_2$ 478.19 |
| 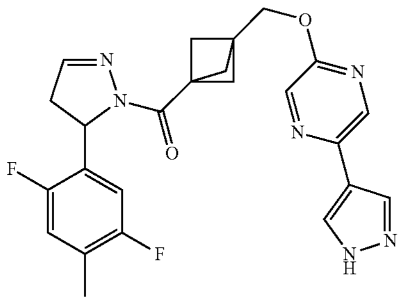 [SMILES: Cc1cc(F)c(C2CC=NN2C(=O)C23CC(COc4cnc(-c5cn[nH]c5)cn4)(C2)C3)cc1F] | (3-(((5-(1H-imidazol-4-yl)pyrazin-2-yl)oxy)methyl)bicyclo[1.1.1]pentan-1-yl)(5-(2,5-difluoro-4-methylphenyl)-4,5-dihydro-1H-pyrazol-1-yl)methanone | $C_{24}H_{22}F_2N_6O_2$ 464.18 |
| 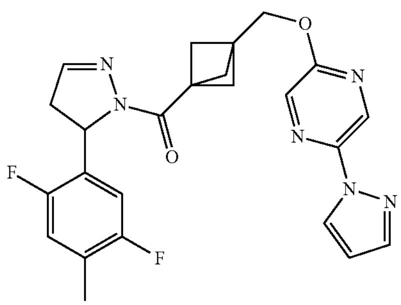 [SMILES: Cc1cc(F)c(C2CC=NN2C(=O)C23CC(COc4cnc(-n5cccn5)cn4)(C2)C3)cc1F] | (3-(((5-(1H-pyrazol-1-yl)pyrazin-2-yl)oxy)methyl)bicyclo[1.1.1]pentan-1-yl)(5-(2,5-difluoro-4-methylphenyl)-4,5-dihydro-1H-pyrazol-1-yl)methanone | $C_{24}H_{22}F_2N_6O_2$ 464.18 |
| 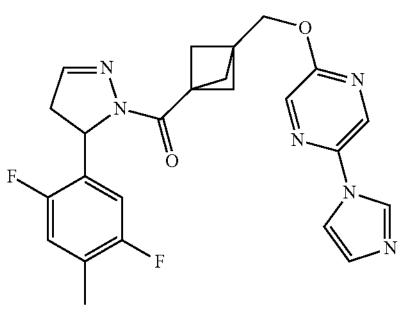 [SMILES: Cc1cc(F)c(C2CC=NN2C(=O)C23CC(COc4cnc(-n5ccnc5)cn4)(C2)C3)cc1F] | (3-(((5-(1H-imidazol-1-yl)pyrazin-2-yl)oxy)methyl)bicyclo[1.1.1]pentan-1-yl)(5-(2,5-difluoro-4-methylphenyl)-4,5-dihydro-1H-pyrazol-1-yl)methanone | $C_{24}H_{22}F_2N_6O_2$ 464.18 |
| 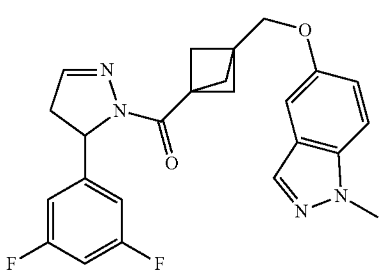 [SMILES: Cn1ncc2cc(OCC34CC(C(=O)N5N=CCC5c5cc(F)cc(F)c5)(C3)C4)ccc21] | (5-(3,5-difluorophenyl)-4,5-dihydro-1H-pyrazol-1-yl)(3-(((1-methyl-1H-indazol-5-yl)oxy)methyl)bicyclo[1.1.1]pentan-1-yl)methanone | $C_{24}H_{22}F_2N_4O_2$ 436.17 |

-continued

| Structure | Name | Formula/ Exact Mass, amu |
|---|---|---|
| 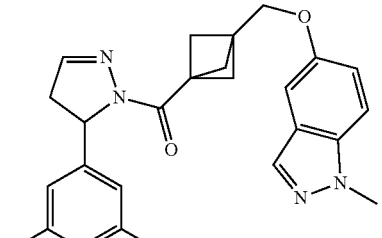 | (5-(3,5-difluorophenyl)-4,5-dihydro-1H-pyrazol-1-yl)(3-(((1-methyl-1H-benzo[d]imidazol-5-yl)oxy)methyl)bicyclo[1.1.1]pentan-1-yl)methanone | $C_{24}H_{22}F_2N_4O_2$ 436.17 |
| 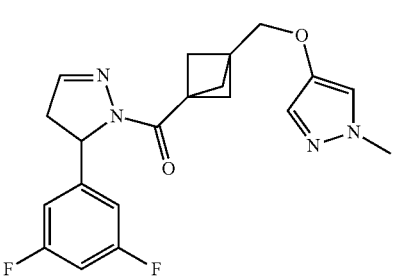 [SMILES: Cn1cc(OCC23CC(C(=O)N4N=CCC4c4cc(F)cc(F)c4)(C2)C3)cn1] | (5-(3,5-difluorophenyl)-4,5-dihydro-1H-pyrazol-1-yl)(3-(((1-methyl-1H-pyrazol-4-yl)oxy)methyl)bicyclo[1.1.1]pentan-1-yl)methanone | $C_{20}H_{20}F_2N_4O$ 386.16 |
| 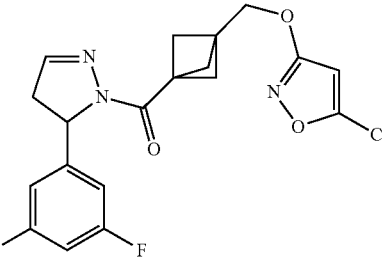 | 3-((3-(5-(3,5-difluorophenyl)-4,5-dihydro-1H-pyrazole-1-carbonyl)bicyclo[1.1.1]pentan-1-yl)methoxy)isoxazole-5-carbonitrile | $C_{20}H_{16}F_2N_4O_3$ 398.12 |
| 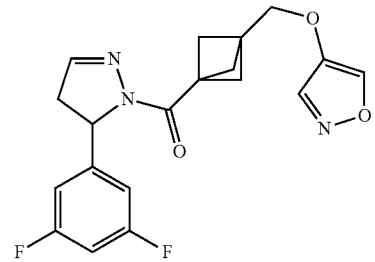 [SMILES: O=C(N1N=CCC1c1cc(F)cc(F)c1)C12CC(COc3cnoc3)(C1)C2] | (5-(3,5-difluorophenyl)-4,5-dihydro-1H-pyrazol-1-yl)(3-((isoxazol-4-yloxy)methyl)bicyclo[1.1.1]pentan-1-yl)methanone | $C_{19}H_{17}F_2N_3O_3$ 373.12 |
| 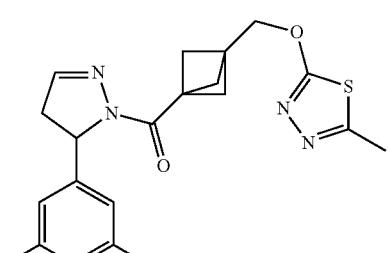 | (5-(3,5-difluorophenyl)-4,5-dihydro-1H-pyrazol-1-yl)(3-(((5-methyl-1,3,4-thiadiazol-2-yl)oxy)methyl)bicyclo[1.1.1]pentan-1-yl)methanone | $C_{19}H_{18}F_2N_4O_2S$ 404.11 |

-continued

| Structure | Name | Formula/Exact Mass, amu |
|---|---|---|
| 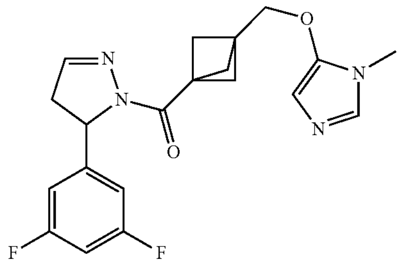 [SMILES: Cn1cncc1OCC12CC(C(=O)N3N=CCC3c3cc(F)cc(F)c3)(C1)C2] | (5-(3,5-difluorophenyl)-4,5-dihydro-1H-pyrazol-1-yl)(3-(((1-methyl-1H-imidazol-5-yl)oxy)methyl)bicyclo[1.1.1]pentan-1-yl)methanone | $C_{20}H_{20}F_2N_4O_2$<br>386.16 |
| 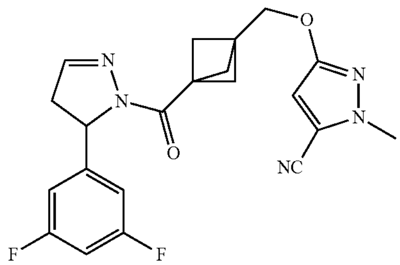 [SMILES: Cn1nc(OCC23CC(C(=O)N4N=CCC4c4cc(F)cc(F)c4)(C2)C3)cc1C#N] | 3-((3-(5-(3,5-difluorophenyl)-4,5-dihydro-1H-pyrazole-1-carbonyl)bicyclo[1.1.1]pentan-1-yl)methoxy)-1-methyl-1H-pyrazole-5-carbonitrile | $C_{21}H_{19}F_2N_5O_2$<br>411.15 |

The activity of the compounds of Examples 1-343 as RIPK1 inhibitors is illustrated in the following assays.

Biological Activity Assays

Compounds described herein have been shown to bind RIPK1 in vitro, and to inhibit phosphorylation of a downstream molecular target in a cellular assay.

ADP-Glo Kinase Assay

In order to measure RIPK1 activity the ADP-Glo kinase assay (Promega, Catalog #V7002) was used to measure the conversion of ATP to ADP. This enzymatic assay was performed in a 384-well white, Optiplate (Perkin Elmer, Catalog #6007299) with assay buffer consisting of 50 mM HEPES pH 7.5 (Gibco, Catalog #15630-080), 50 mM NaCl (Teknova, Catalog #50252), 30 mM $MgCl_2$ (Ambion, Catalog #AM9530G), 1 mM DTT (Santa Cruz Biotechnology, Catalog #sc-29089), 0.05% BSA (Sigma, Catalog #A3059-50G) and 0.02% CHAPS (Sigma, Catalog #C5070-5G). Stock solutions of the test compounds were prepared in 100% DMSO (Sigma, Catalog #D2650) and serially diluted 1:3 using 100% DMSO. Compounds were additionally diluted 1:40 in assay buffer, and 2 µL/well were transferred to the assay plate. 4 µL/well (final concentration of 5 nM) of RIPK1 protein (SignalChem, Catalog #R07-11G-05) diluted in assay buffer and added to the assay plate followed by a 10 minute preincutation at rt. 4 µL/well of ATP (Promega, Catalog #V7002) (final concentration of 50 µM) diluted in assay buffer were then added to the assay plate followed by a 6 h reaction time. Final concentrations of RIPK1 and ATP refer to a 10 µL volume. Luminescence was measured using a BioTek Synergy™ NEO plate reader. $IC_{50}$ values were calculated using a four-parameter logistic curve fit using Genedata Screener software. Results are shown below in Table 2, where the average value across multiple runs is given.

TABLE 7

RIPK1 activity

| Ex. No. | RIPK1 Enzyme Avg IC50 (nM) |
|---|---|
| 1 | 40 |
| 2 | 21190 |
| 3 | 51 |
| 4 | 19 |
| 5 | 17 |
| 6 | 23 |
| 7 | 21 |
| 8 | 28 |
| 9 | 16 |
| 10 | 2912 |
| 11 | 20 |
| 12 | 243 |
| 13 | 1510 |
| 14 | 12 |
| 15 | 22 |
| 16 | 12857 |
| 17 | 570 |
| 18 | 70 |
| 19 | 363 |
| 20 | 1114 |
| 21 | 70 |
| 22 | 11 |
| 23 | 30 |
| 24 | 38845 |
| 25 | (a) |
| 26 | 59 |
| 27 | 14 |
| 28 | 32 |
| 29 | 213 |
| 30 | 124 |
| 31 | 55 |
| 32 | 196 |
| 33 | 466 |
| 34 | 1073 |
| 35 | 4630 |
| 36 | 19254 |
| 37 | (a) |
| 38 | (a) |
| 39 | (a) |
| 40 | 4451 |

TABLE 7-continued

RIPK1 activity

| Ex. No. | RIPK1 Enzyme Avg IC50 (nM) |
|---|---|
| 41 | 31 |
| 42 | 31 |
| 43 | 1702 |
| 44 | 38 |
| 45 | 8593 |
| 46 | 157 |
| 47 | 93 |
| 48 | 186 |
| 49 | 22 |
| 50 | 16 |
| 51 | 22 |
| 52 | 24 |
| 53 | 24 |
| 54 | 409 |
| 55 | 896 |
| 56 | 19 |
| 57 | 32 |
| 58 | 34 |
| 59 | 43 |
| 60 | 44 |
| 61 | 45 |
| 62 | 46 |
| 63 | 104 |
| 64 | 10 |
| 65 | 11 |
| 66 | 16 |
| 67 | 19 |
| 68 | 20 |
| 69 | 22 |
| 70 | 34 |
| 71 | 39 |
| 72 | 78 |
| 73 | 111 |
| 74 | 124 |
| 75 | 323 |
| 76 | 5387 |
| 77 | 7114 |
| 78 | 12951 |
| 79 | 425 |
| 80 | 24732 |
| 81 | 11 |
| 82 | 11 |
| 83 | 16 |
| 84 | 22 |
| 85 | 18 |
| 86 | 19 |
| 87 | 21 |
| 88 | 24 |
| 89 | 25 |
| 90 | (a) |
| 91 | (a) |
| 92 | 56 |
| 93 | 79 |
| 94 | 109 |
| 95 | 151 |
| 96 | 162 |
| 97 | 219 |
| 98 | 240 |
| 99 | 280 |
| 100 | 284 |
| 101 | 486 |
| 102 | 1996 |
| 103 | 2661 |
| 104 | 3046 |
| 105 | (a) |
| 106 | 371 |
| 107 | 183 |
| 108 | 206 |
| 109 | 42 |
| 110 | 134 |
| 111 | 43 |
| 112 | 73 |
| 113 | 4232 |
| 114 | >16667, 8899 |
| 115 | (a) |
| 116 | (a) |
| 117 | (a) |
| 118 | (a) |
| 119 | (a) |
| 120 | (a) |
| 121 | (a) |
| 122 | 998 |
| 123 | 501 |
| 124 | 156 |
| 125 | 2798 |
| 126 | 49 |
| 127 | 158 |
| 128 | 17 |
| 129 | 515 |
| 130 | 238 |
| 131 | 375 |
| 132 | 139 |
| 133 | 20 |
| 134 | 24 |
| 135 | 18 |
| 136 | 20 |
| 137 | 379 |
| 138 | 113 |
| 139 | 95 |
| 140 | 49 |
| 141 | 34 |
| 142 | 79 |
| 143 | 122 |
| 144 | 145 |
| 145 | 169 |
| 146 | 324 |
| 147 | 30 |
| 148 | 80 |
| 149 | 3933 |
| 150 | 5455 |
| 151 | 242 |
| 152 | 98 |
| 153 | 204 |
| 154 | 4860 |
| 155 | 814 |
| 156 | 38 |
| 157 | 42 |
| 158 | 24 |
| 159 | 1123 |
| 160 | 82 |
| 161 | 50 |
| 162 | 46 |
| 163 | 114 |
| 164 | 57 |
| 165 | 27 |
| 166 | 308 |
| 167 | 306 |
| 168 | 865 |
| 169 | 343 |
| 170 | 4672 |
| 171 | 670 |
| 172 | 4347 |
| 173 | 9.1 |
| 174 | 48 |
| 175 | 16 |
| 176 | 19 |
| 177 | 54 |
| 178 | 103 |
| 179 | 9.6 |
| 180 | 392 |
| 184 | 136 |
| 185 | 32 |
| 186 | 113 |
| 187 | 447 |
| 188 | 454 |
| 189 | 27 |
| 190 | 30 |
| 191 | 74 |

TABLE 7-continued

RIPK1 activity

| Ex. No. | RIPK1 Enzyme Avg IC50 (nM) |
|---|---|
| 192 | 80 |
| 193 | 292 |
| 194 | 32 |
| 199 | 8.3 |
| 202 | 32 |
| 208 | 2268 |
| 210 | 9.4 |
| 212 | 11 |
| 213 | 33 |
| 218 | 25 |
| 219 | 47 |
| 222 | 220 |
| 226 | 35 |
| 228 | 433 |
| 230 | 93 |
| 233 | 223 |
| 234 | 211 |
| 248 | 23 |
| 252 | 43 |
| 253 | 51 |
| 255 | 49 |
| 258 | 1013 |
| 260 | 528 |
| 261 | 4522 |
| 320 | 19 |
| 321 | 18 |
| 325 | 21 |
| 326 | 37 |
| 327 | 75 |
| 328 | 116 |
| 330 | 11 |
| 331 | 13 |
| 332 | 19 |
| 333 | 16 |
| 334 | 18 |
| 335 | 18 |
| 336 | 31 |
| 337 | 24 |
| 338 | 26 |

(a) >50,000

Human U937 Cellular Necroptosis Assay

The human monocytic cell line U937 (CRL-1593.2) was purchased from ATCC. The cells were routinely maintained in RPMI-1640 Medium (Gibco, Catalog #11875-093) supplemented with 10% heat inactivated fetal bovine serum (Gibco, Catalog #16140-071), 100 units/mL penicillin and 100 μg/mL streptomycin (Gibco, Catalog #15140-122), in a humidified incubator (37° C., 5% $CO_2$). For the assay, cells were resuspended in RPMI-1640 phenol red free Media (Gibco, Catalog #11835-030) supplemented with 10% fetal bovine serum (Sigma, Catalog #F2442), 100 units/mL penicillin and 100 ug/mL streptomycin. Cells were stimulated with 25 ng/mL human TNFalpha (Cell Sciences, Catalog #CSI15659B) and 25 μM z-VAD-FMK (R&D Systems, Catalog #FMK001) followed by seeding 5000 cells per well in a volume of 40 μL to a white, CulturPlate-384 (Perkin Elmer, Catalog #6007680). Stock solutions of the test compounds were prepared in 100% DMSO (Sigma, Catalog #D2650) and serially diluted 1:3 using 100% DMSO. Compounds were additionally diluted 1:40 in assay medium, and 10 μL/well was transferred to the plate. Following the compound addition the plate was incubated at 37° C. and 5% $CO_2$ for 22 h. After 22 h, viability was assessed with the addition of 20 μL of Cell Titer-Glo 2.0 (Promega, Catalog #G9243). The tissue culture plate was shaken on an orbital shaker at 300 RPM for 15 minutes at rt in the dark. Luminescence was measured using a PerkinElmer Envision™ plate reader. $IC_{50}$ values were calculated using a four-parameter logistic curve fit using Genedata Screener software. Results are shown below in Table 3, where the average value across multiple runs is given.

TABLE 8 hU937 activity

| Ex. No. | hU937 Avg $IC_{50}$ (nM) |
|---|---|
| 3 | 112 |
| 4 | 9 |
| 5 | 20 |
| 6 | 20 |
| 7 | 18 |
| 8 | 51 |
| 9 | 62 |
| 11 | 18 |
| 12 | 887 |
| 14 | 24 |
| 16 | >10000 |
| 18 | 284 |
| 21 | 114 |
| 22 | 5 |
| 23 | 158 |
| 26 | 472 |
| 27 | 167 |
| 28 | 193 |
| 29 | 647 |
| 30 | 708 |
| 31 | 462 |
| 41 | 272 |
| 42 | 51 |
| 43 | 4208 |
| 47 | 1112 |
| 48 | 1295 |
| 49 | 67 |
| 50 | 36 |
| 51 | 40 |
| 52 | 16 |
| 54 | 2641 |
| 55 | 8926 |
| 56 | 63 |
| 57 | 110 |
| 58 | 160 |
| 59 | 226 |
| 60 | 178 |
| 61 | 211 |
| 62 | 133 |
| 63 | 238 |
| 64 | 7 |
| 65 | 44 |
| 67 | 54 |
| 68 | 34 |
| 69 | 44 |
| 70 | 26 |
| 71 | 134 |
| 72 | 98 |
| 73 | 527 |
| 74 | 514 |
| 81 | 12 |
| 82 | 31 |
| 83 | 67 |
| 84 | 3 |
| 85 | 24 |
| 87 | 33 |
| 88 | 94 |
| 89 | 137 |
| 92 | 518 |
| 93 | 398 |
| 94 | 994 |
| 101 | 1343 |
| 106 | 1467 |
| 109 | 470 |
| 110 | 734 |
| 111 | 249 |
| 112 | 285 |
| 124 | 751 |

TABLE 8-continued hU937 activity

| Ex. No. | hU937 Avg IC$_{50}$ (nM) |
|---|---|
| 126 | 440 |
| 127 | 1256 |
| 128 | 48 |
| 129 | 3858 |
| 130 | 1240 |
| 131 | 1925 |
| 132 | 826 |
| 133 | 10 |
| 134 | 46 |
| 135 | 53 |
| 136 | 58 |
| 137 | 2687 |
| 138 | 417 |
| 139 | 493 |
| 140 | 53 |
| 141 | 58 |
| 142 | 750 |
| 143 | 495 |
| 144 | 1184 |
| 145 | 701 |
| 146 | 1916 |
| 147 | 142 |
| 148 | 912 |
| 151 | 1189 |
| 152 | 363 |
| 153 | 553 |
| 155 | 5294 |
| 156 | 159 |
| 157 | 170 |
| 158 | 62 |
| 159 | 3611 |
| 160 | 404 |
| 161 | 157 |
| 162 | 210 |
| 163 | 730 |
| 164 | 214 |
| 165 | 193 |
| 166 | 1971 |
| 167 | 1878 |
| 168 | 6188 |
| 169 | 3313 |
| 170 | 9890 |
| 171 | 3699 |
| 172 | >10000 |
| 173 | 53 |
| 174 | 63 |
| 175 | 47 |
| 176 | 87 |
| 177 | 536 |
| 178 | 228 |
| 184 | 1243 |
| 185 | 77 |
| 186 | 682 |
| 192 | 197 |
| 193 | 1392 |
| 194 | 155 |
| 195 | 1.5 |
| 196 | 631 |
| 197 | 0.77 |
| 198 | 7.4 |
| 199 | 9.3 |
| 200 | 8558 |
| 201 | 7.1 |
| 202 | 18 |
| 203 | 5.5 |
| 204 | 22 |
| 205 | 436 |
| 206 | 109 |
| 207 | 633 |
| 208 | 4300 |
| 209 | 362 |
| 210 | 10 |
| 211 | 16 |
| 212 | 19 |
| 213 | 63 |

TABLE 8-continued hU937 activity

| Ex. No. | hU937 Avg IC$_{50}$ (nM) |
|---|---|
| 214 | 71 |
| 215 | 80 |
| 216 | 92 |
| 217 | 99 |
| 218 | 113 |
| 219 | 292 |
| 220 | 312. |
| 221 | 992 |
| 222 | 1100 |
| 223 | 9745 |
| 224 | 51 |
| 225 | 92 |
| 226 | 51 |
| 227 | 133 |
| 228 | 2405 |
| 229 | 5058 |
| 230 | 407 |
| 231 | 3040 |
| 232 | 8108 |
| 233 | 1194 |
| 234 | 1969 |
| 235 | 339 |
| 236 | 3.8 |
| 237 | 7.8 |
| 238 | 8.4 |
| 239 | 10 |
| 240 | 13 |
| 241 | 18 |
| 242 | 20 |
| 243 | 31 |
| 244 | 37 |
| 245 | 43 |
| 246 | 73 |
| 247 | 81 |
| 248 | 186 |
| 249 | 299 |
| 250 | 267 |
| 251 | 397 |
| 252 | 436 |
| 253 | 479 |
| 254 | 503 |
| 255 | 550 |
| 256 | 895 |
| 257 | 2075 |
| 258 | 3825 |
| 259 | 5452 |
| 260 | 5605 |
| 261 | 9471 |
| 262 | 4672 |
| 263 | 9497 |
| 264 | 12 |
| 265 | 8.3 |
| 266 | 1800 |
| 267 | 3.8 |
| 268 | 3.9 |
| 269 | 5.4 |
| 270 | 16 |
| 271 | 20 |
| 272 | 24 |
| 273 | 30 |
| 274 | 61 |
| 275 | 73 |
| 276 | 76 |
| 277 | 81 |
| 278 | 97 |
| 279 | 104 |
| 280 | 106 |
| 281 | 148 |
| 282 | 153 |
| 283 | 160 |
| 284 | 161 |
| 285 | 164 |
| 286 | 218 |
| 287 | 257 |
| 288 | 276 |

TABLE 8-continued hU937 activity

| Ex. No. | hU937 Avg IC$_{50}$ (nM) |
|---|---|
| 289 | 281 |
| 290 | 445 |
| 291 | 620 |
| 292 | 956 |
| 293 | 1497 |
| 294 | 5613 |
| 295 | 5681 |
| 296 | 5854 |
| 297 | 6059 |
| 298 | 6700 |
| 299 | 7012 |
| 300 | 7419 |
| 301 | 7739 |
| 302 | 9872 |
| 303 | 500 |
| 304 | 6.0 |
| 305 | 6.5 |
| 306 | 6.6 |
| 307 | 8.7 |
| 308 | 11 |
| 309 | 13 |
| 310 | 22 |
| 311 | 40 |
| 312 | 62 |
| 313 | 251 |
| 314 | 475 |
| 315 | 666 |
| 316 | 694 |
| 317 | 8508 |
| 318 | 55 |
| 319 | 21 |
| 320 | 30 |
| 321 | 45 |
| 322 | 60 |
| 323 | 153 |
| 324 | 166 |
| 325 | 193 |
| 326 | 204 |
| 327 | 381 |
| 328 | 409 |
| 329 | 1289 |
| 330 | 21 |
| 331 | 28 |
| 332 | 33 |
| 333 | 36 |
| 334 | 45 |
| 335 | 46 |
| 336 | 55 |
| 337 | 140 |
| 338 | 165 |
| 339 | 453 |
| 340 | 54 |
| 341 | 23 |
| 342 | 380 |
| 344 | 56 |
| 345 | 61 |
| 346 | 16 |

All references, patents or applications, U.S. or foreign, cited in the application are hereby incorporated by reference as if written herein in their entireties. Where any inconsistencies arise, material literally disclosed herein controls.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of structural Formula I:

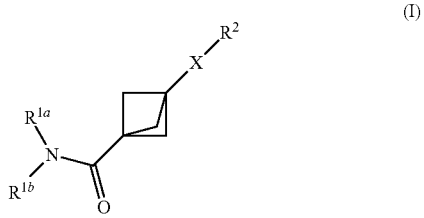

or a salt thereof, wherein:

X is alkylene and is optionally substituted with one or more $R^7$, or X is chosen from carbamoyl, carbonyl, and a bond;

$R^{1a}$ and $R^{1b}$, together with the intervening nitrogen, combine to form a pyrazoline, which is optionally substituted with one $R^3$, and which is optionally substituted with one or more $R^4$;

$R^2$ is chosen from hydrogen, hydroxy, cyano, and halo, or $R^2$ is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl)carbonyl, (cycloalkyl)carbonyl, (heterocycloalkyl)carbonyl, (aryl)carbonyl, (alkyl)amino, (cycloalkyl)amino, (heterocycloalkyl)amino, (aryl)amino, and (heteroaryl)amino, any of which is optionally substituted with one or more $R^5$;

$R^3$ is chosen from aryl, (aryl)oxy, heteroaryl, (heteroaryl)oxy, cycloalkyl, and heterocycloalkyl, any of which is optionally substituted with one or more $R^6$;

each $R^4$ is independently chosen from alkyl, halo, cyano, and hydroxy;

each $R^5$ is independently chosen from halo, cyano, amido, alkyl, alkoxy, cyanoalkyl, hydroxyalkyl, alkoxyalkyl, cycloalkyl, haloalkyl, oxo, P(O)(CH$_3$)$_2$, SO$_2$CH$_3$, aryl optionally substituted with one or more alkyl, and heteroaryl optionally substituted with one or more alkyl;

two $R^5$, together with the intervening atoms, optionally combine to form a cycloalkyl or heterocycloalkyl;

each $R^6$ is independently chosen from halo, alkyl, cycloalkyl, cyano, alkoxy, hydroxy, haloalkyl, hydroxyalkyl, and haloalkoxy; and each $R^7$ is independently chosen from alkyl, cyano, halo, and hydroxy.

2. The compound as recited in claim 1, or a salt thereof, wherein X is alkylene and is optionally substituted with one or more $R^7$.

3. The compound as recited in claim 1, having structural Formula II:

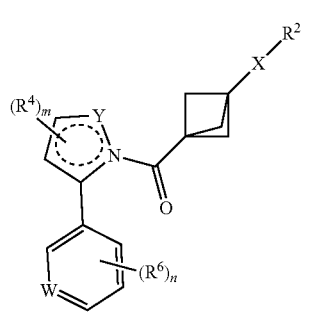

(II)

or a salt thereof, wherein:

m is chosen from 0 and 1;

n is chosen from 0, 1, 2, and 3;

W is chosen from $C(R^{6a})$ and N;

X is alkylene and is optionally substituted with one or more $R^7$, or X is chosen from carbamoyl, carbonyl, and a bond;

Y is chosen from NH and N;

Y and the intervening carbons and nitrogen combine to form a pyrazoline;

$R^2$ is chosen from hydrogen, hydroxy, cyano, and halo, or $R^2$ is chosen from alkyl, amino, cycloalkyl, heterocycloalkyl, aryl, heteroaryl, alkoxy, (cycloalkyl)oxy, (heterocycloalkyl)oxy, (aryl)oxy, (heteroaryl)oxy, (alkyl)carbonyl, (cycloalkyl)carbonyl, (heterocycloalkyl)carbonyl, (aryl)carbonyl, (alkyl)amino, (cycloalkyl)amino, (heterocycloalkyl)amino, (aryl)amino, and (heteroaryl)amino, any of which is optionally substituted with one or more $R^5$;

each $R^4$ is independently chosen from halo, cyano, and hydroxy;

each $R^5$ is independently chosen from halo, cyano, amido, alkyl, alkoxy, hydroxyalkyl, alkoxyalkyl, cycloalkyl, haloalkyl, oxo, $P(O)(CH_3)_2$, $SO_2CH_3$, aryl optionally substituted with one or more alkyl, and heteroaryl optionally substituted with one or more alkyl;

two $R^5$, together with the intervening atoms, optionally combine to form a cycloalkyl or heterocycloalkyl;

each $R^6$ is independently chosen from halo, alkyl, cycloalkyl, cyano, alkoxy, hydroxy, haloalkyl, hydroxyalkyl, and haloalkoxy;

$R^{6a}$ is chosen from H, halo, alkyl, cyano, alkoxy, hydroxy, haloalkyl, and haloalkoxy; and each $R^7$ is independently chosen from alkyl, cyano, halo, and hydroxy.

4. The compound as recited in claim 3, or a salt thereof, wherein Y is N and m is 0.

5. The compound as recited in claim 1, having structural Formula (VII):

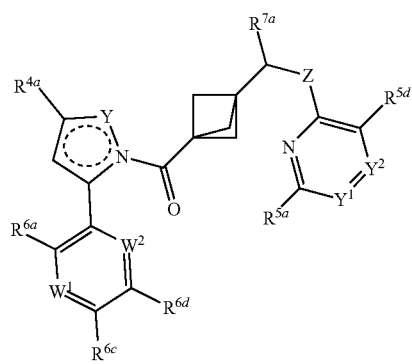

(VII)

or a salt thereof, wherein:

$W^1$ is chosen from $C(R^{6b})$ and N;

$W^2$ is chosen from $C(R^{6e})$ and N;

Y is chosen from NH and N;

Y and the intervening carbons and nitrogen combine to form a pyrazoline;

$Y^1$ is chosen from $C(R^{5b})$ and N;

$Y^2$ is chosen from $C(R^{5c})$ and N;

Z is chosen from O, NH, and $N(CH_3)$;

$R^{4a}$ is chosen from H, halo, cyano, and hydroxy;

$R^{5a}$, $R^{5b}$, $R^{5c}$, and $R^{5d}$ are independently chosen from H, halo, cyano, amido, alkyl, alkoxy, cyanoalkyl, hydroxyalkyl, alkoxyalkyl, cycloalkyl, haloalkyl, $P(O)(CH_3)_2$, $SO_2CH_3$, aryl optionally substituted with one or more alkyl, and heteroaryl optionally substituted with alkyl;

$R^{6a}$, $R^{6b}$, $R^{6c}$, $R^{6d}$, and $R^{6e}$ are independently chosen from H, halo, alkyl, cycloalkyl, cyano, alkoxy, hydroxy, haloalkyl, hydroxyalkyl, and haloalkoxy; and $R^{7a}$ is chosen from H, alkyl, cyano, halo, and hydroxy.

6. The compound as recited in claim 5, or a salt thereof, wherein $R^{5a}$, $R^{5b}$, $R^{5c}$, and $R^{5d}$ are independently chosen from H, halo, cyano, $CONH_2$, $C_{1-6}$alkyl, $C_{1-6}$alkoxy, cyano$C_{1-6}$alkyl, hydroxy$C_{1-6}$alkyl, $C_{1-6}$alkoxy$C_{1-6}$alkyl, $C_{3-7}$cycloalkyl, halo$C_{1-6}$alkyl, $P(O)(CH_3)_2$, $SO_2CH_3$, and 5- to 7-membered heteroaryl optionally substituted with methyl.

7. The compound as recited in claim 1, chosen from:

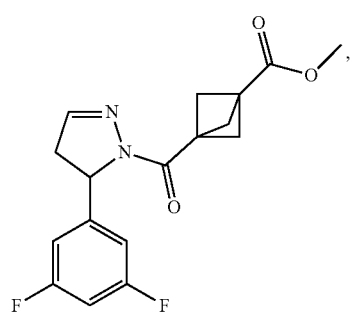

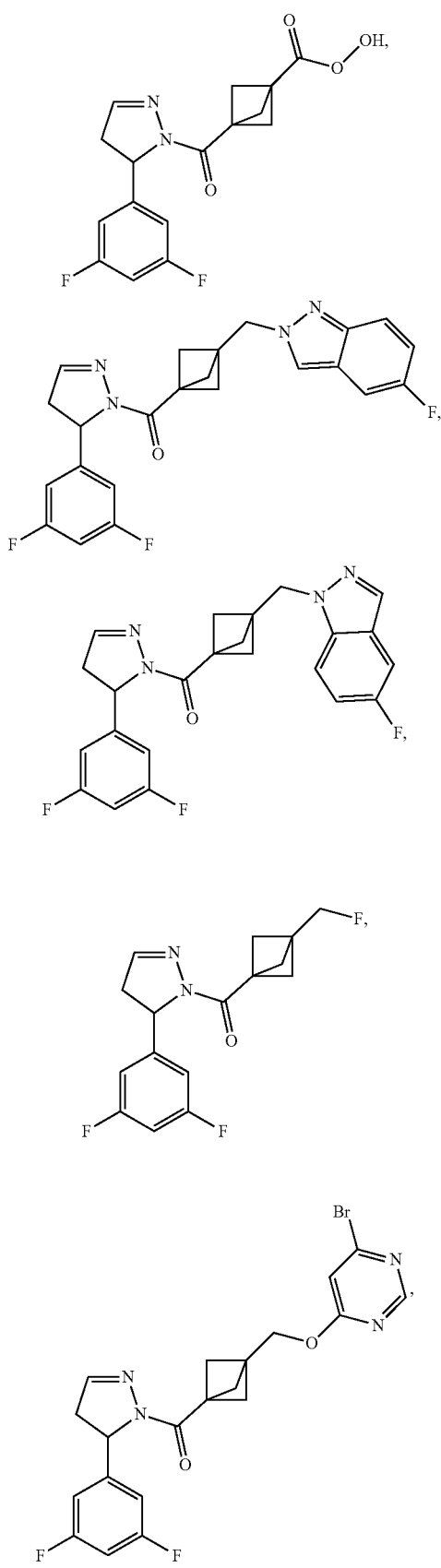

371
-continued
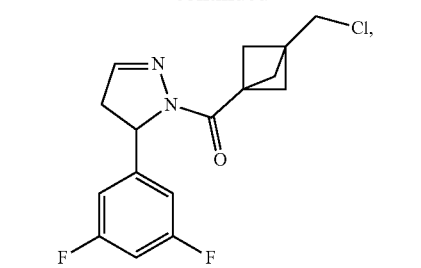
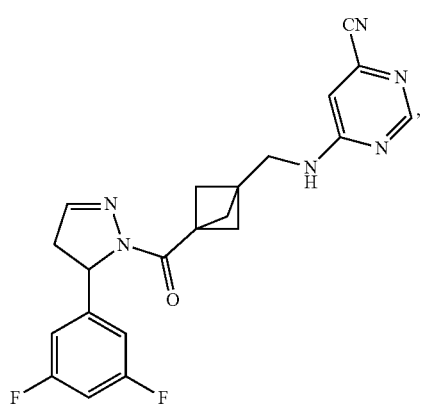
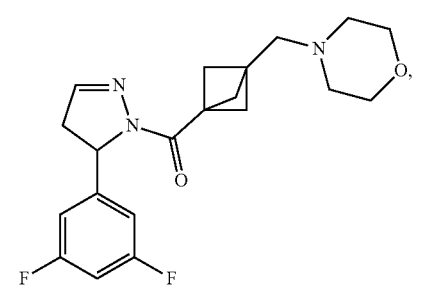
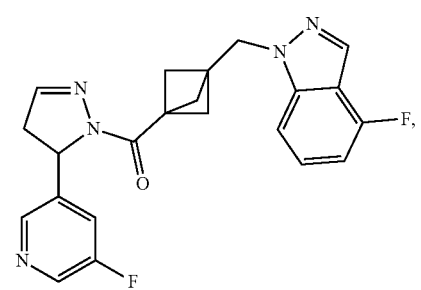
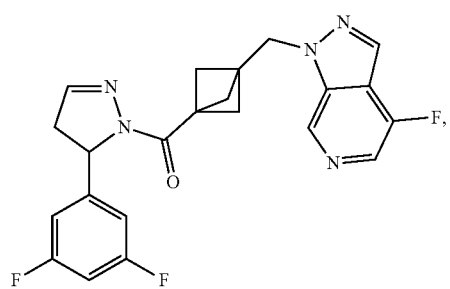
372
-continued
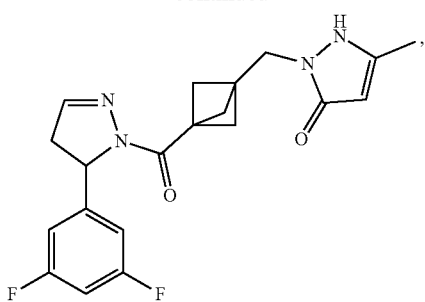
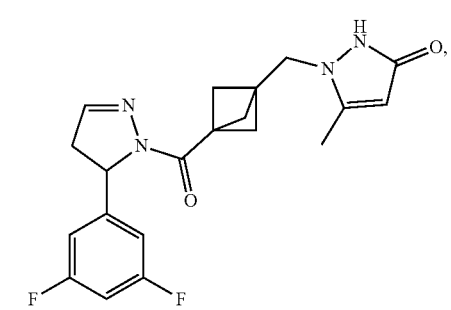
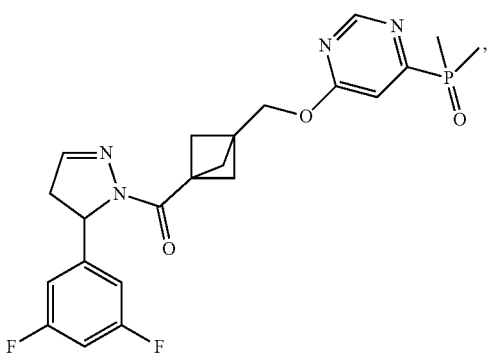
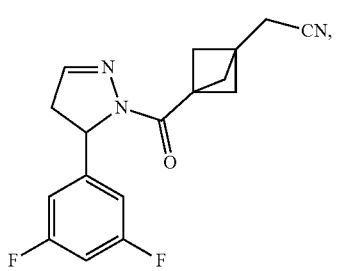
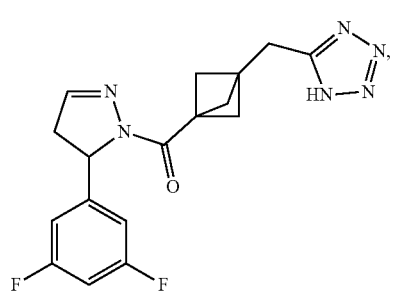

373
-continued
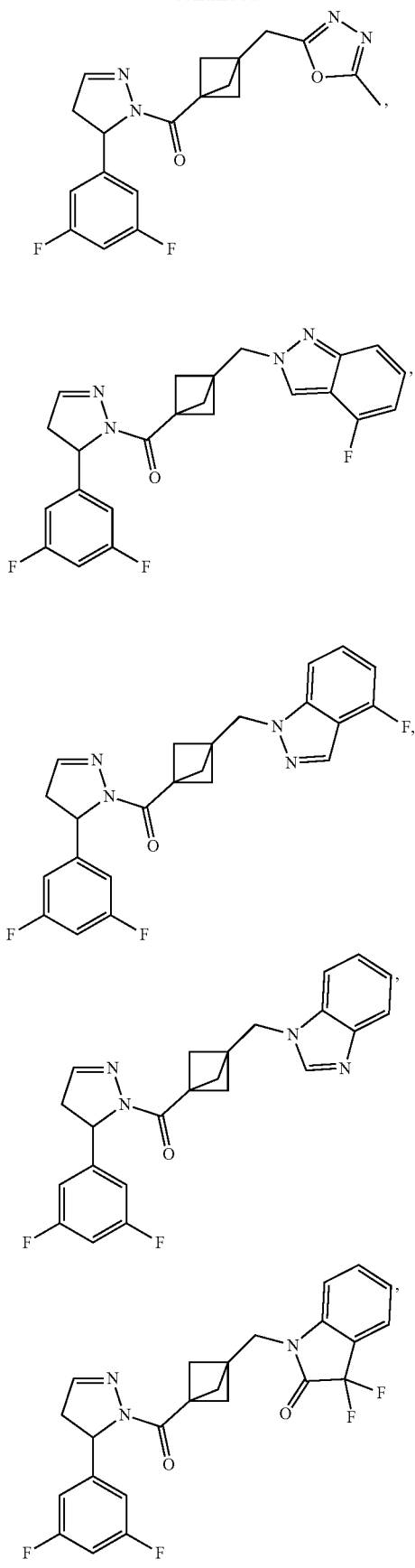
374
-continued
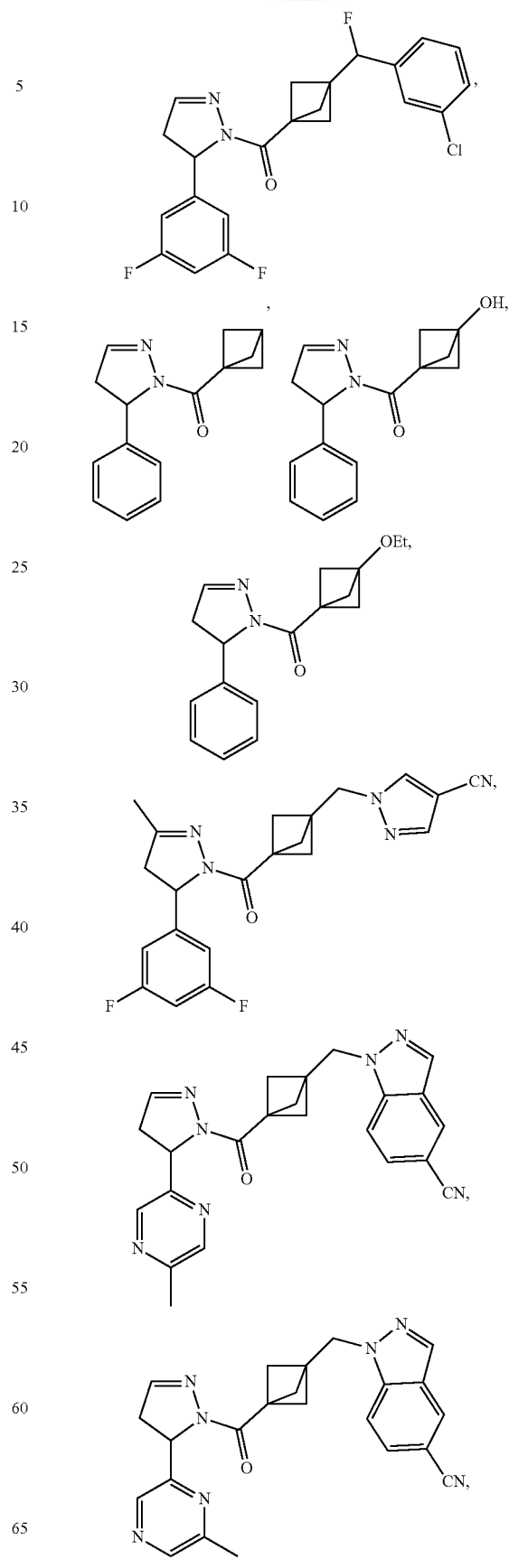

375
-continued
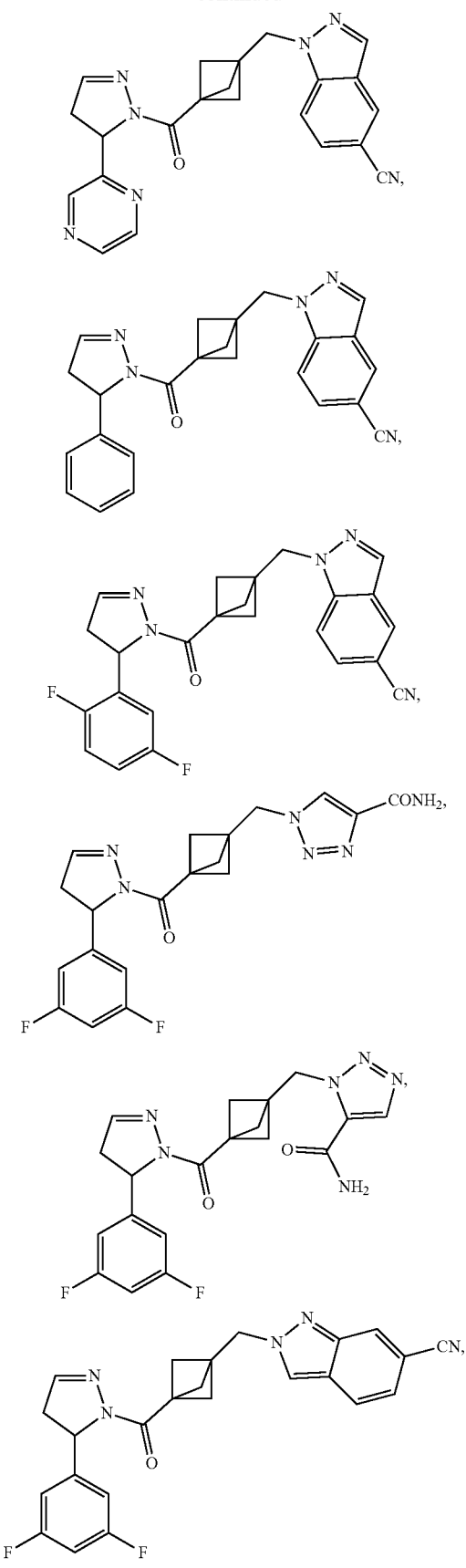
376
-continued
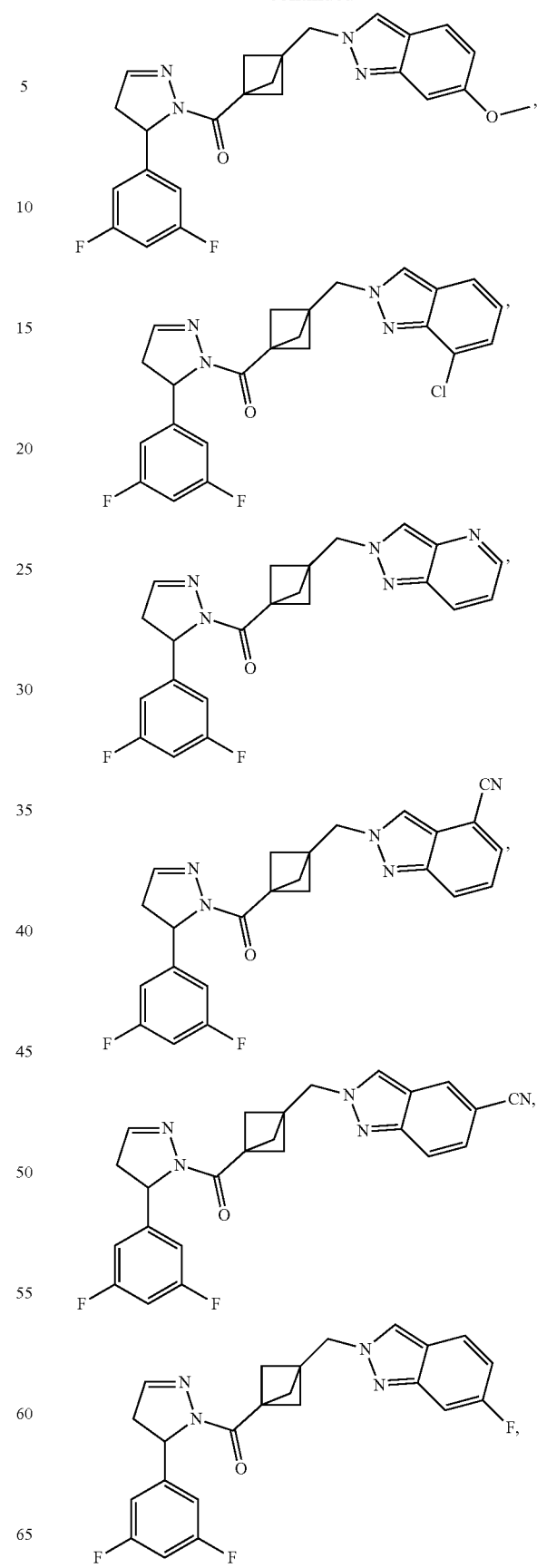

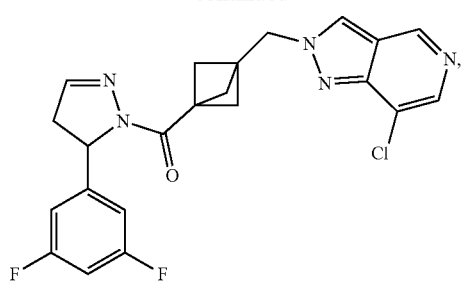
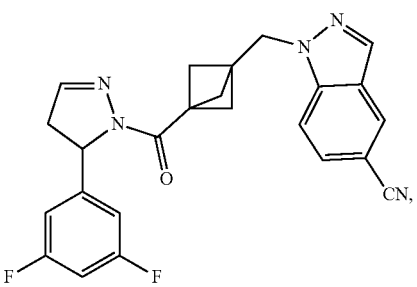
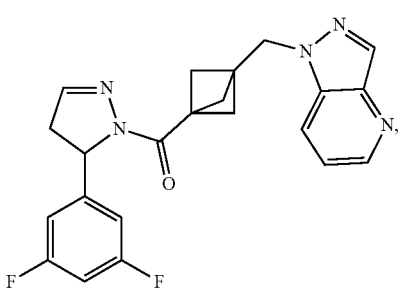
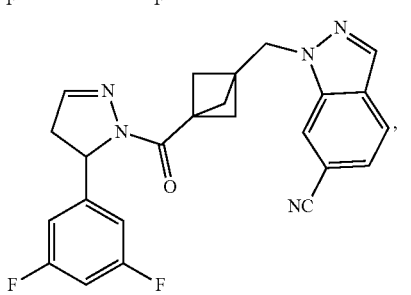
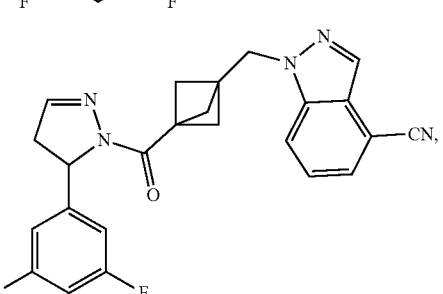
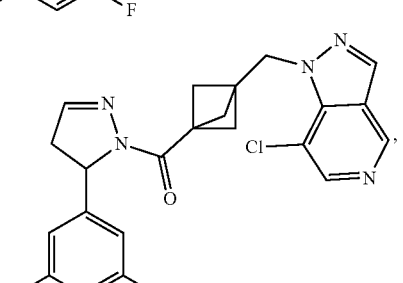
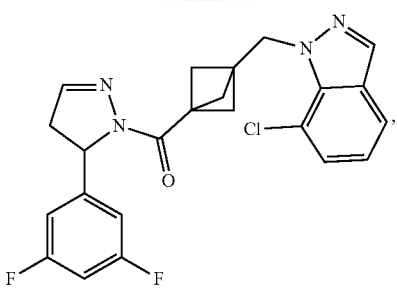
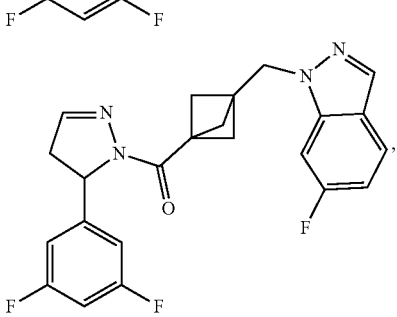
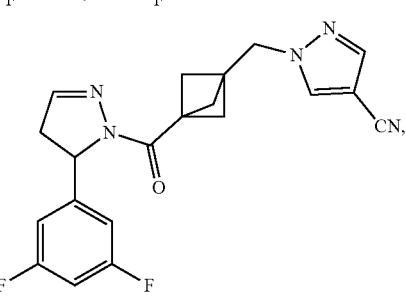
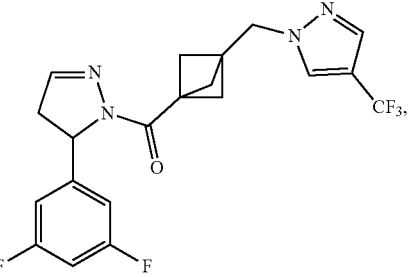
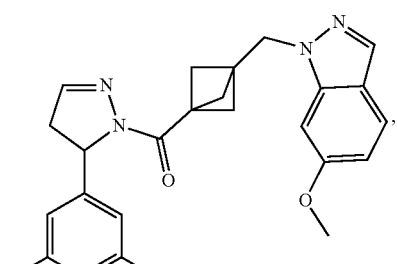
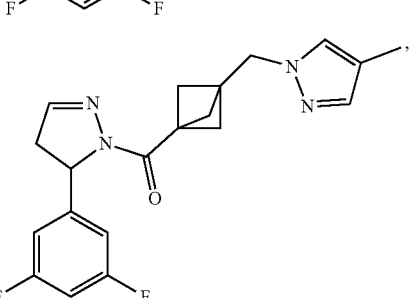

379
-continued
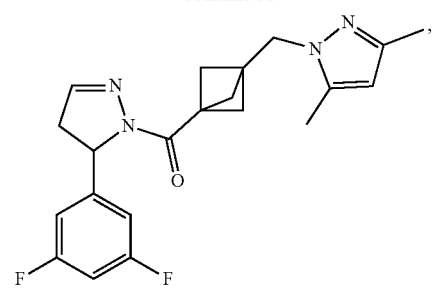
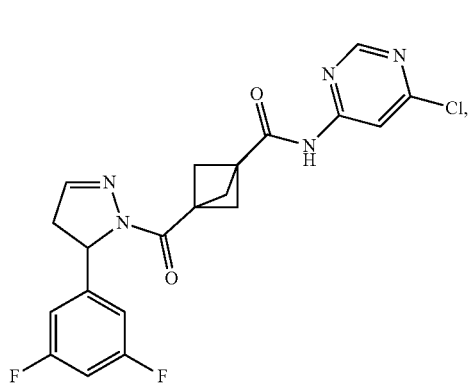
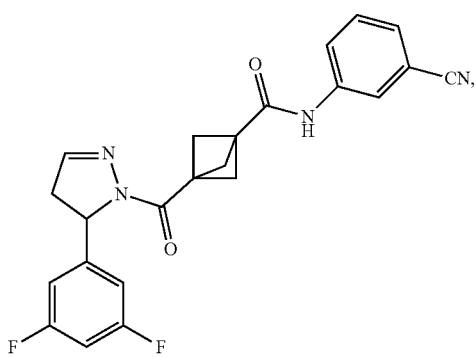
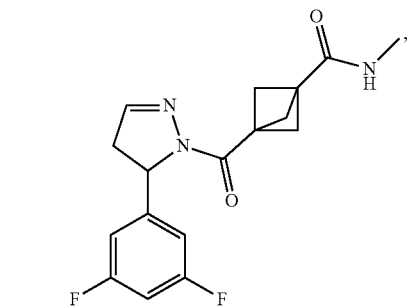
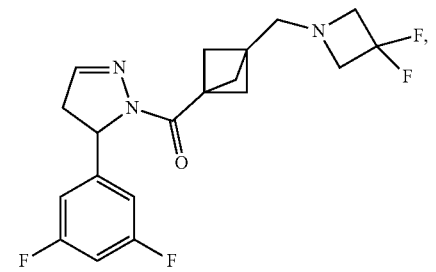
380
-continued
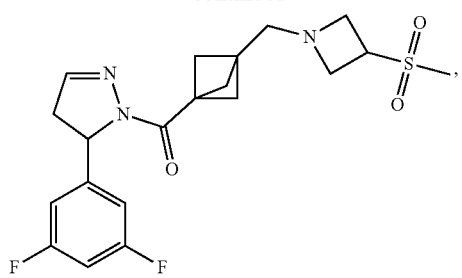
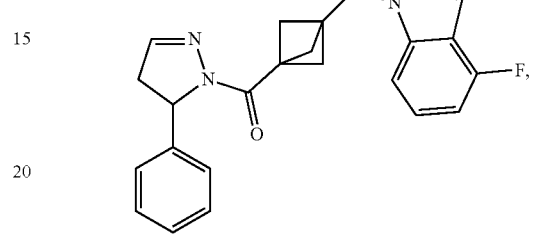
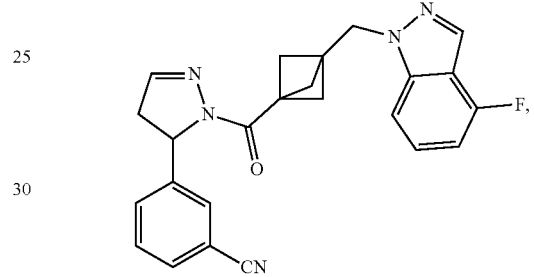
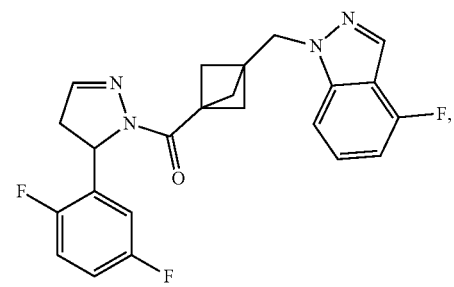
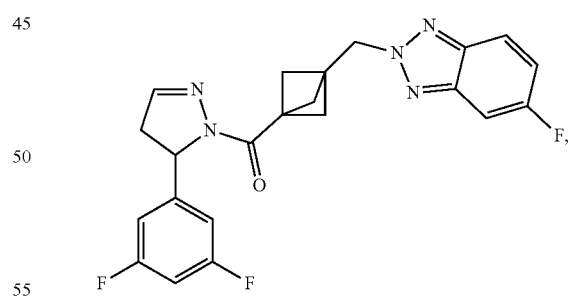
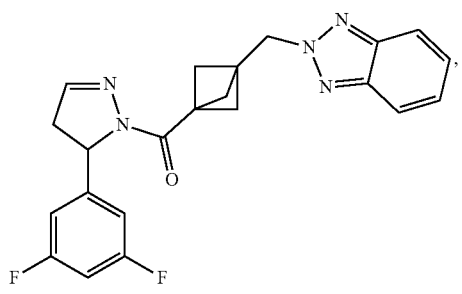

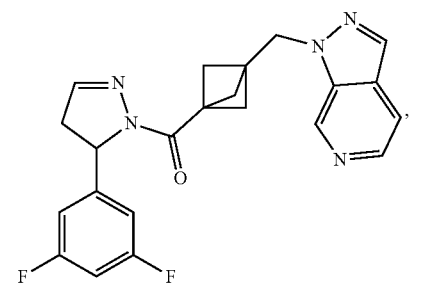
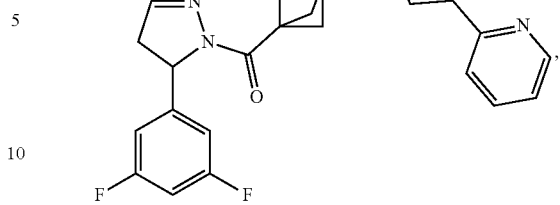
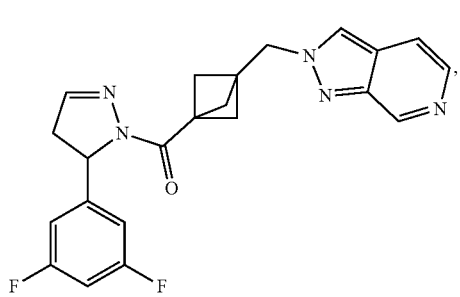
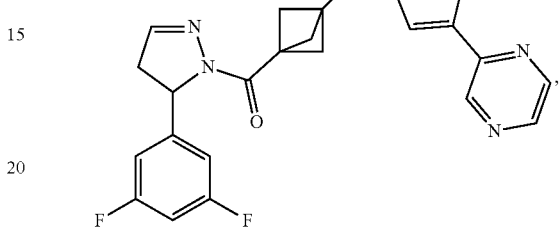
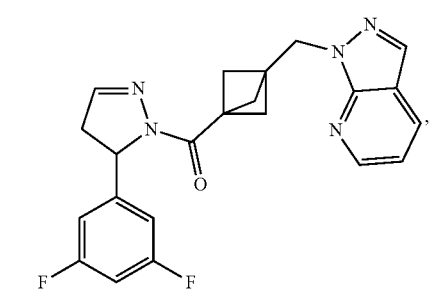
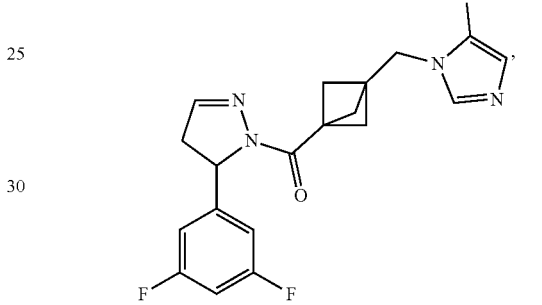
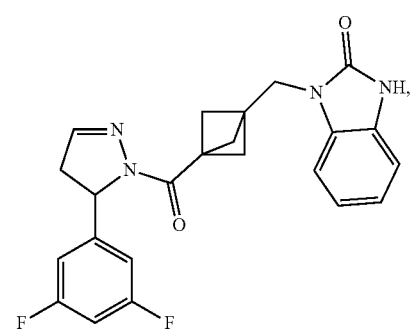
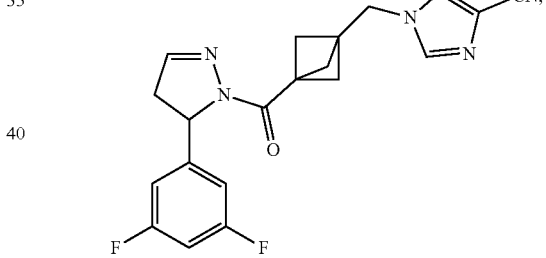
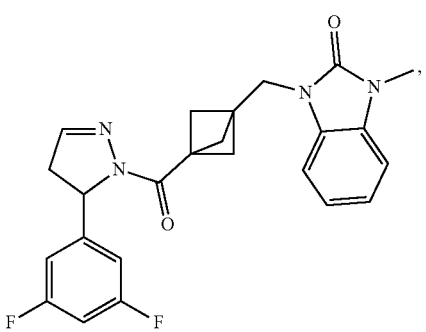
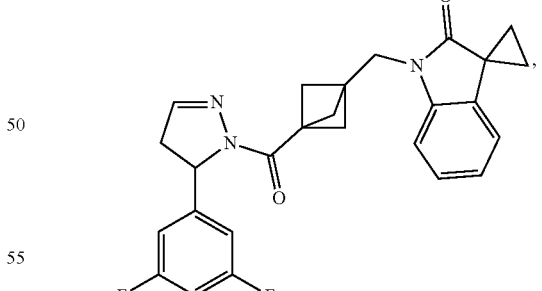
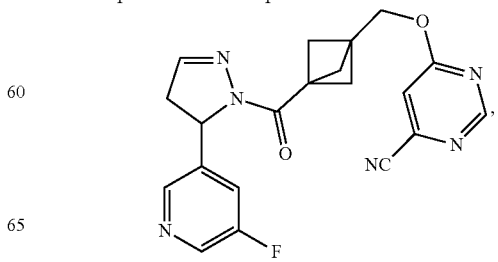

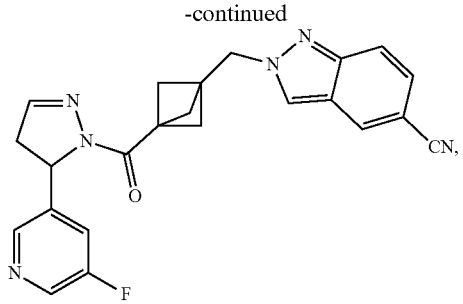
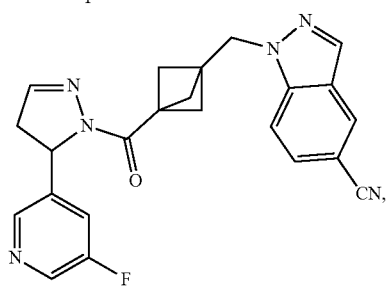
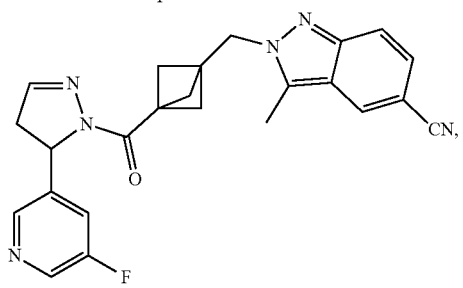
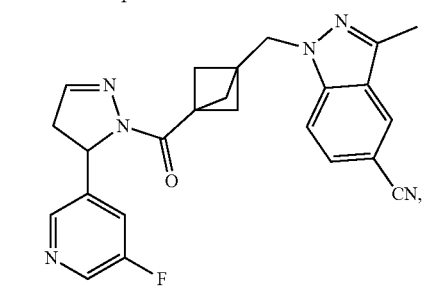
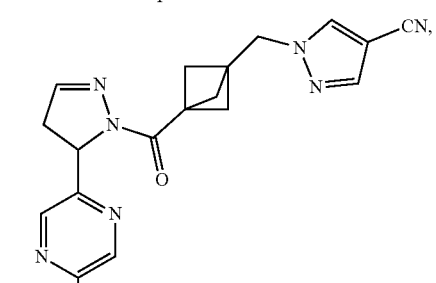
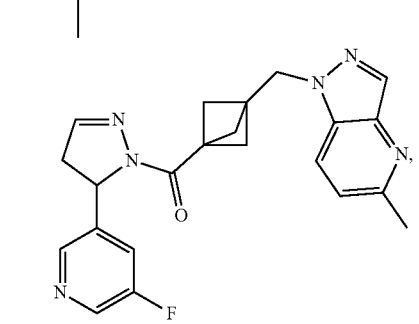
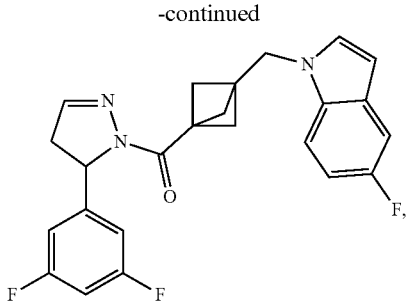
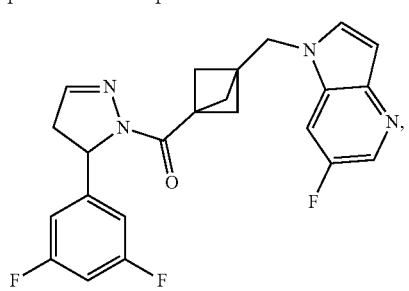
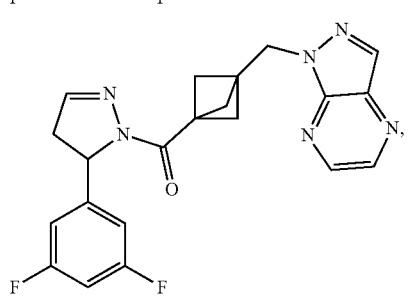
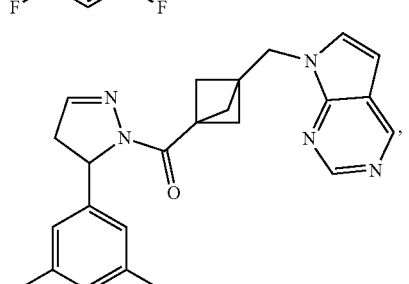
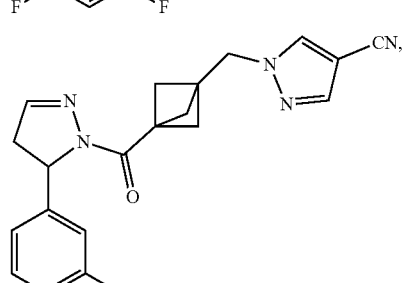
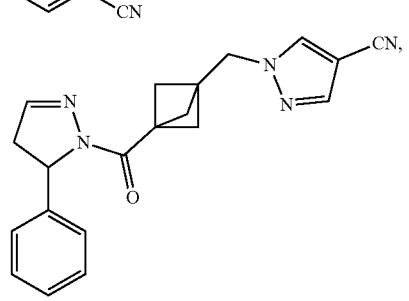

385
-continued
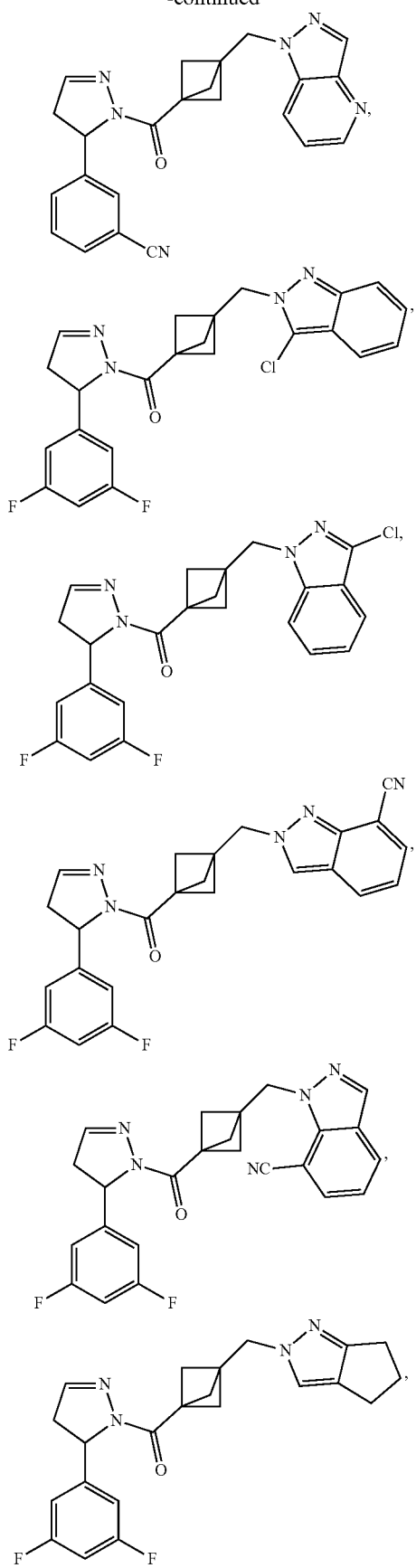
386
-continued
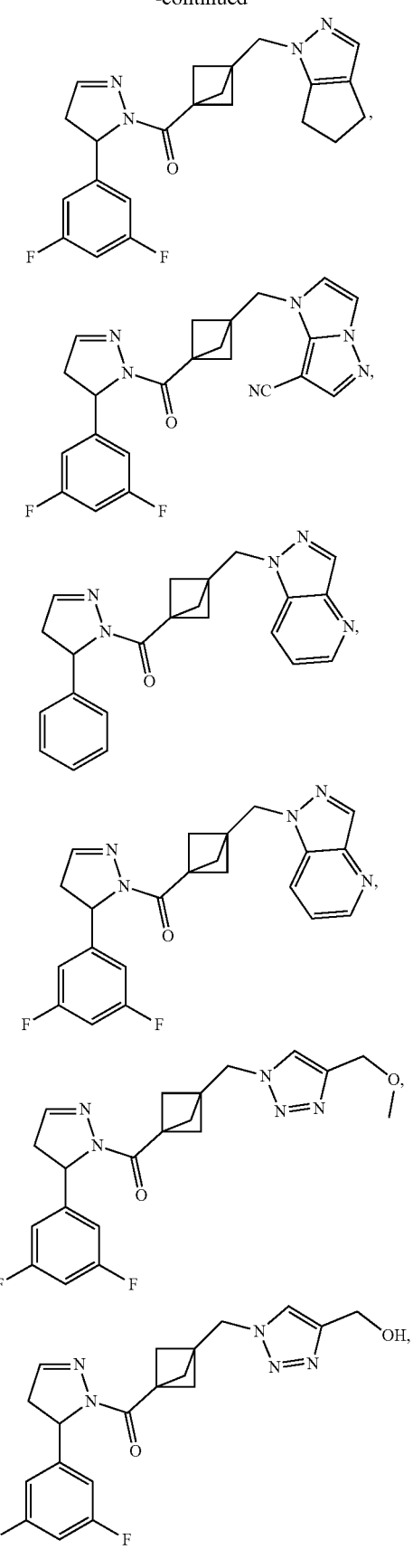

387
-continued
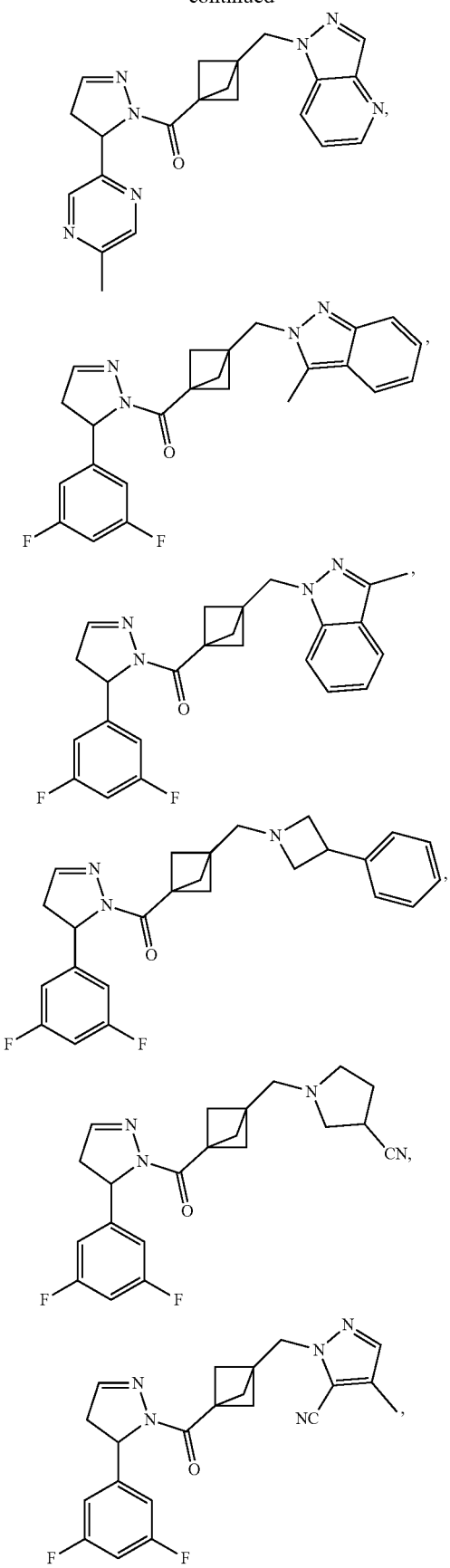
388
-continued
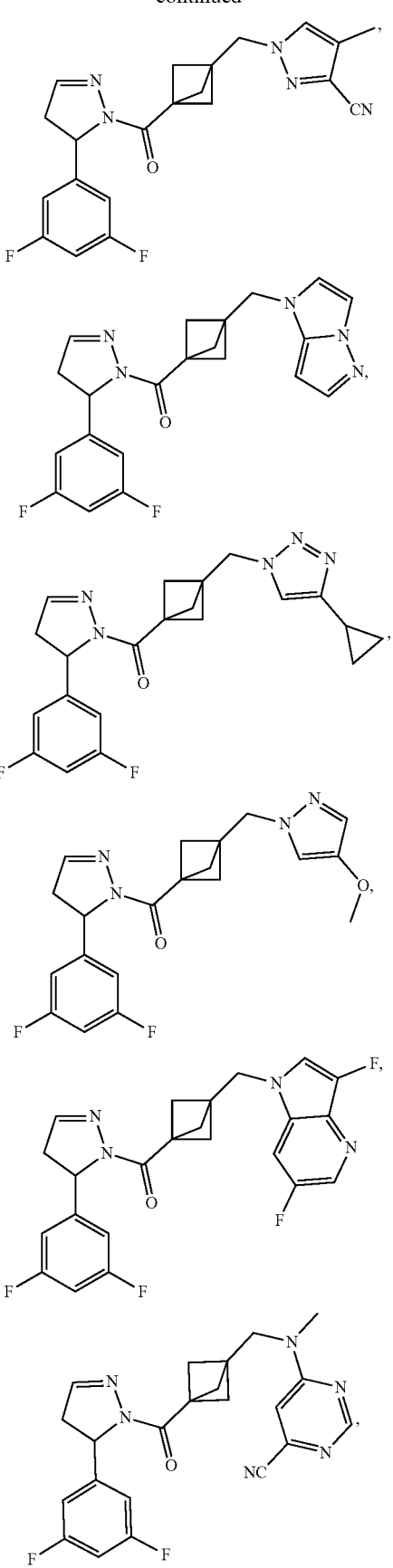

-continued
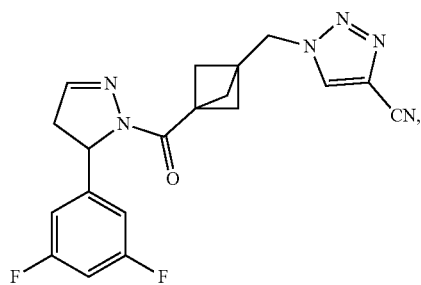
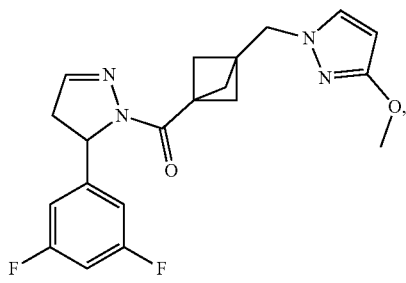
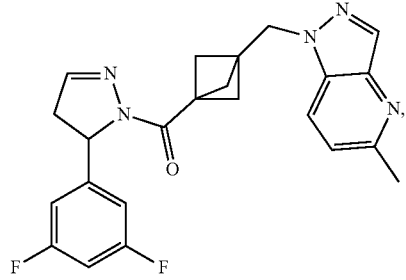
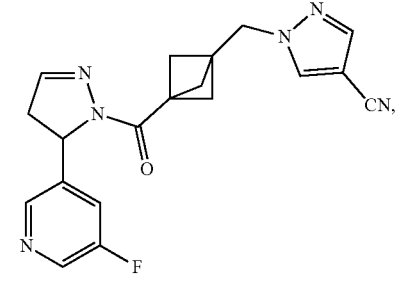
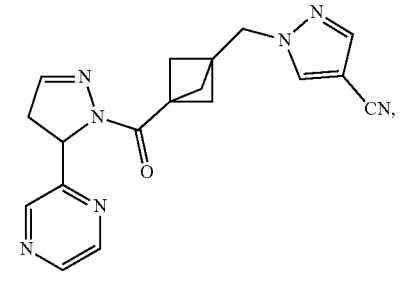
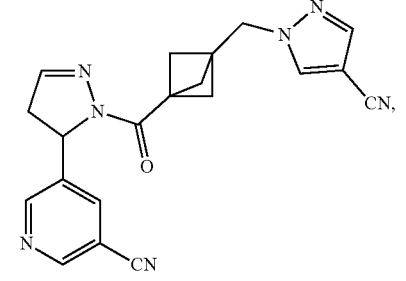
-continued
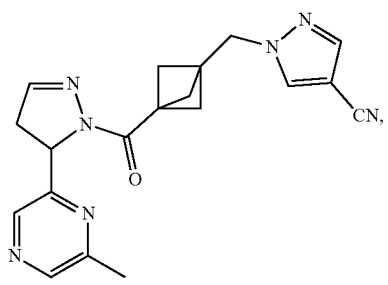
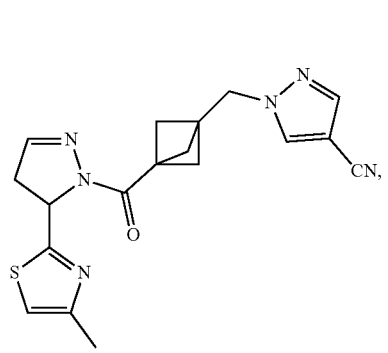
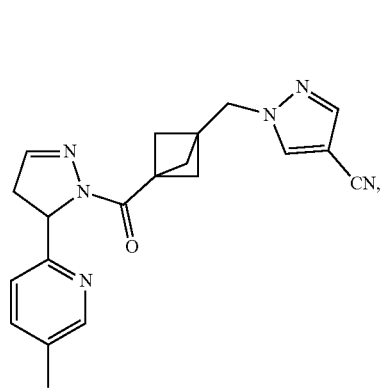
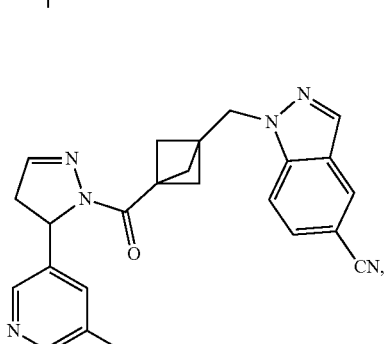
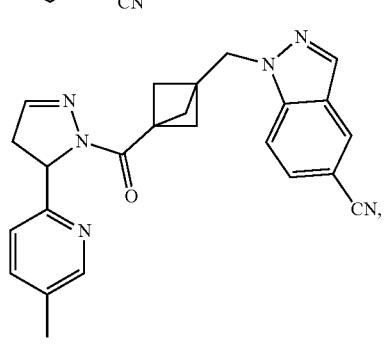

391
-continued
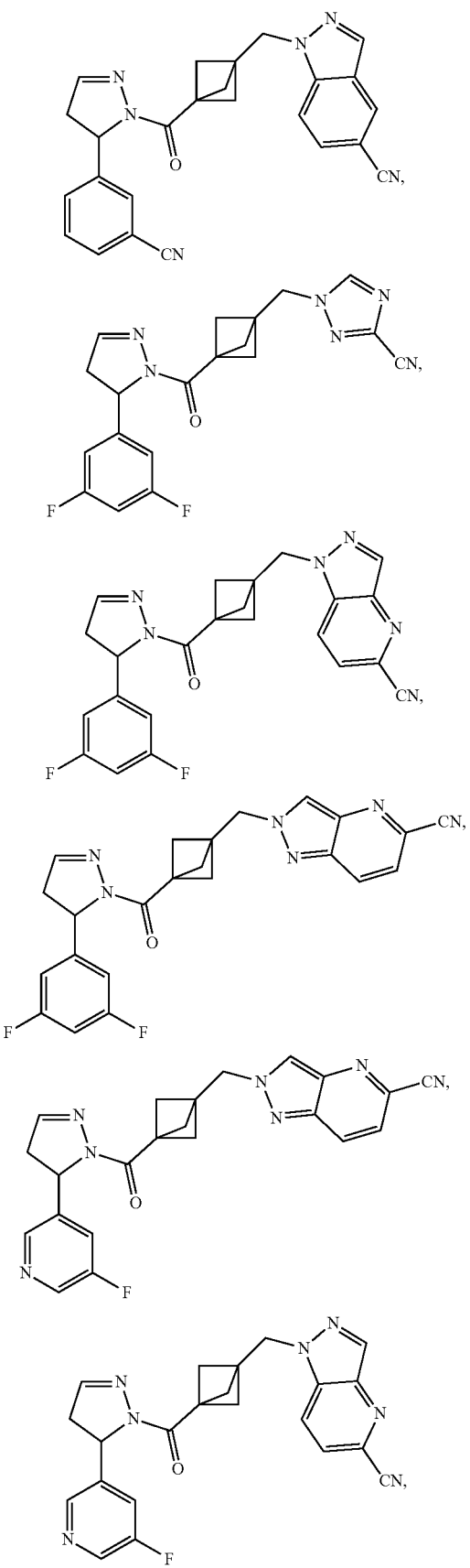
392
-continued
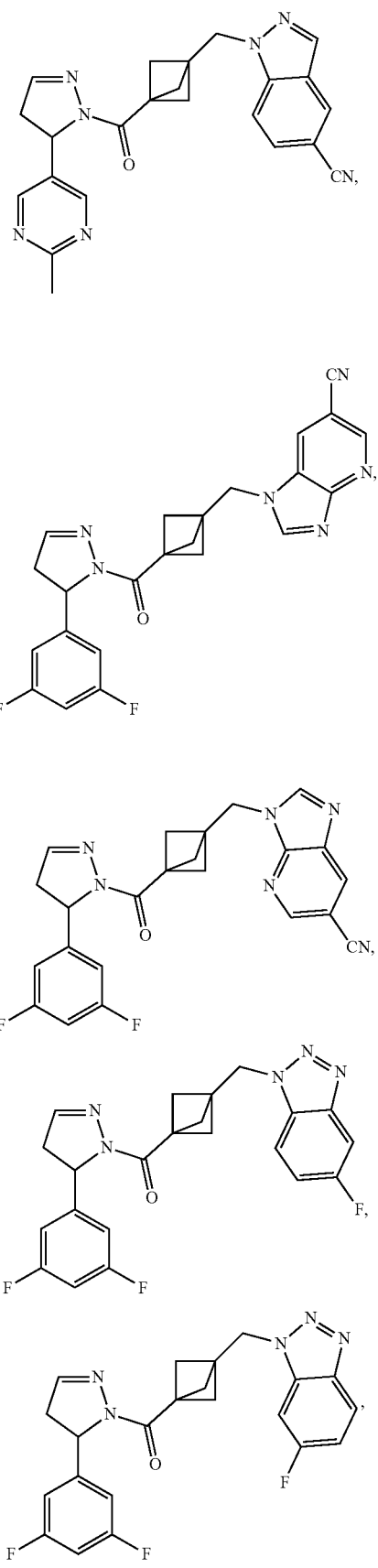

393
-continued
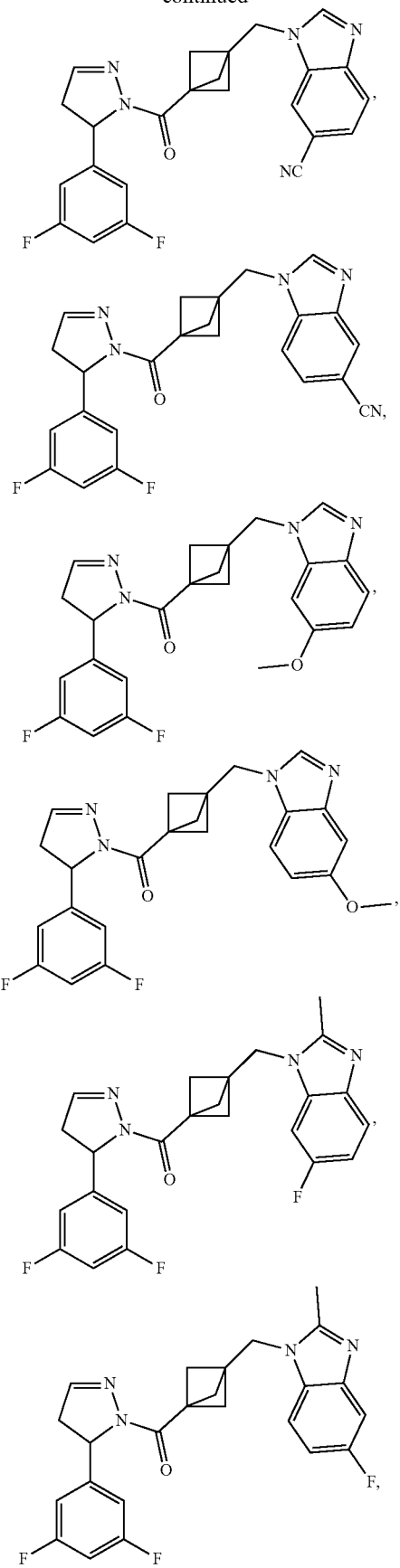
394
-continued
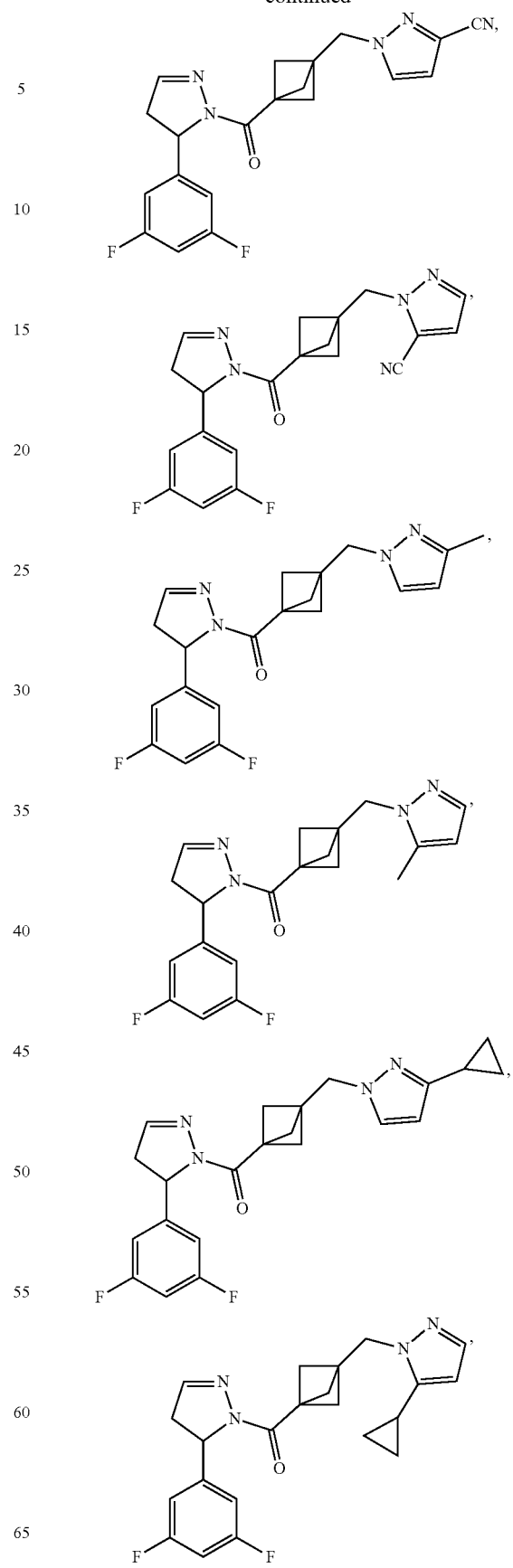

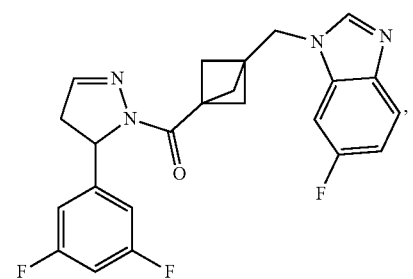
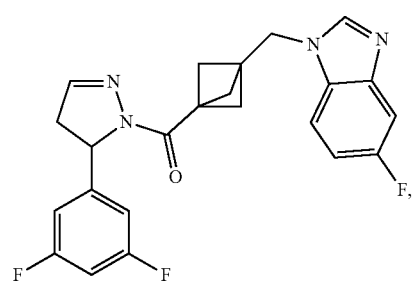
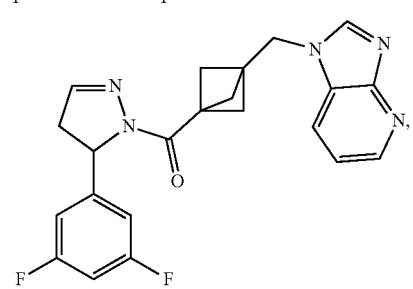
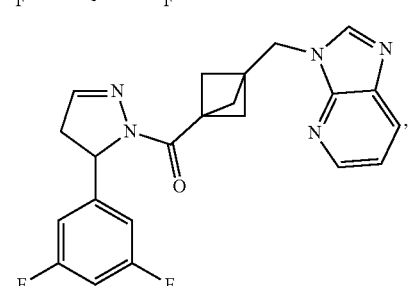
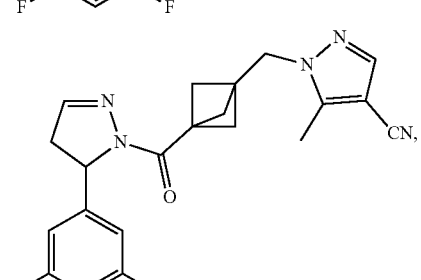
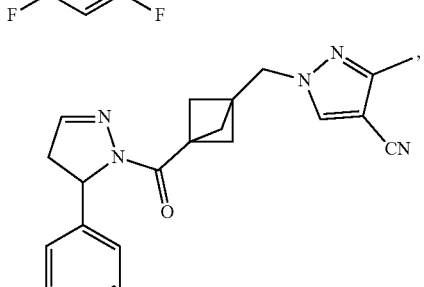
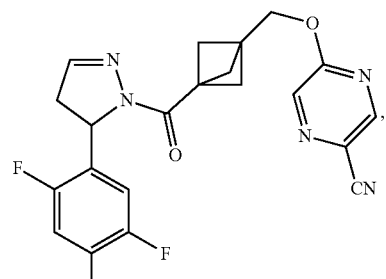
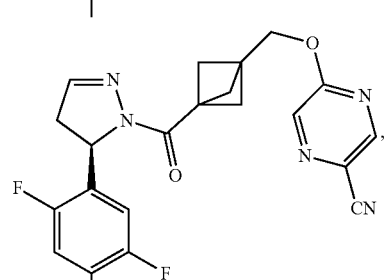
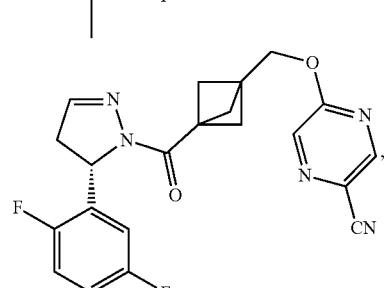
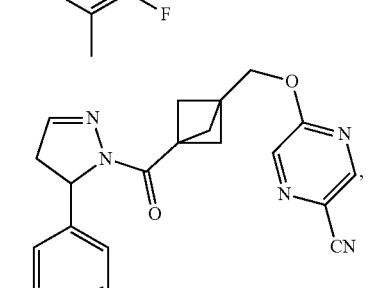
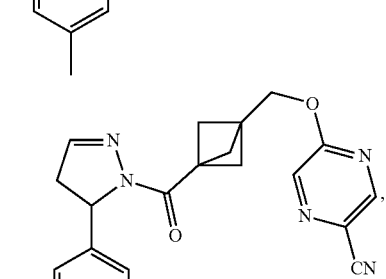
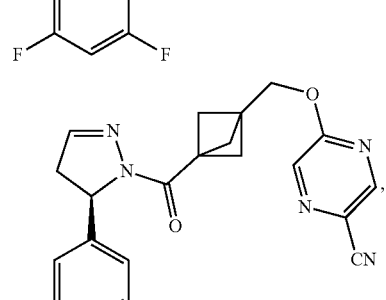

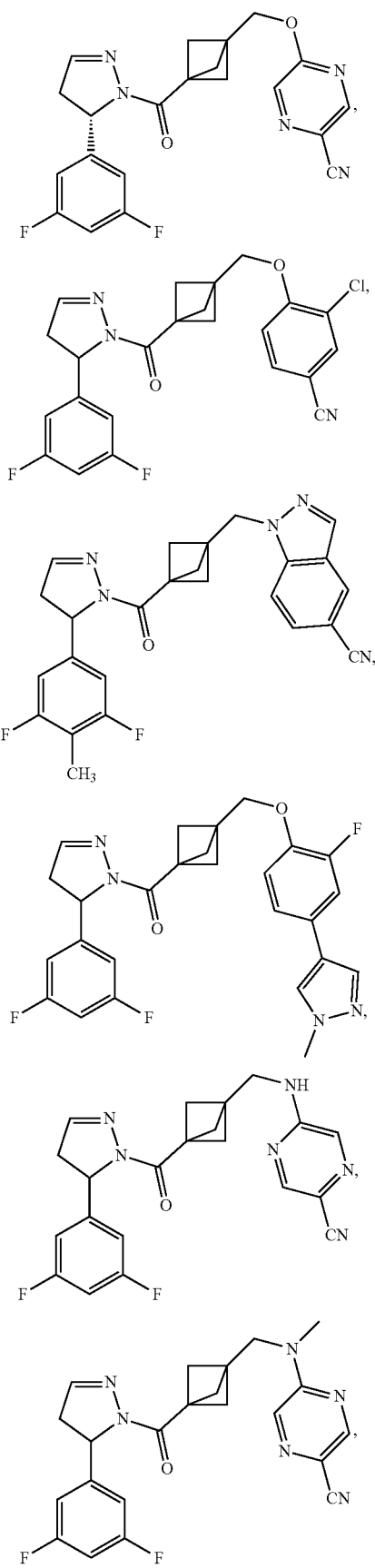
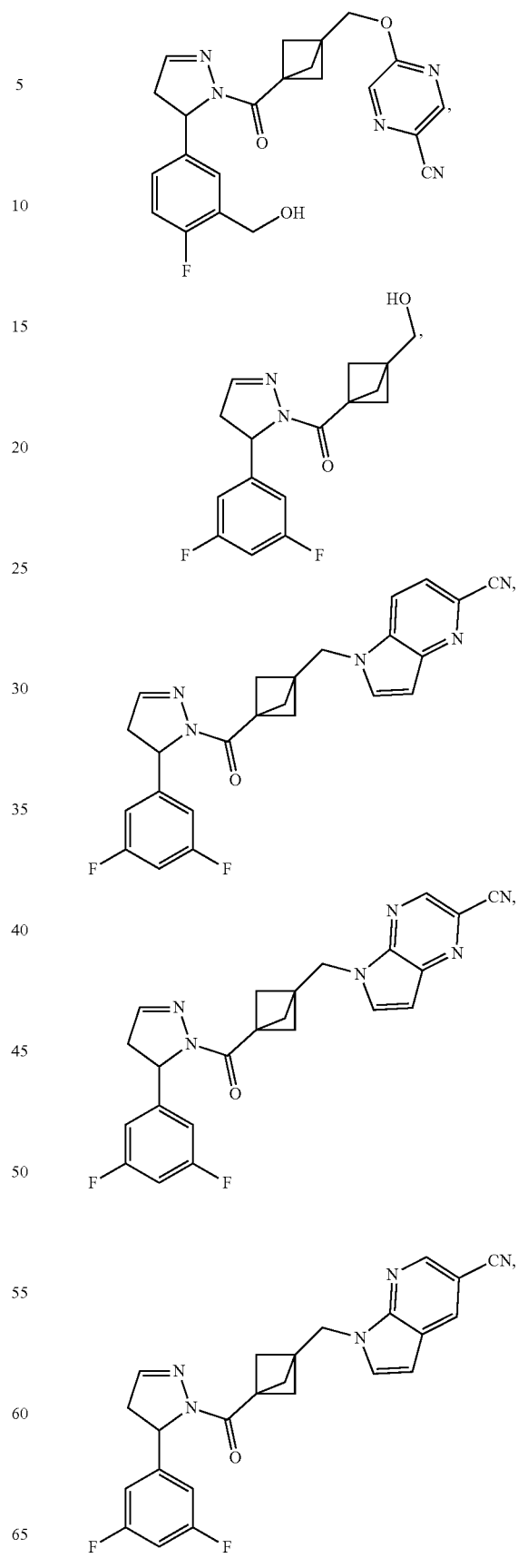

399
-continued
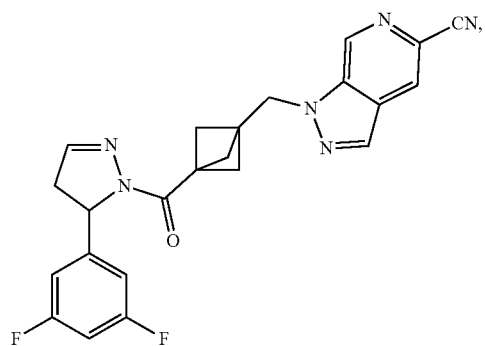
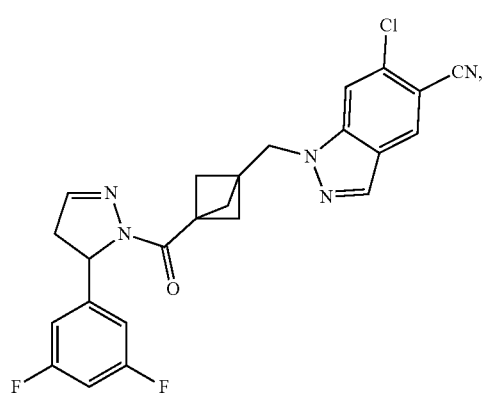
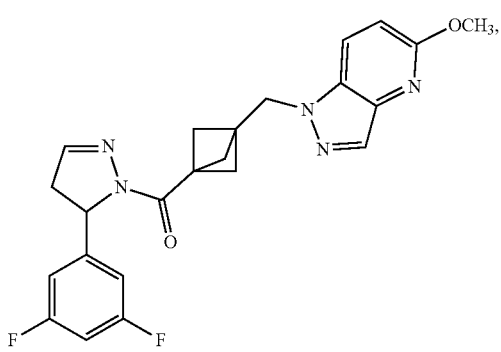
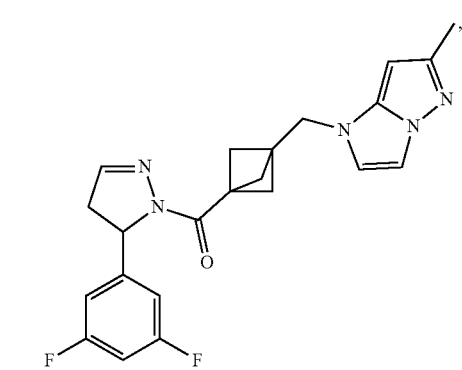
400
-continued
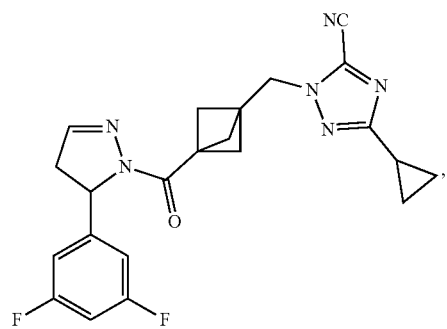
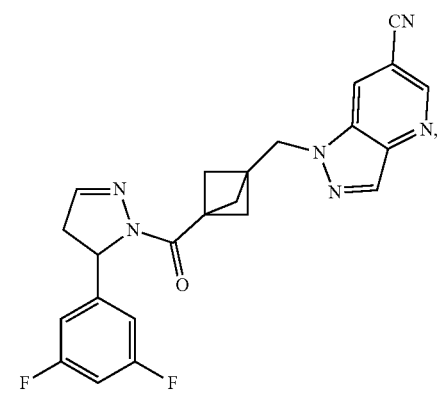
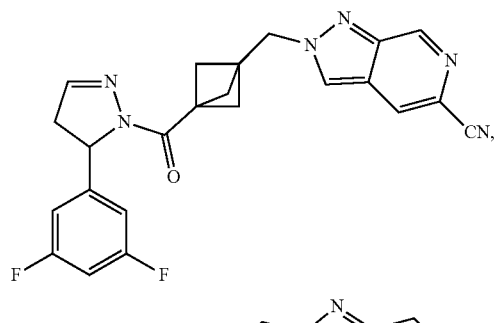
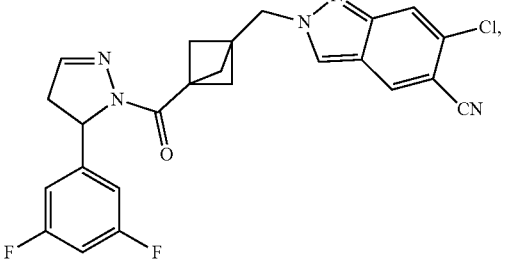
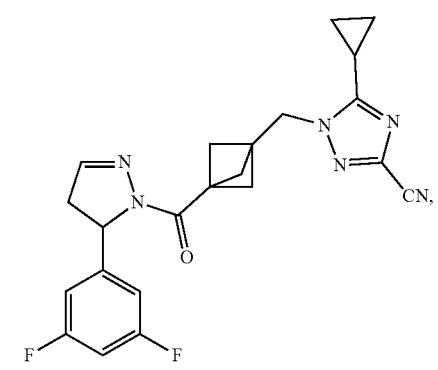

-continued
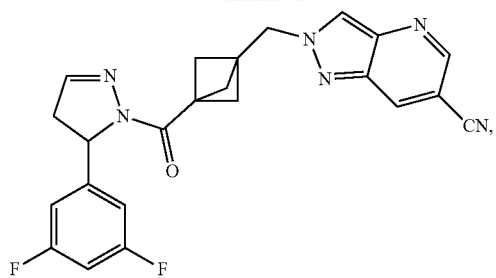
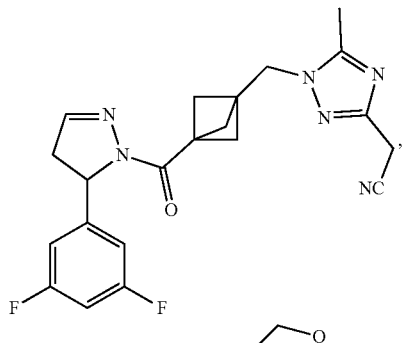
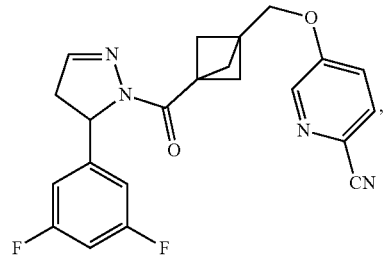
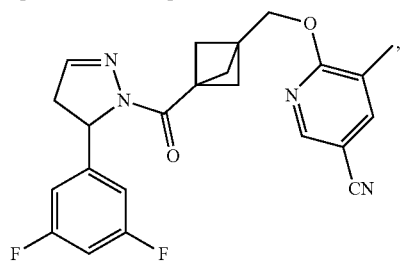
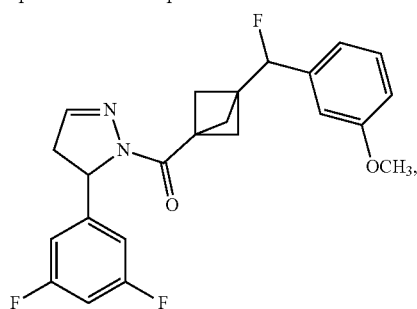
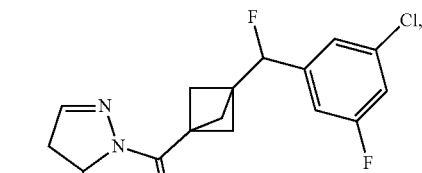
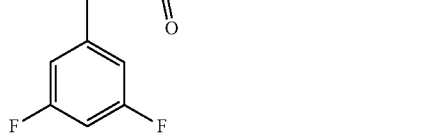
-continued
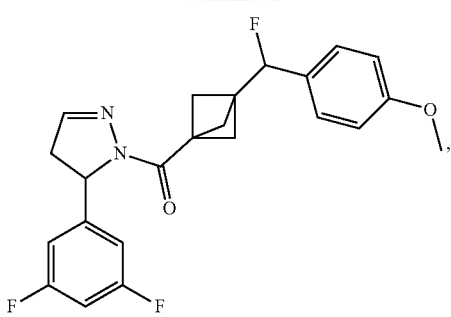
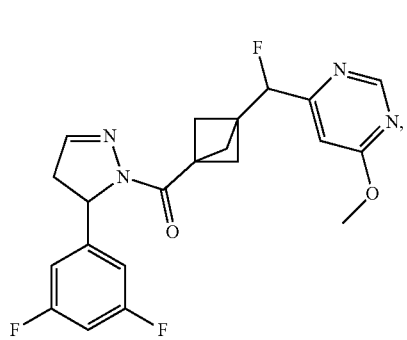
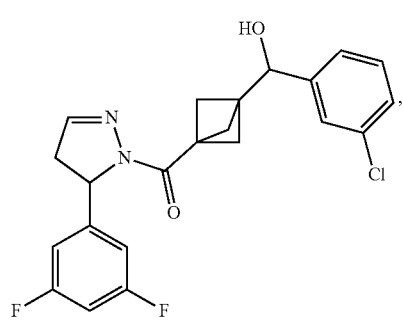
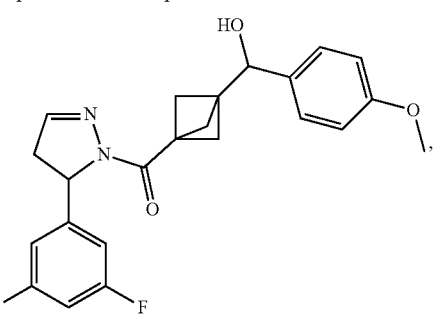
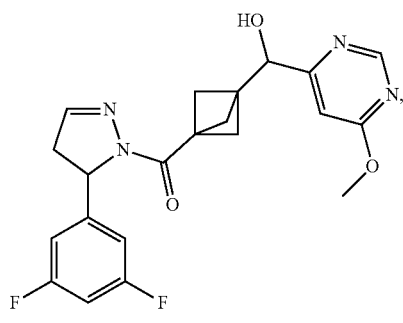

403
-continued
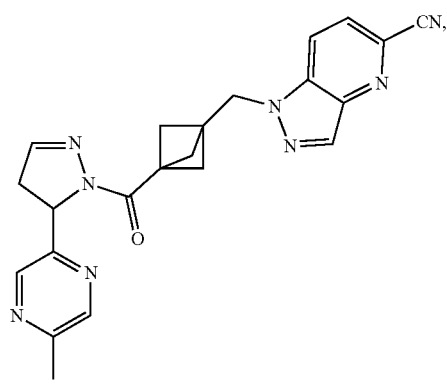
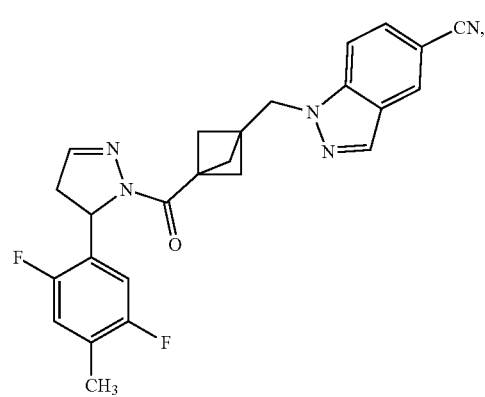
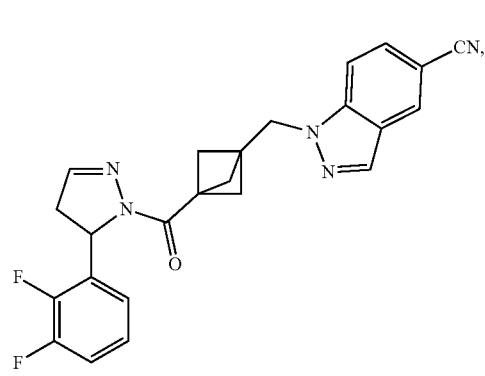
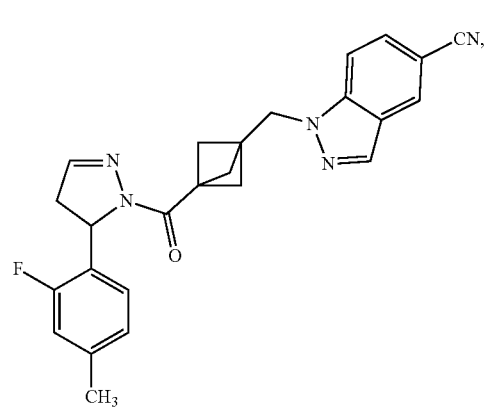
404
-continued
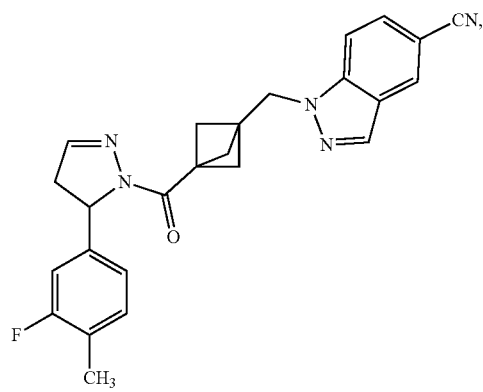
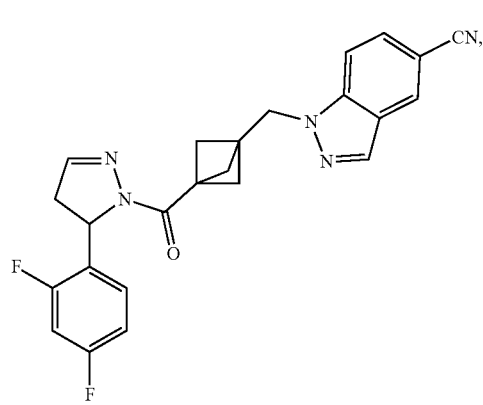
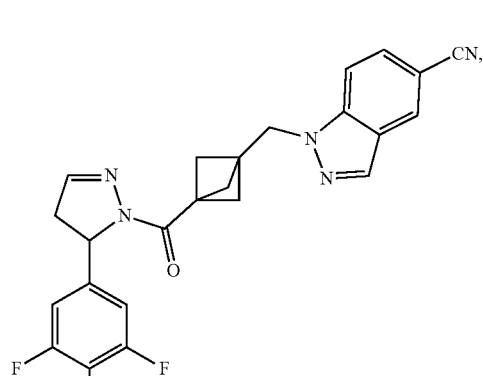
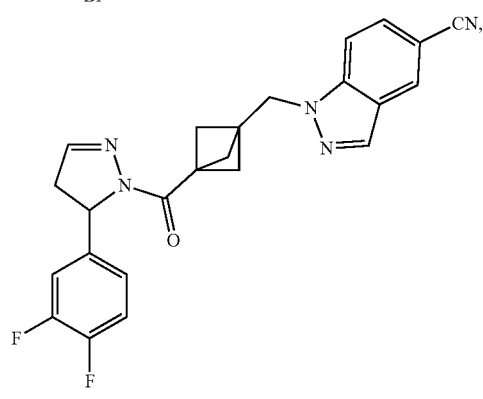

405
-continued
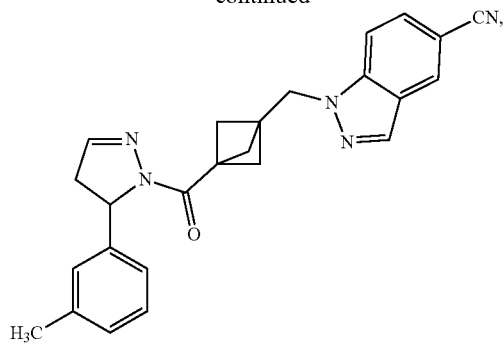
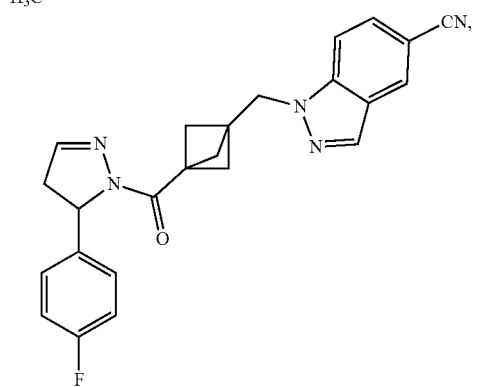
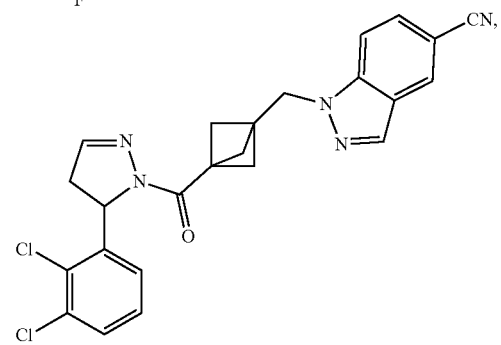
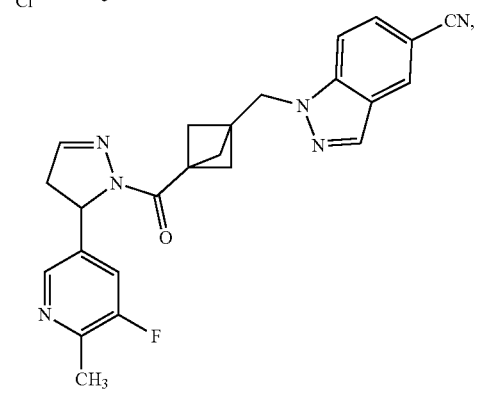
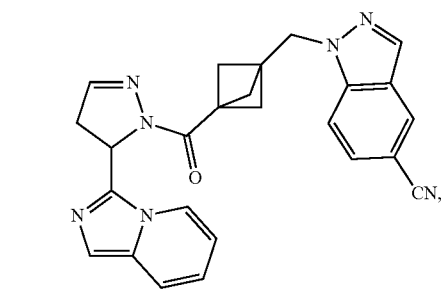
406
-continued
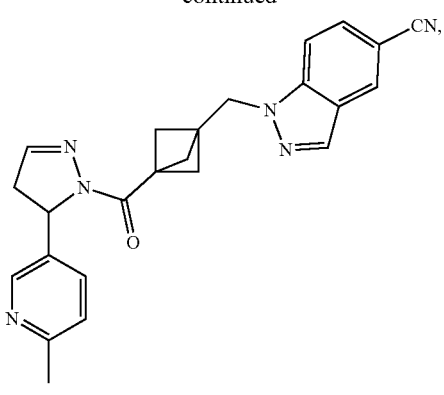
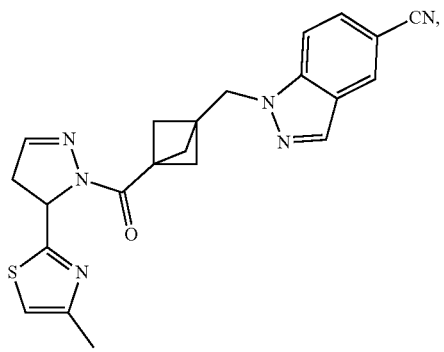
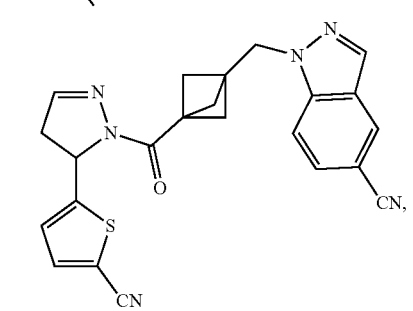
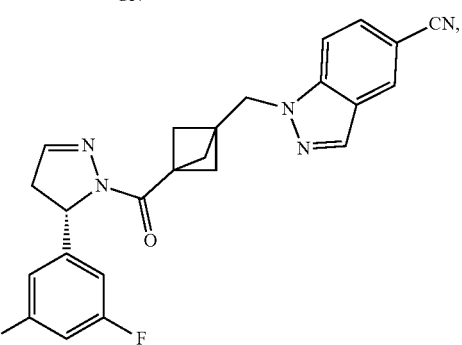
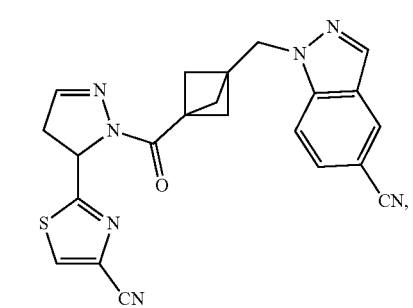

407
-continued
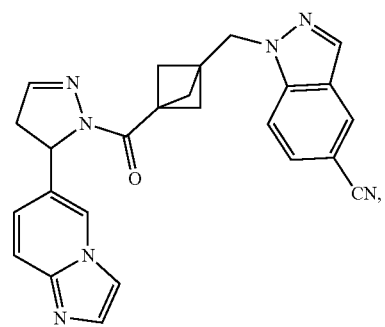
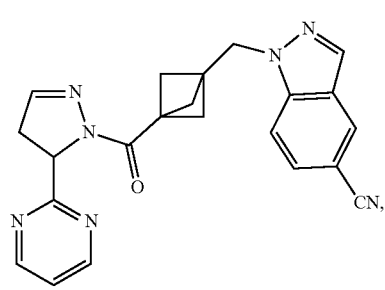
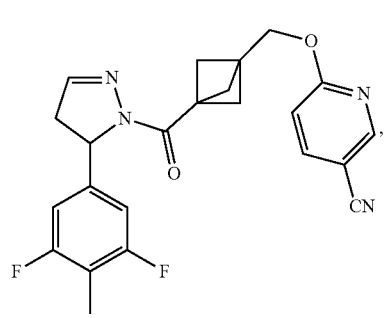
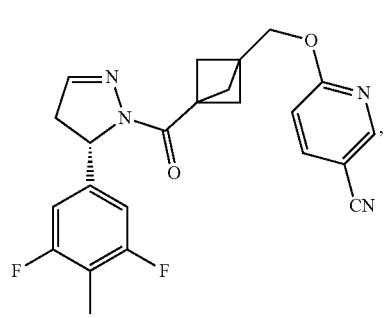
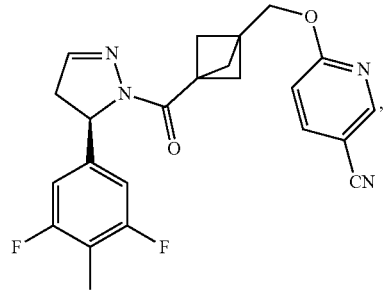
408
-continued
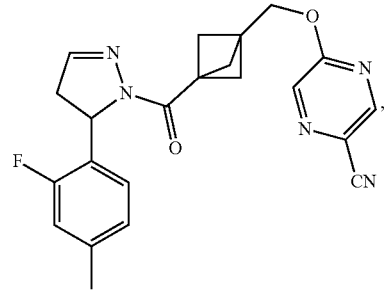
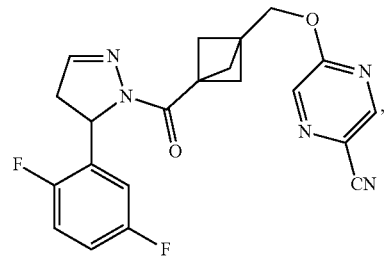
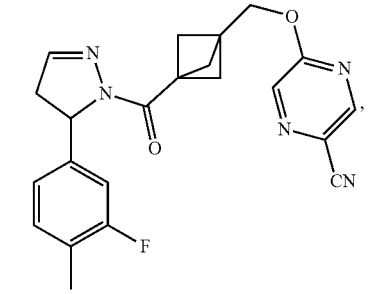
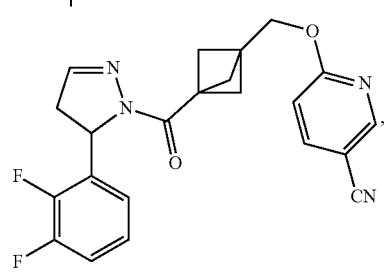
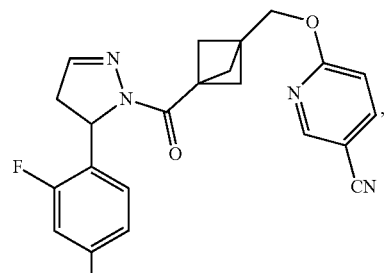
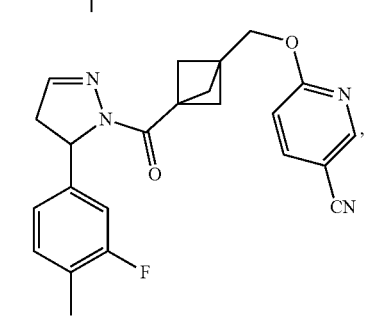

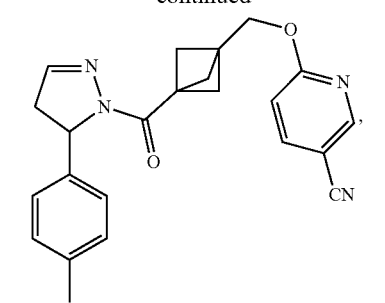
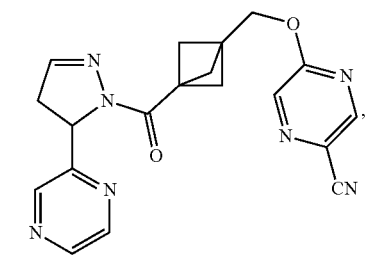
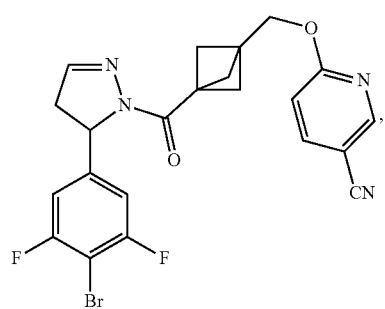
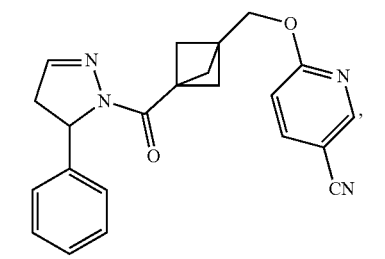
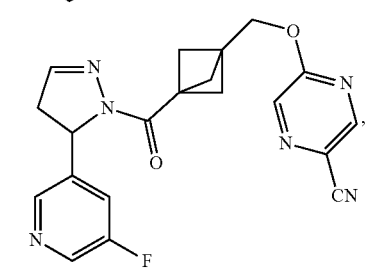
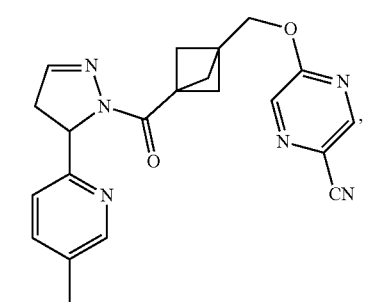
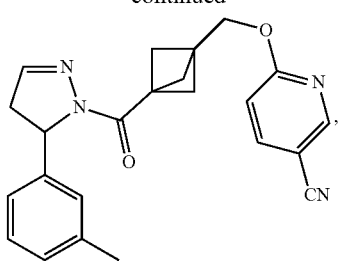
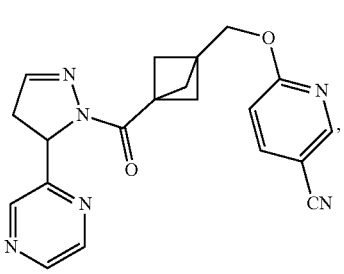
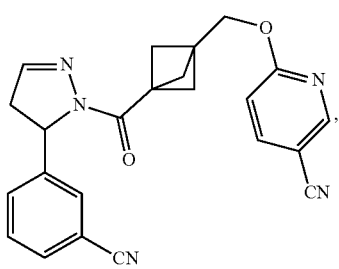
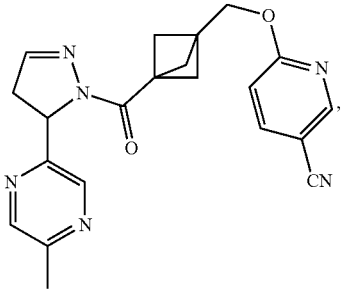
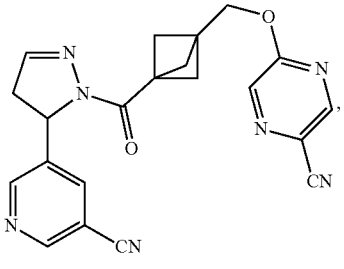
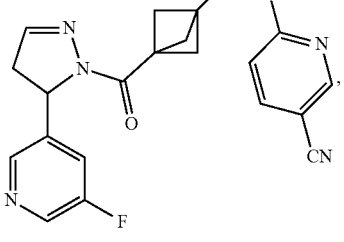

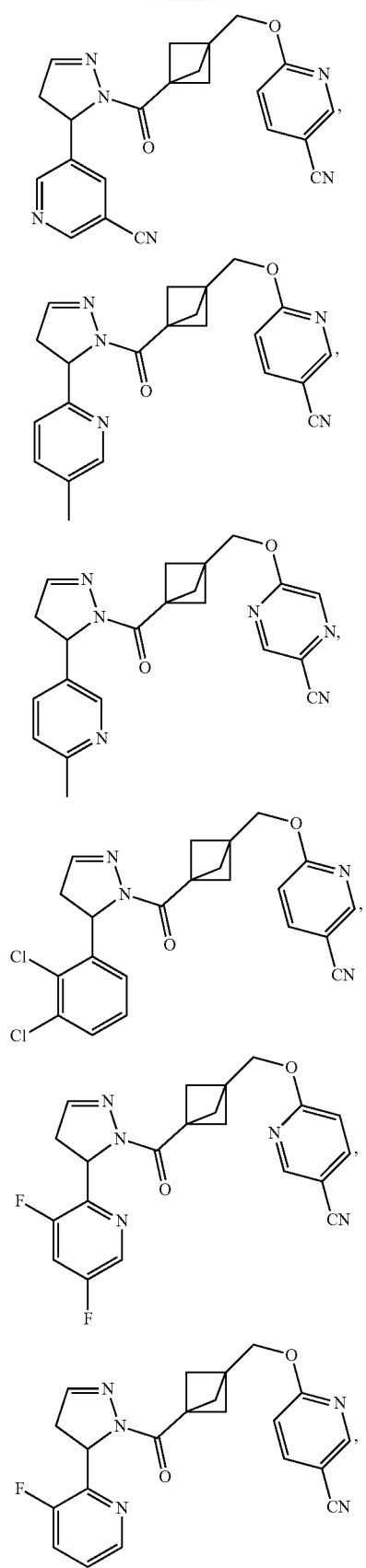
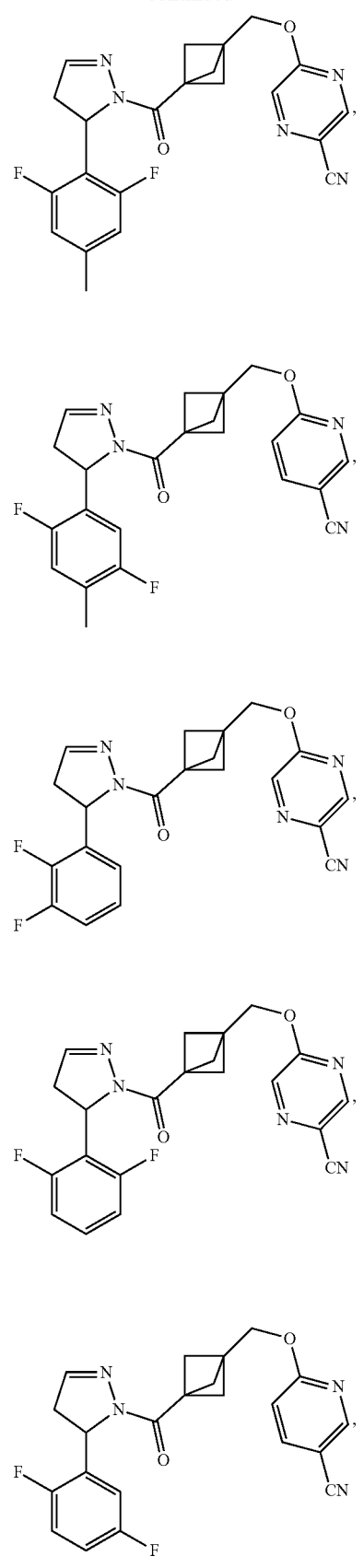

413
-continued
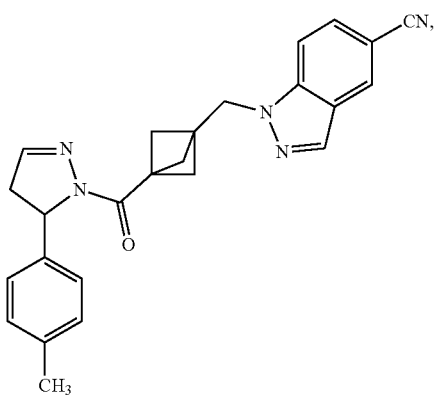
414
-continued
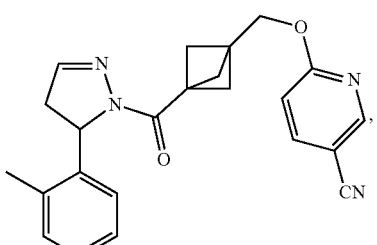
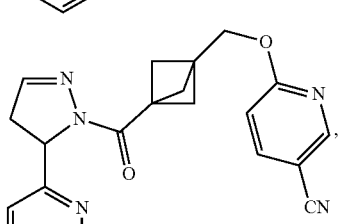
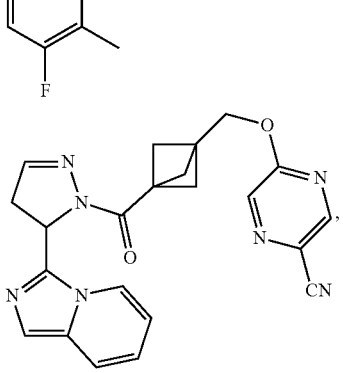
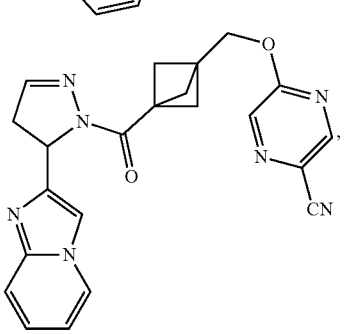
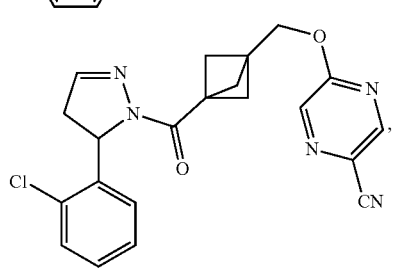
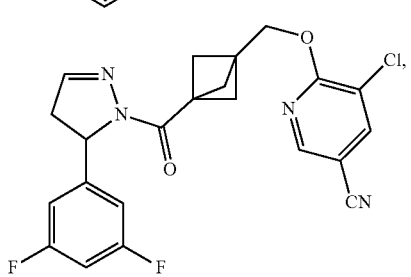

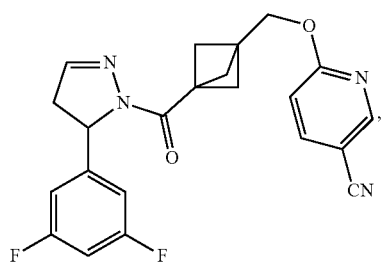
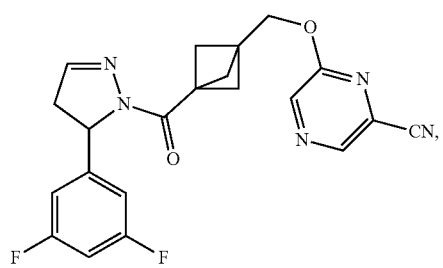
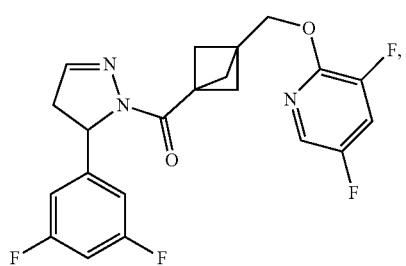
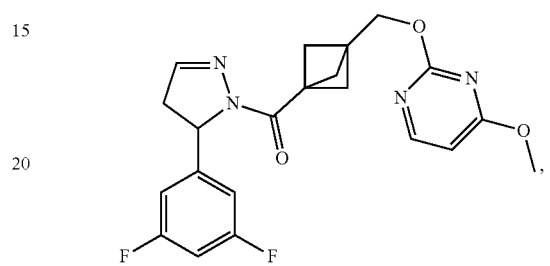
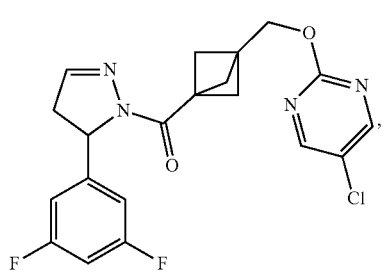
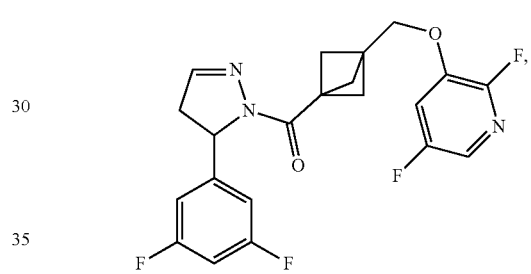
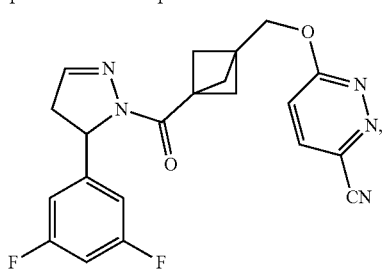
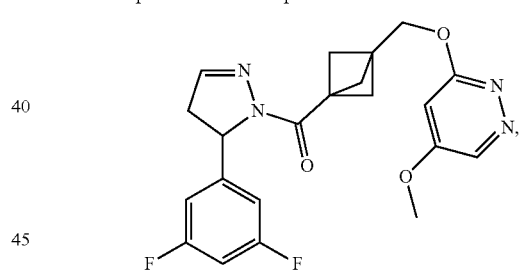
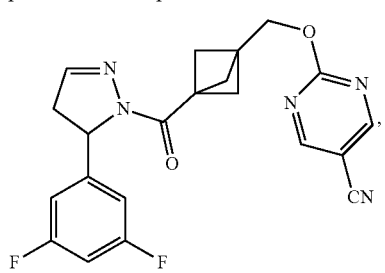
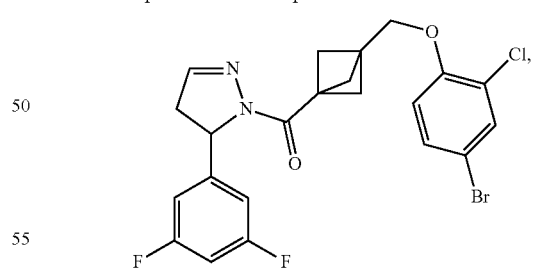
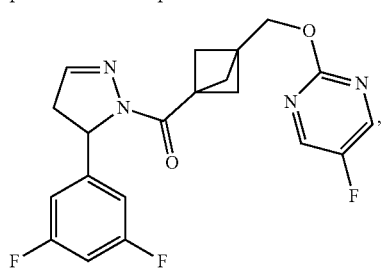
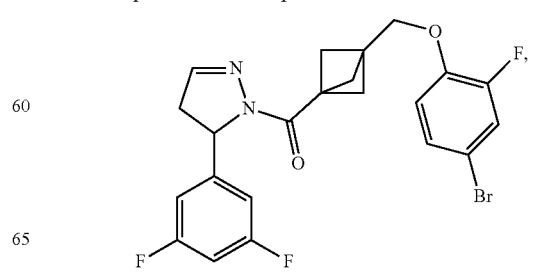

417
-continued
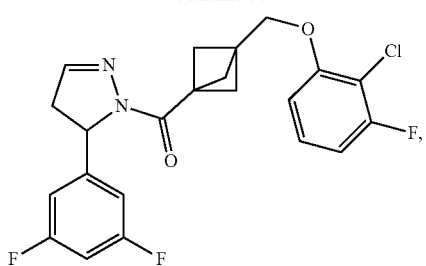
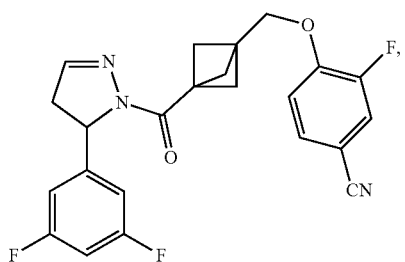
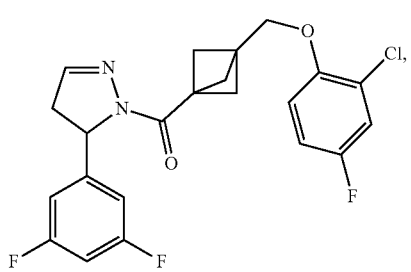
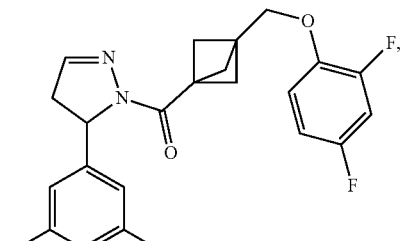
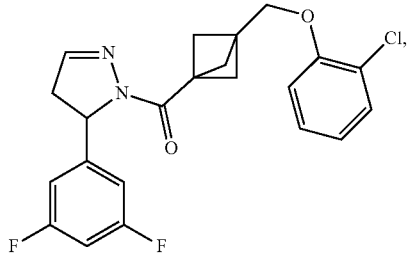
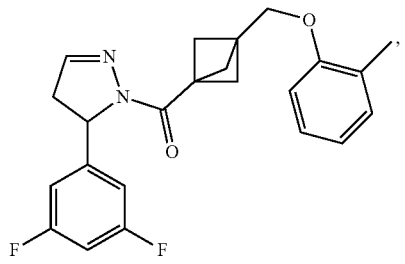
418
-continued
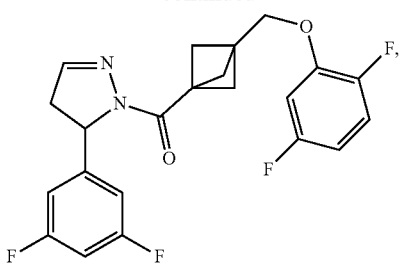
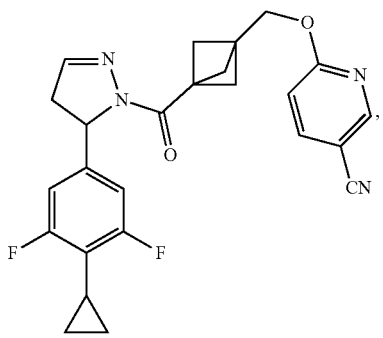
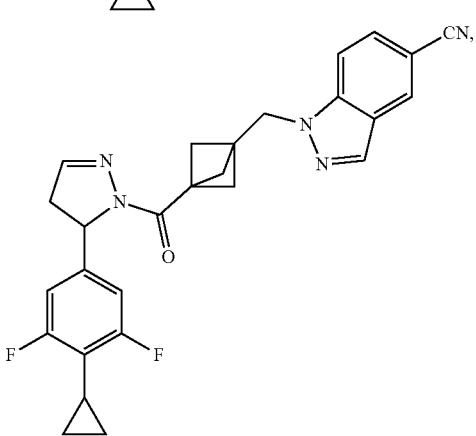
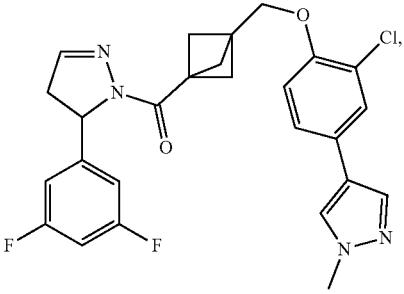
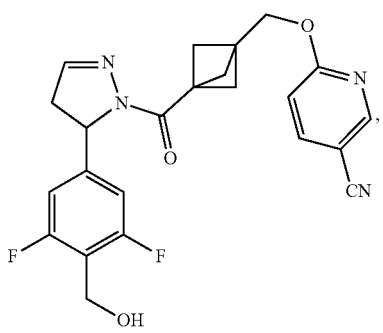

-continued
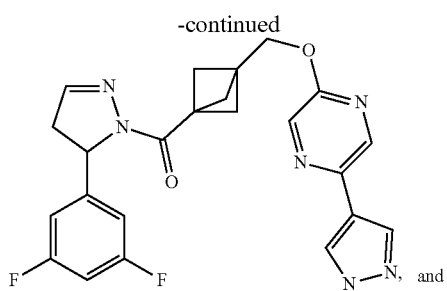, and
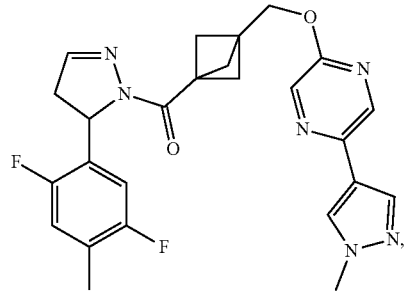,
or a salt thereof.
8. A pharmaceutical composition comprising a compound as recited in claim 1, or a salt thereof, together with a pharmaceutically acceptable carrier.
* * * * *